United States Patent
Boye et al.

(10) Patent No.: US 12,377,169 B2
(45) Date of Patent: Aug. 5, 2025

(54) DUAL AAV-MYO7A VECTORS WITH IMPROVED SAFETY FOR THE TREATMENT OF USH1B

(71) Applicant: University of Florida Research Foundation, Incorporated, Gainesville, FL (US)

(72) Inventors: Shannon E. Boye, Gainesville, FL (US); Sanford L. Boye, Gainesville, FL (US); H. Lee Sweeney, Gainesville, FL (US); Kaitlyn Calabro, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 17/916,308

(22) PCT Filed: Mar. 31, 2021

(86) PCT No.: PCT/US2021/025281
§ 371 (c)(1),
(2) Date: Sep. 30, 2022

(87) PCT Pub. No.: WO2021/202817
PCT Pub. Date: Oct. 7, 2021

(65) Prior Publication Data
US 2023/0149565 A1 May 18, 2023

Related U.S. Application Data

(60) Provisional application No. 63/003,774, filed on Apr. 1, 2020.

(51) Int. Cl.
*A61K 48/00* (2006.01)
*C07K 14/47* (2006.01)
*C12N 15/86* (2006.01)
*A61K 38/00* (2006.01)

(52) U.S. Cl.
CPC ........ *A61K 48/005* (2013.01); *A61K 48/0075* (2013.01); *C07K 14/4716* (2013.01); *C12N 15/86* (2013.01); *A61K 38/00* (2013.01); *C12N 2750/14132* (2013.01); *C12N 2750/14143* (2013.01); *C12N 2800/40* (2013.01)

(58) Field of Classification Search
None
See application file for complete search history.

(56) References Cited

U.S. PATENT DOCUMENTS

| | | | |
|---|---|---|---|
| 8,298,818 B2 | 10/2012 | Boye et al. | |
| 10,214,572 B2 * | 2/2019 | Boye | A61K 48/0066 |
| 11,325,956 B2 | 5/2022 | Boye et al. | |
| 11,525,139 B2 | 12/2022 | Simons et al. | |
| 11,781,145 B2 | 10/2023 | Simons et al. | |
| 11,807,867 B2 | 11/2023 | Simons et al. | |
| 12,188,041 B2 | 1/2025 | Dyka et al. | |
| 2007/0161110 A1 | 7/2007 | Iida et al. | |
| 2010/0003218 A1 | 1/2010 | Duan et al. | |
| 2010/0266551 A1 | 10/2010 | Richard et al. | |
| 2012/0003190 A1 | 1/2012 | Yamoah et al. | |
| 2012/0087862 A1 | 4/2012 | Hood et al. | |
| 2013/0210895 A1 | 8/2013 | Boye et al. | |
| 2014/0249208 A1 | 9/2014 | Bancel et al. | |
| 2014/0256802 A1 | 9/2014 | Boye et al. | |
| 2016/0022836 A1 * | 1/2016 | Banfi | A61P 27/02 514/44 R |
| 2016/0076054 A1 | 3/2016 | Auricchio et al. | |

(Continued)

FOREIGN PATENT DOCUMENTS

| | | |
|---|---|---|
| CA | 3034527 A1 | 3/2018 |
| CN | 110225975 A | 9/2019 |

(Continued)

OTHER PUBLICATIONS

Calabro. Exploring MYO&A function in novel mouse models and improving AAV-Dual Vector gene therapy for Usher Syndrome 1B. PHD dissertation. University of Florida. pp. 1-138 (Year: 2019).*
Barnes et al. JACS 2019,141,9004-9017 (Year: 2019).*
Zhang et al. Nature Communications. 2023. 7534. https://doi.org/10.1038/s41467-023-42747-9. pp. 1-12.*
Printout from https://www.cff.org/research-clinical-trials/types-cftr-mutations#:~:text=. Printed 2024. pp. 1-9.*
[No Author Listed], NCBI Accession No. NM_001632.5. *Homo sapiens* alkaline phosphatase, placental (ALPP), mRNA. https://www.ncbi.nlm.nih.gov/nuccore/1531243738?sat=47&satkey=4899452. Dec. 7, 2018. 4 pages.

(Continued)

*Primary Examiner* — Marcia S Noble
(74) *Attorney, Agent, or Firm* — Wolf, Greenfield & Sacks, P.C.

(57) ABSTRACT

Disclosed are compositions and methods for treating diseases of the mammalian eye, and in particular, complications of the retina associated with Usher syndrome IB (USH1B). Further disclosed are compositions and methods for treating diseases of the mammalian inner ear, and in particular, complications of ear hair cells associated with Usher syndrome IB (USH1B). The disclosure provides improved AAV-based, dual vector systems that facilitate the expression of full-length proteins whose coding sequences exceed that of the polynucleotide packaging capacity of an individual AAV vector. Described herein are modified hybrid dual vector systems that shift the coding sequence for the MYO7A tail domain from the front-half vector to the back-half vector by altering the split point (e.g., from between exons 23 and 24, to between exons 21 and 22), in order to eliminate the production of truncated MYO7A protein. Further described herein are improved, codon-modified hybrid and overlap vector systems in which putative stop codons and residual sequences in non-coding sequences are removed.

14 Claims, 50 Drawing Sheets
Specification includes a Sequence Listing.

(56) References Cited

U.S. PATENT DOCUMENTS

| | | | |
|---|---|---|---|
| 2018/0015172 A1 | 1/2018 | Muzyczka et al. |
| 2019/0002916 A1 | 1/2019 | Kalatzis et al. |
| 2019/0153050 A1 | 5/2019 | Boye et al. |
| 2019/0309326 A1 | 10/2019 | Maclaren et al. |
| 2020/0157573 A1 | 5/2020 | Boye et al. |
| 2021/0130421 A1 | 5/2021 | Boye et al. |
| 2021/0395778 A1 | 12/2021 | Dyka et al. |
| 2024/0011039 A1 | 1/2024 | Simons et al. |

FOREIGN PATENT DOCUMENTS

| | | | | |
|---|---|---|---|---|
| JP | 2016-516424 A | 6/2016 | | |
| JP | 7240675 B2 | 3/2023 | | |
| KR | 10-2007-0004636 A | 1/2007 | | |
| WO | WO 2001/070972 A2 | 9/2001 | | |
| WO | WO 2008/088895 A2 | 7/2008 | | |
| WO | WO 2013/075008 A1 | 5/2013 | | |
| WO | WO 2014/140051 A1 | 9/2014 | | |
| WO | WO-2014170480 A1 * | 10/2014 | ........... | A61K 48/005 |
| WO | WO 2014/193716 A2 | 12/2014 | | |
| WO | WO 2016/131981 A1 | 8/2016 | | |
| WO | WO 2016/139321 A1 | 9/2016 | | |
| WO | WO 2017/049252 A1 | 3/2017 | | |
| WO | WO 2017/100791 A1 | 6/2017 | | |
| WO | WO 2017/216 A1 | 12/2017 | | |
| WO | WO 2018/039375 A1 | 3/2018 | | |
| WO | WO 2018/162748 A1 | 9/2018 | | |
| WO | WO 2018/204734 A1 | 11/2018 | | |
| WO | WO 2019/165292 A1 | 8/2019 | | |
| WO | WO 2019/183641 A1 | 9/2019 | | |
| WO | WO 2020/148458 A1 | 7/2020 | | |
| WO | WO 2021/087296 A1 | 5/2021 | | |

OTHER PUBLICATIONS

[No Author Listed], NCBI Accession No. NP_001274418. OTOF otoferlin isoform e [*Homo sapiens* (human)]. Nov. 17, 2023. 3 pages.

Avraham, What's hot about otoferlin. EMBO J. Dec. 1, 2016;35(23):2502-2504. doi: 10.15252/embj.201695881. Epub Nov. 7, 2016.

Gao et al., The Dystrophin Complex: Structure, Function, and Implications for Therapy. Compr Physiol. Jul. 1, 2015;5(3):1223-39. doi: 10.1002/cphy.c140048. Author Manuscript, 33 pages.

Geleoc et al., Sound strategies for hearing restoration. Science. May 9, 2014;344(6184):1241062. doi: 10.1126/science.1241062.

Hirsch et al., Delivering Transgenic DNA Exceeding the Carrying Capacity of AAV Vectors. Methods Mol Biol. 2016;1382:21-39. doi: 10.1007/978-1-4939-3271-9_2. Author Manuscript, 20 pages.

Lostal et al., Full-length dystrophin reconstitution with adeno-associated viral vectors. Hum Gene Ther. Jun. 2014:25(6):552-62. doi: 10.1089/hum.2013.210. Epub Mar. 31, 2014.

Majewski et al., GT repeats are associated with recombination on human chromosome 22. Genome Res. Aug. 2000;10(8):1108-14. doi: 10.1101/gr.10.8.1108.

Pryadkina et al., A comparison of AAV strategies distinguishes overlapping vectors for efficient systemic delivery of the 6.2 kb Dysferlin coding sequence. Mol Ther Methods Clin Dev. Mar. 25, 2015;2:15009. doi: 10.1038/mtm.2015.9.

Yasunaga et al., OTOF encodes multiple long and short isoforms: genetic evidence that the long ones underlie recessive deafness DFNB9. Am J Hum Genet. Sep. 2000;67(3):591-600. doi: 10.1086/303049. Epub Jul. 19, 2000.

Akil et al., Restoration of hearing in the VGLUT3 knockout mouse using virally mediated gene therapy. Neuron. Jul. 26, 2012;75(2):283-93. doi: 10.1016/j.neuron.2012.05.019.

Extended European Search Report for European Application No. EP 18793935.0 mailed on Feb. 22, 2021.

International Search Report and Written Opinion mailed Jul. 30, 2018 for Application No. PCT/US2018/031009.

International Preliminary Report on Patentability mailed Nov. 14, 2019 for Application No. PCT/US2018/031009.

International Search Report and Written Opinion mailed Feb. 20, 2020 for Application No. PCT/US2019/059549.

International Preliminary Report on Patentability for Application No. PCT/US2019/059549, mailed May 14, 2021.

International Search Report and Written Opinion for International Application No. PCT/US2012/065645 mailed Mar. 29, 2013.

International Preliminary Report on Patentability for International Application No. PCT/US2012/065645 mailed May 30, 2014.

Invitation to Pay Additional Fees for International Application No. PCT/US2021/025281 mailed Jun. 29, 2021.

International Search Report and Written Opinion for International Application No. PCT/US2021/025281 mailed Sep. 10, 2021.

International Preliminary Report on Patentability for International Application No. PCT/US2021/025281 mailed Oct. 13, 2022.

Akil et al., Dual AAV-mediated gene therapy restores hearing in a DFNB9 mouse model. Proc Natl Acad Sci U S A. Mar. 5, 2019;116(10):4496-4501. doi: 10.1073/pnas.1817537116. Epub Feb. 19, 2019.

Alemi et al., Progress Report: AOS Research Grant: Restoration of Hearing in the Otoferlin Knockout Mouse using Viral Gene Therapy. 145th Annual Meeting. American Otological Society, Inc. Apr. 21-22, 2012; p. 68. Available online at: https://www.americanotologicalsociety.org/assets/2012.pdf.

Al-Hussaini et al., Mature retinal pigment epithelium cells are retained in the cell cycle and proliferate in vivo. Mol Vis. 2008;14:1784-91. Epub Oct. 6, 2008.

Allocca et al., Serotype-dependent packaging of large genes in adeno-associated viral vectors results in effective gene delivery in mice. J Clin Invest. May 1, 2008; 118(5): 1955-1964. Published online Apr. 15, 2008. doi: 10.1172/JCI34316.

Al-Moyed et al., A dual-AAV approach restores fast exocytosis and partially rescues auditory function in deaf otoferlin knock-out mice. EMBO Mol Med. Jan. 2019;11(1):e9396. doi: 10.15252/emmm.201809396.

Chen et al., Molecular cloning and domain structure of human myosin-VIIa, the gene product defective in Usher syndrome 1B. Genomics. Sep. 15, 1996;36(3):440-8. doi: 10.1006/geno.1996.0489.

Daya et al., Gene therapy using adeno-associated virus vectors. Clin Microbiol Rev. Oct. 2008;21(4):583-93. doi: 10.1128/CMR.00008-08.

Dong et al., Characterization of genome integrity for oversized recombinant AAV vector. Mol Ther. Jan. 2010;18(1):87-92. doi: 10.1038/mt.2009.258. Epub Nov. 10, 2009.

Duan et al., Circular intermediates of recombinant adeno-associated virus have defined structural characteristics responsible for long-term episomal persistence in muscle tissue. J Virol. Nov. 1998;72(11):8568-77.

Duan et al., Expanding AAV packaging capacity with trans-splicing or overlapping vectors: a quantitative comparison. Mol Ther. Oct. 2001;4(4):383-91.

Dyka et al., Dual adeno-associated virus vectors result in efficient in vitro and in vivo expression of an oversized gene, MYO7A. Hum Gene Ther Methods. Apr. 2014;25(2):166-77. doi: 10.1089/hgtb.2013.212.

GenBank Submission; NIH/NCBI, Accession No. NP_000251. unconventional myosin-VIIa isoform 1 [*Homo sapiens*]. Aug. 14, 2022. 5 pages.

GenBank Submission; NIH/NCBI, Accession No. U39226.1. Human myosin VIIA (USH1B) mRNA, complete cds. Jul. 11, 1996. 5 pages.

Ghosh et al., A hybrid vector system expands adeno-associated viral vector packaging capacity in a transgene-independent manner. Mol Ther. Jan. 2008;16(1):124-30. doi: 10.1038/sj.mt.6300322. Epub Nov. 6, 2007.

Ghosh et al., Efficient transgene reconstitution with hybrid dual AAV vectors carrying the minimized bridging sequences. Hum Gene Ther. Jan. 2011;22(1):77-83. doi: 10.1089/hum.2010.122. Epub Dec. 12, 2010.

(56) References Cited

OTHER PUBLICATIONS

Hashimoto et al., Lentiviral gene replacement therapy of retinas in a mouse model for Usher syndrome type 1B. Gene Therapy. 2007:14;584-594.
Jacobson et al., Usher syndromes due to MYO7A, PCDH15, USH2A or GPR98 mutations share retinal disease mechanism. Hum Mol Genet. Aug. 1, 2008;17(15):2405-15. doi: 10.1093/hmg/ddn140. Epub May 7, 2008.
Lai et al., Evidence for the Failure of Adeno-associated Virus Serotype 5 to Package a Viral Genome ≥8.2 kb. Mol Ther. 2010; 18 1, 75-79. doi:10.1038/mt.2009.256.
Li et al., High-efficiency transduction of fibroblasts and mesenchymal stem cells by tyrosine-mutant AAV2 vectors for their potential use in cellular therapy. Hum Gene Ther. Nov. 2010;21(11):1527-43. doi: 10.1089/hum.2010.005. Epub Oct. 6, 2010.
Lopes et al., Retinal gene therapy with a large MYO7A cDNA using adeno-associated virus. Gene Ther. Aug. 2013;20(8):824-33. doi: 10.1038/gt.2013.3. Epub Jan. 24, 2013. Author Manuscript, 21 pages.
Petrs-Silva et al., Novel properties of tyrosine-mutant AAV2 vectors in the mouse retina. Mol Ther. Feb. 2011;19(2):293-301. doi: 10.1038/mt.2010.234. Epub Nov. 2, 2010.
Trapani et al., Effective delivery of large genes to the retina by dual AAV vectors. EMBO Mol Med. Feb. 2014;6(2):194-211. doi: 10.1002/emmm.201302948. Epub Dec. 15, 2013.
Weil et al., Human myosin VIIA responsible for the Usher 1B syndrome: A predicted membrane-associated motor protein expressed in developing sensory epithelia. Proc Natl Acad Sci U S A. Apr. 16, 1996;93(8):3232-7. doi: 10.1073/pnas.93.8.3232.
Wu et al., Effect of genome size on AAV vector packaging. Mol Ther. Jan. 2010;18(1):80-6. doi: 10.1038/mt.2009.255. Epub Nov. 10, 2009.
Yan et al., Inverted terminal repeat sequences are important for intermolecular recombination and circularization of adeno-associated virus genomes. J Virol. Jan. 2005;79(1):364-79.
Yan et al., Recombinant AAV-mediated gene delivery using dual vector heterodimerization. Methods Enzymol. 2002;346:334-57. doi: 10.1016/s0076-6879(02)46065-x.
Extended European Search Report for European Application No. EP 21781660.2 mailed on Apr. 9, 2024.
[No Author Listed] OTOF sequence comparison of Yasunaga SEQ ID No. 70 with present SEQ ID No. 5 (dated Apr. 12, 24), from U.S. Appl. No. 17/290,082 Office Action, filed Apr. 18, 2024, 5 pages.
McClements et al., A fragmented adeno-associated viral dual vector strategy for treatment of diseases caused by mutations in large genes leads to expression of hybrid transcripts. J Genet Syndr Gene Ther. Nov. 14, 2016;7(5):311. doi: 10.4172/2157-7412.1000311. Author Manuscript, 16 pages.
[No Author Listed] Basics of Sound, the Ear, and Hearing, Hearing Loss: Determining Eligibility for Social Security Benefits. Dobie RA, Van Hemel S, editors. Washington (DC): National Academies Press (US); 2004, p. 42-68.
[No Author Listed] Children's Hospital of Philadelphia Performs First Gene Therapy Procedure to Treat Genetic Hearing Loss in United States, American Academy of Audiology, Accessed online: <https://www.audiology.org/childrens-hospital-of-philadelphia-performs-first-gene-therapy-procedure-to-treat-genetic-hearing-loss-in-united-states/>, dated Jan. 26, 2024 (2 pages).
[No Author Listed] Genetic Hearing Loss With No Associated Abnormalities, Hereditary Hearing Loss and Its Syndromes, Third Edition. Helga V. Toriello and Shelley D. Smith (Eds.), 2013, p. 164-165 (4 pages).
[No Author Listed] GenPept Accession NP_001274418.1, dated Apr. 23, 2017, retrieved from https://www.ncbi.nlm.nih.gov/protein/566559996?sat=46&satkey=73202094, 4 pages.
Ahmed et al., Emerging Gene Therapies for Genetic Hearing Loss. J Assoc Res Otolaryngol. Oct. 2017;18(5):649-670. doi: 10.1007/s10162-017-0634-8. Epub Aug. 16, 2017.
Akil et al., AAV-Mediated Gene Delivery to the Inner Ear. Methods Mol Biol. 2019;1950:271-282. doi: 10.1007/978-1-4939-9139-6_16.
Akil et al., Surgical method for virally mediated gene delivery to the mouse inner ear through the round window membrane. J Vis Exp. Mar. 16, 2015;(97):52187. doi: 10.3791/52187.
Hamosh et al., Otoferlin; OTOF, OMIM. (Apr. 2015) Retrieved via The Wayback Machine, URL: <https://web.archive.org/web/20150729163826/http://omim.org/entry/603681>, 8 pages.
Holt et al., Split otoferlins reunited. EMBO Mol Med. Jan. 2019;11(1):e9995. doi: 10.15252/emmm.201809995.
Kilpatrick et al., Adeno-associated virus-mediated gene delivery into the scala media of the normal and deafened adult mouse ear. Gene Ther. Jun. 2011;18(6):569-78. doi: 10.1038/gt.2010.175. Epub Jan. 6, 2011.
Langouet-Astrie et al., Characterization of intravitreally delivered capsid mutant AAV2-Cre vector to induce tissue-specific mutations in murine retinal ganglion cells. Exp Eye Res. Oct. 2016;151:61-7. doi: 10.1016/j.exer.2016.07.019. Epub Jul. 30, 2016.
Li et al., A novel bispecific molecule delivered by recombinant AAV2 suppresses ocular inflammation and choroidal neovascularization. J Cell Mol Med. Aug. 2017;21(8):1555-1571. doi: 10.1111/jcmm.13086. Epub Mar. 22, 2017.
Liu et al., Specific and efficient transduction of Cochlear inner hair cells with recombinant adeno-associated virus type 3 vector. Mol Ther. Oct. 2005;12(4):725-33. doi: 10.1016/j.ymthe.2005.03.021.
Lopes-Pacheco et al., Self-complementary and tyrosine-mutant rAAV vectors enhance transduction in cystic fibrosis bronchial epithelial cells. Exp Cell Res. Nov. 15, 2018;372(2):99-107. doi: 10.1016/j.yexcr.2018.09.015. Epub Sep. 20, 2018.
Pangrsic et al., Otoferlin: a multi-C2 domain protein essential for hearing. Trends Neurosci. Nov. 2012;35(11):671-80. doi: 10.1016/j.tins.2012.08.002. Epub Sep. 7, 2012.
Petrs-Silva et al., High-efficiency transduction of the mouse retina by tyrosine-mutant AAV serotype vectors. Mol Ther. Mar. 2009;17(3):463-71. doi: 10.1038/mt.2008.269. Epub Dec. 16, 2008.
Roux et al., Otoferlin, defective in a human deafness form, is essential for exocytosis at the auditory ribbon synapse. Cell. Oct. 20, 2006;127(2):277-89. doi: 10.1016/j.cell.2006.08.040.
Suzuki et al., Cochlear gene therapy with ancestral AAV in adult mice: complete transduction of inner hair cells without cochlear dysfunction. Sci Rep. Apr. 3, 2017;7:45524. doi: 10.1038/srep45524.
Tao et al., Delivery of Adeno-Associated Virus Vectors in Adult Mammalian Inner-Ear Cell Subtypes Without Auditory Dysfunction. Hum Gene Ther. Apr. 2018;29(4):492-506. doi: 10.1089/hum.2017.120. Epub Jan. 22, 2018.
Tertrais et al., Viral Transfer of Mini-Otoferlins Partially Restores the Fast Component of Exocytosis and Uncovers Ultrafast Endocytosis in Auditory Hair Cells of Otoferlin Knock-Out Mice. J Neurosci. May 1, 2019;39(18):3394-3411. doi: 10.1523/JNEUROSCI.1550-18.2018. Epub Mar. 4, 2019.
Yoshimura et al., Enhanced viral-mediated cochlear gene delivery in adult mice by combining canal fenestration with round window membrane inoculation. Sci Rep. Feb. 14, 2018;8(1):2980. doi: 10.1038/s41598-018-21233-z. With Supplemental Information (4 pages).
Yoshimura et al., Targeted Allele Suppression Prevents Progressive Hearing Loss in the Mature Murine Model of Human TMC1 Deafness. Mol Ther. Mar. 6, 2019;27(3):681-690. doi: 10.1016/j.ymthe.2018.12.014. Epub Jan. 7, 2019. With Supplemental Information (7 pages).
Zhang et al., Cochlear Gene Therapy for Sensorineural Hearing Loss: Current Status and Major Remaining Hurdles for Translational Success. Front Mol Neurosci. Jun. 26, 2018;11:221. doi: 10.3389/fnmol.2018.00221.
Zhang et al., Temperature sensitive auditory neuropathy. Hear Res. May 2016;335:53-63. doi: 10.1016/j.heares.2016.01.008. Epub Jan. 15, 2016.
Laine et al., Cell cycle regulation in the inner ear sensory epithelia: role of cyclin D1 and cyclin-dependent kinase inhibitors. Dev Biol. Jan. 1, 2010;337(1):134-46. doi: 10.1016/j.ydbio.2009.10.027. Epub Oct. 23, 2009.

(56) References Cited

OTHER PUBLICATIONS

Orthwein et al., A mechanism for the suppression of homologous recombination in G1 cells. Nature. Dec. 17, 2015;528(7582):422-6. doi: 10.1038/nature16142. Epub Dec. 9, 2015. Retraction in: Nature. Jan. 27, 2025. doi: 10.1038/s41586-025-08644-5.

Regalado et al., Some deaf children in China can hear after gene therapy treatment. MIT Technology Review. Oct. 27, 2023. Accessed online: https://www.technologyreview.com/2023/10/27/1082551/gene-treatment-deaf-children-hearing-china/.

EP 21781660.2, dated Apr. 9, 2024, Extended European Search Report.

* cited by examiner

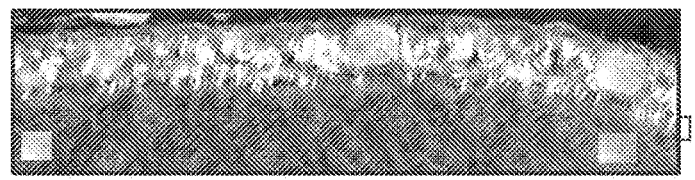
*FIG. 8A*
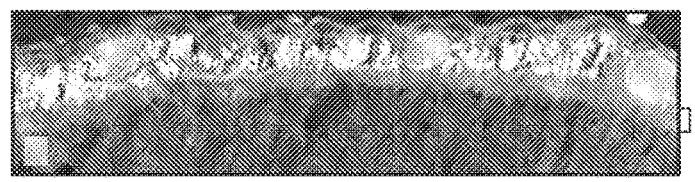
*FIG. 8B*
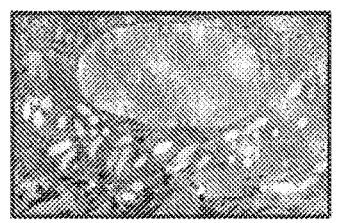   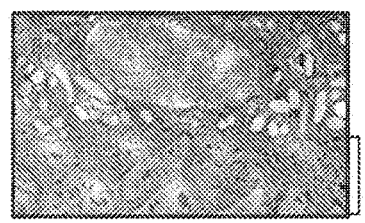
*FIG. 8C*   *FIG. 8D*
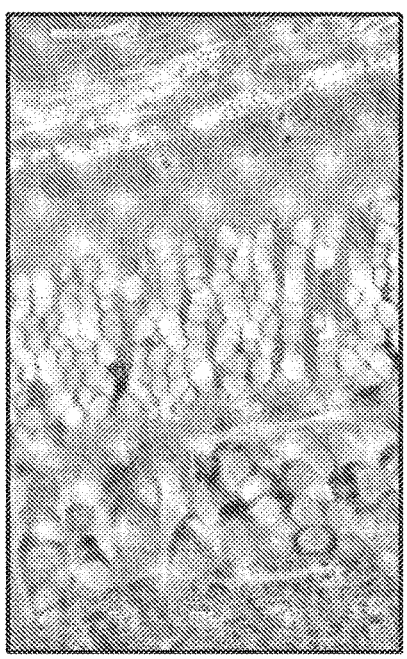   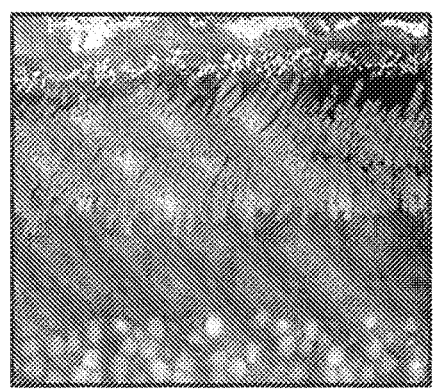
*FIG. 9B*
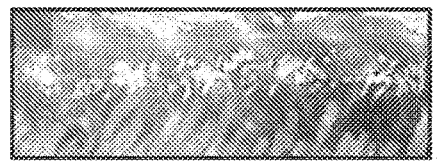
*FIG. 9A*   *FIG. 9C*

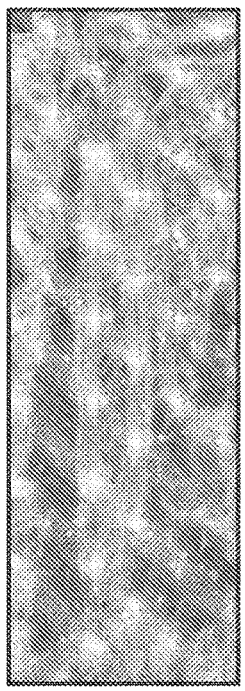 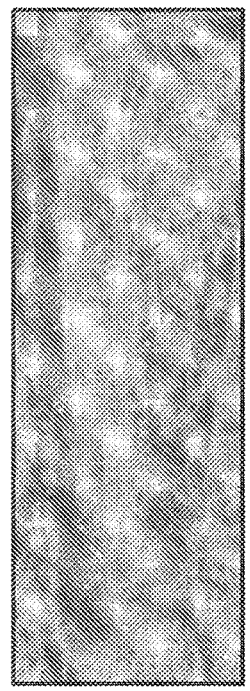 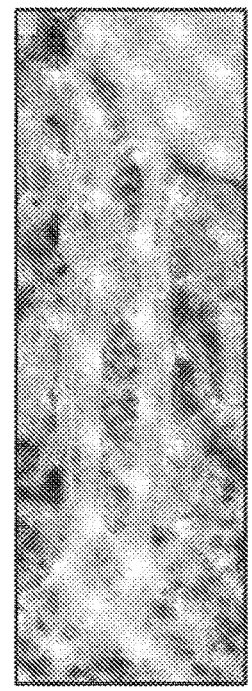 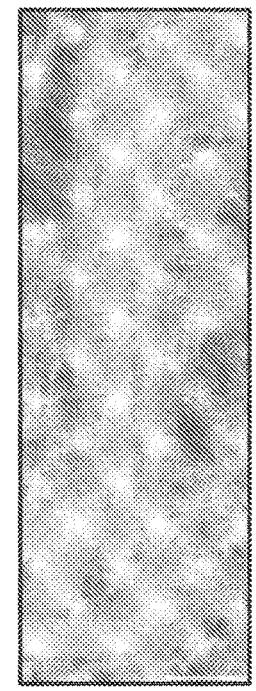
*FIG. 18A*  *FIG. 18B*  *FIG. 18C*  *FIG. 18D*
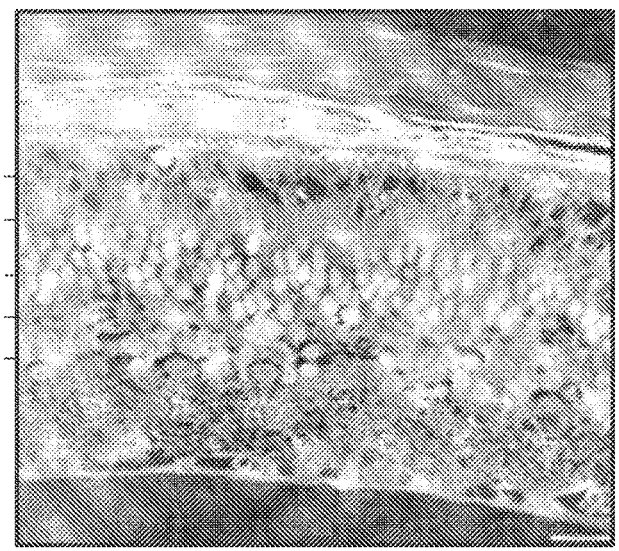
*FIG. 19*

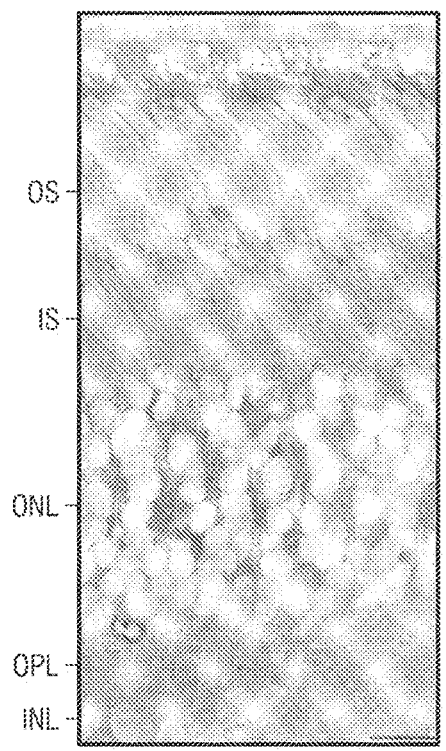
FIG. 20
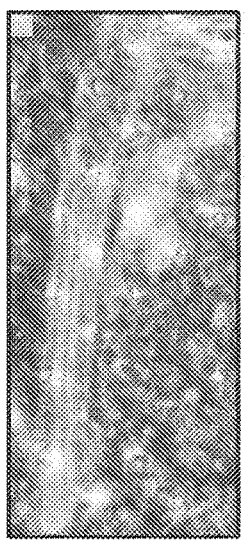 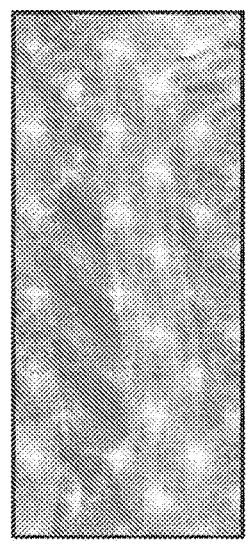 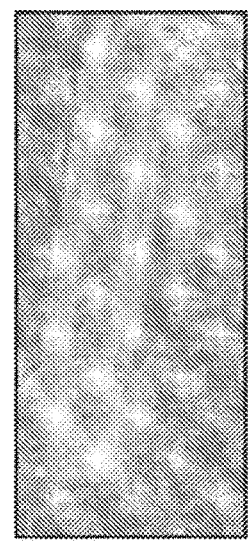 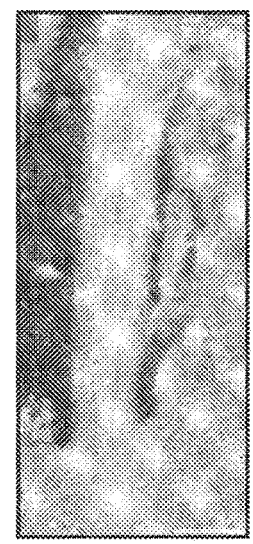
FIG. 21A     FIG. 21B     FIG. 21C     FIG. 21D

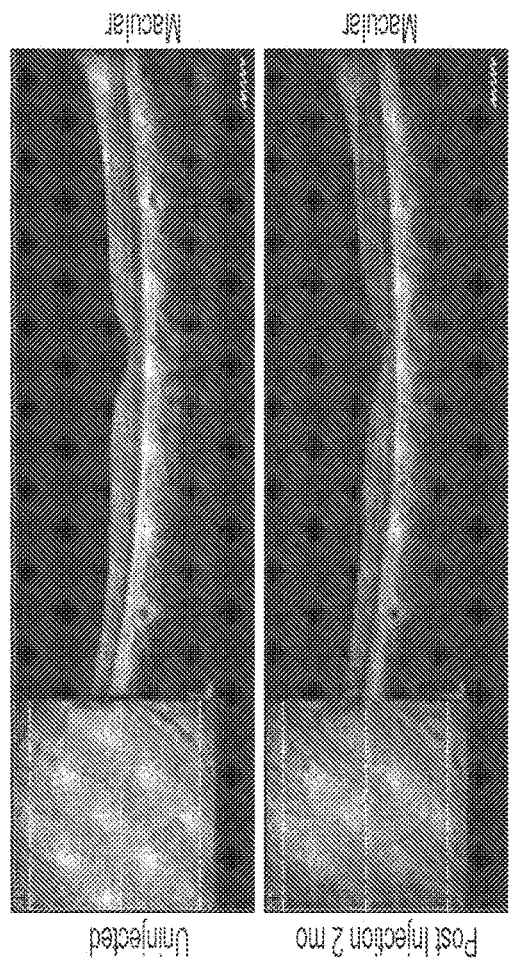
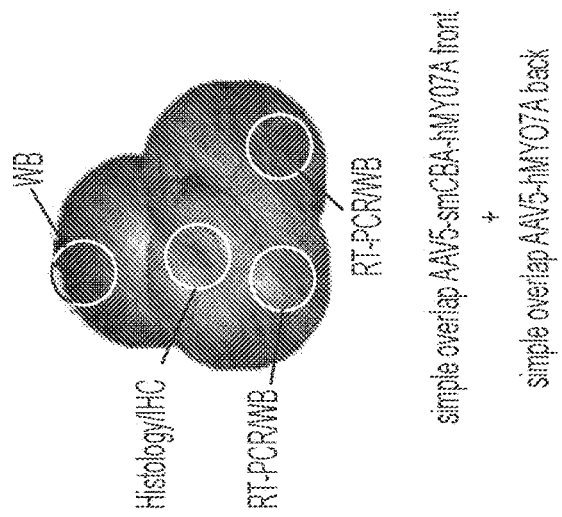
FIG. 41

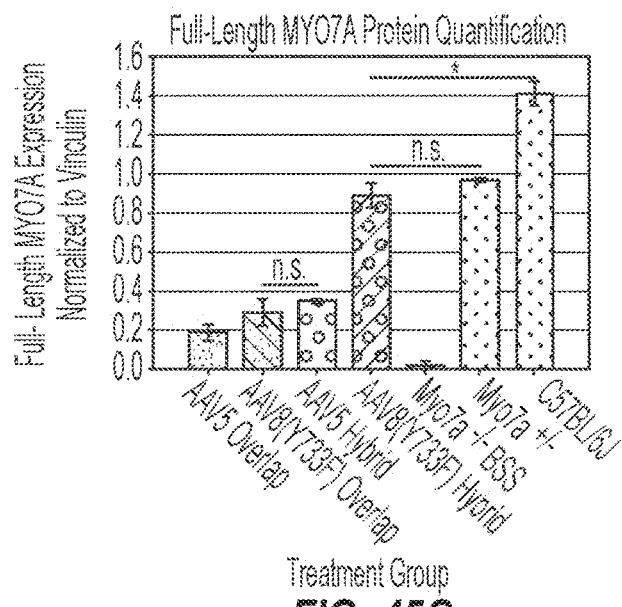

FIG. 45C

| Vector | ITR-ITR length (bp) | Overlap Length (bp) |
|---|---|---|
| smCBA-Overlap Front | 4979 | 1365 |
| Overlap Back | 4937 | |
| smCBA-Overlap Front | 4979 | 1284 |
| Overlap Back-v2.1 | 4801 | |
| smCBA-Overlap-v3 Front | 4614 | 1027 |
| Overlap Back | 4937 | |
| smCBA-Overlap Front | 4979 | 1026 |
| Overlap Back-v3 | 4561 | |
| smCBA-Overlap-v3 Front | 4614 | 945 |
| Overlap Back-v2.1 | 4801 | |
| smCBA-Overlap-v3 Front | 4614 | 687 |
| Overlap-v3 Back | 4561 | |
| smCBA-Overlap-v2-CMv1 Front | 3996 | 361 |
| Overlap Back | 4937 | |
| smCBA-Overlap-v2-CMv1 Front | 3996 | 279 |
| Overlap Back-v2.1 | 4801 | |
| smCBA-Overlap-v2-CMv1 Front | 3996 | 20 |
| Overlap Back-v3 | 4561 | |

FIG. 46

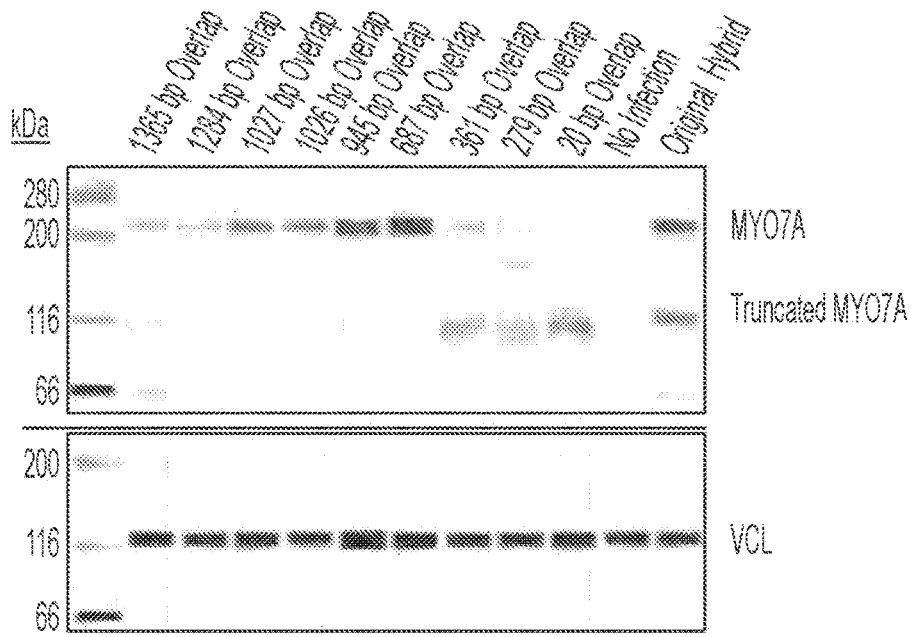

FIG. 48A

| Vector | ITR-ITR length (bp) | Overlap length (bp) |
|---|---|---|
| smCBA-Overlap Front | 4979 | 1365 |
| Overlap Back | 4937 | |
| smCBA-Overlap Front | 4979 | 1284 |
| Overlap Back-v2.1 | 4801 | |
| smCBA-Overlap-v3 Front | 4614 | 1027 |
| Overlap Back | 4937 | |
| smCBA-Overlap Front | 4979 | 1026 |
| Overlap Back v3 | 4561 | |
| smCBA-Overlap-v3 Front | 4614 | 945 |
| Overlap Back-v2.1 | 4801 | |
| smCBA-Overlap-v3 Front | 4614 | 687 |
| Overlap-v3 Back | 4561 | |
| smCBA-Overlap-v2-CMv1 Front | 3996 | 361 |
| Overlap Back | 4937 | |
| smCBA-Overlap-v2-CMv1 Front | 3996 | 279 |
| Overlap Back-v2.1 | 4801 | |
| smCBA-Overlap-v2-CMv1 Front | 3996 | 20 |
| Overlap Back-v3 | 4561 | |

Lead overlap vector pairs: (945 and 687 rows)

FIG. 48B

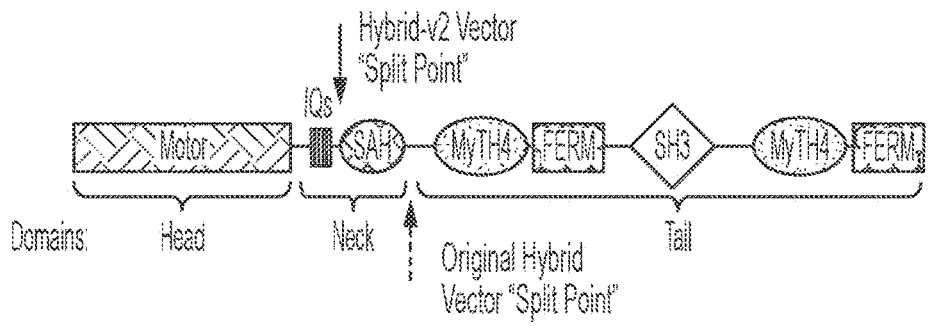

*FIG. 50A*

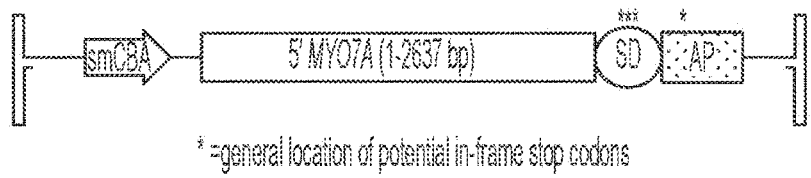

\* =general location of potential in-frame stop codons

*FIG. 50B*

| Vector | ITR-ITR Length (bp): | Codon Modification: |
|---|---|---|
| Original Hybrid Front | 4596 | N/A |
| Original Hybrid Back | 4662 | N/A |
| Hybrid-v2 Front | 4278 | N/A |
| Hybrid-v2 Back | 4981 | N/A |
| Hybrid_CMv1 Front | 4279 | 3 potential stop codons removed from AP intron |
| Hybrid-v2 Back | 4981 | N/A |
| Hybrid_CMv2 Front | 4279 | 3 potential stop codons removed from AP intron; 1 potential stop codon removed from Aphead |
| Hybrid_CMv2 Back | 4982 | 1 potential stop codon removed from Aphead |

*FIG. 50C*

| Vector | ITR-ITR Length (bp): | Codon Modification: | |
|---|---|---|---|
| Hybrid-v2 Front | 4278 | N/A | |
| Hybrid-v2 Back HA MIN | 4890 | N/A | |
| Hybrid-v2 Front | 4278 | N/A | |
| Hybrid-v2 Back noHA MIN | 4859 | N/A | |
| Hybrid_CMv2 Front | 4279 | 3 potential stop codons removed from AP intron; 1 potential stop codon removed from Aphead | Lead hybrid vector pairs |
| Hybrid_CMv2 Back HA MIN | 4891 | 1 potential stop codon removed from Aphead | |
| Hybrid_CMv2 Front | 4279 | 3 potential stop codons removed from AP intron; 1 potential stop codon removed from Aphead | |
| Hybrid_CMv2 Back noHA MIN | 4861 | 1 potential stop codon removed from Aphead | |
| Hybrid_CMv3 Front | 4275 | 3 potential stop codons removed from AP intron; 1 potential stop codon removed from Ap head; 3 potential stop codons removed from 3'UTR/ITR | |
| Hybrid_CMv2 Back HA MIN | 4891 | 1 potential stop codon removed from Aphead | |
| Hybrid_CMv3 Front | 4275 | 3 potential stop codons removed from AP intron; 1 potential stop codon removed from Ap head; 3 potential stop codons removed from 3'UTR/ITR | |
| Hybrid_CMv2 Back noHA MIN | 4861 | 1 potential stop codon removed from Aphead | |

*FIG. 51B*

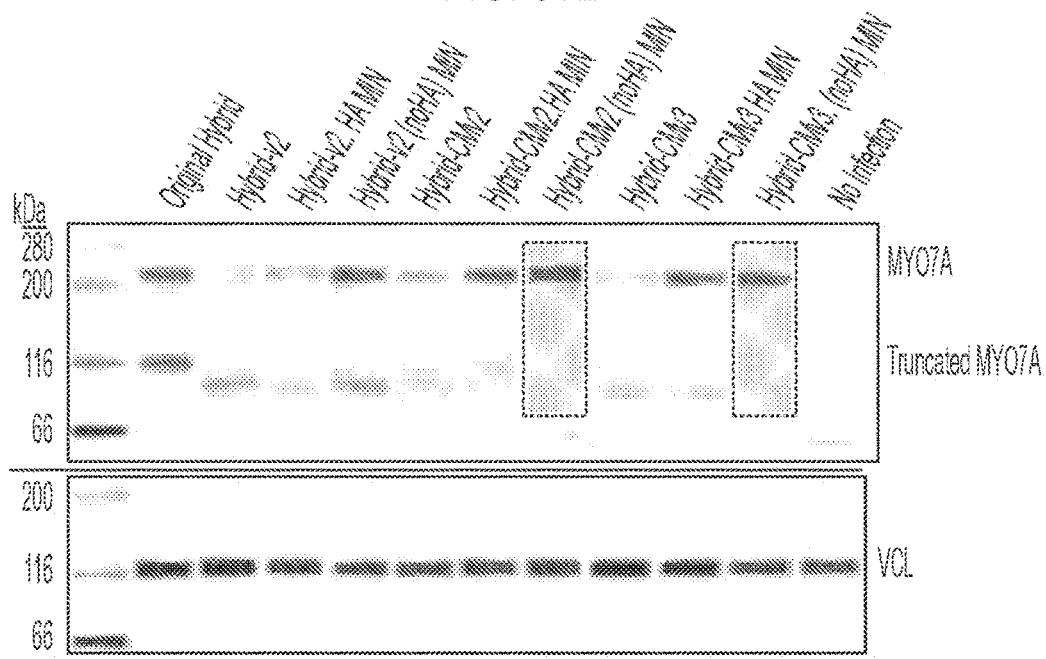

*FIG. 51C*

SEQUENCE LISTING

<160> NUMBER OF SEQ ID NOS: 91

<210> SEQ ID NO 1
<211> LENGTH: 4961
<212> TYPE: DNA
<213> ORGANISM: Artificial Sequence
<220> FEATURE:
<223> OTHER INFORMATION: Synthetic

<400> SEQUENCE: 1

| | | | | | | |
|---|---|---|---|---|---|---|
| ctccctctct | gcgcgctcgc | tcgctcactg | aggccgcccg | ggcaaagccc | gggcgtcggg | 60 |
| cgacctttgg | tcgcccggcc | tcagtgagcg | agcgagcgcg | cagagaggga | gtggccaact | 120 |
| ccatcactag | gggttctcag | atctggcgcg | cccaattcgg | taccctagtt | attaatagta | 180 |
| atcaattacg | gggtcattag | ttcatagccc | atatatggag | ttccgcgtta | cataacttac | 240 |
| ggtaaatggc | ccgcctggct | gaccgcccaa | cgacccccgc | ccattgacgt | caataatgac | 300 |
| gtatgttccc | atagtaacgc | caatagggac | tttccattga | cgtcaatggg | tggactattt | 360 |
| acggtaaact | gcccacttgg | cagtacatca | agtgtatcat | atgccaagta | cgccccctat | 420 |
| tgacgtcaat | gacggtaaat | ggcccgcctg | gcattatgcc | cagtacatga | ccttatggga | 480 |
| ctttcctact | tggcagtaca | tctacgtatt | agtcatcgct | attaccatgg | tcgaggtgag | 540 |
| ccccacgttc | tgcttcactc | tccccatctc | ccccccctcc | ccacccccaa | ttttgtattt | 600 |
| atttattttt | taattatttt | gtgcagcgat | gggggcgggg | gggggggggg | ggcgcgcgcc | 660 |
| aggcggggcg | gggcggggcg | aggggcgggg | cgggcgagg | cggagaggtg | cggcggcagc | 720 |
| caatcagagc | ggcgcgctcc | gaaagtttcc | ttttatggcg | aggcggcggc | ggcggcggcc | 780 |
| ctataaaaag | cgaagcgcgc | ggcggcgggg | agtcgctgcg | cgctgccttc | gccccgtgcc | 840 |
| ccgctccgcc | gccgcctcgc | gccgcccgcc | ccggctctga | ctgaccgcgt | tactcccaca | 900 |
| ggtgagcggg | cgggacggcc | cttctcctcc | gggctgtaat | tagcgcttgg | tttaatgacg | 960 |
| gcttgtttct | tttctgtggc | tgcgtgaaag | ccttgagggg | ctccgggagc | tagagcctct | 1020 |
| gctaaccatg | ttcatgcctt | cttctttttc | ctacagctcc | tgggcaacgt | gctggttatt | 1080 |
| gtgctgtctc | atcattttgg | caaagaattc | tagcggccgc | caccatggtg | attcttcagc | 1140 |
| aggggggacca | tgtgtggatg | gacctgagat | tggggcagga | gttcgacgtg | cccatcgggg | 1200 |
| cggtggtgaa | gctctgcgac | tctgggcagg | tccaggtggt | ggatgatgaa | gacaatgaac | 1260 |
| actggatctc | tccgcagaac | gcaacgcaca | tcaagcctat | gcaccccacg | tcggtccacg | 1320 |
| gcgtggagga | catgatccgc | ctgggggacc | tcaacgaggc | gggcatcttg | cgcaacctgc | 1380 |
| ttatccgcta | ccgggaccac | ctcatctaca | cgtatacggg | ctccatcctg | gtggctgtga | 1440 |
| acccctacca | gctgctctcc | atctactcgc | cagagcacat | ccgccagtat | accaacaaga | 1500 |
| agattgggga | gatgcccccc | cacatctttg | ccattgctga | caactgctac | ttcaacatga | 1560 |
| aacgcaacag | ccgagaccag | tgctgcatca | tcagtgggga | atctgggccc | gggaagacgg | 1620 |
| agagcacaaa | gctgatcctg | cagttcctgg | cagccatcag | tggcagcac | tcgtggattg | 1680 |
| agcagcaggt | cttggaggcc | accccccattc | tggaagcatt | tgggaatgcc | aagaccatcc | 1740 |
| gcaatgacaa | ctcaagccgt | ttcggaaagt | acatcgacat | ccacttcaac | aagcggggcg | 1800 |
| ccatcgaggg | cgcgaagatt | gagcagtacc | tgctggaaaa | gtcacgtgtc | tgtcgccagg | 1860 |
| ccctggatga | aaggaactac | cacgtgttct | actgcatgct | ggagggtatg | agtgaggatc | 1920 |
| agaagaagaa | gctgggcttg | ggccaggcct | ctgactacaa | ctacttggcc | atgggtaact | 1980 |
| gcataacctg | tgagggccgg | gtggacagcc | aggagtacgc | caacatccgc | tccgccatga | 2040 |

```
aggtgctcat gttcactgac accgagaact gggagatctc gaagctcctg gctgccatcc    2100
tgcacctggg caacctgcag tatgaggcac gcacatttga aaacctggat gcctgtgagg    2160
ttctcttctc cccatcgctg gccacagctg catccctgct tgaggtgaac cccccagacc    2220
tgatgagctg cctgactagc cgcaccctca tcacccgcgg ggagacggtg tccaccccac    2280
tgagcaggga acaggcactg gacgtgcgcg acgccttcgt aaaggggatc tacgggcggc    2340
tgttcgtgtg gattgtggac aagatcaacg cagcaattta caagcctccc tcccaggatg    2400
tgaagaactc tcgcaggtcc atcggcctcc tggacatctt tgggtttgag aactttgctg    2460
tgaacagctt tgagcagctc tgcatcaact tcgccaatga gcacctgcag cagttctttg    2520
tgcggcacgt gttcaagctg gagcaggagg aatatgacct ggagagcatt gactggctgc    2580
acatcgagtt cactgacaac caggatgccc tggacatgat tgccaacaag cccatgaaca    2640
tcatctccct catcgatgag gagagcaagt tccccaaggg cacagacacc accatgttac    2700
acaagctgaa ctcccagcac aagctcaacg ccaactacat cccccccaag aacaaccatg    2760
agacccagtt tggcatcaac cattttgcag gcatcgtcta ctatgagacc caaggcttcc    2820
tggagaagaa ccgagacacc ctgcatgggg acattatcca gctggtccac tcctccagga    2880
acaagttcat caagcagatc ttccaggccg atgtcgccat gggcgccgag accaggaagc    2940
gctcgcccac acttagcagc cagttcaagc ggtcactgga gctgctgatg cgcacgctgg    3000
gtgcctgcca gcccttcttt gtgcgatgca tcaagcccaa tgagttcaag aagcccatgc    3060
tgttcgaccg gcacctgtgc gtgcgccagc tgcggtactc aggaatgatg gagaccatcc    3120
gaatccgccg agctggctac cccatccgct acagcttcgt agagtttgtg gagcggtacc    3180
gtgtgctgct gccaggtgtg aagccggcct acaagcaggg cgacctccgc gggacttgcc    3240
agcgcatggc tgaggctgtg ctgggcaccc acgatgactg gcagataggc aaaaccaaga    3300
tctttctgaa ggaccaccat gacatgctgc tggaagtgga gcgggacaaa gccatcaccg    3360
acagagtcat cctccttcag aaagtcatcc ggggattcaa agacaggtct aactttctga    3420
agctgaagaa cgctgccaca ctgatccaga ggcactggcg gggtcacaac tgtaggaaga    3480
actacgggct gatgcgtctg ggcttcctgc ggctgcaggc cctgcaccgc tcccggaagc    3540
tgcaccagca gtaccgcctg gcccgccagc gcatcatcca gttccaggcc cgctgccgcg    3600
cctatctggt gcgcaaggcc ttccgccacc gcctctgggc tgtgctcacc gtgcaggcct    3660
atgcccgggg catgatcgcc cgcaggctgc accaacgcct cagggctgag tatctgtggc    3720
gcctcgaggc tgagaaaatg cggctggcgg aggaagagaa gcttcggaag gagatgagcg    3780
ccaagaaggc caaggaggag gccgagcgca agcatcagga gcgcctggcc cagctggctc    3840
gtgaggacgc tgagcgggag ctgaaggaga aggaggccgc tcggcggaag aaggagctcc    3900
tggagcagat ggaaagggcc cgccatgagc ctgtcaatca ctcagacatg gtggacaaga    3960
tgtttggctt cctgggggact tcaggtggcc tgccaggcca ggagggccag gcacctagtg    4020
gctttgagga cctggagcga gggcggaggg agatggtgga ggaggacctg gatgcagccc    4080
tgccctgcc tgacgaggat gaggaggacc tctctgagta taaatttgcc aagttcgcgg    4140
ccacctactt ccagggggaca accacgcact cctacacccg gcggccactc aaacagccac    4200
tgctctacca tgacgacgag ggtgaccagc tggcagccct ggcggtctgg atcaccatcc    4260
tccgcttcat gggggacctc cctgagccca gtaccacac agccatgagt gatgcagtg    4320
agaagatccc tgtgatgacc aagatttatg agaccctggg caagaagacg tacaagaggg    4380
```

-continued

| | | |
|---|---|---|
| agctgcaggc cctgcagggc gagggcgagg cccagctccc cgagggccag aagaagagca | 4440 | |
| gtgtgaggca caagctggtg catttgactc tgaaaaagaa gtccaagctc acagaggagg | 4500 | |
| tgaccaagag gctgcatgac ggggagtcca cagtgcaggg caacagcatg ctggaggacc | 4560 | |
| ggcccacctc caacctggag aagctgcact tcatcatcgg caatggcatc ctgcggccag | 4620 | |
| cactccggga cgagatctac tgccagatca gcaagcagct gacccacaac ccctccaaga | 4680 | |
| gcagctatgc ccggggctgg attctcgtgt ctctctgcgt gggctgtttc gcccctccg | 4740 | |
| agaagtttgt caagtacctg cggaacttcg ctagcgggca ctagtccgtc gactgttaat | 4800 | |
| taagcatgct ggggagagat ctaggaaacc cctagtgatg gagttggcca ctccctctct | 4860 | |
| gcgcgctcgc tcgctcactg aggccgggcg accaaaggtc gcccgacgcc cgggctttgc | 4920 | |
| ccgggcggcc tcagtgagcg agcgagcgcg cagagaggga g | 4961 | |

<210> SEQ ID NO 2
<211> LENGTH: 4915
<212> TYPE: DNA
<213> ORGANISM: Artificial Sequence
<220> FEATURE:
<223> OTHER INFORMATION: Synthetic

<400> SEQUENCE: 2

| | | |
|---|---|---|
| ctccctctct gcgcgctcgc tcgctcactg aggccgcccg ggcaaagccc gggcgtcggg | 60 | |
| cgacctttgg tcgcccggcc tcagtgagcg agcgagcgcg cagagaggga gtggccaact | 120 | |
| ccatcactag gggttcagat ctggcgcgcc caattggctt cgaattctag cggccgctgc | 180 | |
| ttaagcaggt ctaactttct gaagctgaag aacgctgcca cactgatcca gaggcactgg | 240 | |
| cggggtcaca actgtaggaa gaactacggg ctgatgcgtc tgggcttcct gcggctgcag | 300 | |
| gccctgcacc gctcccggaa gctgcaccag cagtaccgcc tggcccgcca gcgcatcatc | 360 | |
| cagttccagg cccgctgccg cgcctatctg gtgcgcaagg ccttccgcca ccgcctctgg | 420 | |
| gctgtgctca ccgtgcaggc ctatgccgg gcatgatcg cccgcaggct gcaccaacgc | 480 | |
| ctcagggctg agtatctgtg gcgcctcgag gctgagaaaa tgcggctggc ggaggaagag | 540 | |
| aagcttcgga aggagatgag cgccaagaag gccaaggagg aggccgagcg caagcatcag | 600 | |
| gagcgcctgg cccagctggc tcgtgaggac gctgagcggg agctgaagga aaggaggcc | 660 | |
| gctcggcgga agaaggagct cctggagcag atggaaaggg cccgccatga gcctgtcaat | 720 | |
| cactcagaca tggtggacaa gatgtttggc ttcctgggga cttcaggtgg cctgccaggc | 780 | |
| caggagggcc aggcacctag tggctttgag gacctggagc gagggcggag ggagatggtg | 840 | |
| gaggaggacc tggatgcagc cctgccctg cctgacgagg atgaggagga cctctctgag | 900 | |
| tataaattg ccaagttcgc ggccacctac ttccagggga caaccacgca ctcctacacc | 960 | |
| cggcggccac tcaaacagcc actgctctac catgacgacg agggtgacca gctggcagcc | 1020 | |
| ctggcggtct ggatcaccat cctccgcttc atggggggacc tccctgagcc caagtaccac | 1080 | |
| acagccatga gtgatggcag tgagaagatc cctgtgatga ccaagattta tgagaccctg | 1140 | |
| ggcaagaaga cgtacaagag ggagctgcag gccctgcagg gcgagggcga ggcccagctc | 1200 | |
| cccgagggcc agaagaagag cagtgtgagg cacaagctgg tgcatttgac tctgaaaaag | 1260 | |
| aagtccaagc tcacagagga ggtgaccaag aggctgcatg acggggagtc cacagtgcag | 1320 | |
| ggcaacagca tgctggagga ccggcccacc tccaacctgg agaagctgca cttcatcatc | 1380 | |
| ggcaatggca tcctgcggcc agcactccgg gacgagatct actgccagat cagcaagcag | 1440 | |
| ctgacccaca ccccctccaa gagcagctat gcccggggct ggattctcgt gtctctctgc | 1500 | |

```
gtgggctgtt tcgcccctc cgagaagttt gtcaagtacc tgcggaactt catccacggg      1560
ggcccgcccg gctacgcccc gtactgtgag gagcgcctga gaaggacctt tgtcaatggg      1620
acacggacac agccgcccag ctggctggag ctgcaggcca ccaagtccaa gaagccaatc      1680
atgttgcccg tgacattcat ggatgggacc accaagaccc tgctgacgga ctcggcaacc      1740
acggccaagg agctctgcaa cgcgctggcc gacaagatct ctctcaagga ccggttcggg      1800
ttctccctct acattgccct gtttgacaag gtgtcctccc tgggcagcgg cagtgaccac      1860
gtcatggacg ccatctccca gtgcgagcag tacgccaagg agcagggcgc ccaggagcgc      1920 aacgcccct ggaggctctt cttccgcaaa gaggtcttca cgccctggca cagcccctcc      1980
gaggacaacg tggccaccaa cctcatctac cagcaggtgg tgcgaggagt caagtttggg      2040
gagtacaggt gtgagaagga ggacgacctg gctgagctgg cctcccagca gtactttgta      2100
gactatggct ctgagatgat cctggagcgc ctcctgaacc tcgtgcccac ctacatcccc      2160
gaccgcgaga tcacgcccct gaagacgctg gagaagtggg cccagctggc catcgccgcc      2220
cacaagaagg ggatttatgc ccagaggaga actgatgccc agaaggtcaa agaggatgtg      2280
gtcagttatg cccgcttcaa gtggcccttg ctcttctcca ggttttatga agcctacaaa      2340
ttctcaggcc ccagtctccc caagaacgac gtcatcgtgg ccgtcaactg gacgggtgtg      2400
tactttgtgg atgagcagga gcaggtactt ctggagctgt ccttcccaga gatcatggcc      2460
gtgtccagca gcaggggagc gaaaacgacg gcccccagct tcacgctggc caccatcaag      2520
ggggacgaat acaccttcac ctccagcaat gctgaggaca ttcgtgacct ggtggtcacc      2580
ttcctagagg ggctccggaa gagatctaag tatgttgtgg ccctgcagga taaccccaac      2640
cccgcaggcg aggagtcagg cttcctcagc tttgccaagg gagacctcat catcctggac      2700
catgacacgg gcgagcaggt catgaactcg ggctgggcca acggcatcaa tgagaggacc      2760
aagcagcgtg gggacttccc caccgacagt gtgtacgtca tgcccactgt caccatgcca      2820
ccgcgggaga ttgtggccct ggtcaccatg actcccgatc agaggcagga cgttgtccgg      2880
ctcttgcagc tgcgaacggc ggagcccgag gtgcgtgcca agccctacac gctggaggag      2940
ttttcctatg actacttcag gcccccaccc aagcacacgc tgagccgtgt catggtgtcc      3000
aaggcccgag gcaaggaccg gctgtggagc cacacgcggg aaccgctcaa gcaggcgctg      3060
ctcaagaagc tcctgggcag tgaggagctc tcgcaggagg cctgcctggc cttcattgct      3120
gtgctcaagt acatgggcga ctacccgtcc aagaggacac gctccgtcaa cgagctcacc      3180
gaccagatct ttgagggtcc cctgaaagcc gagcccctga aggacgaggc atatgtgcag      3240
atcctgaagc agctgaccga caaccacatc aggtacagcg aggagcgggg ttgggagctg      3300
ctctggctgt gcacgggcct ttttcccacc agcaacatcc tcctgcccca cgtgcagcgc      3360
ttcctgcagt cccgaaagca ctgcccactc gccatcgact gcctgcaacg gctccagaaa      3420
gccctgagaa acgggtcccg gaagtaccct ccgcacctgg tggaggtgga ggccatccag      3480
cacaagacca cccagatttt ccacaaagtc tacttccctg atgacactga cgaggccttc      3540
gaagtggagt ccagcaccaa ggccaaggac ttctgccaga acatcgccac caggctgctc      3600
ctcaagtcct cagagggatt cagcctcttt gtcaaaattg cagacaaggt catcagcgtt      3660
cctgagaatg acttcttctt tgactttgtt cgacacttga cagactggat aaagaaagct      3720
cggcccatca aggacggaat tgtgccctca ctcacctacc aggtgttctt catgaagaag      3780
ctgtggacca ccacggtgcc agggaaggat cccatggccg attccatctt ccactattac      3840
```

| caggagttgc ccaagtatct ccgaggctac cacaagtgca cgcgggagga ggtgctgcag | 3900 |
| ctggggcgc tgatctacag ggtcaagttc gaggaggaca agtcctactt ccccagcatc | 3960 |
| cccaagctgc tgcgggagct ggtgccccag gaccttatcc ggcaggtctc acctgatgac | 4020 |
| tggaagcggt ccatcgtcgc ctacttcaac aagcacgcag ggaagtccaa ggaggaggcc | 4080 |
| aagctggcct tcctgaagct catcttcaag tggcccacct ttggctcagc cttcttcgag | 4140 |
| gtgaagcaaa ctacggagcc aaacttccct gagatcctcc taattgccat caacaagtat | 4200 |
| ggggtcagcc tcatcgatcc caaaacgaag gatatcctca ccactcatcc cttcaccaag | 4260 |
| atctccaact ggagcagcgg caacacctac ttccacatca ccattgggaa cttggtgcgc | 4320 |
| gggagcaaac tgctctgcga cgtcactg ggctacaaga tggatgacct cctgacttcc | 4380 |
| tacattagcc agatgctcac agccatgagc aaacagcggg gctccaggag cggcaagtac | 4440 |
| ccttacgatg taccggatta cgcatgaggt accaagggcg aattctgcag tcgactagag | 4500 |
| ctcgctgatc agcctcgact gtgccttcta gttgccagcc atctgttgtt tgcccctccc | 4560 |
| ccgtgccttc cttgaccctg gaaggtgcca ctcccactgt cctttcctaa taaaatgagg | 4620 |
| aaattgcatc gcattgtctg agtaggtgtc attctattct ggggggtggg gtggggcagg | 4680 |
| acagcaaggg ggaggattgg gaagacaata gcaggcatgc tggggagaga tctgaggact | 4740 |
| agtccgtcga ctgttaatta agcatgctgg ggagagatct aaccccctagt gatggagttg | 4800 |
| gccactccct ctctgcgcgc tcgctcgctc actgaggccg gcgaccaaa ggtcgcccga | 4860 |
| cgcccgggct tgcccgggc ggcctcagtg agcgagcgag cgcgcagaga gggag | 4915 |

<210> SEQ ID NO 3
<211> LENGTH: 4578
<212> TYPE: DNA
<213> ORGANISM: Artificial Sequence
<220> FEATURE:
<223> OTHER INFORMATION: Synthetic

<400> SEQUENCE: 3

| ctccctctct gcgcgctcgc tcgctcactg aggccgcccg ggcaaagccc gggcgtcggg | 60 |
| cgacctttgg tcgcccggcc tcagtgagcg agcgagcgcg cagagaggga gtggccaact | 120 |
| ccatcactag gggttctcag atctggcgcg cccaattcgg taccctagtt attaatagta | 180 |
| atcaattacg gggtcattag ttcatagccc atatatggag ttccgcgtta cataacttac | 240 |
| ggtaaatggc ccgcctggct gaccgcccaa cgacccccgc ccattgacgt caataatgac | 300 |
| gtatgttccc atagtaacgc caatagggac tttccattga cgtcaatggg tggactattt | 360 |
| acggtaaact gcccacttgg cagtacatca agtgtatcat atgccaagta cgccccctat | 420 |
| tgacgtcaat gacggtaaat ggcccgcctg gcattatgcc cagtacatga ccttatggga | 480 |
| ctttcctact tggcagtaca tctacgtatt agtcatcgct attaccatgg tcgaggtgag | 540 |
| ccccacgttc tgcttcactc tccccatctc ccccccctcc caccccccaa ttttgtattt | 600 |
| atttattttt taattatttt gtgcagcgat ggggggcgggg gggggggggg ggcgcgcgcc | 660 |
| aggcggggcg gggcggggcg aggggcgggg cggggcgagg cggagaggtg cggcggcagc | 720 |
| caatcagagc ggcgcgctcc gaaagttttcc tttatggcg aggcggcggc ggcggcggcc | 780 |
| ctataaaaag cgaagcgcgc ggcgggcggg agtcgctgcg cgctgccttc gccccgtgcc | 840 |
| ccgctccgcc gccgcctcgc gccgcccgcc ccggctctga ctgaccgcgt tactcccaca | 900 |
| ggtgagcggg cgggacggcc cttctcctcc gggctgtaat tagcgcttgg tttaatgacg | 960 |
| gcttgttct tttctgtggc tgcgtgaaag ccttgagggg ctccgggagc tagagcctct | 1020 |

```
gctaaccatg ttcatgcctt cttcttttc ctacagctcc tgggcaacgt gctggttatt    1080
gtgctgtctc atcattttgg caaagaattc tagcggccgc caccatggtg attcttcagc    1140
agggggacca tgtgtggatg gacctgagat tggggcagga gttcgacgtg cccatcgggg    1200
cggtggtgaa gctctgcgac tctgggcagg tccaggtggt ggatgatgaa gacaatgaac    1260
actggatctc tccgcagaac gcaacgcaca tcaagcctat gcaccccacg tcggtccacg    1320
gcgtggagga catgatccgc ctgggggacc tcaacgaggc gggcatcttg cgcaacctgc    1380
ttatccgcta ccgggaccac ctcatctaca cgtatacggg ctccatcctg gtggctgtga    1440
acccctacca gctgctctcc atctactcgc cagagcacat ccgccagtat accaacaaga    1500
agattgggga gatgccccccc cacatctttg ccattgctga caactgctac ttcaacatga    1560
aacgcaacag ccgagaccag tgctgcatca tcagtgggga atctggggcc gggaagacgg    1620
agagcacaaa gctgatcctg cagttcctgg cagccatcag tgggcagcac tcgtggattg    1680
agcagcaggt cttggaggcc acccccattc tggaagcatt tgggaatgcc aagaccatcc    1740
gcaatgacaa ctcaagccgt ttcggaaagt acatcgacat ccacttcaac aagcggggcg    1800
ccatcgaggc gcgcaagatt gagcagtacc tgctggaaaa gtcacgtgtc tgtcgccagg    1860
ccctggatga aaggaactac cacgtgttct actgcatgct ggagggtatg agtgaggatc    1920
agaagaagaa gctgggcttg ggccaggcct ctgactacaa ctacttggcc atgggtaact    1980
gcataacctg tgagggccgg gtggacagcc aggagtacgc caacatccgc tccgccatga    2040
aggtgctcat gttcactgac accgagaact gggagatctc gaagctcctg gctgccatcc    2100
tgcacctggg caacctgcag tatgaggcac gcacatttga aaacctggat gcctgtgagg    2160
ttctcttctc cccatcgctg gccacagctg catccctgct tgaggtgaac cccccagacc    2220
tgatgagctg cctgactagc cgcaccctca tcacccgcgg ggagacggtg tccacccccac    2280 tgagcaggga acaggcactg gacgtgcgcg acgccttcgt aaaggggatc tacgggcggc    2340
tgttcgtgtg gattgtggac aagatcaacg cagcaattta caagcctccc tcccaggatg    2400
tgaagaactc tcgcaggtcc atcggcctcc tggacatctt tgggtttgag aactttgctg    2460
tgaacagctt tgagcagctc tgcatcaact tcgccaatga gcacctgcag cagttctttg    2520
tgcggcacgt gttcaagctg gagcaggagg aatatgacct ggagagcatt gactggctgc    2580
acatcgagtt cactgacaac caggatgccc tggacatgat tgccaacaag cccatgaaca    2640
tcatctccct catcgatgag gagagcaagt tccccaaggg cacagacacc accatgttac    2700
acaagctgaa ctcccagcac aagctcaacg ccaactacat ccccccccaag aacaaccatg    2760 agacccagtt tggcatcaac cattttgcag gcatcgtcta ctatgagacc caaggcttcc    2820
tggagaagaa ccgagacacc ctgcatgggg acattatcca gctggtccac tcctccagga    2880
acaagttcat caagcagatc ttccaggccg atgtcgccat gggcgccgag accaggaagc    2940
gctcgcccac acttagcagc cagttcaagc ggtcactgga gctgctgatg cgcacgctgg    3000
gtgcctgcca gccccttcttt gtgcgatgca tcaagcccaa tgagttcaag aagcccatgc    3060
tgttcgaccg gcacctgtgc gtgcgccagc tgcggtactc aggaatgatg gagaccatcc    3120
gaatccgccg agctggctac cccatccgct acagcttcgt agagtttgtg gagcggtacc    3180
gtgtgctgct gccaggtgtg aagccggcct acaagcaggg cgacctccgc gggacttgcc    3240
agcgcatggc tgaggctgtg ctgggcaccc acgatgactg gcagataggc aaaaccaaga    3300
tctttctgaa ggaccaccat gacatgctgc tggaagtgga gcgggacaaa gccatcaccg    3360
```

| | | |
|---|---|---|
| acagagtcat cctccttcag aaagtcatcc ggggattcaa agacaggtct aactttctga | 3420 | |
| agctgaagaa cgctgccaca ctgatccaga ggcactggcg gggtcacaac tgtaggaaga | 3480 | |
| actacgggct gatgcgtctg ggcttcctgc ggctgcaggc cctgcaccgc tcccggaagc | 3540 | |
| tgcaccagca gtaccgcctg gcccgccagc gcatcatcca gttccaggcc cgctgccgcg | 3600 | |
| cctatctggt gcgcaaggcc ttccgccacc gcctctgggc tgtgctcacc gtgcaggcct | 3660 | |
| atgcccgggg catgatcgcc cgcaggctgc accaacgcct cagggctgag tatctgtggc | 3720 | |
| gcctcgaggc tgagaaaatg cggctggcgg aggaagagaa gcttcggaag gagatgagcg | 3780 | |
| ccaagaaggc caaggaggag gccgagcgca agcatcagga gcgcctggcc cagctggctc | 3840 | |
| gtgaggacgc tgagcgggag ctgaaggaga aggaggccgc tcggcggaag aaggagctcc | 3900 | |
| tggagcagat ggaaagggcc cgccatgagc ctgtcaatca ctcagacatg gtggacaaga | 3960 | |
| tgtttggctt cctggggact tcaggtggcc tgccaggcca ggagggccag gcacctagtg | 4020 | |
| gctttgaggt aagtatcaag gttacaagac aggtttaagg agaccaatag aaactgggct | 4080 | |
| tgtcgagaca gagaagactc ttgcgtttct gagctagccc ccggggtgcgc ggcgtcggtg | 4140 | |
| gtgccggcgg ggggcgccag gtcgcaggcg gtgtagggct ccaggcaggc ggcgaaggcc | 4200 | |
| atgacgtgcg ctatgaaggt ctgctcctgc acgccgtgaa ccaggtgcgc ctgcgggccg | 4260 | |
| cgcgcgaaca ccgccacgtc ctcgcctgcg tgggtctctt cgtccagggg cactgctgac | 4320 | |
| tgctgccgat actcggggct cccgctctcg ctctcggtaa catccggccg ggcgccgtcc | 4380 | |
| ttgagcacat agcctggacc gtttcgtcga ctgttaatta agcatgctgg ggagagatct | 4440 | |
| aggaacccct agtgatggag ttggccactc cctctctgcg cgctcgctcg ctcactgagg | 4500 | |
| ccgggcgacc aaaggtcgcc cgacgcccgg gctttgcccg gcggcctca gtgagcgagc | 4560 | |
| gagcgcgcag agagggag | 4578 | |

<210> SEQ ID NO 4
<211> LENGTH: 4646
<212> TYPE: DNA
<213> ORGANISM: Artificial Sequence
<220> FEATURE:
<223> OTHER INFORMATION: Synthetic

<400> SEQUENCE: 4

| | | |
|---|---|---|
| ctccctctct gcgcgctcgc tcgctcactg aggccgcccg gcaaagccc gggcgtcggg | 60 | |
| cgacctttgg tcgcccggcc tcagtgagcg agcgagcgcg cagagaggga gtggccaact | 120 | |
| ccatcactag gggttctcag atctggcgcg cccaattggc ttcgaattct agcggccgcc | 180 | |
| cccgggtgcg cggcgtcggt ggtgccggcg ggggcgcca ggtcgcaggc ggtgtagggc | 240 | |
| tccaggcagg cggcgaaggc catgacgtgc gctatgaagg tctgctcctg cacgccgtga | 300 | |
| accaggtgcg cctgcgggcc gcgcgcgaac accgccacgt cctcgcctgc gtgggtctct | 360 | |
| tcgtccaggg gcactgctga ctgctgccga tactcggggc tcccgctctc gctctcggta | 420 | |
| acatccggcc gggcgccgtc cttgagcaca tagcctggac cgtttcctta agcgacgcat | 480 | |
| gctcgcgata ggcacctatt ggtcttactg acatccactt tgcctttctc tccacaggac | 540 | |
| ctggagcgag ggcggaggga gatggtggag gaggacctgg atgcagccct gccctgcct | 600 | |
| gacgaggatg aggaggacct ctctgagtat aaatttgcca agttcgcggc cacctacttc | 660 | |
| caggggacaa ccacgcactc ctacacccgg cggccactca aacagccact gctctaccat | 720 | |
| gacgacgagg gtgaccagct ggcagccctg cggtctggaa tcaccatcct ccgcttcatg | 780 | |
| ggggacctcc ctgagcccaa gtaccacaca gccatgagtg atggcagtga agatccct | 840 | |

```
gtgatgacca agatttatga daccctgggc aagaagacgt acaagaggga gctgcaggcc    900
ctgcagggcg agggcgaggc ccagctcccc gagggccaga agaagagcag tgtgaggcac    960
aagctggtgc atttgactct gaaaagaag tccaagctca cagaggaggt gaccaagagg    1020
ctgcatgacg gggagtccac agtgcagggc aacagcatgc tggaggaccg gcccacctcc    1080
aacctggaga agctgcactt catcatcggc aatggcatcc tgcggccagc actccgggac    1140
gagatctact gccagatcag caagcagctg acccacaacc cctccaagag cagctatgcc    1200
cggggctgga ttctcgtgtc tctctgcgtg ggctgtttcg ccccctccga agtttgtc     1260
aagtacctgc ggaacttcat ccacggggcc ccgcccggct acgcccccgta ctgtgaggag    1320
cgcctgagaa ggacctttgt caatgggaca cggacacagc cgcccagctg ctggagctg     1380
caggccacca agtccaagaa gccaatcatg ttgcccgtga cattcatgga tgggaccacc    1440
aagaccctgc tgacggactc ggcaaccacg gccaaggagc tctgcaacgc gctggccgac    1500
aagatctctc tcaaggaccg gttcgggttc tccctctaca ttgccctgtt tgacaaggtg    1560
tcctccctgg gcagcggcag tgaccacgtc atggacgcca tctcccagtg cgagcagtac    1620
gccaaggagc agggcgccca ggagcgcaac gccccctgga ggctcttctt ccgcaaagag    1680
gtcttcacgc cctggcacag cccctccgag gacaacgtgg ccaccaacct catctaccag    1740
caggtggtgc gaggagtcaa gtttggggag tacaggtgtg agaaggagga cgacctggct    1800
gagctggcct cccagcagta cttttgtagac tatggctctg agatgatcct ggagcgcctc    1860
ctgaacctcg tgcccaccta catccccgac cgcgagatca cgcccctgaa gacgctggag    1920
aagtgggccc agctggccat cgccgcccac aagaagggga tttatgccca gaggagaact    1980
gatgcccaga aggtcaaaga ggatgtggtc agttatgccc gcttcaagtg gcccttgctc    2040
ttctccaggt tttatgaagc ctacaaattc tcaggcccca gtctcccaa gaacgacgtc     2100
atcgtggccg tcaactggac gggtgtgtac tttgtggatg agcaggagca ggtacttctg    2160
gagctgtcct cccagagat catggccgtg tccagcagca ggggagcgaa aacgacggcc     2220
cccagcttca cgctgccacc catcaagggg gacgaataca ccttcacctc cagcaatgct    2280
gaggacattc gtgacctggt ggtcaccttc ctagaggggg tccggaagag atctaagtat    2340
gttgtggccc tgcaggataa ccccaacccc gcaggcgagg agtcaggctt cctcagcttt    2400
gccaagggag acctcatcat cctggaccat gacacgggcg agcaggtcat gaactcgggc    2460
tgggccaacg gcatcaatga ggaccaag cagcgtgggg acttccccac cgacagtgtg     2520
tacgtcatgc ccactgtcac catgccaccg cgggagattg tggccctggt caccatgact    2580
cccgatcaga ggcaggacgt tgtccggctc ttgcagctgc gaacggcgga gcccgaggtg    2640
cgtgccaagc cctacacgct ggaggagttt cctatgact acttcaggcc cccacccaag    2700
cacacgctga ccgtgtcat ggtgtccaag gcccgaggca aggaccggct gtggagccac    2760
acgcgggaac cgctcaagca ggcgctgctc aagaagctcc tggcagtga ggagctctcg    2820
caggaggcct gcctggcctt cattgctgtg ctcaagtaca tgggcgacta cccgtccaag    2880
aggacacgct ccgtcaacga gctcaccgac cagatctttg agggtcccct gaaagccgag    2940
cccctgaagg acgaggcata tgtgcagatc ctgaagcagc tgaccgacaa ccacatcagg    3000
tacagcgagg agcggggttg ggagctgctc tggctgtgca cgggccttttt cccacccagc    3060
aacatcctcc tgccccacgt gcagcgcttc ctgcagtccc gaaagcactg cccactcgcc    3120
atcgactgcc tgcaacggct ccagaaagcc ctgagaaacg ggtcccggaa gtaccctccg    3180
```

| | | |
|---|---|---|
| cacctggtgg aggtggaggc catccagcac aagaccaccc agattttcca caaagtctac | 3240 |
| ttccctgatg acactgacga ggccttcgaa gtggagtcca gcaccaaggc caaggacttc | 3300 |
| tgccagaaca tcgccaccag gctgctcctc aagtcctcag agggattcag cctctttgtc | 3360 |
| aaaattgcag acaaggtcat cagcgttcct gagaatgact tcttctttga ctttgttcga | 3420 |
| cacttgacag actggataaa gaaagctcgg cccatcaagg acggaattgt gccctcactc | 3480 |
| acctaccagg tgttcttcat gaagaagctg tggaccacca cggtgccagg aaggatccc | 3540 |
| atggccgatt ccatcttcca ctattaccag gagttgccca gtatctccg aggctaccac | 3600 |
| aagtgcacgc gggaggaggt gctgcagctg ggggcgctga tctacagggt caagttcgag | 3660 |
| gaggacaagt cctacttccc cagcatcccc aagctgctgc gggagctggt gccccaggac | 3720 |
| cttatccggc aggtctcacc tgatgactgg aagcggtcca tcgtcgccta cttcaacaag | 3780 |
| cacgcaggga agtccaagga ggaggccaag ctggccttcc tgaagctcat cttcaagtgg | 3840 |
| cccacctttg gctcagcctt cttcgaggtg aagcaaacta cggagccaaa cttccctgag | 3900 |
| atcctcctaa ttgccatcaa caagtatggg gtcagcctca tcgatcccaa aacgaaggat | 3960 |
| atcctcacca ctcatccctt caccaagatc tccaactgga gcagcggcaa cacctacttc | 4020 |
| cacatcacca ttgggaactt ggtgcgcggg agcaaactgc tctgcgagac gtcactgggc | 4080 |
| tacaagatgg atgacctcct gacttcctac attagccaga tgctcacagc catgagcaaa | 4140 |
| cagcggggct ccaggagcgg caagtaccct tacgatgtac cggattacgc atgaggtacc | 4200 |
| aagggcgaat tctgcagtcg actagagctc gctgatcagc ctcgactgtg ccttctagtt | 4260 |
| gccagccatc tgttgtttgc ccctccccg tgccttcctt gaccctggaa ggtgccactc | 4320 |
| ccactgtcct ttcctaataa aatgaggaaa ttgcatcgca ttgtctgagt aggtgtcatt | 4380 |
| ctattctggg gggtggggtg gggcaggaca gcaaggggga ggattgggaa gacaatagca | 4440 |
| ggcatgctgg ggagagatct gaggactagt ccgtcgactg ttaattaagc atgctgggga | 4500 |
| gagatctagg aaaccctag tgatggagtt ggcactccc tctctgcgcg ctcgctcgct | 4560 |
| cactgaggcc gggcgaccaa aggtcgcccg acgcccgggc tttgcccggg cggcctcagt | 4620 |
| gagcgagcga gcgcgcagag agggag | 4646 |

<210> SEQ ID NO 5
<211> LENGTH: 7465
<212> TYPE: DNA
<213> ORGANISM: Homo sapiens

<400> SEQUENCE: 5

| | | |
|---|---|---|
| gctctgggca ggagagagag tgagagacaa gagacacaca cagagagacg gcgaggaagg | 60 |
| gaaagaccca gagggacgcc tagaacgaga cttggagcca gacagaggaa gaggggacgt | 120 |
| gtgtttgcag actggctggg cccgtgaccc agcttcctga gtcctccgtg caggtggcag | 180 |
| ctgtaccagg ctggcaggtc actgagagtg ggcagctggg ccccagaact gtgcctggcc | 240 |
| cagtgggcag caggagctcc tgacttggga ccatggtgat tcttcagcag ggggaccatg | 300 |
| tgtggatgga cctgagattg gggcaggagt tcgacgtgcc catcggggcg gtggtgaagc | 360 |
| tctgcgactc tggcaggtc caggtggtgg atgatgaaga caatgaacac tggatctctc | 420 |
| cgcagaacgc aacgcacatc aagcctatgc accccacgtc ggtccacggc gtggaggaca | 480 |
| tgatccgcct gggggacctc aacgaggcgg gcatcttgcg caacctgctt atccgctacc | 540 |
| gggaccacct catctacacg tatcggggct ccatcctggt ggctgtgaac ccctaccagc | 600 |
| tgctctccat ctactcgcca gagcacatcc gccagtatac caacaagaag attggggaga | 660 |

-continued

```
tgccccccca catctttgcc attgctgaca actgctactt caacatgaaa cgcaacagcc      720
gagaccagtg ctgcatcatc agtggggaat ctggggccgg aaagacgag agcacaaagc      780
```

```
tgccccccca catctttgcc attgctgaca actgctactt caacatgaaa cgcaacagcc      720
gagaccagtg ctgcatcatc agtggggaat ctggggccgg aaagacgag agcacaaagc      780
tgatcctgca gttcctggca gccatcagtg ggcagcactc gtggattgag cagcaggtct      840
tggaggccac ccccattctg gaagcatttg gaatgccaa gaccatccgc aatgacaact      900
caagccgttt cggaaagtac atcgacatcc acttcaacaa gcgggggcgcc atcgagggcg      960
cgaagattga gcagtacctg ctggaaaagt cacgtgtctg tcgccaggcc ctggatgaaa    1020
ggaactacca cgtgttctac tgcatgctgg agggtatgag tgaggatcag aagaagaagc    1080
tgggcttggg ccaggcctct gactacaact acttggccat gggtaactgc ataacctgtg    1140
agggccgggt ggacagccag gagtacgcca acatccgctc cgccatgaag gtgctcatgt    1200
tcactgacac cgagaactgg gagatctcga agctcctggc tgccatcctg cacctgggca    1260
acctgcagta tgaggcacgc acatttgaaa acctggatgc ctgtgaggtt ctcttctccc    1320
catcgctggc cacagctgca tccctgcttg aggtgaaccc cccagacctg atgagctgcc    1380
tgactagccg caccctcatc acccgcgggg agacggtgtc caccccactg agcagggaac    1440
aggcactgga cgtgcgcgac gccttcgtaa aggggatcta cggcggctg ttcgtgtgga    1500
ttgtggacaa gatcaacgca gcaatttaca gcctccctc ccaggatgtg aagaactctc    1560
gcaggtccat cggcctcctg gacatctttg ggtttgagaa cttttgctgtg aacagctttg    1620
agcagctctg catcaacttc gccaatgagc acctgcagca gttctttgtg cggcacgtgt    1680
tcaagctgga gcaggaggaa tatgacctgg agagcattga ctggctgcac atcgagttca    1740
ctgacaacca ggatgccctg acatgatttg ccaacaagcc catgaacatc atctccctca    1800
tcgatgagga gagcaagttc cccaagggca cagacaccac catgttacac aagctgaact    1860
cccagcacaa gctcaacgcc aactacatcc cccccaagaa caaccatgag cccagtttg    1920
gcatcaacca ttttgcaggc atcgtctact atgagcccca aggcttcctg gagaagaacc    1980
gagacaccct gcatggggac attatccagc tggtccactc ctccaggaac aagttcatca    2040
agcagatctt ccaggccgat gtcgccatgg gcgccgagac caggaagcgc tcgcccacac    2100
ttagcagcca gttcaagcgg tcactggagc tgctgatgcg cacgctgggt gcctgccagc    2160
ccttctttgt gcgatgcatc aagcccaatg agttcaagaa gcccatgctg ttcgaccggc    2220
acctgtgcgt gcgccagctg cggtactcag gaatgatgga gccatccga atccgccgag    2280
ctggctaccc catccgctac agcttcgtag agtttgtgga gcggtaccgt gtgctgctgc    2340
caggtgtgaa gccggcctac aagcagggcg acctccgcgg gacttgccag cgcatggctg    2400
aggctgtgct gggcacccac gatgactggc agataggcaa aaccaagatc tttctgaagg    2460
accaccatga catgctgctg gaagtggagc gggacaaagc catcaccgac agagtcatcc    2520
tccttcagaa agtcatccgg ggattcaaag acaggtctaa ctttctgaag ctgaagaacg    2580
ctgccacact gatccagagg cactggcggg gtcacaactg taggaagaac tacgggctga    2640
tgcgtctggg cttcctgcgg ctgcaggccc tgcaccgctc ccggaagctg caccagcagt    2700
accgcctggc ccgccagcgc atcatccagt tccaggcccg ctgccgcgcc tatctggtgc    2760
gcaaggcctt ccgccaccgc ctctgggctg tgctcaccgt gcaggcctat gcccggggca    2820
tgatcgcccg caggctgcac caacgcctca gggctgagta tctgtggcgc ctcgaggctg    2880
agaaaatgcg gctggcggag gaagagaagc ttcggaagga gatgagcgcc aagaaggcca    2940
aggaggaggc cgagcgcaag catcaggagc gcctggccca gctggctcgt gaggacgctg    3000
```

```
agcgggagct gaaggagaag gaggccgctc ggcggaagaa ggagctcctg gagcagatgg    3060
aaagggcccg ccatgagcct gtcaatcact cagacatggt ggacaagatg tttggcttcc    3120
tggggacttc aggtggcctg ccaggccagg agggccaggc acctagtggc tttgaggacc    3180
tggagcgagg gcgagggag atggtggagg aggacctgga tgcagccctg cccctgcctg    3240
acgaggatga ggaggacctc tctgagtata aatttgccaa gttcgcggcc acctacttcc    3300
aggggacaac cacgcactcc tacacccggc ggccactcaa acagccactg ctctaccatg    3360
acgacgaggg tgaccagctg gcagccctgg cggtctggat caccatcctc cgcttcatgg    3420
gggacctccc tgagcccaag taccacacag ccatgagtga tggcagtgag aagatccctg    3480
tgatgaccaa gatttatgag accctgggca agaagacgta caagagggag ctgcaggccc    3540
tgcagggcga gggcgaggcc cagctccccg agggccagaa gaagagcagt gtgaggcaca    3600
agctggtgca tttgactctg aaaaagaagt ccaagctcac agaggaggtg accaagaggc    3660
tgcatgacgg ggagtccaca gtgcagggca acagcatgct ggaggaccgg cccacctcca    3720
acctggagaa gctgcacttc atcatcggca atggcatcct gcggccagca ctccgggacg    3780
agatctactg ccagatcagc aagcagctga cccacaaccc ctccaagagc agctatgccc    3840
ggggctggat tctcgtgtct ctctgcgtgg gctgtttcgc cccctccgag aagtttgtca    3900
agtacctgcg gaacttcatc cacgggggcc cgcccggcta cgccccgtac tgtgaggagc    3960
gcctgagaag gacctttgtc aatgggacac ggacacagcc gcccagctgg ctggagctgc    4020
aggccaccaa gtccaagaag ccaatcatgt tgcccgtgac attcatggat gggaccacca    4080
agaccctgct gacggactcg gcaaccacgg ccaaggagct ctgcaacgcg ctggccgaca    4140
agatctctct caaggaccgg ttcggggttct ccctctacat tgccctgttt gacaaggtgt    4200
cctccctggg cagcggcagt gaccacgtca tggacgccat ctcccagtgc gagcagtacg    4260
ccaaggagca gggcgcccag gagcgcaacg cccccctggag gctcttcttc cgcaaagagg    4320
tcttcacgcc ctggcacagc ccctccgagg acaacgtggc caccaacctc atctaccagc    4380
aggtggtgcg aggagtcaag tttggggagt acaggtgtga aaggaggac gacctggctg    4440 agctggcctc ccagcagtac tttgtagact atggctctga gatgatcctg gagcgcctcc    4500
tgaacctcgt gcccacctac atccccgacc gcagagatcac gcccctgaag acgctggaga    4560
agtgggccca gctggccatc gccgcccaca gaaaggggat ttatgcccag aggagaactg    4620
atgcccagaa ggtcaaagag gatgtggtca gttatgcccg cttcaagtgg cccttgctct    4680
tctccaggtt ttatgaagcc tacaaattct caggcccccag tctcccccaag aacgacgtca    4740 tcgtggccgt caactggacg ggtgtgtact tgtggatga gcaggagcag gtacttctgg    4800
agctgtcctt cccagagatc atggccgtgt ccagcagcag ggagtgccgt gtctggctct    4860
cactgggctg ctctgatctt ggctgtgctg cgcctcactc aggctgggca ggactgaccc    4920
cggcggggcc ctgttctccg tgttggtcct gcagggagc gaaaacgacg cccccagct    4980 tcacgctggc caccatcaag ggggacgaat acaccttcac ctccagtaat gctgaggaca    5040
ttcgtgacct ggtggtcacc ttcctagagg ggctccggaa gagatctaag tatgttgtgg    5100
ccctgcagga taaccccaac cccgcaggcg aggagtcagg cttcctcagc tttgccaagg    5160
gagacctcat catcctggac catgacacgg gcgagcaggt catgaactcg ggctgggca    5220 acggcatcaa tgagaggacc aagcagcgtg gggacttccc caccgactgt gtgtacgtca    5280
tgcccactgt caccatgcca ccgcgggaga ttgtggccct ggtcaccatg actcccgatc    5340
agaggcagga cgttgtccgg ctcttgcagc tgcgaacggc ggagcccgag gtgcgtgcca    5400
```

```
agccctacac gctggaggag ttttcctatg actacttcag gcccccaccc aagcacacgc  5460
tgagccgtgt catggtgtcc aaggcccgag gcaaggaccg gctgtggagc cacacgcggg  5520
aaccgctcaa gcaggcgctg ctcaagaagc tcctgggcag tgaggagctc tcgcaggagg  5580
cctgcctggc cttcattgct gtgctcaagt acatgggcga ctacccgtcc aagaggacac  5640
gctccgtcaa cgagctcacc gaccagatct tgagggtccc cctgaaagcc gagcccctga  5700
aggacgaggc atatgtgcag atcctgaagc agctgaccga caaccacatc aggtacagcg  5760
aggagcgggg ttgggagctg ctctggctgt gcacgggcct tttcccaccc agcaacatcc  5820
tcctgcccca cgtgcagcgc ttcctgcagt cccgaaagca ctgcccactc gccatcgact  5880
gcctgcaacg gctccagaaa gccctgagaa acgggtcccg gaagtaccct ccgcacctgg  5940
tggaggtgga ggccatccag cacaagacca cccagatttt ccacaaggtc tacttccctg  6000
atgacactga cgaggccttc gaagtggagt ccagcaccaa ggccaaggac ttctgccaga  6060
acatcgccac caggctgctc ctcaagtcct cagagggatt cagcctcttt gtcaaaattg  6120
cagacaaggt catcagcgtt cctgagaatg acttcttctt tgactttgtt cgacacttga  6180
cagactggat aaagaaagct cggcccatca aggacgaaat tgtgccctca ctcacctacc  6240
aggtgttctt catgaagaag ctgtggacca ccacggtgcc agggaaggat cccatggccg  6300
attccatctt ccactattac caggagttgc ccaagtatct ccgaggctac acaagtgca  6360
cgcgggagga ggtgctgcag ctgggggcgc tgatctacag ggtcaagttc gaggaggaca  6420
agtcctactt ccccagcatc cccaagctgc tgcgggagct ggtgcccag gaccttatcc  6480
ggcaggtctc acctgatgac tggaagcggt ccatcgtcgc ctacttcaac aagcacgcag  6540
ggaagtccaa ggaggaggcc aagctggcct tcctgaagct catcttcaag tggcccacct  6600
ttggctcagc cttcttcgag gtgaagcaaa ctacggagcc aaacttccct gagatcctcc  6660
taattgccat caacaagtat gggtcagcc tcatcgatcc caaaacgaag gatatcctca  6720
ccactcatcc cttcaccaag atctccaact ggagcagcgg caacacctac ttccacatca  6780
ccattgggaa cttggtgcgc gggagcaaac tgctctgcga cgtcactg ggctacaaga  6840
tggatgacct cctgacttcc tacattagcc agatgctcac agccatgagc aaacagcggg  6900
gctccaggag cggcaagtga acagtcacgg ggaggtgctg gttccatgcc tgctctcgag  6960
gcagcagtgg gttcaggccc atcagctacc cctgcagctg ggaagactt atgccatccc  7020
ggcagcgagg ctgggctggc cagccaccac tgactatacc aactgggcct ctgatgttct  7080
tccagtgagg catctctctg ggatgcagaa cttccctcca tccaccccctc tggcacctgg  7140
gttggtctaa tcctagtttg ctgtggcctt cccggttgtg agagcctgtg atccttagat  7200
gtgtctcctg tttcagacca gccccaccat gcaacttcct ttgactttct gtgtaccact  7260
gggatagagg aatcaagagg acaatctagc tctccatact ttgaacaacc aaatgtgcat  7320
tgaatactct gaaaccgaag ggactggatc tgcaggtggg atgagggaga cagaccactt  7380
ttctatattg cagtgtgaat gctgggcccc tgctcaagtc taccctgatc acctcagggc  7440
ataaagcatg tttcattctc tgaaa                                         7465
```

<210> SEQ ID NO 6
<211> LENGTH: 2215
<212> TYPE: PRT
<213> ORGANISM: Homo sapiens

<400> SEQUENCE: 6

```
Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
            20                  25                  30

Ser Gly Gln Val Gln Val Asp Asp Glu Asp Asn Glu His Trp Ile
        35                  40                  45

Ser Pro Gln Asn Ala Thr His Ile Lys Pro Met His Pro Thr Ser Val
50                  55                  60

His Gly Val Glu Asp Met Ile Arg Leu Gly Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
                100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
        130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Val Leu Glu Ala
                180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
        210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
                260                 265                 270

Gly Gln Ala Ser Asp Tyr Asn Tyr Leu Ala Met Gly Asn Cys Ile Thr
        275                 280                 285

Cys Glu Gly Arg Val Asp Ser Gln Glu Tyr Ala Asn Ile Arg Ser Ala
        290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
                340                 345                 350

Ala Thr Ala Ala Ser Leu Leu Glu Val Asn Pro Pro Asp Leu Met Ser
                355                 360                 365

Cys Leu Thr Ser Arg Thr Leu Ile Thr Arg Gly Glu Thr Val Ser Thr
        370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
```

```
            420                 425                 430
Ile Gly Leu Leu Asp Ile Phe Gly Phe Glu Asn Phe Ala Val Asn Ser
                435                 440                 445
Phe Glu Gln Leu Cys Ile Asn Phe Ala Asn Glu His Leu Gln Gln Phe
                450                 455                 460
Phe Val Arg His Val Phe Lys Leu Glu Gln Glu Glu Tyr Asp Leu Glu
465                 470                 475                 480
Ser Ile Asp Trp Leu His Ile Glu Phe Thr Asp Asn Gln Asp Ala Leu
                485                 490                 495
Asp Met Ile Ala Asn Lys Pro Met Asn Ile Ile Ser Leu Ile Asp Glu
                500                 505                 510
Glu Ser Lys Phe Pro Lys Gly Thr Asp Thr Thr Met Leu His Lys Leu
                515                 520                 525
Asn Ser Gln His Lys Leu Asn Ala Asn Tyr Ile Pro Pro Lys Asn Asn
                530                 535                 540
His Glu Thr Gln Phe Gly Ile Asn His Phe Ala Gly Ile Val Tyr Tyr
545                 550                 555                 560
Glu Thr Gln Gly Phe Leu Glu Lys Asn Arg Asp Thr Leu His Gly Asp
                565                 570                 575
Ile Ile Gln Leu Val His Ser Ser Arg Asn Lys Phe Ile Lys Gln Ile
                580                 585                 590
Phe Gln Ala Asp Val Ala Met Gly Ala Glu Thr Arg Lys Arg Ser Pro
                595                 600                 605
Thr Leu Ser Ser Gln Phe Lys Arg Ser Leu Glu Leu Leu Met Arg Thr
                610                 615                 620
Leu Gly Ala Cys Gln Pro Phe Phe Val Arg Cys Ile Lys Pro Asn Glu
625                 630                 635                 640
Phe Lys Lys Pro Met Leu Phe Asp Arg His Leu Cys Val Arg Gln Leu
                645                 650                 655
Arg Tyr Ser Gly Met Met Glu Thr Ile Arg Ile Arg Arg Ala Gly Tyr
                660                 665                 670
Pro Ile Arg Tyr Ser Phe Val Glu Phe Val Glu Arg Tyr Arg Val Leu
                675                 680                 685
Leu Pro Gly Val Lys Pro Ala Tyr Lys Gln Gly Asp Leu Arg Gly Thr
                690                 695                 700
Cys Gln Arg Met Ala Glu Ala Val Leu Gly Thr His Asp Asp Trp Gln
705                 710                 715                 720
Ile Gly Lys Thr Lys Ile Phe Leu Lys Asp His His Asp Met Leu Leu
                725                 730                 735
Glu Val Glu Arg Asp Lys Ala Ile Thr Asp Arg Val Ile Leu Leu Gln
                740                 745                 750
Lys Val Ile Arg Gly Phe Lys Asp Arg Ser Asn Phe Leu Lys Leu Lys
                755                 760                 765
Asn Ala Ala Thr Leu Ile Gln Arg His Trp Arg Gly His Asn Cys Arg
                770                 775                 780
Lys Asn Tyr Gly Leu Met Arg Leu Gly Phe Leu Arg Leu Gln Ala Leu
785                 790                 795                 800
His Arg Ser Arg Lys Leu His Gln Gln Tyr Arg Leu Ala Arg Gln
                805                 810                 815
Ile Ile Gln Phe Gln Ala Arg Cys Arg Ala Tyr Leu Val Arg Lys Ala
                820                 825                 830
Phe Arg His Arg Leu Trp Ala Val Leu Thr Val Gln Ala Tyr Ala Arg
                835                 840                 845
```

-continued

Gly Met Ile Ala Arg Arg Leu His Gln Arg Leu Arg Ala Glu Tyr Leu
850                 855                 860

Trp Arg Leu Glu Ala Glu Lys Met Arg Leu Ala Glu Glu Glu Lys Leu
865                 870                 875                 880

Arg Lys Glu Met Ser Ala Lys Ala Lys Glu Glu Ala Glu Arg Lys
            885                 890                 895

His Gln Glu Arg Leu Ala Gln Leu Ala Arg Glu Asp Ala Glu Arg Glu
            900                 905                 910

Leu Lys Glu Lys Glu Ala Ala Arg Arg Lys Lys Glu Leu Leu Glu Gln
            915                 920                 925

Met Glu Arg Ala Arg His Glu Pro Val Asn His Ser Asp Met Val Asp
930                 935                 940

Lys Met Phe Gly Phe Leu Gly Thr Ser Gly Gly Leu Pro Gly Gln Glu
945                 950                 955                 960

Gly Gln Ala Pro Ser Gly Phe Glu Asp Leu Glu Arg Gly Arg Arg Glu
            965                 970                 975

Met Val Glu Glu Asp Leu Asp Ala Ala Leu Pro Leu Pro Asp Glu Asp
            980                 985                 990

Glu Glu Asp Leu Ser Glu Tyr Lys Phe Ala Lys Phe Ala Ala Thr Tyr
            995                 1000                1005

Phe Gln Gly Thr Thr Thr His Ser Tyr Thr Arg Arg Pro Leu Lys
1010                1015                1020

Gln Pro Leu Leu Tyr His Asp Asp Glu Gly Asp Gln Leu Ala Ala
1025                1030                1035

Leu Ala Val Trp Ile Thr Ile Leu Arg Phe Met Gly Asp Leu Pro
1040                1045                1050

Glu Pro Lys Tyr His Thr Ala Met Ser Asp Gly Ser Glu Lys Ile
1055                1060                1065

Pro Val Met Thr Lys Ile Tyr Glu Thr Leu Gly Lys Lys Thr Tyr
1070                1075                1080

Lys Arg Glu Leu Gln Ala Leu Gln Gly Glu Gly Glu Ala Gln Leu
1085                1090                1095

Pro Glu Gly Gln Lys Lys Ser Ser Val Arg His Lys Leu Val His
1100                1105                1110

Leu Thr Leu Lys Lys Lys Ser Lys Leu Thr Glu Glu Val Thr Lys
1115                1120                1125

Arg Leu His Asp Gly Glu Ser Thr Val Gln Gly Asn Ser Met Leu
1130                1135                1140

Glu Asp Arg Pro Thr Ser Asn Leu Glu Lys Leu His Phe Ile Ile
1145                1150                1155

Gly Asn Gly Ile Leu Arg Pro Ala Leu Arg Asp Glu Ile Tyr Cys
1160                1165                1170

Gln Ile Ser Lys Gln Leu Thr His Asn Pro Ser Lys Ser Ser Tyr
1175                1180                1185

Ala Arg Gly Trp Ile Leu Val Ser Leu Cys Val Gly Cys Phe Ala
1190                1195                1200

Pro Ser Glu Lys Phe Val Lys Tyr Leu Arg Asn Phe Ile His Gly
1205                1210                1215

Gly Pro Pro Gly Tyr Ala Pro Tyr Cys Glu Glu Arg Leu Arg Arg
1220                1225                1230

Thr Phe Val Asn Gly Thr Arg Thr Gln Pro Pro Ser Trp Leu Glu
1235                1240                1245

-continued

| | | | | | | | | | | | | |
|---|---|---|---|---|---|---|---|---|---|---|---|---|
|Leu|Gln|Ala|Thr|Lys|Ser|Lys|Lys|Pro|Ile|Met|Leu|Pro|Val|Thr|
| |1250| | | | |1255| | | | |1260| | | |

Phe Met Asp Gly Thr Thr Lys Thr Leu Leu Thr Asp Ser Ala Thr
    1265                1270                1275

Thr Ala Lys Glu Leu Cys Asn Ala Leu Ala Asp Lys Ile Ser Leu
    1280                1285                1290

Lys Asp Arg Phe Gly Phe Ser Leu Tyr Ile Ala Leu Phe Asp Lys
    1295                1300                1305

Val Ser Ser Leu Gly Ser Gly Ser Asp His Val Met Asp Ala Ile
    1310                1315                1320

Ser Gln Cys Glu Gln Tyr Ala Lys Glu Gln Gly Ala Gln Glu Arg
    1325                1330                1335

Asn Ala Pro Trp Arg Leu Phe Phe Arg Lys Glu Val Phe Thr Pro
    1340                1345                1350

Trp His Ser Pro Ser Glu Asp Asn Val Ala Thr Asn Leu Ile Tyr
    1355                1360                1365

Gln Gln Val Val Arg Gly Val Lys Phe Gly Glu Tyr Arg Cys Glu
    1370                1375                1380

Lys Glu Asp Asp Leu Ala Glu Leu Ala Ser Gln Gln Tyr Phe Val
    1385                1390                1395

Asp Tyr Gly Ser Glu Met Ile Leu Glu Arg Leu Leu Asn Leu Val
    1400                1405                1410

Pro Thr Tyr Ile Pro Asp Arg Glu Ile Thr Pro Leu Lys Thr Leu
    1415                1420                1425

Glu Lys Trp Ala Gln Leu Ala Ile Ala Ala His Lys Lys Gly Ile
    1430                1435                1440

Tyr Ala Gln Arg Arg Thr Asp Ala Gln Lys Val Lys Glu Asp Val
    1445                1450                1455

Val Ser Tyr Ala Arg Phe Lys Trp Pro Leu Leu Phe Ser Arg Phe
    1460                1465                1470

Tyr Glu Ala Tyr Lys Phe Ser Gly Pro Ser Leu Pro Lys Asn Asp
    1475                1480                1485

Val Ile Val Ala Val Asn Trp Thr Gly Val Tyr Phe Val Asp Glu
    1490                1495                1500

Gln Glu Gln Val Leu Leu Glu Leu Ser Phe Pro Glu Ile Met Ala
    1505                1510                1515

Val Ser Ser Ser Arg Glu Cys Arg Val Trp Leu Ser Leu Gly Cys
    1520                1525                1530

Ser Asp Leu Gly Cys Ala Ala Pro His Ser Gly Trp Ala Gly Leu
    1535                1540                1545

Thr Pro Ala Gly Pro Cys Ser Pro Cys Trp Ser Cys Arg Gly Ala
    1550                1555                1560

Lys Thr Thr Ala Pro Ser Phe Thr Leu Ala Thr Ile Lys Gly Asp
    1565                1570                1575

Glu Tyr Thr Phe Thr Ser Ser Asn Ala Glu Asp Ile Arg Asp Leu
    1580                1585                1590

Val Val Thr Phe Leu Glu Gly Leu Arg Lys Arg Ser Lys Tyr Val
    1595                1600                1605

Val Ala Leu Gln Asp Asn Pro Asn Pro Ala Gly Glu Glu Ser Gly
    1610                1615                1620

Phe Leu Ser Phe Ala Lys Gly Asp Leu Ile Ile Leu Asp His Asp
    1625                1630                1635

Thr Gly Glu Gln Val Met Asn Ser Gly Trp Ala Asn Gly Ile Asn

```
              1640                1645                1650
Glu Arg Thr Lys Gln Arg Gly Asp Phe Pro Thr Asp Cys Val Tyr
          1655                1660                1665

Val Met Pro Thr Val Thr Met Pro Pro Arg Glu Ile Val Ala Leu
          1670                1675                1680

Val Thr Met Thr Pro Asp Gln Arg Gln Asp Val Val Arg Leu Leu
          1685                1690                1695

Gln Leu Arg Thr Ala Glu Pro Glu Val Arg Ala Lys Pro Tyr Thr
          1700                1705                1710

Leu Glu Glu Phe Ser Tyr Asp Tyr Phe Arg Pro Pro Pro Lys His
          1715                1720                1725

Thr Leu Ser Arg Val Met Val Ser Lys Ala Arg Gly Lys Asp Arg
          1730                1735                1740

Leu Trp Ser His Thr Arg Glu Pro Leu Lys Gln Ala Leu Leu Lys
          1745                1750                1755

Lys Leu Leu Gly Ser Glu Glu Leu Ser Gln Glu Ala Cys Leu Ala
          1760                1765                1770

Phe Ile Ala Val Leu Lys Tyr Met Gly Asp Tyr Pro Ser Lys Arg
          1775                1780                1785

Thr Arg Ser Val Asn Glu Leu Thr Asp Gln Ile Phe Glu Gly Pro
          1790                1795                1800

Leu Lys Ala Glu Pro Leu Lys Asp Glu Ala Tyr Val Gln Ile Leu
          1805                1810                1815

Lys Gln Leu Thr Asp Asn His Ile Arg Tyr Ser Glu Glu Arg Gly
          1820                1825                1830

Trp Glu Leu Leu Trp Leu Cys Thr Gly Leu Phe Pro Pro Ser Asn
          1835                1840                1845

Ile Leu Leu Pro His Val Gln Arg Phe Leu Gln Ser Arg Lys His
          1850                1855                1860

Cys Pro Leu Ala Ile Asp Cys Leu Gln Arg Leu Gln Lys Ala Leu
          1865                1870                1875

Arg Asn Gly Ser Arg Lys Tyr Pro Pro His Leu Val Glu Val Glu
          1880                1885                1890

Ala Ile Gln His Lys Thr Thr Gln Ile Phe His Lys Val Tyr Phe
          1895                1900                1905

Pro Asp Asp Thr Asp Glu Ala Phe Glu Val Glu Ser Ser Thr Lys
          1910                1915                1920

Ala Lys Asp Phe Cys Gln Asn Ile Ala Thr Arg Leu Leu Leu Lys
          1925                1930                1935

Ser Ser Glu Gly Phe Ser Leu Phe Val Lys Ile Ala Asp Lys Val
          1940                1945                1950

Ile Ser Val Pro Glu Asn Asp Phe Phe Phe Asp Phe Val Arg His
          1955                1960                1965

Leu Thr Asp Trp Ile Lys Lys Ala Arg Pro Ile Lys Asp Gly Ile
          1970                1975                1980

Val Pro Ser Leu Thr Tyr Gln Val Phe Phe Met Lys Lys Leu Trp
          1985                1990                1995

Thr Thr Thr Val Pro Gly Lys Asp Pro Met Ala Asp Ser Ile Phe
          2000                2005                2010

His Tyr Tyr Gln Glu Leu Pro Lys Tyr Leu Arg Gly Tyr His Lys
          2015                2020                2025

Cys Thr Arg Glu Glu Val Leu Gln Leu Gly Ala Leu Ile Tyr Arg
          2030                2035                2040
```

| | | | | | | | | | | |
|---|---|---|---|---|---|---|---|---|---|---|
| Val | Lys 2045 | Phe | Glu | Asp | Lys 2050 | Ser | Tyr | Phe | Pro | Ser 2055 | Ile | Pro | Lys |

Val Lys Phe Glu Asp Lys Ser Tyr Phe Pro Ser Ile Pro Lys
    2045            2050               2055

Leu Leu Arg Glu Leu Val Pro Gln Asp Leu Ile Arg Gln Val Ser
    2060            2065               2070

Pro Asp Asp Trp Lys Arg Ser Ile Val Ala Tyr Phe Asn Lys His
    2075            2080               2085

Ala Gly Lys Ser Lys Glu Glu Ala Lys Leu Ala Phe Leu Lys Leu
    2090            2095               2100

Ile Phe Lys Trp Pro Thr Phe Gly Ser Ala Phe Phe Glu Val Lys
    2105            2110               2115

Gln Thr Thr Glu Pro Asn Phe Pro Glu Ile Leu Leu Ile Ala Ile
    2120            2125               2130

Asn Lys Tyr Gly Val Ser Leu Ile Asp Pro Lys Thr Lys Asp Ile
    2135            2140               2145

Leu Thr Thr His Pro Phe Thr Lys Ile Ser Asn Trp Ser Ser Gly
    2150            2155               2160

Asn Thr Tyr Phe His Ile Thr Ile Gly Asn Leu Val Arg Gly Ser
    2165            2170               2175

Lys Leu Leu Cys Glu Thr Ser Leu Gly Tyr Lys Met Asp Asp Leu
    2180            2185               2190

Leu Thr Ser Tyr Ile Ser Gln Met Leu Thr Ala Met Ser Lys Gln
    2195            2200               2205

Arg Gly Ser Arg Ser Gly Lys
    2210            2215

<210> SEQ ID NO 7
<211> LENGTH: 6648
<212> TYPE: DNA
<213> ORGANISM: Homo sapiens

<400> SEQUENCE: 7

```
atggtgattc ttcagcaggg ggaccatgtg tggatggacc tgagattggg gcaggagttc      60
gacgtgccca tcggggcggt ggtgaagctc tgcgactctg gcaggtcca ggtggtggat     120
gatgaagaca atgaacactg gatctctccg cagaacgcaa cgcacatcaa gcctatgcac     180
cccacgtcgg tccacggcgt ggaggacatg atccgcctgg ggacctcaa cgaggcgggc     240
atcttgcgca acctgcttat ccgctaccgg gaccacctca tctacacgta tcgggctcc     300
atcctggtgg ctgtgaaccc ctaccagctg ctctccatct actcgccaga gcacatccgc     360
cagtatacca caagaagat tggggagatg ccccccaca tctttgccat tgctgacaac     420
tgctacttca acatgaaacg caacagccga gaccagtgct gcatcatcag tggggaatct     480
ggggccggga agacggagag cacaaagctg atcctgcagt cctggcagc catcagtggg     540
cagcactcgt ggattgagca gcaggtcttg gaggccaccc ccattctgga agcatttggg     600
aatgccaaga ccatccgcaa tgacaactca agccgtttcg gaaagtacat cgacatccac     660
ttcaacaagc ggggcgccat cgagggcgcg aagattgagc agtacctgct ggaaaagtca     720
cgtgtctgtc gccaggccct ggatgaaagg aactaccacg tgttctactg catgctggag     780
ggtatgagtg aggatcagaa gaagaagctg ggcttgggcc aggcctctga ctacaactac     840
ttggccatgg gtaactgcat aacctgtgag ggccgggtgg acagccagga gtacgccaac     900
atccgctccg ccatgaaggt gctcatgttc actgacaccg agaactggga gatctcgaag     960
ctcctggctg ccatcctgca cctgggcaac ctgcagtatg aggcacgcac atttgaaaac    1020
```

```
ctggatgcct gtgaggttct cttctcccca tcgctggcca cagctgcatc cctgcttgag   1080
gtgaaccccc cagacctgat gagctgcctg actagccgca ccctcatcac ccgcggggag   1140
acggtgtcca ccccactgag cagggaacag gcactggacg tgcgcgacgc cttcgtaaag   1200
gggatctacg ggcggctgtt cgtgtggatt gtggacaaga tcaacgcagc aatttacaag   1260
cctccctccc aggatgtgaa gaactctcgc aggtccatcg gcctcctgga catctttggg   1320
tttgagaact tgctgtgaa cagctttgag cagctctgca tcaacttcgc caatgagcac   1380
ctgcagcagt tctttgtgcg gcacgtgttc aagctggagc aggaggaata tgacctggag   1440
agcattgact ggctgcacat cgagttcact gacaaccagg atgccctgga catgattgcc   1500
aacaagccca tgaacatcat ctccctcatc gatgaggaga gcaagttccc caagggcaca   1560
gacaccacca tgttacacaa gctgaactcc cagcacaagc tcaacgccaa ctacatcccc   1620
cccaagaaca accatgagac ccagtttggc atcaaccatt ttgcaggcat cgtctactat   1680
gagacccaag gcttcctgga gaagaaccga cacccctgc atgggacat tatccagctg   1740 gtccactcct ccaggaacaa gttcatcaag cagatcttcc aggccgatgt cgccatgggc   1800
gccgagacca ggaagcgctc gcccacactt agcagccagt tcaagcggtc actggagctg   1860
ctgatgcgca cgctgggtgc ctgccagccc ttctttgtgc gatgcatcaa gcccaatgag   1920
ttcaagaagc ccatgctgtt cgaccggcac ctgtgcgtgc gccagctgcg gtactcagga   1980 atgatgcgaga ccatccgaat ccgccagct ggctacccca tccgctacag cttcgtagag   2040
tttgtggagc ggtaccgtgt gctgctgcca ggtgtgaagc cggcctacaa gcagggcgac   2100
ctccgcggga cttgccagcg catggctgag gctgtgctgg gcacccacga tgactggcag   2160
ataggcaaaa ccaagatctt tctgaaggac caccatgaca tgctgctgga agtggagcgg   2220
gacaaagcca tcaccgacag agtcatcctc cttcagaaag tcatccgggg attcaaagac   2280
aggtctaact ttctgaagct gaagaacgct gccacactga tccagaggca ctggcggggt   2340
cacaactgta ggaagaacta cgggctgatg cgtctgggct tcctgcggct gcaggccctg   2400
caccgctccc ggaagctgca ccagcagtac cgcctggccc gccagcgcat catccagttc   2460
caggcccgct gccgcgccta tctggtgcgc aaggccttcc gccaccgcct ctgggctgtg   2520
ctcaccgtgc aggcctatgc ccggggcatg atcgcccgca ggctgcacca acgcctcagg   2580
gctgagtatc tgtggcgcct cgaggctgag aaaatgcggc tggcggagga agagaagctt   2640
cggaaggaga tgagcgccaa gaaggccaag gaggaggccg agcgcaagca tcaggagcgc   2700
ctggcccagc tggctcgtga ggacgctgag cgggagctga aggagaagga ggccgctcgg   2760
cggaagaagg agctcctgga gcagatggaa agggcccgcc atgagcctgt caatcactca   2820
gacatggtgg acaagatgtt tggcttcctg gggacttcag gtggcctgcc aggccaggag   2880
ggccaggcac ctagtggctt tgaggacctg agcgagggc ggagggagat ggtggaggag   2940
gacctggatg cagccctgcc cctgcctgac gaggatgagg aggacctctc tgagtataaa   3000
tttgccaagt tcgcggccac ctacttccag gggacaacca cgcactccta cacccggcgg   3060
ccactcaaac agccactgct ctaccatgac gacgagggtg accagctggc agccctggcg   3120
gtctggatca ccatcctccg cttcatgggg gacctccctg agcccaagta ccacacagcc   3180
atgagtgatg gcagtgagaa gatccctgtg atgaccaaga tttatgagac cctgggcaag   3240
aagacgtaca gagggagct gcaggccctg caggcgagg gcgaggccca gctccccgag   3300
ggccagaaga gagcagtgt gaggcacaag ctggtgcatt tgactctgaa aaagaagtcc   3360
aagctcacag aggaggtgac caagaggctg catgacgggg agtccacagt gcagggcaac   3420
```

```
agcatgctgg aggaccggcc cacctccaac ctggagaagc tgcacttcat catcggcaat    3480
ggcatcctgc ggccagcact ccgggacgag atctactgcc agatcagcaa gcagctgacc    3540
cacaacccct ccaagagcag ctatgcccgg ggctggattc tcgtgtctct ctgcgtgggc    3600
tgtttcgccc cctccgagaa gtttgtcaag tacctgcgga acttcatcca cggggggccg    3660
cccggctacg ccccgtactg tgaggagcgc ctgagaagga cctttgtcaa tgggacacgg    3720
acacagccgc ccagctggct ggagctgcag gccaccaagt ccaagaagcc aatcatgttg    3780
cccgtgacat tcatggatgg gaccaccaag accctgctga cggactcggc aaccacggcc    3840
aaggagctct gcaacgcgct ggccgacaag atctctctca aggaccggtt cgggttctcc    3900
ctctacattg ccctgtttga caaggtgtcc tccctgggca gcggcagtga ccacgtcatg    3960
gacgccatct cccagtgcga gcagtacgcc aaggagcagg gcgcccagga gcgcaacgcc    4020
ccctggaggc tcttcttccg caaagaggtc ttcacgccct ggcacagccc ctccgaggac    4080
aacgtggcca ccaacctcat ctaccagcag gtggtgcgag gagtcaagtt tggggagtac    4140
aggtgtgaga aggaggacga cctggctgag ctggcctccc agcagtactt tgtagactat    4200
ggctctgaga tgatcctgga gcgcctcctg aacctcgtgc ccacctacat ccccgaccgc    4260
gagatcacgc ccctgaagac gctggagaag tgggcccagc tggccatcgc cgcccacaag    4320
aaggggattt atgcccagag gagaactgat gcccagaagg tcaaagagga tgtggtcagt    4380
tatgcccgct tcaagtggcc cttgctcttc tccaggtttt atgaagccta caaattctca    4440
ggccccagtc tccccaagaa cgacgtcatc gtggccgtca actggacggg tgtgtacttt    4500
gtggatgagc aggagcaggt acttctggag ctgtccttcc cagagatcat ggccgtgtcc    4560
agcagcaggg agtgccgtgt ctggctctca ctgggctgct ctgatcttgg ctgtgctgcg    4620
cctcactcag gctgggcagg actgaccccg gcggggccct gttctccgtg ttggtcctgc    4680
aggggagcga aaacgacggc ccccagcttc acgctggcca ccatcaaggg ggacgaatac    4740
accttcacct ccagtaatgc tgaggacatt cgtgacctgg tggtcacctt cctagagggg    4800
ctccggaaga gatctaagta tgttgtggcc ctgcaggata accccaaccc cgcaggcgag    4860
gagtcaggct tcctcagctt tgccaaggga gacctcatca tcctgaccac cgacacgggc    4920
gagcaggtca tgaactcggg ctgggccaac ggcatcaatg agaggaccaa gcagcgtggg    4980
gacttccccca ccgactgtgt gtacgtcatg cccactgtca ccatgccacc gcgggagatt    5040
gtggccctgg tcaccatgac tcccgatcag aggcaggacg ttgtccggct cttgcagctg    5100
cgaacggcgg agcccgaggt gcgtgccaag ccctacacgc tggaggagtt ttcctatgac    5160
tacttcaggc ccccacccaa gcacacgctg agccgtgtca tggtgtccaa ggcccgaggc    5220
aaggaccggc tgtggagcca cacgcgggaa ccgctcaagc aggcgctgct caagaagctc    5280
ctgggcagtg aggagctctc gcaggaggcc tgcctggcct tcattgctgt gctcaagtac    5340
atgggcgact acccgtccaa gaggacacgc tccgtcaacg agctcaccga ccagatctttc    5400
gagggtcccc tgaaagccga gcccctgaag gacgaggcat atgtgcagat cctgaagcag    5460
ctgaccgaca accacatcag gtacagcgag gagcggggtt gggagctgct ctggctgtgc    5520
acgggccttt tcccacccag caacatcctc ctgcccacg tgcagcgctt cctgcagtcc    5580
cgaaagcact gcccactcgc catcgactgc ctgcaacggc tccagaaagc cctgagaaac    5640
gggtcccgga gtaccctcc gcacctggtg gaggtggagg ccatccagca aagaccacc     5700
cagatttttcc acaaggtcta cttccctgat gacactgacg aggccttcga agtggagtcc    5760
```

-continued

| | |
|---|---|
| agcaccaagg ccaaggactt ctgccagaac atcgccacca ggctgctcct caagtcctca | 5820 |
| gagggattca gcctctttgt caaaattgca gacaaggtca tcagcgttcc tgagaatgac | 5880 |
| ttcttctttg actttgttcg acacttgaca gactggataa agaaagctcg gcccatcaag | 5940 |
| gacggaattg tgccctcact cacctaccag gtgttcttca tgaagaagct gtggaccacc | 6000 |
| acggtgccag ggaaggatcc catggccgat tccatcttcc actattacca ggagttgccc | 6060 |
| aagtatctcc gaggctacca caagtgcacg cgggaggagg tgctgcagct gggggcgctg | 6120 |
| atctacaggg tcaagttcga ggaggacaag tcctacttcc ccagcatccc caagctgctg | 6180 |
| cgggagctgg tgccccagga ccttatccgg caggtctcac ctgatgactg aagcggtcc | 6240 |
| atcgtcgcct acttcaacaa gcacgcaggg aagtccaagg aggaggccaa gctggccttc | 6300 |
| ctgaagctca tcttcaagtg gcccaccttt ggctcagcct tcttcgaggt gaagcaaact | 6360 |
| acggagccaa acttccctga gatcctccta attgccatca caagtatggg ggtcagcctc | 6420 |
| atcgatccca aaacgaagga tatcctcacc actcatccct tcaccaagat ctccaactgg | 6480 |
| agcagcggca acacctactt ccacatcacc attgggaact ggtgcgcgg gagcaaactg | 6540 |
| ctctgcgaga cgtcactggg ctacaagatg gatgacctcc tgacttccta cattagccag | 6600 |
| atgctcacag ccatgagcaa acagcggggc tccaggagcg gcaagtga | 6648 |

<210> SEQ ID NO 8
<211> LENGTH: 2175
<212> TYPE: PRT
<213> ORGANISM: Homo sapiens

<400> SEQUENCE: 8

Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
            20                  25                  30

Ser Gly Gln Val Gln Val Asp Asp Glu Asp Asn Glu His Trp Ile
        35                  40                  45

Ser Pro Gln Asn Ala Thr His Ile Lys Pro Met His Pro Thr Ser Val
    50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
    210                 215                 220

```
Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
            245                 250                 255

Cys Met Leu Glu Gly Met Ser Glu Asp Gln Lys Lys Leu Gly Leu
        260                 265                 270

Gly Gln Ala Ser Asp Tyr Asn Tyr Leu Ala Met Gly Asn Cys Ile Thr
        275                 280                 285

Cys Glu Gly Arg Val Asp Ser Gln Glu Tyr Ala Asn Ile Arg Ser Ala
        290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350

Ala Thr Ala Ala Ser Leu Leu Glu Val Asn Pro Pro Asp Leu Met Ser
        355                 360                 365

Cys Leu Thr Ser Arg Thr Leu Ile Thr Arg Gly Glu Thr Val Ser Thr
        370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
            435                 440                 445

Phe Glu Gln Leu Cys Ile Asn Phe Ala Asn Glu His Leu Gln Gln Phe
450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
            485                 490                 495

Asp Met Ile Ala Asn Lys Pro Met Asn Ile Ile Ser Leu Ile Asp Glu
            500                 505                 510

Glu Ser Lys Phe Pro Lys Gly Thr Asp Thr Thr Met Leu His Lys Leu
        515                 520                 525

Asn Ser Gln His Lys Leu Asn Ala Asn Tyr Ile Pro Pro Lys Asn Asn
530                 535                 540

His Glu Thr Gln Phe Gly Ile Asn His Phe Ala Gly Ile Val Tyr Tyr
545                 550                 555                 560

Glu Thr Gln Gly Phe Leu Glu Lys Asn Arg Asp Thr Leu His Gly Asp
            565                 570                 575

Ile Ile Gln Leu Val His Ser Ser Arg Asn Lys Phe Ile Lys Gln Ile
            580                 585                 590

Phe Gln Ala Asp Val Ala Met Gly Ala Glu Thr Arg Lys Arg Ser Pro
        595                 600                 605

Thr Leu Ser Ser Gln Phe Lys Arg Ser Leu Glu Leu Leu Met Arg Thr
        610                 615                 620

Leu Gly Ala Cys Gln Pro Phe Phe Val Arg Cys Ile Lys Pro Asn Glu
625                 630                 635                 640
```

```
Phe Lys Lys Pro Met Leu Phe Asp Arg His Leu Cys Val Arg Gln Leu
            645                 650                 655

Arg Tyr Ser Gly Met Met Glu Thr Ile Arg Ile Arg Arg Ala Gly Tyr
            660                 665                 670

Pro Ile Arg Tyr Ser Phe Val Glu Phe Val Glu Arg Tyr Arg Val Leu
            675                 680                 685

Leu Pro Gly Val Lys Pro Ala Tyr Lys Gln Gly Asp Leu Arg Gly Thr
            690                 695                 700

Cys Gln Arg Met Ala Glu Ala Val Leu Gly Thr His Asp Asp Trp Gln
705                 710                 715                 720

Ile Gly Lys Thr Lys Ile Phe Leu Lys Asp His His Asp Met Leu Leu
            725                 730                 735

Glu Val Glu Arg Asp Lys Ala Ile Thr Asp Arg Val Ile Leu Leu Gln
            740                 745                 750

Lys Val Ile Arg Gly Phe Lys Asp Arg Ser Asn Phe Leu Lys Leu Lys
            755                 760                 765

Asn Ala Ala Thr Leu Ile Gln Arg His Trp Arg Gly His Asn Cys Arg
            770                 775                 780

Lys Asn Tyr Gly Leu Met Arg Leu Gly Phe Leu Arg Leu Gln Ala Leu
785                 790                 795                 800

His Arg Ser Arg Lys Leu His Gln Gln Tyr Arg Leu Ala Arg Gln Arg
            805                 810                 815

Ile Ile Gln Phe Gln Ala Arg Cys Arg Ala Tyr Leu Val Arg Lys Ala
            820                 825                 830

Phe Arg His Arg Leu Trp Ala Val Leu Thr Val Gln Ala Tyr Ala Arg
            835                 840                 845

Gly Met Ile Ala Arg Arg Leu His Gln Arg Leu Arg Ala Glu Tyr Leu
850                 855                 860

Trp Arg Leu Glu Ala Glu Lys Met Arg Leu Ala Glu Glu Lys Leu
865                 870                 875                 880

Arg Lys Glu Met Ser Ala Lys Lys Ala Lys Glu Glu Ala Glu Arg Lys
            885                 890                 895

His Gln Glu Arg Leu Ala Gln Leu Ala Arg Glu Asp Ala Glu Arg Glu
            900                 905                 910

Leu Lys Glu Lys Glu Ala Ala Arg Arg Lys Lys Glu Leu Leu Glu Gln
            915                 920                 925

Met Glu Arg Ala Arg His Glu Pro Val Asn His Ser Asp Met Val Asp
930                 935                 940

Lys Met Phe Gly Phe Leu Gly Thr Ser Gly Gly Leu Pro Gly Gln Glu
945                 950                 955                 960

Gly Gln Ala Pro Ser Gly Phe Glu Asp Leu Glu Arg Gly Arg Arg Glu
            965                 970                 975

Met Val Glu Glu Asp Leu Asp Ala Ala Leu Pro Leu Pro Asp Glu Asp
            980                 985                 990

Glu Glu Asp Leu Ser Glu Tyr Lys Phe Ala Lys Phe Ala Ala Thr Tyr
            995                 1000                1005

Phe Gln Gly Thr Thr Thr His Ser Tyr Thr Arg Arg Pro Leu Lys
            1010                1015                1020

Gln Pro Leu Leu Tyr His Asp Asp Glu Gly Asp Gln Leu Ala Ala
            1025                1030                1035

Leu Ala Val Trp Ile Thr Ile Leu Arg Phe Met Gly Asp Leu Pro
            1040                1045                1050

Glu Pro Lys Tyr His Thr Ala Met Ser Asp Gly Ser Glu Lys Ile
```

```
              1055              1060              1065
Pro Val Met Thr Lys Ile Tyr Glu Thr Leu Gly Lys Lys Thr Tyr
    1070              1075              1080

Lys Arg Glu Leu Gln Ala Leu Gln Gly Glu Gly Glu Ala Gln Leu
    1085              1090              1095

Pro Glu Gly Gln Lys Lys Ser Ser Val Arg His Lys Leu Val His
    1100              1105              1110

Leu Thr Leu Lys Lys Ser Lys Leu Thr Glu Glu Val Thr Lys
    1115              1120              1125

Arg Leu His Asp Gly Glu Ser Thr Val Gln Gly Asn Ser Met Leu
    1130              1135              1140

Glu Asp Arg Pro Thr Ser Asn Leu Glu Lys Leu His Phe Ile Ile
    1145              1150              1155

Gly Asn Gly Ile Leu Arg Pro Ala Leu Arg Asp Glu Ile Tyr Cys
    1160              1165              1170

Gln Ile Ser Lys Gln Leu Thr His Asn Pro Ser Lys Ser Ser Tyr
    1175              1180              1185

Ala Arg Gly Trp Ile Leu Val Ser Leu Cys Val Gly Cys Phe Ala
    1190              1195              1200

Pro Ser Glu Lys Phe Val Lys Tyr Leu Arg Asn Phe Ile His Gly
    1205              1210              1215

Gly Pro Pro Gly Tyr Ala Pro Tyr Cys Glu Glu Arg Leu Arg Arg
    1220              1225              1230

Thr Phe Val Asn Gly Thr Arg Thr Gln Pro Pro Ser Trp Leu Glu
    1235              1240              1245

Leu Gln Ala Thr Lys Ser Lys Lys Pro Ile Met Leu Pro Val Thr
    1250              1255              1260

Phe Met Asp Gly Thr Thr Lys Thr Leu Leu Thr Asp Ser Ala Thr
    1265              1270              1275

Thr Ala Lys Glu Leu Cys Asn Ala Leu Ala Asp Lys Ile Ser Leu
    1280              1285              1290

Lys Asp Arg Phe Gly Phe Ser Leu Tyr Ile Ala Leu Phe Asp Lys
    1295              1300              1305

Val Ser Ser Leu Gly Ser Gly Ser Asp His Val Met Asp Ala Ile
    1310              1315              1320

Ser Gln Cys Glu Gln Tyr Ala Lys Glu Gln Gly Ala Gln Glu Arg
    1325              1330              1335

Asn Ala Pro Trp Arg Leu Phe Phe Arg Lys Glu Val Phe Thr Pro
    1340              1345              1350

Trp His Ser Pro Ser Glu Asp Asn Val Ala Thr Asn Leu Ile Tyr
    1355              1360              1365

Gln Gln Val Val Arg Gly Val Lys Phe Gly Glu Tyr Arg Cys Glu
    1370              1375              1380

Lys Glu Asp Asp Leu Ala Glu Leu Ala Ser Gln Gln Tyr Phe Val
    1385              1390              1395

Asp Tyr Gly Ser Glu Met Ile Leu Glu Arg Leu Leu Asn Leu Val
    1400              1405              1410

Pro Thr Tyr Ile Pro Asp Arg Glu Ile Thr Pro Leu Lys Thr Leu
    1415              1420              1425

Glu Lys Trp Ala Gln Leu Ala Ile Ala Ala His Lys Lys Gly Ile
    1430              1435              1440

Tyr Ala Gln Arg Arg Thr Asp Ala Gln Lys Val Lys Glu Asp Val
    1445              1450              1455
```

```
Val Ser Tyr Ala Arg Phe Lys Trp Pro Leu Leu Phe Ser Arg Phe
1460                1465                1470

Tyr Glu Ala Tyr Lys Phe Ser Gly Pro Ser Leu Pro Lys Asn Asp
1475                1480                1485

Val Ile Val Ala Val Asn Trp Thr Gly Val Tyr Phe Val Asp Glu
1490                1495                1500

Gln Glu Gln Val Leu Leu Glu Leu Ser Phe Pro Glu Ile Met Ala
1505                1510                1515

Val Ser Ser Ser Arg Gly Ala Lys Thr Thr Ala Pro Ser Phe Thr
1520                1525                1530

Leu Ala Thr Ile Lys Gly Asp Glu Tyr Thr Phe Thr Ser Ser Asn
1535                1540                1545

Ala Glu Asp Ile Arg Asp Leu Val Val Thr Phe Leu Glu Gly Leu
1550                1555                1560

Arg Lys Arg Ser Lys Tyr Val Val Ala Leu Gln Asp Asn Pro Asn
1565                1570                1575

Pro Ala Gly Glu Glu Ser Gly Phe Leu Ser Phe Ala Lys Gly Asp
1580                1585                1590

Leu Ile Ile Leu Asp His Asp Thr Gly Glu Gln Val Met Asn Ser
1595                1600                1605

Gly Trp Ala Asn Gly Ile Asn Glu Arg Thr Lys Gln Arg Gly Asp
1610                1615                1620

Phe Pro Thr Asp Ser Val Tyr Val Met Pro Thr Val Thr Met Pro
1625                1630                1635

Pro Arg Glu Ile Val Ala Leu Val Thr Met Thr Pro Asp Gln Arg
1640                1645                1650

Gln Asp Val Val Arg Leu Leu Gln Leu Arg Thr Ala Glu Pro Glu
1655                1660                1665

Val Arg Ala Lys Pro Tyr Thr Leu Glu Glu Phe Ser Tyr Asp Tyr
1670                1675                1680

Phe Arg Pro Pro Pro Lys His Thr Leu Ser Arg Val Met Val Ser
1685                1690                1695

Lys Ala Arg Gly Lys Asp Arg Leu Trp Ser His Thr Arg Glu Pro
1700                1705                1710

Leu Lys Gln Ala Leu Leu Lys Lys Leu Leu Gly Ser Glu Glu Leu
1715                1720                1725

Ser Gln Glu Ala Cys Leu Ala Phe Ile Ala Val Leu Lys Tyr Met
1730                1735                1740

Gly Asp Tyr Pro Ser Lys Arg Thr Arg Ser Val Asn Glu Leu Thr
1745                1750                1755

Asp Gln Ile Phe Glu Gly Pro Leu Lys Ala Glu Pro Leu Lys Asp
1760                1765                1770

Glu Ala Tyr Val Gln Ile Leu Lys Gln Leu Thr Asp Asn His Ile
1775                1780                1785

Arg Tyr Ser Glu Glu Arg Gly Trp Glu Leu Leu Trp Leu Cys Thr
1790                1795                1800

Gly Leu Phe Pro Pro Ser Asn Ile Leu Leu Pro His Val Gln Arg
1805                1810                1815

Phe Leu Gln Ser Arg Lys His Cys Pro Leu Ala Ile Asp Cys Leu
1820                1825                1830

Gln Arg Leu Gln Lys Ala Leu Arg Asn Gly Ser Arg Lys Tyr Pro
1835                1840                1845
```

Pro His Leu Val Glu Val Glu Ala Ile Gln His Lys Thr Thr Gln
1850                1855                1860

Ile Phe His Lys Val Tyr Phe Pro Asp Asp Thr Asp Glu Ala Phe
1865                1870                1875

Glu Val Glu Ser Ser Thr Lys Ala Lys Asp Phe Cys Gln Asn Ile
1880                1885                1890

Ala Thr Arg Leu Leu Leu Lys Ser Ser Glu Gly Phe Ser Leu Phe
1895                1900                1905

Val Lys Ile Ala Asp Lys Val Leu Ser Val Pro Glu Asn Asp Phe
1910                1915                1920

Phe Phe Asp Phe Val Arg His Leu Thr Asp Trp Ile Lys Lys Ala
1925                1930                1935

Arg Pro Ile Lys Asp Gly Ile Val Pro Ser Leu Thr Tyr Gln Val
1940                1945                1950

Phe Phe Met Lys Lys Leu Trp Thr Thr Thr Val Pro Gly Lys Asp
1955                1960                1965

Pro Met Ala Asp Ser Ile Phe His Tyr Tyr Gln Glu Leu Pro Lys
1970                1975                1980

Tyr Leu Arg Gly Tyr His Lys Cys Thr Arg Glu Val Leu Gln
1985                1990                1995

Leu Gly Ala Leu Ile Tyr Arg Val Lys Phe Glu Glu Asp Lys Ser
2000                2005                2010

Tyr Phe Pro Ser Ile Pro Lys Leu Leu Arg Glu Leu Val Pro Gln
2015                2020                2025

Asp Leu Ile Arg Gln Val Ser Pro Asp Asp Trp Lys Arg Ser Ile
2030                2035                2040

Val Ala Tyr Phe Asn Lys His Ala Gly Lys Ser Lys Glu Glu Ala
2045                2050                2055

Lys Leu Ala Phe Leu Lys Leu Ile Phe Lys Trp Pro Thr Phe Gly
2060                2065                2070

Ser Ala Phe Phe Glu Gln Thr Thr Glu Pro Asn Phe Pro Glu Ile
2075                2080                2085

Leu Leu Ile Ala Ile Asn Lys Tyr Gly Val Ser Leu Ile Asp Pro
2090                2095                2100

Lys Thr Lys Asp Ile Leu Thr Thr His Pro Phe Thr Lys Ile Ser
2105                2110                2115

Asn Trp Ser Ser Gly Asn Thr Tyr Phe His Ile Thr Ile Gly Asn
2120                2125                2130

Leu Val Arg Gly Ser Lys Leu Leu Cys Glu Thr Ser Leu Gly Tyr
2135                2140                2145

Lys Met Asp Asp Leu Leu Thr Ser Tyr Ile Ser Gln Met Leu Thr
2150                2155                2160

Ala Met Ser Lys Gln Arg Gly Ser Arg Ser Gly Lys
2165                2170                2175

<210> SEQ ID NO 9
<211> LENGTH: 39
<212> TYPE: DNA
<213> ORGANISM: Artificial Sequence
<220> FEATURE:
<223> OTHER INFORMATION: Synthetic

<400> SEQUENCE: 9
gcggcggccg ccaccatggt gattcttcag cagggggac          39

```
<210> SEQ ID NO 10
<211> LENGTH: 30
<212> TYPE: DNA
<213> ORGANISM: Artificial Sequence
<220> FEATURE:
<223> OTHER INFORMATION: Synthetic

<400> SEQUENCE: 10
gcggctagcg aagttccgca ggtacttgac                                        30

<210> SEQ ID NO 11
<211> LENGTH: 31
<212> TYPE: DNA
<213> ORGANISM: Artificial Sequence
<220> FEATURE:
<223> OTHER INFORMATION: Synthetic

<400> SEQUENCE: 11
gcgcttaagc aggtctaact ttctgaagct g                                      31

<210> SEQ ID NO 12
<211> LENGTH: 30
<212> TYPE: DNA
<213> ORGANISM: Artificial Sequence
<220> FEATURE:
<223> OTHER INFORMATION: Synthetic

<400> SEQUENCE: 12
gcgggtacct cacttgccgc tcctggagcc                                        30

<210> SEQ ID NO 13
<211> LENGTH: 41
<212> TYPE: DNA
<213> ORGANISM: Artificial Sequence
<220> FEATURE:
<223> OTHER INFORMATION: Synthetic

<400> SEQUENCE: 13
ggcacctagt ggctttgagg taagtatcaa ggttacaaga c                           41

<210> SEQ ID NO 14
<211> LENGTH: 29
<212> TYPE: DNA
<213> ORGANISM: Artificial Sequence
<220> FEATURE:
<223> OTHER INFORMATION: Synthetic

<400> SEQUENCE: 14
gcggctagct cagaaacgca agagtcttc                                         29

<210> SEQ ID NO 15
<211> LENGTH: 22
<212> TYPE: DNA
<213> ORGANISM: Artificial Sequence
<220> FEATURE:
<223> OTHER INFORMATION: Synthetic

<400> SEQUENCE: 15
cttctttgtg cgatgcatca ag                                                22

<210> SEQ ID NO 16
<211> LENGTH: 28
<212> TYPE: DNA
<213> ORGANISM: Artificial Sequence
<220> FEATURE:
<223> OTHER INFORMATION: Synthetic
```

```
<400> SEQUENCE: 16
gcgcttaagc gacgcatgct cgcgatag                                      28

<210> SEQ ID NO 17
<211> LENGTH: 37
<212> TYPE: DNA
<213> ORGANISM: Artificial Sequence
<220> FEATURE:
<223> OTHER INFORMATION: Synthetic

<400> SEQUENCE: 17
cgccctcgct ccaggtcctg tggagagaaa ggcaaag                            37

<210> SEQ ID NO 18
<211> LENGTH: 19
<212> TYPE: DNA
<213> ORGANISM: Artificial Sequence
<220> FEATURE:
<223> OTHER INFORMATION: Synthetic

<400> SEQUENCE: 18
gaacccgaac cggtccttg                                                19

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
gcggctagcc cccgggtgcg cggc                                          24

<210> SEQ ID NO 20
<211> LENGTH: 29
<212> TYPE: DNA
<213> ORGANISM: Artificial Sequence
<220> FEATURE:
<223> OTHER INFORMATION: Synthetic

<400> SEQUENCE: 20
gcggtcgacg aaacggtcca ggctatgtg                                     29

<210> SEQ ID NO 21
<211> LENGTH: 27
<212> TYPE: DNA
<213> ORGANISM: Artificial Sequence
<220> FEATURE:
<223> OTHER INFORMATION: Synthetic

<400> SEQUENCE: 21
gcggcggccg cccccgggtg cgcggcg                                       27

<210> SEQ ID NO 22
<211> LENGTH: 29
<212> TYPE: DNA
<213> ORGANISM: Artificial Sequence
<220> FEATURE:
<223> OTHER INFORMATION: Synthetic

<400> SEQUENCE: 22
gcgcttaagg aaacggtcca ggctatgtg                                     29

<210> SEQ ID NO 23
<211> LENGTH: 40
```

```
<212> TYPE: DNA
<213> ORGANISM: Artificial Sequence
<220> FEATURE:
<223> OTHER INFORMATION: Synthetic

<400> SEQUENCE: 23
caggcaccta gtggctttga ggtaccaggc tagggacagg                              40

<210> SEQ ID NO 24
<211> LENGTH: 28
<212> TYPE: DNA
<213> ORGANISM: Artificial Sequence
<220> FEATURE:
<223> OTHER INFORMATION: Synthetic

<400> SEQUENCE: 24
gcggctagcc gcctgagccc agaagttc                                          28

<210> SEQ ID NO 25
<211> LENGTH: 38
<212> TYPE: DNA
<213> ORGANISM: Artificial Sequence
<220> FEATURE:
<223> OTHER INFORMATION: Synthetic

<400> SEQUENCE: 25
cgccctcgct ccaggtcctg aaggagacaa gaggtatg                               38

<210> SEQ ID NO 26
<211> LENGTH: 29
<212> TYPE: DNA
<213> ORGANISM: Artificial Sequence
<220> FEATURE:
<223> OTHER INFORMATION: Synthetic

<400> SEQUENCE: 26
gcgcttaagc accgcttgtg ttgatcctc                                         29

<210> SEQ ID NO 27
<211> LENGTH: 19
<212> TYPE: DNA
<213> ORGANISM: Artificial Sequence
<220> FEATURE:
<223> OTHER INFORMATION: Synthetic

<400> SEQUENCE: 27
gccagggaag gatcccatg                                                    19

<210> SEQ ID NO 28
<211> LENGTH: 57
<212> TYPE: DNA
<213> ORGANISM: Artificial Sequence
<220> FEATURE:
<223> OTHER INFORMATION: Synthetic

<400> SEQUENCE: 28
gcgggtacct catgcgtaat ccggtacatc gtaagggtac ttgccgctcc tggagcc          57

<210> SEQ ID NO 29
<211> LENGTH: 24
<212> TYPE: DNA
<213> ORGANISM: Artificial Sequence
<220> FEATURE:
<223> OTHER INFORMATION: Synthetic

<400> SEQUENCE: 29
```

```
agcttcgtag agtttgtgga gcgg                                            24
```

<210> SEQ ID NO 30
<211> LENGTH: 19
<212> TYPE: DNA
<213> ORGANISM: Artificial Sequence
<220> FEATURE:
<223> OTHER INFORMATION: Synthetic

<400> SEQUENCE: 30

```
gaggggcaaa caacagatg                                                  19
```

<210> SEQ ID NO 31
<211> LENGTH: 4262
<212> TYPE: DNA
<213> ORGANISM: Artificial Sequence
<220> FEATURE:
<223> OTHER INFORMATION: Synthetic

<400> SEQUENCE: 31

```
ctccctctct gcgcgctcgc tcgctcactg aggccgcccg ggcaaagccc gggcgtcggg     60
cgacctttgg tcgcccggcc tcagtgagcg agcgagcgcg cagagaggga gtggccaact    120
ccatcactag gggttctcag atctggcgcg cccaattcgg taccctagtt attaatagta    180
atcaattacg gggtcattag ttcatagccc atatatggag ttccgcgtta cataacttac    240
ggtaaatggc ccgcctggct gaccgcccaa cgacccccgc ccattgacgt caataatgac    300
gtatgttccc atagtaacgc caatagggac tttccattga cgtcaatggg tggactattt    360
acggtaaact gcccacttgg cagtacatca agtgtatcat atgccaagta cgccccctat    420
tgacgtcaat gacggtaaat ggcccgcctg gcattatgcc cagtacatga ccttatggga    480
ctttcctact tggcagtaca tctacgtatt agtcatcgct attaccatgg tcgaggtgag    540
ccccacgttc tgcttcactc tccccatctc ccccccctcc ccacccccaa ttttgtattt    600
atttattttt taattatttt gtgcagcgat ggggggcgggg ggggggggggg ggcgcgcgcc    660
aggcggggcg ggcgggggcg aggggcgggg cggggcgagg cggagaggtg cggcggcagc    720
caatcagagc ggcgcgctcc gaaagtttcc ttttatggcg aggcggcggc ggcggcggcc    780
ctataaaaag cgaagcgcgc ggcgggcggg agtcgctgcg acgctgcctt cgccccgtgc    840
cccgctccgc cgccgcctcg cgccgcccgc cccggctctg actgaccgcg ttactcccac    900
aggtgagcgg gcgggacggc ccttctcctc cgggctgtaa ttagcgcttg gtttaatgac    960
ggcttgtttc ttttctgtgg ctgcgtgaaa gccttgaggg gctccgggag ctagagcctc   1020
tgctaaccat gttcatgcct tcttcttttt cctacagctc ctgggcaacg tgctggttat   1080
tgtgctgtct catcattttg gcaaagaatt ctagcggccg ccaccatggt gattcttcag   1140
caggggacc atgtgtggat ggacctgaga ttggggcagg agttcgacgt gcccatcggg   1200
gcggtggtga agctctgcga ctctgggcag gtccaggtgg tggatgatga agacaatgaa   1260
cactggatct ctccgcagaa cgcaacgcac atcaagccta tgcaccccac gtcggtccac   1320
ggcgtggagg acatgatccg cctgggggac ctcaacgagg cgggcatctt gcgcaacctg   1380
cttatccgct accgggacca cctcatctac acgtatacgg gctccatcct ggtgctgtg    1440
aaccccctacc agctgctctc catctactcg ccagagcaca tccgccagta taccaacaag   1500
aagattgggg gatgccccc ccacatcttt gccattgctg acactgcta cttcaacatg   1560
aaacgcaaca gccgagacca gtgctgcatc atcagtgggg aatctgggc cgggaagacg   1620
gagagcacaa agctgatcct gcagttcctg gcagccatca gtgggcagca ctcgtggatt   1680
```

```
gagcagcagg tcttggaggc caccccatt  ctggaagcat ttgggaatgc caagaccatc  1740
cgcaatgaca actcaagccg tttcggaaag tacatcgaca tccacttcaa caagcggggc  1800
gccatcgagg gcgcgaagat tgagcagtac ctgctggaaa agtcacgtgt ctgtcgccag  1860
gccctggatg aaaggaacta ccacgtgttc tactgcatgc tggagggtat gagtgaggat  1920
cagaagaaga agctgggctt gggccaggcc tctgactaca actacttggc catgggtaac  1980
tgcataacct gtgagggccg ggtggacagc caggagtacg ccaacatccg ctccgccatg  2040
aaggtgctca tgttcactga caccgagaac tgggagatct cgaagctcct ggctgccatc  2100
ctgcacctgg gcaacctgca gtatgaggca cgcacatttg aaaacctgga tgcctgtgag  2160
gttctcttct ccccatcgct ggccacagct gcatccctgc ttgaggtgaa ccccccagac  2220
ctgatgagct gcctgactag ccgcaccctc atcacccgcg gggagacggt gtccacccca  2280
ctgagcaggg aacaggcact ggacgtgcgc gacgccttcg taaagggat ctacgggcgg  2340
ctgttcgtgt ggattgtgga caagatcaac gcagcaattt acaagcctcc ctcccaggat  2400
gtgaagaact ctcgcaggtc catcggcctc ctggacatct ttgggtttga aactttgct   2460
gtgaacagct ttgagcagct ctgcatcaac ttcgccaatg agcacctgca gcagttcttt  2520
gtgcggcacg tgttcaagct ggagcaggag gaatatgacc tggagagcat tgactggctg  2580
cacatcgagt tcactgacaa ccaggatgcc ctggacatga ttgccaacaa gcccatgaac  2640
atcatctccc tcatcgatga ggagagcaag ttccccaagg gcacagacac caccatgtta  2700
cacaagctga actcccagca caagctcaac gccaactaca tccccccccaa gaacaaccat  2760
gagacccagt ttggcatcaa ccattttgca ggcatcgtct actatgagac ccaaggcttc  2820
ctggagaaga accagacaca cctgcatggg acattatcc  agctggtcca ctcctccagg  2880
aacaagttca tcaagcagat cttccaggcc gatgtcgcca tgggcgccga gaccaggaag  2940
cgctcgccca cacttagcag ccagttcaag cggtcactgg agctgctgat gcgcacgctg  3000
ggtgcctgcc agcccttctt tgtgcgatgc atcaagccca atgagttcaa gaagcccatg  3060
ctgttcgacc ggcacctgtg cgtgcgccag ctgcggtact caggaatgat ggagaccatc  3120
cgaatccgcc gagctggcta ccccatccgc tacagcttcg tagagtttgt ggagcggtac  3180
cgtgtgctgc tgccaggtgt gaagccggcc tacaagcagg gcgacctccg cgggacttgc  3240
cagcgcatgg ctgaggctgt gctgggcacc cacgatgact ggcagatagg caaaaccaag  3300
atctttctga aggaccacca tgacatgctg ctggaagtgg agcgggacaa agccatcacc  3360
gacagagtca tcctccttca gaaagtcatc cggggattca agacaggtc  taactttctg  3420
aagctgaaga acgctgccac actgatccag aggcactggc ggggtcacaa ctgtaggaag  3480
aactacgggc tgatgcgtct gggcttcctg cggctgcagg ccctgcaccg ctcccggaag  3540
ctgcaccagc agtaccgcct ggcccgccag cgcatcatcc agttccaggc ccgctgccgc  3600
gcctatctgt gcgcaaggc cttccgccac cgcctctggg ctgtgctcac cgtgcaggcc  3660
tatgcccggg gcatgatcgc ccgcaggctg caccaacgcc tcagggctga ggtaagtatc  3720
aaggttacaa gacaggttta aggagaccaa tagaaactgg gcttgtcgag acagagaaga  3780
ctcttgcgtt tctgagctag cccccgggtg cgcggcgtcg gtggtgccgg cggggggcgc  3840
caggtcgcag gcggtgtagg gctccaggca ggcggcgaag gccatgacgt gcgctatgaa  3900
ggtctgctcc tgcacgccgt gaaccaggtg cgcctgcggg ccgcgcgcga acaccgccac  3960
gtcctcgcct gcgtgggtct cttcgtccag gggcactgct gactgctgcc gatactcggg  4020
```

```
gctcccgctc tcgctctcgg taacatccgg ccgggcgccg tccttgagca catagcctgg    4080
accgtttcgt cgactgttaa ttaagcatgc tggggagaga tctaggaaac ccctagtgat    4140
ggagttggcc actccctctc tgcgcgctcg ctcgctcact gaggccgggc gaccaaaggt    4200
cgcccgacgc ccgggctttg cccgggcggc tcagtgagc gagcgagcgc gcagagaggg    4260
ag                                                                   4262
```

<210> SEQ ID NO 32
<211> LENGTH: 4965
<212> TYPE: DNA
<213> ORGANISM: Artificial Sequence
<220> FEATURE:
<223> OTHER INFORMATION: Synthetic

<400> SEQUENCE: 32

```
ctccctctct gcgcgctcgc tcgctcactg aggccgcccg ggcaaagccc gggcgtcggg      60
cgacctttgg tcgcccggcc tcagtgagcg agcgagcgcg cagagaggga gtggccaact    120
ccatcactag gggttctcag atctggcgcg cccaattggc ttcgaattct agcggccgcc    180
cccgggtgcg cggcgtcggt ggtgccggcg ggggcgcca ggtcgcaggc ggtgtagggc     240
tccaggcagg cggcgaaggc catgacgtgc gctatgaagg tctgctcctg cacgccgtga    300
accaggtgcg cctgcgggcc gcgcgcgaac accgccacgt cctcgcctgc gtgggtctct    360
tcgtccaggg gcactgctga ctgctgccga tactcggggc tcccgctctc gctctcggta    420
acatccggcc gggcgccgtc cttgagcaca tagcctggac cgtttccttg agcgacgcat    480
gctcgcgata ggcaccctatt ggtcttactg acatccactt tgcctttctc tccacagtat    540
ctgtggcgcc tcgaggctga gaaaatgcgg ctggcggagg aagagaagct tcggaaggag    600 atgagccgcca agaaggccaa ggaggaggcc gagcgcaagc atcaggagcg cctggcccag    660
ctggctcgtg aggacgctga gcgggagctg aaggagaagg aggccgctcg gcggaagaag    720
gagctcctgg agcagatgga aagggcccgc catgagcctg tcaatcactc agacatggtg    780
gacaagatgt ttggcttcct ggggacttca ggtggcctgc caggccagga gggccaggca    840
cctagtggct ttgaggacct ggagcgaggg cggagggaga tggtggagga ggacctggat    900
gcagccctgc ccctgcctga cgaggatgag gaggacctct ctgagtataa atttgccaag    960
ttcgcggcca cctacttcca ggggacaacc acgcactcct acacccggcg gccactcaaa   1020
cagccactgc tctaccatga cgacgagggt gaccagctgg cagccctggc ggtctggatc   1080
accatcctcc gcttcatggg ggacctccct gagcccaagt accacacagc catgagtgat   1140
ggcagtgaga agatccctgt gatgaccaag atttatgaga ccctgggcaa gagacgtac   1200 aagagggagc tgcaggccct gcagggcgag ggcgaggccc agctccccga gggcagaag   1260 aagagcagtg tgaggcacaa gctggtgcat ttgactctga aaagaagtc caagctcaca   1320 gaggaggtga ccaagaggct gcatgacggg agtccacag tgcagggcaa cagcatgctg   1380
gaggaccggc ccacctccaa cctggagaag ctgcacttca tcatcggcaa tggcatcctg   1440
cggccagcac tccgggacga tatctactgc cagatcagca gcagctgac ccacaacccc   1500 tccaagagca gctatgcccg ggctggatt tcgtgtctc tctgcgtggg ctgtttcgcc   1560
ccctccgaga agtttgtcaa gtacctgcgg aacttcatcc acggggcc gcccggctac   1620 gccccgtact gtgaggagcg cctgagaagg accttttgtca atgggacacg gacacagccg   1680
cccagctggc tggagctgca ggccaccaag tccaagaagc caatcatgtt gcccgtgaca   1740
ttcatggatg ggaccaccaa gacccgtctg acggactcgg caaccacggc caaggagctc   1800
```

| | |
|---|---|
| tgcaacgcgc tggccgacaa gatctctctc aaggaccggt tcgggttctc cctctacatt | 1860 |
| gccctgtttg acaaggtgtc ctccctgggc agcggcagtg accacgtcat ggacgccatc | 1920 |
| tcccagtgcg agcagtacgc caaggagcag ggcgcccagg agcgcaacgc ccctggagg | 1980 |
| ctcttcttcc gcaaagaggt cttcacgccc tggcacagcc cctccgagga caacgtggcc | 2040 |
| accaacctca tctaccagca ggtggtgcga ggagtcaagt ttggggagta caggtgtgag | 2100 |
| aaggaggacg acctggctga gctggcctcc cagcagtact ttgtagacta tggctctgag | 2160 |
| atgatcctgg agcgcctcct gaacctcgtg cccacctaca tccccgaccg cgagatcacg | 2220 |
| cccctgaaga cgctggagaa gtgggcccag ctggccatcg ccgcccacaa gaagggatt | 2280 |
| tatgcccaga ggagaactga tgcccagaag gtcaaagagg atgtggtcag ttatgcccgc | 2340 |
| ttcaagtggc ccttgctctt ctccaggttt tatgaagcct acaaattctc aggccccagt | 2400 |
| ctccccaaga cgacgtcat cgtggccgtc aactggacgg gtgtgtactt tgtggatgag | 2460 |
| caggagcagg tacttctgga gctgtccttc ccagagatca tggccgtgtc cagcagcagg | 2520 |
| ggagcgaaaa cgacggcccc cagcttcacg ctggccacca tcaaggggga cgaatacacc | 2580 |
| ttcacctcca gcaatgctga ggacattcgt gacctggtgg tcaccttcct agaggggctc | 2640 |
| cggaagagat ctaagtatgt tgtggccctg caggataacc ccaaccccgc aggcgaggag | 2700 |
| tcaggcttcc tcagctttgc caagggagac ctcatcatcc tggaccatga cacgggcgag | 2760 |
| caggtcatga actcgggctg ggccaacggc atcaatgaga ggaccaagca gcgtggggac | 2820 |
| ttccccaccg acagtgtgta cgtcatgccc actgtcacca tgccaccgcg ggagattgtg | 2880 |
| gccctggtca ccatgactcc cgatcagagg caggacgttg tccggctctt gcagctgcga | 2940 |
| acggcggagc ccgaggtgcg tgccaagccc tacacgctgg aggagttttc ctatgactac | 3000 |
| ttcaggcccc cacccaagca cacgctgagc cgtgtcatgg tgtccaaggc ccgaggcaag | 3060 |
| gaccggctgt ggagccacac gcgggaaccg ctcaagcagg cgctgctcaa gaagctcctg | 3120 |
| ggcagtgagg agctctcgca ggaggcctgc ctggccttca ttgctgtgct caagtacatg | 3180 |
| ggcgactacc cgtccaagag gacacgctcc gtcaacgagc tcaccgacca gatctttgag | 3240 |
| ggtcccctga agccgagcc cctgaaggac gaggcatatg tgcagatcct gaagcagctg | 3300 |
| accgacaacc acatcaggta cagcgaggag cggggttggg agctgctctg gctgtgcacg | 3360 |
| ggcctttcc cacccagcaa catcctcctg ccccacgtgc agcgcttcct gcagtcccga | 3420 |
| aagcactgcc cactcgccat cgactgcctg caacggctcc agaaagccct gagaaacggg | 3480 |
| tccccggaagt accctccgca cctggtggag gtggaggcca tccagcacaa gaccacccag | 3540 |
| attttccaca aagtctactt ccctgatgac actgacgagg ccttcgaagt ggagtccagc | 3600 |
| accaaggcca aggacttctg ccagaacatc gccaccaggc tgctcctcaa gtcctcagag | 3660 |
| ggattcagcc tctttgtcaa aattgcagac aaggtcatca gcgttcctga gaatgacttc | 3720 |
| ttctttgact tgttcgaca cttgacagac tggataaaga agctcggcc catcaaggac | 3780 |
| ggaattgtgc cctcactcac ctaccaggtg ttcttcatga agaagctgtg gaccaccacg | 3840 |
| gtgccaggga aggatcccat ggccgattcc atcttccact attaccagga gttgcccaag | 3900 |
| tatctccgag gctaccacaa gtgcacgcgg gaggaggtg tgcagctggg ggcgctgatc | 3960 |
| tacagggtca agttcgagga ggacaagtcc tacttcccca gcatccccaa gctgctgcgg | 4020 |
| gagctggtgc cccaggacct tatccggcag gtctcacctg atgactggaa gcggtccatc | 4080 |
| gtcgcctact tcaacaagca cgcagggaag tccaaggagg aggccaagct ggccttcctg | 4140 |

| | |
|---|---:|
| aagctcatct tcaagtggcc caccttttggc tcagccttct tcgaggtgaa gcaaactacg | 4200 |
| gagccaaact tccctgagat cctcctaatt gccatcaaca agtatggggt cagcctcatc | 4260 |
| gatcccaaaa cgaaggatat cctcaccact catcccttca ccaagatctc caactggagc | 4320 |
| agcggcaaca cctacttcca catcaccatt gggaacttgg tgcgcgggag caaactgctc | 4380 |
| tgcgagacgt cactgggcta caagatggat gacctcctga cttcctacat tagccagatg | 4440 |
| ctcacagcca tgagcaaaca gcggggctcc aggagcggca agtaccctta cgatgtaccg | 4500 |
| gattacgcat gaggtaccaa ggcgaattc tgcagtcgac tagagctcgc tgatcagcct | 4560 |
| cgactgtgcc ttctagttgc cagccatctg ttgtttgccc ctcccccgtg ccttccttga | 4620 |
| ccctggaagg tgccactccc actgtccttt cctaataaaa tgaggaaatt gcatcgcatt | 4680 |
| gtctgagtag tgtcattct attctggggg gtggggtggg gcaggacagc aagggggagg | 4740 |
| attgggaaga caatagcagg catgctgggg agagatctgg aggactagtc cgtcgactgt | 4800 |
| taattaagca tgctggggag agatctagga accccctagt gatggagttg gccactccct | 4860 |
| ctctgcgcgc tcgctcgctc actgaggccg gcgaccaaa ggtcgcccga cgcccgggct | 4920 |
| ttgcccgggc ggcctcagtg agcgagcgag cgcgcagaga gggag | 4965 |

<210> SEQ ID NO 33
<211> LENGTH: 4262
<212> TYPE: DNA
<213> ORGANISM: Artificial Sequence
<220> FEATURE:
<223> OTHER INFORMATION: Synthetic

<400> SEQUENCE: 33

| | |
|---|---:|
| ctccctctct gcgcgctcgc tcgctcactg aggccgcccg ggcaaagccc gggcgtcggg | 60 |
| cgacctttgg tcgcccggcc tcagtgagcg agcgagcgcg cagagaggga gtggccaact | 120 |
| ccatcactag gggttctcag atctggcgcg cccaattcgg taccctagtt attaatagta | 180 |
| atcaattacg gggtcattag ttcatagccc atatatggag ttccgcgtta cataacttac | 240 |
| ggtaaatggc ccgcctggct gaccgcccaa cgacccccgc ccattgacgt caataatgac | 300 |
| gtatgttccc atagtaacgc caatagggac tttccattga cgtcaatggg tggactattt | 360 |
| acggtaaact gcccacttgg cagtacatca agtgtatcat atgccaagta cgccccctat | 420 |
| tgacgtcaat gacggtaaat ggcccgcctg gcattatgcc cagtacatga ccttatggga | 480 |
| ctttcctact tggcagtaca tctacgtatt agtcatcgct attaccatgg tcgaggtgag | 540 |
| ccccacgttc tgcttcactc tccccatctc cccccctcc ccaccccaa ttttgtattt | 600 |
| atttattttt taattatttt gtgcagcgat ggggggggg ggggggggg ggcgcgcgcc | 660 |
| aggcggggcg gggcggggcg aggggcgggg cgggggcgagg cggagaggtg cggcggcagc | 720 |
| caatcagagc ggcgcgctcc gaaagtttcc ttttatggcg aggcggcggc ggcggcggcc | 780 |
| ctataaaaag cgaagcgcgc ggcgggcggg agtcgctgcg cgctgccttc gccccgtgcc | 840 |
| ccgctccgcc gccgcctcgc gccgcccgcc ccggctctga ctgaccgcgt tactcccaca | 900 |
| ggtgagcggg cgggacggcc cttctcctcc gggctgtaat tagcgcttgg tttaatgacg | 960 |
| gcttgtttct tttctgtggc tgcgtgaaag ccttgagggg ctccgggagc tagagcctct | 1020 |
| gctaaccatg ttcatgcctt cttcttttcc ctacagctcc tgggcaacgt gctggttatt | 1080 |
| gtgctgtctc atcatttttgg caaagaattc tagcggccgc caccatggtg attcttcagc | 1140 |
| aggggggacca tgtgtggatg gacctgagat tgggcaggaa gttcgacgtg cccatcgggg | 1200 |
| cggtggtgaa gctctgcgac tctgggcagg tccaggtggt ggatgatgaa gacaatgaac | 1260 |

```
actggatctc tccgcagaac gcaacgcaca tcaagcctat gcaccccacg tcggtccacg    1320
gcgtggagga catgatccgc ctgggggacc tcaacgaggc gggcatcttg cgcaacctgc    1380
ttatccgcta ccgggaccac ctcatctaca cgtatacggg ctccatcctg gtggctgtga    1440
acccctacca gctgctctcc atctactcgc cagagcacat ccgccagtat accaacaaga    1500
agattgggga gatgcccccc cacatctttg ccattgctga caactgctac ttcaacatga    1560
aacgcaacag ccgagaccag tgctgcatca tcagtgggga atctgggcc gggaagacgg     1620 agagcacaaa gctgatcctg cagttcctgg cagccatcag tgggcagcac tcgtggattg    1680
agcagcaggt cttggaggcc acccccattc tggaagcatt tgggaatgcc aagaccatcc    1740
gcaatgacaa ctcaagccgt ttcggaaagt acatcgacat ccacttcaac aagcggggcg    1800
ccatcgaggg cgcgaagatt gagcagtacc tgctggaaaa gtcacgtgtc tgtcgccagg    1860
ccctggatga aaggaactac cacgtgttct actgcatgct ggagggtatg agtgaggatc    1920
agaagaagaa gctgggcttg gccaggcct ctgactacaa ctacttggcc atgggtaact     1980
gcataacctg tgagggccgg gtggacagcc aggagtacgc caacatccgc tccgccatga    2040
aggtgctcat gttcactgac accgagaact gggagatctc gaagctcctg gctgccatcc    2100
tgcacctggg caacctgcag tatgaggcac gcacatttga aaacctggat gcctgtgagg    2160
ttctcttctc cccatcgctg gccacagctg catccctgct tgaggtgaac cccccagacc    2220
tgatgagctg cctgactagc cgcacccctca tcacccgcgg ggagacggtg tccacccac    2280 tgagcaggga acaggcactg gacgtgcgcg acgccttcgt aaagggggatc tacgggcggc    2340 tgttcgtgtg gattgtggac aagatcaacg cagcaattta caagcctccc tcccaggatg    2400
tgaagaactc tcgcaggtcc atcggcctcc tggacatctt tgggtttgag aactttgctg    2460
tgaacagctt tgagcagctc tgcatcaact tcgccaatga gcacctgcag cagttctttg    2520
tgcggcacgt gttcaagctg gagcaggagg aatatgacct ggagagcatt gactggctgc    2580
acatcgagtt cactgacaac caggatgccc tggacatgat tgccaacaag cccatgaaca    2640
tcatctccct catcgatgag gagagcaagt tccccaaggg cacagacacc accatgttac    2700
acaagctgaa ctcccagcac aagctcaacg ccaactacat cccccccaag aacaaccatg    2760
agacccagtt tggcatcaac cattttgcag gcatcgtcta ctatgagacc caaggcttcc    2820
tggagaagaa ccgagacacc ctgcatgggg acattatcca gctggtccac tcctccagga    2880
acaagttcat caagcagatc ttccaggccg atgtcgccat gggcgccgag accaggaagc    2940
gctcgcccac acttagcagc cagttcaagc ggtcactgga gctgctgatg cgcacgctgg    3000
gtgcctgcca gcccttcttt gtgcgatgca tcaagcccaa tgagttcaag aagcccatgc    3060
tgttcgaccg gcacctgtgc gtgcgccagc tgcggtactc aggaatgatg gagaccatcc    3120
gaatccgccg agctggctac cccatccgct acagcttcgt agagtttgtg gagcggtacc    3180
gtgtgctgct gccaggtgtg aagcggcct acaagcaggg cgacctccgc gggacttgcc     3240
agcgcatggc tgaggctgtg ctgggcaccc acgatgactg gcagataggc aaaaccaaga    3300
tctttctgaa ggaccaccat gacatgctgc tggaagtgga gcgggacaaa gccatcaccg    3360
acagagtcat cctccttcag aaagtcatcc ggggattcaa agacaggtct aactttctga    3420
agctgaagaa cgctgccaca ctgatccaga ggcactggcg gggtcacaac tgtaggaaga    3480
actacgggct gatgcgtctg ggcttcctgc ggctgcaggc cctgcaccgc tcccggaagc    3540
tgcaccagca gtaccgcctg gcccgccagc gcatcatcca gttccaggcc cgctgccgcg    3600
```

```
cctatctggt gcgcaaggcc ttccgccacc gcctctgggc tgtgctcacc gtgcaggcct    3660
atgcccgggg catgatcgcc cgcaggctgc accaacgcct cagggctgag gtaagtatca    3720
aggttacaag acaggttaac ggagaccaat tgaaactggg cttgtcgaga cagagaagac    3780
tcttgcgttt cagcgctagc ccccgggtgc gcggcgtcgg tggtgccggc gggggcgcc     3840 aggtcgcagg cggtgtaggg ctccaggcag gcggcgaagg ccatgacgtg cgctatgaag    3900
gtctgctcct gcacgccgtg aaccaggtgc gcctgcgggc cgcgcgcgaa caccgccacg    3960
tcctcgcctg cgtgggtctc ttcgtccagg ggcactgctg actgctgccg atactcgggg    4020
ctcccgctct cgctctcggt aacatccggc cgggcgccgt ccttgagcac atagcctgga    4080
ccgtttcgtc gactgttaat taagcatgct ggggagagat ctgaggaaac ccctagtgat    4140
ggagttggcc actccctctc tgcgcgctcg ctcgctcact gaggccgggc gaccaaaggt    4200
cgcccgacgc ccgggctttg cccgggcggc ctcagtgagc gagcgagcgc gcagagaggg    4260
ag                                                                   4262
```

<210> SEQ ID NO 34
<211> LENGTH: 4259
<212> TYPE: DNA
<213> ORGANISM: Artificial Sequence
<220> FEATURE:
<223> OTHER INFORMATION: Synthetic

<400> SEQUENCE: 34

```
ctccctctct gcgcgctcgc tcgctcactg aggccgcccg ggcaaagccc gggcgtcggg     60
cgacctttgg tcgcccggcc tcagtgagcg agcgagcgcg cagagaggga gtggccaact    120
ccatcactag gggttctcag atctggcgcg cccaattcgg taccctagtt attaatagta    180
atcaattacg gggtcattag ttcatagccc atatatggag ttccgcgtta cataacttac    240
ggtaaatggc ccgcctggct gaccgcccaa cgacccccgc ccattgacgt caataatgac    300
gtatgttccc atagtaacgc caatagggac tttccattga cgtcaatggg tggactattt    360
acggtaaact gcccacttgg cagtacatca agtgtatcat atgccaagta cgccccctat    420
tgacgtcaat gacggtaaat ggcccgcctg gcattatgcc cagtacatga ccttatggga    480
ctttcctact tggcagtaca tctacgtatt agtcatcgct attaccatgg tcgaggtgag    540
ccccacgttc tgcttcactc tccccatctc ccccccctcc ccacccccaa ttttgtattt    600
atttattttt taattatttt gtgcagcgat gggggcgggg ggggggggg ggcgcgcgcc    660 aggcggggcg gggcggggcg aggggcgggg cgggcgagg cggagaggtg cggcggcagc    720
caatcagagc ggcgcgctcc gaaagtttcc ttttatggcg aggcggcggc ggcggcggcc    780
ctataaaaag cgaagcgcgc ggcggcggg agtcgctgcg cgctgccttc gccccgtgcc    840
ccgctccgcc gccgcctcgc gccgcccgcc ccggctctga ctgaccgcgt tactcccaca    900
ggtgagcggg cgggacggcc cttctcctcc gggctgtaat tagcgcttgg tttaatgacg    960
gcttgtttct tttctgtggc tgcgtgaaag ccttgagggg ctccgggagc tagagcctct   1020
gctaaccatg ttcatgcctt cttctttttc ctacagctcc tgggcaacgt gctggttatt   1080
gtgctgtctc atcattttgg caaagaattc tagcggccgc caccatggtg attcttcagc   1140 aggggggacca tgtgtggatg gacctgagat tggggcagga gttcgacgtg cccatcgggg   1200
cggtggtgaa gctctgcgac tctgggcagg tccaggtggt ggatgatgaa gacaatgaac   1260
actggatctc tccgcagaac gcaacgcaca tcaagcctat gcaccccacg tcggtccacg   1320
gcgtggagga catgatccgc ctgggggacc tcaacgaggc gggcatcttg cgcaacctgc   1380
```

```
ttatccgcta ccgggaccac ctcatctaca cgtatacggg ctccatcctg gtggctgtga    1440
acccctacca gctgctctcc atctactcgc cagagcacat ccgccagtat accaacaaga    1500
agattgggga gatgccccc cacatctttg ccattgctga caactgctac ttcaacatga     1560
aacgcaacag ccgagaccag tgctgcatca tcagtgggga atctggggcc gggaagacgg    1620
agagcacaaa gctgatcctg cagttcctgg cagccatcag tgggcagcac tcgtggattg    1680
agcagcaggt cttggaggcc accccattc tggaagcatt tgggaatgcc aagaccatcc     1740
gcaatgacaa ctcaagccgt ttcggaaagt acatcgacat ccacttcaac aagcggggcg    1800
ccatcgaggg cgcgaagatt gagcagtacc tgctggaaaa gtcacgtgtc tgtcgccagg    1860
ccctggatga aggaactac cacgtgttct actgcatgct ggagggtatg agtgaggatc      1920
agaagaagaa gctgggcttg ggccaggcct ctgactacaa ctacttggcc atgggtaact    1980
gcataacctg tgagggccgg gtggacagcc aggagtacgc caacatccgc tccgccatga    2040
aggtgctcat gttcactgac accgagaact gggagatctc gaagctcctg gctgccatcc    2100
tgcacctggg caacctgcag tatgaggcac gcacatttga aaacctggat gcctgtgagg    2160
ttctcttctc cccatcgctg gccacagctg catccctgct tgaggtgaac cccccagacc    2220
tgatgagctg cctgactagc cgcacccctca tcaccgcgg ggagacggtg tccaccccac     2280
tgagcaggga acaggcactg gacgtgcgcg acgccttcgt aaaggggatc tacgggcggc    2340
tgttcgtgtg gattgtggac aagatcaacg cagcaattta caagcctccc tcccaggatg    2400
tgaagaactc tcgcaggtcc atcggcctcc tggacatctt tgggttgag aactttgctg      2460 tgaacagctt tgagcagctc tgcatcaact tcgccaatga gcacctgcag cagttctttg    2520
tgcggcacgt gttcaagctg gagcaggagg aatatgacct ggagagcatt gactggctgc    2580
acatcgagtt cactgacaac caggatgccc tggacatgat tgccaacaag cccatgaaca    2640
tcatctccct catcgatgag gagagcaagt tccccaaggg cacagacacc accatgttac    2700
acaagctgaa ctcccagcac aagctcaacg ccaactacat ccccccccaag aacaaccatg    2760 agacccagtt tggcatcaac cattttgcag gcatcgtcta ctatgagacc caaggcttcc    2820
tggagaagaa ccgagacacc ctgcatgggg acattatcca gctggtccac tcctccagga    2880
acaagttcat caagcagatc ttccaggccg atgtcgccat gggcgccgag accaggaagc    2940
gctcgcccac acttagcagc cagttcaagc ggtcactgga gctgctgatg cgcacgctgg    3000
gtgcctgcca gcccttcttt gtgcgatgca tcaagcccaa tgagttcaag aagcccatgc    3060
tgttcgaccg gcacctgtgc gtgcgccagc tgcggtactc aggaatgatg gagaccatcc    3120
gaatccgccg agctggctac cccatccgct acagcttcgt agagtttgtg gagcggtacc    3180
gtgtgctgct gccaggtgtg aagcggcct acaagcaggg cgacctccgc gggacttgcc      3240
agcgcatggc tgaggctgtg ctgggcaccc acgatgactg gcagataggc aaaaccaaga    3300
tctttctgaa ggaccaccat gacatgctgc tggaagtgga gcgggacaaa gccatcaccg    3360
acagagtcat cctccttcag aaagtcatcc ggggattcaa agacaggtct aactttctga    3420
agctgaagaa cgctgccaca ctgatccaga ggcactggcg gggtcacaac tgtaggaaga    3480
actacgggct gatgcgtctg ggcttcctgc ggctgcaggc cctgcaccgc tcccggaagc    3540
tgcaccagca gtaccgcctg gcccgccagc gcatcatcca gttccaggcc cgctgccgcg    3600
cctatctggt gcgcaaggcc ttccgccacc gcctctgggc tgtgctcacc gtgcaggcct    3660
atgcccgggg catgatcgcc cgcaggctgc accaacgcct cagggctgag gtaagtatca    3720
```

| | |
|---|---|
| aggttacaag acaggttaac ggagaccaat tgaaactggg cttgtcgaga cagagaagac | 3780 |
| tcttgcgttt cagcgctagc ccccgggtgc gcggcgtcgg tggtgccggc gggggcgcc | 3840 |
| aggtcgcagg cggtgtaggg ctccaggcag gcggcgaagg ccatgacgtg cgctatgaag | 3900 |
| gtctgctcct gcacgccgtg aaccaggtgc gcctgcgggc cgcgcgcgaa caccgccacg | 3960 |
| tcctcgcctg cgtgggtctc ttcgtccagg ggcactgcgc actgctgccg atactcgggg | 4020 |
| ctcccgctct cgctctcggt aacatccggc cgggcgccgt ccttgagcac atagcctgga | 4080 |
| ccgtttcgtc gactgttaat taagcatgct ggggagagat ctgtaacccc tagtgatgga | 4140 |
| gttggccact ccctctctgc gcgctcgctc gctcactgag gccgggcgac caaaggtcgc | 4200 |
| ccgacgcccg ggctttgccc gggcggcctc agtgagcgag cgagcgcgca gagagggag | 4259 |

<210> SEQ ID NO 35
<211> LENGTH: 4964
<212> TYPE: DNA
<213> ORGANISM: Artificial Sequence
<220> FEATURE:
<223> OTHER INFORMATION: Synthetic

<400> SEQUENCE: 35

| | |
|---|---|
| ctccctctct gcgcgctcgc tcgctcactg aggccgcccg gcaaagccc gggcgtcggg | 60 |
| cgacctttgg tcgcccggcc tcagtgagcg agcgagcgcg cagagaggga gtggccaact | 120 |
| ccatcactag gggttcagat ctggcgcgcc caattggctt cgaattctag cggccgcccc | 180 |
| cgggtgcgcg cgtcggtgg tgccggcggg gggcgccagg tcgcaggcgg tgtagggctc | 240 |
| caggcaggcg gcgaaggcca tgacgtgcgc tatgaaggtc tgctcctgca cgccgtgaac | 300 |
| caggtgcgcc tgcgggccgc gcgcgaacac cgccacgtcc tcgcctgcgt gggtctcttc | 360 |
| gtccaggggc actgcgcact gctgccgata ctcggggctc ccgctctcgc tctcggtaac | 420 |
| atccggccgg cgccgtcct tgagcacata gcctggaccg tttctcttaa gcgacgcatg | 480 |
| ctcgcgatag gcacctattg gtcttactga catccacttt gcctttctct ccacagtatc | 540 |
| tgtgcgcct cgaggctgag aaaatgcggc tggcggagga agagaagctt cggaaggaga | 600 |
| tgagcgccaa gaaggccaag gaggaggccg agcgcaagca tcaggagcgc ctggcccagc | 660 |
| tggctcgtga ggacgctgag cgggagctga aggagaagga ggccgctcgg cggaagaagg | 720 |
| agctcctgga gcagatggaa agggcccgcc atgagcctgt caatcactca gacatggtgg | 780 |
| acaagatgtt tggcttcctg ggacttcag gtggcctgcc aggccaggag ggccaggcac | 840 |
| ctagtggctt tgaggacctg gagcgagggc ggagggagat ggtggaggag gacctggatg | 900 |
| cagccctgcc cctgcctgac gaggatgagg aggacctctc tgagtataaa tttgccaagt | 960 |
| tcgcggccac ctacttccag gggacaacca cgcactccta cacccggcgg ccactcaaac | 1020 |
| agccactgct ctaccatgac gacgagggtg accagctggc agccctggcg gtctggatca | 1080 |
| ccatcctccg cttcatgggg gacctccctg agcccaagta ccacacagcc atgagtgatg | 1140 |
| gcagtgagaa gatccctgtg atgaccaaga tttatgagac cctgggcaag aagacgtaca | 1200 |
| agagggagct gcaggccctg cagggcgagg gcgaggccca gctccccgag ggccagaaga | 1260 |
| agagcagtgt gaggcacaag ctggtgcatt tgactctgaa aaagaagtcc aagctcacag | 1320 |
| aggaggtgac caagaggctg catgacgggg agtccacagt gcagggcaac agcatgctgg | 1380 |
| aggaccggcc cacctccaac ctggagaagc tgcacttcat catcggcaat ggcatcctgc | 1440 |
| ggccagcact ccgggacgag atctactgcc agatcagcaa gcagctgacc cacaaccccc | 1500 |
| ccaagagcag ctatgcccgg ggctggattc tcgtgtctct ctgcgtgggc tgtttcgccc | 1560 |

```
cctccgagaa gtttgtcaag tacctgcgga acttcatcca cggggcccg cccggctacg    1620 ccccgtactg tgaggagcgc ctgagaagga cctttgtcaa tgggacacgg acacagccgc    1680
ccagctggct ggagctgcag gccaccaagt ccaagaagcc aatcatgttg cccgtgacat    1740
tcatggatgg gaccaccaag accctgctga cggactcggc aaccacggcc aaggagctct    1800
gcaacgcgct ggccgacaag atctctctca aggaccggtt cgggttctcc ctctacattg    1860
ccctgtttga caaggtgtcc tccctgggca gcggcagtga ccacgtcatg gacgccatct    1920
cccagtgcga gcagtacgcc aaggagcagg gcgcccagga gcgcaacgcc cctggaggc    1980 tcttcttccg caaagaggtc ttcacgccct ggcacagccc ctccgaggac aacgtggcca    2040
ccaacctcat ctaccagcag gtggtgcgag gagtcaagtt tggggagtac aggtgtgaga    2100
aggaggacga cctggctgag ctggcctccc agcagtactt tgtagactat ggctctgaga    2160
tgatcctgga gcgcctcctg aacctcgtgc ccacctacat ccccgaccgc gagatcacgc    2220
ccctgaagac gctggagaag tgggcccagc tggccatcgc cgcccacaag aaggggattt    2280
atgcccagag gagaactgat gcccagaagg tcaaagagga tgtggtcagt tatgcccgct    2340
tcaagtggcc cttgctcttc tccaggtttt atgaagccta caaattctca ggccccagtc    2400
tccccaagaa cgacgtcatc gtggccgtca actggacggg tgtgtacttt gtggatgagc    2460
aggagcaggt acttctggag ctgtccttcc cagagatcat ggccgtgtcc agcagcaggg    2520
gagcgaaaac gacggccccc agcttcacgc tggccaccat caagggggac gaatacacct    2580
tcacctccag caatgctgag gacattcgtg acctggtggt caccttccta gagggggctcc    2640 ggaagagatc taagtatgtt gtggccctgc aggataaccc caaccccgca ggcgaggagt    2700
caggcttcct cagcttttgcc aagggagacc tcatcatcct ggaccatgac acgggcgagc    2760
aggtcatgaa ctcgggctgg gccaacggca tcaatgagag gaccaagcag cgtgggggact    2820 tccccaccga cagtgtgtac gtcatgccca ctgtcaccat gccaccgcgg gagattgtgg    2880
ccctggtcac catgactccc gatcagaggc aggacgttgt ccggctcttg cagctgcgaa    2940
cggcggagcc cgaggtgcgt gccaagccct acacgctgga ggagtttttcc tatgactact    3000 tcaggccccc acccaagcac acgctgagcc gtgtcatggt gtccaaggcc cgaggcaagg    3060
accggctgtg gagccacacg cgggaaccgc tcaagcaggc gctgctcaag aagctcctgg    3120
gcagtgagga gctctcgcag gaggcctgcc tggccttcat tgctgtgctc aagtacatgg    3180
gcgactaccc gtccaagagg acacgctccg tcaacgagct caccgaccag atctttgagg    3240
gtcccctgaa agccgagccc ctgaaggacg aggcatatgt gcagatcctg aagcagctga    3300
ccgacaacca catcaggtac agcgaggagc ggggttggga gctgctctgg ctgtgcacgg    3360
gccttttccc acccagcaac atcctcctgc ccacgtgca gcgcttcctg cagtcccgaa    3420
agcactgccc actcgccatc gactgcctgc aacggctcca gaaagccctg agaaacgggt    3480
cccggaagta ccctccgcac ctggtggagg tggaggccat ccagcacaag accacccaga    3540
ttttccacaa agtctacttc cctgatgaca ctgacgaggc cttcgaagtg gagtccagca    3600
ccaaggccaa ggacttctgc cagaacatcg ccaccaggct gctcctcaag tcctcagagg    3660
gattcagcct ctttgtcaaa attgcagaca aggtcatcag cgttcctgag aatgacttct    3720
tcttgacttt tgttcgacac ttgacagact ggataaagaa agctcggccc atcaaggacg    3780
gaattgtgcc ctcactcacc taccaggtgt tcttcatgaa gaagctgtgg accaccacgg    3840
tgccagggaa ggatcccatg gccgattcca tcttccacta ttaccaggag ttgcccaagt    3900
```

```
atctccgagg ctaccacaag tgcacgcggg aggaggtgct gcagctgggg gcgctgatct    3960
acagggtcaa gttcgaggag acaagtcct acttccccag catccccaag ctgctgcggg     4020
agctggtgcc ccaggacctt atccggcagg tctcacctga tgactggaag cggtccatcg    4080
tcgcctactt caacaagcac gcagggaagt ccaaggagga ggccaagctg gccttcctga    4140
agctcatctt caagtggccc acctttggct cagccttctt cgaggtgaag caaactacgg    4200
agccaaactt ccctgagatc ctcctaattg ccatcaacaa gtatgggctc agcctcatcg    4260
atcccaaaac gaaggatatc ctcaccactc atcccttcac caagatctcc aactggagca    4320
gcggcaacac ctacttccac atcaccattg gaacttggt gcgcgggagc aaactgctct    4380
gcgagacgtc actgggctac aagatggatg acctcctgac ttcctacatt agccagatgc    4440
tcacagccat gagcaaacag cggggctcca ggagcggcaa gtaccttac gatgtaccgg    4500
attacgcatg aggtaccaag ggcgaattct gcagtcgact agagctcgct gatcagcctc    4560
gactgtgcct tctagttgcc agccatctgt tgtttgcccc tcccccgtgc cttccttgac    4620
cctggaaggt gccactccca ctgtcctttc ctaataaaat gaggaaattg catcgcattg    4680
tctgagtagg tgtcattcta ttctgggggg tggggtgggg caggacagca agggggagga    4740
ttgggaagac aatagcaggc atgctgggga gagatctgga ggactagtcc gtcgactgtt    4800
aattaagcat gctggggaga gatctaggaa acccctagtg atggagttgg ccactccctc    4860
tctgcgcgct cgctcgctca ctgaggccgg gcgaccaaag gtcgcccgac gcccgggctt    4920
tgcccgggcg gcctcagtga gcgagcgagc gcgcagagag ggag                    4964
```

<210> SEQ ID NO 36
<211> LENGTH: 3949
<212> TYPE: DNA
<213> ORGANISM: Artificial Sequence
<220> FEATURE:
<223> OTHER INFORMATION: Synthetic

<400> SEQUENCE: 36

```
ctccctctct gcgcgctcgc tcgctcactg aggccgcccg ggcaaagccc gggcgtcggg      60
cgacctttgg tcgcccggcc tcagtgagcg agcgagcgcg cagagaggga gtggccaact    120
ccatcactag gggttctcag atctggcgcg cccaattcgg taccctagtt attaatagta    180
atcaattacg gggtcattag ttcatagccc atatatggag ttccgcgtta cataacttac    240
ggtaaatggc ccgcctggct gaccgcccaa cgacccccgc ccattgacgt caataatgac    300
gtatgttccc atagtaacgc caatagggac tttccattga cgtcaatggg tggactattt    360
acggtaaact gcccacttgg cagtacatca agtgtatcat atgccaagta cgccccctat    420
tgacgtcaat gacggtaaat ggcccgcctg gcattatgcc cagtacatga ccttatggga    480
ctttcctact tggcagtaca tctacgtatt agtcatcgct attaccatgg tcgaggtgag    540
ccccacgttc tgcttcactc tccccatctc ccccccctcc ccacccccaa ttttgtattt    600
atttattttt taattatttt gtgcagcgat ggggcgggg ggggggggg ggcgcgcgcc      660
aggcggggcg gggcggggcg aggggcgggg cggggcgagg cggagaggtg cggcggcagc    720
caatcagagc ggcgcgctcc gaaagtttcc ttttatggcg aggcggcggc ggcggcggcc    780
ctataaaaag cgaagcgcgc ggcgggcggg agtcgctgcg cgctgccttc gccccgtgcc    840
ccgctccgcc gccgcctcgc gccgcccgcc ccggctctga ctgaccgcgt tactcccaca    900
ggtgagcggg cgggacggcc cttctcctcc gggctgtaat tagcgcttgg tttaatgacg    960
gcttgttttct tttctgtggc tgcgtgaaag ccttgagggg ctccgggagc tagagcctct   1020
```

-continued

```
gctaaccatg ttcatgcctt cttcttttc ctacagctcc tgggcaacgt gctggttatt     1080
gtgctgtctc atcattttgg caaagaattc tagcggccgc caccatggtg attcttcagc     1140
aggggggacca tgtgtggatg gacctgagat tggggcagga gttcgacgtg cccatcgggg    1200
cggtggtgaa gctctgcgac tctgggcagg tccaggtggt ggatgatgaa gacaatgaac    1260
actggatctc tccgcagaac gcaacgcaca tcaagcctat gcaccccacg tcggtccacg    1320
gcgtggagga catgatccgc ctgggggacc tcaacgaggc gggcatcttg cgcaacctgc    1380
ttatccgcta ccgggaccac ctcatctaca cgtatacggg ctccatcctg gtggctgtga    1440
accctacca gctgctctcc atctactcgc cagagcacat ccgccagtat accaacaaga    1500
agattgggga gatgcccccc cacatctttg ccattgctga caactgctac ttcaacatga    1560
aacgcaacag ccgagaccag tgctgcatca tcagtgggga atctgggccc gggaagacgg    1620
agagcacaaa gctgatcctg cagttcctgg cagccatcag tgggcagcac tcgtggattg    1680
agcagcaggt cttggaggcc accccattc tggaagcatt tgggaatgcc aagaccatcc    1740
gcaatgacaa ctcaagccgt ttcggaaagt acatcgacat ccacttcaac aagcggggcg    1800
ccatcgaggc gcgcaagatt gagcagtacc tgctggaaaa gtcacgtgtc tgtcgccagg    1860
ccctggatga aaggaactac cacgtgttct actgcatgct ggagggtatg agtgaggatc    1920
agaagaagaa gctgggcttg gccaggcct ctgactacaa ctacttggcc atgggtaact    1980
gcataacctg tgagggccgg gtggacagcc aggagtacgc caacatccgc tccgccatga    2040
aggtgctcat gttcactgac accgagaact gggagatctc gaagctcctg gctgccatcc    2100
tgcacctggg caacctgcag tatgaggcac gcacatttga aaacctggat gcctgtgagg    2160
ttctcttctc cccatcgctg gccacagctg catccctgct tgaggtgaac cccccagacc    2220
tgatgagctg cctgactagc cgcaccctca tcacccgcgg ggagacggtg tccacccccac    2280
tgagcaggga acaggcactg gacgtgcgcg acgccttcgt aaaggggatc tacgggcggc    2340
tgttcgtgtg gattgtggac aagatcaacg cagcaattta caagcctccc tcccaggatg    2400
tgaagaactc tcgcaggtcc atcggcctcc tggacatctt tgggttttgag aactttgctg    2460
tgaacagctt tgagcagctc tgcatcaact tcgccaatga gcacctgcag cagttcttg    2520
tgcggcacgt gttcaagctg gagcaggagg aatatgacct ggagagcatt gactggctgc    2580
acatcgagtt cactgacaac caggatgccc tggacatgat tgccaacaag cccatgaaca    2640
tcatctccct catcgatgag gagagcaagt tccccaaggg cacagacacc accatgttac    2700
acaagctgaa ctcccagcac aagctcaacg ccaactacat ccccccccaag aacaaccatg    2760
agacccagtt tggcatcaac cattttgcag gcatcgtcta ctatgagacc caaggcttcc    2820
tggagaagaa ccgagacacc ctgcatgggg acattatcca gctggtccac tcctccagga    2880
acaagttcat caagcagatc ttccaggccg atgtcgccat gggcgccgag accaggaagc    2940
gctcgcccac acttagcagc cagttcaagc ggtcactgga gctgctgatg cgcacgctgg    3000
gtgcctgcca gcccttcttt gtgcgatgca tcaagcccaa tgagttcaag aagcccatgc    3060
tgttcgaccg gcacctgtgc gtgcgccagc tgcggtactc aggaatgatg gagaccatcc    3120
gaatccgccg agctggctac cccatccgct acagcttcgt agagtttgtg gagcggtacc    3180
gtgtgctgct gccaggtgtg aagccggcct acaagcaggg cgacctccgc gggacttgcc    3240
agcgcatggc tgaggctgtg ctgggcaccc acgatgactg gcagataggc aaaaccaaga    3300
tctttctgaa ggaccaccat gacatgctgc tggaagtgga gcgggacaaa gccatcaccg    3360
```

| | |
|---|---|
| acagagtcat cctccttcag aaagtcatcc ggggattcaa agacaggtct aactttctga | 3420 |
| agctgaagaa cgctgccaca ctgatccaga ggcactggcg gggtcacaac tgtaggaaga | 3480 |
| actacgggct gatgcgtctg ggcttcctgc ggctgcaggc cctgcaccgc tcccggaagc | 3540 |
| tgcaccagca gtaccgcctg gcccgccagc gcatcatcca gttccaggcc cgctgccgcg | 3600 |
| cctatctggt gcgcaaggcc ttccgccacc gcctctgggc tgtgctcacc gtgcaggcct | 3660 |
| atgcccgggg catgatcgcc cgcaggctgc accaacgcct cagggctgag tatctgtggc | 3720 |
| gcctcgaggc tgagaaaatg cggctggcgg aggaagagaa gcttagagga tcctcccgtc | 3780 |
| gactgtttaa gcatgctggg gagagatctg aggaaacccc tagtgatgga gttggccact | 3840 |
| ccctctctgc gcgctcgctc gctcactgag gccgggcgac caaaggtcgc ccgacgcccg | 3900 |
| ggctttgccc gggcggcctc agtgagcgag cgagcgcgca gagagggag | 3949 |

<210> SEQ ID NO 37
<211> LENGTH: 3960
<212> TYPE: DNA
<213> ORGANISM: Artificial Sequence
<220> FEATURE:
<223> OTHER INFORMATION: Synthetic

<400> SEQUENCE: 37

| | |
|---|---|
| ctccctctct gcgcgctcgc tcgctcactg aggccgcccg ggcaaagccc gggcgtcggg | 60 |
| cgacctttgg tcgcccggcc tcagtgagcg agcgagcgcg cagagaggga gtggccaact | 120 |
| ccatcactag gggttctcag atctggcgcg cccaattcgg taccctagtt attaatagta | 180 |
| atcaattacg gggtcattag ttcatagccc atatatggag ttccgcgtta cataacttac | 240 |
| ggtaaatggc ccgcctggct gaccgcccaa cgacccccgc ccattgacgt caataatgac | 300 |
| gtatgttccc atagtaacgc caatagggac tttccattga cgtcaatggg tggactattt | 360 |
| acggtaaact gcccacttgg cagtacatca agtgtatcat atgccaagta cgccccctat | 420 |
| tgacgtcaat gacggtaaat ggcccgcctg gcattatgcc cagtacatga ccttatggga | 480 |
| ctttcctact tggcagtaca tctacgtatt agtcatcgct attaccatgg tcgaggtgag | 540 |
| ccccacgttc tgcttcactc tccccatctc ccccccctcc caccccccaa ttttgtattt | 600 |
| atttattttt taattatttt gtgcagcgat gggggcgggg ggggggggcg ggcgcgcgcc | 660 |
| aggcggggcg gggcggggcg aggggcgggg cgggcgagg cggagaggtg cggcggcagc | 720 |
| caatcagagc ggcgcgctcc gaaagtttcc ttttatggcg aggcggcggc ggcggcggcc | 780 |
| ctataaaaag cgaagcgcgc ggcgggcggg agtcgctgcg cgctgccttc gccccgtgcc | 840 |
| ccgctccgcc gccgcctcgc gccgcccgcc ccggctctga ctgaccgcgt tactcccaca | 900 |
| ggtgagcggg cgggacggcc cttctcctcc gggctgtaat tagcgcttgg tttaatgacg | 960 |
| gcttgtttct tttctgtggc tgcgtgaaag ccttgagggg ctccgggagc tagagcctct | 1020 |
| gctaaccatg ttcatgcctt cttcttttc ctacagctcc tgggcaacgt gctggttatt | 1080 |
| gtgctgtctc atcattttgg caaagaattc tagcggccgc caccatggtg attcttcagc | 1140 |
| agggggacca tgtgtggatg gacctgagat tggggcagga gttcgacgtg cccatcgggg | 1200 |
| cggtggtgaa gctctgcgac tctgggcagg tccaggtggt ggatgatgaa gacaatgaac | 1260 |
| actggatctc tccgcagaac gcaacgcaca tcaagcctat gcaccccacg tcggtccacg | 1320 |
| gcgtggagga catgatccgc ctgggggacc tcaacgaggc gggcatcttg cgcaacctgc | 1380 |
| ttatccgcta ccgggaccac ctcatctaca cgtatacggg ctccatcctg gtggctgtga | 1440 |
| accccctacca gctgctctcc atctactcgc cagagcacat ccgccagtat accaacaaga | 1500 |

```
agattgggga gatgcccccc cacatctttg ccattgctga caactgctac ttcaacatga  1560
aacgcaacag ccgagaccag tgctgcatca tcagtgggga atctgggcc gggaagacgg    1620
agagcacaaa gctgatcctg cagttcctgg cagccatcag tgggcagcac tcgtggattg   1680
agcagcaggt cttggaggcc acccccattc tggaagcatt tgggaatgcc aagaccatcc   1740
gcaatgacaa ctcaagccgt ttcggaaagt acatcgacat ccacttcaac aagcggggcg   1800
ccatcgaggg cgcgaagatt gagcagtacc tgctggaaaa gtcacgtgtc tgtcgccagg   1860
ccctggatga aaggaactac cacgtgttct actgcatgct ggagggtatg agtgaggatc   1920
agaagaagaa gctgggcttg ggccaggcct ctgactacaa ctacttggcc atgggtaact   1980
gcataacctg tgagggccgg gtggacagcc aggagtacgc caacatccgc tccgccatga   2040
aggtgctcat gttcactgac accgagaact gggagatctc gaagctcctg gctgccatcc   2100
tgcacctggg caacctgcag tatgaggcac gcacatttga aaacctggat gcctgtgagg   2160
ttctcttctc cccatcgctg gccacagctg catccctgct tgaggtgaac ccccagacc    2220
tgatgagctg cctgactagc cgcacccctca tcacccgcgg ggagacggtg tccacccac   2280
tgagcaggga acaggcactg gacgtgcgcg acgccttcgt aaagggatc tacgggcggc    2340
tgttcgtgtg gattgtggac aagatcaacg cagcaattta caagcctccc tcccaggatg   2400
tgaagaactc tcgcaggtcc atcggcctcc tggacatctt tgggtttgag aactttgctg   2460
tgaacagctt tgagcagctc tgcatcaact tcgccaatga gcacctgcag cagttctttg   2520
tgcggcacgt gttcaagctg gagcaggagg aatatgacct ggagagcatt gactggctgc   2580
acatcgagtt cactgacaac caggatgccc tggacatgat tgccaacaag cccatgaaca   2640
tcatctccct catcgatgag gagagcaagt tccccaaggg cacagacacc accatgttac   2700
acaagctgaa ctcccagcac aagctcaacg ccaactacat ccccccccaag aacaaccatg   2760
agacccagtt tggcatcaac cattttgcag gcatcgtcta ctatgagacc caaggcttcc   2820
tggagaagaa ccgagacacc ctgcatgggg acattatcca gctggtccac tcctccagga   2880
acaagttcat caagcagatc ttccaggccg atgtcgccat gggcgccgag accaggaagc   2940
gctcgcccac acttagcagc cagttcaagc ggtcactgga gctgctgatg cgcacgctgg   3000
gtgcctgcca gcccttcttt gtgcgatgca tcaagcccaa tgagttcaag aagcccatgc   3060
tgttcgaccg gcacctgtgc gtgcgccagc tgcggtactc aggaatgatg gagaccatcc   3120
gaatccgccg agctggctac cccatccgct acagcttcgt agagtttgtg gagcggtacc   3180
gtgtgctgct gccaggtgtg aagccggcct acaagcaggg cgacctccgc gggacttgcc   3240
agcgcatggc tgaggctgtg ctgggcaccc acgatgactg gcagataggc aaaaccaaga   3300
tctttctgaa ggaccaccat gacatgctgc tggaagtgga gcgggacaaa gccatcaccg   3360
acagagtcat cctccttcag aaagtcatcc ggggattcaa agacaggtct aactttctga   3420
agctgaagaa cgctgccaca ctgatccaga ggcactggcg gggtcacaac tgtaggaaga   3480
actacgggct gatgcgtctg ggcttcctgc ggctgcaggc cctgcaccgc tcccggaagc   3540
tgcaccagca gtaccgcctg gcccgccagc gcatcatcca gttccaggcc cgctgccgcg   3600
cctatctggt gcgcaaggcc ttccgccacc gcctctgggc tgtgctcacc gtgcaggcct   3660
atgcccgggg catgatcgcc cgcaggctgc accaacgcct cagggctgag tatctgtggc   3720
gcctcgaggc tgaaaaatg cggctggcgg aggaagagaa gctttgaaag tgacattagg   3780
ctcccgtcga ctgttaatta agcatgctgg ggagagatct gaggaaaccc ctagtgatgg   3840
```

| | |
|---|---|
| agttggccac tccctctctg cgcgctcgct cgctcactga ggccgggcga ccaaaggtcg | 3900 |
| cccgacgccc gggctttgcc cgggcggcct cagtgagcga gcgagcgcgc agagagggag | 3960 |

<210> SEQ ID NO 38
<211> LENGTH: 4793
<212> TYPE: DNA
<213> ORGANISM: Artificial Sequence
<220> FEATURE:
<223> OTHER INFORMATION: Synthetic

<400> SEQUENCE: 38

| | |
|---|---|
| ctccctctct gcgcgctcgc tcgctcactg aggccgcccg gcaaagccc gggcgtcggg | 60 |
| cgacctttgg tcgcccggcc tcagtgagcg agcgagcgcg cagagaggga gtggccaact | 120 |
| ccatcactag gggttcagat ctggcgcgcc ggatccgggc tgatgcgtct gggcttcctg | 180 |
| cggctgcagg ccctgcaccg ctcccggaag ctgcaccagc agtaccgcct ggcccgccag | 240 |
| cgcatcatcc agttccaggc ccgctgccgc gcctatctgg tgcgcaaggc cttccgccac | 300 |
| cgcctctggg ctgtgctcac cgtgcaggcc tatgcccggg gcatgatcgc ccgcaggctg | 360 |
| caccaacgcc tcagggctga gtatctgtgg cgcctcgagg ctgagaaaat gcggctggcg | 420 |
| gaggaagaga agcttcggaa ggagatgagc gccaagaagg ccaaggagga ggccgagcgc | 480 |
| aagcatcagg agcgcctggc ccagctggct cgtgaggacg ctgagcggga gctgaaggag | 540 |
| aaggaggccg ctcggcggaa gaaggagctc ctggagcaga tggaaagggc cgccatgag | 600 |
| cctgtcaatc actcagacat ggtggacaag atgtttggct tcctggggac ttcaggtggc | 660 |
| ctgccaggcc aggagggcca ggcacctagt ggctttgagg acctggagcg agggcggagg | 720 |
| gagatggtgg aggaggacct ggatgcagcc ctgccctgc ctgacgagga tgaggaggac | 780 |
| ctctctgagt ataaatttgc caagttcgcg gccacctact ccaggggac aaccacgcac | 840 |
| tcctacaccc ggcggccact caaacagcca ctgctctacc atgacgacga gggtgaccag | 900 |
| ctggcagccc tggcggtctg gatcaccatc ctccgcttca tgggggacct ccctgagccc | 960 |
| aagtaccaca cagccatgag tgatggcagt gagaagatcc ctgtgatgac caagatttat | 1020 |
| gagaccctgg gcaagaagac gtacaagagg gagctgcagg ccctgcaggg cgagggcgag | 1080 |
| gcccagctcc ccgagggcca agaagagagc agtgtgaggc acaagctggt gcatttgact | 1140 |
| ctgaaaaaga gtccaagct cacagaggag gtgaccaaga gctgcatga cggggagtcc | 1200 |
| acagtgcagg gcaacagcat gctggaggac cggcccacct ccaacctgga gaagctgcac | 1260 |
| ttcatcatcg gcaatggcat cctgcggcca gcactccggg acgagatcta ctgccagatc | 1320 |
| agcaagcagc tgacccacaa ccctccaag agcagctatg cccggggctg gattctcgtg | 1380 |
| tctctctgcg tgggctgttt cgccccctcc gagaagtttg tcaagtacct gcggaacttc | 1440 |
| atccacgggg gcccgcccgg ctacgccccg tactgtgagg agcgcctgag aaggaccttt | 1500 |
| gtcaatggga cacggacaca gccgcccagc tggctggagc tgcaggccac caagtccaag | 1560 |
| aagccaatca tgttgcccgt gacattcatg gatgggacca ccaagaccct gctgacggac | 1620 |
| tcggcaacca cggccaagga gctctgcaac gcgctggccg acaagatctc tctcaaggac | 1680 |
| cggttcgggt tctccctcta cattgccctg tttgacaagg tgtcctccct gggcagcggc | 1740 |
| agtgaccacg tcatggacgc catctcccag tgcgagcagt acgccaagga gcagggcgcc | 1800 |
| caggagcgca acgcccctg gaggctcttc ttccgcaaag aggtcttcac gccctggcac | 1860 |
| agccctccg aggacaacgt ggccaccaac ctcatctacc agcaggtggt gcgaggagtc | 1920 |
| aagtttgggg agtacaggtg tgagaaggag gacgacctgg ctgagctggc ctcccagcag | 1980 |

```
tactttgtag actatggctc tgagatgatc ctggagcgcc tcctgaacct cgtgcccacc    2040
tacatccccg accgcgagat cacgcccctg aagacgctgg agaagtgggc ccagctggcc    2100
atcgccgccc acaagaaggg gatttatgcc cagaggagaa ctgatgccca gaaggtcaaa    2160
gaggatgtgg tcagttatgc ccgcttcaag tggcccttgc tcttctccag gttttatgaa    2220
gcctacaaat tctcaggccc cagtctcccc aagaacgacg tcatcgtggc cgtcaactgg    2280
acgggtgtgt actttgtgga tgagcaggag caggtacttc tggagctgtc cttcccagag    2340
atcatggccg tgtccagcag caggggagcg aaaacgacgg cccccagctt cacgctggcc    2400
accatcaagg gggacgaata caccttcacc tccagcaatg ctgaggacat cgtgacctg     2460
gtggtcacct tcctagaggg gctccggaag agatctaagt atgttgtggc cctgcaggat    2520
aaccccaacc ccgcaggcga ggagtcaggc ttcctcagct tgccaagggg agacctcatc    2580
atcctggacc atgacacggg cgagcaggtc atgaactcgg gctgggccaa cggcatcaat    2640
gagaggacca agcagcgtgg ggacttcccc accgacagtg tgtacgtcat gcccactgtc    2700
accatgccac cgcgggagat tgtggccctg gtcaccatga ctcccgatca gaggcaggac    2760
gttgtccggc tcttgcagct gcgaacggcg gagcccgagg tgcgtgccaa gcccctacacg   2820
ctggaggagt tttcctatga ctacttcagg cccccaccca agcacacgct gagccgtgtc    2880
atggtgtcca aggcccgagg caaggaccgg ctgtggagcc acacgcggga accgctcaag    2940
caggcgctgc tcaagaagct cctgggcagt gaggagctct cgcaggaggc ctgcctggcc    3000
ttcattgctg tgctcaagta catgggcgac tacccgtcca agaggacacg ctccgtcaac    3060
gagctcaccg accagatctt tgagggtccc ctgaaagccg agccctgaa ggacgaggca     3120
tatgtgcaga tcctgaagca gctgaccgac aaccacatca ggtacagcga ggagcggggt    3180
tgggagctgc tctggctgtg cacgggcctt ttcccaccca gcaacatcct cctgcccac     3240
gtgcagcgct tcctgcagtc ccgaaagcac tgcccactcg ccatcgactg cctgcaacgg    3300
ctccagaaag ccctgagaaa cgggtcccgg aagtaccctc cgcacctggt ggaggtggag    3360
gccatccagc acaagaccac ccagatttc cacaaagtct acttccctga tgacactgac     3420
gaggccttcg aagtggagtc cagcaccaag gccaaggact tctgcagaa catcgccacc     3480
aggctgctcc tcaagtcctc agagggattc agcctcttg tcaaaattgc agacaaggtc    3540
atcagcgttc tgagaatga cttcttcttt gactttgttc gacacttgac agactggata    3600
aagaaagctc ggcccatcaa ggacggaatt gtgccctcac tcacctacca ggtgttcttc    3660
atgaagaagc tgtggaccac cacggtgcca ggaaggatc ccatggccga ttccatcttc     3720
cactattacc aggagttgcc caagtatctc cgaggctacc acaagtgcac gcgggaggag    3780
gtgctgcagc tgggggcgct gatctacagg gtcaagttcg aggaggacaa gtcctacttc    3840
cccagcatcc ccaagctgct gcgggagctg tgccccagg accttatccg gcaggtctca    3900
cctgatgact ggaagcggtc catcgtcgcc tacttcaaca gcacgcagg gaagtccaag    3960
gaggaggcca agctggcctt cctgaagctc atcttcaagt ggcccacctt tggctcagcc    4020
ttcttcgagg tgaagcaaac tacggagcca acttccctg agatcctcct aattgccatc    4080
aacaagtatg gggtcagcct catcgatccc aaaacgaagg atatcctcac cactcatccc    4140
ttcaccaaga tctccaactg gagcagcggc aacacctact ccacatcac cattgggaac    4200
ttggtgcgcg ggagcaaact gctctgcgag acgtcactgg gctacaagat ggatgacctc    4260
ctgacttcct acattagcca gatgctcaca gccatgagca aacagcgggg ctccaggagc    4320
```

```
ggcaagtacc cttacgatgt accggattac gcatgaggta ccaagggcga attctgcagt    4380
cgactagagc tcgctgatca gcctcgactg tgccttctag ttgccagcca tctgttgttt    4440
gcccctcccc cgtgccttcc ttgaccctgg aaggtgccac tcccactgtc ctttcctaat    4500
aaaatgagga aattgcatcg cattgtctga gtaggtgtca ttctattctg gggggtgggg    4560
tggggcagga cagcaagggg gaggattggg aagacaatag caggcatgct ggggagagat    4620
ctgaggatcc ttaattaagc atgctgggga gagatctgaa cccctagtga tggagttggc    4680
cactccctct ctgcgcgctc gctcgctcac tgaggccggg cgaccaaagg tcgcccgacg    4740
cccgggcttt gcccgggcgg cctcagtgag cgagcgagcg cgcagagagg gag           4793

<210> SEQ ID NO 39
<211> LENGTH: 361
<212> TYPE: DNA
<213> ORGANISM: Artificial Sequence
<220> FEATURE:
<223> OTHER INFORMATION: Synthetic

<400> SEQUENCE: 39
caggtctaac tttctgaagc tgaagaacgc tgccacactg atccagaggc actggcgggg    60
tcacaactgt aggaagaact acgggctgat gcgtctgggc ttcctgcggc tgcaggccct   120
gcaccgctcc cggaagctgc accagcagta ccgcctggcc cgccagcgca tcatccagtt   180
ccaggcccgc tgccgcgcct atctggtgcg caaggccttc cgccaccgcc tctgggctgt   240
gctcaccgtg caggcctatg cccggggcat gatcgcccgc aggctgcacc aacgcctcag   300
ggctgagtat ctgtggcgcc tcgaggctga aaaatgcggc tggcggagg aagagaagct    360 t                                                                  361

<210> SEQ ID NO 40
<211> LENGTH: 111
<212> TYPE: DNA
<213> ORGANISM: Artificial Sequence
<220> FEATURE:
<223> OTHER INFORMATION: Synthetic

<400> SEQUENCE: 40
caacgcctca gggctgaggt aagtatcaag gttacaagac aggtttaagg agaccaatag    60
aaactgggct tgtcgagaca gagaagactc ttgcgtttct gagctagccc c             111

<210> SEQ ID NO 41
<211> LENGTH: 111
<212> TYPE: DNA
<213> ORGANISM: Artificial Sequence
<220> FEATURE:
<223> OTHER INFORMATION: Synthetic

<400> SEQUENCE: 41
caacgcctca gggctgaggt aagtatcaag gttacaagac aggttaacgg agaccaattg    60
aaactgggct tgtcgagaca gagaagactc ttgcgtttca gcgctagccc c             111

<210> SEQ ID NO 42
<211> LENGTH: 78
<212> TYPE: DNA
<213> ORGANISM: Artificial Sequence
<220> FEATURE:
<223> OTHER INFORMATION: Synthetic

<400> SEQUENCE: 42
ccgcaggctg caccaacgcc tcagggctga ggtaagtatc aaggttacaa gacaggttaa    60
```
cggagaccaa ttgaaact                                                          78

<210> SEQ ID NO 43
<211> LENGTH: 79
<212> TYPE: DNA
<213> ORGANISM: Artificial Sequence
<220> FEATURE:
<223> OTHER INFORMATION: Synthetic

<400> SEQUENCE: 43
aacggagacc aattgaaact gggcttgtcg agacagagaa gactcttgcg tttcagcgct     60
agcccccggg tgcgcggcg                                                         79

<210> SEQ ID NO 44
<211> LENGTH: 4845
<212> TYPE: DNA
<213> ORGANISM: Artificial Sequence
<220> FEATURE:
<223> OTHER INFORMATION: Synthetic

<400> SEQUENCE: 44
ctccctctct gcgcgctcgc tcgctcactg aggccgcccg ggcaaagccc gggcgtcggg     60
cgacctttgg tcgcccggcc tcagtgagcg agcgagcgcg cagagaggga gtggccaact    120
ccatcactag gggttctcag atctggcgcg ccccccgggt gcgcggcgtc ggtggtgccg    180
gcggggggcg ccaggtcgca ggcggtgtag ggctccaggc aggcggcgaa ggccatgacg    240
tgcgctatga aggtctgctc ctgcacgccg tgaaccaggt gcgcctgcgg gccgcgcgcg    300
aacaccgcca cgtcctcgcc tgcgtgggtc tcttcgtcca ggggcactgc gcactgctgc    360
cgatactcgg ggctcccgct ctcgctctcg gtaacatccg gccgggcgcc gtccttgagc    420
acatagcctg gaccgtttct cttaagcgac gcatgctcgc gataggcacc tattggtctt    480
actgacatcc actttgcctt tctctccaca gtatctgtgg cgcctcgagg ctgagaaaat    540
gcggctggcg gaggaagaga agcttcggaa ggagatgagc gccaagaagg ccaaggagga    600
ggccgagcgc aagcatcagg agcgcctggc ccagctggct cgtgaggacg ctgagcggga    660
gctgaaggag aaggaggccg ctcggcgaa gaaggagctc ctggagcaga tggaaagggc    720
ccgccatgag cctgtcaatc actcagacat ggtggacaag atgtttggct tcctggggac    780
ttcaggtggc ctgccaggcc aggagggcca ggcacctagt ggctttgagg acctggagcg    840
agggcggagg gagatggtgg aggaggacct ggatgcagcc ctgccctgc ctgacgagga    900 tgaggaggac ctctctgagt ataaatttgc caagttcgcg ccacctacct ccagggac    960 aaccacgcac tcctacaccc ggcggccact caaacagcca ctgctctacc atgacgacga   1020
gggtgaccag ctggcagccc tggcggtctg gatcaccatc ctccgcttca tgggggacct   1080
ccctgagccc aagtaccaca gccatgagtg atggcagt gagaagatcc ctgtgatgac   1140
caagatttat gagaccctgg gcaagaagac gtacaagagg gagctgcagg ccctgcaggg   1200
cgagggcgag gccagctcc ccgagggcca aagaagagc agtgtgaggc acaagctggt   1260
gcatttgact ctgaaaaaga agtccaagct cacagaggag gtgaccaaga ggctgcatga   1320
cggggagtcc acagtgcagg gcaacagcat gctggaggac cggcccacct ccaacctgga   1380
gaagctgcac ttcatcatcg gcaatggcat cctgcggcca gcactccggg acgagatcta   1440
ctgccagatc agcaagcagc tgaccccaca ccctccaag agcagctatg cccggggctg   1500
gattctcgtg tctctctgcg tgggctgttt cgccccctcc gagaagtttg tcaagtacct   1560

-continued

```
gcggaacttc atccacgggg gcccgcccgg ctacgccccg tactgtgagg agcgcctgag    1620
aaggaccttt gtcaatggga cacggacaca gccgcccagc tggctggagc tgcaggccac    1680
caagtccaag aagccaatca tgttgcccgt gacattcatg gatgggacca ccaagaccct    1740
gctgacggac tcggcaacca cggccaagga gctctgcaac gcgctggccg acaagatctc    1800
tctcaaggac cggttcgggt tctccctcta cattgccctg tttgacaagg tgtcctccct    1860
gggcagcgga agtgaccacg tcatggacgc catctcccag tgcgagcagt acgccaagga    1920
gcagggcgcc caggagcgca cgcccctg gaggctcttc ttccgcaaag aggtcttcac    1980
gccctggcac agcccctccg aggacaacgt ggccaccaac ctcatctacc agcaggtggt    2040
gcgaggagtc aagtttgggg agtacaggtg tgagaaggag gacgacctgg ctgagctggc    2100
ctcccagcag tactttgtag actatggctc tgagatgatc ctggagcgcc tcctgaacct    2160
cgtgcccacc tacatccccg accgcgagat cacgcccctg aagacgctgg agaagtgggc    2220
ccagctggcc atcgccgccc acaagaaggg gatttatgcc cagaggagaa ctgatgccca    2280
gaaggtcaaa gaggatgtgg tcagttatgc ccgcttcaag tggcccttgc tcttctccag    2340
gttttatgaa gcctacaaat ctctcaggcc cagtctcccc aagaacgacg tcatcgtggc    2400
cgtcaactgg acgggtgtgt actttgtgga tgagcaggag caggtacttc tggagctgtc    2460
cttcccagag atcatggccg tgtccagcag caggggagcg aaaacgacgg cccccagctt    2520
cacgctggcc accatcaagg gggacgaata caccttcacc tccagcaatg ctgaggacat    2580
tcgtgacctg gtggtcacct tcctagaggg gctccggaag agatctaagt atgttgtggc    2640
cctgcaggat aaccccaacc ccgcaggcga ggagtcaggc ttcctcagct ttgccaaggg    2700
agacctcatc atcctggacc atgacacggg cgagcaggtc atgaactcgg gctgggccaa    2760
cggcatcaat gagaggacca agcagcgtgg ggacttcccc accgacagtg tgtacgtcat    2820
gcccactgtc accatgccac cgcgggagat tgtggccctg tcaccatga ctcccgatca    2880 gaggcaggac gttgtccggc tcttgcagct gcgaacggcg gagcccgagg tgcgtgccaa    2940
gccctacacg ctggaggagt tttcctatga ctacttcagg cccccaccca gcacacgct    3000 gagccgtgtc atggtgtcca aggcccgagg caaggaccgg ctgtggagcc acacgcggga    3060
accgctcaag caggcgctgc tcaagaagct cctgggcagt gaggagctct cgcaggaggc    3120
ctgcctggcc ttcattgctg tgctcaagta catgggcgac tacccgtcca agaggacacg    3180
ctccgtcaac gagctcaccg accagatctt tgagggtccc ctgaaagccg agcccctgaa    3240
ggacgaggca tatgtgcaga tcctgaagca gctgaccgac aaccacatca ggtacagcga    3300
ggagcggggt tgggagctgc tctggctgtg cacgggcctt ttcccaccca gcaacatcct    3360
cctgccccac gtgcagcgct tcctgcagtc ccgaaagcac tgcccactcg ccatcgactg    3420
cctgcaacgg ctccagaaag ccctgagaaa cgggtcccgg aagtaccctc cgcacctggt    3480
ggaggtggag gccatccagc acaagaccac ccagatttc cacaaagtct acttccctga    3540
tgacactgac gaggccttcg aagtggagtc cagcaccaag gccaaggact ctgccagaa    3600 catcgccacc aggctgctcc tcaagtcctc agagggattc agcctctttg tcaaaattgc    3660
agacaaggtc atcagcgttc ctgagaatga cttcttcttt gactttgttc gacacttgac    3720
agactggata aagaaagctc ggcccatcaa ggacggaatt gtgccctcac tcacctacca    3780
ggtgttcttc atgaagaagc tgtggaccac cacggtgcca gggaaggatc ccatggccga    3840
ttccatcttc cactattacc aggagttgcc caagtatctc cgaggctacc acaagtgcac    3900 gcggggaggag gtgctgcagc tgggggcgct gatctacagg gtcaagttcg aggaggacaa    3960
```

| | |
|---|---|
| gtcctacttc cccagcatcc ccaagctgct gcgggagctg gtgccccagg accttatccg | 4020 |
| gcaggtctca cctgatgact ggaagcggtc catcgtcgcc tacttcaaca agcacgcagg | 4080 |
| gaagtccaag gaggaggcca agctggcctt cctgaagctc atcttcaagt ggcccacctt | 4140 |
| tggctcagcc ttcttcgagg tgaagcaaac tacggagcca aacttccctg agatcctcct | 4200 |
| aattgccatc aacaagtatg gggtcagcct catcgatccc aaaacgaagg atatcctcac | 4260 |
| cactcatccc ttcaccaaga tctccaactg gagcagcggc aacacctact tccacatcac | 4320 |
| cattgggaac ttggtgcgcg ggagcaaact gctctgcgag acgtcactgg gctacaagat | 4380 |
| ggatgaccct ctgacttcct acattagcca gatgctcaca gccatgagca acagcgggg | 4440 |
| ctccaggagc ggcaagagag ctcgctgatc agcctcgact gtgccttcta gttgccagcc | 4500 |
| atctgttgtt tgcccctccc ccgtgccttc cttgaccctg gaaggtgcca ctcccactgt | 4560 |
| cctttcctaa taaaatgagg aaattgcatc gcattgtctg agtaggtgtc attctattct | 4620 |
| ggggggtggg gtggggcagg acagcaaggg ggaggattgg gaagacaata gcaggcattt | 4680 |
| aattaagcat gctggggaga gatctgagga accccctagt gatggagttg gccactccct | 4740 |
| ctctgcgcgc tcgctcgctc actgaggccg gcgaccaaa ggtcgcccga cgcccgggct | 4800 |
| ttgcccgggc ggcctcagtg agcgagcgag cgcgcagaga gggag | 4845 |

<210> SEQ ID NO 45
<211> LENGTH: 1366
<212> TYPE: DNA
<213> ORGANISM: Artificial Sequence
<220> FEATURE:
<223> OTHER INFORMATION: Synthetic

<400> SEQUENCE: 45

| | |
|---|---|
| caggtctaac tttctgaagc tgaagaacgc tgccacactg atccagaggc actggcgggg | 60 |
| tcacaactgt aggaagaact acgggctgat gcgtctgggc ttcctgcggc tgcaggccct | 120 |
| gcaccgctcc cggaagctgc accagcagta ccgcctggcc cgccagcgca tcatccagtt | 180 |
| ccaggcccgc tgccgcgcct atctggtgcg caaggcctttc cgccaccgcc tctgggctgt | 240 |
| gctcaccgtg caggcctatg cccggggcat gatcgcccgc aggctgcacc aacgcctcag | 300 |
| ggctgagtat ctgtggcgcc tcgaggctga gaaaatgcgg ctggcggagg aagagaagct | 360 |
| tcggaaggag atgagcgcca agaaggccaa ggaggaggcc gagcgcaagc atcaggagcg | 420 |
| cctggcccag ctggctcgtg aggacgctga gcgggagctg aaggagaagg aggccgctcg | 480 |
| gcggaagaag gagctcctgg agcagatgga aagggcccgc catgagcctg tcaatcactc | 540 |
| agacatggtg gacaagatgt ttggcttcct ggggacttca ggtggcctgc aggccagga | 600 |
| gggccaggca cctagtggct ttgaggacct ggagcgaggg cggagggaga tggtggagga | 660 |
| ggacctggat gcagccctgc ccctgcctga cgaggatgag gaggacctct ctgagtataa | 720 |
| atttgccaag ttcgcggcca cctacttcca ggggacaacc acgcactcct acacccggcg | 780 |
| gccactcaaa cagccactgc tctaccatga cgacgagggt gaccagctgg cagccctggc | 840 |
| ggtctggatc accatcctcc gcttcatggg ggacctccct gagcccaagt accacacagc | 900 |
| catgagtgat ggcagtgaga agatccctgt gatgaccaag atttatgaga ccctgggcaa | 960 |
| gaagacgtac aagagggagc tgcaggccct gcagggcgag ggcgaggccc agctccccga | 1020 |
| gggccagaag aagagcagtg tgaggcacaa gctggtgcat ttgactctga aaaagaagtc | 1080 |
| caagctcaca gaggaggtga ccaagaggct gcatgacggg gagtccacag tgcagggcaa | 1140 |

```
cagcatgctg gaggaccggc ccacctccaa cctggagaag ctgcacttca tcatcggcaa   1200
tggcatcctg cggccagcac tccgggacga gatctactgc cagatcagca agcagctgac   1260
ccacaacccc tccaagagca gctatgcccg gggctggatt ctcgtgtctc tctgcgtggg   1320
ctgtttcgcc ccctccgaga agtttgtcaa gtacctgcgg aacttc                  1366
```

```
<210> SEQ ID NO 46
<211> LENGTH: 4259
<212> TYPE: DNA
<213> ORGANISM: Artificial Sequence
<220> FEATURE:
<223> OTHER INFORMATION: Synthetic

<400> SEQUENCE: 46
ctccctctct gcgcgctcgc tcgctcactg aggccgcccg ggcaaagccc gggcgtcggg     60
cgacctttgg tcgcccggcc tcagtgagcg agcgagcgcg cagagaggga gtggccaact    120
ccatcactag gggttctcag atctggcgcg cccaattcgg taccctagtt attaatagta    180
atcaattacg gggtcattag ttcatagccc atatatggag ttccgcgtta cataacttac    240
ggtaaatggc ccgcctggct gaccgcccaa cgacccccgc ccattgacgt caataatgac    300
gtatgttccc atagtaacgc caatagggac tttccattga cgtcaatggg tggactattt    360
acggtaaact gcccacttgg cagtacatca agtgtatcat atgccaagta cgccccctat    420
tgacgtcaat gacggtaaat ggcccgcctg gcattatgcc cagtacatga ccttatggga    480
ctttcctact tggcagtaca tctacgtatt agtcatcgct attaccatgg tcgaggtgag    540
ccccacgttc tgcttcactc tccccatctc ccccccctcc ccacccccaa ttttgtattt    600
atttattttt taattatttt gtgcagcgat gggggcgggg ggggggggggg ggcgcgcgcc    660 aggcggggcg gggcggggcg aggggcgggg cgggggcgagg cggagaggtg cggcggcagc    720
caatcagagc ggcgcgctcc gaaagtttcc ttttatggcg aggcggcggc ggcggcggcc    780
ctataaaaag cgaagcgcgc ggcgggcggg agtcgctgcg acgctgcctt cgccccgtgc    840
cccgctccgc cgccgcctcg cgccgcccgc cccggctctg actgaccgcg ttactcccac    900
aggtgagcgg gcgggacggc ccttctcctc cgggctgtaa ttagcgcttg gtttaatgac    960
ggcttgtttc ttttctgtgg ctgcgtgaaa gccttgaggg gctccgggag ctagagcctc   1020
tgctaaccat gttcatgcct tcttcttttt cctacagctc ctgggcaacg tgctggttat   1080
tgtgctgtct catcattttg gcaaagaatt ctagcggccg ccaccatggt gattcttcag   1140 caggggggacc atgtgtggat ggacctgaga ttggggcagg agttcgacgt gcccatcggg   1200
gcggtggtga agctctgcga ctctgggcag gtccaggtgg tggatgatga agacaatgaa   1260
cactggatct ctccgcagaa cgcaacgcac atcaagccta tgcacccac gtcggtccac   1320 ggcgtggagg acatgatccg cctggggac ctcaacgagg cgggcatctt gcgcaacctg   1380
cttatccgct accgggacca cctcatctac acgtatacgg gctccatcct ggtggctgtg   1440
aacccctacc agctgctctc catctactcg ccagagcaca tccgcagta taccaacaag   1500 aagattgggg agatgccccc ccacatcttt gccattgctg acaactgcta cttcaacatg   1560
aaacgcaaca gccgagacca gtgctgcatc atcagtgggg aatctggggc cgggaagacg   1620
gagagcacaa agctgatcct gcagttcctg gcagccatca gtgggcagca ctcgtggatt   1680
gagcagcagg tcttggaggc cacccccatt ctggaagcat tgggaatgc caagaccatc   1740 cgcaatgaca actcaagccg tttcggaaag tacatcgaca tccacttcaa caagggggc   1800 gccatcgagg gcgcgaagat tgagcagtac ctgctggaaa agtcacgtgt ctgtcgccag   1860
```

```
gccctggatg aaaggaacta ccacgtgttc tactgcatgc tggagggtat gagtgaggat      1920
cagaagaaga agctgggctt gggccaggcc tctgactaca actacttggc catgggtaac      1980
tgcataacct gtgagggccg ggtggacagc caggagtacg ccaacatccg ctccgccatg      2040
aaggtgctca tgttcactga caccgagaac tgggagatct cgaagctcct ggctgccatc      2100
ctgcacctgg gcaacctgca gtatgaggca cgcacatttg aaaacctgga tgcctgtgag      2160
gttctcttct cccatcgct ggccacagct gcatccctgc ttgaggtgaa ccccccagac       2220
ctgatgagct gcctgactag ccgcacccte atcacccgcg gggagacggt gtccacccca      2280
ctgagcaggg aacaggcact ggacgtgcgc gacgccttcg taaagggat ctacgggcgg       2340 ctgttcgtgt ggattgtgga caagatcaac gcagcaattt acaagcctcc ctcccaggat     2400
gtgaagaact ctcgcaggtc catcggcctc ctggacatct ttgggtttga aactttgct     2460 gtgaacagct ttgagcagct ctgcatcaac ttcgccaatg agcacctgca gcagttcttt     2520
gtgcggcacg tgttcaagct ggagcaggag gaatatgacc tggagagcat tgactggctg    2580
cacatcgagt tcactgacaa ccaggatgcc ctggacatga ttgccaacaa gcccatgaac    2640
atcatctccc tcatcgatga gggagagcaag ttccccaagg gcacagacac caccatgtta  2700
cacaagctga actcccagca aagctcaac gccaactaca tcccccccaa gaacaaccat    2760
gagacccagt ttggcatcaa ccattttgca ggcatcgtct actatgagac ccaaggcttc   2820
ctggagaaga accgagacac cctgcatggg gacattatcc agctggtcca ctcctccagg   2880
aacaagttca tcaagcagat cttccaggcc gatgtcgcca tgggcgccga gaccaggaag   2940
cgctcgccca cacttagcag ccagttcaag cggtcactgg agctgctgat gcgcacgctg   3000
ggtgcctgcc agcccttctt tgtgcgatgc atcaagccca atgagttcaa gaagcccatg   3060
ctgttcgacc ggcacctgtg cgtgcgccag ctgcggtact caggaatgat ggagaccatc   3120
cgaatccgcc gagctggcta ccccatccgc tacagcttcg tagagtttgt ggagcggtac   3180
cgtgtgctgc tgccaggtgt gaagccggcc tacaagcagg gcgacctccg cgggacttgc   3240
cagcgcatgg ctgaggctgt gctgggcacc cacgatgact ggcagatagg caaaaccaag   3300
atctttctga aggaccacca tgacatgctg ctggaagtgg agcgggacaa agccatcacc   3360
gacagagtca tcctccttca gaaagtcatc cggggattca agacaggtc taactttctg    3420 aagctgaaga acgctgccac actgatccag aggcactggc ggggtcacaa ctgtaggaag   3480
aactacgggc tgatgcgtct gggcttcctg cggctgcagg ccctgcaccg ctcccggaag   3540
ctgcaccagc agtaccgcct ggcccgccag cgcatcatcc agttccaggc ccgctgccgc   3600
gcctatctgg tgcgcaaggc cttccgccac cgcctctggg ctgtgctcac cgtgcaggcc   3660
tatgcccggg gcatgatcgc ccgcaggctg caccaacgcc tcagggctga ggtaagtatc   3720
aaggttacaa gacaggttaa cggagaccaa ttgaaactgg gcttgtcgag acagagaaga   3780
ctcttgcgtt tcagcgctag cccccgggtg cgcggcgtcg tggtgccgg cggggggcgc    3840 caggtcgcag gcggtgtagg gctccaggca ggcggcgaag gccatgacgt gcgctatgaa    3900
ggtctgctcc tgcacgccgt gaaccaggtg cgcctgcggg ccgcgcgcga acaccgccac   3960
gtcctcgcct gcgtgggtct cttcgtccag ggcactgcg cactgctgcc gatactcggg     4020
gctcccgctc tcgctctcgg taacatccgg ccgggcgccg tccttgagca catagcctgg   4080
accgtttcgt cgacggatcc gcatgctggg gagagatctg aggaaacccc tagtgatgga   4140
gttggccact ccctctctgc gcgctcgctc gctcactgag gccgggcgac caaaggtcgc   4200
```

```
ccgacgcccg ggctttgccc gggcggcctc agtgagcgag cgagcgcgca gagagggag    4259
```

<210> SEQ ID NO 47
<211> LENGTH: 4875
<212> TYPE: DNA
<213> ORGANISM: Artificial Sequence
<220> FEATURE:
<223> OTHER INFORMATION: Synthetic

<400> SEQUENCE: 47

```
ctccctctct gcgcgctcgc tcgctcactg aggccgcccg ggcaaagccc gggcgtcggg      60
cgacctttgg tcgcccggcc tcagtgagcg agcgagcgcg cagagaggga gtggccaact     120
ccatcactag gggttctcag atctggcgcg ccccccgggt gcgcggcgtc ggtggtgccg     180
gcggggggcg ccaggtcgca ggcggtgtag ggctccaggc aggcggcgaa ggccatgacg     240
tgcgctatga aggtctgctc ctgcacgccg tgaaccaggt gcgcctgcgg gccgcgcgcg     300
aacaccgcca cgtcctcgcc tgcgtgggtc tcttcgtcca gggcactgc gcactgctgc     360
cgatactcgg ggctcccgct ctcgctctcg gtaacatccg gccgggcgcc gtccttgagc     420
acatagcctg accgtttct cttaagcgac gcatgctcgc gataggcacc tattggtctt     480
actgacatcc actttgcctt tctctccaca gtatctgtgg cgcctcgagg ctgagaaaat     540
gcggctggcg gaggaagaga agcttcggaa ggagatgagc gccaagaagg ccaaggagga     600
ggccgagcgc aagcatcagg agcgcctggc ccagctggct cgtgaggacg ctgagcggga     660
gctgaaggag aaggaggccg ctcggcggaa gaggagctc ctggagcaga tggaaagggc     720
ccgccatgag cctgtcaatc actcagacat ggtggacaag atgtttggct tcctggggac     780
ttcaggtggc ctgccaggcc aggagggcca ggcacctagt ggctttgagg acctggagcg     840
agggcggagg gagatggtgg aggaggacct ggatgcagcc ctgccctgc ctgacgagga     900
tgaggaggac ctctctgagt ataaatttgc caagttcgcg gccacctact ccaggggac     960
aaccacgcac tcctacaccc ggcggccact caaacagcca ctgctctacc atgacgacga    1020
gggtgaccag ctggcagccc tggcggtctg gatcaccatc ctccgcttca tggggacct    1080
ccctgagccc aagtaccaca cagccatgag tgatggcagt gagaagatcc ctgtgatgac    1140
caagatttat gagaccctgg gcaagaagac gtacaagagg gagctgcagg ccctgcaggg    1200
cgagggcgag gcccagctcc ccagggcca agaagagagc agtgtgaggc acaagctggt    1260
gcatttgact ctgaaaaaga agtccaagct cacagaggag gtgaccaaga ggctgcatga    1320
cggggagtcc acagtgcagg gcaacagcat gctggaggac cggcccaccct ccaacctgga    1380
gaagctgcac ttcatcatcg gcaatggcat cctgcggcca gcactccggg acgagatcta    1440
ctgccagatc agcaagcagc tgacccacaa cccctccaag agcagctatg cccggggctg    1500
gattctcgtg tctctctgcg tgggctgttt cgcccctcc gagaagtttg tcaagtacct    1560
gcggaacttc atccacgggg gcccgcccgg ctacgccccg tactgtgagg agcgcctgag    1620
aaggaccttt gtcaatggga cacggacaca gccgcccagc tggctggagc tgcaggccac    1680
caagtccaag aagccaatca tgttgcccgt gacattcatg gatgggacca ccaagaccct    1740
gctgacggac tcggcaacca cggccaagga gctctgcaac gcgctggccg acaagatctc    1800
tctcaaggac cggttcgggt tctccctcta cattgccctg tttgacaagg tgtcctccct    1860
gggcagcggc agtgaccacg tcatggacgc catctcccag tgcgagcagt acgccaagga    1920
gcagggcgcc caggagcgca acgcccctg gaggctcttc ttccgcaaag aggtcttcac    1980
gccctggcac agccctccg aggacaacgt ggccaccaac ctcatctacc agcaggtggt    2040
```

```
gcgaggagtc aagtttgggg agtacaggtg tgagaaggag gacgacctgg ctgagctggc   2100
ctcccagcag tactttgtag actatggctc tgagatgatc ctggagcgcc tcctgaacct   2160
cgtgcccacc tacatccccg accgcgagat cacgcccctg aagacgctgg agaagtgggc   2220
ccagctggcc atcgccgccc acaagaaggg gatttatgcc cagaggagaa ctgatgccca   2280
gaaggtcaaa gaggatgtgg tcagttatgc ccgcttcaag tggcccttgc tcttctccag   2340
gttttatgaa gcctacaaat tctcaggccc cagtctcccc aagaacgacg tcatcgtggc   2400
cgtcaactgg acgggtgtgt actttgtgga tgagcaggag caggtacttc tggagctgtc   2460
cttcccagag atcatggccg tgtccagcag caggggagcg aaaacgacgg cccccagctt   2520
cacgctggcc accatcaagg gggacgaata caccttcacc tccagcaatg ctgaggacat   2580
tcgtgacctg gtggtcacct cctagagggg gctccggaag agatctaagt atgttgtggc   2640
cctgcaggat aaccccaacc ccgcaggcga ggagtcaggc ttcctcagct tgccaagggg   2700
agacctcatc atcctggacc atgacacggg cgagcaggtc atgaactcgg gctgggccaa   2760
cggcatcaat gagaggacca agcagcgtgg ggacttcccc accgacagtg tgtacgtcat   2820
gcccactgtc accatgccac cgcgggagat tgtggccctg gtcaccatga ctcccgatca   2880
gaggcaggac gttgtccggc tcttgcagct gcgaacggcg gagcccgagg tgcgtgccaa   2940
gccctacacg ctggaggagt tttcctatga ctacttcagg ccccacccca agcacacgct   3000
gagccgtgtc atggtgtcca aggcccgagg caaggaccgg ctgtggagcc acgcgggga   3060
accgctcaag caggcgctgc tcaagaagct cctgggcagt gaggagctct cgcaggaggc   3120
ctgcctggcc ttcattgctg tgctcaagta catgggcgac tacccgtcca agaggacacg   3180
ctccgtcaac gagctcaccg accagatctt tgagggtccc ctgaaagccg agcccctgaa   3240
ggacgaggca tatgtgcaga tcctgaagca gctgaccgac aaccacatca ggtacagcga   3300
ggagcggggt tgggagctgc tctggctgtg cacgggcctt ttcccaccca gcaacatcct   3360
cctgccccac gtgcagcgct tcctgcagtc ccgaaagcac tgcccactcg ccatcgactg   3420
cctgcaacgg ctccagaaag ccctgagaaa cgggtcccgg aagtaccctc cgcacctggt   3480
ggaggtggag gccatccagc acaagaccac ccagattttc cacaaagtct acttccctga   3540
tgacactgac gaggccttcg aagtggagtc cagcaccaag gccaaggact ctgccagaa   3600
catcgccacc aggctgctcc tcaagtcctc agagggattc agcctctttg tcaaaattgc   3660
agacaaggtc atcagcgttc tgagaatgac cttcttcttt gactttgttc gacacttgac   3720
agactggata aagaaagctc ggcccatcaa ggacggaatt gtgccctcac tcacctacca   3780
ggtgttcttc atgaagaagc tgtggaccac cacggtgcca gggaaggatc ccatggccga   3840
ttccatcttc cactattacc aggagttgcc caagtatctc cgaggctacc acaagtgcac   3900
gcgggaggag gtgctgcagc tggggcgct gatctacagg gtcaagttcg aggaggacaa   3960
gtcctacttc cccagcatcc ccaagctgct gcggagctg gtgccccagg accttatccg   4020
gcaggtctca cctgatgact ggaagcggtc catcgtcgcc tacttcaaca gcacgcagg   4080
gaagtccaag gaggaggcca agctggcctt cctgaagctc atcttcaagt ggcccaccct   4140
tggctcagcc ttcttcgagg tgaagcaaac tacgagcca aacttccctg agatcctcct   4200
aattgccatc aacaagtatg gggtcagcct catcgatccc aaaacgaagg atatcctcac   4260
cactcatccc ttcaccaaga tctccaactg gagcagcggc aacacctact tccacatcac   4320
cattgggaac ttggtgcgcg ggagcaaact gctctgcgag acgtcactgg gctacaagat   4380
```

| | |
|---|---|
| ggatgacctc ctgacttcct acattagcca gatgctcaca gccatgagca acagcgggg | 4440 |
| ctccaggagc ggcaagtacc cttacgatgt accggattac gcatgaagag ctcgctgatc | 4500 |
| agcctcgact gtgccttcta gttgccagcc atctgttgtt tgcccctccc ccgtgccttc | 4560 |
| cttgaccctg gaaggtgcca ctcccactgt cctttcctaa taaaatgagg aaattgcatc | 4620 |
| gcattgtctg agtaggtgtc attctattct ggggggtggg gtggggcagg acagcaaggg | 4680 |
| ggaggattgg gaagacaata gcaggcattt aattaagcat gctggggaga gatctgagga | 4740 |
| aaccctagt gatggagttg ccactccct ctctgcgcgc tcgctcgctc actgaggccg | 4800 |
| ggcgaccaaa ggtcgcccga cgcccgggct tgcccgggc ggcctcagtg agcgagcgag | 4860 |
| cgcgcagaga gggag | 4875 |

<210> SEQ ID NO 48
<211> LENGTH: 4874
<212> TYPE: DNA
<213> ORGANISM: Artificial Sequence
<220> FEATURE:
<223> OTHER INFORMATION: Synthetic

<400> SEQUENCE: 48

| | |
|---|---|
| ctccctctct gcgcgctcgc tcgctcactg aggccgcccg ggcaaagccc gggcgtcggg | 60 |
| cgacctttgg tcgcccggcc tcagtgagcg agcgagcgcg cagagaggga gtggccaact | 120 |
| ccatcactag gggttctcag atctggcgcg cccccgggt gcgcggcgtc ggtggtgccg | 180 |
| gcgggggcg ccaggtcgca ggcggtgtag ggctccaggc aggcggcgaa ggccatgacg | 240 |
| tgcgctatga aggtctgctc ctgcacgccg tgaaccaggt gcgcctgcgg gccgcgcgcg | 300 |
| aacaccgcca cgtcctcgcc tgcgtgggtc tcttcgtcca ggggcactgc tgactgctgc | 360 |
| cgatactcgg ggctcccgct ctcgctctcg gtaacatccg gccgggcgcc gtccttgagc | 420 |
| acatagcctg gaccgtttcc ttaagcgacg catgctcgcg ataggcacct attggtctta | 480 |
| ctgacatcca ctttgccttt ctctccacag tatctgtggc gcctcgaggc tgagaaaatg | 540 |
| cggctggcgg aggaagagaa gcttcggaag gagatgagcg ccaagaaggc caaggaggag | 600 |
| gccgagcgca gcatcagga gcgcctggcc cagctggctc gtgaggacgc tgagcggag | 660 |
| ctgaaggaga aggaggccgc tcggcggaag aaggagctcc tggagcagat ggaaagggcc | 720 |
| cgccatgagc ctgtcaatca ctcagacatg gtggacaaga tgtttggctt cctggggact | 780 |
| tcaggtggcc tgccaggcca ggagggccag gcacctagtg gctttgagga cctggagcga | 840 |
| gggcggaggg agatggtgga ggaggacctg atgcagcccc tgcccctgcc tgacgaggat | 900 |
| gaggaggacc tctctgagta taaatttgcc aagttcgcgg ccacctactt ccaggggaca | 960 |
| accacgcact cctacaccg gcggccactc aaacagccac tgctctacca tgacgacgag | 1020 |
| ggtgaccagc tggcagccct ggcggtctgg atcaccatcc tccgcttcat gggggacctc | 1080 |
| cctgagccca gtaccacac agccatgagt gatggcagtg agaagatccc tgtgatgacc | 1140 |
| aagatttatg agaccctggg caagaagacg tacaagaggg agctgcaggc cctgcagggc | 1200 |
| gagggcgagg cccagctccc cgagggccag aagaagagca gtgtgaggca caagctggtg | 1260 |
| catttgactc tgaaaagaa gtccaagctc acagaggagg tgaccaagag gctgcatgac | 1320 |
| ggggagtcca cagtgcaggg caacagcatg ctggaggacc ggcccacctc aacctggag | 1380 |
| aagctgcact tcatcatcgg caatggcatc ctgcggccag cactccggga cgagatctac | 1440 |
| tgccagatca gcaagcagct gacccacaac ccctccaaga gcagctatgc ccggggctgg | 1500 |
| attctcgtgt ctctctgcgt gggctgtttc gcccctccg agaagtttgt caagtacctg | 1560 |

```
cggaacttca tccacggggg cccgcccggc tacgccccgt actgtgagga gcgcctgaga    1620
aggacctttg tcaatgggac acggacacag ccgcccagct ggctggagct gcaggccacc    1680
aagtccaaga agccaatcat gttgcccgtg acattcatgg atgggaccac caagaccctg    1740
ctgacggact cggcaaccac ggccaaggag ctctgcaacg cgctggccga caagatctct    1800
ctcaaggacc ggttcgggtt ctccctctac attgccctgt tgacaaggt gtcctccctg     1860 ggcagcggca gtgaccacgt catggacgcc atctcccagt gcgagcagta cgccaaggag    1920
cagggcgccc aggagcgcaa cgcccctgg aggctcttct ccgcaaaga ggtcttcacg      1980 ccctggcaca gcccctccga ggacaacgtg gccaccaacc tcatctacca gcaggtggtg    2040
cgaggagtca gtttggggga gtacaggtgt gagaaggagg acgacctggc tgagctggcc    2100
tcccagcagt actttgtaga ctatggctct gagatgatcc tggagcgcct cctgaacctc    2160
gtgcccacct acatccccga ccgcgagatc acgcccctga gacgctggga aagtgggcc    2220 cagctggcca tcgccgccca caagaagggg atttatgccc agaggagaac tgatgcccag    2280
aaggtcaaag aggatgtggt cagttatgcc cgcttcaagt ggcccttgct cttctccagg    2340
ttttatgaag cctacaaatt ctcaggcccc agtctcccca gaacgacgt catcgtggcc     2400 gtcaactgga cgggtgtgta ctttgtggat gagcaggagc aggtacttct ggagctgtcc    2460
ttcccagaga tcatggccgt gtccagcagc agggggagcga aaacgacggc ccccagcttc    2520
acgctggcca ccatcaaggg ggacgaatac accttcacct ccagcaatgc tgaggacatt    2580
cgtgacctgg tggtcaccct cctagagggg ctccggaaga gatctaagta tgttgtggcc    2640
ctgcaggata accccaaccc cgcaggcgag gagtcaggct tcctcagctt tgccaaggga    2700
gacctcatca tcctggacca tgacacgggc gagcaggtca tgaactcggg ctgggccaac    2760
ggcatcaatg agaggaccaa gcagcgtggg gacttcccca ccgacagtgt gtacgtcatg    2820
cccactgtca ccatgccacc gcgggagatt gtggccctgg tcaccatgac tcccgatcag    2880
aggcaggacg ttgtccggct cttgcagctg cgaacggcgg agcccgaggt gcgtgccaag    2940
ccctacacgc tggaggagtt ttcctatgac tacttcaggc ccccacccaa gcacacgctg    3000
agccgtgtca tggtgtccaa ggcccgaggc aaggaccggc tgtggagcca cacgcgggaa    3060
ccgctcaagc aggcgctgct caagaagctc ctgggcagtg aggagctctc gcaggaggcc    3120
tgcctggcct tcattgctgt gctcaagtac atgggcgact acccgtccaa gaggacacgc    3180
tccgtcaacg agctcaccga ccagatcttt gagggtcccc tgaaagccga gcccctgaag    3240
gacgaggcat atgtgcagat cctgaagcag ctgaccgaca ccacatcag gtacagcgag     3300 gagcggggtt gggagctgct ctggctgtgc acgggccttt tcccacccag caacatcctc    3360
ctgccccacg tgcagcgctt cctgcagtcc cgaaagcact gcccactcgc catcgactgc    3420
ctgcaacggc tccagaaagc cctgagaaac gggtcccgga gtaccctcc gcacctggtg    3480 gaggtggagg ccatccagca aagaccacc cagattttcc acaaagtcta cttccctgat    3540
gacactgacg aggccttcga agtggagtcc agcaccaagg ccaaggactt ctgccagaac    3600
atcgccacca ggctgctcct caagtcctca gagggattca gcctctttgt caaaattgca    3660
gacaaggtca tcagcgttcc tgagaatgac ttcttctttg actttgttcg acacttgaca    3720
gactggataa agaaagctcg gccatcaag acggaattg tgccctcact cacctaccag      3780
gtgttcttca tgaagaagct gtggaccacc acggtgccag ggaaggatcc catggccgat    3840
tccatcttcc actattacca ggagttgccc aagtatctcc gaggctacca caagtgcacg    3900
```

| | |
|---|---:|
| cgggaggagg tgctgcagct gggggcgctg atctacaggg tcaagttcga ggaggacaag | 3960 |
| tcctacttcc ccagcatccc caagctgctg cgggagctgg tgccccagga ccttatccgg | 4020 |
| caggtctcac ctgatgactg gaagcggtcc atcgtcgcct acttcaacaa gcacgcaggg | 4080 |
| aagtccaagg aggaggccaa gctggccttc ctgaagctca tcttcaagtg cccacccttt | 4140 |
| ggctcagcct tcttcgaggt gaagcaaact acggagccaa acttccctga gatcctccta | 4200 |
| attgccatca acaagtatgg ggtcagcctc atcgatccca aaacgaagga tatcctcacc | 4260 |
| actcatccct tcaccaagat ctccaactgg agcagcggca cacctactt ccacatcacc | 4320 |
| attgggaact tggtgcgcgg gagcaaactg ctctgcgaga cgtcactggg ctacaagatg | 4380 |
| gatgacctcc tgacttccta cattagccag atgctcacag ccatgagcaa acagcggggc | 4440 |
| tccaggagcg gcaagtaccc ttacgatgta ccggattacg catgaagagc tcgctgatca | 4500 |
| gcctcgactg tgccttctag ttgccagcca tctgttgttt gcccctcccc cgtgccttcc | 4560 |
| ttgaccctgg aaggtgccac tcccactgtc ctttcctaat aaaatgagga aattgcatcg | 4620 |
| cattgtctga gtaggtgtca ttctattctg ggggtgggg tggggcagga cagcaagggg | 4680 |
| gaggattggg aagacaatag caggcattta attaagcatg ctggggagag atctgaggaa | 4740 |
| accccctagtg atggagttgg ccactccctc tctgcgcgct cgctcgctca ctgaggccgg | 4800 |
| gcgaccaaag gtcgcccgac gcccgggctt tgcccgggcg gcctcagtga gcgagcgagc | 4860 |
| gcgcagagag ggag | 4874 |

<210> SEQ ID NO 49
<211> LENGTH: 4843
<212> TYPE: DNA
<213> ORGANISM: Artificial Sequence
<220> FEATURE:
<223> OTHER INFORMATION: Synthetic

<400> SEQUENCE: 49

| | |
|---|---:|
| ctccctctct gcgcgctcgc tcgctcactg aggccgcccg gcaaagccc gggcgtcggg | 60 |
| cgacctttgg tcgcccggcc tcagtgagcg agcgagcgcg cagagaggga gtggccaact | 120 |
| ccatcactag gggttctcag atctggcgcg cccccccgggt gcgcggcgtc ggtggtgccg | 180 |
| gcggggggcg ccaggtcgca ggcggtgtag ggctccaggc aggcggcgaa ggccatgacg | 240 |
| tgcgctatga aggtctgctc ctgcacgccg tgaaccaggt gcgcctgcgg gccgcgcgcg | 300 |
| aacaccgcca cgtcctcgcc tgcgtgggtc tcttcgtcca ggggcactgc tgactgctgc | 360 |
| cgatactcgg ggctcccgct ctcgctctcg gtaacatccg gccgggcgcc gtccttgagc | 420 |
| acatagcctg gaccgtttcc ttaagcgacg catgctcgcg ataggcacct attggtctta | 480 |
| ctgacatcca ctttgccttt ctctccacag tatctgtggc gcctcgaggc tgagaaaatg | 540 |
| cggctggcgg aggaagagaa gcttcggaag gagatgagcg ccaagaaggc caaggaggag | 600 |
| gccgagcgca gcatcagga gcgcctggcc cagctggctc gtgaggacgc tgagcgggag | 660 |
| ctgaaggaga aggaggccgc tcggcggaag aaggagctcc tggagcagat ggaaagggcc | 720 |
| cgccatgagc ctgtcaatca ctcagacatg gtggacaaga tgtttggctt cctggggact | 780 |
| tcaggtggcc tgccaggcca ggagggccag gcacctagtg gctttgagga cctgagcga | 840 |
| gggcggaggg agatggtgga ggaggacctg gatgcagccc tgccctgcc tgacgaggat | 900 |
| gaggaggacc tctctgagta taaatttgcc aagttcgcgg ccaccactt ccaggggaca | 960 |
| accacgcact cctacacccg gcggccactc aaacagccac tgctctacca tgacgacgag | 1020 |
| ggtgaccagc tggcagccct ggcggtctgg atcaccatcc tccgcttcat gggggacctc | 1080 |

```
cctgagccca agtaccacac agccatgagt gatggcagtg agaagatccc tgtgatgacc    1140
aagatttatg agaccctggg caagaagacg tacaagaggg agctgcaggc cctgcagggc    1200
gagggcgagg cccagctccc cgagggccag aagaagagca gtgtgaggca caagctggtg    1260
catttgactc tgaaaaagaa gtccaagctc acagaggagg tgaccaagag gctgcatgac    1320
ggggagtcca cagtgcaggg caacagcatg ctggaggacc ggcccacctc caacctggag    1380
aagctgcact tcatcatcgg caatggcatc ctgcggccag cactccggga cgagatctac    1440
tgccagatca gcaagcagct gacccacaac ccctccaaga gcagctatgc ccggggctgg    1500
attctcgtgt ctctctgcgt gggctgtttc gccccctccg agaagtttgt caagtacctg    1560
cggaacttca tccacggggg cccgcccggc tacgccccgt actgtgagga gcgcctgaga    1620
aggacctttg tcaatgggac acggacacag ccgcccagct ggctggagct gcaggccacc    1680
aagtccaaga agccaatcat gttgcccgtg acattcatgg atgggaccac caagaccctg    1740
ctgacggact cggcaaccac ggccaaggag ctctgcaacg cgctggccga caagatctct    1800
ctcaaggacc ggttcgggtt ctccctctac attgccctgt tgacaaggt gtcctccctg    1860 ggcagcggca gtgaccacgt catggacgcc atctcccagt gcgagcagta cgccaaggag    1920
cagggcgccc aggagcgcaa cgccccctgg aggctcttct ccgcaaaga ggtcttcacg    1980 ccctggcaca gcccctccga ggacaacgtg gccaccaacc tcatctacca gcaggtggtg    2040
cgaggagtca agtttgggga gtacaggtgt gagaaggagg acgacctggc tgagctggcc    2100
tcccagcagt actttgtaga ctatggctct gagatgatcc tggagcgcct cctgaacctc    2160
gtgcccacct acatccccga ccgcgagatc acgcccctga gacgctggaa gaagtgggcc    2220
cagctggcca tcgccgccca caagaagggg atttatgccc agaggagaac tgatgcccag    2280
aaggtcaaag aggatgtggt cagttatgcc cgcttcaagt ggcccttgct cttctccagg    2340
ttttatgaag cctacaaatt ctcaggcccc agtctcccca gaacgacgt catcgtggcc    2400 gtcaactgga cgggtgtgta ctttgtggat gagcaggagc aggtacttct ggagctgtcc    2460
ttcccagaga tcatggccgt gtccagcagc aggggagcga aaacgacggc ccccagcttc    2520
acgctggcca ccatcaaggg ggacgaatac accttcacct ccagcaatgc tgaggacatt    2580
cgtgacctgg tggtcacctt cctagagggg ctccggaaga gatctaagta tgttgtggcc    2640
ctgcaggata cccccaaccc cgcaggcgag gagtcaggct cctcagcttt gccaagggag    2700
gacctcatca tcctggacca tgacacgggc gagcaggtca tgaactcggg ctgggccaac    2760
ggcatcaatg agaggaccaa gcagcgtggg gacttcccca ccgacagtgt gtacgtcatg    2820
cccactgtca ccatgccacc gcgggagatt gtggccctgg tcaccatgac tcccgatcag    2880
aggcaggacg ttgtccggct cttgcagctg cgaacggcgg agcccgaggt gcgtgccaag    2940
ccctacacgc tggaggagtt ttcctatgac tacttcaggc ccccacccaa gcacacgctg    3000
agccgtgtca tggtgtccaa ggcccgaggc aaggaccggc tgtggagcca cacgcgggaa    3060
ccgctcaagc aggcgctgct caagaagctc ctgggcagtg aggagctctc gcaggaggcc    3120
tgcctggcct tcattgctgt gctcaagtac atgggcgact accgtccaa gaggacacgc    3180 tccgtcaacg agctcaccga ccagatcttt gagggtcccc tgaaagccga gcccctgaag    3240
gacgaggcat atgtgcagat cctgaagcag ctgaccgaca accacatcag gtacagcgag    3300
gagcggggtt gggagctgct ctggctgtgc acgggccttt tcccacccag caacatcctc    3360
ctgccccacg tgcagcgctt cctgcagtcc cgaaagcact gcccactcgc catcgactgc    3420
```

| | |
|---|---|
| ctgcaacggc tccagaaagc cctgagaaac gggtcccgga agtaccctcc gcacctggtg | 3480 |
| gaggtggagg ccatccagca caagaccacc cagattttcc acaaagtcta cttccctgat | 3540 |
| gacactgacg aggccttcga agtggagtcc agcaccaagg ccaaggactt ctgccagaac | 3600 |
| atcgccacca ggctgctcct caagtcctca gagggattca gcctcttTgt caaaattgca | 3660 |
| gacaaggtca tcagcgttcc tgagaatgac ttcttctttg actttgttcg acacttgaca | 3720 |
| gactggataa agaaagctcg gcccatcaag gacggaattg tgccctcact cacctaccag | 3780 |
| gtgttcttca tgaagaagct gtggaccacc acggtgccag ggaaggatcc catggccgat | 3840 |
| tccatcttcc actattacca ggagttgccc aagtatctcc gaggctacca caagtgcacg | 3900 |
| cgggaggagg tgctgcagct gggggcgctg atctacaggg tcaagttcga ggaggacaag | 3960 |
| tcctacttcc ccagcatccc caagctgctg cgggagctgg tgccccagga ccttatccgg | 4020 |
| caggtctcac ctgatgactg gaagcggtcc atcgtcgcct acttcaacaa gcacgcaggg | 4080 |
| aagtccaagg aggaggccaa gctggccttc ctgaagctca tcttcaagtg cccaccttt | 4140 |
| ggctcagcct tcttcgaggt gaagcaaact acggagccaa acttccctga tcctcccta | 4200 |
| attgccatca acaagtatgg ggtcagcctc atcgatccca aaacgaagga tatcctcacc | 4260 |
| actcatccct tcaccaagat ctccaactgg agcagcggca cacctactt ccacatcacc | 4320 |
| attgggaact tggtgcgcgg gagcaaactg ctctgcgaga cgtcactggg ctacaagatg | 4380 |
| gatgacctcc tgacttccta cattagccag atgctcacag ccatgagcaa acagcggggc | 4440 |
| tccaggagcg gcaagagagc tcgctgatca gcctcgactg tgccttctag ttgccagcca | 4500 |
| tctgttgttt gccCctcccc cgtgccttcc ttgaccctgg aaggtgccac tcccactgtc | 4560 |
| ctttcctaat aaaatgagga aattgcatcg cattgtctga gtaggtgtca ttctattctg | 4620 |
| gggggtgggg tggggcagga cagcaagggg gaggattggg aagacaatag caggcattta | 4680 |
| attaagcatg ctggggagag atctaggaaa cccctagtga tggagttggc cactccctct | 4740 |
| ctgcgcgctc gctcgctcac tgaggccggg cgaccaaagg tcgcccgacg cccgggcttt | 4800 |
| gcccgggcgg cctcagtgag cgagcgagcg cgcagagagg gag | 4843 |

<210> SEQ ID NO 50
<211> LENGTH: 4591
<212> TYPE: DNA
<213> ORGANISM: Artificial Sequence
<220> FEATURE:
<223> OTHER INFORMATION: Synthetic

<400> SEQUENCE: 50

| | |
|---|---|
| ctccctctct gcgcgctcgc tcgctcactg aggccgcccg ggcaaagccc gggcgtcggg | 60 |
| cgacctttgg tcgcccggcc tcagtgagcg agcgagcgcg cagagaggga gtggccaact | 120 |
| ccatcactag gggttcagat ctggcgcgcc caattcggta ccctagttat taatagtaat | 180 |
| caattacggg gtcattagtt catagcccat atatggagtt ccgcgttaca aacttacgg | 240 |
| taaatggccc gcctggctga ccgcccaacg acccccgccc attgacgtca ataatgacgt | 300 |
| atgttcccat agtaacgcca atagggactt tccattgacg tcaatgggtg gactatttac | 360 |
| ggtaaactgc ccacttggca gtacatcaag tgtatcatat gccaagtacg cccCctattg | 420 |
| acgtcaatga cggtaaatgg cccgcctggc attatgccca gtacatgacc ttatgggact | 480 |
| ttcctacttg gcagtacatc tacgtattag tcatcgctat taccatggtc gaggtgagcc | 540 |
| ccacgttctg cttcactctc cccatctccc cccctcccc accccaatt ttgtatttat | 600 |
| ttatttttta attattttgt gcagcgatgg gggcggggg gggggggg cgcgcgccag | 660 |

```
gcggggcggg gcggggcgag gggcggggcg gggcgaggcg gagaggtgcg gcggcagcca    720
atcagagcgg cgcgctccga aagtttcctt ttatggcgag gcggcggcgg cggcggccct    780
ataaaaagcg aagcgcgcgg cgggcgggag tcgctgcgcg ctgccttcgc cccgtgcccc    840
gctccgccgc cgcctcgcgc cgcccgcccc ggctctgact gaccgcgtta ctcccacagg    900
tgagcgggcg ggacggccct tctcctccgg gctgtaatta gcgcttggtt taatgacggc    960
ttgtttcttt tctgtggctg cgtgaaagcc ttgaggggct ccgggagcta gagcctctgc   1020
taaccatgtt catgccttct tcttttcct acagctcctg gcaacgtgc tggttattgt    1080
gctgtctcat cattttggca aagaattcta gcggccgcca ccatggtgat tcttcagcag   1140
ggggaccatg tgtggatgga cctgagattg gggcaggagt tcgacgtgcc catcggggcg   1200
gtggtgaagc tctgcgactc tgggcaggtc caggtggtgg atgatgaaga caatgaacac   1260
tggatctctc cgcagaacgc aacgcacatc aagcctatgc accccacgtc ggtccacggc   1320
gtggaggaca tgatccgcct gggggacctc aacgaggcgg gcatcttgcg caacctgctt   1380
atccgctacc gggaccacct catctacacg tatacgggct ccatcctggt ggctgtgaac   1440
ccctaccagc tgctctccat ctactcgcca gagcacatcc gccagtatac caacaagaag   1500
attggggaga tgccccccca catctttgcc attgctgaca actgctactt caacatgaaa   1560
cgcaacagcc gagaccagtg ctgcatcatc agtgggaat ctgggccgg gaagacggag   1620
agcacaaagc tgatcctgca gttcctggca gccatcagtg ggcagcactc gtggattgag   1680
cagcaggtct tggaggccac ccccattctg gaagcatttg ggaatgccaa gaccatccgc   1740
aatgacaact caagccgttt cggaaagtac atcgacatcc acttcaacaa gcggggcgcc   1800
atcgagggcg cgaagattga gcagtacctg ctggaaaagt cacgtgtctg tcgccaggcc   1860
ctggatgaaa ggaactacca cgtgttctac tgcatgctgg agggtatgag tgaggatcag   1920
aagaagaagc tgggcttggg ccaggcctct gactacaact acttggccat gggtaactgc   1980
ataacctgtg agggccgggt ggacagccag gagtacgcca acatccgctc cgccatgaag   2040
gtgctcatgt tcactgacac cgagaactgg gagatctcga agctcctggc tgccatcctg   2100
cacctgggca acctgcagta tgaggcacgc acatttgaaa acctggatgc ctgtgaggtt   2160
ctcttctccc catcgctggc cacagctgca tccctgcttg aggtgaaccc cccagacctg   2220
atgagctgcc tgactagccg caccctcatc acccgcgggg agacggtgtc caccccactg   2280
agcagggaac aggcactgga cgtgcgcgac gccttcgtaa aggggatcta cgggcggctg   2340
ttcgtgtgga ttgtgacaa gatcaacgca gcaatttaca gcctccctc ccaggatgtg   2400
aagaactctc gcaggtccat cggcctcctg gacatctttg ggtttgagaa ctttgctgtg   2460
aacagctttg agcagctctg catcaacttc gccaatgagc acctgcagca gttctttgtg   2520
cggcacgtgt tcaagctgga gcaggaggaa tatgacctgg agagcattga ctggctgcac   2580
atcgagttca ctgacaacca ggatgccctg gacatgattg ccaacaagcc catgaacatc   2640
atctccctca tcgatgagga gagcaagttc cccaagggca cagacaccac catgttacac   2700
aagctgaact cccagcacaa gctcaacgcc aactacatcc cccccaagaa caaccatgag   2760
acccagtttg gcatcaacca ttttgcaggc atcgtctact atgagaccca aggcttcctg   2820
gagaagaacc gagacaccct gcatgggac attatccagc tggtccactc ctccaggaac   2880
aagttcatca gcagatctt ccaggccgat gtcgccatgg gcgccgagac caggaagcgc   2940
tcgcccacac ttagcagcca gttcaagcgg tcactggagc tgctgatgcg cacgctgggt   3000
```

| | |
|---|---:|
| gcctgccagc ccttctttgt gcgatgcatc aagcccaatg agttcaagaa gcccatgctg | 3060 |
| ttcgaccggc acctgtgcgt gcgccagctg cggtactcag gaatgatgga gaccatccga | 3120 |
| atccgccgag ctggctaccc catccgctac agcttcgtag agtttgtgga gcggtaccgt | 3180 |
| gtgctgctgc caggtgtgaa gccggcctac aagcagggcg acctccgcgg acttgccag | 3240 |
| cgcatggctg aggctgtgct gggcacccac gatgactggc agataggcaa aaccaagatc | 3300 |
| tttctgaagg accaccatga catgctgctg gaagtggagc gggacaaagc catcaccgac | 3360 |
| agagtcatcc tccttcagaa agtcatccgg ggattcaaag acaggtctaa ctttctgaag | 3420 |
| ctgaagaacg ctgccacact gatccagagg cactggcggg gtcacaactg taggaagaac | 3480 |
| tacgggctga tgcgtctggg cttcctgcgg ctgcaggccc tgcaccgctc ccggaagctg | 3540 |
| caccagcagt accgcctggc ccgccagcgc atcatccagt tccaggcccg ctgccgcgcc | 3600 |
| tatctggtgc gcaaggcctt ccgccaccgc ctctgggctg tgctcaccgt gcaggcctat | 3660 |
| gcccggggca tgatcgcccg caggctgcac caacgcctca gggctgagta tctgtggcgc | 3720 |
| ctcgaggctg agaaaatgcg gctggcgag gaagagaagc ttcggaagga gatgagcgcc | 3780 |
| aagaaggcca aggaggaggc cgagcgcaag catcaggagc gcctggccca gctggctcgt | 3840 |
| gaggacgctg agcgggagct gaaggagaag gaggccgctc ggcggaagaa ggagctcctg | 3900 |
| gagcagatgg aaagggcccg ccatgagcct gtcaatcact cagacatggt ggacaagatg | 3960 |
| tttggcttcc tggggacttc aggtggcctg ccaggccagg agggccaggc acctagtggc | 4020 |
| tttgaggacc tggagcgagg gcggagggag atggtggagg aggacctgga tgcagccctg | 4080 |
| ccctgcctg acgaggatga ggaggacctc tctgagtata aatttgccaa gttcgcggcc | 4140 |
| acctacttcc aggggacaac cacgcactcc tacacccggc ggccactcaa acagccactg | 4200 |
| ctctaccatg acgacgaggg tgaccagctg gcagccctgg cggtctggat caccatcctc | 4260 |
| cgcttcatgg gggacctccc tgagcccaag taccacacag ccatgagtga tggcagtgag | 4320 |
| aagatccctg tgatgaccaa gatttatgag accctgggca agaagactga caagagggag | 4380 |
| ctgcaggccc tgcagggcga gggcgaggcc cagctccccg agggccagtt aattaagcat | 4440 |
| gctggggaga gatctgaacc cctagtgatg gagttggcca ctccctctct gcgcgctcgc | 4500 |
| tcgctcactg aggccgggcg accaaaggtc gcccgacgcc cgggctttgc ccgggcggcc | 4560 |
| tcagtgagcg agcgagcgcg cagagaggga g | 4591 |

<210> SEQ ID NO 51
<211> LENGTH: 4541
<212> TYPE: DNA
<213> ORGANISM: Artificial Sequence
<220> FEATURE:
<223> OTHER INFORMATION: Synthetic

<400> SEQUENCE: 51

| | |
|---|---:|
| ctccctctct gcgcgctcgc tcgctcactg aggccgcccg gcaaagccc gggcgtcggg | 60 |
| cgacctttgg tcgcccggcc tcagtgagcg agcgagcgcg cagagaggga gtggccaact | 120 |
| ccatcactag gggttcagat ctggcgcgcc ctggcggagg aagagaagct tcggaaggag | 180 |
| atgagcgcca agaaggccaa ggaggaggcc gagcgcaagc atcaggagcg cctggcccag | 240 |
| ctggctcgtg aggacgctga gcgggagctg aaggagaagg aggccgctcg gcggaagaag | 300 |
| gagctcctgg agcagatgga aagggcccgc catgagcctg tcaatcactc agacatggtg | 360 |
| gacaagatgt ttggcttcct ggggacttca ggtggcctgc caggccagga gggccaggca | 420 |
| cctagtggct ttgaggacct ggagcgaggg cggagggaga tggtggagga ggacctggat | 480 |

```
gcagccctgc ccctgcctga cgaggatgag gaggacctct ctgagtataa atttgccaag    540
ttcgcggcca cctacttcca ggggacaacc acgcactcct acacccggcg gccactcaaa    600
cagccactgc tctaccatga cgacgagggt gaccagctgg cagccctggc ggtctggatc    660
accatcctcc gcttcatggg ggacctccct gagcccaagt accacacagc catgagtgat    720
ggcagtgaga agatccctgt gatgaccaag atttatgaga ccctgggcaa gaagacgtac    780
aagagggagc tgcaggccct gcagggcgag ggcgaggccc agctccccga gggccagaag    840
aagagcagtg tgaggcacaa gctggtgcat tgactctga aaaagaagtc caagctcaca    900
gaggaggtga ccaagaggct gcatgacggg gagtccacag tgcagggcaa cagcatgctg    960
gaggaccggc ccacctccaa cctggagaag ctgcacttca tcatcggcaa tggcatcctg   1020
cggccagcac tccgggacga gatctactgc cagatcagca agcagctgac ccacaacccc   1080
tccaagagca gctatgcccg ggctggatt ctcgtgtctc tctgcgtggg ctgtttcgcc    1140
ccctccgaga agtttgtcaa gtacctgcgg aacttcatcc acgggggccc gcccggctac   1200
gccccgtact gtgaggagcg cctgagaagg acctttgtca atgggacacg gacacagccg   1260
cccagctggc tggagctgca ggccaccaag tccaagaagc caatcatgtt gcccgtgaca   1320
ttcatggatg ggaccaccaa gaccctgctg acggactcgg caaccacggc caaggagctc   1380
tgcaacgcgc tggccgacaa gatctctctc aaggaccggt tcgggttctc cctctacatt   1440
gccctgtttg acaaggtgtc ctccctgggc agcggcagtg accacgtcat ggacgccatc   1500
tcccagtgcg agcagtacgc caaggagcag ggcgcccagg agcgcaacgc ccctggagg    1560 ctcttcttcc gcaaagaggt cttcacgccc tggcacagcc cctccgagga caacgtggcc   1620
accaacctca tctaccagca ggtggtgcga ggagtcaagt ttggggagta caggtgtgag   1680
aaggaggacg acctggctga gctggcctcc cagcagtact ttgtagacta tggctctgag   1740
atgatcctgg agcgcctcct gaacctcgtg cccacctaca tccccgaccg cgagatcacg   1800
cccctgaaga cgctggagaa gtgggcccag ctggccatcg ccgcccacaa gaagggggatt   1860 tatgcccaga ggagaactga tgcccagaag gtcaaagagg atgtggtcag ttatgcccgc   1920
ttcaagtggc ccttgctctt ctccaggttt tatgaagcct acaaattctc aggccccagt   1980
ctccccaaga cgacgtcat cgtggccgtc aactggacgg tgtgtacttt tgtggatgag    2040
caggagcagg tacttctgga gctgtccttc ccagagatca tggccgtgtc cagcagcagg   2100
ggagcgaaaa cgacggcccc cagcttcacg ctggccacca tcaagggggga cgaatacacc   2160 ttcacctcca gcaatgctga ggacattcgt gacctggtgg tcaccttcct agaggggctc   2220
cggaagagat ctaagtatgt tgtggccctg caggataacc ccaaccccgc aggcgaggag   2280
tcaggcttcc tcagctttgc caaggggagac ctcatcatcc tggaccatga cacgggcgag   2340
caggtcatga actcgggctg ggccaacggc atcaatgaga ggaccaagca gcgtggggac   2400
ttccccaccg acagtgtgta cgtcatgccc actgtcacca tgccaccgcg ggagattgtg   2460
gccctggtca ccatgactcc cgatcagagg caggacgttg tccggctctt gcagctgcga   2520
acggcggagc ccgaggtgcg tgccaagccc tacacgctgg aggagttttc ctatgactac   2580
ttcaggcccc cacccaagca cacgctgagc cgtgtcatgt gtccaaggc ccgaggcaag   2640 gaccggctgt ggagccacac gcgggaaccg ctcaagcagg cgctgctcaa gaagctcctg   2700
ggcagtgagg agctctcgca ggaggcctgc ctggccttca ttgctgtgct caagtacatg   2760
ggcgactacc cgtccaagag gacacgctcc gtcaacgagc tcaccgacca gatctttgag   2820
```

-continued

```
ggtcccctga aagccgagcc cctgaaggac gaggcatatg tgcagatcct gaagcagctg    2880
accgacaacc acatcaggta cagcgaggag cggggttggg agctgctctg gctgtgcacg    2940
ggccttttcc cacccagcaa catcctcctg ccccacgtgc agcgcttcct gcagtcccga    3000
aagcactgcc cactcgccat cgactgcctg caacggctcc agaaagccct gagaaacggg    3060
tcccggaagt accctccgca cctggtggag gtggaggcca tccagcacaa gaccacccag    3120
attttccaca aagtctactt ccctgatgac actgacgagg ccttcgaagt ggagtccagc    3180
accaaggcca aggacttctg ccagaacatc gccaccaggc tgctcctcaa gtcctcagag    3240
ggattcagcc tctttgtcaa aattgcagac aaggtcatca gcgttcctga aatgacttc     3300
ttctttgact ttgttcgaca cttgacagac tggataaaga aagctcggcc catcaaggac    3360
ggaattgtgc cctcactcac ctaccaggtg ttcttcatga agaagctgtg gaccaccacg    3420
gtgccaggga aggatcccat ggccgattcc atcttccact attaccagga gttgcccaag    3480
tatctccgag ctaccacaa gtgcacgcgg gaggaggtgc tgcagctggg ggcgctgatc    3540
tacagggtca agttcgagga ggacaagtcc tacttcccca gcatccccaa gctgctgcgg    3600
gagctggtgc cccaggacct tatccggcag gtctcacctg atgactggaa gcggtccatc    3660
gtcgcctact tcaacaagca cgcagggaag tccaaggagg aggccaagct ggccttcctg    3720
aagctcatct tcaagtggcc cacctttggc tcagccttct tcgaggtgaa gcaaactacg    3780
gagccaaact tccctgagat cctcctaatt gccatcaaca gtatggggt cagcctcatc    3840
gatcccaaaa cgaaggatat cctcaccact catcccttca ccaagatctc caactggagc    3900
agcggcaaca cctacttcca catcaccatt gggaacttgg tgcgcgggag caaactgctc    3960
tgcgagacgt cactgggcta caagatggat gacctcctga cttcctacat tagccagatg    4020
ctcacagcca tgagcaaaca gcggggctcc aggagcggca agtaccctta cgatgtaccg    4080
gattacgcat gaggtaccaa gggcgaattc tgcagtcgac tagagctcgc tgatcagcct    4140
cgactgtgcc ttctagttgc cagccatctg ttgtttgccc ctcccccgtg ccttccttga    4200
ccctggaagg tgccactccc actgtccttt cctaataaaa tgaggaaatt gcatcgcatt    4260
gtctgagtag gtgtcattct attctgggggg gtggggtggg gcaggacagc aaggggggagg    4320
attgggaaga caatagcagg catgctgggg agagatctga ggactagtcc gtcgactgtt    4380
aattaagcat gctggggaga gatctgaacc cctagtgatg gagttggcca ctccctctct    4440
gcgcgctcgc tcgctcactg aggccgggcg accaaaggtc gcccgacgcc cgggctttgc    4500
ccgggcggcc tcagtgagcg agcgagcgcg cagagaggga g                        4541
```

<210> SEQ ID NO 52
<211> LENGTH: 1366
<212> TYPE: DNA
<213> ORGANISM: Artificial Sequence
<220> FEATURE:
<223> OTHER INFORMATION: Synthetic

<400> SEQUENCE: 52

```
caggtctaac tttctgaagc tgaagaacgc tgccacactg atccagaggc actggcgggg      60
tcacaactgt aggaagaact acgggctgat gcgtctgggc ttcctgcggc tgcaggccct    120
gcaccgctcc cggaagctgc accagcagta ccgcctggcc cgccagcgca tcatccagtt    180
ccaggcccgc tgccgcgcct atctggtgcg caaggccttc cgccaccgcc tctgggctgt    240
gctcaccgtg caggcctatg cccggggcat gatcgcccgc aggctgcacc aacgcctcag    300
ggctgagtat ctgtggcgcc tcgaggctga gaaaatgcgg ctggcggagg aagagaagct    360
```

```
tcggaaggag atgagcgcca agaaggccaa ggaggaggcc gagcgcaagc atcaggagcg      420
cctggcccag ctggctcgtg aggacgctga gcgggagctg aaggagaagg aggccgctcg      480
gcggaagaag gagctcctgg agcagatgga aagggcccgc catgagcctg tcaatcactc      540
agacatggtg gacaagatgt ttggcttcct ggggacttca ggtggcctgc caggccagga      600
gggccaggca cctagtggct tgaggacct ggagcgaggg cggagggaga tggtggagga       660
ggacctggat gcagccctgc ccctgcctga cgaggatgag gaggacctct ctgagtataa      720
atttgccaag ttcgcggcca cctacttcca ggggacaacc acgcactcct acacccggcg      780
gccactcaaa cagccactgc tctaccatga cgacagggt gaccagctgg cagccctggc       840
ggtctggatc accatcctcc gcttcatggg ggacctccct gagcccaagt accacacagc      900
catgagtgat ggcagtgaga agatccctgt gatgaccaag atttatgaga ccctgggcaa      960
gaagacgtac aagagggagc tgcaggccct gcagggcgag ggcgaggccc agctccccga     1020
gggccagaag aagagcagtg tgaggcacaa gctggtgcat ttgactctga aaaagaagtc     1080
caagctcaca gaggaggtga ccaagaggct gcatgacggg gagtccacag tgcagggcaa     1140
cagcatgctg gaggaccggc ccacctccaa cctggagaag ctgcacttca tcatcggcaa     1200
tggcatcctg cggccagcac tccgggacga gatctactgc cagatcagca agcagctgac     1260
ccacaacccc tccaagagca gctatgcccg gggctggatt ctcgtgtctc tctgcgtggg     1320
ctgtttcgcc ccctccgaga gtttgtcaa gtacctgcgg aacttc                    1366

<210> SEQ ID NO 53
<211> LENGTH: 1284
<212> TYPE: DNA
<213> ORGANISM: Artificial Sequence
<220> FEATURE:
<223> OTHER INFORMATION: Synthetic

<400> SEQUENCE: 53
gggctgatgc gtctgggctt cctgcggctg caggccctgc accgctcccg gaagctgcac       60
cagcagtacc gcctggcccg ccagcgcatc atccagttcc aggcccgctg ccgcgcctat      120
ctggtgcgca aggccttccg ccaccgcctc tgggctgtgc tcaccgtgca ggcctatgcc      180
cggggcatga tcgcccgcag gctgcaccaa cgcctcaggg ctgagtatct gtggcgcctc      240
gaggctgaga aaatgcggct ggcggaggaa gagaagcttc ggaaggagat gagcgccaag      300
aaggccaagg aggaggccga gcgcaagcat caggagcgcc tggcccagct ggctcgtgag      360
gacgctgagc gggagctgaa ggagaaggag gccgctcggc ggaagaagga gctcctggag      420
cagatggaaa gggcccgcca tgagcctgtc aatcactcag acatggtgga caagatgttt      480
ggcttcctgg ggacttcagg tggcctgcca ggccaggagg ccaggcacc tagtggcttt       540 gaggacctgg agcgagggcg agggagatg gtggaggagg acctggatgc agccctgccc       600
ctgcctgacg aggatgagga ggacctctct gagtataaat ttgccaagtt cgcggccacc      660
tacttccagg ggacaaccac gcactcctac acccggcggc cactcaaaca gccactgctc      720
taccatgacg acgagggtga ccagctggca gccctggcgg tctggatcac catcctccgc      780
ttcatggggg acctccctga gcccaagtac cacacagcca tgagtgatgg cagtgagaag      840
atccctgtga tgaccaagat ttatgagacc ctgggcaaga gacgtacaa gagggagctg       900 caggccctgc agggcgaggg cgaggcccag ctccccgagg gccagaagaa gagcagtgtg      960
aggcacaagc tggtgcattt gactctgaaa aagaagtcca agctcacaga ggaggtgacc     1020
```

| aagaggctgc atgacgggga gtccacagtg cagggcaaca gcatgctgga ggaccggccc | 1080 |
| acctccaacc tggagaagct gcacttcatc atcggcaatg catcctgcg gccagcactc | 1140 |
| cgggacgaga tctactgcca gatcagcaag cagctgaccc acaacccctc caagagcagc | 1200 |
| tatgcccggg gctggattct cgtgtctctc tgcgtgggct gtttcgcccc ctccgagaag | 1260 |
| tttgtcaagt acctgcggaa cttc | 1284 |

<210> SEQ ID NO 54
<211> LENGTH: 1027
<212> TYPE: DNA
<213> ORGANISM: Artificial Sequence
<220> FEATURE:
<223> OTHER INFORMATION: Synthetic

<400> SEQUENCE: 54

| caggtctaac tttctgaagc tgaagaacgc tgccacactg atccagaggc actggcgggg | 60 |
| tcacaactgt aggaagaact acgggctgat gcgtctgggc ttcctgcggc tgcaggccct | 120 |
| gcaccgctcc cggaagctgc accagcagta ccgcctggcc cgccagcgca tcatccagtt | 180 |
| ccaggcccgc tgccgcgcct atctggtgcg caaggccttc cgccaccgcc tctgggctgt | 240 |
| gctcaccgtg caggcctatg cccggggcat gatcgcccgc aggctgcacc aacgcctcag | 300 |
| ggctgagtat ctgtggcgcc tcgaggctga aaaatgcgg ctggcggagg aagagaagct | 360 |
| tcggaaggag atgagcgcca agaaggccaa ggaggaggcc gagcgcaagc atcaggagcg | 420 |
| cctggcccag ctggctcgtg aggacgctga gcggagctg aaggagaagg aggccgctcg | 480 |
| gcggaagaag gagctcctgg agcagatgga aagggcccgc catgagcctg tcaatcactc | 540 |
| agacatggtg gacaagatgt ttggcttcct ggggacttca ggtggcctgc aggccagga | 600 |
| gggccaggca cctagtggct ttgaggacct ggagcgaggg cggagggaga tggtggagga | 660 |
| ggacctggat gcagccctgc ccctgcctga cgaggatgag gaggacctct ctgagtataa | 720 |
| atttgccaag ttcgcggcca cctacttcca ggggacaacc acgcactcct acacccggcg | 780 |
| gccactcaaa cagccactgc tctaccatga cgacgagggt gaccagctgg cagccctggc | 840 |
| ggtctggatc accatcctcc gcttcatggg ggacctccct gagcccaagt accacacagc | 900 |
| catgagtgat ggcagtgaga agatccctgt gatgaccaag atttatgaga ccctgggcaa | 960 |
| gaagacgtac aagagggagc tgcaggccct gcagggcgag ggcgaggccc agctcccga | 1020 |
| gggccag | 1027 |

<210> SEQ ID NO 55
<211> LENGTH: 1026
<212> TYPE: DNA
<213> ORGANISM: Artificial Sequence
<220> FEATURE:
<223> OTHER INFORMATION: Synthetic

<400> SEQUENCE: 55

| ctggcggagg aagagaagct tcggaaggag atgagcgcca agaaggccaa ggaggaggcc | 60 |
| gagcgcaagc atcaggagcg cctggcccag ctggctcgtg aggacgctga gcggagctg | 120 |
| aaggagaagg aggccgctcg gcggaagaag gagctcctgg agcagatgga aagggcccgc | 180 |
| catgagcctg tcaatcactc agacatggtg gacaagatgt ttggcttcct ggggacttca | 240 |
| ggtggcctgc aggccagga gggccaggca cctagtggct ttgaggacct ggagcgaggg | 300 |
| cggagggaga tggtggagga ggacctggat gcagccctgc ccctgcctga cgaggatgag | 360 |
| gaggacctct ctgagtataa atttgccaag ttcgcggcca cctacttcca ggggacaacc | 420 |

```
acgcactcct acacccggcg gccactcaaa cagccactgc tctaccatga cgacgagggt      480
gaccagctgg cagccctggc ggtctggatc accatcctcc gcttcatggg ggacctccct      540
gagcccaagt accacacagc catgagtgat ggcagtgaga agatccctgt gatgaccaag      600
atttatgaga ccctgggcaa gaagacgtac aagagggagc tgcaggccct gcagggcgag      660
ggcgaggccc agctccccga gggccagaag aagagcagtg tgaggcacaa gctggtgcat      720
ttgactctga aaagaagtc caagctcaca gaggaggtga ccaagaggct gcatgacggg       780
gagtccacag tgcagggcaa cagcatgctg gaggaccggc ccacctccaa cctggagaag      840
ctgcacttca tcatcggcaa tggcatcctg cggccagcac tccgggacga gatctactgc      900
cagatcagca agcagctgac ccacaacccc tccaagagca gctatgcccg ggctggatt      960 ctcgtgtctc tctgcgtggg ctgtttcgcc ccctccgaga gtttgtcaa gtacctgcgg      1020 aacttc                                                                1026
```

<210> SEQ ID NO 56
<211> LENGTH: 945
<212> TYPE: DNA
<213> ORGANISM: Artificial Sequence
<220> FEATURE:
<223> OTHER INFORMATION: Synthetic

<400> SEQUENCE: 56

```
gggctgatgc gtctgggctt cctgcggctg caggccctgc accgctcccg gaagctgcac       60
cagcagtacc gcctggcccg ccagcgcatc atccagttcc aggcccgctg ccgcgcctat      120
ctggtgcgca aggccttccg ccaccgcctc tgggctgtgc tcaccgtgca ggcctatgcc      180
cggggcatga tcgcccgcag gctgcaccaa cgcctcaggg ctgagtatct gtggcgcctc      240
gaggctgaga aaatgcggct ggcggaggaa gagaagcttc ggaaggagat gagcgccaag      300
aaggccaagg aggaggccga gcgcaagcat caggagcgcc tggcccagct ggctcgtgag      360
gacgctgagc gggagctgaa ggagaaggag gccgctcggc ggaagaagga gctcctggag      420
cagatggaaa gggcccgcca tgagcctgtc aatcactcag acatggtgga caagatgttt      480
ggcttcctgg ggacttcagg tggcctgcca ggccaggagg ccaggcacc tagtggcttt       540 gaggacctgg agcgagggcg gagggagatg gtggaggagg acctggatgc agccctgccc      600
ctgcctgacg aggatgagga ggacctctct gagtataaat tgccaagttt cgcggccacc      660
tacttccagg ggacaaccac gcactcctac acccggcggc cactcaaaca gccactgctc      720
taccatgacg acgagggtga ccagctggca gccctggcgg tctggatcac catcctccgc      780
ttcatggggg acctccctga gcccaagtac cacacagcca tgagtgatgg cagtgagaag      840
atccctgtga tgaccaagat ttatgagacc ctgggcaaga gacgtacaa gagggagctg       900 caggccctgc agggcgaggg cgaggcccag ctccccgagg gccag                      945
```

<210> SEQ ID NO 57
<211> LENGTH: 687
<212> TYPE: DNA
<213> ORGANISM: Artificial Sequence
<220> FEATURE:
<223> OTHER INFORMATION: Synthetic

<400> SEQUENCE: 57

```
ctggcggagg aagagaagct tcggaaggag atgagcgcca agaaggccaa ggaggaggcc       60
gagcgcaagc atcaggagcg cctggcccag ctggctcgtg aggacgctga gcgggagctg      120
```

```
aaggagaagg aggccgctcg gcggaagaag gagctcctgg agcagatgga aagggcccgc      180
catgagcctg tcaatcactc agacatggtg gacaagatgt ttggcttcct ggggacttca      240
ggtggcctgc caggccagga gggccaggca cctagtggct ttgaggacct ggagcgaggg      300
cggagggaga tggtggagga ggacctggat gcagccctgc ccctgcctga cgaggatgag      360
gaggacctct ctgagtataa atttgccaag ttcgcggcca cctacttcca ggggacaacc      420
acgcactcct acaccggcg gccactcaaa cagccactgc tctaccatga cgacgagggt       480
gaccagctgg cagccctggc ggtctggatc accatcctcc gcttcatggg ggacctccct      540
gagcccaagt accacacagc catgagtgat ggcagtgaga agatccctgt gatgaccaag      600
atttatgaga ccctgggcaa gaagacgtac aagagggagc tgcaggccct gcagggcgag      660
ggcgaggccc agctccccga gggccag                                         687
```

```
<210> SEQ ID NO 58
<211> LENGTH: 279
<212> TYPE: DNA
<213> ORGANISM: Artificial Sequence
<220> FEATURE:
<223> OTHER INFORMATION: Synthetic

<400> SEQUENCE: 58
gggctgatgc gtctgggctt cctgcggctg caggccctgc accgctcccg gaagctgcac      60
cagcagtacc gcctggcccg ccagcgcatc atccagttcc aggcccgctg ccgcgcctat     120
ctggtgcgca aggccttccg ccaccgcctc tgggctgtgc tcaccgtgca ggcctatgcc     180
cggggcatga tcgcccgcag gctgcaccaa cgcctcaggg ctgagtatct gtggcgcctc     240
gaggctgaga aaatgcggct ggcggaggaa gagaagctt                            279
```

```
<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
tggcggagga agagaagctt                                                  20
```

```
<210> SEQ ID NO 60
<211> LENGTH: 135
<212> TYPE: DNA
<213> ORGANISM: Artificial Sequence
<220> FEATURE:
<223> OTHER INFORMATION: Synthetic

<400> SEQUENCE: 60
ctccctctct gcgcgctcgc tcgctcactg aggccgcccg gcaaagccc gggcgtcggg       60 cgacctttgg tcgcccggcc tcagtgagcg agcgagcgcg cagagaggga gtggccaact    120
ccatcactag gggtt                                                      135
```

```
<210> SEQ ID NO 61
<211> LENGTH: 135
<212> TYPE: DNA
<213> ORGANISM: Artificial Sequence
<220> FEATURE:
<223> OTHER INFORMATION: Synthetic

<400> SEQUENCE: 61 aaccccctagt gatggagttg gccactccct ctctgcgcgc tcgctcgctc actgaggccg     60
```

```
ggcgaccaaa ggtcgcccga cgcccgggct tgcccgggc ggcctcagtg agcgagcgag    120
cgcgcagaga gggag                                                    135
```

<210> SEQ ID NO 62
<211> LENGTH: 880
<212> TYPE: PRT
<213> ORGANISM: Artificial Sequence
<220> FEATURE:
<223> OTHER INFORMATION: Synthetic

<400> SEQUENCE: 62

```
Met Val Ile Leu Gln Gln Gly Asp His Val Trp Met Asp Leu Arg Leu
1               5                   10                  15

Gly Gln Glu Phe Asp Val Pro Ile Gly Ala Val Lys Leu Cys Asp
            20                  25                  30

Ser Gly Gln Val Gln Val Asp Asp Glu Asp Asn Glu His Trp Ile
        35                  40                  45

Ser Pro Gln Asn Ala Thr His Ile Lys Pro Met His Pro Thr Ser Val
    50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
    210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
            260                 265                 270

Gly Gln Ala Ser Asp Tyr Asn Tyr Leu Ala Met Gly Asn Cys Ile Thr
        275                 280                 285

Cys Glu Gly Arg Val Asp Ser Gln Glu Tyr Ala Asn Ile Arg Ser Ala
    290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
```

```
            340                 345                 350
Ala Thr Ala Ala Ser Leu Leu Glu Val Asn Pro Pro Asp Leu Met Ser
            355                 360                 365

Cys Leu Thr Ser Arg Thr Leu Ile Thr Arg Gly Glu Thr Val Ser Thr
    370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
        435                 440                 445

Phe Glu Gln Leu Cys Ile Asn Phe Ala Asn His Leu Gln Gln Phe
    450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
                485                 490                 495

Asp Met Ile Ala Asn Lys Pro Met Asn Ile Ile Ser Leu Ile Asp Glu
            500                 505                 510

Glu Ser Lys Phe Pro Lys Gly Thr Asp Thr Thr Met Leu His Lys Leu
        515                 520                 525

Asn Ser Gln His Lys Leu Asn Ala Asn Tyr Ile Pro Pro Lys Asn Asn
    530                 535                 540

His Glu Thr Gln Phe Gly Ile Asn His Phe Ala Gly Ile Val Tyr Tyr
545                 550                 555                 560

Glu Thr Gln Gly Phe Leu Glu Lys Asn Arg Asp Thr Leu His Gly Asp
                565                 570                 575

Ile Ile Gln Leu Val His Ser Ser Arg Asn Lys Phe Ile Lys Gln Ile
            580                 585                 590

Phe Gln Ala Asp Val Ala Met Gly Ala Glu Thr Arg Lys Arg Ser Pro
        595                 600                 605

Thr Leu Ser Ser Gln Phe Lys Arg Ser Leu Glu Leu Leu Met Arg Thr
    610                 615                 620

Leu Gly Ala Cys Gln Pro Phe Phe Val Arg Cys Ile Lys Pro Asn Glu
625                 630                 635                 640

Phe Lys Lys Pro Met Leu Phe Asp Arg His Leu Cys Val Arg Gln Leu
                645                 650                 655

Arg Tyr Ser Gly Met Met Glu Thr Ile Arg Ile Arg Arg Ala Gly Tyr
            660                 665                 670

Pro Ile Arg Tyr Ser Phe Val Glu Phe Val Glu Arg Tyr Arg Val Leu
        675                 680                 685

Leu Pro Gly Val Lys Pro Ala Tyr Lys Gln Gly Asp Leu Arg Gly Thr
    690                 695                 700

Cys Gln Arg Met Ala Glu Ala Val Leu Gly Thr His Asp Asp Trp Gln
705                 710                 715                 720

Ile Gly Lys Thr Lys Ile Phe Leu Lys Asp His His Asp Met Leu Leu
                725                 730                 735

Glu Val Glu Arg Asp Lys Ala Ile Thr Asp Arg Val Ile Leu Leu Gln
            740                 745                 750

Lys Val Ile Arg Gly Phe Lys Asp Arg Ser Asn Phe Leu Lys Leu Lys
        755                 760                 765
```

```
Asn Ala Ala Thr Leu Ile Gln Arg His Trp Arg Gly His Asn Cys Arg
        770                 775                 780
Lys Asn Tyr Gly Leu Met Arg Leu Gly Phe Leu Arg Leu Gln Ala Leu
785                 790                 795                 800
His Arg Ser Arg Lys Leu His Gln Gln Tyr Arg Leu Ala Arg Gln Arg
                805                 810                 815
Ile Ile Gln Phe Gln Ala Arg Cys Arg Ala Tyr Leu Val Arg Lys Ala
                820                 825                 830
Phe Arg His Arg Leu Trp Ala Val Leu Thr Val Gln Ala Tyr Ala Arg
            835                 840                 845
Gly Met Ile Ala Arg Arg Leu His Gln Arg Leu Arg Ala Glu Tyr Leu
            850                 855                 860
Trp Arg Leu Glu Ala Glu Lys Met Arg Leu Ala Glu Glu Lys Leu
865                 870                 875                 880
```

<210> SEQ ID NO 63
<211> LENGTH: 2640
<212> TYPE: DNA
<213> ORGANISM: Artificial Sequence
<220> FEATURE:
<223> OTHER INFORMATION: Synthetic

<400> SEQUENCE: 63

```
atggtgattc ttcagcaggg ggaccatgtg tggatggacc tgagattggg gcaggagttc    60
gacgtgccca tcggggcggt ggtgaagctc tgcgactctg gcaggtccaa ggtggtggat   120
gatgaagaca atgaacactg gatctctccg cagaacgcaa cgcacatcaa gcctatgcac   180
cccacgtcgg tccacggcgt ggaggacatg atccgcctgg ggacctcaac gaggcgggc   240
atcttgcgca acctgcttat ccgctaccgg gaccacctca tctacacgta tacgggctcc   300
atcctggtgg ctgtgaaccc ctaccagctg ctctccatct actcgccaga gcacatccgc   360
cagtatacca caagaagat gggagatg ccccccaca tctttgccat gctgacaac       420
tgctacttca acatgaaacg caacagccga gaccagtgct gcatcatcag tggggaatct   480
ggggccggga gacggagag cacaaagctg atcctgcagt tcctggcagc catcagtggg   540
cagcactcgt ggattgagca gcaggtcttg gaggccaccc ccattctgga agcatttggg   600
aatgccaaga ccatccgcaa tgacaactca agccgtttcg gaaagtacat cgacatccac   660
ttcaacaagc ggggcgccat cgagggcgcg aagattgagc agtacctgct ggaaaagtca   720
cgtgtctgtc gccaggcct ggatgaaagg aactaccacg tgttctactg catgctggag    780
ggtatgagtg aggatcagaa gaagaagctg ggcttgggcc aggcctctga ctacaactac   840
ttggccatgg gtaactgcat aacctgtgag ggcggtgg acagccagga gtacgccaac    900
atccgctccg ccatgaaggt gctcatgttc actgacaccg gaactggga gatctcgaag   960
ctcctggctg ccatcctgca cctgggcaac ctgcagtatg aggcacgcac atttgaaaac  1020
ctggatgcct gtgaggttct cttctcccca tcgctggcca cagctgcatc cctgcttgag  1080
gtgaacccc cagacctgat gagctgcctg actagccgca ccctcatcac ccgcggggag  1140
acggtgtcca ccccactgag cagggaacag gcactgacg tgcgcgacgc cttcgtaaag  1200
gggatctacg gcggctgttt cgtgtggatt gtggacaaga tcaacgcagc aatttacaag  1260
cctccctccc aggatgtgaa gaactctcgc aggtccatcg gcctcctgga catctttggg  1320
tttgagaact tgctgtgaa cagctttgag cagctctgca tcaacttcgc caatgagcac  1380
ctgcagcagt tctttgtgcg gcacgtgttc aagctggagc aggaggaata tgacctggag  1440
```

```
agcattgact ggctgcacat cgagttcact gacaaccagg atgccctgga catgattgcc   1500
aacaagccca tgaacatcat ctccctcatc gatgaggaga gcaagttccc caagggcaca   1560
gacaccacca tgttacacaa gctgaactcc cagcacaagc tcaacgccaa ctacatcccc   1620
cccaagaaca accatgagac ccagtttggc atcaaccatt ttgcaggcat cgtctactat   1680
gagacccaag gcttcctgga gaagaaccga gacaccctgc atgggacat tatccagctg   1740 gtccactcct ccaggaacaa gttcatcaag cagatcttcc aggccgatgt cgccatgggc   1800
gccgagacca ggaagcgctc gcccacactt agcagccagt tcaagcggtc actggagctg   1860
ctgatgcgca cgctgggtgc ctgccagccc ttctttgtgc gatgcatcaa gcccaatgag   1920
ttcaagaagc ccatgctgtt cgaccggcac ctgtgcgtgc gccagctgcg gtactcagga   1980
atgatggaga ccatccgaat ccgccgagct ggctacccca tccgctacag cttcgtagag   2040
tttgtggagc ggtaccgtgt gctgctgcca ggtgtgaagc cggcctacaa gcagggcgac   2100
ctccgcggga cttgccagcg catggctgag gctgtgctgg caccacga tgactggcag   2160 ataggcaaaa ccaagatctt tctgaaggac caccatgaca tgctgctgga agtggagcgg   2220
gacaaagcca tcaccgacag agtcatcctc cttcagaaag tcatccgggg attcaaagac   2280
aggtctaact ttctgaagct gaagaacgct gccacactga tccagaggca ctggcggggt   2340
cacaactgta ggaagaacta cgggctgatg cgtctgggct tcctgcggct gcaggccctg   2400
caccgctccc ggaagctgca ccagcagtac cgcctggccc gccagcgcat catccagttc   2460
caggcccgct gccgcgccta tctggtgcgc aaggccttcc gccaccgcct ctgggctgtg   2520
ctcaccgtgc aggcctatgc ccggggcatg atcgcccgca ggctgcacca acgcctcagg   2580
gctgagtatc tgtggcgcct cgaggctgag aaaatgcggc tggcggagga agagaagctt   2640

<210> SEQ ID NO 64
<211> LENGTH: 952
<212> TYPE: DNA
<213> ORGANISM: Artificial Sequence
<220> FEATURE:
<223> OTHER INFORMATION: Synthetic

<400> SEQUENCE: 64
aattcggtac cctagttatt aatagtaatc aattacgggg tcattagttc atagcccata     60
tatggagttc cgcgttacat aacttacggt aaatggcccg cctggctgac cgcccaacga    120 ccccgccca ttgacgtcaa taatgacgta tgttcccata gtaacgccaa tagggacttt    180
ccattgacgt caatgggtgg actatttacg gtaaactgcc cacttggcag tacatcaagt    240
gtatcatatg ccaagtacgc cccctattga cgtcaatgac ggtaaatggc ccgcctggca    300
ttatgcccag tacatgacct tatgggactt tcctacttgg cagtacatct acgtattagt    360
catcgctatt accatggtcg aggtgagccc cacgttctgc ttcactctcc ccatctcccc    420
cccctcccca cccccaattt tgtatttatt tattttttaa ttattttgtg cagcgatggg    480 ggcgggggg ggggggggc gcgcgccagg cggggcgggg cggggcgagg ggcggggcgg    540
ggcgaggcgg agaggtgcgg cggcagccaa tcagagcggc gcgctccgaa agtttccttt    600 tatgcgagg cggcggcggc ggcggcccta taaaaagcga agcgcgcggc gggcgggagt    660
cgctgcgcgc tgccttcgcc ccgtgccccg ctccgccgcc gcctcgcgcc gcccgccccg    720
gctctgactg accgcgttac tcccacaggt gagcgggcgg gacggccctt ctcctccggg    780
ctgtaattag cgcttggttt aatgacggct tgtttctttt ctgtggctgc gtgaaagcct    840
```

```
tgaggggctc cgggagctag agcctctgct aaccatgttc atgccttctt cttttccta    900 cagctcctgg gcaacgtgct ggttattgtg ctgtctcatc attttggcaa ag           952
```

<210> SEQ ID NO 65
<211> LENGTH: 1102
<212> TYPE: PRT
<213> ORGANISM: Artificial Sequence
<220> FEATURE:
<223> OTHER INFORMATION: Synthetic

<400> SEQUENCE: 65

```
Met Val Ile Leu Gln Gln Gly Asp His Val Trp Met Asp Leu Arg Leu
1               5                   10                  15

Gly Gln Glu Phe Asp Val Pro Ile Gly Ala Val Lys Leu Cys Asp
            20                  25                  30

Ser Gly Gln Val Gln Val Asp Asp Glu Asp Asn Glu His Trp Ile
        35                  40                  45

Ser Pro Gln Asn Ala Thr His Ile Lys Pro Met His Pro Thr Ser Val
    50                  55                  60

His Gly Val Glu Asp Met Ile Arg Leu Gly Asp Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
    210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
            260                 265                 270

Gly Gln Ala Ser Asp Tyr Asn Tyr Leu Ala Met Gly Asn Cys Ile Thr
        275                 280                 285

Cys Glu Gly Arg Val Asp Ser Gln Glu Tyr Ala Asn Ile Arg Ser Ala
    290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350
```

-continued

```
Ala Thr Ala Ala Ser Leu Leu Glu Val Asn Pro Pro Asp Leu Met Ser
        355                 360                 365
Cys Leu Thr Ser Arg Thr Leu Ile Thr Arg Gly Glu Thr Val Ser Thr
    370                 375                 380
Pro Leu Ser Arg Glu Gln Ala Leu Asp Val Arg Asp Ala Phe Val Lys
385                 390                 395                 400
Gly Ile Tyr Gly Arg Leu Phe Val Trp Ile Val Asp Lys Ile Asn Ala
            405                 410                 415
Ala Ile Tyr Lys Pro Pro Ser Gln Asp Val Lys Asn Ser Arg Arg Ser
            420                 425                 430
Ile Gly Leu Leu Asp Ile Phe Gly Phe Glu Asn Phe Ala Val Asn Ser
            435                 440                 445
Phe Glu Gln Leu Cys Ile Asn Phe Ala Asn Glu His Leu Gln Gln Phe
        450                 455                 460
Phe Val Arg His Val Phe Lys Leu Glu Gln Glu Glu Tyr Asp Leu Glu
465                 470                 475                 480
Ser Ile Asp Trp Leu His Ile Glu Phe Thr Asp Asn Gln Asp Ala Leu
                485                 490                 495
Asp Met Ile Ala Asn Lys Pro Met Asn Ile Ile Ser Leu Ile Asp Glu
            500                 505                 510
Glu Ser Lys Phe Pro Lys Gly Thr Asp Thr Thr Met Leu His Lys Leu
        515                 520                 525
Asn Ser Gln His Lys Leu Asn Ala Asn Tyr Ile Pro Pro Lys Asn Asn
    530                 535                 540
His Glu Thr Gln Phe Gly Ile Asn His Phe Ala Gly Ile Val Tyr Tyr
545                 550                 555                 560
Glu Thr Gln Gly Phe Leu Glu Lys Asn Arg Asp Thr Leu His Gly Asp
                565                 570                 575
Ile Ile Gln Leu Val His Ser Ser Arg Asn Lys Phe Ile Lys Gln Ile
            580                 585                 590
Phe Gln Ala Asp Val Ala Met Gly Ala Glu Thr Arg Lys Arg Ser Pro
        595                 600                 605
Thr Leu Ser Ser Gln Phe Lys Arg Ser Leu Glu Leu Leu Met Arg Thr
    610                 615                 620
Leu Gly Ala Cys Gln Pro Phe Phe Val Arg Cys Ile Lys Pro Asn Glu
625                 630                 635                 640
Phe Lys Lys Pro Met Leu Phe Asp Arg His Leu Cys Val Arg Gln Leu
                645                 650                 655
Arg Tyr Ser Gly Met Met Glu Thr Ile Arg Ile Arg Arg Ala Gly Tyr
            660                 665                 670
Pro Ile Arg Tyr Ser Phe Val Glu Phe Val Glu Arg Tyr Arg Val Leu
            675                 680                 685
Leu Pro Gly Val Lys Pro Ala Tyr Lys Gln Gly Asp Leu Arg Gly Thr
        690                 695                 700
Cys Gln Arg Met Ala Glu Ala Val Leu Gly Thr His Asp Asp Trp Gln
705                 710                 715                 720
Ile Gly Lys Thr Lys Ile Phe Leu Lys Asp His His Asp Met Leu Leu
                725                 730                 735
Glu Val Glu Arg Asp Lys Ala Ile Thr Asp Arg Val Ile Leu Leu Gln
            740                 745                 750
Lys Val Ile Arg Gly Phe Lys Asp Arg Ser Asn Phe Leu Lys Leu Lys
        755                 760                 765
```

Asn Ala Ala Thr Leu Ile Gln Arg His Trp Arg Gly His Asn Cys Arg
    770                 775                 780

Lys Asn Tyr Gly Leu Met Arg Leu Gly Phe Leu Arg Leu Gln Ala Leu
785                 790                 795                 800

His Arg Ser Arg Lys Leu His Gln Gln Tyr Arg Leu Ala Arg Gln Arg
            805                 810                 815

Ile Ile Gln Phe Gln Ala Arg Cys Arg Ala Tyr Leu Val Arg Lys Ala
        820                 825                 830

Phe Arg His Arg Leu Trp Ala Val Leu Thr Val Gln Ala Tyr Ala Arg
    835                 840                 845

Gly Met Ile Ala Arg Arg Leu His Gln Arg Leu Arg Ala Glu Tyr Leu
850                 855                 860

Trp Arg Leu Glu Ala Glu Lys Met Arg Leu Ala Glu Glu Lys Leu
865                 870                 875                 880

Arg Lys Glu Met Ser Ala Lys Lys Ala Lys Glu Ala Glu Arg Lys
            885                 890                 895

His Gln Glu Arg Leu Ala Gln Leu Ala Arg Glu Asp Ala Glu Arg Glu
        900                 905                 910

Leu Lys Glu Lys Glu Ala Ala Arg Arg Lys Lys Glu Leu Leu Glu Gln
    915                 920                 925

Met Glu Arg Ala Arg His Glu Pro Val Asn His Ser Asp Met Val Asp
930                 935                 940

Lys Met Phe Gly Phe Leu Gly Thr Ser Gly Gly Leu Pro Gly Gln Glu
945                 950                 955                 960

Gly Gln Ala Pro Ser Gly Phe Glu Asp Leu Glu Arg Gly Arg Arg Glu
            965                 970                 975

Met Val Glu Glu Asp Leu Asp Ala Ala Leu Pro Leu Pro Asp Glu Asp
        980                 985                 990

Glu Glu Asp Leu Ser Glu Tyr Lys Phe Ala Lys Phe Ala Ala Thr Tyr
    995                 1000                1005

Phe Gln Gly Thr Thr Thr His Ser Tyr Thr Arg Arg Pro Leu Lys
    1010                1015                1020

Gln Pro Leu Leu Tyr His Asp Asp Glu Gly Asp Gln Leu Ala Ala
    1025                1030                1035

Leu Ala Val Trp Ile Thr Ile Leu Arg Phe Met Gly Asp Leu Pro
    1040                1045                1050

Glu Pro Lys Tyr His Thr Ala Met Ser Asp Gly Ser Glu Lys Ile
    1055                1060                1065

Pro Val Met Thr Lys Ile Tyr Glu Thr Leu Gly Lys Lys Thr Tyr
    1070                1075                1080

Lys Arg Glu Leu Gln Ala Leu Gln Gly Glu Gly Glu Ala Gln Leu
    1085                1090                1095

Pro Glu Gly Gln
    1100

<210> SEQ ID NO 66
<211> LENGTH: 3306
<212> TYPE: DNA
<213> ORGANISM: Artificial Sequence
<220> FEATURE:
<223> OTHER INFORMATION: Synthetic

<400> SEQUENCE: 66
atggtgattc ttcagcaggg ggaccatgtg tggatggacc tgagattggg gcaggagttc    60
gacgtgccca tcggggcggt ggtgaagctc tgcgactctg gcaggtcca ggtggtggat    120

-continued

```
gatgaagaca atgaacactg gatctctccg cagaacgcaa cgcacatcaa gcctatgcac      180
cccacgtcgg tccacggcgt ggaggacatg atccgcctgg gggacctcaa cgaggcgggc      240
atcttgcgca acctgcttat ccgctaccgg gaccacctca tctacacgta tacgggctcc      300
atcctggtgg ctgtgaaccc ctaccagctg ctctccatct actcgccaga gcacatccgc      360
cagtatacca acaagaagat tggggagatg ccccccacca tctttgccat tgctgacaac      420
tgctacttca acatgaaacg caacagccga gaccagtgct gcatcatcag tggggaatct      480
ggggccggga agacggagag cacaaagctg atcctgcagt tcctggcagc catcagtggg      540
cagcactcgt ggattgagca gcaggtcttg gaggccaccc ccattctgga agcatttggg      600
aatgccaaga ccatccgcaa tgacaactca agccgtttcg gaaagtacat cgacatccac      660
ttcaacaagc ggggcgccat cgagggcgcg aagattgagc agtacctgct ggaaaagtca      720
cgtgtctgtc gccaggccct ggatgaaagg aactaccacg tgttctactg catgctggag      780
ggtatgagtg aggatcagaa gaagaagctg ggcttgggcc aggcctctga ctacaactac      840
ttggccatgg gtaactgcat aacctgtgag ggccgggtgg acagccagga gtacgccaac      900
atccgctccg ccatgaaggt gctcatgttc actgacaccg agaactggga gatctcgaag      960
ctcctggctg ccatcctgca cctgggcaac ctgcagtatg aggcacgcac atttgaaaac      1020
ctggatgcct gtgaggttct cttctcccca tcgctggcca cagctgcatc cctgcttgag      1080 gtgaacccc cagacctgat gagctgcctg actagccgca ccctcatcac ccgcggggag      1140
acggtgtcca ccccactgag cagggaacag gcactggacg tgcgcgacgc cttcgtaaag      1200
gggatctacg gcggctgtt cgtgtggatt gtggacaaga tcaacgcagc aatttacaag      1260
cctccctccc aggatgtgaa gaactctcgc aggtccatcg gcctcctgga catctttggg      1320
tttgagaact ttgctgtgaa cagctttgag cagctctgca tcaacttcgc caatgagcac      1380
ctgcagcagt tctttgtgcg gcacgtgttc aagctggagc aggaggaata tgacctggag      1440
agcattgact ggctgcacat cgagttcact gacaaccagg atgccctgga catgattgcc      1500
aacaagccca tgaacatcat ctccctcatc gatgaggaga gcaagttccc caagggcaca      1560
gacaccacca tgttacacaa gctgaactcc agcacaagc tcaacgccaa ctacatcccc      1620
cccaagaaca accatgagac ccagtttggc atcaaccatt ttgcaggcat cgtctactat      1680
gagacccaag gcttcctgga aagaaccga gacaccctgc atgggacat tatccagctg      1740 gtccactcct ccaggaacaa gttcatcaag cagatcttcc aggccgatgt cgccatgggc      1800
gccgagacca ggaagcgctc gcccacactt agcagccagt tcaagcggtc actggagctg      1860
ctgatgcgca cgctgggtgc ctgccagccc ttctttgtgc gatgcatcaa gcccaatgag      1920
ttcaagaagc ccatgctgtt cgaccggcac ctgtgcgtgc ccagctgcg gtactcagga      1980 atgatggaga ccatccgaat ccgccgagct ggctacccca tccgctacag cttcgtagag      2040 tttgtgggagc ggtaccgtgt gctgctgcca ggtgtgaagc cggcctacaa gcagggcgac      2100
ctccgcggga cttgccagcg catggctgag gctgtgctgg cacccacga tgactggcag      2160 ataggcaaaa ccaagatctt tctgaaggac accatgaca tgctgctgga agtggagcgg      2220
gacaaagcca tcaccgacag agtcatcctc cttcagaaag tcatccgggg attcaaagac      2280
aggtctaact ttctgaagct gaagaacgct gccacactga tccagaggca ctggcggggt      2340
cacaactgta ggaagaacta cgggctgatg cgtctgggct tcctgcggct gcaggccctg      2400
caccgctccc ggaagctgca ccagcagtac cgcctggccc gccagcgcat catccagttc      2460
```

-continued

```
caggcccgct gccgcgccta tctggtgcgc aaggccttcc gccaccgcct ctgggctgtg    2520
ctcaccgtgc aggcctatgc ccggggcatg atcgcccgca ggctgcacca acgcctcagg    2580
gctgagtatc tgtggcgcct cgaggctgag aaaatgcggc tggcggagga agagaagctt    2640
cggaaggaga tgagcgccaa gaaggccaag gaggaggccg agcgcaagca tcaggagcgc    2700
ctggcccagc tggctcgtga ggacgctgag cgggagctga aggagaagga ggccgctcgg    2760
cggaagaagg agctcctgga gcagatggaa agggcccgcc atgagcctgt caatcactca    2820
gacatggtgg acaagatgtt tggcttcctg gggacttcag gtggcctgcc aggccaggag    2880
ggccaggcac ctagtggctt tgaggacctg agcgagggc ggagggagat ggtgaggag    2940 gacctggatg cagccctgcc cctgcctgac gaggatgagg aggacctctc tgagtataaa    3000
tttgccaagt cgcggccac ctacttccag gggacaacca cgcactccta caccggcgg    3060 ccactcaaac agccactgct ctaccatgac gacgagggtg accagctggc agccctggcg    3120
gtctggatca ccatcctccg cttcatgggg gacctccctg agcccaagta ccacacagcc    3180
atgagtgatg gcagtgagaa gatccctgtg atgaccaaga tttatgagac cctgggcaag    3240
aagacgtaca agagggagct gcaggccctg cagggcgagg cgaggcccca gctccccgag    3300
ggccag                                                                3306
```

```
<210> SEQ ID NO 67
<211> LENGTH: 2905
<212> TYPE: PRT
<213> ORGANISM: Artificial Sequence
<220> FEATURE:
<223> OTHER INFORMATION: Synthetic

<400> SEQUENCE: 67

Ala Thr Gly Gly Thr Gly Ala Thr Thr Cys Thr Thr Cys Ala Gly Cys
1               5                   10                  15

Ala Gly Gly Gly Gly Ala Cys Cys Ala Thr Gly Thr Gly Thr Gly
            20                  25                  30

Gly Ala Thr Gly Gly Ala Cys Cys Thr Gly Ala Gly Ala Thr Thr Gly
        35                  40                  45

Gly Gly Gly Cys Ala Gly Gly Ala Gly Thr Thr Cys Gly Ala Cys Gly
    50                  55                  60

Thr Gly Cys Cys Ala Thr Cys Gly Gly Gly Cys Gly Gly Thr
65                  70                  75                  80

Gly Gly Thr Gly Ala Ala Gly Cys Thr Cys Thr Gly Cys Gly Ala Cys
                85                  90                  95

Thr Cys Thr Gly Gly Gly Cys Ala Gly Gly Thr Cys Cys Ala Gly Gly
            100                 105                 110

Thr Gly Gly Thr Gly Gly Ala Thr Gly Ala Thr Gly Ala Ala Gly Ala
        115                 120                 125

Cys Ala Ala Thr Gly Ala Ala Cys Ala Cys Thr Gly Gly Ala Thr Cys
    130                 135                 140

Thr Cys Thr Cys Cys Gly Cys Ala Gly Ala Ala Cys Gly Cys Ala Ala
145                 150                 155                 160

Cys Gly Cys Ala Cys Ala Thr Cys Ala Ala Gly Cys Cys Thr Ala Thr
                165                 170                 175

Gly Cys Ala Cys Cys Cys Ala Cys Gly Thr Cys Gly Gly Thr Cys
            180                 185                 190

Cys Ala Cys Gly Gly Cys Gly Thr Gly Gly Ala Gly Gly Ala Cys Ala
        195                 200                 205
```

```
Thr Gly Ala Thr Cys Cys Gly Cys Thr Gly Gly Gly Gly Ala
    210             215             220

Cys Cys Thr Cys Ala Ala Cys Gly Ala Gly Cys Gly Gly Cys
225             230             235             240

Ala Thr Cys Thr Thr Gly Cys Gly Cys Ala Ala Cys Thr Gly Cys
            245             250             255

Thr Thr Ala Thr Cys Cys Gly Cys Thr Ala Cys Cys Gly Gly Ala
            260             265             270

Cys Cys Ala Cys Cys Thr Cys Ala Thr Cys Thr Ala Cys Ala Cys Gly
        275             280             285

Thr Ala Thr Ala Cys Gly Gly Gly Cys Thr Cys Cys Ala Thr Cys Cys
    290             295             300

Thr Gly Gly Thr Gly Gly Cys Thr Gly Thr Gly Ala Ala Cys Cys Cys
305             310             315             320

Cys Thr Ala Cys Cys Ala Gly Cys Thr Gly Cys Thr Cys Thr Cys Cys
            325             330             335

Ala Thr Cys Thr Ala Cys Thr Cys Gly Cys Cys Ala Gly Ala Gly Cys
            340             345             350

Ala Cys Ala Thr Cys Cys Gly Cys Cys Ala Gly Thr Ala Thr Ala Cys
            355             360             365

Cys Ala Ala Cys Ala Ala Gly Ala Ala Gly Ala Thr Thr Gly Gly Gly
        370             375             380

Gly Ala Gly Ala Thr Gly Cys Cys Cys Cys Cys Ala Cys Ala
385             390             395             400

Thr Cys Thr Thr Thr Gly Cys Cys Ala Thr Thr Gly Cys Thr Gly Ala
            405             410             415

Cys Ala Ala Cys Thr Gly Cys Thr Ala Cys Thr Thr Cys Ala Ala Cys
            420             425             430

Ala Thr Gly Ala Ala Ala Cys Gly Cys Ala Ala Cys Ala Gly Cys Cys
            435             440             445

Gly Ala Gly Ala Cys Cys Ala Gly Thr Gly Cys Thr Gly Cys Ala Thr
        450             455             460

Cys Ala Thr Cys Ala Gly Thr Gly Gly Gly Ala Ala Thr Cys Thr
465             470             475             480

Gly Gly Gly Gly Cys Cys Gly Gly Ala Ala Gly Ala Cys Gly Gly
            485             490             495

Ala Gly Ala Gly Cys Ala Cys Ala Ala Ala Gly Cys Thr Gly Ala Thr
        500             505             510

Cys Cys Thr Gly Cys Ala Gly Thr Thr Cys Cys Thr Gly Gly Cys Ala
    515             520             525

Gly Cys Cys Ala Thr Cys Ala Gly Thr Gly Gly Cys Ala Gly Cys
530             535             540

Ala Cys Thr Cys Gly Thr Gly Gly Ala Thr Thr Gly Ala Gly Cys Ala
545             550             555             560

Gly Cys Ala Gly Gly Thr Cys Thr Thr Gly Gly Ala Gly Gly Cys Cys
            565             570             575

Ala Cys Cys Cys Cys Ala Thr Thr Cys Thr Gly Gly Ala Ala Gly
            580             585             590

Cys Thr Thr Thr Gly Gly Gly Ala Ala Thr Gly Cys Cys Ala Ala
            595             600             605

Gly Ala Cys Cys Ala Thr Cys Cys Gly Cys Ala Ala Thr Gly Ala Cys
        610             615             620

Ala Ala Cys Thr Cys Ala Ala Gly Cys Cys Gly Thr Thr Thr Cys Gly
```

-continued

```
625                 630                 635                 640

Gly Ala Ala Ala Gly Thr Ala Cys Ala Thr Cys Gly Ala Cys Ala Thr
                645                 650                 655

Cys Cys Ala Cys Thr Thr Cys Ala Ala Cys Ala Ala Gly Cys Gly Gly
            660                 665                 670

Gly Gly Cys Gly Cys Cys Ala Thr Cys Gly Ala Gly Gly Gly Cys Gly
        675                 680                 685

Cys Gly Ala Ala Gly Ala Thr Thr Gly Ala Gly Cys Ala Gly Thr Ala
    690                 695                 700

Cys Cys Thr Gly Cys Thr Gly Gly Ala Ala Ala Ala Gly Thr Cys Ala
705                 710                 715                 720

Cys Gly Thr Gly Thr Cys Thr Gly Thr Cys Gly Cys Cys Ala Gly Gly
                725                 730                 735

Cys Cys Cys Thr Gly Gly Ala Thr Gly Ala Ala Ala Gly Gly Ala Ala
            740                 745                 750

Cys Thr Ala Cys Cys Ala Cys Gly Thr Gly Thr Thr Cys Thr Ala Cys
        755                 760                 765

Thr Gly Cys Ala Thr Gly Cys Thr Gly Gly Ala Gly Gly Gly Thr Ala
    770                 775                 780

Thr Gly Ala Gly Thr Gly Ala Gly Gly Ala Thr Cys Ala Gly Ala Ala
785                 790                 795                 800
Gly Ala Ala Gly Ala Ala Gly Cys Thr Gly Gly Gly Cys Thr Thr Gly
                805                 810                 815

Gly Gly Cys Cys Ala Gly Gly Cys Cys Thr Cys Thr Gly Ala Cys Thr
            820                 825                 830

Ala Cys Ala Ala Cys Thr Ala Cys Thr Thr Gly Gly Cys Cys Ala Thr
        835                 840                 845

Gly Gly Gly Thr Ala Ala Cys Thr Gly Cys Ala Thr Ala Ala Cys Cys
    850                 855                 860

Thr Gly Thr Gly Ala Gly Gly Gly Cys Cys Gly Gly Gly Thr Gly Gly
865                 870                 875                 880
Ala Cys Ala Gly Cys Cys Ala Gly Gly Ala Gly Thr Ala Cys Gly Cys
                885                 890                 895

Cys Ala Ala Cys Ala Thr Cys Cys Gly Cys Thr Cys Cys Gly Cys Cys
            900                 905                 910

Ala Thr Gly Ala Ala Gly Gly Thr Gly Cys Thr Cys Ala Thr Gly Thr
        915                 920                 925

Thr Cys Ala Cys Thr Gly Ala Cys Ala Cys Cys Gly Ala Gly Ala Ala
    930                 935                 940

Cys Thr Gly Gly Gly Ala Gly Ala Thr Cys Thr Cys Gly Ala Ala Gly
945                 950                 955                 960
Cys Thr Cys Cys Thr Gly Gly Cys Thr Gly Cys Cys Ala Thr Cys Cys
                965                 970                 975

Thr Gly Cys Ala Cys Cys Thr Gly Gly Gly Cys Ala Ala Cys Cys Thr
            980                 985                 990

Gly Cys Ala Gly Thr Ala Thr Gly  Ala Gly Gly Cys Ala  Cys Gly Cys
        995                 1000                1005

Ala Cys  Ala Thr Thr Thr Gly  Ala Ala Ala Ala Cys  Cys Thr Gly
    1010                1015                1020

Gly Ala  Thr Gly Cys Cys Thr  Gly Thr Gly Ala Gly  Gly Thr Thr
    1025                1030                1035

Cys Thr  Cys Thr Thr Cys Thr  Cys Cys Cys Cys Ala  Thr Cys Gly
    1040                1045                1050
```

Cys Thr Gly Gly Cys Cys Ala Cys Ala Gly Cys Thr Gly Cys Ala
1055                1060                1065

Thr Cys Cys Cys Thr Gly Cys Thr Thr Gly Ala Gly Gly Thr Gly
1070                1075                1080

Ala Ala Cys Cys Cys Cys Cys Ala Gly Ala Cys Cys Thr Gly
1085                1090                1095

Ala Thr Gly Ala Gly Cys Thr Gly Cys Cys Thr Gly Ala Cys Thr
1100                1105                1110

Ala Gly Cys Cys Gly Cys Ala Cys Cys Thr Cys Ala Thr Cys
1115                1120                1125

Ala Cys Cys Cys Gly Cys Gly Gly Gly Ala Gly Ala Cys Gly
1130                1135                1140

Gly Thr Gly Thr Cys Cys Ala Cys Cys Cys Cys Ala Cys Thr Gly
1145                1150                1155

Ala Gly Cys Ala Gly Gly Ala Ala Cys Ala Gly Gly Cys Ala
1160                1165                1170

Cys Thr Gly Gly Ala Cys Gly Thr Gly Cys Gly Cys Gly Ala Cys
1175                1180                1185

Gly Cys Cys Thr Thr Cys Gly Thr Ala Ala Ala Gly Gly Gly Gly
1190                1195                1200

Ala Thr Cys Thr Ala Cys Gly Gly Cys Gly Gly Cys Thr Gly
1205                1210                1215

Thr Thr Cys Gly Thr Gly Thr Gly Gly Ala Thr Thr Gly Thr Gly
1220                1225                1230

Gly Ala Cys Ala Ala Gly Ala Thr Cys Ala Ala Cys Gly Cys Ala
1235                1240                1245

Gly Cys Ala Ala Thr Thr Thr Ala Cys Ala Ala Gly Cys Cys Thr
1250                1255                1260

Cys Cys Cys Thr Cys Cys Ala Gly Gly Ala Thr Gly Thr Gly
1265                1270                1275

Ala Ala Gly Ala Ala Cys Thr Cys Thr Cys Gly Cys Ala Gly Gly
1280                1285                1290

Thr Cys Cys Ala Thr Cys Gly Gly Cys Cys Thr Cys Cys Thr Gly
1295                1300                1305

Gly Ala Cys Ala Thr Cys Thr Thr Gly Gly Gly Thr Thr Thr
1310                1315                1320

Gly Ala Gly Ala Ala Cys Thr Thr Gly Cys Thr Gly Thr Gly
1325                1330                1335

Ala Ala Cys Ala Gly Cys Thr Thr Gly Ala Gly Cys Ala Gly
1340                1345                1350

Cys Thr Cys Thr Gly Cys Ala Thr Cys Ala Ala Cys Thr Thr Cys
1355                1360                1365

Gly Cys Cys Ala Ala Thr Gly Ala Gly Cys Ala Cys Cys Thr Gly
1370                1375                1380

Cys Ala Gly Cys Ala Gly Thr Thr Cys Thr Thr Thr Gly Thr Gly
1385                1390                1395

Cys Gly Gly Cys Ala Cys Gly Thr Gly Thr Thr Cys Ala Ala Gly
1400                1405                1410

Cys Thr Gly Gly Ala Gly Cys Ala Gly Gly Ala Gly Gly Ala Ala
1415                1420                1425

Thr Ala Thr Gly Ala Cys Cys Thr Gly Gly Ala Gly Ala Gly Cys
1430                1435                1440

-continued

```
Ala Thr Thr Gly Ala Cys Thr Gly Gly Cys Thr Gly Cys Ala Cys
    1445            1450             1455

Ala Thr Cys Gly Ala Gly Thr Thr Cys Ala Cys Thr Gly Ala Cys
    1460            1465             1470

Ala Ala Cys Cys Ala Gly Gly Ala Thr Gly Cys Cys Cys Thr Gly
    1475            1480             1485

Gly Ala Cys Ala Thr Gly Ala Thr Thr Gly Cys Cys Ala Ala Cys
    1490            1495             1500

Ala Ala Gly Cys Cys Cys Ala Thr Gly Ala Ala Cys Ala Thr Cys
    1505            1510             1515

Ala Thr Cys Thr Cys Cys Thr Cys Ala Thr Cys Gly Ala Thr
    1520            1525             1530

Gly Ala Gly Gly Ala Gly Ala Gly Cys Ala Ala Gly Thr Thr Cys
    1535            1540             1545

Cys Cys Cys Ala Ala Gly Gly Gly Cys Ala Cys Ala Gly Ala Cys
    1550            1555             1560

Ala Cys Cys Ala Cys Cys Ala Thr Gly Thr Thr Ala Cys Ala Cys
    1565            1570             1575

Ala Ala Gly Cys Thr Gly Ala Ala Cys Thr Cys Cys Cys Ala Gly
    1580            1585             1590

Cys Ala Cys Ala Ala Gly Cys Thr Cys Ala Ala Cys Gly Cys Cys
    1595            1600             1605

Ala Ala Cys Thr Ala Cys Ala Thr Cys Cys Cys Cys Cys Cys Cys
    1610            1615             1620

Ala Ala Gly Ala Ala Cys Ala Ala Cys Cys Ala Thr Gly Ala Gly
    1625            1630             1635

Ala Cys Cys Cys Ala Gly Thr Thr Gly Gly Cys Ala Thr Cys
    1640            1645             1650

Ala Ala Cys Cys Ala Thr Thr Thr Gly Cys Ala Gly Gly Cys
    1655            1660             1665

Ala Thr Cys Gly Thr Cys Thr Ala Cys Thr Ala Thr Gly Ala Gly
    1670            1675             1680

Ala Cys Cys Cys Ala Ala Gly Gly Cys Thr Thr Cys Cys Thr Gly
    1685            1690             1695

Gly Ala Gly Ala Ala Gly Ala Ala Cys Cys Gly Ala Gly Ala Cys
    1700            1705             1710

Ala Cys Cys Cys Thr Gly Cys Ala Thr Gly Gly Gly Ala Cys
    1715            1720             1725

Ala Thr Thr Ala Thr Cys Cys Ala Gly Cys Thr Gly Gly Thr Cys
    1730            1735             1740

Cys Ala Cys Thr Cys Cys Thr Cys Cys Ala Gly Gly Ala Ala Cys
    1745            1750             1755

Ala Ala Gly Thr Thr Cys Ala Thr Cys Ala Ala Gly Cys Ala Gly
    1760            1765             1770

Ala Thr Cys Thr Thr Cys Cys Ala Gly Gly Cys Cys Gly Ala Thr
    1775            1780             1785

Gly Thr Cys Gly Cys Cys Ala Thr Gly Gly Cys Gly Cys Cys
    1790            1795             1800

Gly Ala Gly Ala Cys Cys Ala Gly Gly Ala Ala Gly Cys Gly Cys
    1805            1810             1815

Thr Cys Gly Cys Cys Ala Cys Ala Cys Thr Thr Ala Gly Cys
    1820            1825             1830

Ala Gly Cys Cys Ala Gly Thr Thr Cys Ala Ala Gly Cys Gly Gly
```

-continued

```
    1835                1840                1845

Thr Cys  Ala Cys Thr Gly Gly  Ala Gly Cys Thr Gly  Cys Thr Gly
    1850                1855                1860

Ala Thr  Gly Cys Gly Cys Ala  Cys Gly Cys Thr Gly  Gly Gly Thr
    1865                1870                1875

Gly Cys  Cys Thr Gly Cys Cys  Ala Gly Cys Cys Cys  Thr Thr Cys
    1880                1885                1890

Thr Thr  Thr Gly Thr Gly Cys  Gly Ala Thr Gly Cys  Ala Thr Cys
    1895                1900                1905

Ala Ala  Gly Cys Cys Cys Ala  Ala Thr Gly Ala Gly  Thr Thr Cys
    1910                1915                1920

Ala Ala  Gly Ala Ala Gly Cys  Cys Cys Ala Thr Gly  Cys Thr Gly
    1925                1930                1935

Thr Thr  Cys Gly Ala Cys Cys  Gly Gly Cys Ala Cys  Cys Thr Gly
    1940                1945                1950

Thr Gly  Cys Gly Thr Gly Cys  Gly Cys Cys Ala Gly  Cys Thr Gly
    1955                1960                1965

Cys Gly  Gly Thr Ala Cys Thr  Cys Ala Gly Gly Ala  Ala Thr Gly
    1970                1975                1980

Ala Thr  Gly Gly Ala Gly Ala  Cys Cys Ala Thr Cys  Cys Gly Ala
    1985                1990                1995

Ala Thr  Cys Cys Gly Cys Cys  Gly Ala Gly Cys Thr  Gly Gly Cys
    2000                2005                2010

Thr Ala  Cys Cys Cys Cys Ala  Thr Cys Cys Gly Cys  Thr Ala Cys
    2015                2020                2025

Ala Gly  Cys Thr Thr Cys Gly  Thr Ala Gly Ala Gly  Thr Thr Thr
    2030                2035                2040

Gly Thr  Gly Gly Ala Gly Cys  Gly Gly Thr Ala Cys  Cys Gly Thr
    2045                2050                2055

Gly Thr  Gly Cys Thr Gly Cys  Thr Gly Cys Cys Ala  Gly Gly Thr
    2060                2065                2070

Gly Thr  Gly Ala Ala Gly Cys  Cys Gly Gly Cys Cys  Thr Ala Cys
    2075                2080                2085

Ala Ala  Gly Cys Ala Gly Gly  Gly Cys Gly Ala Cys  Cys Thr Cys
    2090                2095                2100

Cys Gly  Cys Gly Gly Gly Ala  Cys Thr Thr Gly Cys  Cys Ala Gly
    2105                2110                2115

Cys Gly  Cys Ala Thr Gly Gly  Cys Thr Gly Ala Gly  Gly Cys Thr
    2120                2125                2130

Gly Thr  Gly Cys Thr Gly Gly  Gly Cys Ala Cys Cys  Cys Ala Cys
    2135                2140                2145

Gly Ala  Thr Gly Ala Cys Thr  Gly Gly Cys Ala Gly  Ala Thr Ala
    2150                2155                2160

Gly Gly  Cys Ala Ala Ala Ala  Cys Cys Ala Ala Gly  Ala Thr Cys
    2165                2170                2175

Thr Thr  Thr Cys Thr Gly Ala  Ala Gly Gly Ala Cys  Cys Ala Cys
    2180                2185                2190

Cys Ala  Thr Gly Ala Cys Ala  Thr Gly Cys Thr Gly  Cys Thr Gly
    2195                2200                2205

Gly Ala  Ala Gly Thr Gly Gly  Ala Gly Cys Gly Gly  Gly Ala Cys
    2210                2215                2220

Ala Ala  Ala Gly Cys Cys Ala  Thr Cys Ala Cys Cys  Gly Ala Cys
    2225                2230                2235
```

```
Ala Gly  Ala Gly Thr Cys Ala  Thr Cys Cys Thr  Cys Thr Thr
    2240             2245              2250

Cys Ala  Gly Ala Ala Ala Gly  Thr Cys Ala Thr  Cys Cys Gly Gly
    2255             2260              2265

Gly Gly  Ala Thr Thr Cys Ala  Ala Ala Gly Ala  Cys Ala Gly Gly
    2270             2275              2280

Thr Cys  Thr Ala Ala Cys Thr  Thr Thr Cys Thr  Gly Ala Ala Gly
    2285             2290              2295

Cys Thr  Gly Ala Ala Gly Ala  Ala Cys Gly Cys  Thr Gly Cys Cys
    2300             2305              2310

Ala Cys  Ala Cys Thr Gly Ala  Thr Cys Cys Ala  Gly Ala Gly Gly
    2315             2320              2325

Cys Ala  Cys Thr Gly Gly Cys  Gly Gly Gly Thr  Cys Ala Cys
    2330             2335              2340

Ala Ala  Cys Thr Gly Thr Ala  Gly Gly Ala Ala  Gly Ala Ala Cys
    2345             2350              2355

Thr Ala  Cys Gly Gly Gly Cys  Thr Gly Ala Thr  Gly Cys Gly Thr
    2360             2365              2370

Cys Thr  Gly Gly Gly Cys Thr  Thr Cys Thr Gly  Cys Gly Gly
    2375             2380              2385

Cys Thr  Gly Cys Ala Gly Gly  Cys Cys Cys Thr  Gly Cys Ala Cys
    2390             2395              2400

Cys Gly  Cys Thr Cys Cys Cys  Gly Gly Ala Ala  Gly Cys Thr Gly
    2405             2410              2415

Cys Ala  Cys Cys Ala Gly Cys  Ala Gly Thr Ala  Cys Cys Gly Cys
    2420             2425              2430

Cys Thr  Gly Gly Cys Cys Cys  Gly Cys Cys Ala  Gly Cys Gly Cys
    2435             2440              2445

Ala Thr  Cys Ala Thr Cys Cys  Ala Gly Thr Thr  Cys Cys Ala Gly
    2450             2455              2460

Gly Cys  Cys Cys Gly Cys Thr  Gly Cys Cys Gly  Cys Gly Cys Cys
    2465             2470              2475

Thr Ala  Thr Cys Thr Gly Gly  Thr Gly Cys Gly  Cys Ala Ala Gly
    2480             2485              2490

Gly Cys  Cys Thr Thr Cys Cys  Gly Cys Cys Ala  Cys Cys Gly Cys
    2495             2500              2505

Cys Thr  Cys Thr Gly Gly Gly  Cys Thr Gly Thr  Gly Cys Thr Cys
    2510             2515              2520

Ala Cys  Cys Gly Thr Gly Cys  Ala Gly Gly Cys  Cys Thr Ala Thr
    2525             2530              2535

Gly Cys  Cys Cys Gly Gly Gly  Gly Cys Ala Thr  Gly Ala Thr Cys
    2540             2545              2550

Gly Cys  Cys Cys Gly Cys Ala  Gly Gly Cys Thr  Gly Cys Ala Cys
    2555             2560              2565

Cys Ala  Ala Cys Gly Cys Cys  Thr Cys Ala Gly  Gly Gly Cys Thr
    2570             2575              2580

Gly Ala  Gly Thr Ala Thr Cys  Thr Gly Thr Gly  Gly Cys Gly Cys
    2585             2590              2595

Cys Thr  Cys Gly Ala Gly Gly  Cys Thr Gly Ala  Gly Ala Ala Ala
    2600             2605              2610

Ala Thr  Gly Cys Gly Gly Cys  Thr Gly Gly Cys  Gly Gly Ala Gly
    2615             2620              2625
```

```
Gly Ala Ala Gly Ala Gly Ala Ala Gly Cys Thr Thr Cys Gly Gly
        2630                2635                2640

Ala Ala Gly Gly Ala Gly Ala Thr Gly Ala Gly Cys Gly Cys Cys
    2645                2650                2655

Ala Ala Gly Ala Ala Gly Gly Cys Cys Ala Ala Gly Gly Ala Gly
        2660                2665                2670

Gly Ala Gly Gly Cys Cys Gly Ala Gly Cys Gly Cys Ala Ala Gly
    2675                2680                2685

Cys Ala Thr Cys Ala Gly Gly Ala Gly Cys Gly Cys Cys Thr Gly
        2690                2695                2700

Gly Cys Cys Cys Ala Gly Cys Thr Gly Gly Cys Thr Cys Gly Thr
    2705                2710                2715

Gly Ala Gly Gly Ala Cys Gly Cys Thr Gly Ala Gly Cys Gly Gly
        2720                2725                2730

Gly Ala Gly Cys Thr Gly Ala Ala Gly Gly Ala Gly Ala Ala Gly
    2735                2740                2745

Gly Ala Gly Gly Cys Cys Gly Cys Thr Cys Gly Gly Cys Gly Gly
        2750                2755                2760

Ala Ala Gly Ala Ala Gly Gly Ala Gly Cys Thr Cys Cys Thr Gly
    2765                2770                2775

Gly Ala Gly Cys Ala Gly Ala Thr Gly Gly Ala Ala Ala Gly Gly
        2780                2785                2790

Gly Cys Cys Cys Gly Cys Cys Ala Thr Gly Ala Gly Cys Cys Thr
    2795                2800                2805

Gly Thr Cys Ala Ala Thr Cys Ala Cys Thr Cys Ala Gly Ala Cys
        2810                2815                2820

Ala Thr Gly Gly Thr Gly Gly Ala Cys Ala Ala Gly Ala Thr Gly
    2825                2830                2835

Thr Thr Thr Gly Gly Cys Thr Thr Cys Cys Thr Gly Gly Gly Gly
        2840                2845                2850

Ala Cys Thr Thr Cys Ala Gly Gly Thr Gly Gly Cys Cys Thr Gly
    2855                2860                2865

Cys Cys Ala Gly Gly Cys Cys Ala Gly Gly Ala Gly Gly Gly Cys
        2870                2875                2880

Cys Ala Gly Gly Cys Ala Cys Thr Ala Gly Thr Gly Gly Cys
    2885                2890                2895

Thr Thr Thr Gly Ala Gly Gly
        2900                2905

<210> SEQ ID NO 68
<211> LENGTH: 968
<212> TYPE: PRT
<213> ORGANISM: Artificial Sequence
<220> FEATURE:
<223> OTHER INFORMATION: Synthetic

<400> SEQUENCE: 68

Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
            20                  25                  30

Ser Gly Gln Val Gln Val Val Asp Asp Glu Asp Asn Glu His Trp Ile
        35                  40                  45

Ser Pro Gln Asn Ala Thr His Ile Lys Pro Met His Pro Thr Ser Val
    50                  55                  60
```

```
His Gly Val Glu Asp Met Ile Arg Leu Gly Asp Leu Asn Glu Ala Gly
 65                  70                  75                  80

Ile Leu Arg Asn Leu Leu Ile Arg Tyr Arg Asp His Leu Ile Tyr Thr
                 85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
    210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
            260                 265                 270

Gly Gln Ala Ser Asp Tyr Asn Tyr Leu Ala Met Gly Asn Cys Ile Thr
        275                 280                 285

Cys Glu Gly Arg Val Asp Ser Gln Glu Tyr Ala Asn Ile Arg Ser Ala
    290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350

Ala Thr Ala Ala Ser Leu Leu Glu Val Asn Pro Pro Asp Leu Met Ser
        355                 360                 365

Cys Leu Thr Ser Arg Thr Leu Ile Thr Arg Gly Glu Thr Val Ser Thr
    370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
        435                 440                 445

Phe Glu Gln Leu Cys Ile Asn Phe Ala Asn Glu His Leu Gln Gln Phe
    450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
```

```
                     485                 490                 495
Asp Met Ile Ala Asn Lys Pro Met Asn Ile Ile Ser Leu Ile Asp Glu
                500                 505                 510
Glu Ser Lys Phe Pro Lys Gly Thr Asp Thr Thr Met Leu His Lys Leu
                515                 520                 525
Asn Ser Gln His Lys Leu Asn Ala Asn Tyr Ile Pro Pro Lys Asn Asn
            530                 535                 540
His Glu Thr Gln Phe Gly Ile Asn His Phe Ala Gly Ile Val Tyr Tyr
545                 550                 555                 560
Glu Thr Gln Gly Phe Leu Glu Lys Asn Arg Asp Thr Leu His Gly Asp
                565                 570                 575
Ile Ile Gln Leu Val His Ser Ser Arg Asn Lys Phe Ile Lys Gln Ile
                580                 585                 590
Phe Gln Ala Asp Val Ala Met Gly Ala Glu Thr Arg Lys Arg Ser Pro
            595                 600                 605
Thr Leu Ser Ser Gln Phe Lys Arg Ser Leu Glu Leu Leu Met Arg Thr
            610                 615                 620
Leu Gly Ala Cys Gln Pro Phe Phe Val Arg Cys Ile Lys Pro Asn Glu
625                 630                 635                 640
Phe Lys Lys Pro Met Leu Phe Asp Arg His Leu Cys Val Arg Gln Leu
                645                 650                 655
Arg Tyr Ser Gly Met Met Glu Thr Ile Arg Ile Arg Arg Ala Gly Tyr
                660                 665                 670
Pro Ile Arg Tyr Ser Phe Val Glu Phe Val Glu Arg Tyr Arg Val Leu
                675                 680                 685
Leu Pro Gly Val Lys Pro Ala Tyr Lys Gln Gly Asp Leu Arg Gly Thr
            690                 695                 700
Cys Gln Arg Met Ala Glu Ala Val Leu Gly Thr His Asp Asp Trp Gln
705                 710                 715                 720
Ile Gly Lys Thr Lys Ile Phe Leu Lys Asp His His Asp Met Leu Leu
                725                 730                 735
Glu Val Glu Arg Asp Lys Ala Ile Thr Asp Arg Val Ile Leu Leu Gln
            740                 745                 750
Lys Val Ile Arg Gly Phe Lys Asp Arg Ser Asn Phe Leu Lys Leu Lys
            755                 760                 765
Asn Ala Ala Thr Leu Ile Gln Arg His Trp Arg Gly His Asn Cys Arg
            770                 775                 780
Lys Asn Tyr Gly Leu Met Arg Leu Gly Phe Leu Arg Leu Gln Ala Leu
785                 790                 795                 800
His Arg Ser Arg Lys Leu His Gln Gln Tyr Arg Leu Ala Arg Gln Arg
                805                 810                 815
Ile Ile Gln Phe Gln Ala Arg Cys Arg Ala Tyr Leu Val Arg Lys Ala
                820                 825                 830
Phe Arg His Arg Leu Trp Ala Val Leu Thr Val Gln Ala Tyr Ala Arg
                835                 840                 845
Gly Met Ile Ala Arg Arg Leu His Gln Arg Leu Arg Ala Glu Tyr Leu
            850                 855                 860
Trp Arg Leu Glu Ala Glu Lys Met Arg Leu Ala Glu Glu Glu Lys Leu
865                 870                 875                 880
Arg Lys Glu Met Ser Ala Lys Lys Ala Lys Glu Glu Ala Glu Arg Lys
                885                 890                 895
His Gln Glu Arg Leu Ala Gln Leu Ala Arg Glu Asp Ala Glu Arg Glu
                900                 905                 910
```

Leu Lys Glu Lys Glu Ala Ala Arg Arg Lys Lys Glu Leu Leu Glu Gln
        915                 920                 925

Met Glu Arg Ala Arg His Glu Pro Val Asn His Ser Asp Met Val Asp
    930                 935                 940

Lys Met Phe Gly Phe Leu Gly Thr Ser Gly Gly Leu Pro Gly Gln Glu
945                 950                 955                 960

Gly Gln Ala Pro Ser Gly Phe Glu
                965

<210> SEQ ID NO 69
<211> LENGTH: 287
<212> TYPE: DNA
<213> ORGANISM: Artificial Sequence
<220> FEATURE:
<223> OTHER INFORMATION: Synthetic

<400> SEQUENCE: 69
ccccgggtgc gcggcgtcgg tggtgccggc gggggcgcc aggtcgcagg cggtgtaggg    60
ctccaggcag gcggcgaagg ccatgacgtg cgctatgaag gtctgctcct gcacgccgtg   120
aaccaggtgc gcctgcgggc cgcgcgcgaa caccgccacg tcctcgcctg cgtgggtctc   180
ttcgtccagg ggcactgctg actgctgccg atactcgggg ctcccgctct cgctctcggt   240
aacatccggc cgggcgccgt ccttgagcac atagcctgga ccgtttc                 287

<210> SEQ ID NO 70
<211> LENGTH: 287
<212> TYPE: DNA
<213> ORGANISM: Artificial Sequence
<220> FEATURE:
<223> OTHER INFORMATION: Synthetic

<400> SEQUENCE: 70
ccccgggtgc gcggcgtcgg tggtgccggc gggggcgcc aggtcgcagg cggtgtaggg    60
ctccaggcag gcggcgaagg ccatgacgtg cgctatgaag gtctgctcct gcacgccgtg   120
aaccaggtgc gcctgcgggc cgcgcgcgaa caccgccacg tcctcgcctg cgtgggtctc   180
ttcgtccagg ggcactgcgc actgctgccg atactcgggg ctcccgctct cgctctcggt   240
aacatccggc cgggcgccgt ccttgagcac atagcctgga ccgtttc                 287

<210> SEQ ID NO 71
<211> LENGTH: 3627
<212> TYPE: DNA
<213> ORGANISM: Artificial Sequence
<220> FEATURE:
<223> OTHER INFORMATION: 72

<400> SEQUENCE: 71
gacctggagc gagggcggag ggagatggtg gaggaggacc tggatgcagc cctgccctg    60 cctgacgagg atgaggagga cctctctgag tataaatttg ccaagttcgc ggccacctac   120
ttccagggga caaccacgca ctcctacacc cggcggccac tcaaacagcc actgctctac   180
catgacgacg agggtgacca gctggcagcc ctggcggtct ggatcaccat cctccgcttc   240
atgggggacc tccctgagcc caagtaccac acagccatga gtgatggcag tgagaagatc   300
cctgtgatga ccaagattta tgagaccctg gcaagaaga cgtacaagag ggagctgcag   360
gccctgcagg gcgagggcga ggcccagctc cccgagggcc agaagaagag cagtgtgagg   420
cacaagctgg tgcatttgac tctgaaaaag aagtccaagc tcacagagga ggtgaccaag   480

-continued

| | |
|---|---|
| aggctgcatg acggggagtc cacagtgcag ggcaacagca tgctggagga ccggcccacc | 540 |
| tccaacctgg agaagctgca cttcatcatc ggcaatggca tcctgcggcc agcactccgg | 600 |
| gacgagatct actgccagat cagcaagcag ctgacccaca cccctccaa gagcagctat | 660 |
| gcccggggct ggattctcgt gtctctctgc gtgggctgtt tcgcccctc cgagaagttt | 720 |
| gtcaagtacc tgcggaactt catccacggg ggcccgcccg gctacgcccc gtactgtgag | 780 |
| gagcgcctga gaaggacctt tgtcaatggg acacggacac agccgcccag ctggctggag | 840 |
| ctgcaggcca ccaagtccaa gaagccaatc atgttgcccg tgacattcat ggatgggacc | 900 |
| accaagaccc tgctgacgga ctcggcaacc acggccaagg agctctgcaa cgcgctggcc | 960 |
| gacaagatct ctctcaagga ccggttcggg ttctccctct acattgccct gtttgacaag | 1020 |
| gtgtcctccc tgggcagcgg cagtgaccac gtcatggacg ccatctccca gtgcgagcag | 1080 |
| tacgccaagg agcagggcgc ccaggagcgc aacgcccct ggaggctctt cttccgcaaa | 1140 |
| gaggtcttca cgccctggca cagcccctcc gaggacaacg tggccaccaa cctcatctac | 1200 |
| cagcaggtgt gcgaggagt caagtttggg gagtacaggt gtgagaagga ggacgacctg | 1260 |
| gctgagctgg cctcccagca gtactttgta gactatggct ctgagatgat cctggagcgc | 1320 |
| ctcctgaacc tcgtgcccac ctacatcccc gaccgcgaga tcacgcccct gaagacgctg | 1380 |
| gagaagtggg cccagctggc catcgccgcc cacaagaagg ggatttatgc ccagaggaga | 1440 |
| actgatgccc agaaggtcaa agaggatgtg gtcagttatg cccgcttcaa gtggcccttg | 1500 |
| ctcttctcca ggttttatga agcctacaaa ttctcaggcc ccagtctccc caagaacgac | 1560 |
| gtcatcgtgg ccgtcaactg gacggtgtgt actttgtgg atgagcagga gcaggtactt | 1620 |
| ctggagctgt ccttcccaga gatcatggcc gtgtccagca gcggggagc gaaaacgacg | 1680 |
| gcccccagct tcacgctggc caccatcaag ggggacgaat acaccttcac ctccagcaat | 1740 |
| gctgaggaca ttcgtgacct ggtggtcacc ttcctagagg ggctccggaa gagatctaag | 1800 |
| tatgttgtgg ccctgcagga taaccccaac cccgcaggcg aggagtcagg cttcctcagc | 1860 |
| tttgccaagg gagacctcat catcctggac catgacacgg gcgagcaggt catgaactcg | 1920 |
| ggctgggcca acggcatcaa tgagaggacc aagcagcgtg gggacttccc caccgacagt | 1980 |
| gtgtacgtca tgcccactgt caccatgcca ccgcgggaga ttgtggccct ggtcaccatg | 2040 |
| actcccgatc agaggcagga cgttgtccgg ctcttgcagc tgcgaacggc ggagcccgag | 2100 |
| gtgcgtgcca agccctacac gctggaggag ttttcctatg actacttcag gccccaccc | 2160 |
| aagcacacgc tgagccgtgt catggtgtcc aaggcccgag gcaaggaccg gctgtggagc | 2220 |
| cacacgcggg aaccgctcaa gcaggcgctg ctcaagaagc tcctgggcag tgaggagctc | 2280 |
| tcgcaggagg cctgcctggc cttcattgct gtgctcaagt acatgggcga ctacccgtcc | 2340 |
| aagaggacac gctccgtcaa cgagctcacc gaccagatct ttgagggtcc cctgaaagcc | 2400 |
| gagcccctga aggacgaggc atatgtgcag atcctgaagc agctgaccga caaccacatc | 2460 |
| aggtacagcg aggagcgggg ttgggagctg ctctggctgt gcacgggcct tttcccaccc | 2520 |
| agcaacatcc tcctgcccca cgtgcagcgc ttcctgcagt cccgaaagca ctgcccactc | 2580 |
| gccatcgact gcctgcaacg gctccagaaa gccctgagaa acgggtcccg gaagtaccct | 2640 |
| ccgcacctgg tggaggtgga ggccatccag cacaagacca cccagatttt ccacaaagtc | 2700 |
| tacttccctg atgacactga cgaggccttc gaagtggagt ccagcaccaa ggccaaggac | 2760 |
| ttctgccaga catcgccac caggctgctc ctcaagtcct cagagggatt cagcctctttt | 2820 |
| gtcaaaattg cagacaaggt catcagcgtt cctgagaatg acttcttctt tgactttgtt | 2880 |

```
cgacacttga cagactggat aaagaaagct cggcccatca aggacggaat tgtgccctca    2940
ctcacctacc aggtgttctt catgaagaag ctgtggacca ccacggtgcc agggaaggat    3000
cccatggccg attccatctt ccactattac caggagttgc ccaagtatct ccgaggctac    3060
cacaagtgca cgcgggagga ggtgctgcag ctggggcgc tgatctacag ggtcaagttc     3120
gaggaggaca agtcctactt ccccagcatc cccaagctgc tgcgggagct ggtgcccag     3180 gaccttatcc ggcaggtctc acctgatgac tggaagcggt ccatcgtcgc ctacttcaac    3240
aagcacgcag ggaagtccaa ggaggaggcc aagctggcct tcctgaagct catcttcaag    3300
tggcccacct ttggctcagc cttcttcgag gtgaagcaaa ctacggagcc aaacttccct    3360
gagatcctcc taattgccat caacaagtat ggggtcagcc tcatcgatcc caaaacgaag    3420
gatatcctca ccactcatcc cttccaccaag atctccaact ggagcagcgg caacacctac   3480
ttccacatca ccattgggaa cttggtgcgc gggagcaaac tgctctgcga cgtcactg     3540 ggctacaaga tggatgacct cctgacttcc tacattagcc agatgctcac agccatgagc    3600
aaacagcggg gctccaggag cggcaag                                        3627

<210> SEQ ID NO 72
<211> LENGTH: 30
<212> TYPE: DNA
<213> ORGANISM: Artificial Sequence
<220> FEATURE:
<223> OTHER INFORMATION: Synthetic

<400> SEQUENCE: 72
taccCttacg atgtaccgga ttacgcatga                                       30

<210> SEQ ID NO 73
<211> LENGTH: 2586
<212> TYPE: DNA
<213> ORGANISM: Artificial Sequence
<220> FEATURE:
<223> OTHER INFORMATION: Synthetic

<400> SEQUENCE: 73
atggtgattc ttcagcaggg ggaccatgtg tggatggacc tgagattggg gcaggagttc      60
gacgtgccca tcggggcggt ggtgaagctc tgcgactctg gcaggtcca ggtggtggat     120 gatgaagaca atgaacactg gatctctccg cagaacgcaa cgcacatcaa gcctatgcac    180
cccacgtcgg tccacggcgt ggaggacatg atccgcctgg gggacctcaa cgaggcgggc    240
atcttgcgca acctgcttat ccgctaccgg gaccacctca tctacacgta tacgggctcc    300
atcctggtgg ctgtgaaccc ctaccagctg ctctccatct actcgccaga gcacatccgc    360
cagtatacca caagaagat tggggagatg ccccccaca tctttgccat tgctgacaac     420
tgctacttca acatgaaacg caacagccga ccagtgctg catcatcag tggggaatct     480 ggggccggga agacgagag cacaaagctg atcctgcagt tcctggcagc catcagtggg    540
cagcactcgt ggattgagca gcaggtcttg gaggccaccc ccattctgga agcatttggg    600
aatgccaaga ccatccgcaa tgacaactca agccgtttcg gaaagtacat cgacatccac    660
ttcaacaagc ggggcgccat cgagggcgcg aagattgagc agtacctgct ggaaaagtca    720
cgtgtctgtc gccaggccct ggatgaaagg aactaccacg tgttctactg catgctggag    780
ggtatgagtg aggatcagaa gaagaagctg ggcttgggcc aggcctctga ctacaactac    840
ttggccatgg gtaactgcat aacctgtgag ggccgggtgg acagccagga gtacgccaac    900
```

| | |
|---|---|
| atccgctccg ccatgaaggt gctcatgttc actgacaccg agaactggga gatctcgaag | 960 |
| ctcctggctg ccatcctgca cctgggcaac ctgcagtatg aggcacgcac atttgaaaac | 1020 |
| ctggatgcct gtgaggttct cttctcccca tcgctggcca cagctgcatc cctgcttgag | 1080 |
| gtgaaccccc cagacctgat gagctgcctg actagccgca ccctcatcac ccgcggggag | 1140 |
| acggtgtcca ccccactgag cagggaacag gcactggacg tgcgcgacgc cttcgtaaag | 1200 |
| gggatctacg gcggctgtt cgtgtggatt gtggacaaga tcaacgcagc aatttacaag | 1260 |
| cctccctccc aggatgtgaa gaactctcgc aggtccatcg gcctcctgga catctttggg | 1320 |
| tttgagaact tgctgtgaa cagctttgag cagctctgca tcaacttcgc caatgagcac | 1380 |
| ctgcagcagt tctttgtgcg gcacgtgttc aagctggagc aggaggaata tgacctggag | 1440 |
| agcattgact ggctgcacat cgagttcact gacaaccagg atgccctgga catgattgcc | 1500 |
| aacaagccca tgaacatcat ctccctcatc gatgaggaga gcaagttccc caagggcaca | 1560 |
| gacaccacca tgttacacaa gctgaactcc cagcacaagc tcaacgccaa ctacatcccc | 1620 |
| cccaagaaca accatgagac ccagtttggc atcaaccatt ttgcaggcat cgtctactat | 1680 |
| gagacccaag gcttcctgga gaagaaccga gacaccctgc atggggacat tatccagctg | 1740 |
| gtccactcct ccaggaacaa gttcatcaag cagatcttcc aggccgatgt cgccatgggc | 1800 |
| gccgagacca ggaagcgctc gcccacactt agcagccagt tcaagcggtc actggagctg | 1860 |
| ctgatgcgca cgctgggtgc ctgccagccc ttctttgtgc gatgcatcaa gcccaatgag | 1920 |
| ttcaagaagc ccatgctgtt cgaccggcac ctgtgcgtgc gccagctgcg gtactcagga | 1980 |
| atgatggaga ccatccgaat ccgccgagct ggctacccca tccgctacag cttcgtagag | 2040 |
| tttgtggagc ggtaccgtgt gctgctgcca ggtgtgaagc cggcctacaa gcagggcgac | 2100 |
| ctccgcggga cttgccagcg catggctgag gctgtgctgg caccacga tgactggcag | 2160 |
| ataggcaaaa ccaagatctt tctgaaggac caccatgaca tgctgctgga agtggagcgg | 2220 |
| gacaaagcca tcaccgacag agtcatcctc cttcagaaag tcatccgggg attcaaagac | 2280 |
| aggtctaact ttctgaagct gaagaacgct gccacactga tccagaggca ctggcggggt | 2340 |
| cacaactgta ggaagaacta cgggctgatg cgtctgggct tcctgcggct gcaggccctg | 2400 |
| caccgctccc ggaagctgca ccagcagtac cgcctggccc gccagcgcat catccagttc | 2460 |
| caggcccgct gccgcgccta tctggtgcgc aaggccttcc gccaccgcct ctgggctgtg | 2520 |
| ctcaccgtgc aggcctatgc ccggggcatg atcgcccgca ggctgcacca acgcctcagg | 2580 |
| gctgag | 2586 |

```
<210> SEQ ID NO 74
<211> LENGTH: 862
<212> TYPE: PRT
<213> ORGANISM: Artificial Sequence
<220> FEATURE:
<223> OTHER INFORMATION: Synthetic

<400> SEQUENCE: 74

Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
                20                  25                  30

Ser Gly Gln Val Gln Val Val Asp Asp Glu Asp Asn Glu His Trp Ile
        35                  40                  45

Ser Pro Gln Asn Ala Thr His Ile Lys Pro Met His Pro Thr Ser Val
    50                  55                  60
```

```
His Gly Val Glu Asp Met Ile Arg Leu Gly Asp Leu Asn Glu Ala Gly
 65                  70                  75                  80

Ile Leu Arg Asn Leu Leu Ile Arg Tyr Arg Asp His Leu Ile Tyr Thr
                 85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125

Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Gln Val Leu Glu Ala
            180                 185                 190

Thr Pro Ile Leu Glu Ala Phe Gly Asn Ala Lys Thr Ile Arg Asn Asp
        195                 200                 205

Asn Ser Ser Arg Phe Gly Lys Tyr Ile Asp Ile His Phe Asn Lys Arg
210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
            260                 265                 270

Gly Gln Ala Ser Asp Tyr Asn Tyr Leu Ala Met Gly Asn Cys Ile Thr
        275                 280                 285

Cys Glu Gly Arg Val Asp Ser Gln Glu Tyr Ala Asn Ile Arg Ser Ala
    290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350

Ala Thr Ala Ala Ser Leu Leu Glu Val Asn Pro Pro Asp Leu Met Ser
        355                 360                 365

Cys Leu Thr Ser Arg Thr Leu Ile Thr Arg Gly Glu Thr Val Ser Thr
    370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
        435                 440                 445

Phe Glu Gln Leu Cys Ile Asn Phe Ala Asn Glu His Leu Gln Gln Phe
    450                 455                 460

Phe Val Arg His Val Phe Lys Leu Glu Gln Glu Glu Tyr Asp Leu Glu
465                 470                 475                 480
```

```
Ser Ile Asp Trp Leu His Ile Glu Phe Thr Asp Asn Gln Asp Ala Leu
                485                 490                 495
Asp Met Ile Ala Asn Lys Pro Met Asn Ile Ile Ser Leu Ile Asp Glu
            500                 505                 510
Glu Ser Lys Phe Pro Lys Gly Thr Asp Thr Thr Met Leu His Lys Leu
        515                 520                 525
Asn Ser Gln His Lys Leu Asn Ala Asn Tyr Ile Pro Pro Lys Asn Asn
    530                 535                 540
His Glu Thr Gln Phe Gly Ile Asn His Phe Ala Gly Ile Val Tyr Tyr
545                 550                 555                 560
Glu Thr Gln Gly Phe Leu Glu Lys Asn Arg Asp Thr Leu His Gly Asp
                565                 570                 575
Ile Ile Gln Leu Val His Ser Ser Arg Asn Lys Phe Ile Lys Gln Ile
            580                 585                 590
Phe Gln Ala Asp Val Ala Met Gly Ala Glu Thr Arg Lys Arg Ser Pro
        595                 600                 605
Thr Leu Ser Ser Gln Phe Lys Arg Ser Leu Glu Leu Leu Met Arg Thr
    610                 615                 620
Leu Gly Ala Cys Gln Pro Phe Phe Val Arg Cys Ile Lys Pro Asn Glu
625                 630                 635                 640
Phe Lys Lys Pro Met Leu Phe Asp Arg His Leu Cys Val Arg Gln Leu
                645                 650                 655
Arg Tyr Ser Gly Met Met Glu Thr Ile Arg Ile Arg Arg Ala Gly Tyr
            660                 665                 670
Pro Ile Arg Tyr Ser Phe Val Glu Phe Val Glu Arg Tyr Arg Val Leu
        675                 680                 685
Leu Pro Gly Val Lys Pro Ala Tyr Lys Gln Gly Asp Leu Arg Gly Thr
    690                 695                 700
Cys Gln Arg Met Ala Glu Ala Val Leu Gly Thr His Asp Asp Trp Gln
705                 710                 715                 720
Ile Gly Lys Thr Lys Ile Phe Leu Lys Asp His His Asp Met Leu Leu
                725                 730                 735
Glu Val Glu Arg Asp Lys Ala Ile Thr Asp Arg Val Ile Leu Leu Gln
            740                 745                 750
Lys Val Ile Arg Gly Phe Lys Asp Arg Ser Asn Phe Leu Lys Leu Lys
        755                 760                 765
Asn Ala Ala Thr Leu Ile Gln Arg His Trp Arg Gly His Asn Cys Arg
    770                 775                 780
Lys Asn Tyr Gly Leu Met Arg Leu Gly Phe Leu Arg Leu Gln Ala Leu
785                 790                 795                 800
His Arg Ser Arg Lys Leu His Gln Gln Tyr Arg Leu Ala Arg Gln Arg
                805                 810                 815
Ile Ile Gln Phe Gln Ala Arg Cys Arg Ala Tyr Leu Val Arg Lys Ala
            820                 825                 830
Phe Arg His Arg Leu Trp Ala Val Leu Thr Val Gln Ala Tyr Ala Arg
        835                 840                 845
Gly Met Ile Ala Arg Arg Leu His Gln Arg Leu Arg Ala Glu
    850                 855                 860

<210> SEQ ID NO 75
<211> LENGTH: 3945
<212> TYPE: DNA
<213> ORGANISM: Artificial Sequence
<220> FEATURE:
<223> OTHER INFORMATION: Synthetic
```

<400> SEQUENCE: 75

```
tatctgtggc gcctcgaggc tgagaaaatg cggctggcgg aggaagagaa gcttcggaag        60
gagatgagcg ccaagaaggc caaggaggag gccgagcgca agcatcagga gcgcctggcc       120
cagctggctc gtgaggacgc tgagcgggag ctgaaggaga aggaggccgc tcggcggaag       180
aaggagctcc tggagcagat ggaaagggcc cgccatgagc ctgtcaatca ctcagacatg       240
gtggacaaga tgtttggctt cctggggact tcaggtggcc tgccaggcca ggagggccag       300
gcacctagtg gctttgagga cctggagcga gggcggaggg agatggtgga ggaggacctg       360
gatgcagccc tgcccctgcc tgacgaggat gaggaggacc tctctgagta taaatttgcc       420
aagttcgcgg ccacctactt ccaggggaca accacgcact cctacacccg gcggccactc       480
aaacagccac tgctctacca tgacgacgag ggtgaccagc tggcagccct ggcggtctgg       540
atcaccatcc tccgcttcat ggggaccctc cctgagccca gtaccacac agccatgagt       600
gatggcagtg agaagatccc tgtgatgacc aagatttatg agaccctggg caagaagacg       660
tacaagaggg agctgcaggc cctgcaggc gagggcgagg cccagctccc cgagggccag       720
aagaagagca gtgtgaggca caagctggtg catttgactc tgaaaaagaa gtccaagctc       780
acagaggagg tgaccaagag gctgcatgac ggggagtcca cagtgcaggg caacagcatg       840
ctggaggacc ggcccacctc caacctggag aagctgcact tcatcatcgg caatggcatc       900
ctgcggccag cactccggga cgagatctac tgccagatca gcaagcagct gacccacaac       960
ccctccaaga gcagctatgc ccggggctgg attctcgtgt ctctctgcgt gggctgtttc      1020
gccccctccg agaagtttgt caagtacctg cggaacttca tccacggggg cccgcccggc      1080
tacgccccgt actgtgagga gcgcctgaga aggacctttg tcaatgggac acggacacag      1140
ccgcccagct ggctggagct gcaggccacc aagtccaaga agccaatcat gttgcccgtg      1200
acattcatgg atgggaccac caagaccctg ctgacggact cggcaaccac ggccaaggag      1260
ctctgcaacg cgctggccga caagatctct ctcaaggacc ggttcgggtt ctccctctac      1320
attgccctgt ttgacaaggt gtcctccctg gcagcggca gtgaccacgt catggacgcc      1380
atctcccagt gcgagcagta cgccaaggag caggcgccc aggagcgcaa cgcccctgg      1440
aggctcttct tccgcaaaga ggtcttcacg ccctggcaca gccctccga ggacaacgtg      1500
gccaccaacc tcatctacca gcaggtggtg cgaggagtca gtttggggga gtacaggtgt      1560
gagaaggagg acgacctggc tgagctggcc tcccagcagt actttgtaga ctatggctct      1620
gagatgatcc tggagcgcct cctgaacctc gtgcccacct acatccccga ccgcgagatc      1680
acgcccctga gacgctggga gaagtgggcc cagctggcca tcgccgccca caagaagggg      1740
atttatgccc agaggagaac tgatgcccag aaggtcaaag aggatgtggt cagttatgcc      1800
cgcttcaagt ggcccttgct cttctccagg ttttatgaag cctacaaatt ctcaggcccc      1860
agtctcccca gaacgacgt catcgtggcc gtcaactgga cgggtgtgta ctttgtggat      1920
gagcaggagc aggtacttct ggagctgtcc ttcccagaga tcatggccgt gtccagcagc      1980
aggggagcga aaacgacggc ccccagcttc acgctggcca ccatcaaggg ggacgaatac      2040
accttcacct ccagcaatgc tgaggacatt cgtgacctgg tggtcacctt cctagagggg      2100
ctccggaaga gatctaagta tgttgtggcc ctgcaggata ccccaacccc gcaggcgag      2160
gagtcaggct cctcagcttt gccaagggga gacctcatca tcctggacca tgacacgggc      2220
gagcaggtca tgaactcggg ctgggccaac ggcatcaatg agaggaccaa gcagcgtggg      2280
```

```
gacttcccca ccgacagtgt gtacgtcatg cccactgtca ccatgccacc gcgggagatt    2340
gtggccctgg tcaccatgac tcccgatcag aggcaggacg ttgtccggct cttgcagctg    2400
cgaacggcgg agcccgaggt gcgtgccaag ccctacacgc tggaggagtt ttcctatgac    2460
tacttcaggc ccccacccaa gcacacgctg agccgtgtca tggtgtccaa ggcccgaggc    2520
aaggaccggc tgtggagcca cacgcgggaa ccgctcaagc aggcgctgct caagaagctc    2580
ctgggcagtg aggagctctc gcaggaggcc tgcctggcct tcattgctgt gctcaagtac    2640
atgggcgact acccgtccaa gaggacacgc tccgtcaacg agctcaccga ccagatcttt    2700
gagggtcccc tgaaagccga gcccctgaag gacgaggcat atgtgcagat cctgaagcag    2760
ctgaccgaca accacatcag gtacagcgag gagcggggtt gggagctgct ctggctgtgc    2820
acggcctttt ccccacccag caacatcctc ctgccccacg tgcagcgctt cctgcagtcc    2880
cgaaagcact gcccactcgc catcgactgc ctgcaacggc tccagaaagc cctgagaaac    2940
gggtcccgga agtaccctcc gcacctggtg gaggtggagg ccatccagca aagaccacc    3000 cagattttcc acaaagtcta cttccctgat gacactgacg aggccttcga agtggagtcc    3060
agcaccaagg ccaaggactt ctgccagaac atcgccacca ggctgctcct caagtcctca    3120
gagggattca gcctctttgt caaaattgca gacaaggtca tcagcgttcc tgagaatgac    3180
ttcttctttg actttgttcg acacttgaca gactggataa agaaagctcg gcccatcaag    3240
gacggaattg tgccctcact cacctaccag gtgttcttca tgaagaagct gtggaccacc    3300
acggtgccag ggaaggatcc catggccgat tccatcttcc actattacca ggagttgccc    3360
aagtatctcc gaggctacca caagtgcacg cgggaggagg tgctgcagct gggggcgctg    3420
atctacaggg tcaagttcga ggaggacaag tcctacttcc ccagcatccc caagctgctg    3480
cgggagctgt tgccccagga ccttatccgg caggtctcac ctgatgactg gagcggtcc    3540 atcgtcgcct acttcaacaa gcacgcaggg aagtccaagg aggaggccaa gctggccttc    3600
ctgaagctca tcttcaagtg gcccaccttt ggctcagcct tcttcgaggt gaagcaaact    3660
acggagccaa acttccctga tcctcccta attgccatca caagtatgg ggtcagcctc    3720 atcgatccca aaacgaagga tatcctcacc actcatccct tcaccaagat ctccaactgg    3780
agcagcggca cacctactt ccacatcacc attgggaact tggtgcgcgg gagcaaactg    3840
ctctgcgaga cgtcactggg ctacaagatg atgaccctcc tgacttccta cattagccag    3900
atgctcacag ccatgagcaa acagcggggc tccaggagcg gcaag                    3945
```

<210> SEQ ID NO 76  
<211> LENGTH: 1315  
<212> TYPE: PRT  
<213> ORGANISM: Artificial Sequence  
<220> FEATURE:  
<223> OTHER INFORMATION: Synthetic

<400> SEQUENCE: 76

```
Tyr Leu Trp Arg Leu Glu Ala Glu Lys Met Arg Leu Ala Glu Glu Glu
1               5                   10                  15

Lys Leu Arg Lys Glu Met Ser Ala Lys Ala Lys Glu Glu Ala Glu
            20                  25                  30

Arg Lys His Gln Glu Arg Leu Ala Gln Leu Ala Arg Glu Asp Ala Glu
        35                  40                  45

Arg Glu Leu Lys Glu Lys Glu Ala Ala Arg Arg Lys Lys Glu Leu Leu
    50                  55                  60

Glu Gln Met Glu Arg Ala Arg His Glu Pro Val Asn His Ser Asp Met
```

```
                65                  70                  75                  80
Val Asp Lys Met Phe Gly Phe Leu Gly Thr Ser Gly Gly Leu Pro Gly
                        85                  90                  95

Gln Glu Gly Gln Ala Pro Ser Gly Phe Glu Asp Leu Glu Arg Gly Arg
                100                 105                 110

Arg Glu Met Val Glu Asp Leu Asp Ala Ala Leu Pro Leu Pro Asp
                115                 120                 125

Glu Asp Glu Asp Leu Ser Glu Tyr Lys Phe Ala Lys Phe Ala Ala
            130                 135                 140

Thr Tyr Phe Gln Gly Thr Thr His Ser Tyr Thr Arg Arg Pro Leu
145                 150                 155                 160

Lys Gln Pro Leu Leu Tyr His Asp Asp Glu Gly Asp Gln Leu Ala Ala
                165                 170                 175

Leu Ala Val Trp Ile Thr Ile Leu Arg Phe Met Gly Asp Leu Pro Glu
                180                 185                 190

Pro Lys Tyr His Thr Ala Met Ser Asp Gly Ser Glu Lys Ile Pro Val
                195                 200                 205

Met Thr Lys Ile Tyr Glu Thr Leu Gly Lys Lys Thr Tyr Lys Arg Glu
                210                 215                 220

Leu Gln Ala Leu Gln Gly Glu Gly Glu Ala Gln Leu Pro Glu Gly Gln
225                 230                 235                 240

Lys Lys Ser Ser Val Arg His Lys Leu Val His Leu Thr Leu Lys Lys
                245                 250                 255

Lys Ser Lys Leu Thr Glu Glu Val Thr Lys Arg Leu His Asp Gly Glu
                260                 265                 270

Ser Thr Val Gln Gly Asn Ser Met Leu Glu Asp Arg Pro Thr Ser Asn
                275                 280                 285

Leu Glu Lys Leu His Phe Ile Ile Gly Asn Gly Ile Leu Arg Pro Ala
                290                 295                 300

Leu Arg Asp Glu Ile Tyr Cys Gln Ile Ser Lys Gln Leu Thr His Asn
305                 310                 315                 320

Pro Ser Lys Ser Ser Tyr Ala Arg Gly Trp Ile Leu Val Ser Leu Cys
                325                 330                 335

Val Gly Cys Phe Ala Pro Ser Glu Lys Phe Val Lys Tyr Leu Arg Asn
                340                 345                 350

Phe Ile His Gly Gly Pro Pro Gly Tyr Ala Pro Tyr Cys Glu Glu Arg
                355                 360                 365

Leu Arg Arg Thr Phe Val Asn Gly Thr Arg Thr Gln Pro Pro Ser Trp
                370                 375                 380

Leu Glu Leu Gln Ala Thr Lys Ser Lys Lys Pro Ile Met Leu Pro Val
385                 390                 395                 400

Thr Phe Met Asp Gly Thr Thr Lys Thr Leu Leu Thr Asp Ser Ala Thr
                405                 410                 415

Thr Ala Lys Glu Leu Cys Asn Ala Leu Ala Asp Lys Ile Ser Leu Lys
                420                 425                 430

Asp Arg Phe Gly Phe Ser Leu Tyr Ile Ala Leu Phe Asp Lys Val Ser
                435                 440                 445

Ser Leu Gly Ser Gly Ser Asp His Val Met Asp Ala Ile Ser Gln Cys
                450                 455                 460

Glu Gln Tyr Ala Lys Glu Gln Gly Ala Gln Glu Arg Asn Ala Pro Trp
465                 470                 475                 480

Arg Leu Phe Phe Arg Lys Glu Val Phe Thr Pro Trp His Ser Pro Ser
                485                 490                 495
```

Glu Asp Asn Val Ala Thr Asn Leu Ile Tyr Gln Gln Val Val Arg Gly
            500                 505                 510

Val Lys Phe Gly Glu Tyr Arg Cys Glu Lys Glu Asp Leu Ala Glu
        515                 520                 525

Leu Ala Ser Gln Gln Tyr Phe Val Asp Tyr Gly Ser Glu Met Ile Leu
    530                 535                 540

Glu Arg Leu Leu Asn Leu Val Pro Thr Tyr Ile Pro Asp Arg Glu Ile
545                 550                 555                 560

Thr Pro Leu Lys Thr Leu Glu Lys Trp Ala Gln Leu Ala Ile Ala Ala
            565                 570                 575

His Lys Lys Gly Ile Tyr Ala Gln Arg Arg Thr Asp Ala Gln Lys Val
        580                 585                 590

Lys Glu Asp Val Val Ser Tyr Ala Arg Phe Lys Trp Pro Leu Leu Phe
        595                 600                 605

Ser Arg Phe Tyr Glu Ala Tyr Lys Phe Ser Gly Pro Ser Leu Pro Lys
        610                 615                 620

Asn Asp Val Ile Val Ala Val Asn Trp Thr Gly Val Tyr Phe Val Asp
625                 630                 635                 640

Glu Gln Glu Gln Val Leu Leu Glu Leu Ser Phe Pro Glu Ile Met Ala
                645                 650                 655

Val Ser Ser Ser Arg Gly Ala Lys Thr Thr Ala Pro Ser Phe Thr Leu
            660                 665                 670

Ala Thr Ile Lys Gly Asp Glu Tyr Thr Phe Thr Ser Ser Asn Ala Glu
        675                 680                 685

Asp Ile Arg Asp Leu Val Val Thr Phe Leu Glu Gly Leu Arg Lys Arg
        690                 695                 700

Ser Lys Tyr Val Val Ala Leu Gln Asp Asn Pro Asn Pro Ala Gly Glu
705                 710                 715                 720

Glu Ser Gly Phe Leu Ser Phe Ala Lys Gly Asp Leu Ile Ile Leu Asp
                725                 730                 735

His Asp Thr Gly Glu Gln Val Met Asn Ser Gly Trp Ala Asn Gly Ile
            740                 745                 750

Asn Glu Arg Thr Lys Gln Arg Gly Asp Phe Pro Thr Asp Ser Val Tyr
        755                 760                 765

Val Met Pro Thr Val Thr Met Pro Pro Arg Glu Ile Val Ala Leu Val
770                 775                 780

Thr Met Thr Pro Asp Gln Arg Gln Asp Val Val Arg Leu Leu Gln Leu
785                 790                 795                 800

Arg Thr Ala Glu Pro Glu Val Arg Ala Lys Pro Tyr Thr Leu Glu Glu
            805                 810                 815

Phe Ser Tyr Asp Tyr Phe Arg Pro Pro Lys His Thr Leu Ser Arg
        820                 825                 830

Val Met Val Ser Lys Ala Arg Gly Lys Asp Arg Leu Trp Ser His Thr
    835                 840                 845

Arg Glu Pro Leu Lys Gln Ala Leu Leu Lys Leu Leu Gly Ser Glu
            850                 855                 860

Glu Leu Ser Gln Glu Ala Cys Leu Ala Phe Ile Ala Val Leu Lys Tyr
865                 870                 875                 880

Met Gly Asp Tyr Pro Ser Lys Arg Thr Arg Ser Val Asn Glu Leu Thr
                885                 890                 895

Asp Gln Ile Phe Glu Gly Pro Leu Lys Ala Glu Pro Leu Lys Asp Glu
            900                 905                 910

```
Ala Tyr Val Gln Ile Leu Lys Gln Leu Thr Asp Asn His Ile Arg Tyr
            915                 920                 925

Ser Glu Glu Arg Gly Trp Glu Leu Leu Trp Leu Cys Thr Gly Leu Phe
        930                 935                 940

Pro Pro Ser Asn Ile Leu Leu Pro His Val Gln Arg Phe Leu Gln Ser
945                 950                 955                 960

Arg Lys His Cys Pro Leu Ala Ile Asp Cys Leu Gln Arg Leu Gln Lys
                965                 970                 975

Ala Leu Arg Asn Gly Ser Arg Lys Tyr Pro Pro His Leu Val Glu Val
            980                 985                 990

Glu Ala Ile Gln His Lys Thr Thr Gln Ile Phe His Lys Val Tyr Phe
        995                 1000                1005

Pro Asp Asp Thr Asp Glu Ala Phe Glu Val Glu Ser Ser Thr Lys
    1010                1015                1020

Ala Lys Asp Phe Cys Gln Asn Ile Ala Thr Arg Leu Leu Leu Lys
    1025                1030                1035

Ser Ser Glu Gly Phe Ser Leu Phe Val Lys Ile Ala Asp Lys Val
    1040                1045                1050

Ile Ser Val Pro Glu Asn Asp Phe Phe Phe Asp Phe Val Arg His
    1055                1060                1065

Leu Thr Asp Trp Ile Lys Lys Ala Arg Pro Ile Lys Asp Gly Ile
    1070                1075                1080

Val Pro Ser Leu Thr Tyr Gln Val Phe Phe Met Lys Lys Leu Trp
    1085                1090                1095

Thr Thr Thr Val Pro Gly Lys Asp Pro Met Ala Asp Ser Ile Phe
    1100                1105                1110

His Tyr Tyr Gln Glu Leu Pro Lys Tyr Leu Arg Gly Tyr His Lys
    1115                1120                1125

Cys Thr Arg Glu Glu Val Leu Gln Leu Gly Ala Leu Ile Tyr Arg
    1130                1135                1140

Val Lys Phe Glu Glu Asp Lys Ser Tyr Phe Pro Ser Ile Pro Lys
    1145                1150                1155

Leu Leu Arg Glu Leu Val Pro Gln Asp Leu Ile Arg Gln Val Ser
    1160                1165                1170

Pro Asp Asp Trp Lys Arg Ser Ile Val Ala Tyr Phe Asn Lys His
    1175                1180                1185

Ala Gly Lys Ser Lys Glu Glu Ala Lys Leu Ala Phe Leu Lys Leu
    1190                1195                1200

Ile Phe Lys Trp Pro Thr Phe Gly Ser Ala Phe Phe Glu Val Lys
    1205                1210                1215

Gln Thr Thr Glu Pro Asn Phe Pro Glu Ile Leu Leu Ile Ala Ile
    1220                1225                1230

Asn Lys Tyr Gly Val Ser Leu Ile Asp Pro Lys Thr Lys Asp Ile
    1235                1240                1245

Leu Thr Thr His Pro Phe Thr Lys Ile Ser Asn Trp Ser Ser Gly
    1250                1255                1260

Asn Thr Tyr Phe His Ile Thr Ile Gly Asn Leu Val Arg Gly Ser
    1265                1270                1275

Lys Leu Leu Cys Glu Thr Ser Leu Gly Tyr Lys Met Asp Asp Leu
    1280                1285                1290

Leu Thr Ser Tyr Ile Ser Gln Met Leu Thr Ala Met Ser Lys Gln
    1295                1300                1305

Arg Gly Ser Arg Ser Gly Lys
```

<210> SEQ ID NO 77
<211> LENGTH: 4170
<212> TYPE: DNA
<213> ORGANISM: Artificial Sequence
<220> FEATURE:
<223> OTHER INFORMATION: Synthetic

<400> SEQUENCE: 77

| | | | | | |
|---|---|---|---|---|---|
| gggctgatgc | gtctgggctt | cctgcggctg | caggccctgc | accgctcccg | gaagctgcac | 60 |
| cagcagtacc | gcctggcccg | ccagcgcatc | atccagttcc | aggcccgctg | ccgcgcctat | 120 |
| ctggtgcgca | aggccttccg | ccaccgcctc | tgggctgtgc | tcaccgtgca | ggcctatgcc | 180 |
| cggggcatga | tcgcccgcag | gctgcaccaa | cgcctcaggg | ctgagtatct | gtggcgcctc | 240 |
| gaggctgaga | aaatgcggct | ggcggaggaa | gagaagcttc | ggaaggagat | gagcgccaag | 300 |
| aaggccaagg | aggaggccga | gcgcaagcat | caggagcgcc | tgcccagct | ggctcgtgag | 360 |
| gacgctgagc | gggagctgaa | ggagaaggag | gccgctcggc | ggaagaagga | gctcctggag | 420 |
| cagatggaaa | gggcccgcca | tgagcctgtc | aatcactcag | acatggtgga | caagatgttt | 480 |
| ggcttcctgg | ggacttcagg | tggcctgcca | ggccaggagg | gccaggcacc | tagtggcttt | 540 |
| gaggacctgg | agcgagggcg | gagggagatg | gtggaggagg | acctggatgc | agccctgccc | 600 |
| ctgcctgacg | aggatgagga | ggacctctct | gagtataaat | tgccaagtt | cgcggccacc | 660 |
| tacttccagg | ggacaaccac | gcactcctac | acccggcggc | cactcaaaca | gccactgctc | 720 |
| taccatgacg | acgagggtga | ccagctggca | gccctggcgg | tctggatcac | catcctccgc | 780 |
| ttcatggggg | acctccctga | gcccaagtac | cacacagcca | tgagtgatgg | cagtgagaag | 840 |
| atccctgtga | tgaccaagat | ttatgagacc | ctgggcaaga | gacgtacaa | gagggagctg | 900 |
| caggccctgc | agggcgaggg | cgaggcccag | ctccccgagg | gccagaagaa | gagcagtgtg | 960 |
| aggcacaagc | tggtgcattt | gactctgaaa | aagaagtcca | agctcacaga | ggaggtgacc | 1020 |
| aagaggctgc | atgacgggga | gtccacagtg | cagggcaaca | gcatgctgga | ggaccggccc | 1080 |
| acctccaacc | tggagaagct | gcacttcatc | atcggcaatg | catcctgcg | ccagcactc | 1140 |
| cgggacgaga | tctactgcca | gatcagcaag | cagctgaccc | acaaccctc | caagagcagc | 1200 |
| tatgcccggg | gctggattct | cgtgtctctc | tgcgtgggct | gtttcgcccc | ctccgagaag | 1260 |
| tttgtcaagt | acctgcggaa | cttcatccac | gggggcccgc | ccggctacgc | cccgtactgt | 1320 |
| gaggagcgcc | tgagaaggac | ctttgtcaat | gggacacgga | cacagccgcc | cagctggctg | 1380 |
| gagctgcagg | ccaccaagtc | caagaagcca | atcatgttgc | ccgtgacatt | catggatggg | 1440 |
| accaccaaga | ccctgctgac | ggactcggca | accacggcca | aggagctctg | caacgcgctg | 1500 |
| gccgacaaga | tctctctcaa | ggaccggttc | gggttctccc | tctacattgc | cctgtttgac | 1560 |
| aaggtgtcct | ccctgggcag | cggcagtgac | cacgtcatgg | acgccatctc | ccagtgcgag | 1620 |
| cagtacgcca | aggagcaggg | cgcccaggag | cgcaacgccc | cctggaggct | cttcttccgc | 1680 |
| aaagaggtct | tcacgccctg | gcacagcccc | tccgaggaca | cgtggccac | caacctcatc | 1740 |
| taccagcagg | tggcgcgagg | agtcaagttt | ggggagtaca | ggtgtgagaa | ggaggacgac | 1800 |
| ctggctgagc | tggcctccca | gcagtacttt | gtagactatg | gctctgagat | gatcctggag | 1860 |
| cgcctcctga | acctcgtgcc | cacctacatc | cccgaccgcg | agatcacgcc | cctgaagacg | 1920 |
| ctggagaagt | gggcccagct | ggccatcgcc | gcccacaaga | aggggattta | tgcccagagg | 1980 |
| agaactgatg | cccagaaggt | caaagaggat | gtggtcagtt | atgcccgctt | caagtggccc | 2040 |

```
ttgctcttct ccaggtttta tgaagcctac aaattctcag gccccagtct ccccaagaac    2100
gacgtcatcg tggccgtcaa ctggacgggt gtgtactttg tggatgagca ggagcaggta    2160
cttctggagc tgtccttccc agagatcatg gccgtgtcca gcagcagggg agcgaaaacg    2220
acggccccca gcttcacgct ggccaccatc aaggggacg aatacacctt cacctccagc     2280
aatgctgagg acattcgtga cctggtggtc accttcctag aggggctccg gaagagatct    2340
aagtatgttg tggccctgca ggataacccc aaccccgcag gcgaggagtc aggcttcctc    2400
agctttgcca agggagacct catcatcctg gaccatgaca cgggcgagca ggtcatgaac    2460
tcgggctggg ccaacggcat caatgagagg accaagcagc gtgggacttt ccccaccgac    2520
agtgtgtacg tcatgcccac tgtcaccatg ccaccgcggg agattgtggc cctggtcacc    2580
atgactcccg atcagaggca ggacgttgtc cggctcttgc agctgcgaac ggcggagccc    2640
gaggtgcgtg ccaagcccta cacgctggag gagttttcct atgactactt caggccccca    2700
cccaagcaca cgctgagccg tgtcatggtg tccaaggccc gaggcaagga ccggctgtgg    2760
agccacacgc gggaaccgct caagcaggcg ctgctcaaga agctcctggg cagtgaggag    2820
ctctcgcagg aggcctgcct ggccttcatt gctgtgctca gtacatgggg cgactacccg    2880
tccaagagga cacgctccgt caacgagctc accgaccaga tctttgaggg tcccctgaaa    2940
gccgagcccc tgaaggacga ggcatatgtg cagatcctga gcagctgac cgacaaccac    3000
atcaggtaca gcgaggagcg gggttgggag ctgctctggc tgtgcacggg ccttttccca    3060
cccagcaaca tcctcctgcc ccacgtgcag cgcttcctgc agtcccgaaa gcactgccca    3120
ctcgccatcg actgcctgca acggctccag aaagccctga gaaacgggtc ccggaagtac    3180
cctccgcacc tggtggaggt ggaggccatc cagcacaaga ccacccagat tttccacaaa    3240
gtctacttcc ctgatgacac tgacgaggcc ttcgaagtgg agtccagcac caaggccaag    3300
gacttctgcc agaacatcgc caccaggctg ctcctcaagt cctcagaggg attcagcctc    3360
tttgtcaaaa ttgcagacaa ggtcatcagc gttcctgaga atgacttctt ctttgacttt    3420
gttcgacact tgacagactg gataaagaaa gctcggccca tcaaggacgg aattgtgccc    3480
tcactcacct accaggtgtt cttcatgaag aagctgtgga ccaccacggt gcagggaag    3540
gatcccatgg ccgattccat cttccactat taccaggagt tgcccaagta tctccgaggc    3600
taccacaagt gcacgcggga ggaggtgctg cagctggggg cgctgatcta cagggtcaag    3660
ttcgaggagg acaagtccta cttccccagc atccccaagc tgctgcggga gctggtgccc    3720
caggacctta tccggcaggt ctcacctgat gactggaagc ggtccatcgt cgcctacttc    3780
aacaagcacg cagggaagtc caaggaggag gccaagctgg ccttcctgaa gctcatcttc    3840
aagtggccca cctttggctc agccttcttc gaggtgaagc aaactacgga ccaaacttc    3900
cctgagatcc tcctaattgc catcaacaag tatggggtca gcctcatcga tcccaaaacg    3960
aaggatatcc tcaccactca tcccttcacc aagatctcca actggagcag cggcaacacc    4020
tacttccaca tcaccattgg gaacttggtg cgcgggagca aactgctctg cgagacgtca    4080
ctgggctaca agatggatga cctcctgact tcctacatta gccagatgct cacagccatg    4140
agcaaacagc ggggctccag gagcggcaag                                     4170
```

<210> SEQ ID NO 78
<211> LENGTH: 1390
<212> TYPE: PRT
<213> ORGANISM: Artificial Sequence
<220> FEATURE:

<223> OTHER INFORMATION: Synthetic

<400> SEQUENCE: 78

```
Gly Leu Met Arg Leu Gly Phe Leu Arg Leu Gln Ala Leu His Arg Ser
1               5                   10                  15

Arg Lys Leu His Gln Gln Tyr Arg Leu Ala Arg Gln Arg Ile Ile Gln
            20                  25                  30

Phe Gln Ala Arg Cys Arg Ala Tyr Leu Val Arg Lys Ala Phe Arg His
        35                  40                  45

Arg Leu Trp Ala Val Leu Thr Val Gln Ala Tyr Ala Arg Gly Met Ile
    50                  55                  60

Ala Arg Arg Leu His Gln Arg Leu Arg Ala Glu Tyr Leu Trp Arg Leu
65                  70                  75                  80

Glu Ala Glu Lys Met Arg Leu Ala Glu Glu Lys Leu Arg Lys Glu
                85                  90                  95

Met Ser Ala Lys Lys Ala Lys Glu Glu Ala Glu Arg Lys His Gln Glu
                100                 105                 110

Arg Leu Ala Gln Leu Ala Arg Glu Asp Ala Glu Arg Glu Leu Lys Glu
            115                 120                 125

Lys Glu Ala Ala Arg Arg Lys Lys Glu Leu Leu Glu Gln Met Glu Arg
130                 135                 140

Ala Arg His Glu Pro Val Asn His Ser Asp Met Val Asp Lys Met Phe
145                 150                 155                 160

Gly Phe Leu Gly Thr Ser Gly Gly Leu Pro Gly Gln Glu Gly Gln Ala
                165                 170                 175

Pro Ser Gly Phe Glu Asp Leu Glu Arg Gly Arg Arg Glu Met Val Glu
            180                 185                 190

Glu Asp Leu Asp Ala Ala Leu Pro Leu Pro Asp Glu Asp Glu Glu Asp
        195                 200                 205

Leu Ser Glu Tyr Lys Phe Ala Lys Phe Ala Ala Thr Tyr Phe Gln Gly
    210                 215                 220

Thr Thr Thr His Ser Tyr Thr Arg Arg Pro Leu Lys Gln Pro Leu Leu
225                 230                 235                 240

Tyr His Asp Asp Glu Gly Asp Gln Leu Ala Ala Leu Ala Val Trp Ile
                245                 250                 255

Thr Ile Leu Arg Phe Met Gly Asp Leu Pro Glu Pro Lys Tyr His Thr
            260                 265                 270

Ala Met Ser Asp Gly Ser Glu Lys Ile Pro Val Met Thr Lys Ile Tyr
        275                 280                 285

Glu Thr Leu Gly Lys Lys Thr Tyr Lys Arg Glu Leu Gln Ala Leu Gln
    290                 295                 300

Gly Glu Gly Glu Ala Gln Leu Pro Glu Gly Gln Lys Lys Ser Ser Val
305                 310                 315                 320

Arg His Lys Leu Val His Leu Thr Leu Lys Lys Ser Lys Leu Thr
                325                 330                 335

Glu Glu Val Thr Lys Arg Leu His Asp Gly Glu Ser Thr Val Gln Gly
            340                 345                 350

Asn Ser Met Leu Glu Asp Arg Pro Thr Ser Asn Leu Glu Lys Leu His
        355                 360                 365

Phe Ile Ile Gly Asn Gly Ile Leu Arg Pro Ala Leu Arg Asp Glu Ile
    370                 375                 380

Tyr Cys Gln Ile Ser Lys Gln Leu Thr His Asn Pro Ser Lys Ser Ser
385                 390                 395                 400
```

```
Tyr Ala Arg Gly Trp Ile Leu Val Ser Leu Cys Val Gly Cys Phe Ala
                405                 410                 415
Pro Ser Glu Lys Phe Val Lys Tyr Leu Arg Asn Phe Ile His Gly Gly
            420                 425                 430
Pro Pro Gly Tyr Ala Pro Tyr Cys Glu Glu Arg Leu Arg Arg Thr Phe
            435                 440                 445
Val Asn Gly Thr Arg Thr Gln Pro Pro Ser Trp Leu Glu Leu Gln Ala
    450                 455                 460
Thr Lys Ser Lys Lys Pro Ile Met Leu Pro Val Thr Phe Met Asp Gly
465                 470                 475                 480
Thr Thr Lys Thr Leu Leu Thr Asp Ser Ala Thr Thr Ala Lys Glu Leu
                485                 490                 495
Cys Asn Ala Leu Ala Asp Lys Ile Ser Leu Lys Asp Arg Phe Gly Phe
            500                 505                 510
Ser Leu Tyr Ile Ala Leu Phe Asp Lys Val Ser Ser Leu Gly Ser Gly
            515                 520                 525
Ser Asp His Val Met Asp Ala Ile Ser Gln Cys Glu Gln Tyr Ala Lys
    530                 535                 540
Glu Gln Gly Ala Gln Glu Arg Asn Ala Pro Trp Arg Leu Phe Phe Arg
545                 550                 555                 560
Lys Glu Val Phe Thr Pro Trp His Ser Pro Ser Glu Asp Asn Val Ala
                565                 570                 575
Thr Asn Leu Ile Tyr Gln Gln Val Val Arg Gly Val Lys Phe Gly Glu
            580                 585                 590
Tyr Arg Cys Glu Lys Glu Asp Asp Leu Ala Glu Leu Ala Ser Gln Gln
    595                 600                 605
Tyr Phe Val Asp Tyr Gly Ser Glu Met Ile Leu Glu Arg Leu Leu Asn
610                 615                 620
Leu Val Pro Thr Tyr Ile Pro Asp Arg Glu Ile Thr Pro Leu Lys Thr
625                 630                 635                 640
Leu Glu Lys Trp Ala Gln Leu Ala Ile Ala Ala His Lys Lys Gly Ile
                645                 650                 655
Tyr Ala Gln Arg Arg Thr Asp Ala Gln Lys Val Lys Glu Asp Val Val
            660                 665                 670
Ser Tyr Ala Arg Phe Lys Trp Pro Leu Leu Phe Ser Arg Phe Tyr Glu
    675                 680                 685
Ala Tyr Lys Phe Ser Gly Pro Ser Leu Pro Lys Asn Asp Val Ile Val
690                 695                 700
Ala Val Asn Trp Thr Gly Val Tyr Phe Val Asp Glu Gln Glu Gln Val
705                 710                 715                 720
Leu Leu Glu Leu Ser Phe Pro Glu Ile Met Ala Val Ser Ser Ser Arg
                725                 730                 735
Gly Ala Lys Thr Thr Ala Pro Ser Phe Thr Leu Ala Thr Ile Lys Gly
            740                 745                 750
Asp Glu Tyr Thr Phe Thr Ser Ser Asn Ala Glu Asp Ile Arg Asp Leu
    755                 760                 765
Val Val Thr Phe Leu Glu Gly Leu Arg Lys Arg Ser Lys Tyr Val Val
770                 775                 780
Ala Leu Gln Asp Asn Pro Asn Pro Ala Gly Glu Ser Gly Phe Leu
785                 790                 795                 800
Ser Phe Ala Lys Gly Asp Leu Ile Ile Leu Asp His Asp Thr Gly Glu
                805                 810                 815
Gln Val Met Asn Ser Gly Trp Ala Asn Gly Ile Asn Glu Arg Thr Lys
```

```
                820             825             830
Gln Arg Gly Asp Phe Pro Thr Asp Ser Val Tyr Val Met Pro Thr Val
            835             840             845
Thr Met Pro Pro Arg Glu Ile Val Ala Leu Val Thr Met Thr Pro Asp
850             855             860
Gln Arg Gln Asp Val Val Arg Leu Leu Gln Leu Arg Thr Ala Glu Pro
865             870             875             880
Glu Val Arg Ala Lys Pro Tyr Thr Leu Glu Glu Phe Ser Tyr Asp Tyr
            885             890             895
Phe Arg Pro Pro Lys His Thr Leu Ser Arg Val Met Val Ser Lys
            900             905             910
Ala Arg Gly Lys Asp Arg Leu Trp Ser His Thr Arg Glu Pro Leu Lys
            915             920             925
Gln Ala Leu Leu Lys Lys Leu Leu Gly Ser Glu Leu Ser Gln Glu
            930             935             940
Ala Cys Leu Ala Phe Ile Ala Val Leu Lys Tyr Met Gly Asp Tyr Pro
945             950             955             960
Ser Lys Arg Thr Arg Ser Val Asn Glu Leu Thr Asp Gln Ile Phe Glu
            965             970             975
Gly Pro Leu Lys Ala Glu Pro Leu Lys Asp Glu Ala Tyr Val Gln Ile
            980             985             990
Leu Lys Gln Leu Thr Asp Asn His  Ile Arg Tyr Ser Glu  Glu Arg Gly
            995             1000            1005
Trp Glu  Leu Leu Trp Leu Cys  Thr Gly Leu Phe Pro  Pro Ser Asn
    1010            1015            1020
Ile Leu  Leu Pro His Val Gln  Arg Phe Leu Gln Ser  Arg Lys His
    1025            1030            1035
Cys Pro  Leu Ala Ile Asp Cys  Leu Gln Arg Leu Gln  Lys Ala Leu
    1040            1045            1050
Arg Asn  Gly Ser Arg Lys Tyr  Pro Pro His Leu Val  Glu Val Glu
    1055            1060            1065
Ala Ile  Gln His Lys Thr Thr  Gln Ile Phe His Lys  Val Tyr Phe
    1070            1075            1080
Pro Asp  Asp Thr Asp Glu Ala  Phe Glu Val Glu Ser  Ser Thr Lys
    1085            1090            1095
Ala Lys  Asp Phe Cys Gln Asn  Ile Ala Thr Arg Leu  Leu Leu Lys
    1100            1105            1110
Ser Ser  Glu Gly Phe Ser Leu  Phe Val Lys Ile Ala  Asp Lys Val
    1115            1120            1125
Ile Ser  Val Pro Glu Asn Asp  Phe Phe Phe Asp Phe  Val Arg His
    1130            1135            1140
Leu Thr  Asp Trp Ile Lys Lys  Ala Arg Pro Ile Lys  Asp Gly Ile
    1145            1150            1155
Val Pro  Ser Leu Thr Tyr Gln  Val Phe Phe Met Lys  Lys Leu Trp
    1160            1165            1170
Thr Thr  Thr Val Pro Gly Lys  Asp Pro Met Ala Asp  Ser Ile Phe
    1175            1180            1185
His Tyr  Tyr Gln Glu Leu Pro  Lys Tyr Leu Arg Gly  Tyr His Lys
    1190            1195            1200
Cys Thr  Arg Glu Glu Val Leu  Gln Leu Gly Ala Leu  Ile Tyr Arg
    1205            1210            1215
Val Lys  Phe Glu Glu Asp Lys  Ser Tyr Phe Pro Ser  Ile Pro Lys
    1220            1225            1230
```

```
Leu Leu Arg Glu Leu Val Pro Gln Asp Leu Ile Arg Gln Val Ser
    1235            1240                1245

Pro Asp Asp Trp Lys Arg Ser Ile Val Ala Tyr Phe Asn Lys His
    1250            1255                1260

Ala Gly Lys Ser Lys Glu Glu Ala Lys Leu Ala Phe Leu Lys Leu
    1265            1270                1275

Ile Phe Lys Trp Pro Thr Phe Gly Ser Ala Phe Phe Glu Val Lys
    1280            1285                1290

Gln Thr Thr Glu Pro Asn Phe Pro Glu Ile Leu Leu Ile Ala Ile
    1295            1300                1305

Asn Lys Tyr Gly Val Ser Leu Ile Asp Pro Lys Thr Lys Asp Ile
    1310            1315                1320

Leu Thr Thr His Pro Phe Thr Lys Ile Ser Asn Trp Ser Ser Gly
    1325            1330                1335

Asn Thr Tyr Phe His Ile Thr Ile Gly Asn Leu Val Arg Gly Ser
    1340            1345                1350

Lys Leu Leu Cys Glu Thr Ser Leu Gly Tyr Lys Met Asp Asp Leu
    1355            1360                1365

Leu Thr Ser Tyr Ile Ser Gln Met Leu Thr Ala Met Ser Lys Gln
    1370            1375                1380

Arg Gly Ser Arg Ser Gly Lys
    1385            1390

<210> SEQ ID NO 79
<211> LENGTH: 120
<212> TYPE: PRT
<213> ORGANISM: Artificial Sequence
<220> FEATURE:
<223> OTHER INFORMATION: Synthetic

<400> SEQUENCE: 79

Arg Ser Asn Phe Leu Lys Leu Lys Asn Ala Ala Thr Leu Ile Gln Arg
1               5                   10                  15

His Trp Arg Gly His Asn Cys Arg Lys Asn Tyr Gly Leu Met Arg Leu
                20                  25                  30

Gly Phe Leu Arg Leu Gln Ala Leu His Arg Ser Arg Lys Leu His Gln
            35                  40                  45

Gln Tyr Arg Leu Ala Arg Gln Arg Ile Ile Gln Phe Gln Ala Arg Cys
        50                  55                  60

Arg Ala Tyr Leu Val Arg Lys Ala Phe Arg His Arg Leu Trp Ala Val
65                  70                  75                  80

Leu Thr Val Gln Ala Tyr Ala Arg Gly Met Ile Ala Arg Leu His
                85                  90                  95

Gln Arg Leu Arg Ala Glu Tyr Leu Trp Arg Leu Glu Ala Glu Lys Met
                100                 105                 110

Arg Leu Ala Glu Glu Glu Lys Leu
            115                 120

<210> SEQ ID NO 80
<211> LENGTH: 3912
<212> TYPE: DNA
<213> ORGANISM: Artificial Sequence
<220> FEATURE:
<223> OTHER INFORMATION: 81

<400> SEQUENCE: 80
ctggcggagg aagagaagct tcggaaggag atgagcgcca agaaggccaa ggaggaggcc    60
```

-continued

```
gagcgcaagc atcaggagcg cctggcccag ctggctcgtg aggacgctga gcgggagctg     120
aaggagaagg aggccgctcg gcggaagaag gagctcctgg agcagatgga aagggcccgc     180
catgagcctg tcaatcactc agacatggtg acaagatgt ttggcttcct ggggacttca      240
ggtggcctgc caggccagga gggccaggca cctagtggct tgaggacct ggagcgaggg      300 cggagggaga tggtggagga ggacctggat gcagccctgc ccctgcctga cgaggatgag     360
gaggacctct ctgagtataa atttgccaag ttcgcggcca cctacttcca ggggacaacc     420
acgcactcct acacccggcg gccactcaaa cagccactgc tctaccatga cgacgagggt     480
gaccagctgg cagccctggc ggtctggatc accatcctcc gcttcatggg ggacctccct     540
gagcccaagt accacacagc catgagtgat ggcagtgaga agatccctgt gatgaccaag     600
atttatgaga ccctgggcaa gaagacgtac aagagggagc tgcaggccct gcagggcgag     660
ggcgaggccc agctccccga gggccagaag aagagcagtg tgaggcacaa gctggtgcat     720
ttgactctga aaagaagtc caagctcaca gaggaggtga ccaagaggct gcatgacggg      780
gagtccacag tgcagggcaa cagcatgctg gaggaccggc ccacctccaa cctggagaag     840
ctgcacttca tcatcggcaa tggcatcctg cggccagcac tccgggacga gatctactgc     900
cagatcagca agcagctgac ccacaacccc tccaagagca gctatgcccg ggctggatt      960 ctcgtgtctc tctgcgtggg ctgtttcgcc ccctccgaga gtttgtcaa gtacctgcgg     1020 aacttcatcc acggggccc gccggctac gccccgtact gtgaggagcg cctgagaagg      1080
acctttgtca atgggacacg gacacagccg cccagctggc tggagctgca ggccaccaag     1140
tccaagaagc caatcatgtt gcccgtgaca ttcatggatg ggaccaccaa gaccctgctg     1200
acggactcgg caaccacggc caaggagctc tgcaacgcgc tggccgacaa gatctctctc     1260
aaggaccggt tcgggttctc cctctacatt gccctgtttg acaaggtgtc ctccctgggc     1320
agcggcagtg accacgtcat ggacgccatc tcccagtgcg agcagtacgc caaggagcag     1380
ggcgcccagg agcgcaacgc cccctggagg ctcttcttcc gcaaagaggt cttcacgccc     1440
tggcacagcc cctccgagga caacgtggcc accaacctca tctaccagca ggtggtgcga     1500
ggagtcaagt ttggggagta caggtgtgag aaggaggacg acctggctga gctggcctcc     1560
cagcagtact ttgtagacta tggctctgag atgatcctgg agcgcctcct gaacctcgtg     1620
cccacctaca tccccgaccg cgagatcacg cccctgaaga cgctggagaa gtgggcccag     1680
ctggccatcg ccgcccacaa gaagggggatt tatgcccaga ggagaactga tgcccagaag     1740
gtcaaagagg atgtggtcag ttatgcccgc ttcaagtggc ccttgctctt ctccaggttt      1800
tatgaagcct acaaattctc aggccccagt ctccccaaga cgacgtcat cgtggccgtc      1860 aactggacgg tgtgtactt tgtggatgag caggagcagg tacttctgga gctgtccttc      1920
ccagagatca tggccgtgtc cagcagcagg ggagcgaaaa cgacggcccc cagcttcacg     1980
ctggccacca tcaaggggga cgaatacacc ttcacctcca gcaatgctga ggacattcgt     2040
gacctggtgg tcaccttcct agaggggctc cggaagagat ctaagtatgt tgtggccctg     2100
caggataacc ccaaccccgc aggcgaggag tcaggcttcc tcagctttgc aagggagac      2160 ctcatcatcc tggaccatga cacgggcgag caggtcatga actcgggctg ggccaacggc     2220
atcaatgaga ggaccaagca gcgtgggac ttccccaccg acagtgtgta cgtcatgccc      2280
actgtcacca tgccaccgcg ggagattgtg ccctggtca ccatgactcc cgatcagagg      2340
caggacgttg tccggctctt gcagctgcga acggcggagc ccgaggtgcg tgccaagccc     2400
```

```
tacacgctgg aggagttttc ctatgactac ttcaggcccc cacccaagca cacgctgagc    2460
cgtgtcatgg tgtccaaggc ccgaggcaag gaccggctgt ggagccacac gcgggaaccg    2520
ctcaagcagg cgctgctcaa gaagctcctg ggcagtgagg agctctcgca ggaggcctgc    2580
ctggccttca ttgctgtgct caagtacatg ggcgactacc cgtccaagag gacacgctcc    2640
gtcaacgagc tcaccgacca gatctttgag ggtcccctga agccgagcc cctgaaggac    2700 gaggcatatg tgcagatcct gaagcagctg accgacaacc acatcaggta cagcgaggag    2760
cggggttggg agctgctctg ctgtgcacg ggccttttcc acccagcaa catcctcctg    2820 ccccacgtgc agcgcttcct gcagtcccga aagcactgcc cactcgccat cgactgcctg    2880
caacggctcc agaaagccct gagaaacggg tcccggaagt accctccgca cctggtggag    2940
gtggaggcca tccagcacaa gaccacccag attttccaca aagtctactt ccctgatgac    3000
actgacgagg ccttcgaagt ggagtccagc accaaggcca aggacttctg ccagaacatc    3060
gccaccaggc tgctcctcaa gtcctcagag ggattcagcc tctttgtcaa aattgcagac    3120
aaggtcatca gcgttcctga gaatgacttc ttctttgact tgttcgaca cttgacagac    3180 tggataaaga aagctcggcc catcaaggac ggaattgtgc cctcactcac ctaccaggtg    3240
ttcttcatga agaagctgtg gaccaccacg gtgccaggga aggatccat ggccgattcc    3300 atcttccact attaccagga gttgcccaag tatctccgag gctaccacaa gtgcacgcgg    3360
gaggaggtgc tgcagctggg ggcgctgatc tacagggtca agttcgagga ggacaagtcc    3420
tacttcccca gcatccccaa gctgctgcgg gagctggtgc cccaggacct tatccggcag    3480
gtctcacctg atgactggaa gcggtccatc gtcgcctact caacaagca cgcagggaag    3540 tccaaggagg aggccaagct ggccttcctg aagctcatct tcaagtggcc cacctttggc    3600
tcagccttct tcgaggtgaa gcaaactacg gagccaaact ccctgagat cctcctaatt    3660 gccatcaaca gtatgggggt cagcctcatc gatcccaaaa cgaaggatat cctcaccact    3720
catcccttca ccaagatctc caactggagc agcggcaaca cctacttcca catcaccatt    3780
gggaacttgg tgcgcgggag caaactgctc tgcgagacgt cactgggcta caagatggat    3840
gacctcctga cttcctacat tagccagatg ctcacagcca tgagcaaaca gcggggctcc    3900
aggagcggca ag                                                       3912
```

<210> SEQ ID NO 81
<211> LENGTH: 1304
<212> TYPE: PRT
<213> ORGANISM: Artificial Sequence
<220> FEATURE:
<223> OTHER INFORMATION: Synthetic

<400> SEQUENCE: 81

```
Leu Ala Glu Glu Glu Lys Leu Arg Lys Glu Met Ser Ala Lys Lys Ala
1               5                   10                  15

Lys Glu Glu Ala Glu Arg Lys His Gln Glu Arg Leu Ala Gln Leu Ala
            20                  25                  30

Arg Glu Asp Ala Glu Arg Glu Leu Lys Glu Lys Glu Ala Ala Arg Arg
        35                  40                  45

Lys Lys Glu Leu Leu Glu Gln Met Glu Arg Ala Arg His Glu Pro Val
    50                  55                  60

Asn His Ser Asp Met Val Asp Lys Met Phe Gly Phe Leu Gly Thr Ser
65                  70                  75                  80

Gly Gly Leu Pro Gly Gln Glu Gly Gln Ala Pro Ser Gly Phe Glu Asp
            85                  90                  95
```

```
Leu Glu Arg Gly Arg Arg Glu Met Val Glu Asp Leu Asp Ala Ala
            100                 105                 110

Leu Pro Leu Pro Asp Glu Asp Glu Asp Leu Ser Glu Tyr Lys Phe
            115                 120                 125

Ala Lys Phe Ala Ala Thr Tyr Phe Gln Gly Thr Thr Thr His Ser Tyr
130                 135                 140

Thr Arg Arg Pro Leu Lys Gln Pro Leu Leu Tyr His Asp Asp Glu Gly
145                 150                 155                 160

Asp Gln Leu Ala Ala Leu Ala Val Trp Ile Thr Ile Leu Arg Phe Met
                165                 170                 175

Gly Asp Leu Pro Glu Pro Lys Tyr His Thr Ala Met Ser Asp Gly Ser
            180                 185                 190

Glu Lys Ile Pro Val Met Thr Lys Ile Tyr Glu Thr Leu Gly Lys Lys
            195                 200                 205

Thr Tyr Lys Arg Glu Leu Gln Ala Leu Gln Gly Glu Gly Glu Ala Gln
210                 215                 220

Leu Pro Glu Gly Gln Lys Lys Ser Ser Val Arg His Lys Leu Val His
225                 230                 235                 240

Leu Thr Leu Lys Lys Lys Ser Lys Leu Thr Glu Glu Val Thr Lys Arg
                245                 250                 255

Leu His Asp Gly Glu Ser Thr Val Gln Gly Asn Ser Met Leu Glu Asp
            260                 265                 270

Arg Pro Thr Ser Asn Leu Glu Lys Leu His Phe Ile Ile Gly Asn Gly
            275                 280                 285

Ile Leu Arg Pro Ala Leu Arg Asp Glu Ile Tyr Cys Gln Ile Ser Lys
            290                 295                 300

Gln Leu Thr His Asn Pro Ser Lys Ser Ser Tyr Ala Arg Gly Trp Ile
305                 310                 315                 320

Leu Val Ser Leu Cys Val Gly Cys Phe Ala Pro Ser Glu Lys Phe Val
                325                 330                 335

Lys Tyr Leu Arg Asn Phe Ile His Gly Gly Pro Pro Gly Tyr Ala Pro
            340                 345                 350

Tyr Cys Glu Glu Arg Leu Arg Arg Thr Phe Val Asn Gly Thr Arg Thr
            355                 360                 365

Gln Pro Pro Ser Trp Leu Glu Leu Gln Ala Thr Lys Ser Lys Lys Pro
370                 375                 380

Ile Met Leu Pro Val Thr Phe Met Asp Gly Thr Thr Lys Thr Leu Leu
385                 390                 395                 400

Thr Asp Ser Ala Thr Thr Ala Lys Glu Leu Cys Asn Ala Leu Ala Asp
                405                 410                 415

Lys Ile Ser Leu Lys Asp Arg Phe Gly Phe Ser Leu Tyr Ile Ala Leu
            420                 425                 430

Phe Asp Lys Val Ser Ser Leu Gly Ser Gly Ser Asp His Val Met Asp
            435                 440                 445

Ala Ile Ser Gln Cys Glu Gln Tyr Ala Lys Glu Gln Gly Ala Gln Glu
            450                 455                 460

Arg Asn Ala Pro Trp Arg Leu Phe Phe Arg Lys Glu Val Phe Thr Pro
465                 470                 475                 480

Trp His Ser Pro Ser Glu Asp Asn Val Ala Thr Asn Leu Ile Tyr Gln
                485                 490                 495

Gln Val Val Arg Gly Val Lys Phe Gly Glu Tyr Arg Cys Glu Lys Glu
            500                 505                 510
```

Asp Asp Leu Ala Glu Leu Ala Ser Gln Gln Tyr Phe Val Asp Tyr Gly
            515                 520                 525

Ser Glu Met Ile Leu Glu Arg Leu Leu Asn Leu Val Pro Thr Tyr Ile
530                 535                 540

Pro Asp Arg Glu Ile Thr Pro Leu Lys Thr Leu Glu Lys Trp Ala Gln
545                 550                 555                 560

Leu Ala Ile Ala Ala His Lys Lys Gly Ile Tyr Ala Gln Arg Arg Thr
                565                 570                 575

Asp Ala Gln Lys Val Lys Glu Asp Val Ser Tyr Ala Arg Phe Lys
            580                 585                 590

Trp Pro Leu Leu Phe Ser Arg Phe Tyr Glu Ala Tyr Lys Phe Ser Gly
            595                 600                 605

Pro Ser Leu Pro Lys Asn Asp Val Ile Val Ala Val Asn Trp Thr Gly
        610                 615                 620

Val Tyr Phe Val Asp Glu Gln Glu Gln Val Leu Leu Glu Leu Ser Phe
625                 630                 635                 640

Pro Glu Ile Met Ala Val Ser Ser Arg Gly Ala Lys Thr Thr Ala
                645                 650                 655

Pro Ser Phe Thr Leu Ala Thr Ile Lys Gly Asp Glu Tyr Thr Phe Thr
                660                 665                 670

Ser Ser Asn Ala Glu Asp Ile Arg Asp Leu Val Val Thr Phe Leu Glu
            675                 680                 685

Gly Leu Arg Lys Arg Ser Lys Tyr Val Val Ala Leu Gln Asp Asn Pro
            690                 695                 700

Asn Pro Ala Gly Glu Glu Ser Gly Phe Leu Ser Phe Ala Lys Gly Asp
705                 710                 715                 720

Leu Ile Ile Leu Asp His Asp Thr Gly Glu Gln Val Met Asn Ser Gly
                725                 730                 735

Trp Ala Asn Gly Ile Asn Glu Arg Thr Lys Gln Arg Gly Asp Phe Pro
                740                 745                 750

Thr Asp Ser Val Tyr Val Met Pro Thr Val Thr Met Pro Pro Arg Glu
            755                 760                 765

Ile Val Ala Leu Val Thr Met Thr Pro Asp Gln Arg Gln Asp Val Val
770                 775                 780

Arg Leu Leu Gln Leu Arg Thr Ala Glu Pro Glu Val Arg Ala Lys Pro
785                 790                 795                 800

Tyr Thr Leu Glu Glu Phe Ser Tyr Asp Tyr Phe Arg Pro Pro Lys
                805                 810                 815

His Thr Leu Ser Arg Val Met Val Ser Lys Ala Arg Gly Lys Asp Arg
            820                 825                 830

Leu Trp Ser His Thr Arg Glu Pro Leu Lys Gln Ala Leu Leu Lys Lys
            835                 840                 845

Leu Leu Gly Ser Glu Glu Leu Ser Gln Glu Ala Cys Leu Ala Phe Ile
850                 855                 860

Ala Val Leu Lys Tyr Met Gly Asp Tyr Pro Ser Lys Arg Thr Arg Ser
865                 870                 875                 880

Val Asn Glu Leu Thr Asp Gln Ile Phe Glu Gly Pro Leu Lys Ala Glu
                885                 890                 895

Pro Leu Lys Asp Glu Ala Tyr Val Gln Ile Leu Lys Gln Leu Thr Asp
            900                 905                 910

Asn His Ile Arg Tyr Ser Glu Glu Arg Gly Trp Glu Leu Leu Trp Leu
            915                 920                 925

Cys Thr Gly Leu Phe Pro Pro Ser Asn Ile Leu Leu Pro His Val Gln

```
                930         935         940
Arg Phe Leu Gln Ser Arg Lys His Cys Pro Leu Ala Ile Asp Cys Leu
945                 950                 955                 960

Gln Arg Leu Gln Lys Ala Leu Arg Asn Gly Ser Arg Lys Tyr Pro Pro
            965                 970                 975

His Leu Val Glu Val Glu Ala Ile Gln His Lys Thr Thr Gln Ile Phe
            980                 985                 990

His Lys Val Tyr Phe Pro Asp Asp Thr Asp Glu Ala Phe Glu Val Glu
        995                 1000                1005

Ser Ser Thr Lys Ala Lys Asp Phe Cys Gln Asn Ile Ala Thr Arg
    1010                1015                1020

Leu Leu Leu Lys Ser Ser Glu Gly Phe Ser Leu Phe Val Lys Ile
    1025                1030                1035

Ala Asp Lys Val Ile Ser Val Pro Glu Asn Asp Phe Phe Phe Asp
    1040                1045                1050

Phe Val Arg His Leu Thr Asp Trp Ile Lys Lys Ala Arg Pro Ile
    1055                1060                1065

Lys Asp Gly Ile Val Pro Ser Leu Thr Tyr Gln Val Phe Phe Met
    1070                1075                1080

Lys Lys Leu Trp Thr Thr Thr Val Pro Gly Lys Asp Pro Met Ala
    1085                1090                1095

Asp Ser Ile Phe His Tyr Tyr Gln Glu Leu Pro Lys Tyr Leu Arg
    1100                1105                1110

Gly Tyr His Lys Cys Thr Arg Glu Glu Val Leu Gln Leu Gly Ala
    1115                1120                1125

Leu Ile Tyr Arg Val Lys Phe Glu Glu Asp Lys Ser Tyr Phe Pro
    1130                1135                1140

Ser Ile Pro Lys Leu Leu Arg Glu Leu Val Pro Gln Asp Leu Ile
    1145                1150                1155

Arg Gln Val Ser Pro Asp Asp Trp Lys Arg Ser Ile Val Ala Tyr
    1160                1165                1170

Phe Asn Lys His Ala Gly Lys Ser Lys Glu Glu Ala Lys Leu Ala
    1175                1180                1185

Phe Leu Lys Leu Ile Phe Lys Trp Pro Thr Phe Gly Ser Ala Phe
    1190                1195                1200

Phe Glu Val Lys Gln Thr Thr Glu Pro Asn Phe Pro Glu Ile Leu
    1205                1210                1215

Leu Ile Ala Ile Asn Lys Tyr Gly Val Ser Leu Ile Asp Pro Lys
    1220                1225                1230

Thr Lys Asp Ile Leu Thr Thr His Pro Phe Thr Lys Ile Ser Asn
    1235                1240                1245

Trp Ser Ser Gly Asn Thr Tyr Phe His Ile Thr Ile Gly Asn Leu
    1250                1255                1260

Val Arg Gly Ser Lys Leu Leu Cys Glu Thr Ser Leu Gly Tyr Lys
    1265                1270                1275

Met Asp Asp Leu Leu Thr Ser Tyr Ile Ser Gln Met Leu Thr Ala
    1280                1285                1290

Met Ser Lys Gln Arg Gly Ser Arg Ser Gly Lys
    1295                1300
```

<210> SEQ ID NO 82
<211> LENGTH: 455
<212> TYPE: PRT
<213> ORGANISM: Artificial Sequence
<220> FEATURE:
<223> OTHER INFORMATION: Synthetic

<400> SEQUENCE: 82

```
Arg Ser Asn Phe Leu Lys Leu Lys Asn Ala Ala Thr Leu Ile Gln Arg
1               5                   10                  15

His Trp Arg Gly His Asn Cys Arg Lys Asn Tyr Gly Leu Met Arg Leu
            20                  25                  30

Gly Phe Leu Arg Leu Gln Ala Leu His Arg Ser Arg Lys Leu His Gln
        35                  40                  45

Gln Tyr Arg Leu Ala Arg Gln Arg Ile Ile Gln Phe Gln Ala Arg Cys
    50                  55                  60

Arg Ala Tyr Leu Val Arg Lys Ala Phe Arg His Arg Leu Trp Ala Val
65                  70                  75                  80

Leu Thr Val Gln Ala Tyr Ala Arg Gly Met Ile Ala Arg Arg Leu His
                85                  90                  95

Gln Arg Leu Arg Ala Glu Tyr Leu Trp Arg Leu Glu Ala Glu Lys Met
            100                 105                 110

Arg Leu Ala Glu Glu Glu Lys Leu Arg Lys Glu Met Ser Ala Lys Lys
        115                 120                 125

Ala Lys Glu Glu Ala Glu Arg Lys His Gln Glu Arg Leu Ala Gln Leu
    130                 135                 140

Ala Arg Glu Asp Ala Glu Arg Glu Leu Lys Glu Lys Glu Ala Ala Arg
145                 150                 155                 160

Arg Lys Lys Glu Leu Leu Glu Gln Met Glu Arg Ala Arg His Glu Pro
                165                 170                 175

Val Asn His Ser Asp Met Val Asp Lys Met Phe Gly Phe Leu Gly Thr
            180                 185                 190

Ser Gly Gly Leu Pro Gly Gln Gly Gln Ala Pro Ser Gly Phe Glu
        195                 200                 205

Asp Leu Glu Arg Gly Arg Arg Glu Met Val Glu Glu Asp Leu Asp Ala
    210                 215                 220

Ala Leu Pro Leu Pro Asp Glu Asp Glu Glu Asp Leu Ser Glu Tyr Lys
225                 230                 235                 240

Phe Ala Lys Phe Ala Ala Thr Tyr Phe Gln Gly Thr Thr Thr His Ser
                245                 250                 255

Tyr Thr Arg Arg Pro Leu Lys Gln Pro Leu Leu Tyr His Asp Asp Glu
            260                 265                 270

Gly Asp Gln Leu Ala Ala Leu Ala Val Trp Ile Thr Ile Leu Arg Phe
        275                 280                 285

Met Gly Asp Leu Pro Glu Pro Lys Tyr His Thr Ala Met Ser Asp Gly
    290                 295                 300

Ser Glu Lys Ile Pro Val Met Thr Lys Ile Tyr Glu Thr Leu Gly Lys
305                 310                 315                 320

Lys Thr Tyr Lys Arg Glu Leu Gln Ala Leu Gln Gly Glu Gly Glu Ala
                325                 330                 335

Gln Leu Pro Glu Gly Gln Lys Lys Ser Ser Val Arg His Lys Leu Val
            340                 345                 350

His Leu Thr Leu Lys Lys Lys Ser Lys Leu Thr Glu Glu Val Thr Lys
        355                 360                 365

Arg Leu His Asp Gly Glu Ser Thr Val Gln Gly Asn Ser Met Leu Glu
    370                 375                 380

Asp Arg Pro Thr Ser Asn Leu Glu Lys Leu His Phe Ile Ile Gly Asn
385                 390                 395                 400
```

```
Gly Ile Leu Arg Pro Ala Leu Arg Asp Glu Ile Tyr Cys Gln Ile Ser
                405                 410                 415

Lys Gln Leu Thr His Asn Pro Ser Lys Ser Ser Tyr Ala Arg Gly Trp
            420                 425                 430

Ile Leu Val Ser Leu Cys Val Gly Cys Phe Ala Pro Ser Glu Lys Phe
        435                 440                 445

Val Lys Tyr Leu Arg Asn Phe
    450                 455

<210> SEQ ID NO 83
<211> LENGTH: 428
<212> TYPE: PRT
<213> ORGANISM: Artificial Sequence
<220> FEATURE:
<223> OTHER INFORMATION: Synthetic

<400> SEQUENCE: 83

Gly Leu Met Arg Leu Gly Phe Leu Arg Leu Gln Ala Leu His Arg Ser
1               5                   10                  15

Arg Lys Leu His Gln Gln Tyr Arg Leu Ala Arg Gln Arg Ile Ile Gln
            20                  25                  30

Phe Gln Ala Arg Cys Arg Ala Tyr Leu Val Arg Lys Ala Phe Arg His
        35                  40                  45

Arg Leu Trp Ala Val Leu Thr Val Gln Ala Tyr Ala Arg Gly Met Ile
    50                  55                  60

Ala Arg Arg Leu His Gln Arg Leu Arg Ala Glu Tyr Leu Trp Arg Leu
65                  70                  75                  80

Glu Ala Glu Lys Met Arg Leu Ala Glu Glu Lys Leu Arg Lys Glu
                85                  90                  95

Met Ser Ala Lys Lys Ala Lys Glu Glu Ala Glu Arg Lys His Gln Glu
            100                 105                 110

Arg Leu Ala Gln Leu Ala Arg Glu Asp Ala Glu Arg Glu Leu Lys Glu
        115                 120                 125

Lys Glu Ala Ala Arg Arg Lys Lys Glu Leu Leu Glu Gln Met Glu Arg
    130                 135                 140

Ala Arg His Glu Pro Val Asn His Ser Asp Met Val Asp Lys Met Phe
145                 150                 155                 160

Gly Phe Leu Gly Thr Ser Gly Gly Leu Pro Gly Gln Glu Gly Gln Ala
                165                 170                 175

Pro Ser Gly Phe Glu Asp Leu Glu Arg Gly Arg Arg Glu Met Val Glu
            180                 185                 190

Glu Asp Leu Asp Ala Ala Leu Pro Leu Pro Asp Glu Asp Glu Glu Asp
        195                 200                 205

Leu Ser Glu Tyr Lys Phe Ala Lys Phe Ala Ala Thr Tyr Phe Gln Gly
    210                 215                 220

Thr Thr Thr His Ser Tyr Thr Arg Arg Pro Leu Lys Gln Pro Leu Leu
225                 230                 235                 240

Tyr His Asp Asp Glu Gly Asp Gln Leu Ala Ala Leu Ala Val Trp Ile
                245                 250                 255

Thr Ile Leu Arg Phe Met Gly Asp Leu Pro Glu Pro Lys Tyr His Thr
            260                 265                 270

Ala Met Ser Asp Gly Ser Glu Lys Ile Pro Val Met Thr Lys Ile Tyr
        275                 280                 285

Glu Thr Leu Gly Lys Lys Thr Tyr Lys Arg Glu Leu Gln Ala Leu Gln
    290                 295                 300
```

```
Gly Glu Gly Glu Ala Gln Leu Pro Glu Gly Gln Lys Lys Ser Ser Val
305                 310                 315                 320

Arg His Lys Leu Val His Leu Thr Leu Lys Lys Ser Lys Leu Thr
            325                 330                 335

Glu Glu Val Thr Lys Arg Leu His Asp Gly Glu Ser Thr Val Gln Gly
            340                 345                 350

Asn Ser Met Leu Glu Asp Arg Pro Thr Ser Asn Leu Glu Lys Leu His
            355                 360                 365

Phe Ile Ile Gly Asn Gly Ile Leu Arg Pro Ala Leu Arg Asp Glu Ile
370                 375                 380

Tyr Cys Gln Ile Ser Lys Gln Leu Thr His Asn Pro Ser Lys Ser Ser
385                 390                 395                 400

Tyr Ala Arg Gly Trp Ile Leu Val Ser Leu Cys Val Gly Cys Phe Ala
            405                 410                 415

Pro Ser Glu Lys Phe Val Lys Tyr Leu Arg Asn Phe
            420                 425

<210> SEQ ID NO 84
<211> LENGTH: 342
<212> TYPE: PRT
<213> ORGANISM: Artificial Sequence
<220> FEATURE:
<223> OTHER INFORMATION: Synthetic

<400> SEQUENCE: 84

Arg Ser Asn Phe Leu Lys Leu Lys Asn Ala Ala Thr Leu Ile Gln Arg
1               5                   10                  15

His Trp Arg Gly His Asn Cys Arg Lys Asn Tyr Gly Leu Met Arg Leu
            20                  25                  30

Gly Phe Leu Arg Leu Gln Ala Leu His Arg Ser Arg Lys Leu His Gln
            35                  40                  45

Gln Tyr Arg Leu Ala Arg Gln Arg Ile Ile Gln Phe Gln Ala Arg Cys
        50                  55                  60

Arg Ala Tyr Leu Val Arg Lys Ala Phe Arg His Arg Leu Trp Ala Val
65                  70                  75                  80

Leu Thr Val Gln Ala Tyr Ala Arg Gly Met Ile Ala Arg Arg Leu His
                85                  90                  95

Gln Arg Leu Arg Ala Glu Tyr Leu Trp Arg Leu Glu Ala Glu Lys Met
            100                 105                 110

Arg Leu Ala Glu Glu Glu Lys Leu Arg Lys Glu Met Ser Ala Lys Lys
            115                 120                 125

Ala Lys Glu Glu Ala Glu Arg Lys His Gln Glu Arg Leu Ala Gln Leu
        130                 135                 140

Ala Arg Glu Asp Ala Glu Arg Glu Leu Lys Lys Glu Ala Ala Arg
145                 150                 155                 160

Arg Lys Lys Glu Leu Leu Glu Gln Met Glu Arg Ala Arg His Glu Pro
                165                 170                 175

Val Asn His Ser Asp Met Val Asp Lys Met Phe Gly Phe Leu Gly Thr
            180                 185                 190

Ser Gly Gly Leu Pro Gly Gln Glu Gly Gln Ala Pro Ser Gly Phe Glu
            195                 200                 205

Asp Leu Glu Arg Gly Arg Arg Glu Met Val Glu Glu Asp Leu Asp Ala
        210                 215                 220

Ala Leu Pro Leu Pro Asp Glu Asp Glu Glu Asp Leu Ser Glu Tyr Lys
225                 230                 235                 240
```

```
Phe Ala Lys Phe Ala Ala Thr Tyr Phe Gln Gly Thr Thr Thr His Ser
                245                 250                 255

Tyr Thr Arg Arg Pro Leu Lys Gln Pro Leu Leu Tyr His Asp Asp Glu
            260                 265                 270

Gly Asp Gln Leu Ala Ala Leu Ala Val Trp Ile Thr Ile Leu Arg Phe
        275                 280                 285

Met Gly Asp Leu Pro Glu Pro Lys Tyr His Thr Ala Met Ser Asp Gly
    290                 295                 300

Ser Glu Lys Ile Pro Val Met Thr Lys Ile Tyr Glu Thr Leu Gly Lys
305                 310                 315                 320

Lys Thr Tyr Lys Arg Glu Leu Gln Ala Leu Gln Gly Glu Gly Glu Ala
                325                 330                 335

Gln Leu Pro Glu Gly Gln
            340

<210> SEQ ID NO 85
<211> LENGTH: 342
<212> TYPE: PRT
<213> ORGANISM: Artificial Sequence
<220> FEATURE:
<223> OTHER INFORMATION: Synthetic

<400> SEQUENCE: 85

Leu Ala Glu Glu Lys Leu Arg Lys Glu Met Ser Ala Lys Lys Ala
1               5                   10                  15

Lys Glu Glu Ala Glu Arg Lys His Gln Glu Arg Leu Ala Gln Leu Ala
                20                  25                  30

Arg Glu Asp Ala Glu Arg Glu Leu Lys Glu Lys Glu Ala Ala Arg Arg
            35                  40                  45

Lys Lys Glu Leu Leu Glu Gln Met Glu Arg Ala Arg His Glu Pro Val
50                  55                  60

Asn His Ser Asp Met Val Asp Lys Met Phe Gly Phe Leu Gly Thr Ser
65                  70                  75                  80

Gly Gly Leu Pro Gly Gln Glu Gly Gln Ala Pro Ser Gly Phe Glu Asp
                85                  90                  95

Leu Glu Arg Gly Arg Arg Glu Met Val Glu Asp Leu Asp Ala Ala
            100                 105                 110

Leu Pro Leu Pro Asp Glu Asp Glu Asp Leu Ser Glu Tyr Lys Phe
            115                 120                 125

Ala Lys Phe Ala Ala Thr Tyr Phe Gln Gly Thr Thr Thr His Ser Tyr
    130                 135                 140

Thr Arg Arg Pro Leu Lys Gln Pro Leu Leu Tyr His Asp Asp Glu Gly
145                 150                 155                 160

Asp Gln Leu Ala Ala Leu Ala Val Trp Ile Thr Ile Leu Arg Phe Met
                165                 170                 175

Gly Asp Leu Pro Glu Pro Lys Tyr His Thr Ala Met Ser Asp Gly Ser
            180                 185                 190

Glu Lys Ile Pro Val Met Thr Lys Ile Tyr Glu Thr Leu Gly Lys Lys
        195                 200                 205

Thr Tyr Lys Arg Glu Leu Gln Ala Leu Gln Gly Glu Gly Glu Ala Gln
    210                 215                 220

Leu Pro Glu Gly Gln Lys Lys Ser Ser Val Arg His Lys Leu Val His
225                 230                 235                 240

Leu Thr Leu Lys Lys Lys Ser Lys Leu Thr Glu Glu Val Thr Lys Arg
                245                 250                 255
```

```
Leu His Asp Gly Glu Ser Thr Val Gln Gly Asn Ser Met Leu Glu Asp
            260                 265                 270

Arg Pro Thr Ser Asn Leu Glu Lys Leu His Phe Ile Ile Gly Asn Gly
            275                 280                 285

Ile Leu Arg Pro Ala Leu Arg Asp Glu Ile Tyr Cys Gln Ile Ser Lys
            290                 295                 300

Gln Leu Thr His Asn Pro Ser Lys Ser Tyr Ala Arg Gly Trp Ile
305                 310                 315                 320

Leu Val Ser Leu Cys Val Gly Cys Phe Ala Pro Ser Glu Lys Phe Val
                    325                 330                 335

Lys Tyr Leu Arg Asn Phe
            340

<210> SEQ ID NO 86
<211> LENGTH: 315
<212> TYPE: PRT
<213> ORGANISM: Artificial Sequence
<220> FEATURE:
<223> OTHER INFORMATION: Synthetic

<400> SEQUENCE: 86

Gly Leu Met Arg Leu Gly Phe Leu Arg Leu Gln Ala Leu His Arg Ser
1               5                   10                  15

Arg Lys Leu His Gln Gln Tyr Arg Leu Ala Arg Gln Arg Ile Ile Gln
            20                  25                  30

Phe Gln Ala Arg Cys Arg Ala Tyr Leu Val Lys Ala Phe Arg His
            35                  40                  45

Arg Leu Trp Ala Val Leu Thr Val Gln Ala Tyr Ala Arg Gly Met Ile
    50                  55                  60

Ala Arg Arg Leu His Gln Arg Leu Arg Ala Glu Tyr Leu Trp Arg Leu
65                  70                  75                  80

Glu Ala Glu Lys Met Arg Leu Ala Glu Glu Lys Leu Arg Lys Glu
                85                  90                  95

Met Ser Ala Lys Lys Ala Lys Glu Glu Ala Glu Arg Lys His Gln Glu
            100                 105                 110

Arg Leu Ala Gln Leu Ala Arg Glu Asp Ala Glu Arg Glu Leu Lys Glu
            115                 120                 125

Lys Glu Ala Ala Arg Arg Lys Lys Glu Leu Leu Glu Gln Met Glu Arg
    130                 135                 140

Ala Arg His Glu Pro Val Asn His Ser Asp Met Val Asp Lys Met Phe
145                 150                 155                 160

Gly Phe Leu Gly Thr Ser Gly Gly Leu Pro Gly Gln Glu Gly Gln Ala
                165                 170                 175

Pro Ser Gly Phe Glu Asp Leu Glu Arg Gly Arg Glu Met Val Glu
            180                 185                 190

Glu Asp Leu Asp Ala Ala Leu Pro Leu Pro Glu Asp Glu Glu Asp
            195                 200                 205

Leu Ser Glu Tyr Lys Phe Ala Lys Phe Ala Ala Thr Tyr Phe Gln Gly
    210                 215                 220

Thr Thr Thr His Ser Tyr Thr Arg Arg Pro Leu Lys Gln Pro Leu Leu
225                 230                 235                 240

Tyr His Asp Asp Glu Gly Asp Gln Leu Ala Ala Leu Ala Val Trp Ile
                245                 250                 255

Thr Ile Leu Arg Phe Met Gly Asp Leu Pro Glu Pro Lys Tyr His Thr
            260                 265                 270
```

```
Ala Met Ser Asp Gly Ser Glu Lys Ile Pro Val Met Thr Lys Ile Tyr
        275                 280                 285

Glu Thr Leu Gly Lys Lys Thr Tyr Lys Arg Glu Leu Gln Ala Leu Gln
        290                 295                 300

Gly Glu Gly Glu Ala Gln Leu Pro Glu Gly Gln
305                 310                 315

<210> SEQ ID NO 87
<211> LENGTH: 229
<212> TYPE: PRT
<213> ORGANISM: Artificial Sequence
<220> FEATURE:
<223> OTHER INFORMATION: Synthetic

<400> SEQUENCE: 87

Leu Ala Glu Glu Lys Leu Arg Lys Glu Met Ser Ala Lys Lys Ala
1               5                   10                  15

Lys Glu Glu Ala Glu Arg Lys His Gln Glu Arg Leu Ala Gln Leu Ala
            20                  25                  30

Arg Glu Asp Ala Glu Arg Glu Leu Lys Glu Lys Glu Ala Ala Arg Arg
        35                  40                  45

Lys Lys Glu Leu Leu Glu Gln Met Glu Arg Ala Arg His Glu Pro Val
50                  55                  60

Asn His Ser Asp Met Val Asp Lys Met Phe Gly Phe Leu Gly Thr Ser
65                  70                  75                  80

Gly Gly Leu Pro Gly Gln Glu Gly Gln Ala Pro Ser Gly Phe Glu Asp
                85                  90                  95

Leu Glu Arg Gly Arg Arg Glu Met Val Glu Glu Asp Leu Asp Ala Ala
            100                 105                 110

Leu Pro Leu Pro Asp Glu Asp Glu Glu Asp Leu Ser Glu Tyr Lys Phe
        115                 120                 125

Ala Lys Phe Ala Ala Thr Tyr Phe Gln Gly Thr Thr Thr His Ser Tyr
130                 135                 140

Thr Arg Arg Pro Leu Lys Gln Pro Leu Leu Tyr His Asp Asp Glu Gly
145                 150                 155                 160

Asp Gln Leu Ala Ala Leu Ala Val Trp Ile Thr Ile Leu Arg Phe Met
                165                 170                 175

Gly Asp Leu Pro Glu Pro Lys Tyr His Thr Ala Met Ser Asp Gly Ser
            180                 185                 190

Glu Lys Ile Pro Val Met Thr Lys Ile Tyr Glu Thr Leu Gly Lys Lys
        195                 200                 205

Thr Tyr Lys Arg Glu Leu Gln Ala Leu Gln Gly Glu Gly Glu Ala Gln
    210                 215                 220

Leu Pro Glu Gly Gln
225

<210> SEQ ID NO 88
<211> LENGTH: 93
<212> TYPE: PRT
<213> ORGANISM: Artificial Sequence
<220> FEATURE:
<223> OTHER INFORMATION: Synthetic

<400> SEQUENCE: 88

Gly Leu Met Arg Leu Gly Phe Leu Arg Leu Gln Ala Leu His Arg Ser
1               5                   10                  15

Arg Lys Leu His Gln Gln Tyr Arg Leu Ala Arg Gln Arg Ile Ile Gln
```

```
                   20                  25                  30

Phe Gln Ala Arg Cys Arg Ala Tyr Leu Val Arg Lys Ala Phe Arg His
                35                  40                  45

Arg Leu Trp Ala Val Leu Thr Val Gln Ala Tyr Ala Arg Gly Met Ile
            50                  55                  60

Ala Arg Arg Leu His Gln Arg Leu Arg Ala Glu Tyr Leu Trp Arg Leu
65                  70                  75                  80

Glu Ala Glu Lys Met Arg Leu Ala Glu Glu Lys Leu
                85                  90

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
tggcggagga agagaagctt                                                   20

<210> SEQ ID NO 90
<211> LENGTH: 2640
<212> TYPE: DNA
<213> ORGANISM: Artificial Sequence
<220> FEATURE:
<223> OTHER INFORMATION: Synthetic

<400> SEQUENCE: 90
atggtgattc ttcagcaggg ggaccatgtg tggatggacc tgagattggg gcaggagttc        60
gacgtgccca tcggggcggt ggtgaagctc tgcgactctg gcaggtccaa ggtggtggat       120
gatgaagaca atgaacactg gatctctccg cagaacgcaa cgcacatcaa gcctatgcac       180
cccacgtcgg tccacggcgt ggaggacatg atccgcctgg gggacctcaa cgaggcgggc       240
atcttgcgca acctgcttat ccgctaccgg gaccacctca tctacacgta tcgggctcc        300 atcctggtgg ctgtgaaccc ctaccagctg ctctccatct actcgccaga gcacatccgc       360
cagtatacca acaagaagat tggggagatg ccccccccaca tctttgccat tgctgacaac       420
tgctacttca acatgaaacg caacagccga gaccagtgct gcatcatcag tggggaatct       480
ggggccggga agacggagag cacaaagctg atcctgcagt tcctggcagc catcagtggg       540
cagcactcgt ggattgagca gcaggtcttg gaggccaccc ccattctgga agcatttggg       600
aatgccaaga ccatccgcaa tgacaactca agccgtttcg gaaagtacat cgacatccac       660
ttcaacaagc ggggcgccat cgagggcgcg aagattgagc agtacctgct ggaaaagtca       720
cgtgtctgtc gccaggccct ggatgaaagg aactaccacg tgttctactg catgctggag       780
ggtatgagtg aggatcagaa aagaagctg gcttgggcc aggcctctga ctacaactac       840
ttggccatgg gtaactgcat aacctgtgag ggccgggtgg acagccagga gtacgccaac       900
atccgctccg ccatgaaggt gctcatgttc actgacaccg agaactggga gatctcgaag       960
ctcctggctg ccatcctgca cctgggcaac ctgcagtatg aggcacgcac atttgaaaac      1020
ctggatgcct gtgaggttct cttctcccca tcgctggcca cagctgcatc cctgcttgag      1080 gtgaacccc cagacctgat gagctgcctg actagccgca ccctcatcac ccgcggggag      1140
acggtgtcca ccccactgag cagggaacag gcactggacg tgcgcgacgc cttcgtaaag      1200
gggatctacg gcggctgtt cgtgtggatt gtggacaaga tcaacgcagc aatttacaag      1260
cctccctccc aggatgtgaa gaactctcgc aggtccatcg gcctcctgga catctttggg      1320
```

```
tttgagaact ttgctgtgaa cagctttgag cagctctgca tcaacttcgc caatgagcac    1380
ctgcagcagt tctttgtgcg gcacgtgttc aagctggagc aggaggaata tgacctggag    1440
agcattgact ggctgcacat cgagttcact gacaaccagg atgccctgga catgattgcc    1500
aacaagccca tgaacatcat ctccctcatc gatgaggaga gcaagttccc caagggcaca    1560
gacaccacca tgttacacaa gctgaactcc cagcacaagc tcaacgccaa ctacatcccc    1620
cccaagaaca accatgagac ccagtttggc atcaaccatt ttgcaggcat cgtctactat    1680
gagacccaag gcttcctgga agaaccga gacaccctgc atggggacat tatccagctg    1740
gtccactcct ccaggaacaa gttcatcaag cagatcttcc aggccgatgt cgccatgggc    1800
gccgagacca ggaagcgctc gcccacactt agcagccagt tcaagcggtc actggagctg    1860
ctgatgcgca cgctgggtgc ctgccagccc ttctttgtgc gatgcatcaa gcccaatgag    1920
ttcaagaagc ccatgctgtt cgaccggcac ctgtgcgtgc gccagctgcg gtactcagga    1980
atgatggaga ccatccgaat ccgccgagct ggctacccca tccgctacag cttcgtagag    2040
tttgtggagc ggtaccgtgt gctgctgcca ggtgtgaagc cggcctacaa gcagggcgac    2100
ctccgcggga cttgccagcg catggctgag gctgtgctgg caccacga tgactggcag    2160
ataggcaaaa ccaagatctt tctgaaggac caccatgaca tgctgctgga agtggagcgg    2220
gacaaagcca tcaccgacag agtcatcctc cttcagaaag tcatccgggg attcaaagac    2280
aggtctaact ttctgaagct gaagaacgct gccacactga tccagaggca ctggcggggt    2340
cacaactgta ggaagaacta cgggctgatg cgtctgggct tcctgcggct gcaggccctg    2400
caccgctccc ggaagctgca ccagcagtac cgcctggccc gccagcgcat catccagttc    2460
caggcccgct gccgcgccta tctggtgcgc aaggccttcc gccaccgcct ctgggctgtg    2520
ctcaccgtgc aggcctatgc ccggggcatg atcgcccgca ggctgcacca acgcctcagg    2580
gctgagtatc tgtggcgcct cgaggctgag aaaatgcggc tggcggagga agagaagctt    2640
```

<210> SEQ ID NO 91  
<211> LENGTH: 880  
<212> TYPE: PRT  
<213> ORGANISM: Artificial Sequence  
<220> FEATURE:  
<223> OTHER INFORMATION: Synthetic

<400> SEQUENCE: 91

```
Met Val Ile Leu Gln Gln Gly Asp His Val Trp Met Asp Leu Arg Leu
1               5                   10                  15

Gly Gln Glu Phe Asp Val Pro Ile Gly Ala Val Val Lys Leu Cys Asp
            20                  25                  30

Ser Gly Gln Val Gln Val Asp Asp Glu Asp Asn Glu His Trp Ile
        35                  40                  45

Ser Pro Gln Asn Ala Thr His Ile Lys Pro Met His Pro Thr Ser Val
    50                  55                  60

His Gly Val Glu Asp Met Ile Arg Leu Gly Leu Asn Glu Ala Gly
65                  70                  75                  80

Ile Leu Arg Asn Leu Leu Ile Arg Tyr Arg Asp His Leu Ile Tyr Thr
                85                  90                  95

Tyr Thr Gly Ser Ile Leu Val Ala Val Asn Pro Tyr Gln Leu Leu Ser
            100                 105                 110

Ile Tyr Ser Pro Glu His Ile Arg Gln Tyr Thr Asn Lys Lys Ile Gly
        115                 120                 125
```

```
Glu Met Pro Pro His Ile Phe Ala Ile Ala Asp Asn Cys Tyr Phe Asn
    130                 135                 140

Met Lys Arg Asn Ser Arg Asp Gln Cys Cys Ile Ile Ser Gly Glu Ser
145                 150                 155                 160

Gly Ala Gly Lys Thr Glu Ser Thr Lys Leu Ile Leu Gln Phe Leu Ala
                165                 170                 175

Ala Ile Ser Gly Gln His Ser Trp Ile Glu Gln Val Leu Glu Ala
            180                 185                 190

Thr Pro Ile Leu Glu Ala Phe Gly Asn Ala Lys Thr Ile Arg Asn Asp
            195                 200                 205

Asn Ser Ser Arg Phe Gly Lys Tyr Ile Asp Ile His Phe Asn Lys Arg
210                 215                 220

Gly Ala Ile Glu Gly Ala Lys Ile Glu Gln Tyr Leu Leu Glu Lys Ser
225                 230                 235                 240

Arg Val Cys Arg Gln Ala Leu Asp Glu Arg Asn Tyr His Val Phe Tyr
                245                 250                 255

Cys Met Leu Glu Gly Met Ser Glu Asp Gln Lys Lys Lys Leu Gly Leu
            260                 265                 270

Gly Gln Ala Ser Asp Tyr Asn Tyr Leu Ala Met Gly Asn Cys Ile Thr
        275                 280                 285

Cys Glu Gly Arg Val Asp Ser Gln Glu Tyr Ala Asn Ile Arg Ser Ala
    290                 295                 300

Met Lys Val Leu Met Phe Thr Asp Thr Glu Asn Trp Glu Ile Ser Lys
305                 310                 315                 320

Leu Leu Ala Ala Ile Leu His Leu Gly Asn Leu Gln Tyr Glu Ala Arg
                325                 330                 335

Thr Phe Glu Asn Leu Asp Ala Cys Glu Val Leu Phe Ser Pro Ser Leu
            340                 345                 350

Ala Thr Ala Ala Ser Leu Leu Glu Val Asn Pro Pro Asp Leu Met Ser
        355                 360                 365

Cys Leu Thr Ser Arg Thr Leu Ile Thr Arg Gly Glu Thr Val Ser Thr
    370                 375                 380

Pro Leu Ser Arg Glu Gln Ala Leu Asp Val Arg Asp Ala Phe Val Lys
385                 390                 395                 400

Gly Ile Tyr Gly Arg Leu Phe Val Trp Ile Val Asp Lys Ile Asn Ala
                405                 410                 415

Ala Ile Tyr Lys Pro Pro Ser Gln Asp Val Lys Asn Ser Arg Arg Ser
            420                 425                 430

Ile Gly Leu Leu Asp Ile Phe Gly Phe Glu Asn Phe Ala Val Asn Ser
        435                 440                 445

Phe Glu Gln Leu Cys Ile Asn Phe Ala Asn Glu His Leu Gln Gln Phe
450                 455                 460

Phe Val Arg His Val Phe Lys Leu Glu Gln Glu Glu Tyr Asp Leu Glu
465                 470                 475                 480

Ser Ile Asp Trp Leu His Ile Glu Phe Thr Asp Asn Gln Asp Ala Leu
                485                 490                 495

Asp Met Ile Ala Asn Lys Pro Met Asn Ile Ile Ser Leu Ile Asp Glu
            500                 505                 510

Glu Ser Lys Phe Pro Lys Gly Thr Asp Thr Thr Met Leu His Lys Leu
        515                 520                 525

Asn Ser Gln His Lys Leu Asn Ala Asn Tyr Ile Pro Pro Lys Asn Asn
    530                 535                 540

His Glu Thr Gln Phe Gly Ile Asn His Phe Ala Gly Ile Val Tyr Tyr
```

```
545                 550                 555                 560

Glu Thr Gln Gly Phe Leu Glu Lys Asn Arg Asp Thr Leu His Gly Asp
                565                 570                 575

Ile Ile Gln Leu Val His Ser Ser Arg Asn Lys Phe Ile Lys Gln Ile
                580                 585                 590

Phe Gln Ala Asp Val Ala Met Gly Ala Glu Thr Arg Lys Arg Ser Pro
                595                 600                 605

Thr Leu Ser Ser Gln Phe Lys Arg Ser Leu Glu Leu Leu Met Arg Thr
    610                 615                 620

Leu Gly Ala Cys Gln Pro Phe Phe Val Arg Cys Ile Lys Pro Asn Glu
625                 630                 635                 640

Phe Lys Lys Pro Met Leu Phe Asp Arg His Leu Cys Val Arg Gln Leu
                645                 650                 655

Arg Tyr Ser Gly Met Met Glu Thr Ile Arg Ile Arg Arg Ala Gly Tyr
                660                 665                 670

Pro Ile Arg Tyr Ser Phe Val Glu Phe Val Glu Arg Tyr Arg Val Leu
                675                 680                 685

Leu Pro Gly Val Lys Pro Ala Tyr Lys Gln Gly Asp Leu Arg Gly Thr
    690                 695                 700

Cys Gln Arg Met Ala Glu Ala Val Leu Gly Thr His Asp Asp Trp Gln
705                 710                 715                 720

Ile Gly Lys Thr Lys Ile Phe Leu Lys Asp His His Asp Met Leu Leu
                725                 730                 735

Glu Val Glu Arg Asp Lys Ala Ile Thr Asp Arg Val Ile Leu Leu Gln
                740                 745                 750

Lys Val Ile Arg Gly Phe Lys Asp Arg Ser Asn Phe Leu Lys Leu Lys
                755                 760                 765

Asn Ala Ala Thr Leu Ile Gln Arg His Trp Arg Gly His Asn Cys Arg
    770                 775                 780

Lys Asn Tyr Gly Leu Met Arg Leu Gly Phe Leu Arg Leu Gln Ala Leu
785                 790                 795                 800

His Arg Ser Arg Lys Leu His Gln Gln Tyr Arg Leu Ala Arg Gln Arg
                805                 810                 815

Ile Ile Gln Phe Gln Ala Arg Cys Arg Ala Tyr Leu Val Arg Lys Ala
                820                 825                 830

Phe Arg His Arg Leu Trp Ala Val Leu Thr Val Gln Ala Tyr Ala Arg
                835                 840                 845

Gly Met Ile Ala Arg Arg Leu His Gln Arg Leu Arg Ala Glu Tyr Leu
    850                 855                 860

Trp Arg Leu Glu Ala Glu Lys Met Arg Leu Ala Glu Glu Lys Leu
865                 870                 875                 880
```

DUAL AAV-MYO7A VECTORS WITH IMPROVED SAFETY FOR THE TREATMENT OF USH1B

RELATED APPLICATIONS

This Application is a national stage filing under 35 U.S.C. § 371 of International Patent Application Serial No. PCT/US2021/025281, filed Mar. 31, 2021, which claims the benefit of the filing date of U.S. Provisional Application No. 63/003,774, filed Apr. 1, 2020, the entire contents of each of which are incorporated herein by reference in their entirety.

REFERENCE TO A SEQUENCE LISTING SUBMITTED AS A TEXT FILE VIA EFS-WEB

This application contains a sequence listing which has been submitted in ASCII format via EFS-Web and is hereby incorporated by reference in its entirety. Said ASCII copy, created on Sep. 29, 2022, is named U120270039US01-SEQ-KSB and is 351,960 bytes in size.

NON-FEDERAL SUPPORT

This invention was made in whole or in part from funding under grant award number TA-GT-0419-0774-UFL-GH received from the Foundation for Fighting Blindness, and under agreement number AGR00018211, received from Atsena Therapeutics, Inc.

BACKGROUND OF THE DISCLOSURE

Recombinant AAV has emerged as a useful gene delivery vehicle to treat retinal disease. However, one limitation of AAV is its relatively small DNA packaging capacity-approximately 4.7 kilobases (KB). Thus, standard AAV vector systems are unsuitable for addressing diseases in which large genes are mutated or otherwise dysfunctional, such as Usher syndrome. A solution is needed in order to package large genes into AAV vector systems and safely deliver gene therapy treatment to patients.

SUMMARY OF THE DISCLOSURE

The disclosure relates generally to the fields of molecular biology and virology, and in particular, to the development of gene delivery vehicles. Disclosed are improved rAAV dual vector and polynucleotide vector systems, and compositions useful in delivering a variety of nucleic acid segments, including those encoding therapeutic proteins, polypeptides, peptides, antisense oligonucleotides, or ribozyme constructs to selected host cells for use in various gene-therapy regimens. Further disclosed are recombinant viral particles, isolated host cells, and pharmaceutical compositions comprising any of these rAAV dual vector and polynucleotide vector systems. Methods are also provided for preparing and using the improved rAAV dual vector systems disclosed herein in a variety of viral-based gene therapies, and in particular, for the treatment and/or amelioration of symptoms of Myosin VII-deficiency, including, without limitation, the treatment of human Usher syndrome type IB. Further provided herein are methods of treatment or amelioration of a disease or condition involving the administration of rAAV dual vector systems that encode the MYO7A protein and result in reduced cytotoxicities than previously available vector systems. In some aspects, provided are methods of administering a vector system, whereby an amount of truncated MYO7A protein and/or associated cytotoxicity is minimized. In some embodiments, the therapeutic polypeptide is not a myosin polypeptide.

In various aspects, the methods of treatment and pharmaceutical compositions provided herein are intended for administration to one or both eyes of a subject, e.g., a human or animal subject. In further various aspects, the methods of treatment and pharmaceutical compositions provided herein are intended for administration to one or both ears of a subject, e.g., a human or animal subject.

The disclosure provides materials and methods for gene therapy of diseases, such as Usher syndrome. Usher syndrome, including types I (e.g., USH1B), II, and III, is a condition that results in sensory impairment, specifically in the visual, auditory, and vestibular systems. The sensory loss that accompanies Usher syndrome can be present even at birth, and gets progressively worse with age.

The most common form of Usher syndrome, USH1B, is a severe autosomal-recessive, deaf-blindness disorder caused by mutations in the MyosinVIIa gene. Patients are born deaf due to insufficient expression of human Myosin VII protein (MYO7A) and/or mutations in the gene causing protein malfunction. Blindness occurs from a progressive retinal degeneration that begins within the first decade of life. MYO7A protein is expressed in photoreceptors and retinal pigment epithelium (RPE), and is involved in opsin transport through photoreceptor cilia and the movement of RPE melanosomes. A study showed that photoreceptors (PRs) may be the initial site of disease, and that defects in an adhesion belt structure that sits around the photoreceptor outer segment in humans may cause the retinal degeneration seen in USH1B patients (Sahly, et al., 2012). The coding region for the MYO7A protein, however, is 6534 or 6648 nucleotides in length (depending on the isoform), making traditional AAV vector systems unsuitable for gene therapy of USH1B.

While there are currently no treatments available for this condition, gene therapy offers promise for recovering/maintaining function within the visual, auditory, and vestibular systems. Previously, Allocca et al. (2008) published results suggesting that AAV5 serotype vectors were capable of packaging genomes of up to 8.9 KB in size, and that these vectors expressed full-length proteins when delivered in vivo. In Allocca et al. (2008), the authors expressed full-length MYO7A protein from an AAV5 vector containing the CMV promoter driving hMYO7A. Subsequent studies confirmed that these 'oversized' AAV5 vectors did indeed drive full-length protein expression, however the genetic content of each vector capsid was found to be limited only to ~5 KB of DNA, and not the 8.7 KB originally reported by Allocca et al. (2008) (Lai et al., 2010; Dong et al., 2010; Wu et al., 2010). These vector capsids were shown to contain a "heterogeneous mixture" of truncated vector genomes (e.g., the 5' end of the gene, the 3' end of the gene, or a mixture of the two with an internal sequence deletion). Additionally, these oversized/heterogeneous vectors exhibited poor packaging efficiency (for example, resulting in low-vector titers) and low transduction efficiency when compared to matched reporter vectors of standard size (<5 KB) (Wu et al., 2010).

Using the 'heterogeneous' system as described in Lai et al. (2010), Dong et al. (2010) and Wu et al. (2010), vectors containing portions of the MYO7A transgene were packaged despite the observed poor packaging efficiency, and proof-of-concept results were demonstrated in the shaker-1 mouse model of USH1B. The therapeutic results achieved with the heterogeneous AAV-hMYO7A vectors were comparable to previous gene replacement results using a lentivirus-based hMYO7A vector (Hashimoto et al., 2007). This lentivirus-MYO7A vector is under development by Oxford BioMedica in collaboration with Sanofi-Aventis for a phase I/II clinical trial of USH1B, marketed under the name UshStat® LentiVector®. Lentivirus is regarded as a vector platform that is not well-suited for infecting post-mitotic (for example, non-dividing) cells. Furthermore, although the vector is suitable for transducing RPE, many studies have shown it to be ineffective at transducing adult photoreceptors. Because photoreceptors (PRs) may be the initial site of disease (Sahly, et al., 2012), the exclusive targeting by UshStat® of RPE cells may not bring about a complete or effective therapy, although this remains to be seen in human clinical trials.

Because of the excellent safety profile and encouraging reports of efficacy in the AAV gene therapy trials for LCA2/RPE65, there has been continuing interest in creating an AAV-based system for treating USH1B patients. The inventors have previously characterized AAV dual vector platforms for use in treating USH1B patients, also described herein. The original dual vector systems designed by the inventors (e.g., the "first generation" dual vector systems) have successfully demonstrated that mRNA arising from the system is 100% accurate relative to what would be predicted by correct homologous recombination of the front and back vector pairs, making them useful as gene therapy delivery vector systems. These vectors are described in US Patent Publication Nos. 2019/0153050 and 2014/0256802, each of which is incorporated herein by reference in its entirety.

This disclosure is based, at least in part, on the observation that some of the previous dual vector platforms resulted in the production of truncated MYO7A protein that was correlated with production of a truncated fragment of the MYO7A protein within the cell. Specifically, loss of retinal structure/function was observed following injection of a previous, first-generation dual vector hybrid system into mouse retina, which may have been attributable to the gain of function exerted by truncated MYO7A protein containing a portion of the tail domain. Hybrid vector systems contain both recombinogenic and spliceosome-recognition sequences that enable two paths through which the two halves of the polynucleotide vector system can combine in a cell to make a full-length polynucleotide. Hybrid vector systems are thus modular and versatile alternatives to simple overlap and simple trans-splicing dual vector systems. Described herein are modified dual hybrid vector systems that shift (all of, or a portion of) the coding sequence for the MYO7A tail domain from the front-half vector to the back-half vector by altering the split point (e.g., from between exons 23 and 24, to between exons 21 and 22) in order to eliminate the production of a truncated MYO7A protein and any associated cytotoxicity (for example, a gain of function toxicity observed in the retina). Further described herein are modified dual overlap vector systems that shift the coding sequence for the MYO7A tail domain from the front-half vector to the back-half vector by altering the overlapping coding sequence among the two vector halves.

Further described herein are codon-modified hybrid and overlap vector systems in which putative stop codons in non-coding sequences are removed. Further described herein are modified overlap vector systems that contain altered and/or reduced lengths of the overlapping coding sequence between the two vectors. Further described herein are modified hybrid vector systems that contain reductions in the lengths of the back half vector.

This disclosure is also based, at least in part, on the improvement of a previous, first-generation dual vector overlap system to increase transduction efficiency in the retina. In some embodiments, the disclosed improvements encompass the shortening of 5' (front) and/or 3' (back) AAV vectors in the system to increase rAAV particle packaging efficiencies.

In some embodiments, the disclosed rAAV vectors comprise a transgene encoding a MYO7A protein, e.g., human MYO7A protein. In some embodiments, the disclosed rAAV vectors comprise transgenes that encode other proteins relevant to Usher syndrome. In some embodiments, the disclosed rAAV vectors comprise transgenes that encode other proteins relevant to other ocular or aural diseases, disorders, or conditions.

Accordingly, aspects of the disclosure provide modified dual AAV vector systems that permit expression of full-length proteins, whose coding sequence exceeds the polynucleotide packaging capacity of an individual AAV vector.

Thus, in some aspects, provided herein are hybrid dual vector systems. Provided herein are polynucleotide vector systems comprising: i) a first AAV vector polynucleotide comprising an inverted terminal repeat at each end of the polynucleotide, and between the inverted terminal repeats a promoter followed by a partial coding sequence that encodes an N-terminal part of a myosin polypeptide followed by a splice donor (SD) site and an intron, and ii) a second AAV vector polynucleotide comprising an inverted terminal repeat at each end of the polynucleotide, and between the inverted terminal repeats an intron and a splice acceptor (SA) site for the intron, wherein the intron sequence in the first and second AAV vectors comprises a polynucleotide sequence that overlaps, and wherein the split point between the first and second AAV vector polynucleotide sequences is between exon 21 and exon 22 of the hMYO7A gene (see FIGS. 22D and 22E). Provided herein are hybrid polynucleotide systems in which the N-terminal part of the myosin polypeptide does not comprise the single-alpha helix (SAH) domain of the myosin polypeptide (e.g., in which the first AAV vector polynucleotide comprises a partial coding sequence that does not encode the SAH domain of the myosin polypeptide). In some embodiments, the intron sequence that overlaps comprises an alkaline phosphatase intron. Further provided herein are polynucleotide vector systems wherein the first AAV vector polynucleotide comprises the nucleotide sequence of SEQ ID NO: 33 or 34, and the second AAV vector polynucleotide comprises the nucleotide sequence of SEQ ID NO: 32, 35, or 44.

In other aspects, provided herein are overlap dual vector systems. Provided herein are polynucleotide vector systems comprising: i) a first AAV vector polynucleotide comprising an inverted terminal repeat at each end of the polynucleotide, and between the inverted terminal repeats a promoter followed by a partial coding sequence that encodes an N-terminal part of a myosin polypeptide, and ii) a second AAV vector polynucleotide comprising an inverted terminal repeat at each end of the polynucleotide, and between the inverted terminal repeats a partial coding sequence that encodes a C-terminal part of the myosin polypeptide, wherein the polynucleotide sequence encoding the polypeptide sequence in the first and second AAV vectors comprises a polynucleotide sequence that overlaps, and wherein the C-terminal part of the myosin polypeptide comprises the single-alpha helix (SAH) domain of the myosin polypeptide. Further provided herein are polynucleotide vector systems wherein the first AAV vector polynucleotide comprises a nucleic acid sequence at least about 80%, at least 85%, at least 90%, at least 95%, at least 98%, or at least 99% identical to the nucleotide sequence of SEQ ID NO: 36, and the second AAV vector polynucleotide comprises a nucleic acid sequence at least about 80%, at least 85%, at least 90%, at least 95%, at least 98%, or at least 99% identical to the nucleotide sequence of SEQ ID NO: 38.

In some aspects, provided herein are polynucleotide vector systems comprising: i) a first AAV vector polynucleotide comprising an inverted terminal repeat at each end of the polynucleotide, and between the inverted terminal repeats a promoter followed by a partial coding sequence that encodes an N-terminal part of a myosin polypeptide, and ii) a second AAV vector polynucleotide comprising an inverted terminal repeat at each end of the polynucleotide, and between the inverted terminal repeats a partial coding sequence that encodes a C-terminal part of the myosin polypeptide, wherein the polynucleotide sequence encoding the polypeptide sequence in the first and second AAV vectors comprises a polynucleotide sequence that overlaps, and wherein (i) the first AAV vector polynucleotide comprises a nucleic acid sequence at least about 80%, at least 85%, at least 90%, at least 95%, at least 98%, or at least 99% identical to SEQ ID NO: 63, 90, or 66, and (ii) the second AAV vector polynucleotide comprises a nucleic acid sequence at least about 80% at least 85%, at least 90%, at least 95%, at least 98%, or at least 99% identical to SEQ ID NO: 77 or 80.

Provided herein are polynucleotide vector systems comprising: i) a first AAV vector polynucleotide comprising an inverted terminal repeat at each end of the polynucleotide, and between the inverted terminal repeats a promoter followed by a partial coding sequence that encodes an N-terminal part of a myosin polypeptide, and ii) a second AAV vector polynucleotide comprising an inverted terminal repeat at each end of the polynucleotide, and between the inverted terminal repeats a partial coding sequence that encodes a C-terminal part of the myosin polypeptide, wherein the polynucleotide sequence encoding the polypeptide sequence in the first and second AAV vectors comprises a polynucleotide sequence that overlaps, and wherein (i) the first AAV vector polynucleotide comprises a nucleotide sequence selected from SEQ ID NOs: 63, 90, and 66, and (ii) the second AAV vector polynucleotide comprises a nucleotide sequence selected from SEQ ID NOs: 77 and 80.

Provided herein are polynucleotide vector systems comprising: i) a first AAV vector polynucleotide comprising an inverted terminal repeat at each end of the polynucleotide, and between the inverted terminal repeats a promoter followed by a partial coding sequence that encodes an N-terminal part of a myosin polypeptide, and ii) a second AAV vector polynucleotide comprising an inverted terminal repeat at each end of the polynucleotide, and between the inverted terminal repeats a partial coding sequence that encodes a C-terminal part of the myosin polypeptide, wherein the polynucleotide sequence encoding the polypeptide sequence in the first and second AAV vectors comprises a polynucleotide sequence that overlaps, and wherein (i) the first AAV vector polynucleotide encodes an amino acid sequence at least about 80%, at least 85%, at least 90%, at least 95%, at least 98%, or at least 99% identical to the amino acid sequence of SEQ ID NO: 62, 91, or 65, and (ii) the second AAV vector polynucleotide encodes an amino acid sequence at least about 80%, at least 85%, at least 90%, at least 95%, at least 98%, or at least 99% identical to the amino acid sequence of SEQ ID NO: 78 or 81.

Provided herein are polynucleotide vector systems comprising: i) a first AAV vector polynucleotide comprising an inverted terminal repeat at each end of the polynucleotide, and between the inverted terminal repeats a promoter followed by a partial coding sequence that encodes an N-terminal part of a myosin polypeptide, and ii) a second AAV vector polynucleotide comprising an inverted terminal repeat at each end of the polynucleotide, and between the inverted terminal repeats a partial coding sequence that encodes a C-terminal part of the myosin polypeptide, wherein the polynucleotide sequence encoding the polypeptide sequence in the first and second AAV vectors comprises a polynucleotide sequence that overlaps, and wherein the polynucleotide sequence that overlaps comprises a nucleotide sequence at least about 80%, at least 85%, at least 90%, at least 95%, at least 98%, or at least 99% identical to a sequence selected from any one of SEQ ID NOs: 39 and 52-59.

Provided herein are polynucleotide vector systems comprising: i) a first AAV vector polynucleotide comprising an inverted terminal repeat at each end of the polynucleotide, and between the inverted terminal repeats a promoter followed by a partial coding sequence that encodes an N-terminal part of a myosin polypeptide, and ii) a second AAV vector polynucleotide comprising an inverted terminal repeat at each end of the polynucleotide, and between the inverted terminal repeats a partial coding sequence that encodes a C-terminal part of the myosin polypeptide, wherein the polynucleotide sequence encoding the polypeptide sequence in the first and second AAV vectors comprises a polynucleotide sequence that overlaps, and wherein the polynucleotide sequence that overlaps comprises a sequence encoding any one of SEQ ID NOs: 79 and 82-89.

Provided herein are polynucleotide vector systems comprising: i) a first AAV vector polynucleotide comprising an inverted terminal repeat at each end of the polynucleotide, and between the inverted terminal repeats a promoter followed by a partial coding sequence that encodes an N-terminal part of a myosin polypeptide followed by a splice donor site and a first intron, and ii) a second AAV vector polynucleotide comprising an inverted terminal repeat at each end of the polynucleotide, and between the inverted terminal repeats a second intron and a splice acceptor site for the first intron, wherein the nucleotide sequences of the first and second introns (collectively referred to herein as "the intron sequence") comprise a polynucleotide sequence that overlaps, and wherein the first and/or second intron sequence comprises a nucleic acid sequence at least about 80% at least 85%, at least 90%, at least 95%, at least 98%, or at least 99% identical to SEQ ID NO: 69 or SEQ ID NO: 70.

Provided herein are polynucleotide vector systems comprising: i) a first AAV vector polynucleotide comprising an inverted terminal repeat at each end of the polynucleotide, and between the inverted terminal repeats a promoter followed by a partial coding sequence that encodes an N-terminal part of a myosin polypeptide followed by a splice donor site and a first intron, and ii) a second AAV vector polynucleotide comprising an inverted terminal repeat at each end of the polynucleotide, and between the inverted terminal repeats a second intron and a splice acceptor site for the first intron, wherein the nucleotide sequences of the first and second introns comprise a polynucleotide sequence that overlaps, and wherein the split point between the first and second AAV vector polynucleotide sequences is between two exons of the gene encoding the therapeutic protein.

Provided herein are polynucleotide vector systems comprising: i) a first AAV vector polynucleotide comprising an inverted terminal repeat at each end of the polynucleotide, and between the inverted terminal repeats a promoter followed by a partial coding sequence that encodes an N-terminal part of a myosin polypeptide followed by a splice donor site and a first intron, and ii) a second AAV vector polynucleotide comprising an inverted terminal repeat at each end of the polynucleotide, and between the inverted terminal repeats a second intron and a splice acceptor site for the first intron, wherein the nucleotide sequences of the first and second introns comprise a polynucleotide sequence that overlaps, and wherein (i) the first AAV vector polynucleotide comprises a nucleic acid sequence at least about 80%, at least 85%, at least 90%, at least 95%, at least 98%, or at least 99% identical to SEQ ID NOs: 31, 33, 34, and 46, and (ii) the second AAV vector polynucleotide comprises a nucleic acid sequence at least about 80%, at least 85%, at least 90%, at least 95%, at least 98%, or at least 99% identical to SEQ ID NOs: 32, 35, 44, and 47-49.

Provided herein are polynucleotide vector systems comprising: i) a first AAV vector polynucleotide comprising an inverted terminal repeat at each end of the polynucleotide, and between the inverted terminal repeats a promoter followed by a partial coding sequence that encodes an N-terminal part of a myosin polypeptide followed by a splice donor site and a first intron, and ii) a second AAV vector polynucleotide comprising an inverted terminal repeat at each end of the polynucleotide, and between the inverted terminal repeats a second intron and a splice acceptor site for the first intron, wherein the nucleotide sequences of the first and second introns comprise a polynucleotide sequence that overlaps, and wherein (i) the first AAV vector polynucleotide comprises a nucleic acid sequence at least about 80%, at least 85%, at least 90%, at least 95%, at least 98%, or at least 99% identical to the nucleotide sequence of SEQ ID NO: 33, and (ii) the second AAV vector polynucleotide comprises a nucleic acid sequence at least about 80%, at least 85%, at least 90%, at least 95%, at least 98%, or at least 99% identical to the nucleotide sequence of SEQ ID NO: 32.

Provided herein are polynucleotide vector systems comprising: i) a first AAV vector polynucleotide comprising an inverted terminal repeat at each end of the polynucleotide, and between the inverted terminal repeats a promoter followed by a partial coding sequence that encodes an N-terminal part of a myosin polypeptide followed by a splice donor site and a first intron, and ii) a second AAV vector polynucleotide comprising an inverted terminal repeat at each end of the polynucleotide, and between the inverted terminal repeats a second intron and a splice acceptor site for the first intron, wherein the nucleotide sequences of the first and second introns comprise a polynucleotide sequence that overlaps, and wherein (i) the first AAV vector polynucleotide comprises a nucleic acid sequence at least about 80%, at least 85%, at least 90%, at least 95%, at least 98%, or at least 99% identical to the nucleotide sequence of SEQ ID NO: 34, and (ii) the second AAV vector polynucleotide comprises a nucleic acid sequence at least about 80%, at least 85%, at least 90%, at least 95%, at least 98%, or at least 99% identical to the nucleotide sequence of SEQ ID NO: 35.

Provided herein are polynucleotide vector systems comprising: i) a first AAV vector polynucleotide comprising an inverted terminal repeat at each end of the polynucleotide, and between the inverted terminal repeats a promoter followed by a partial coding sequence that encodes an N-terminal part of a myosin polypeptide followed by a splice donor site and a first intron, and ii) a second AAV vector polynucleotide comprising an inverted terminal repeat at each end of the polynucleotide, and between the inverted terminal repeats a second intron and a splice acceptor site for the first intron, wherein the nucleotide sequences of the first and second introns comprise a polynucleotide sequence that overlaps, and wherein (i) the first AAV vector polynucleotide comprises a nucleic acid sequence at least about 80%, at least 85%, at least 90%, at least 95%, at least 98%, or at least 99% identical to the nucleotide sequence of SEQ ID NO: 34, and (ii) the second AAV vector polynucleotide comprises a nucleic acid sequence at least about 80%, at least 85%, at least 90%, at least 95%, at least 98%, or at least 99% identical to the nucleotide sequence of SEQ ID NO: 44.

BRIEF DESCRIPTION OF THE DRAWINGS

For promoting an understanding of the principles of the disclosure, reference will now be made to the embodiments, or examples, illustrated in the drawings and specific language will be used to describe the same. It will nevertheless be understood that no limitation of the scope of the disclosure is thereby intended. Any alterations and further modifications in the described embodiments, and any further applications of the principles of the disclosure as described herein are contemplated as would normally occur to one of ordinary skill in the art to which the disclosure relates.

FIGS. 8A-8D show differences in RPE melanosome localization in wild type vs. shaker-1 mice. In wild type mice, RPE melanosome apically migrate towards photoreceptor outer segments (FIG. 8A) whereas this phenomenon fails to occur in mice lacking MYO7A (shaker-1), as seen in (FIG. 8B). To the right is a high magnification image of single RPE cells from either a wild type (FIG. 8C) or shaker-1 (FIG. 8D) mouse showing this phenomenon up close.

FIGS. 9A-9C show that apical migration of RPE melanosomes is restored in shaker-1 mice injected with an exemplary Overlap Dual Vector System. Electron microscopy reveals that melanosomes of untreated shaker-1 mice do not apically migrate (FIG. 9A). In shaker-1 mice injected with exemplary overlap vectors (packaged in AAV2), RPE melanosomes migrate apically towards photoreceptors, which can be seen here in both low- and high-magnification images (FIGS. 9B and 9C).

FIG. 10A is a diagram of the viral vector encoding human MYO7A cDNA. FIG. 10B is a western blot of WT eyecup (lane 1), primary RPE cultures derived from MYO7A-null mice and infected with AAV2-MYO7A (lane 2) or AAV5-MYO7A (lane 3), or not infected (lane 4), and primary RPE cultures derived from MYO7A$^{+/-}$ mice (lane 5). All lanes were immunolabeled with antibodies against actin (as a loading indicator of relative protein loading) and MYO7A. FIGS. 10C-10F are immunofluorescence images of primary RPE cell cultures. Cells derived from MYO7A-null mice that were not infected (FIG. 10C), from MYO7A$^{+/-}$ mice (FIG. 10D), or from MYO7A-null mice infected with either 1×AAV2-MYO7A (FIG. 10E) or 1×AAV5-MYO7A (FIG. 10F). Scale=10 µm.

FIGS. 11A-11E show EM images of MYO7A immunogold labelling of the connecting cilium and pericilium from rod photoreceptors in a MYO7A-null retina. FIG. 11A is a longitudinal section from an untreated MYO7A-null retina (background label only). FIG. 11B and FIG. 11C are longitudinal sections from MYO7A-null retinas treated with AAV2-MYO7A (FIG. 11B) or AAV5-MYO7A (FIG. 11C). Scale=50 nm. FIG. 11D and FIG. 11E are transverse sections of connecting cilia from rod photoreceptors in MYO7A-null retinas treated with AAV2-MYO7A (FIG. 11D) or AAV5-MYO7A (FIG. 11E). Scale=50 nm. FIG. 11F and FIG. 11G show EM images of RPE cells from MYO7A-null retinas treated with AAV2-MYO7A (FIG. 11F) or AAV5-MYO7A (FIG. 11G). Scale=500 nm. Areas indicated by rectangles are enlarged in FIG. 11F-1 and FIG. 11G-1 to show MYO7A immunogold labeling (indicated by circles). Scale=50 nm. FIG. 11H and FIG. 11I show EM image of a longitudinal section of the connecting cilium and pericilium from a rod (FIG. 11H) and a cone (FIG. 11I) photoreceptor in a MYO7A-null retina, treated with AAV2-MYO7A. The section was double-labeled with MYO7A (12-nm gold) and rod opsin (15-nm gold) antibodies. Rod outer segments were labeled with the opsin antibody, while cones were identified by lack of rod opsin labeling in their outer segments. The sections show just the base of the outer segments. Nearly all the label in the connecting cilium is MYO7A, even in the rod. Scale=50 nm. FIGS. 11J-11M are bar graphs indicating MYO7A immunogold particle density in the rod photoreceptor cilium and pericilium (FIG. 11J and FIG. 11L) and in the RPE (FIG. 11K and FIG. 11M), following treatment with AAV2-MYO7A (FIG. 11J and FIG. 11K) or AAV5-MYO7A (FIG. 11L and FIG. 11M) at different concentrations. n=3 animals per condition. Bars indicate SEM.

FIG. 12E illustrates a region distant from injection site, where all RPE cells lacked melanosomes in their apical processes. Brackets on left side indicate RPE apical processes. Scale=25 µm. FIG. 12F is a diagram of an eyecup, indicating the relative locations of the images shown in FIGS. 12A-12E. ONH indicates the optic nerve head.

FIG. 14A-1 and FIG. 14A-2 illustrate a diagram of the overlapping AAV2-MYO7A dual vectors. The overlapping region contains 1365 bases. FIG. 14B is a Western blot of proteins from primary RPE cultures derived from MYO7A-null mice that were either not infected (lane 1), or infected with AAV2-MYO7A (overlap dual) (lane 2); primary RPE cultures derived from MYO7A$^{+/-}$ mice (lane 3); WT eyecup (lane 4); HEK293 cells transfected with pTR-smCBA-MYO7A (lane 5). All lanes were immunolabeled with anti-MYO7A and anti-actin. FIGS. 14C-14F show immunofluorescence of cultured RPE cells transduced with AAV2-MYO7A (overlap dual). FIGS. 14C-14E show primary RPE cultures derived from MYO7A-null mice and ARPE19 (FIG. 14F) cells. Scale=10 µm. FIG. 14G is a bar graph indicating the distribution of MYO7A immunogold particle density among RPE cells from retinas of MYO7A-null mice, injected with AAV2-MYO7A(dual). n=3 animals.

FIG. 15A shows light microscopy of a semithin section from a treated MYO7A-null mouse retina. The region shown is near the injection site. Arrows indicate melanosomes in the apical processes. White lines indicate cells that still show the MYO7A-null phenotype, with an absence of melanosomes in the apical processes. Scale=50 µm. FIG. 15B is a low-magnification immunoEM image of RPE from a retina treated with AAV2-MYO7A (overlap dual). As in FIG. 15A, the white line indicated a region that still showed the MYO7A-null phenotype. Rectangle 'c', includes melanosomes in the apical region, indicating a corrected RPE cell. Scale=500 nm. FIGS. 15C-15E show higher-magnification images of regions outlined by the rectangles shown in FIG. 15B. MYO7A immunogold particles are indicated by circles. Scale=50 nm. FIG. 15F is a bar graph illustrating MYO7A immunogold particle density measured in RPE cells from MYO7A-null retinas, WT retinas, or from MYO7A-null retinas treated with AAV2-MYO7A (overlap dual) and determined to be corrected or not corrected by the location of their apical melanosomes. n=3 animals per condition. Bars indicate SEM. FIG. 15G is an immunoEM image of a rod photoreceptor cilium double-labeled with antibodies against MYO7A (small gold particles) and against rod opsin (large gold particles). MYO7A labeling is associated with the connecting cilium and periciliary membrane, indicating expression and correct localization of MYO7A. While this region is devoid of opsin labeling, which is restricted to the disk membranes, it is consistent with the wild type (WT) phenotype, thus indicating correction of the mutant phenotype. Scale=300 nm.

FIGS. 18A-18D show MYO7A expression in the connecting cilium and pericilium of rod photoreceptors from MYO7A-null retinas injected with diluted AAV2-MYO7A (FIG. 18A and FIG. 18B) or AAV5-MYO7A (FIG. 18C and FIG. 18D); (FIG. 18A and FIG. 18C) 1:10, (FIG. 18B and FIG. 18D) 1:100. Scale=200 nm.

FIG. 19 shows the structural preservation of injected MYO7A-null retinas. Light microscopy of the photoreceptor layer 3 weeks after injection with 10×AAV5-MYO7A. Scale=15 μm.

FIG. 20 shows structural preservation of injected MYO7A-null retinas. Light microscopy of photoreceptor layer 3 months after injection with 1×AAV2-MYO7A. Scale=10 μm.

FIGS. 21A-21D show correction of abnormal levels of opsin in the connecting cilium and pericilium of rod photoreceptors following subretinal injections with AAV2-MYO7A or AAV5-MYO7A. ImmunoEMs from WT retina (FIG. 21A), MYO7A-null retinas treated with 1×AAV2-MYO7A (FIG. 21B) or 1×AAV5-MYO7A (FIG. 21C), and from an untreated MYO7A-null retina (FIG. 21D) labeled with anti-rod opsin and 12-nm gold-conjugated secondary antibody. Scale=200 nm.

FIG. 22A is a fragmented AAV (fAAV) vector. FIG. 22B shows simple overlap: the 1365-bp shared between the two vectors is shaded gray. FIG. 22C is a trans-splicing vector. FIG. 22D shows an AP hybrid vector: the 270-bp element shared between the two vectors is marked with diagonal gradient shading (⅓ APhead as described by Ghosh et al., 2011). FIG. 22E shows the native intron hybrid vectors utilizing a 250-bp sequence of MYO7A intron 23. 3' MYO7A is the 3'-portion of MYO7A; 5' MYO7A is the 5'-portion of MYO7A; AAV is adeno-associated virus; AP is alkaline phosphatase; intron=intron 23 of MYO7A; pA=polyadenylation signal; SA=splice-acceptor site; SD=splice-donor site; and smCBA refers to a (truncated) chimeric cytomegalovirus immediate early/chicken β-actin chimeric promoter.

FIG. 23A shows human embryonic kidney (HEK293) cells expressing human MYO7A after infection with simple overlap vectors (MOI of 10,000 for both vectors) packaged in AAV2 (tripleY-F). Equal amounts of protein were separated on 7.5% sodium dodecyl sulfate (SDS) polyacrylamide gel electrophoresis (PAGE) and stained for MYO7A. FIG. 23B shows HEK293 cells infected with AAV2 (tripleY-F) at MOIs of 10,000, 2,000, and 400. FIG. 23C is a time-course assay of MYO7A expressed in HEK293 cells. Cells were harvested 3-7 days after infection. MOI=multiplicity of infection; T=HEK293 cells transfected with full-length MYO7A plasmid; U=untreated HEK293 cells.

FIG. 29A shows the resultant protein expression following simple overlap or AP hybrid dual vector injections. Myo7a−/− mice were injected with 5.0×10$^8$ vector genomes (vg) total (2.5×10$^8$ vg each) of either the simple overlap or AP hybrid dual vectors. All vector expression was driven by the smCBA promoter. Retinas were collected and analyzed at 6 weeks post-injection. FIG. 29B shows the quantification of the full-length MYO7A expression normalized to vinculin (VCL) for multiple treatment groups.

FIG. 31A is a bar graph showing the average MYO7A front half transcript expression at 6 weeks post-injection. FIG. 31B shows the Western Blot results at 6 weeks post-injection, using VCL as a loading control. All vectors were delivered at 5.0×10$^8$ vg.

FIG. 35A shows the Western Blot results of the original hybrid, with a split site between exons 23 and 24 ("Ex23/24"), and the second generation hybrid, with a split site between exons 21 and 22 ("Ex21/22"), using VCL as a loading control. FIG. 35B illustrates the normalized full-length MYO7A expression. NI indicates "not injected".

FIG. 36A shows the Western Blot results, using VCL as a loading control. FIG. 36B shows p-values for the comparison of full-length protein expression between exons 21/22 and exons 23/24 in the hybrid vector systems. FIG. 36C displays the normalized MYO7A expression relative to WT. Hybrid vectors were encapsidated and administered in AAV5 and AAV8(Y733F) virions, and the MYO7A expression associated with each serotype was measured and normalized to WT.

FIG. 37A shows the second generation hybrid vector system, with a split site between exons 21 and 22. AP sequences act as a polyA and/or splicing signal. FIG. 37B shows the overlap vectors with the potential in-frame stop codons from the 3' end (downstream of the MYO7A N-terminal fragment) in the front hybrid vector plasmid removed.

FIG. 39A shows the Western blot results of the original hybrid (exons 23/24) front, second generation hybrid (exons 21/22) front, and the hybrid CMv1 (exons 21/22) front. As used herein, "CMv1" (or "COv2") refers to the human codon-modified version 1 hybrid vector. FIG. 39B is a bar graph showing the truncated MYO7A expression normalized to vinculin.

FIG. 41 shows the nonhuman primate data for the expression of AAV-mediated MYO7A transcript in macaque retina and tolerability of dual AAV5-MYO7A vectors in subretinally injected macaque retinas. Vectors were delivered at titers of 4×10$^8$ vg each (8×10$^8$ vg total).

FIGS. 45A-45C show two different dual AAV vector platforms that drive full-length MYO7A expression. FIG. 45A contains schematics depicting the overlap and hybrid dual AAV vector platforms. FIGS. 45B and 45C show the amount of MYO7A produced from the original hybrid and overlap vectors following encapsidation in AAV5 or AAV8 (Y733F) virions. VCL marker was used as a control.

FIG. 46 shows improved (third generation) overlap dual vectors that show increased packaging efficiency.

FIGS. 48A and 48B show overlap vectors compared using the Protein Simple Jess quantification system through use of a capillary-based Western blot tool. FIG. 48A shows the expression of MYO7A and truncated MYO7A from various overlap vectors. FIG. 48B shows a table describing the overlap length and the respective ITR-ITR length (bp).

FIG. 49A shows MYO7A expression normalized to VCL relative to the original hybrid vectors. FIG. 49B shows the degree of expression of truncated MYO7A protein normalized to VCL relative to the original hybrid vectors.

FIGS. 50A-50D show improved hybrid dual vectors that provide reduced cytotoxicity and greater safety. FIG. 50A shows Hybrid-V2 with altered 'split point' such that no neck/tail domain is encoded by the front half vector. FIG. 50B shows a schematic of the hybrid vectors. Four potential in-frame stop codons were modified in the Hybrid-V2 front half vector sequence. All codon modifications were made on the Hybrid-V2 MIN background. FIG. 50C shows a table describing the modifications made to each vector, and the respective ITR to ITR (ITR-ITR) length (in bp). FIG. 50D shows a comparison of production of full-length MYO7A and truncated MYO7A fragment against the original hybrid vectors.

FIGS. 51A-51E show improved hybrid dual vectors for safety. FIG. 51A shows Hybrid-V2 back MIN, Hybrid-CMv2 back MIN, and an exemplary vector representing Hybrid-V2 back MIN HA and Hybrid-CMv2 back MIN HA. In the Hybrid back MIN vectors, an 'unneeded legacy' sequence was removed from the back half vector to ensure the vector size did not exceed packaging capacity. FIG. 51B shows a table describing the codon modifications made to each vector, and the respective ITR-ITR length (bp). FIGS. 51C-E show that reducing the size of back half vectors leads to increased expression of full length MYO7A from hybrid vectors.

DETAILED DESCRIPTION OF THE DISCLOSURE

Illustrative embodiments of the disclosure are described below. The disclosure provides compositions and methods for genetic therapy of diseases and conditions, such as Usher syndrome 1B (USH1B). Aspects of the disclosure concern AAV-based dual vector systems that allow for expression of full-length proteins whose coding sequence exceeds the polynucleotide packaging capacity of individual AAV vectors. Aspects of this disclosure provide AAV-based dual vector systems for expression in the retina of the eyes of the subject, or the hair cells of the inner ear of a subject. Accordingly, provided herein are methods for treatment of ocular and aural symptoms associated with USH1B, as well as other diseases and disorders. The disclosure provides nucleic acid vectors of an overlap vector system and nucleic acid vectors of a hybrid vector system.

Figure 1:
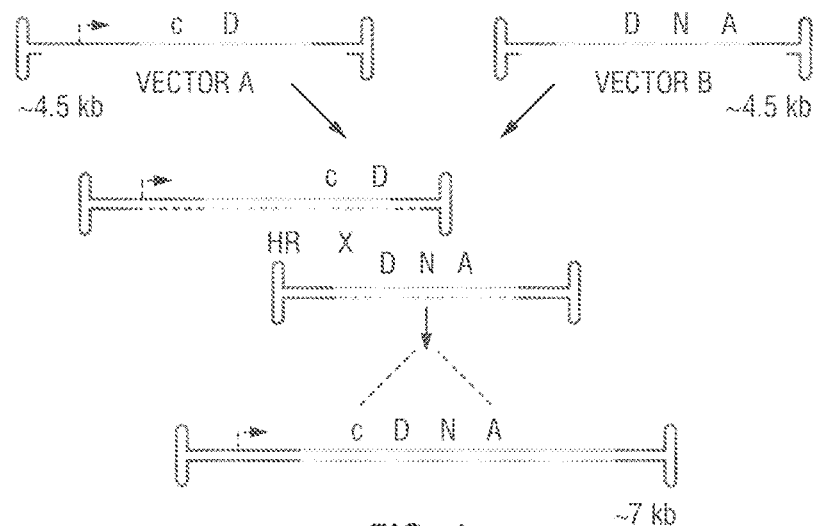
FIG. 1 shows the formation of complete gene cassette from dual AAV vectors via homologous recombination.
Figure 44:
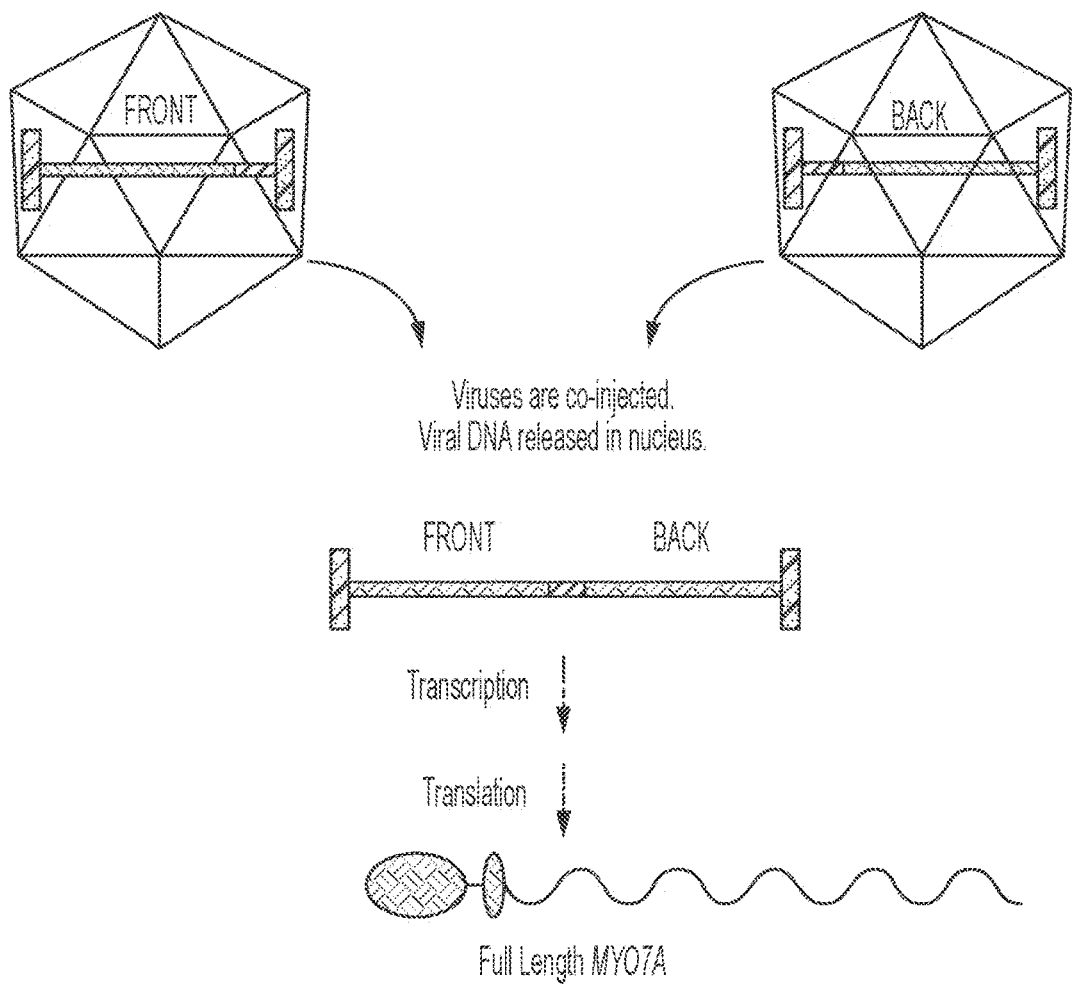
FIG. 44 is a schematic that shows the dual AAV vector approach for the delivery of MYO7A gene therapy. The MYO7A cDNA is split into two halves and each half is delivered via a separate AAV vector, delivered in separate AAV particles that are co-injected. The gene halves recombine in each cell to form full-length MYO7A.

Multiple distinct, AAV-based, dual vector systems have been created and disclosed herein for use in gene replacement therapies, including, for example, in the treatment of USH1B in human patients. In particular embodiments, a vector system of the disclosure employs two discrete AAV vectors that each packages a maximal-size DNA molecule (for example, ~4.5 to 4.8 Kb). The two vectors are co-administered to selected recipient cells to reconstitute the full-length, biologically-active, MYO7A polypeptide. In these constructs, a portion of overlapping nucleic acid sequence is common to each of the vector genomes (see FIG. 1). When co-delivered to suitable cells (FIG. 44), the overlapping sequence region facilitates the proper concatamerization of the two partial gene cassettes. These gene cassettes then undergo homologous recombination to produce a full-length gene cassette within the cells (see FIG. 1). Exemplary shared components of exemplary embodiments of the dual vector systems include the use of AAV inverted terminal repeats (ITR), the small (truncated) version of the chimeric CMV/chicken β-actin promoter (smCBA), human MYO7A (hMYO7A) cDNA sequence and the SV40 polyadenylation (pA) signal.

In some embodiments, the polynucleotide vector and vector systems provided herein do not comprise any of the nucleotide sequences of SEQ ID NOs: 1-4. In exemplary embodiments, the overlap vectors of the disclosure do not comprise any of SEQ ID NOs: 1 and 2. In exemplary embodiments, the hybrid vectors of the disclosure do not comprise any of the nucleotide sequences of SEQ ID NOs: 3 and 4. In some embodiments, the vectors of the disclosure do not comprise the nucleotide sequence of SEQ ID NO: 67 or NO: 71.

Overlap Vector System

In some aspects, overlap dual AAV vector systems are provided. In some embodiments, the overlap vector systems of the disclosure do not produce a truncated MYO7A protein fragment following administration to a mouse or a subject.

In one aspect of the disclosure, an overlap vector system of the disclosure includes:

i) a first AAV vector polynucleotide comprising an inverted terminal repeat at each end (5' and 3' end) of the polynucleotide, and between the inverted terminal repeats a suitable promoter followed by (for example, 3' to the promoter) a partial coding sequence that encodes an N-terminal part of a selected full-length polypeptide, and ii) a second AAV vector polynucleotide comprising an inverted terminal repeat at each end (for example, the 5'- and 3'-ends) of the polynucleotide, and between the inverted terminal repeats a partial coding sequence that encodes a C-terminal portion of the selected full-length polypeptide, and optionally followed by a polyadenylation (pA) sequence. The coding sequences in the first and second vectors when combined encode the selected full-length polypeptide, or a functional fragment or variant thereof. The polypeptide encoding sequence in the first and second AAV vectors comprises sequence that overlaps.

In some embodiments of the provided overlap vector systems, the selected full-length polypeptide is a myosin polypeptide. In some embodiments, the myosin polypeptide is human myosin VII A (hMYO7A). In some embodiments, the myosin polypeptide is human myosin VII B (hMYO7B). In some embodiments, the myosin polypeptide is myosin 7 (VII) isoform II. Isoform II (2) of hMYO7A (NM_001127180) encodes a 2175-amino acid protein (250.2 kDa) and lacks an in-frame segment in the coding region (a portion of exon 35), relative to isoform I (see Chen et al., 1996; Weil et al., 1996). In some embodiments, the myosin polypeptide is another myosin isoform or a functional fragment thereof. In particular embodiments, full-length myosin 7A or isoform II is encoded in the provided vector systems. The peptide sequence of isoform II is set forth as SEQ ID NO: 8.

In some embodiments, the selected full-length polypeptide is selected from ABCA4 (Stargardt disease), CEP290 (LCA10), EYS (Retinitis Pigmentosa), RP1 (Retinitis Pigmentosa), ALMS1 (Alstrom syndrome), CDH23 (Usher syndrome 1D), PCDH15 (Usher syndrome 1F), and USH-ERIN (USH2A) Usher syndrome 2A). In some embodiments, the selected full-length polypeptide is selected from DMD (Duchenne muscular dystrophy), CFTR (Cystic fibrosis), GDE (Glycogen storage disease III), DYSF (dysferlinopathies), OTOF (neurosensory nonsyndromic recessive deafness) and F8 (Hemophilia A). The diseases and disorders associated with each of these genes are provided in parentheses. In some embodiments, the selected full-length polypeptide is encoded by a gene of about 6 Kb to about 9 Kb in length. In some embodiments, the selected full-length polypeptide is encoded by a gene of about 7 Kb to about 8 Kb in length.

The inventors have also discovered that hMYO7A overlapping regions, e.g., SEQ ID NOs: 39 and 53-59, may be used as the polynucleotide sequence that overlaps in additional overlap dual vectors expressing large genes (other than MYO7A). Accordingly, in some embodiments, overlap dual vectors expressing portions (or halves) of a large gene selected from ABCA4, CEP290, EYS, RP1, ALMS1, CDH23, PCDH15, USH1C, USH1G, USH2A, DNFB31, DMD, CFTR, GDE, DYSF, F8, and DFNB2, contain an overlap region that comprises a part of the hMYO7A gene in the polynucleotide sequence that overlaps. These overlap vectors express a large gene other than MYO7A and that comprises a nucleotide sequence having at least 80%, 85%, 90%, 95%, 98%, or 99% identity to any one of SEQ ID NOs: 39 and 52-59. Such overlap vectors may comprise an overlapping region that contains the nucleotide sequence of any one of SEQ ID NOs: 39 and 53-59, e.g., SEQ ID NO: 56 or 57.

In some embodiments, the selected full-length polypeptide is expressed in one or more photoreceptor cells. In some embodiments, the selected full-length polypeptide is expressed in one or more cells that do not comprise photoreceptor cells. In some embodiments, the selected full-length polypeptide is expressed in one or more hair cells, e.g., hair cells of the auditory system or the vestibular system.

In some embodiments, the C-terminal part of the selected full-length polypeptide (e.g., the myosin polypeptide) comprises the single-alpha helix (SAH) domain of the selected full-length polypeptide.

In some embodiments, the first AAV vector polynucleotide comprises the nucleotide sequence of SEQ ID NO: 1, or a functional fragment and/or variant thereof, and the second AAV vector polynucleotide comprises the nucleotide sequence of SEQ ID NO: 2, or a functional fragment and/or variant thereof.

Figure 2:
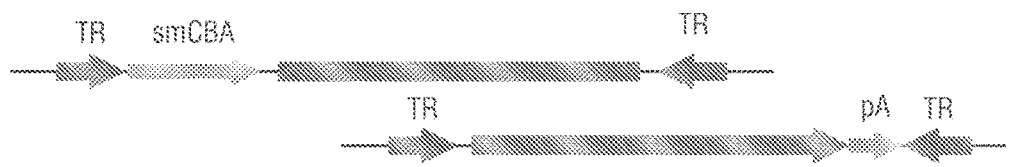
FIG. 2 shows a schematic of the two vector components that make up the Overlap Dual Vector System in accordance with one aspect of the disclosure.

In some embodiments, the first generation overlap vector (for example, the AAV vector polynucleotide comprising the nucleotide sequence of SEQ ID NO: 1, or a functional fragment and/or variant thereof, and/or the second AAV vector polynucleotide comprising the nucleotide sequence of SEQ ID NO: 2, or a functional fragment and/or variant thereof) contains nucleotides 1 through 3644 of MYO7A cDNA from the ATG in the 5' vector and/or nucleotides 2279 through 6534 in the 3' vector. In some embodiments, the fragments are amplified with P1 and P3 by polymerase chain reaction (PCR) and cloned into the 5' vector via NotI and NheI and the 3' vector with P3 (AflII) and P4 (KpnI), respectively. The resulting two vector plasmids share 1365 bp of overlapping MYO7A sequence (FIG. 2), and the overlap between the sequences ends at the split point between exons 23 and 24.

In some embodiments, a portion of the coding sequence present at the 3'-end of the coding sequence of the first generation overlap vector is identical or substantially identical with a portion of the coding sequence present at the 5'-end of the coding sequence of the first generation overlap vector. In particular embodiments, the sequence overlap between the first and second AAV (first generation) overlap vectors of the disclosure is between about 500 and about 3,000 nucleotides; between about 1,000 and about 2,000 nucleotides; between about 1,200 and about 1,800 nucleotides; or between about 1,300 and about 1,400 nucleotides.

In particular embodiments, the sequence overlap between the first and second AAV overlap vectors of the disclosure is 1284 bp, 1027 bp, 1026 bp, 945 bp, 687 bp, 361 bp, 279 bp, or 20 bp in length. In particular embodiments, the sequence overlap between the first and second AAV overlap vectors of the disclosure has a length that is within 1, 2, 3, 4, 5, 6, 7, 8, 9, or 10 nucleotides different from 1284 bp, 1027 bp, 1026 bp, 945 bp, 687 bp, 361 bp, 279 bp, or 20 bp. In some embodiments, the sequence overlap is 945 bp, 687 bp, or 361 bp.

In particular embodiments, the sequence overlap of the first generation overlap vector system is about 1,350 nucleotides. In an exemplary embodiment, the sequence overlap of the first generation overlap vector system is 1,365 nucleotides. In particular embodiments, the polynucleotide sequence that overlaps comprises SEQ ID NO: 45. In particular embodiments, the polypeptide encoded is wild type or functional human myosin VIIa (hMYO7A). Amino acid sequences of wild type and functional hMYO7A polypeptides, and polynucleotides encoding them, are known in the art (see, e.g., GenBank accession numbers NP_000251 and U39226.1). In particular embodiments, a hMYO7A polypeptide comprises the amino acid sequence shown in SEQ ID NO: 6 or SEQ ID NO: 8, or a functional fragment or a variant thereof. In particular embodiments, the hMYO7A polypeptide is encoded by the nucleotide sequence shown in SEQ ID NO: 5 or SEQ ID NO: 7.

Codon-Modified Overlap Vectors

Figure 37A:
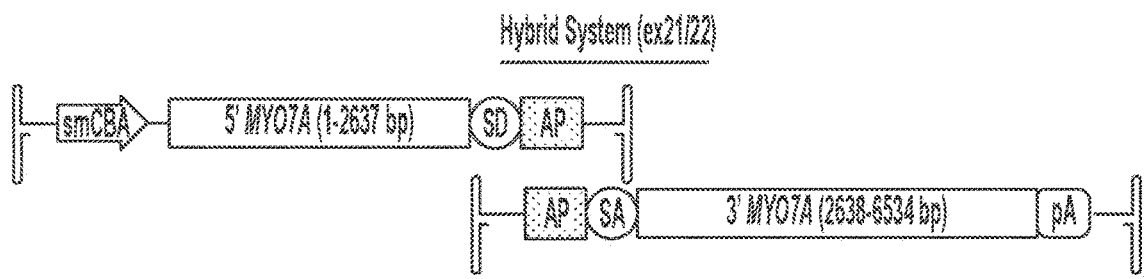
FIGS. 37A-37B show schematics of an exemplary second generation MYO7A polynucleotide vector systems of the disclosure.
Figure 37B:
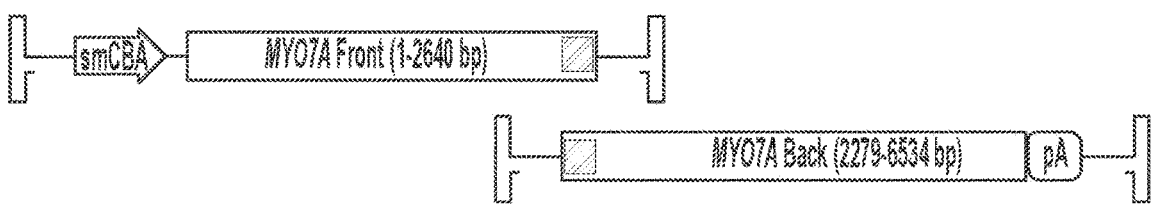

In some embodiments of the disclosed overlap vector systems, a codon-modified overlap vector is provided. In some embodiments, the first generation overlap front-half vector ("AAV-smCBA-hMYO7A-NT") is shortened. All coding sequences corresponding to the tail domain of MYO7A was removed from the front half vector, thus reducing the size of the overlap region to 361 bp (SEQ ID NO: 39). (This vector does not generate a truncated MYO7A fragment containing a tail, or SAH, domain.) The vector was also altered so that all potential (or putative) stop codons were removed. (See FIG. 37B.) The resultant vector is the CMv1 overlap front-half vector ("AAV-smCBA-hMYO7A- noDimNT-CMv1"). Accordingly, the overlap vector system of the disclosure may comprise a CMv1 overlap vector system.

In some embodiments, an overlap vector having an altered (e.g., a shortened) overlapping coding sequence is provided. In such embodiments, an overlap vector containing an overlap sequence in the MYO7A gene or another gene that is less than 1365 bp in length is provided. In these systems, the length of the overlapping sequence is reduced to a certain point, therefore ensuring neither vector genome is pushing the packaging capacity of AAV capsid (4.7-4.9 kb), leads to increased expression of full length MYO7A. If the overlap length is too small (<361 bp), full length MYO7A expression is reduced, and truncated protein appears. Overlap vectors containing 687 or 945 bp of overlapping MYO7A sequence produce as much or more full-length MYO7A as original hybrid vectors. (See FIGS. 48A, 48B, 49A, and 49B.) Such vectors may be referred to herein as "V3" or $3^{rd}$ generation overlap vectors. In exemplary embodiments, overlap vectors containing 687 or 945 bp of overlapping MYO7A sequence are exemplified.

Accordingly, provided herein are polynucleotide vector systems wherein the polynucleotide sequence that overlaps comprises a nucleotide sequence selected from any one of SEQ ID NOs: 39 and 52-59. In some embodiments, the polynucleotide sequence that overlaps comprises a nucleotide sequence selected from any one of SEQ ID NOs: 39, 56, and 57. In exemplary embodiments, the polynucleotide sequence that overlaps comprises the sequence of SEQ ID NO: 56 or 57. In some embodiments, the length between the inverted terminal repeats at each end of the first AAV vector polynucleotide is about 4615 nucleotides (nt) or fewer. In some embodiments, the length between the inverted terminal repeats at each end of the second AAV vector polynucleotide is about 4800 nt or fewer. In some embodiments, the length between the inverted terminal repeats at each end of the second AAV vector polynucleotide is about 4560 nt.

Thus, in some embodiments, the polynucleotide vector system of the disclosure is a CMv1 overlap system. In some embodiments, the vector system is an overlap V2 ($2^{nd}$ generation) system. In some embodiments, the vector system is a V3 overlap ($3^{rd}$ generation) system. Any of the disclosed front-half overlap vectors may be combined with any of the disclosed back-half overlap vectors in the compositions of the disclosure. The resulting third generation overlap front half vector ("AAV-smCBA-hMYO7A-NT-long-v3") is set forth as SEQ ID NO: 50. The resulting third generation overlap back half vector, inclusive of an HA tag, is set forth as SEQ ID NO: 51.

Accordingly, in some aspects, provided herein are polynucleotide vector systems comprising:

i) a first AAV vector polynucleotide comprising an inverted terminal repeat at each end of the polynucleotide, and between the inverted terminal repeats a promoter followed by a partial coding sequence that encodes an N-terminal part of a myosin polypeptide, and ii) a second AAV vector polynucleotide comprising an inverted terminal repeat at each end of the polynucleotide, and between the inverted terminal repeats a partial coding sequence that encodes a C-terminal part of the myosin polypeptide, wherein the polynucleotide sequence encoding the polypeptide sequence in the first and second AAV vectors comprises a polynucleotide sequence that overlaps, and wherein the first AAV vector polynucleotide comprises a nucleotide sequence selected from SEQ ID NOs: 36, 37, and 50;

and the second AAV vector polynucleotide comprises a nucleotide sequence selected from SEQ ID NOs: 38 and 51. In exemplary embodiments, the first AAV vector polynucleotide comprises the nucleotide sequence of SEQ ID NO: 50, and the second AAV vector polynucleotide comprises the nucleotide sequence of SEQ ID NO: 51. In some embodiments, the first AAV vector polynucleotide comprises the nucleotide sequence of SEQ ID NO: 50, and the second AAV vector polynucleotide comprises the nucleotide sequence of SEQ ID NO: 38. In some embodiments, the first AAV vector polynucleotide comprises the nucleotide sequence of SEQ ID NO: 36, and the second AAV vector polynucleotide comprises the nucleotide sequence of SEQ ID NO: 38.

In some embodiments, the first AAV vector polynucleotide comprises a partial coding sequence that does not encode the single-alpha helix (SAH) domain of the selected full-length polypeptide. In some embodiments, the first AAV vector polynucleotide of the second generation overlap vector comprises the nucleotide sequence of SEQ ID NO: 37, or a functional fragment and/or variant thereof, and the second AAV vector polynucleotide of the second generation overlap vector comprises the nucleotide sequence of SEQ ID NO: 38, or a functional fragment and/or variant thereof.

In some embodiments, the second generation overlap vector (for example, the AAV vector polynucleotide comprising the nucleotide sequence of SEQ ID NO: 37, or a functional fragment and/or variant thereof, and/or the second AAV vector polynucleotide comprising the nucleotide sequence of SEQ ID NO: 38, or a functional fragment and/or variant thereof) contains nucleotides 1 through 2640 of MYO7A cDNA from the ATG in the 5' vector and/or nucleotides 2279 through 6534 in the 3' vector. In some embodiments, the fragments are amplified with P1 and P3 by polymerase chain reaction (PCR) and cloned into the 5' vector via NotI and NheI and the 3' vector with P3 (AflII) and P4 (KpnI), respectively. The resulting two vector plasmids share 361 bp of overlapping MYO7A sequence (FIG. 37), and the overlap between the sequences ends at the split point between exons 21 and 22.

In some embodiments, the polynucleotide sequence that overlaps does not comprise any portion of exon 23 of the hMYO7A gene. In some embodiments, the polynucleotide sequence that overlaps does not comprise exon 23 in full (e.g., 100% of exon 23). In some embodiments, the polynucleotide sequence that overlaps comprises a portion of exon 17, exon 18 in full, exon 19 in full, exon 20 in full, and a portion of exon 21 of the hMYO7A gene. In some embodiments, the polynucleotide sequence that overlaps comprises a portion of exon 17, a portion of exon 18, a portion of exon 19, a portion of exon 20, and/or a portion of exon 21 of the hMYO7A gene. As used herein, a "portion" may comprise e.g. at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, etc. of the exon and/or intron sequence.

In some embodiments, a portion of the coding sequence present at the 3'-end of the coding sequence of the first vector of the second generation overlap vector is identical or substantially identical with a portion of the coding sequence present at the 5'-end of the coding sequence of the second vector of the second generation overlap vector. In particular embodiments, the sequence overlap between the first and second AAV vectors is between about 1 and about 500 nucleotides; between about 100 and about 200 nucleotides; between about 200 and about 300 nucleotides; or between about 300 and about 400 nucleotides.

In particular embodiments, the sequence overlap of the second generation overlap vector system is about 350 nucleotides. In an exemplary embodiment, the sequence overlap of the second generation overlap vector system is 361 nucleotides. In particular embodiments, the polynucleotide sequence that overlaps comprises SEQ ID NO: 39. In particular embodiments, the polypeptide encoded is wild type or functional human myosin VIIa (hMYO7A). Amino acid sequences of wild type and functional hMYO7A polypeptides, and polynucleotides encoding them, are known in the art (see, e.g., GenBank accession numbers NP_000251 and U39226.1). In particular embodiments, a hMYO7A polypeptide comprises the amino acid sequence shown in SEQ ID NO: 6 or SEQ ID NO: 8, or a functional fragment or a variant thereof. In particular embodiments, the hMYO7A polypeptide is encoded by the nucleotide sequence shown in SEQ ID NO: 5 or SEQ ID NO: 7.

```
SEQ ID NO: 5 is a nucleotide sequence encoding a human myosin VIIa polypeptide
(protein coding sequence is nucleotides 273-6920);
GCTCTGGGCAGGAGAGAGAGTGAGAGACAAGAGACACACAGAGAGACGGCG

AGGAAGGGAAAGACCCAGAGGGACGCCTAGAACGAGACTTGGAGCCAGACAGA

GGAAGAGGGGACGTGTGTTTGCAGACTGGCTGGGCCCGTGACCCAGCTTCCTGAG

TCCTCCGTGCAGGTGGCAGCTGTACCAGGCTGGCAGGTCACTGAGAGTGGGCAGC

TGGGCCCCAGAACTGTGCCTGGCCCAGTGGGCAGCAGGAGCTCCTGACTTGGGAC

CATGGTGATTCTTCAGCAGGGGACCATGTGTGGATGGACCTGAGATTGGGGCAG

GAGTTCGACGTGCCCATCGGGGCGGTGGTGAAGCTCTGCGACTCTGGGCAGGTCC

AGGTGGTGGATGATGAAGACAATGAACACTGGATCTCTCCGCAGAACGCAACGC

ACATCAAGCCTATGCACCCCACGTCGGTCCACGGCGTGGAGGACATGATCCGCCT

GGGGGACCTCAACGAGGCGGGCATCTTGCGCAACCTGCTTATCCGCTACCGGGAC

CACCTCATCTACACGTATACGGGCTCCATCCTGGTGGCTGTGAACCCCTACCAGCT

GCTCTCCATCTACTCGCCAGAGCACATCCGCCAGTATACCAACAAGAAGATTGGG

GAGATGCCCCCCCACATCTTTGCCATTGCTGACAACTGCTACTTCAACATGAAAC

GCAACAGCCGAGACCAGTGCTGCATCATCAGTGGGGAATCTGGGGCCGGGAAGA

CGGAGAGCACAAAGCTGATCCTGCAGTTCCTGGCAGCCATCAGTGGGCAGCACTC

GTGGATTGAGCAGCAGGTCTTGGAGGCCACCCCCATTCTGGAAGCATTTGGGAAT

GCCAAGACCATCCGCAATGACAACTCAAGCCGTTTCGGAAAGTACATCGACATCC

ACTTCAACAAGCGGGGCGCCATCGAGGGCGCGAAGATTGAGCAGTACCTGCTGG

AAAAGTCACGTGTCTGTCGCCAGGCCCTGGATGAAAGGAACTACCACGTGTTCTA

CTGCATGCTGGAGGGTATGAGTGAGGATCAGAAGAAGAAGCTGGGCTTGGGCCA

GGCCTCTGACTACAACTACTTGGCCATGGGTAACTGCATAACCTGTGAGGGCCGG

GTGGACAGCCAGGAGTACGCCAACATCCGCTCCGCCATGAAGGTGCTCATGTTCA

CTGACACCGAGAACTGGGAGATCTCGAAGCTCCTGGCTGCCATCCTGCACCTGGG

CAACCTGCAGTATGAGGCACGCACATTTGAAAACCTGGATGCCTGTGAGGTTCTC

TTCTCCCCATCGCTGGCCACAGCTGCATCCCTGCTTGAGGTGAACCCCCCAGACCT

GATGAGCTGCCTGACTAGCCGCACCCTCATCACCCGCGGGGAGACGGTGTCCACC

CCACTGAGCAGGGAACAGGCACTGGACGTGCGCGACGCCTTCGTAAAGGGGATC

TACGGGCGGCTGTTCGTGTGGATTGTGGACAAGATCAACGCAGCAATTTACAAGC

CTCCCTCCCAGGATGTGAAGAACTCTCGCAGGTCCATCGGCCTCCTGGACATCTTT

GGGTTTGAGAACTTTGCTGTGAACAGCTTTGAGCAGCTCTGCATCAACTTCGCCA

ATGAGCACCTGCAGCAGTTCTTTGTGCGGCACGTGTTCAAGCTGGAGCAGGAGGA

ATATGACCTGGAGAGCATTGACTGGCTGCACATCGAGTTCACTGACAACCAGGAT
```

```
-continued
GCCCTGGACATGATTGCCAACAAGCCCATGAACATCATCTCCCTCATCGATGAGG
AGAGCAAGTTCCCCAAGGGCACAGACACCACCATGTTACACAAGCTGAACTCCC
AGCACAAGCTCAACGCCAACTACATCCCCCCCAAGAACAACCATGAGACCCAGTT
TGGCATCAACCATTTTGCAGGCATCGTCTACTATGAGACCCAAGGCTTCCTGGAG
AAGAACCGAGACACCCTGCATGGGACATTATCCAGCTGGTCCACTCCTCCAGGA
ACAAGTTCATCAAGCAGATCTTCCAGGCCGATGTCGCCATGGGCGCCGAGACCAG
GAAGCGCTCGCCCACACTTAGCAGCCAGTTCAAGCGGTCACTGGAGCTGCTGATG
CGCACGCTGGGTGCCTGCCAGCCCTTCTTTGTGCGATGCATCAAGCCCAATGAGT
TCAAGAAGCCCATGCTGTTCGACCGGCACCTGTGCGTGCGCCAGCTGCGGTACTC
AGGAATGATGGAGACCATCCGAATCCGCCGAGCTGGCTACCCCATCCGCTACAGC
TTCGTAGAGTTTGTGGAGCGGTACCGTGTGCTGCTGCCAGGTGTGAAGCCGGCCT
ACAAGCAGGGCGACCTCCGCGGGACTTGCCAGCGCATGGCTGAGGCTGTGCTGG
GCACCCACGATGACTGGCAGATAGGCAAAACCAAGATCTTTCTGAAGGACCACC
ATGACATGCTGCTGGAAGTGGAGCGGGACAAAGCCATCACCGACAGAGTCATCC
TCCTTCAGAAAGTCATCCGGGGATTCAAAGACAGGTCTAACTTTCTGAAGCTGAA
GAACGCTGCCACACTGATCCAGAGGCACTGGCGGGGTCACAACTGTAGGAAGAA
CTACGGGCTGATGCGTCTGGGCTTCCTGCGGCTGCAGGCCCTGCACCGCTCCCGG
AAGCTGCACCAGCAGTACCGCCTGGCCCGCCAGCGCATCATCCAGTTCCAGGCCC
GCTGCCGCGCCTATCTGGTGCGCAAGGCCTTCCGCCACCGCCTCTGGGCTGTGCTC
ACCGTGCAGGCCTATGCCCGGGGCATGATCGCCCGCAGGCTGCACCAACGCCTCA
GGGCTGAGTATCTGTGGCGCCTCGAGGCTGAGAAAATGCGGCTGGCGGAGGAAG
AGAAGCTTCGGAAGGAGATGAGCGCCAAGAAGGCCAAGGAGGAGGCCGAGCGC
AAGCATCAGGAGCGCCTGGCCCAGCTGGCTCGTGAGGACGCTGAGCGGGAGCTG
AAGGAGAAGGAGGCCGCTCGGCGGAAGAAGGAGCTCCTGGAGCAGATGGAAAG
GGCCCGCCATGAGCCTGTCAATCACTCAGACATGGTGGACAAGATGTTTGGCTTC
CTGGGGACTTCAGGTGGCCTGCCAGGCCAGGAGGGCCAGGCACCTAGTGGCTTTG
AGGACCTGGAGCGAGGGCGGAGGGAGATGGTGGAGGAGGACCTGGATGCAGCC
CTGCCCCTGCCTGACGAGGATGAGGAGGACCTCTCTGAGTATAAATTTGCCAAGT
TCGCGGCCACCTACTTCCAGGGGACAACCACGCACTCCTACACCCGGCGGCCACT
CAAACAGCCACTGCTCTACCATGACGACGAGGGTGACCAGCTGGCAGCCCTGGC
GGTCTGGATCACCATCCTCCGCTTCATGGGGGACCTCCCTGAGCCCAAGTACCAC
ACAGCCATGAGTGATGGCAGTGAGAAGATCCCTGTGATGACCAAGATTTATGAG
ACCCTGGGCAAGAAGACGTACAAGAGGGAGCTGCAGGCCCTGCAGGGCGAGGGC
GAGGCCCAGCTCCCCGAGGGCCAGAAGAAGAGCAGTGTGAGGCACAAGCTGGTG
CATTTGACTCTGAAAAAGAAGTCCAAGCTCACAGAGGAGGTGACCAAGAGGCTG
CATGACGGGGAGTCCACAGTGCAGGGCAACAGCATGCTGGAGGACCGGCCCACC
TCCAACCTGGAGAAGCTGCACTTCATCATCGGCAATGGCATCCTGCGGCCAGCAC
TCCGGGACGAGATCTACTGCCAGATCAGCAAGCAGCTGACCCACAACCCCTCCAA
GAGCAGCTATGCCCGGGGCTGGATTCTCGTGTCTCTCTGCGTGGGCTGTTTCGCCC
CCTCCGAGAAGTTTGTCAAGTACCTGCGGAACTTCATCCACGGGGGCCCGCCCGG
```

-continued

```
CTACGCCCCGTACTGTGAGGAGCGCCTGAGAAGGACCTTTGTCAATGGGACACGG
ACACAGCCGCCCAGCTGGCTGGAGCTGCAGGCCACCAAGTCCAAGAAGCCAATC
ATGTTGCCCGTGACATTCATGGATGGGACCACCAAGACCCTGCTGACGGACTCGG
CAACCACGGCCAAGGAGCTCTGCAACGCGCTGGCCGACAAGATCTCTCTCAAGG
ACCGGTTCGGGTTCTCCCTCTACATTGCCCTGTTTGACAAGGTGTCCTCCCTGGGC
AGCGGCAGTGACCACGTCATGGACGCCATCTCCCAGTGCGAGCAGTACGCCAAG
GAGCAGGGCGCCCAGGAGCGCAACGCCCCCTGGAGGCTCTTCTTCCGCAAAGAG
GTCTTCACGCCCTGGCACAGCCCCTCCGAGGACAACGTGGCCACCAACCTCATCT
ACCAGCAGGTGGTGCGAGGAGTCAAGTTTGGGGAGTACAGGTGTGAGAAGGAGG
ACGACCTGGCTGAGCTGGCCTCCCAGCAGTACTTTGTAGACTATGGCTCTGAGAT
GATCCTGGAGCGCCTCCTGAACCTCGTGCCCACCTACATCCCCGACCGCGAGATC
ACGCCCCTGAAGACGCTGGAGAAGTGGGCCCAGCTGGCCATCGCCGCCCACAAG
AAGGGGATTTATGCCCAGAGGAGAACTGATGCCCAGAAGGTCAAAGAGGATGTG
GTCAGTTATGCCCGCTTCAAGTGGCCCTTGCTCTTCTCCAGGTTTTATGAAGCCTA
CAAATTCTCAGGCCCCAGTCTCCCCAAGAACGACGTCATCGTGGCCGTCAACTGG
ACGGGTGTGTACTTTGTGGATGAGCAGGAGCAGGTACTTCTGGAGCTGTCCTTCC
CAGAGATCATGGCCGTGTCCAGCAGCAGGGAGTGCCGTGTCTGGCTCTCACTGGG
CTGCTCTGATCTTGGCTGTGCTGCGCCTCACTCAGGCTGGGCAGGACTGACCCCG
GCGGGGCCCTGTTCTCCGTGTTGGTCCTGCAGGGGAGCGAAAACGACGGCCCCCA
GCTTCACGCTGGCCACCATCAAGGGGGACGAATACACCTTCACCTCCAGTAATGC
TGAGGACATTCGTGACCTGGTGGTCACCTTCCTAGAGGGGCTCCGGAAGAGATCT
AAGTATGTTGTGGCCCTGCAGGATAACCCCAACCCCGCAGGCGAGGAGTCAGGCT
TCCTCAGCTTTGCCAAGGGAGACCTCATCATCCTGGACCATGACACGGGCGAGCA
GGTCATGAACTCGGGCTGGGCCAACGGCATCAATGAGAGGACCAAGCAGCGTGG
GGACTTCCCCACCGACTGTGTGTACGTCATGCCCACTGTCACCATGCCACCGCGG
GAGATTGTGGCCCTGGTCACCATGACTCCCGATCAGAGGCAGGACGTTGTCCGGC
TCTTGCAGCTGCGAACGGCGGAGCCCGAGGTGCGTGCCAAGCCCTACACGCTGGA
GGAGTTTTCCTATGACTACTTCAGGCCCCCACCCAAGCACACGCTGAGCCGTGTC
ATGGTGTCCAAGGCCCGAGGCAAGGACCGGCTGTGGAGCCACACGCGGGAACCG
CTCAAGCAGGCGCTGCTCAAGAAGCTCCTGGGCAGTGAGGAGCTCTCGCAGGAG
GCCTGCCTGGCCTTCATTGCTGTGCTCAAGTACATGGGCGACTACCCGTCCAAGA
GGACACGCTCCGTCAACGAGCTCACCGACCAGATCTTTGAGGGTCCCCTGAAAGC
CGAGCCCCTGAAGGACGAGGCATATGTGCAGATCCTGAAGCAGCTGACCGACAA
CCACATCAGGTACAGCGAGGAGCGGGGTTGGGAGCTGCTCTGGCTGTGCACGGG
CCTTTTCCCACCCAGCAACATCCTCCTGCCCCACGTGCAGCGCTTCCTGCAGTCCC
GAAAGCACTGCCCACTCGCCATCGACTGCCTGCAACGGCTCCAGAAAGCCCTGAG
AAACGGGTCCCGGAAGTACCCTCCGCACCTGGTGGAGGTGGAGGCCATCCAGCA
CAAGACCACCCAGATTTTCCACAAGGTCTACTTCCCTGATGACACTGACGAGGCC
TTCGAAGTGGAGTCCAGCACCAAGGCCAAGGACTTCTGCCAGAACATCGCCACCA
GGCTGCTCCTCAAGTCCTCAGAGGGATTCAGCCTCTTTGTCAAAATTGCAGACAA
GGTCATCAGCGTTCCTGAGAATGACTTCTTCTTTGACTTTGTTCGACACTTGACAG
```

```
ACTGGATAAAGAAAGCTCGGCCCATCAAGGACGGAATTGTGCCCTCACTCACCTA
CCAGGTGTTCTTCATGAAGAAGCTGTGGACCACCACGGTGCCAGGGAAGGATCCC
ATGGCCGATTCCATCTTCCACTATTACCAGGAGTTGCCCAAGTATCTCCGAGGCTA
CCACAAGTGCACGCGGGAGGAGGTGCTGCAGCTGGGGGCGCTGATCTACAGGGT
CAAGTTCGAGGAGGACAAGTCCTACTTCCCCAGCATCCCCAAGCTGCTGCGGGAG
CTGGTGCCCCAGGACCTTATCCGGCAGGTCTCACCTGATGACTGGAAGCGGTCCA
TCGTCGCCTACTTCAACAAGCACGCAGGGAAGTCCAAGGAGGAGGCCAAGCTGG
CCTTCCTGAAGCTCATCTTCAAGTGGCCCACCTTTGGCTCAGCCTTCTTCGAGGTG
AAGCAAACTACGGAGCCAAACTTCCCTGAGATCCTCCTAATTGCCATCAACAAGT
ATGGGGTCAGCCTCATCGATCCCAAAACGAAGGATATCCTCACCACTCATCCCTT
CACCAAGATCTCCAACTGGAGCAGCGGCAACACCTACTTCCACATCACCATTGGG
AACTTGGTGCGCGGGAGCAAACTGCTCTGCGAGACGTCACTGGGCTACAAGATG
GATGACCTCCTGACTTCCTACATTAGCCAGATGCTCACAGCCATGAGCAAACAGC
GGGGCTCCAGGAGCGGCAAGTGAACAGTCACGGGGAGGTGCTGGTTCCATGCCT
GCTCTCGAGGCAGCAGTGGGTTCAGGCCCATCAGCTACCCCTGCAGCTGGGGAAG
ACTTATGCCATCCCGGCAGCGAGGCTGGGCTGGCCAGCCACCACTGACTATACCA
ACTGGGCCTCTGATGTTCTTCCAGTGAGGCATCTCTCTGGGATGCAGAACTTCCCT
CCATCCACCCCTCTGGCACCTGGGTTGGTCTAATCCTAGTTTGCTGTGGCCTTCCC
GGTTGTGAGAGCCTGTGATCCTTAGATGTGTCTCCTGTTTCAGACCAGCCCCACCA
TGCAACTTCCTTTGACTTTCTGTGTACCACTGGGATAGAGGAATCAAGAGGACAA
TCTAGCTCTCCATACTTTGAACAACCAAATGTGCATTGAATACTCTGAAACCGAA
GGGACTGGATCTGCAGGTGGGATGAGGGAGACAGACCACTTTTCTATATTGCAGT
GTGAATGCTGGGCCCCTGCTCAAGTCTACCCTGATCACCTCAGGGCATAAAGCAT
GTTTCATTCTCTGAAA
```

SEQ ID NO: 6 is the amino acid sequence of the human myosin VIIa polypeptide encoded by nucleotides 273-6920 of SEQ ID NO: 5;

```
MVILQQGDHVWMDLRLGQEFDVPIGAVVKLCDSGQVQVVDDEDNEHWISPQNATH
IKPMHPTSVHGVEDMIRLGDLNEAGILRNLLIRYRDHLIYTYTGSILVAVNPYQLLSIY
SPEHIRQYTNKKIGEMPPHIFAIADNCYFNMKRNSRDQCCIISGESGAGKTESTKLILQ
FLAAISGQHSWIEQQVLEATPILEAFGNAKTIRNDNSSRFGKYIDIHFNKRGAIEGAKIE
QYLLEKSRVCRQALDERNYHVFYCMLEGMSEDQKKKLGLGQASDYNYLAMGNCIT
CEGRVDSQEYANIRSAMKVLMFTDTENWEISKLLAAILHLGNLQYEARTFENLDACE
VLFSPSLATAASLLEVNPPDLMSCLTSRTLITRGETVSTPLSREQALDVRDAFVKGIYG
RLFVWIVDKINAAIYKPPSQDVKNSRRSIGLLDIFGFENFAVNSFEQLCINFANEHLQQ
FFVRHVFKLEQEEYDLESIDWLHIEFTDNQDALDMIANKPMNIISLIDEESKFPKGTDT
TMLHKLNSQHKLNANYIPPKNNHETQFGINHFAGIVYYETQGFLEKNRDTLHGDIIQL
VHSSRNKFIKQIFQADVAMGAETRKRSPTLSSQFKRSLELLMRTLGACQPFFVRCIKP
NEFKKPMLFDRHLCVRQLRYSGMMETIRIRRAGYPIRYSFVEFVERYRVLLPGVKPA
YKQGDLRGTCQRMAEAVLGTHDDWQIGKTKIFLKDHHDMLLEVERDKAITDRVILL
QKVIRGFKDRSNFLKLKNAATLIQRHWRGHNCRKNYGLMRLGFLRLQALHRSRKLH
QQYRLARQRIIQFQARCRAYLVRKAFRHRLWAVLTVQAYARGMIARRLHQRLRAEY
```

LWRLEAEKMRLAEEEKLRKEMSAKKAKEEAERKHQERLAQLAREDAERELKEKEA

ARRKKELLEQMERARHEPVNHSDMVDKMFGFLGTSGGLPGQEGQAPSGFEDLERGR

REMVEEDLDAALPLPDEDEEDLSEYKFAKFAATYFQGTTTHSYTRRPLKQPLLYHDD

EGDQLAALAVWITILRFMGDLPEPKYHTAMSDGSEKIPVMTKIYETLGKKTYKRELQ

ALQGEGEAQLPEGQKKSSVRHKLVHLTLKKKSKLTEEVTKRLHDGESTVQGNSMLE

DRPTSNLEKLHFIIGNGILRPALRDEIYCQISKQLTHNPSKSSYARGWILVSLCVGCFAP

SEKFVKYLRNFIHGGPPGYAPYCEERLRRTFVNGTRTQPPSWLELQATKSKKPIMLPV

TFMDGTTKTLLTDSATTAKELCNALADKISLKDRFGFSLYIALFDKVSSLGSGSDHV

MDAISQCEQYAKEQGAQERNAPWRLFFRKEVFTPWHSPSEDNVATNLIYQQVVRGV

KFGEYRCEKEDDLAELASQQYFVDYGSEMILERLLNLVPTYIPDREITPLKTLEKWAQ

LAIAAHKKGIYAQRRTDAQKVKEDVVSYARFKWPLLFSRFYEAYKFSGPSLPKNDVI

VAVNWTGVYFVDEQEQVLLELSFPEIMAVSSSRECRVWLSLGCSDLGCAAPHSGWA

GLTPAGPCSPCWSCRGAKTTAPSFTLATIKGDEYTFTSSNAEDIRDLVVTFLEGLRKR

SKYVVALQDNPNPAGEESGFLSFAKGDLIILDHDTGEQVMNSGWANGINERTKQRG

DFPTDCVYVMPTVTMPPREIVALVTMTPDQRQDVVRLLQLRTAEPEVRAKPYTLEEF

SYDYFRPPPKHTLSRVMVSKARGKDRLWSHTREPLKQALLKKLLGSEELSQEACLAF

IAVLKYMGDYPSKRTRSVNELTDQIFEGPLKAEPLKDEAYVQILKQLTDNHIRYSEER

GWELLWLCTGLFPPSNILLPHVQRFLQSRKHCPLAIDCLQRLQKALRNGSRKYPPHL

VEVEAIQHKTTQIFHKVYFPDDTDEAFEVESSTKAKDFCQNIATRLLLKSSEGFSLFVK

IADKVISVPENDFFFDFVRHLTDWIKKARPIKDGIVPSLTYQVFFMKKLWTTTVPGKD

PMADSIFHYYQELPKYLRGYHKCTREEVLQLGALIYRVKFEEDKSYFPSIPKLLRELV

PQDLIRQVSPDDWKRSIVAYFNKHAGKSKEEAKLAFLKLIFKWPTFGSAFFEVKQTTE

PNFPEILLIAINKYGVSLIDPKTKDILTTHPFTKISNWSSGNTYFHITIGNLVRGSKLLCE

TSLGYKMDDLLTSYISQMLTAMSKQRGSRSGK

SEQ ID NO: 7 is a nucleotide sequence that encodes a human myosin VIIa polypeptide;
ATGGTGATTCTTCAGCAGGGGGACCATGTGTGGATGGACCTGAGATTGGGGCAGG

AGTTCGACGTGCCCATCGGGGCGGTGGTGAAGCTCTGCGACTCTGGGCAGGTCCA

GGTGGTGGATGATGAAGACAATGAACACTGGATCTCTCCGCAGAACGCAACGCA

CATCAAGCCTATGCACCCCACGTCGGTCCACGGCGTGGAGGACATGATCCGCCTG

GGGGACCTCAACGAGGCGGGCATCTTGCGCAACCTGCTTATCCGCTACCGGGACC

ACCTCATCTACACGTATACGGGCTCCATCCTGGTGGCTGTGAACCCCTACCAGCT

GCTCTCCATCTACTCGCCAGAGCACATCCGCCAGTATACCAACAAGAAGATTGGG

GAGATGCCCCCCCACATCTTTGCCATTGCTGACAACTGCTACTTCAACATGAAAC

GCAACAGCCGAGACCAGTGCTGCATCATCAGTGGGGAATCTGGGGCCGGAAGA

CGGAGAGCACAAAGCTGATCCTGCAGTTCCTGGCAGCCATCAGTGGGCAGCACTC

GTGGATTGAGCAGCAGGTCTTGGAGGCCACCCCCATTCTGGAAGCATTTGGGAAT

GCCAAGACCATCCGCAATGACAACTCAAGCCGTTTCGGAAAGTACATCGACATCC

ACTTCAACAAGCGGGGCGCCATCGAGGGCGCGAAGATTGAGCAGTACCTGCTGG

AAAAGTCACGTGTCTGTCGCCAGGCCCTGGATGAAAGGAACTACCACGTGTTCTA

CTGCATGCTGGAGGGTATGAGTGAGGATCAGAAGAAGAAGCTGGGCTTGGGCCA

GGCCTCTGACTACAACTACTTGGCCATGGGTAACTGCATAACCTGTGAGGGCCGG

-continued

```
GTGGACAGCCAGGAGTACGCCAACATCCGCTCCGCCATGAAGGTGCTCATGTTCA

CTGACACCGAGAACTGGGAGATCTCGAAGCTCCTGGCTGCCATCCTGCACCTGGG

CAACCTGCAGTATGAGGCACGCACATTTGAAAACCTGGATGCCTGTGAGGTTCTC

TTCTCCCCATCGCTGGCCACAGCTGCATCCCTGCTTGAGGTGAACCCCCCAGACCT

GATGAGCTGCCTGACTAGCCGCACCCTCATCACCCGCGGGGAGACGGTGTCCACC

CCACTGAGCAGGGAACAGGCACTGGACGTGCGCGACGCCTTCGTAAAGGGGATC

TACGGGCGGCTGTTCGTGTGGATTGTGGACAAGATCAACGCAGCAATTTACAAGC

CTCCCTCCCAGGATGTGAAGAACTCTCGCAGGTCCATCGGCCTCCTGGACATCTTT

GGGTTTGAGAACTTTGCTGTGAACAGCTTTGAGCAGCTCTGCATCAACTTCGCCA

ATGAGCACCTGCAGCAGTTCTTTGTGCGGCACGTGTTCAAGCTGGAGCAGGAGGA

ATATGACCTGGAGAGCATTGACTGGCTGCACATCGAGTTCACTGACAACCAGGAT

GCCCTGGACATGATTGCCAACAAGCCCATGAACATCATCTCCCTCATCGATGAGG

AGAGCAAGTTCCCCAAGGGCACAGACACCACCATGTTACACAAGCTGAACTCCC

AGCACAAGCTCAACGCCAACTACATCCCCCCCAAGAACAACCATGAGACCCAGTT

TGGCATCAACCATTTTGCAGGCATCGTCTACTATGAGACCCAAGGCTTCCTGGAG

AAGAACCGAGACACCCTGCATGGGACATTATCCAGCTGGTCCACTCCTCCAGGA

ACAAGTTCATCAAGCAGATCTTCCAGGCCGATGTCGCCATGGGCGCCGAGACCAG

GAAGCGCTCGCCCACACTTAGCAGCCAGTTCAAGCGGTCACTGGAGCTGCTGATG

CGCACGCTGGGTGCCTGCCAGCCCTTCTTTGTGCGATGCATCAAGCCCAATGAGT

TCAAGAAGCCCATGCTGTTCGACCGGCACCTGTGCGTGCGCCAGCTGCGGTACTC

AGGAATGATGGAGACCATCCGAATCCGCCGAGCTGGCTACCCCATCCGCTACAGC

TTCGTAGAGTTTGTGGAGCGGTACCGTGTGCTGCTGCCAGGTGTGAAGCCGGCCT

ACAAGCAGGGCGACCTCCGCGGGACTTGCCAGCGCATGGCTGAGGCTGTGCTGG

GCACCCACGATGACTGGCAGATAGGCAAAACCAAGATCTTTCTGAAGGACCACC

ATGACATGCTGCTGGAAGTGGAGCGGGACAAAGCCATCACCGACAGAGTCATCC

TCCTTCAGAAAGTCATCCGGGGATTCAAAGACAGGTCTAACTTTCTGAAGCTGAA

GAACGCTGCCACACTGATCCAGAGGCACTGGCGGGGTCACAACTGTAGGAAGAA

CTACGGGCTGATGCGTCTGGGCTTCCTGCGGCTGCAGGCCCTGCACCGCTCCCGG

AAGCTGCACCAGCAGTACCGCCTGGCCCGCCAGCGCATCATCCAGTTCCAGGCCC

GCTGCCGCGCCTATCTGGTGCGCAAGGCCTTCCGCCACCGCCTCTGGGCTGTGCTC

ACCGTGCAGGCCTATGCCCGGGGCATGATCGCCCGCAGGCTGCACCAACGCCTCA

GGGCTGAGTATCTGTGGCGCCTCGAGGCTGAGAAAATGCGGCTGGCGGAGGAAG

AGAAGCTTCGGAAGGAGATGAGCGCCAAGAAGGCCAAGGAGGAGGCCGAGCGC

AAGCATCAGGAGCGCCTGGCCCAGCTGGCTCGTGAGGACGCTGAGCGGGAGCTG

AAGGAGAAGGAGGCCGCTCGGCGGAAGAAGGAGCTCCTGGAGCAGATGGAAAG

GGCCCGCCATGAGCCTGTCAATCACTCAGACATGGTGGACAAGATGTTTGGCTTC

CTGGGGACTTCAGGTGGCCTGCCAGGCCAGGAGGGCCAGGCACCTAGTGGCTTTG

AGGACCTGGAGCGAGGGCGGAGGGAGATGGTGGAGGAGGACCTGGATGCAGCC

CTGCCCCTGCCTGACGAGGATGAGGAGGACCTCTCTGAGTATAAATTTGCCAAGT

TCGCGGCCACCTACTTCCAGGGGACAACCACGCACTCCTACACCCGGCGGCCACT
```

```
                         -continued
CAAACAGCCACTGCTCTACCATGACGACGAGGGTGACCAGCTGGCAGCCCTGGC

GGTCTGGATCACCATCCTCCGCTTCATGGGGGACCTCCCTGAGCCCAAGTACCAC

ACAGCCATGAGTGATGGCAGTGAGAAGATCCCTGTGATGACCAAGATTTATGAG

ACCCTGGGCAAGAAGACGTACAAGAGGGAGCTGCAGGCCCTGCAGGGCGAGGGC

GAGGCCCAGCTCCCCGAGGGCCAGAAGAAGAGCAGTGTGAGGCACAAGCTGGTG

CATTTGACTCTGAAAAAGAAGTCCAAGCTCACAGAGGAGGTGACCAAGAGGCTG

CATGACGGGGAGTCCACAGTGCAGGGCAACAGCATGCTGGAGGACCGGCCCACC

TCCAACCTGGAGAAGCTGCACTTCATCATCGGCAATGGCATCCTGCGGCCAGCAC

TCCGGGACGAGATCTACTGCCAGATCAGCAAGCAGCTGACCCACAACCCCTCCAA

GAGCAGCTATGCCCGGGGCTGGATTCTCGTGTCTCTCTGCGTGGGCTGTTTCGCCC

CCTCCGAGAAGTTTGTCAAGTACCTGCGGAACTTCATCCACGGGGCCCGCCCGG

CTACGCCCCGTACTGTGAGGAGCGCCTGAGAAGGACCTTTGTCAATGGGACACGG

ACACAGCCGCCCAGCTGGCTGGAGCTGCAGGCCACCAAGTCCAAGAAGCCAATC

ATGTTGCCCGTGACATTCATGGATGGGACCACCAAGACCCTGCTGACGGACTCGG

CAACCACGGCCAAGGAGCTCTGCAACGCGCTGGCCGACAAGATCTCTCTCAAGG

ACCGGTTCGGGTTCTCCCTCTACATTGCCCTGTTTGACAAGGTGTCCTCCCTGGGC

AGCGGCAGTGACCACGTCATGGACGCCATCTCCCAGTGCGAGCAGTACGCCAAG

GAGCAGGGCGCCCAGGAGCGCAACGCCCCTGGAGGCTCTTCTTCCGCAAAGAG

GTCTTCACGCCCTGGCACAGCCCTCCGAGGACAACGTGGCCACCAACCTCATCT

ACCAGCAGGTGGTGCGAGGAGTCAAGTTTGGGGAGTACAGGTGTGAGAAGGAGG

ACGACCTGGCTGAGCTGGCCTCCCAGCAGTACTTTGTAGACTATGGCTCTGAGAT

GATCCTGGAGCGCCTCCTGAACCTCGTGCCCACCTACATCCCCGACCGCGAGATC

ACGCCCCTGAAGACGCTGGAGAAGTGGGCCCAGCTGGCCATCGCCGCCCACAAG

AAGGGGATTTATGCCCAGAGGAGAACTGATGCCCAGAAGGTCAAAGAGGATGTG

GTCAGTTATGCCCGCTTCAAGTGGCCCTTGCTCTTCTCCAGGTTTTATGAAGCCTA

CAAATTCTCAGGCCCCAGTCTCCCCAAGAACGACGTCATCGTGGCCGTCAACTGG

ACGGGTGTGTACTTTGTGGATGAGCAGGAGCAGGTACTTCTGGAGCTGTCCTTCC

CAGAGATCATGGCCGTGTCCAGCAGCAGGGAGTGCCGTGTCTGGCTCTCACTGGG

CTGCTCTGATCTTGGCTGTGCTGCGCCTCACTCAGGCTGGGCAGGACTGACCCCG

GCGGGGCCCTGTTCTCCGTGTTGGTCCTGCAGGGGAGCGAAAACGACGGCCCCCA

GCTTCACGCTGGCCACCATCAAGGGGGACGAATACACCTTCACCTCCAGTAATGC

TGAGGACATTCGTGACCTGGTGGTCACCTTCCTAGAGGGGCTCCGGAAGAGATCT

AAGTATGTTGTGGCCCTGCAGGATAACCCCAACCCCGCAGGCGAGGAGTCAGGCT

TCCTCAGCTTTGCCAAGGGAGACCTCATCATCCTGGACCATGACACGGGCGAGCA

GGTCATGAACTCGGGCTGGGCCAACGGCATCAATGAGAGGACCAAGCAGCGTGG

GGACTTCCCCACCGACTGTGTGTACGTCATGCCCACTGTCACCATGCCACCGCGG

GAGATTGTGGCCCTGGTCACCATGACTCCCGATCAGAGGCAGGACGTTGTCCGGC

TCTTGCAGCTGCGAACGGCGGAGCCCGAGGTGCGTGCCAAGCCCTACACGCTGGA

GGAGTTTTCCTATGACTACTTCAGGCCCCCACCCAAGCACACGCTGAGCCGTGTC

ATGGTGTCCAAGGCCCGAGGCAAGGACCGGCTGTGGAGCCACACGCGGGAACCG

CTCAAGCAGGCGCTGCTCAAGAAGCTCCTGGGCAGTGAGGAGCTCTCGCAGGAG
```

```
GCCTGCCTGGCCTTCATTGCTGTGCTCAAGTACATGGGCGACTACCCGTCCAAGA

GGACACGCTCCGTCAACGAGCTCACCGACCAGATCTTTGAGGGTCCCCTGAAAGC

CGAGCCCCTGAAGGACGAGGCATATGTGCAGATCCTGAAGCAGCTGACCGACAA

CCACATCAGGTACAGCGAGGAGCGGGGTTGGGAGCTGCTCTGGCTGTGCACGGG

CCTTTTCCCACCCAGCAACATCCTCCTGCCCCACGTGCAGCGCTTCCTGCAGTCCC

GAAAGCACTGCCCACTCGCCATCGACTGCCTGCAACGGCTCCAGAAAGCCCTGAG

AAACGGGTCCCGGAAGTACCCTCCGCACCTGGTGGAGGTGGAGGCCATCCAGCA

CAAGACCACCCAGATTTTCCACAAGGTCTACTTCCCTGATGACACTGACGAGGCC

TTCGAAGTGGAGTCCAGCACCAAGGCCAAGGACTTCTGCCAGAACATCGCCACCA

GGCTGCTCCTCAAGTCCTCAGAGGGATTCAGCCTCTTTGTCAAAATTGCAGACAA

GGTCATCAGCGTTCCTGAGAATGACTTCTTCTTTGACTTTGTTCGACACTTGACAG

ACTGGATAAAGAAAGCTCGGCCCATCAAGGACGGAATTGTGCCCTCACTCACCTA

CCAGGTGTTCTTCATGAAGAAGCTGTGGACCACCACGGTGCCAGGGAAGGATCCC

ATGGCCGATTCCATCTTCCACTATTACCAGGAGTTGCCCAAGTATCTCCGAGGCTA

CCACAAGTGCACGCGGGAGGAGGTGCTGCAGCTGGGGGCGCTGATCTACAGGGT

CAAGTTCGAGGAGGACAAGTCCTACTTCCCCAGCATCCCCAAGCTGCTGCGGGAG

CTGGTGCCCCAGGACCTTATCCGGCAGGTCTCACCTGATGACTGGAAGCGGTCCA

TCGTCGCCTACTTCAACAAGCACGCAGGGAAGTCCAAGGAGGAGGCCAAGCTGG

CCTTCCTGAAGCTCATCTTCAAGTGGCCCACCTTTGGCTCAGCCTTCTTCGAGGTG

AAGCAAACTACGGAGCCAAACTTCCCTGAGATCCTCCTAATTGCCATCAACAAGT

ATGGGGTCAGCCTCATCGATCCCAAAACGAAGGATATCCTCACCACTCATCCCTT

CACCAAGATCTCCAACTGGAGCAGCGGCAACACCTACTTCCACATCACCATTGGG

AACTTGGTGCGCGGGAGCAAACTGCTCTGCGAGACGTCACTGGGCTACAAGATG

GATGACCTCCTGACTTCCTACATTAGCCAGATGCTCACAGCCATGAGCAAACAGC

GGGGCTCCAGGAGCGGCAAGTGA

SEQ ID NO: 8 is an amino acid sequence of a human myosin VIIa polypeptide
(isoform 2);
MVILQQGDHVWMDLRLGQEFDVPIGAVVKLCDSGQVQVVDDEDNEHWISPQNATH

IKPMHPTSVHGVEDMIRLGDLNEAGILRNLLIRYRDHLIYTYTGSILVAVNPYQLLSIY

SPEHIRQYTNKKIGEMPPHIFAIADNCYFNMKRNSRDQCCIISGESGAGKTESTKLILQ

FLAAISGQHSWIEQQVLEATPILEAFGNAKTIRNDNSSRFGKYIDIHFNKRGAIEGAKIE

QYLLEKSRVCRQALDERNYHVFYCMLEGMSEDQKKKLGLGQASDYNYLAMGNCIT

CEGRVDSQEYANIRSAMKVLMFTDTENWEISKLLAAILHLGNLQYEARTFENLDACE

VLFSPSLATAASLLEVNPPDLMSCLTSRTLITRGETVSTPLSREQALDVRDAFVKGIYG

RLFVWIVDKINAAIYKPPSQDVKNSRRSIGLLDIFGFENFAVNSFEQLCINFANEHLQQ

FFVRHVFKLEQEEYDLESIDWLHIEFTDNQDALDMIANKPMNIISLIDEESKFPKGTDT

TMLHKLNSQHKLNANYIPPKNNHETQFGINHFAGIVYYETQGFLEKNRDTLHGDIIQL

VHSSRNKFIKQIFQADVAMGAETRKRSPTLSSQFKRSLELLMRTLGACQPFFVRCIKP

NEFKKPMLFDRHLCVRQLRYSGMMETIRIRRAGYPIRYSFVEFVERYRVLLPGVKPA

YKQGDLRGTCQRMAEAVLGTHDDWQIGKTKIFLKDHHDMLLEVERDKAITDRVILL

QKVIRGFKDRSNFLKLKNAATLIQRHWRGHNCRKNYGLMRLGFLRLQALHRSRKLH
```

-continued

```
QQYRLARQRIIQFQARCRAYLVRKAFRHRLWAVLTVQAYARGMIARRLHQRLRAEY

LWRLEAEKMRLAEEEKLRKEMSAKKAKEEAERKHQERLAQLAREDAERELKEKEA

ARRKKELLEQMERARHEPVNHSDMVDKMFGFLGTSGGLPGQEGQAPSGFEDLERGR

REMVEEDLDAALPLPDEDEEDLSEYKFAKFAATYFQGTTTHSYTRRPLKQPLLYHDD

EGDQLAALAVWITILRFMGDLPEPKYHTAMSDGSEKIPVMTKIYETLGKKTYKRELQ

ALQGEGEAQLPEGQKKSSVRHKLVHLTLKKKSKLTEEVTKRLHDGESTVQGNSMLE

DRPTSNLEKLHFIIGNGILRPALRDEIYCQISKQLTHNPSKSSYARGWILVSLCVGCFAP

SEKFVKYLRNFIHGGPPGYAPYCEERLRRTFVNGTRTQPPSWLELQATKSKKPIMLPV

TFMDGTTKTLLTDSATTAKELCNALADKISLKDRFGFSLYIALFDKVSSLGSGSDHV

MDAISQCEQYAKEQGAQERNAPWRLFFRKEVFTPWHSPSEDNVATNLIYQQVVRGV

KFGEYRCEKEDDLAELASQQYFVDYGSEMILERLLNLVPTYIPDREITPLKTLEKWAQ

LAIAAHKKGIYAQRRTDAQKVKEDVVSYARFKWPLLFSRFYEAYKFSGPSLPKNDVI

VAVNWTGVYFVDEQEQVLLELSFPEIMAVSSSRGAKTTAPSFTLATIKGDEYTFTSSN

AEDIRDLVVTFLEGLRKRSKYVVALQDNPNPAGEESGFLSFAKGDLIILDHDTGEQV

MNSGWANGINERTKQRGDFPTDSVYVMPTVTMPPREIVALVTMTPDQRQDVVRLL

QLRTAEPEVRAKPYTLEEFSYDYFRPPPKHTLSRVMVSKARGKDRLWSHTREPLKQA

LLKKLLGSEELSQEACLAFIAVLKYMGDYPSKRTRSVNELTDQIFEGPLKAEPLKDEA

YVQILKQLTDNHIRYSEERGWELLWLCTGLFPPSNILLPHVQRFLQSRKHCPLAIDCL

QRLQKALRNGSRKYPPHLVEVEAIQHKTTQIFHKVYFPDDTDEAFEVESSTKAKDFC

QNIATRLLLKSSEGFSLFVKIADKVLSVPENDFFFDFVRHLTDWIKKARPIKDGIVPSL

TYQVFFMKKLWTTTVPGKDPMADSIFHYYQELPKYLRGYHKCTREEVLQLGALIYR

VKFEEDKSYFPSIPKLLRELVPQDLIRQVSPDDWKRSIVAYFNKHAGKSKEEAKLAFL

KLIFKWPTFGSAFFEQTTEPNFPEILLIAINKYGVSLIDPKTKDILTTHPFTKISNWSSGN

TYFHITIGNLVRGSKLLCETSLGYKMDDLLTSYISQMLTAMSKQRGSRSGK
```

CMv1 Overlap Vector System

Some embodiments contemplate the overlapping vector system as described herein, with one or more substitutions made in the 3' untranslated region downstream of the MYO7A partial coding sequence, and before the 3' AAV inverted terminal repeat. In some embodiments, these substitutions are intended to remove potential (or putative) in-frame stop codons. In some embodiments, these substitutions remove one or more putative stop codons in a non-coding sequence. In particular embodiments, the substitutions remove one or more putative stop codons in the 3' untranslated region between the partial coding sequence encoding the C-terminal part of the polypeptide and the 3' AAV inverted terminal repeat of the second AAV vector polynucleotide (e.g., downstream of the MYO7A N-terminal fragment). In some embodiments, the one or more putative stop codons are removed and replaced with a "stuffer" sequence (see FIG. 43). In some embodiments, the first AAV vector polynucleotide thus comprises a partial coding sequence that does not encode the single-alpha helix (SAH) domain of the selected full-length polypeptide.

As a result of these substitutions, a front-half vector is created having the nucleotide sequence comprising SEQ ID NO: 36. In such embodiments, overlap vector systems of the disclosure may comprise:

(i) a first AAV vector polynucleotide comprising an inverted terminal repeat at each end of the polynucleotide, and between the inverted terminal repeats a promoter followed by a partial coding sequence that encodes an N-terminal part of a selected full-length polypeptide; and (ii) a second AAV vector polynucleotide comprising an inverted terminal repeat at each end of the polynucleotide, and between the inverted terminal repeats a partial coding sequence that encodes a C-terminal part of the selected full-length polypeptide. In some embodiments, the second AAV vector polynucleotide is followed by a polyadenylation (pA) signal sequence. The coding sequences in the first and second vectors when combined encode the selected full-length polypeptide, or a functional fragment or variant thereof. The polypeptide encoding sequence in the first and second AAV vectors comprises sequence that overlaps.

In some embodiments, the C-terminal part of the selected full-length polypeptide (e.g., the myosin polypeptide) comprises the single-alpha helix (SAH) domain of the selected full-length polypeptide.

In some embodiments, the polynucleotide sequence that overlaps comprises SEQ ID NO: 39. In particular embodiments, the sequence overlap between the first and second AAV vectors is between about 1 and about 500 nucleotides; between about 100 and about 200 nucleotides; between about 200 and about 300 nucleotides; or between about 300 and about 400 nucleotides. In particular embodiments, the sequence overlap of the second generation overlap vector system is about 350 nucleotides. In an exemplary embodiment, the sequence overlap of the second generation overlap vector system is 361 nucleotides.

In some embodiments, the polynucleotide sequence that overlaps does not comprise any portion of exon 23 of the hMYO7A gene. In some embodiments, the polynucleotide sequence that overlaps does not comprise exon 23 in full (e.g., 100% of exon 23). In some embodiments, the polynucleotide sequence that overlaps comprises a portion of exon 17, exon 18 in full, exon 19 in full, exon 20 in full, and a portion of exon 21 of the hMYO7A gene. In some embodiments, the polynucleotide sequence that overlaps comprises a portion of exon 17, a portion of exon 18, a portion of exon 19, a portion of exon 20, and/or a portion of exon 21 of the hMYO7A gene. As used herein, a "portion" may comprise e.g. at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, etc. of the exon and/or intron.

In an exemplary embodiment, the first AAV vector polynucleotide comprises the nucleotide sequence of SEQ ID NO: 36, or a functional fragment and/or variant thereof, and the second AAV vector polynucleotide comprises the nucleotide sequence of SEQ ID NO: 38, or a functional fragment and/or variant thereof.

In some embodiments, first AAV vector polynucleotide comprises a partial coding sequence that does not encode the single-alpha helix (SAH) domain of the selected full-length (e.g. myosin) polypeptide. In some embodiments, the second AAV vector polynucleotide is followed by a polyadenylation (pA) signal sequence.

In some embodiments, any vector of the overlap polynucleotide vector systems described in the disclosure may be administered by parenteral administration, such as intravenous, intramuscular, intraocular, intranasal, etc. The vector can be administered in vivo, in vitro or ex vivo.

In some embodiments, any vector of the overlap polynucleotide vector systems described herein may be administered to the eye. In particular embodiments, a vector is administered to the eye of a subject by subretinal injection. In some embodiments, any vector of the hybrid polynucleotide vector systems described herein may be administered to the ear.

In some embodiments, any vector of the hybrid polynucleotide vector systems described herein the polynucleotide vector system is administered to the ear of a subject, e.g., by a round window injection or during cochlear implant surgery.

SEQ ID NO: 5 is a nucleotide sequence encoding a human myosin VIIa polypeptide (protein coding sequence is nucleotides 273-6920), the sequence of which is disclosed herein;

SEQ ID NO: 6 is the amino acid sequence of the human myosin VIIa polypeptide encoded by nucleotides 273-6920 of SEQ ID NO: 5, the sequence of which is disclosed herein;

SEQ ID NO: 7 is a nucleotide sequence that encodes a human myosin VIIa polypeptide, the sequence of which is disclosed herein;

SEQ ID NO: 8 is an amino acid sequence of a human myosin VIIa polypeptide (isoform 2), the sequence of which is disclosed herein.

Some aspects of the disclosed overlap vectors contemplate a virus or a recombinant viral particle comprising the first AAV vector polynucleotide or the second AAV vector polynucleotide as described herein. In particular embodiments, the first AAV vector polynucleotide comprises SEQ ID NO: 36, and the second AAV vector polynucleotide comprises SEQ ID NO: 38. In some embodiments, the virus or recombinant viral particle is characterized as an adeno-associated virus (AAV) or an infectious AAV viral particle. In some embodiments, the recombinant AAV viral particle includes one or more tyrosine-to-phenylalanine (Y-F) mutations in a capsid protein of the virus or virion. Tyrosine-to-phenylalanine (Y-F) mutations in a capsid protein of the virus or virion at amino acid position 733 are specifically contemplated herein (for example, AAV8 Y733F).

In some embodiments, the virus or virion is packaged in an AAV5, AAV7, AAV8, AAV9, AAV44.9, AAV44.9 (E531D), AAV2(4pMut), AAVAnc80, AAVrh.8, AAVrh.8R, AAV9-PHP.B, AAV9-PHP.eB, AAVrh.10, or AAVrh.74 capsid. In some embodiments, the viral particle comprises an AAV1, AAV2, AAV3, AAV4, AAV5, AAV6, AAV7, AAV8, AAV9, AAV10, AAV7m8, AAV-DJ, AAV2/2-MAX, AAVSHh10, AAVSHh10Y, AAV3b, AAVLK03, AAV8PB2, AAV1(E531K), AAV6(D532N), AAV6-3pmut, AAV2G9, AAV44.9, AAV44.9(E531D), AAVrh.8, AAVrh.8R, AAV9-PHP.B, and/or AAVAnc80 capsid. In exemplary embodiments, the virion is packaged in an AAV44.9(E531D) capsid variant.

In some embodiments, the overlap polynucleotide vector systems described herein use a tissue-specific promoter. In some embodiments, the systems use a promoter that mediates expression in the eye. In some embodiments, the systems use a promoter that mediates expression in the ear.

In some embodiments, the overlap polynucleotide vector systems described herein use any one of the following promoters: a cytomegalovirus (CMV) promoter, an elongation factor-1 alpha (EF-1 alpha) promoter, a cone arrestin promoter, a chimeric CMV β actin promoter (CBA), a truncated chimeric CMV β actin (smCBA), a human myosin 7a gene-derived promoter, a cone transducin a (TαC) gene-derived promoter, a rhodopsin promoter, a cGMP-phosphodiesterase β-subunit promoter, human or mouse rhodopsin promoter, a human rhodopsin kinase (hGRK1) promoter, a synapsin promoter, a glial fibrillary acidic protein (GFAP) promoter, a rod specific IRBP promoter, a RPE-specific vitelliform macular dystrophy-2 [VMD2] promoter, and combinations thereof. In some embodiments, the polynucleotide vector system described herein uses a human rhodopsin kinase (hGRK1) promoter. In some embodiments, the polynucleotide vector system uses a cone arrestin promoter.

In some embodiments for delivery to the eyes (retina) of a subject, the disclosed overlap polynucleotide vector systems use a cytomegalovirus (CMV) promoter. In some embodiments, the polynucleotide vector system uses an EF-1 alpha promoter. In some embodiments for delivery to the ears (hair cells) of a subject, the polynucleotide vector system uses a synapsin or GFAP promoter (see Lee et al., Hearing Research).

Hybrid Vector Systems

In some aspects, hybrid dual AAV vector systems are provided. These hybrid vector systems drive higher levels of full length MYO7A than overlap vectors and produce truncated protein from the front half vector. The hybrid front half vector leads to reduced retinal function in subretinally injected mice. (See FIGS. 15B-E.) In various embodiments, the hybrid vector systems of the disclosure do not produce a truncated MYO7A protein fragment following administration to a mouse or a subject.

Altering the split point, codon modifying the front half vector, and/or minimizing the length of the back half vector leads to production of full-length MYO7A at levels equal to or above that seen with the first generation hybrid vectors. The improved vectors provided herein generate far less undesired truncated protein side product. from the front half vector. In some embodiments, production of the truncated protein is eliminated, partially or completely.

In some aspects of the disclosure, a hybrid vector system of the disclosure includes:

(i) a first AAV vector polynucleotide comprising an inverted terminal repeat at each end (for example, the 5'-end and the 3'-end) of the polynucleotide, and between the inverted terminal repeats a suitable promoter followed by (for example, 3' to the promoter) a partial coding sequence that encodes an N-terminal part of a selected full-length polypeptide followed by a splice donor site and an intron, and (ii) a second AAV vector polynucleotide comprising an inverted terminal repeat at each end (5'-end and 3'-end) of the polynucleotide, and between the inverted terminal repeats an intron and a splice acceptor site for the intron, optionally followed by a partial coding sequence that encodes a C-terminal part of the selected full-length polypeptide, optionally followed by a polyadenylation (pA) signal sequence. The intron sequence in the first and second AAV vectors comprises sequence that overlaps.

In some embodiments, the split point between the first and second AAV vector polynucleotide sequences is between exon 21 and exon 22 of the hMYO7A gene.

In an exemplary embodiment, the first AAV vector polynucleotide comprises the nucleotide sequence of SEQ ID NO: 31, or a functional fragment and/or variant thereof, and the second AAV vector polynucleotide comprises the nucleotide sequence of SEQ ID NO: 32, or a functional fragment and/or variant thereof.

The coding sequences in the first and second vectors when combined encode the selected full-length polypeptide, or a functional fragment or variant thereof. In some embodiments, the selected full-length polypeptide is hMYO7A. In some embodiments, the selected full-length polypeptide is hMYO7B. In some embodiments, the selected full-length polypeptide is isoform II of hMYO7A. In some embodiments, the polynucleotide sequence corresponding to the tail domain of the MYO7A protein is removed from the first AAV vector polynucleotide.

It will be appreciated that this disclosure is not limited to delivery of full-length myosin 7A polypeptide or myosin 7A-encoding nucleotides. In some embodiments, the selected full-length polypeptide is selected from ABCA4 (Stargardt disease), CEP290 (LCA10), EYS (Retinitis Pigmentosa), RP1 (Retinitis Pigmentosa), ALMS1 (Alstrom syndrome), CDH23 (Usher syndrome 1D), PCDH15 (Usher syndrome 1F), and USH2A (Usher syndrome 2A). In some embodiments, the selected full-length polypeptide is selected from DMD (Duchenne muscular dystrophy), CFTR (Cystic fibrosis), GDE (Glycogen storage disease III), DYSF (dysferlinopathies), OTOF (neurosensory nonsyndromic recessive deafness) and F8 (Hemophilia A). In some embodiments, the selected full-length polypeptide is not OTOF.

In some embodiments, all or part of the intron sequence present at the 3'-end of the coding sequence of the first vector is identical or substantially identical with all or part of the intron sequence present at the 5'-end of the coding sequence of the second vector. In some embodiments, intron sequence overlap between the first and second AAV vectors is several hundred nucleotides in length. In particular embodiments, the intron sequence overlap is about 50 to about 500 nucleotides or so in length; alternatively between about 200 and about 300 nucleotides or so in length.

In particular embodiments, the intron sequence utilized in any vector system of the disclosure is a sequence of an intron naturally present in the genomic sequence of the gene encoding the selected polypeptide. In some embodiments, characterized as the native intron hybrid vectors, the intron is intron 23 of the hMYO7A gene. In particular embodiments, the polypeptide encoded is hMYO7A, or a functional fragment thereof, and the intron is a partial sequence of full intron 23 of the hMYO7A gene. In particular embodiments, the polypeptide encoded is hMYO7A, or a functional fragment thereof, and the intron is the full intron 23 of the hMYO7A gene.

In some embodiments of the native intron hybrid vectors as described herein, the recombinogenic sequence of the dual vector system comprises partial sequences of exon 21, exon 22, and/or exon 23 of the hMYO7A gene. In some embodiments of the native intron hybrid vectors as described herein, the dual vector system comprising partial sequences of exon 21, exon 22, and/or exon 23 of the hMYO7A gene utilizes a partial sequence of a full native intron. In some embodiments, the native intron is intron 23 of the hMYO7A gene. Thus, in some embodiments, the intron sequence is a partial sequence of full intron 23 of the hMYO7A gene. As used herein, a "partial sequence" may comprise e.g. at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, etc. of the exon and/or intron sequence. In some embodiments, the first and/or second intron sequence comprises a sequence of an intron naturally present in the genomic sequence of the gene encoding a myosin polypeptide. In some embodiments, the intron sequence is a partial sequence of full intron 23 of the hMYO7A gene.

A number of strategies have been devised to overcome the issue of random concatemerization and thereby increase specificity as well as efficiency of dual vector platforms. First, the addition of a highly-recombinogenic sequence such as that used in the AP hybrid vector here has resulted in significantly increased protein expression compared with the trans-splicing system. Ghosh et al. (2011) provide a detailed analysis of the 270-bp AP sequence used in this study as well as other sequences derived from AP that direct recombination and lead to significant improvement over trans-splicing vectors. The finding that AP hybrid vectors are more efficient than trans-splicing vectors supports that the AP sequence directs at least some of the concatemerization events toward the proper orientation with recombination then occurring via this sequence or via the ITRs. The APhead domain in particular can mediate appropriate head-to-tail concatemerization following re-combination of the dual vectors in the cell. Regardless, with more concatemers properly aligned, the AP hybrid system mediates a more-efficient expression of MYO7A. (Another approach for directing concatemerization is the use of single-strand oligonucleotides that are capable of tethering the back end of the 5' vector and the front end of the 3' vector together (Hirsch et al., 2009); however, this strategy requires efficient delivery of the oligonucleotide to the nucleus of the target cells timed with the dual vectors.) Finally, dual vectors utilizing mismatched ITRs can be used to direct concatemerization in a head-to-tail orientation (Yan et al., 2005), although the process may require further optimization of the AAV packaging machinery.

Figure 45A:
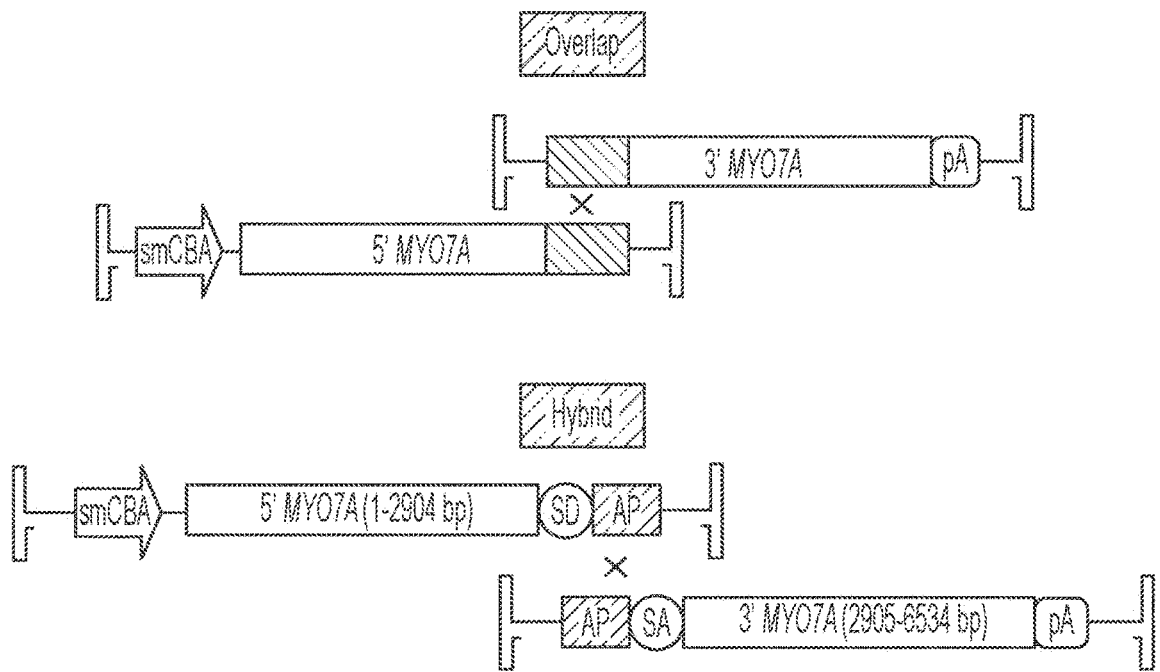
Figure 45B:
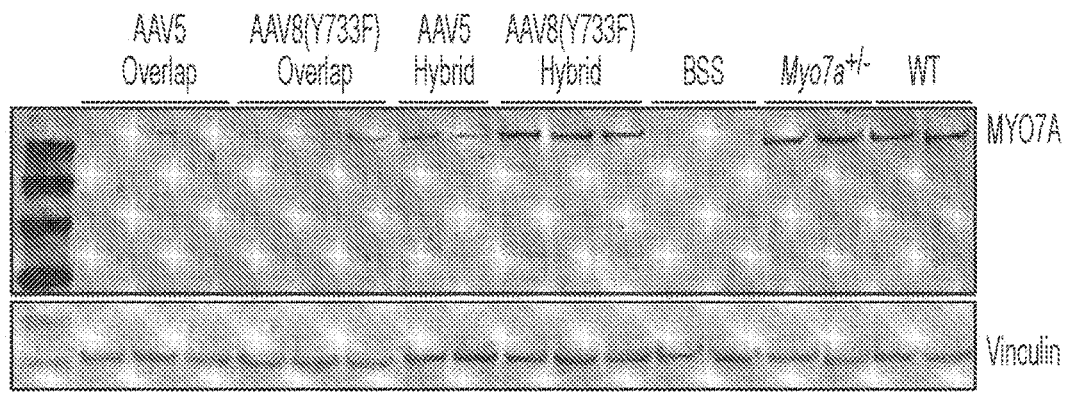

Accordingly, in some embodiments, the intron sequence utilized in the vector system of the disclosure is a sequence of an intron that is not naturally present in the genomic sequence of a gene encoding the selected polypeptide. In particular embodiments, the intron is a synthetic alkaline phosphatase (AP) intron. The intron sequences utilized in the vector system of the disclosure can comprise splice donor and splice acceptor sequences. In some embodiments, the intron sequence is a recombinogenic, intronic sequence (for example, the AK sequence of the F1 phage as shown in Trapani, et al. 2014). In these embodiments, the hybrid vectors, characterized as the second generation hybrid vectors described herein, rely on both ITR-mediated concatemerization and homologous recombination mediated by the AK sequence for the reconstitution of the full-length expression cassette. Thus, in some embodiments, the intron sequence is the AK sequence of the F1 phage. Accordingly, in some embodiments of the disclosed hybrid vectors, the vectors comprise one or more AP intronic spliceosome recognition sites, such as one or more AP splice acceptor (APSA) domains or AP splice donor (APSD) domains. In exemplary embodiments, these vectors comprise an APSA and an APSD. In some embodiments, the front half vector contains an APSA and the back half vector contains an APSD. In some embodiments, the front half vector contains an APSD and the back half vector contains an APSA. See FIGS. 37A and 45A.

Accordingly, in exemplary embodiments, the hybrid vector pairs contain an APhead-encoding sequence as part of the AP intron. In some embodiments of the disclosed hybrid vectors, the vectors comprise an intronic sequence comprising a nucleotide sequence having at least 85%, 90%, 92.5%, 95%, 98%, or 99% identity to either of SEQ ID NO: 69 or 70. In some embodiments of the disclosed hybrid vectors, the vectors comprise the nucleotide sequence of SEQ ID NO: 69 or 70 (APhead sequence).

Polypeptides other than hMYO7A that are contemplated for delivery using any of the disclosed hybrid vectors include, but are not limited to, harmonin (Uniprot Q9Y6N9), cadherin 23 (Uniprot Q9H251), protocadherin 15 (Uniprot Q96QU1), and usherin (USH2A) (Uniprot O75445). In some embodiments, the selected full-length polypeptide is encoded by a gene of about 5 Kb to about 10 Kb in length. In some embodiments, the selected full-length polypeptide is encoded by a gene of about 6 Kb to about 9 Kb in length. In some embodiments, the selected full-length polypeptide is encoded by a gene of about 7 Kb to about 8 Kb in length. In some embodiments, hybrid dual vectors expressing portions (or halves) of a large gene contain a sequence between the first intron and second intron of the first and second AAV vector polynucleotides, respectively; and a large gene other than MYO7A and that comprises a nucleotide sequence having at least 80%, 85%, 90%, 95%, 98%, or 99% identity to any one of SEQ ID NOs: 39 and 52-59. In some embodiments, these hybrid vectors an intronic sequence containing the nucleotide sequence of any one of SEQ ID NOs: 39 and 53-59, e.g., SEQ ID NO: 56 or 57. The large gene may be selected from ABCA4, CEP290, EYS, RP1, ALMS1, CDH23, PCDH15, USH1C, USH1G, USH2A, DNFB31, DMD, CFTR, GDE, DYSF, F8, and DFNB2. These hybrid vectors encoding non-MYO7A (e.g., ABCA4) genes may contain an overlapping region identified through the improved overlap vectors provided herein as the recombinogenic sequence, in place of the recombinogenic APhead sequence/domain. The overlapping regions of these hybrid vectors are flanked by splice acceptor and/or splice donor sequences, such that the overlapping region is spliced out, and does not code for any MYO7A protein.

In some embodiments, the hybrid vector system of the first generation contains a split point between exons 23 and 24, wherein the sequence corresponding to the tail domain of the MYO7A protein is contained within the front-half vector represented by SEQ ID NO: 3. The back-half vector of this exon 23/24 hybrid vector system is shown in SEQ ID NO: 4. In some embodiments, the second generation hybrid vector system contains a split point located between exons 21 and 22, wherein the sequence corresponding to the tail domain of the MYO7A protein is removed from the front-half vector of the exon 23/24 hybrid vector system, thereby generating the second generation hybrid front-half vector (SEQ ID NO: 31).

Thus, in an exemplified embodiment, the first AAV vector polynucleotide comprises the nucleotide sequence of SEQ ID NO: 31, or a functional fragment and/or variant thereof, and the second AAV vector polynucleotide comprises the nucleotide sequence of SEQ ID NO: 32, or a functional fragment and/or variant thereof, and the intronic sequence is the AK sequence of the F1 phage.

In some embodiments, the split point between the first and second AAV vector polynucleotide sequences is between exon 21 and exon 22 of the hMYO7A gene. In some embodiments, the split point between the first and second AAV vector polynucleotide sequences is between exon 22 and exon 23 of the hMYO7A gene.

In some embodiments, the split point between the first and second AAV vector polynucleotide sequences is not between exon 23 and exon 24 of the hMYO7A gene. In exemplary embodiments, the hybrid vectors of the disclosure do not comprise any of the nucleotide sequences of SEQ ID NOs: 3 and 4.

CMv1 Hybrid Vector System

Some embodiments contemplate a hybrid vector system as described herein, wherein substitutions are made in a noncoding sequence of the vector (e.g., the 3' untranslated region (3' UTR) downstream of the MYO7A partial coding sequence, and before the 3' AAV inverted terminal repeat of the inverted terminal repeat pairs of the first and/or second vector polynucleotide). In some embodiments, the substitutions are positioned in putative stop codons, such that these potential stop codons are removed. In some embodiments, one or more potential stop codons are removed by installing one or more nucleotide substitutions in the alkaline phosphatase (AP) intronic splice donor sequence ("AP intron") of the front-half vector (for example, the front-half vector comprising SEQ ID NO: 31). In some embodiments, three potential stop codons are modified within the alkaline phosphatase intronic splice donor sequence of the front-half vector. As a result of the modification of these putative stop codons in the APhead sequence, a modified front-half vector is created comprising SEQ ID NO: 33. See FIG. 42.

Accordingly, in some embodiments, a hybrid vector system of the disclosure comprises:

i) a first AAV vector polynucleotide comprising an inverted terminal repeat at each end of the polynucleotide, and between the inverted terminal repeats a promoter followed by a partial coding sequence that encodes an N-terminal part of a selected full-length polypeptide followed by a splice donor site and an intron; and ii) a second AAV vector polynucleotide comprising an inverted terminal repeat at each end of the polynucleotide, and between the inverted terminal repeats an intron and a splice acceptor site for the intron, and optionally followed by a partial coding sequence that encodes a C-terminal part of the selected full-length polypeptide, followed by a polyadenylation (pA) signal sequence. The intron sequence in the first and second AAV vectors comprises sequence that overlaps. In an exemplary embodiment, the first AAV vector polynucleotide comprises the nucleotide sequence of SEQ ID NO: 33, or a functional fragment and/or variant thereof, and the second AAV vector polynucleotide comprises the nucleotide sequence of SEQ ID NO: 32, or a functional fragment and/or variant thereof.

CMv2 Hybrid Vector System

Still other embodiments contemplate the hybrid vector system as described herein, with one additional putative in-frame stop codon modified in the front-half vector (for example, the front-half vector comprising SEQ ID NO: 33). In some embodiments, the modification comprises the installation of a substitution into the APhead sequence of the front-half vector that removes a putative stop codon from this sequence. As a result of this modification and removal of this putative stop codon, a further modified front-half vector is created comprising SEQ ID NO: 34.

Upon modification of the additional putative in-frame stop codon as described herein, some embodiments consider making complementary changes to the back-half vector (for example, the back-half vector comprising SEQ ID NO: 32), where the identical codon is also modified in the back-half vector. Thus, in some embodiments, the modification comprises the installation of a substitution into the APhead sequence of the back-half vector that removes a putative stop codon from this sequence. As a result of the modification of this additional stop codon, a modified back-half vector is created comprising SEQ ID NO: 35. See FIG. 42.

As such, in the CMv1 vector, three potential in-frame stop codons in the AP intron are removed. In the CMv2 vector, these same three potential stop codons in the AP intron were removed, and one potential stop codon from the APhead coding sequence was removed.

Therefore, in particular embodiments, a hybrid vector system of the disclosure comprises:

i) a first AAV vector polynucleotide comprising an inverted terminal repeat at each end of the polynucleotide, and between the inverted terminal repeats a promoter followed by a partial coding sequence that encodes an N-terminal part of a selected full-length polypeptide followed by a splice donor site and an intron; and ii) a second AAV vector polynucleotide comprising an inverted terminal repeat at each end of the polynucleotide, and between the inverted terminal repeats an intron and a splice acceptor site for the intron, and optionally followed by a partial coding sequence that encodes a C-terminal part of the selected full-length polypeptide, followed by a polyadenylation (pA) signal sequence. The intron sequence in the first and second AAV vectors comprises sequence that overlaps. In an exemplary embodiment, the first AAV vector polynucleotide comprises the nucleotide sequence of SEQ ID NO: 34, or a functional fragment and/or variant thereof, and the second AAV vector polynucleotide comprises the nucleotide sequence of SEQ ID NO: 35, or a functional fragment and/or variant thereof.

V2 MIN and CMv2 MIN Hybrid Vector Systems (Also Known as CMv2.1 Hybrid Vector System)

When the split point is altered from the junction between exons 23 and 24, as in the first-generation hybrid vector system, to the junction between exons 21 and 22, as in the second-generation hybrid vector system, additional portions of the MYO7A sequence are shifted to the back-half second-generation hybrid vector. Because of this, in some embodiments the second-generation back-half hybrid vector is close to, but does not exceed, the AAV packaging limit. Accordingly, in some embodiments, the modified back-half vector comprising SEQ ID NO: 35 may be further modified to remove any residual (extra), non-essential sequences, such as restriction enzyme sites and tag sequences, from the 3' end of the construct. These residual sequences are sometimes referred to as "unseeded legacy" sequences. The resulting modified back-half vector comprises SEQ ID NO: 49. This vector system is known as the "V2 MIN" or "V2-back MIN" hybrid system. In some embodiments, this system contains an HA tag ("V2 MIN HA"). The V2 MIN HA vector is set forth as SEQ ID NO: 48. The V2 MIN back-half vector is 122 bp shorter than the first-generation hybrid back-half vectors (4981 bp vs. 4861 bp).

In some embodiments, a vector is provided in which unseeded legacy sequences are removed, and one or more substitutions in non-coding sequences are installed. In some embodiments, these one or more substitutions are positioned in putative stop codons, such that these potential stop codons are removed. In some embodiments, one or more potential stop codons are removed by installing one or more nucleotide substitutions in the APhead sequence of the front-half vector. In some embodiments, the one or more putative stop codons are removed and replaced with a "stuffer" sequence (see FIG. 43).

In some embodiments, three potential stop codons are modified within the alkaline phosphatase intron sequence of the front-half vector. In some embodiments, one putative stop codon is modified (removed) by installing one or more substitutions in the APhead sequence of the front-half vector. As a result of the modification of these putative stop codons in the APhead sequence, the modified front-half vector of SEQ ID NO: 34 was generated.

In some embodiments, one putative stop codon is likewise modified in the APhead sequence of the back-half vector. As a result of the modification of this putative stop codon in the APhead sequence, the modified back-half vector of SEQ ID NO: 44 was generated.

This vector system is known as the CMv2 MIN system. In some embodiments, this system contains an HA tag ("CMv2 MIN HA"). The CMv2 MIN HA vector is set forth as SEQ ID NO: 47. The CMv2 MIN back-half vector is 121 bp shorter than the first-generation hybrid back-half vectors (4982 bp vs. 4861 bp).

Thus, in some embodiments, a hybrid vector system of the disclosure comprises:

i) a first AAV vector polynucleotide comprising an inverted terminal repeat at each end of the polynucleotide, and between the inverted terminal repeats a promoter followed by a partial coding sequence that encodes an N-terminal part of a selected full-length polypeptide followed by a splice donor site and an intron; and ii) a second AAV vector polynucleotide comprising an inverted terminal repeat at each end of the polynucleotide, and between the inverted terminal repeats an intron and a splice acceptor site for the intron, and optionally followed by a partial coding sequence that encodes a C-terminal part of the selected full-length polypeptide, followed by a polyadenylation (pA) signal sequence. The intron sequence in the first and second AAV vectors comprises sequence that overlaps. In an exemplary embodiment, the first AAV vector polynucleotide comprises the nucleotide sequence of SEQ ID NO: 34, or a functional fragment and/or variant thereof, and the second AAV vector polynucleotide comprises the nucleotide sequence of SEQ ID NO: 44, or a functional fragment and/or variant thereof. In some embodiments, the first AAV vector polynucleotide comprises the nucleotide sequence of SEQ ID NO: 34, or a functional fragment and/or variant thereof, and the second AAV vector polynucleotide comprises the nucleotide sequence of SEQ ID NO: 47, or a functional fragment and/or variant thereof. In some embodiments, the first AAV vector polynucleotide comprises the nucleotide sequence of SEQ ID NO: 34, or a functional fragment and/or variant thereof, and the second AAV vector polynucleotide comprises the nucleotide sequence of SEQ ID NO: 48, or a functional fragment and/or variant thereof.

CMv3 MIN Hybrid Vector Systems

Still other embodiments contemplate the hybrid vector system as described herein, with three additional in-frame stop codons modified in the front-half vector. In some embodiments, one or more nucleotide substitutions (e.g., three substitutions) are made in the 3′UTR or ITR downstream of the MYO7A coding sequence. Accordingly, in some embodiments, a front-half vector is provided in which one in-frame stop codon in the APhead sequence, three in-frame stop codons in the AP intron sequence, and three in-frame stop codons in the 3′ UTR sequence have been removed through the installation of substitutions. As a result of the modification of these putative stop codons, a further modified front-half vector is created comprising SEQ ID NO: 46 ("AAV-smCBA-hMYO7A-NT-Ex21-APSD-AP-head-CMv3", or simply "CMv3 hybrid system"). In exemplary embodiments, the CMv3 hybrid system is a CMv3 MIN system in that residual, unseeded legacy sequences (e.g., restriction enzyme sites) have been removed. In some embodiments, the CMv3 system has a HA tag.

Therefore, in an exemplary embodiment, the first AAV vector polynucleotide comprises the nucleotide sequence of SEQ ID NO: 46, or a functional fragment and/or variant thereof, and the second AAV vector polynucleotide comprises the nucleotide sequence of SEQ ID NO: 35, or a functional fragment and/or variant thereof.

Thus, in some embodiments, the polynucleotide vector system of the disclosure is a CMv3 hybrid system. In some embodiments, the vector system is a CMv3 MIN system. In some embodiments, the vector system is a CMv2 system. In some embodiments, the vector system is a CMv2 MIN system. In some embodiments, the vector system is a CMv1 or CMv1 MIN system. Any of the disclosed front-half hybrid vectors may be combined with any of the disclosed back-half hybrid vectors in the compositions of the disclosure.

In exemplary embodiments, polynucleotide vector systems are provided that comprise:

i) a first AAV vector polynucleotide comprising an inverted terminal repeat at each end of the polynucleotide, and between the inverted terminal repeats a promoter followed by a partial coding sequence that encodes an N-terminal part of a myosin polypeptide followed by a splice donor site and an intron, and ii) a second AAV vector polynucleotide comprising an inverted terminal repeat at each end of the polynucleotide, and between the inverted terminal repeats an intron and a splice acceptor site for the intron, wherein the intron sequence in the first and second AAV vectors comprises a polynucleotide sequence that overlaps, and wherein the first AAV vector polynucleotide comprises a nucleotide sequence selected from SEQ ID NOs: 31, 33, 34, and 46;

and the second AAV vector polynucleotide comprises a nucleotide sequence selected from SEQ ID NOs: 32, 35, 44, and 47-49.

In some embodiments of the hybrid vector systems described herein, the selected full-length polypeptide is a myosin polypeptide. In some embodiments, the myosin polypeptide is human myosin VII A (hMYO7A). In some embodiments, the myosin polypeptide is human myosin VII B (hMYO7B). In some embodiments, the myosin polypeptide is myosin 7 (VII) isoform II. In some embodiments, the myosin polypeptide is another myosin isoform or a functional fragment thereof. In particular embodiments, full-length myosin 7A or isoform II is encoded in the provided vector systems.

In some embodiments, the C-terminal part of the selected full-length polypeptide (e.g., the myosin polypeptide) comprises the single-alpha helix (SAH) domain of the selected full-length polypeptide.

The coding sequences in the first and second vectors when combined encode the selected full-length polypeptide, or a functional fragment or variant thereof. Accordingly, in some embodiments, all or part of the intron sequence present at the 3′-end of the coding sequence of the first vector is identical or substantially identical with all or part of the intron sequence present at the 5′-end of the coding sequence of the second vector.

Some embodiments of the hybrid vectors described herein contemplate a virus or a recombinant viral particle comprising the first AAV vector polynucleotide or the second AAV vector polynucleotide as described herein. In particular embodiments, the first AAV vector polynucleotide comprises SEQ ID NO: 33, and the second AAV vector polynucleotide comprises SEQ ID NO: 32. In some embodiments, the virus or recombinant viral particle is characterized as an adeno-associated virus (AAV) or an infectious AAV viral particle. In some embodiments, the recombinant AAV viral particle includes one or more tyrosine-to-phenylalanine (Y-F) mutations in a capsid protein of the virus or virion. Tyrosine-to-phenylalanine (Y-F) mutations in a capsid protein of the virus or virion at amino acid position 733 are specifically contemplated herein (for example, AAV8 Y733F). Likewise, tyrosine-to-phenylalanine (Y-F) mutations in a capsid protein of the virus or virion at amino acid position 731 are specifically contemplated herein (for example, AAV44.9(Y731F)).

In some embodiments, the virus or virion is packaged in an AAV5, AAV7, AAV8, AAV9, AAV44.9, AAV44.9 (E531D), AAV2(4pMut), AAVAnc80, AAVrh.8, AAVrh.8R, AAV9-PHP.B, AAV9-PHP.eB, AAVrh.10, or AAVrh.74 capsid. In some embodiments, the viral particle comprises an AAV1, AAV2, AAV3, AAV4, AAV5, AAV6, AAV7, AAV8, AAV9, AAV10, AAV7m8, AAV-DJ, AAV2/2-MAX, AAVSHh10, AAVSHh10Y, AAV3b, AAVLK03, AAV8PB2, AAV1(E531K), AAV6(D532N), AAV6-3pmut, AAV2G9, AAV44.9, AAV44.9(E531D), AAVrh.8, AAVrh.8R, AAV9-PHP.B, or an AAVAnc80 capsid. In exemplary embodiments for delivery to the retina, the virion is packaged in an AAV44.9(E531D) capsid variant. In exemplary embodiments for delivery to the hair cells of the ear, the virion is packaged in an AAV9-PHP.B capsid variant.

In some embodiments, the hybrid polynucleotide vector systems described herein use a tissue-specific promoter. In some embodiments, the systems use a promoter that mediates expression in the eye. In some embodiments, the systems use a promoter that mediates expression in the ear.

In some embodiments, the hybrid polynucleotide vector systems described herein use any one of the following promoters: a cytomegalovirus (CMV) promoter, an elongation factor-1 alpha (EF-1 alpha) promoter, a cone arrestin promoter, a chimeric CMV β actin (smCBA) promoter, a human myosin 7a gene-derived promoter, a cone transducin a (TαC) gene-derived promoter, a rhodopsin promoter, a cGMP-phosphodiesterase β-subunit promoter, human or mouse rhodopsin promoter, a human rhodopsin kinase (hGRK1) promoter, a synapsin promoter, a glial fibrillary acidic protein (GFAP) promoter, a rod specific IRBP promoter, a RPE-specific vitelliform macular dystrophy-2 [VMD2] promoter, and combinations thereof. In some embodiments, the polynucleotide vector system described herein uses a human rhodopsin kinase (hGRK1) promoter. In some embodiments, the polynucleotide vector system uses a cone arrestin promoter. In some embodiments, the polynucleotide vector system uses a cytomegalovirus (CMV) promoter. In some embodiments for delivery to the eyes (retina) of a subject, the disclosed overlap polynucleotide vector systems use a cytomegalovirus (CMV) promoter.

In some embodiments for delivery to the retina, the hybrid polynucleotide vector system uses an EF-1 alpha promoter. In some embodiments for delivery to the ears (hair cells) of a subject, the polynucleotide vector system uses a synapsin or GFAP promoter (see Lee et al., Hearing Research).

Each embodiment contained with the "hybrid vectors" section and as described herein is specifically contemplated for each hybrid vector system described, for example the vector system wherein the split point between the first and second AAV vector polynucleotide sequences is between exon 21 and exon 22 of the hMYO7A gene; the vector system wherein the split point between the first and second AAV vector polynucleotide sequences is between exon 22 and exon 23 of the hMYO7A gene; the vector system with a front-half vector comprising the nucleotide sequence of SEQ ID NO: 31 and a back-half vector comprising the nucleotide sequence of SEQ ID NO: 32; the vector system with a front-half vector comprising the nucleotide sequence of SEQ ID NO: 33 and a back-half vector comprising the nucleotide sequence of SEQ ID NO: 32; the vector system with a front-half vector comprising the nucleotide sequence of SEQ ID NO: 34 and a back-half vector comprising the nucleotide sequence of SEQ ID NO: 35; and/or the vector system with a front-half vector comprising the nucleotide sequence of SEQ ID NO: 34 and a back-half vector comprising the nucleotide sequence of SEQ ID NO: 44.

In some embodiments, any vector of the hybrid polynucleotide vector systems described in the disclosure may be administered by parenteral administration, such as intravenous, intramuscular, intraocular, intranasal, or (intra-)utricle injection, etc. The vector can be administered in vivo, in vitro or ex vivo.

In some embodiments, any vector of the hybrid polynucleotide vector systems described herein may be administered to the eye. In particular embodiments, a vector is administered to the eye of a subject by subretinal injection.

In some embodiments, any vector of the hybrid polynucleotide vector systems described herein may be administered to the ear.

In some embodiments, any vector of the hybrid polynucleotide vector systems described herein the polynucleotide vector system is administered to the ear of a subject, e.g., by a round window injection or during cochlear implant surgery.

The methods of the disclosure can be used with humans and other animals. Animals contemplated within the scope of the disclosure include, for example, dogs, cats, rabbits, ferrets, guinea pigs, hamsters, pigs, monkeys or other primates, mice, gerbils, horses, mules, donkeys, burros, cattle, cows, pigs, sheep, and alligators. As used herein, the terms "patient" and "subject" are used interchangeably and are intended to include such human and non-human species, including human and non-human cells. Likewise, in vitro methods of the disclosure may also be performed on cells of one or more human or non-human, mammalian species, including human and non-human cells.

Components of Exemplary Dual AAV Vectors

Any of the dual polynucleotide vector systems of the disclosure may be used in conjunction with an AAV vector system known in the art. In treating some diseases, it may be preferable to administer the rAAV vector construct a single time, while in the management or treatment of other diseases or conditions, it may be desirable to provide two or more administrations of the vector constructs to the patient in one or more administration periods. In such circumstances, the AAV vector-based therapeutics may be provided successively in one or more daily, weekly, monthly, or less-frequent periods, as may be necessary to achieve treatment, or amelioration of one or more symptoms of the disease or disorder being treated. In some embodiments, the vector may be provided to one or both eyes by one or more administrations of an infectious adeno-associated viral particle, an rAAV virion, or a plurality of infectious rAAV particles in an amount and for a time sufficient to treat or ameliorate one or more symptoms of the disease or condition being treated.

In particular embodiments, the disclosure provides rAAV particles been derived from a number of different serotypes, including, for example, those selected from the group consisting of AAV1, AAV2, AAV3, AAV4, AAV5, AAV6, AAV7, AAV8, AAV9, and AAV10. In exemplary embodiments, particles derived from AAV2, AAV5 and AAV8 serotype vectors are utilized. In particular embodiments, particles having an AAV8(Y733F) or AAV2(tripleY-F) capsid are used. Accordingly, the disclosure provides recombinant AAV particles derived from, e.g., AAV8(Y733F) or AAV2(tripleY-F), that comprise overlap and hybrid polynucleotide vector systems. In some embodiments, the serotype of the AAV vector is not AAV6 or AAV2.

Additional exemplary capsids include AAV2, AAV6, and capsids derived from AAV2 and AAV6. Such capsids include AAV7m8, AAV-DJ, AAV2/2-MAX, AAVSHh10, AAVSHh10Y, AAV3b, AAVLK03, AAV8PB2, AAV1 (E531K), AAV6(D532N), AAV6-3pmut, AAV2G9, AAV44.9, AAV44.9(E531D), AAVrh.8, AAVrh.8R, AAV9-PHP.B, and/or AAVAnc80. In some embodiments, the virus or virion is packaged in an AAV5, AAV7, AAV8, AAV9, AAV44.9, AAV44.9(E531D), AAV2(4pMut), AAVAnc80, AAVrh.8, AAVrh.8R, AAV9-PHP.B, AAVrh.10, or AAVrh.74 capsid.

The AAV-DJ capsid is described in Grimm et al., *J. Virol.*, 2008, 5887-5911 and Katada et al., (2019), Evaluation of AAV-DJ vector for retinal gene therapy, *PeerJ* 7:e6317, each of which is herein incorporated by reference. The AAV7m8 capsid, which is closely related to AAV-DJ, is described in Dalkara, et al. *Sci Transl Med.* 2013; 5(189):189ra76, herein incorporated by reference. The AAV2/2-MAX capsid is described in Reid, Ertel & Lipinski, Improvement of Photoreceptor Targeting via Intravitreal Delivery in Mouse and Human Retina Using Combinatory rAAV2 Capsid Mutant Vectors, *Invest. Ophthalmol Vis Sci.* 2017; 58:6429-6439, herein incorporated by reference. The AAV2/2-MAX capsid comprises five point mutations, Y272F, Y444F, Y500F, Y730F, T491V. The AAV1(E531K) capsid is described in Boye et al., Impact of Heparin Sulfate Binding on Transduction of Retina by Recombinant Adeno-Associated Virus Vectors, *J. Virol.* 90:4215-4231 (2016), herein incorporated by reference. The AAVSHh10 and AAV6(D532N) capsids, both derivatives of AAV6, are described in Klimczak et al., (2009) A Novel Adeno-Associated Viral Variant for Efficient and Selective Intravitreal Transduction of Rat Muller Cells, *PLoS ONE* 4(10): e746, herein incorporated by reference. The AAV6-3pmut (also known as AAV6(TM6) and AAV6 (Y705+Y731F+T492V)) capsid is described in Rosario et al., Microglia-specific targeting by novel capsid-modified AAV6 vectors, *Mol Ther Methods Clin Dev.* (2016); 13(3): 16026 and International Patent Publication No. 2016/126857, each of which are herein incorporated by reference.

Additional capsids suitable for use with the disclosed methods include the following: capsids comprising non-native amino acid substitutions at amino acid residues of a wild-type AAV2 capsid, wherein the non-native amino acid substitutions comprise one or more of Y272F, Y444F, T491V, Y500F, Y700F, Y704F and Y730F; capsids comprising non-native amino acid substitutions at amino acid residues of a wild-type AAV6 capsid, wherein the non-native amino acid substitutions comprise one or more of Y445F, Y705F, Y731F, T492V and S663V. In certain embodiments, the capsid comprises AAV2G9, a variant of AAV2.

In other embodiments, the capsid comprises a non-native amino acid substitution at amino acid residue 533 or 733 of a wild-type AAV8 capsid, wherein the non-native amino acid substitution is E533K, Y733F, or a combination thereof. The AAV8(Y733F) capsid is described in Doroudchi et al., *Amer. Soc. of Gene & Cell Ther.* 19(7): 1220-29 (2011). In certain embodiments of the disclosed methods, the capsid comprises AAV8PB2, a variant of AAV8.

In other embodiments, the capsid comprises non-native amino acid substitutions of a wild-type AAV2 capsid comprising one or more of the following mutations:
 (a) Y444F;
 (b) Y444F+Y500F+Y730F;
 (c) Y272F+Y444F+Y500F+Y730F;
 (d) Y444F+Y500F+Y730F+T491V; or
 (e) Y272F+Y444F+Y500F+Y730F+T491V.

In other embodiments, the capsid comprises non-native amino acid substitutions of a wild-type AAV6 capsid, comprising one or more of the following mutations:
 (a) Y445F;
 (b) Y705F+Y731F;
 (c) T492V;
 (d) Y705F+Y731F+T492V;
 (e) S663V; or
 (f) S663V+T492V.

Additional capsids suitable for use with the disclosed methods are described in International Patent Publication No. WO 2018/156654, published Aug. 30, 2018, herein incorporated by reference in its entirety. In particular embodiments, the rAAV particles of the disclosed invention comprise one of the following capsids: DGE-DF (also known as 'V1V4 VR-V'), P2-V2, P2-V3, P2-V1 (also known as ME-B), and P2-V1(Y-F+T-V) (also known as ME-B(Y-F+T-V)). In still other embodiments, the rAAV particles may comprise a capsid selected from AAV6 (3pMut) or AAV2(quadYF+T-V). In still other embodiments, the rAAV particles of the disclosed methods may comprise any of the capsid variants described in International Patent Publication No. WO 2018/156654.

In particular embodiments, disclosed herein are rAAV particles which may comprise a DGE-DF capsid, P2-V2 capsid, P2-V3 capsid, P2-V1 capsid (also known as ME-B), or P2-V1(Y-F+T-V) capsid for the enhanced transduction of said rAAV particles in retinal cells. In other embodiments, the disclosed rAAV particles may comprise a capsid selected from AAV2(Y444F), AAV2(Y444F+Y500F+Y730F), AAV2(Y272F+Y444F+Y500F+Y730F), AAV2(Y444F+Y500F+Y730F+T491V) and AAV2(Y272F+Y444F+Y500F+Y730F+T491V), AAV6(Y445F), AAV6(Y705F+Y731F), AAV6(Y705F+Y731F+T492V), AAV6(S663V), AAV6(T492V) or AAV6(S663V+T492V).

Exemplary inverted terminal repeat (ITR) sequences used in any AAV vector systems of the disclosure may comprise any AAV ITR. The ITRs used in an AAV vector can be the same or different. In particular embodiments, the ITR may be obtained from an AAV serotype 2 (AAV2), AAV serotype 5 (AAV5), AAV serotype 7 (AAV7), AAV serotype 8 (AAV8), AAV serotype 44.9 (AAV44.9), or a variant thereof, such as AAV serotype 44.9(E531D) and 44.9(Y73IF) (see PCT Application No. PCT/US2020/14838, filed Jan. 23, 2020, herein incorporated by reference). An AAV vector of the disclosure can comprise different AAV ITRs. In a non-limiting example, a vector may comprise an ITR of AAV2 and an ITR of AAV5. AAV ITR sequences are well known in the art (see, e.g., GenBank Accession Nos. AF043303.1; NC_001401.2; J01901.1; JN898962.1; K01624.1; and K01625.1). The AAV dual vector systems disclosed herein are able to efficiently express a therapeutic gene that is larger than what may ordinarily be packaged within a single AAV vector.

Accordingly, in some aspects the disclosure provides a virus or virion comprising any of the polynucleotides or vectors of the disclosure. In particular embodiments, the virus or virion is an AAV virus. Methods for preparing viruses and virions comprising a heterologous polynucleotide or vector are known in the art. In the case of AAV, cells can be co-infected or transfected with adenovirus or polynucleotide vectors comprising adenovirus genes suitable for AAV helper function. Examples of materials and methods are described, for example, in U.S. Pat. Nos. 8,137,962 and 6,967,018 (each of which is incorporated herein by reference).

In particular embodiments, the AAV serotype provides for one or more tyrosine to phenylalanine (Y-F) mutations on the capsid surface. In particular embodiments, the AAV is an AAV8 serotype having a tyrosine-to-phenylalanine (Y-F) mutation at position 733 (Y733F). The abilities to produce full-length MYO7A protein for second-generation hybrid and overlap vectors encapsidated in AAV5 and AAV8 (Y733F) virions is shown in FIGS. 36A-36C and 45B. AAV8(Y733F) virions outperformed AAV5 virions, as measured by Western blot (see FIG. 45B).

Figure 5:
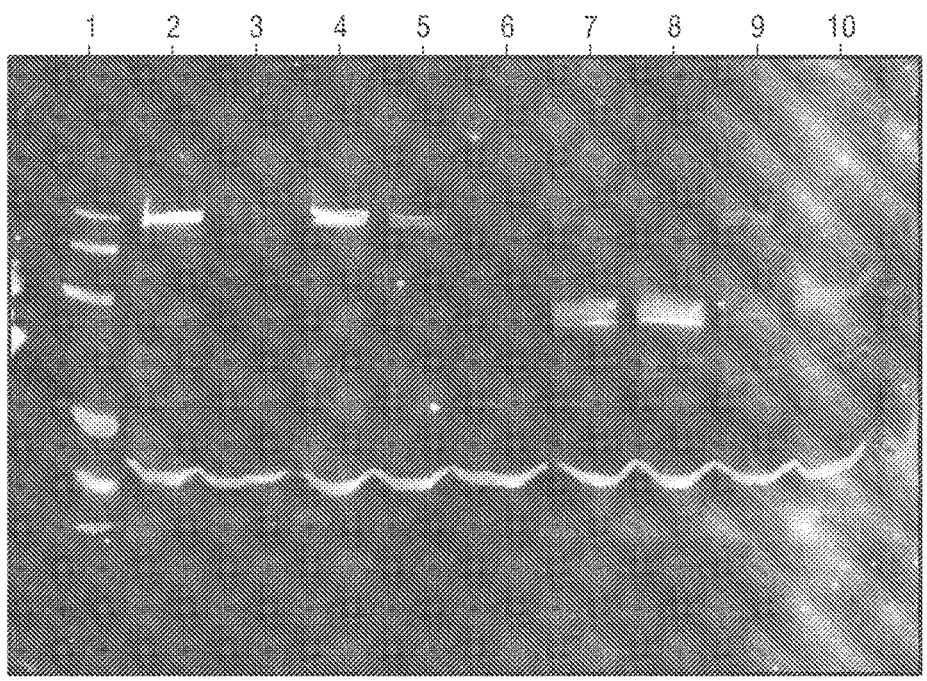
FIG. 5 shows an immunoblot to detect the presence of MYO7A in infected or transfected HEK293 cells. Heterogeneous vectors are compared to all three dual vector systems. Dual vectors were packaged either in AAV2 or in AAV2 (triple mutant) capsids. The triple mutant contains three tyrosine-to-phenylalanine mutations on the capsid surface. For all three dual vector systems, infections were performed with either a) the front-half (N-terminal) and back-half (C-terminal) vectors; or b) the front-half vectors alone (to confirm the presence or absence of a truncated protein product expressed from the promoter-containing N-terminal vectors).

In some embodiments, a triple-mutant AAV8 vector, which contains tyrosine-to-phenylalanine Tyr-Phe mutations at positions Y733F, Y500F, and Y730F, respectively, is used (see FIG. 5). In other embodiments, a triple-mutant AAV8 vector, which contains tyrosine-to-phenylalanine Tyr-Phe mutations at positions Y447F, Y733F, and T494V (e.g. AAV8(Y447F+Y733F+T494F)) is used.

In exemplary embodiments, the rAAV particles of the disclosure may comprise a transgene, or heterologous nucleic acid, that is too large for delivery in standard AAV systems. Exemplary transgenes encode at least one diagnostic or therapeutic protein or polypeptide selected from the group consisting of a molecular marker, photosensitive opsins, including, without limitation, rhodopsin, melanopsin, cone opsins, channel rhodopsins, bacterial or archaea-associated opsins, an adrenergic agonist, an anti-apoptosis factor, an apoptosis inhibitor, a cytokine receptor, a cytokine, a cytotoxin, an erythropoietic agent, a glutamic acid decarboxylase, a glycoprotein, a growth factor, a growth factor receptor, a hormone, a hormone receptor, an interferon, an interleukin, an interleukin receptor, a kinase, a kinase inhibitor, a nerve growth factor, a netrin, a neuroactive peptide, a neuroactive peptide receptor, a neurogenic factor, a neurogenic factor receptor, a neurophilin, a neurotrophic factor, a neurotrophin, a neurotrophin receptor, an N-methyl-D-aspartate antagonist, a plexin, a protease, a protease inhibitor, a protein decarboxylase, a protein kinase, a protein kinase inhibitor, a proteolytic protein, a proteolytic protein inhibitor, a semaphorin, a semaphorin receptor, a serotonin transport protein, a serotonin uptake inhibitor, a serotonin receptor, a serpin, a serpin receptor, a tumor suppressor, and any combination thereof.

In some embodiments, the transgene is hMYO7A, which encodes a human myosin VIIa polypeptide. In particular embodiments, a hMYO7A polypeptide comprises the amino acid sequence shown in SEQ ID NO: 6 or SEQ ID NO: 8, or a functional fragment or a variant thereof. In particular embodiments, the hMYO7A polypeptide is encoded by the nucleotide sequence set forth in SEQ ID NO: 5 or SEQ ID NO: 7.

In some embodiments, the transgene is USH1C, CDH23, PCDH15 and USH1G, all of which are associated with Usher syndrome type I. In some embodiments, the transgene is USH2A or DFNB31, both of which are associated with Usher syndrome type II. In some embodiments, the transgene is ABCA4, CEP290, EYS, RP1, ALMS1, CDH23, PCDH15, DFNB2 or USHERIN.

In some embodiments, administration of any of the disclosed polynucleotide vectors to the eye of a subject in need thereof restores vision loss, partially or completely. The transgene may comprise a human MYO7A. These administrations may provide a partial or complete restoration of melanosome apical migration in retinal pigment epithelium (RPE) cells.

In some embodiments, the production of the therapeutic agent encoded by the transgene of any of the disclosed polynucleotide vector systems in cells of the eye (such as retinal cells or RPE cells) provides one or more of the following therapeutic endpoints: a) preserves one or more photoreceptor cells or one or more RPE cells, b) restores one or more rod- and/or cone-mediated functions, c) restores visual behavior in one or both eyes, or d) any combination thereof. In particular embodiments, production of the therapeutic agent in the disclosed methods preserves one or more PR cells, such as retinal ganglion cells, bipolar cells, Müller glial cells or astrocyte cells, or RPE cells.

In some embodiments, production of the therapeutic agent persists in the one or more photoreceptor cells or the one or more RPE cells substantially for a period of at least three months, at least six months, at least nine months, or at least a year or more, following an initial administration of any of the disclosed rAAV polynucleotide vector system into the one or both eyes of the mammal.

In some embodiments, administration of any of the disclosed polynucleotide vectors to the inner ear of a subject in need thereof restores hearing loss, partially or completely. In some embodiments, administration to the inner ear restores age-related hearing loss. The transgene may comprise a human MYO7A. These administrations may provide a partial or complete restoration of vestibular function in the inner ears. In some embodiments, any of the disclosed hybrid or overlap vectors may be administered to a vestibular hair cell, an inner ear hair cell, an outer ear hair cell, or a combination thereof.

In this manner, the polynucleotide vector systems and compositions thereof of the disclosure may be used to treat or ameliorate symptoms of USH1B (Usher Syndrome type 1B) in the eyes and/or inner ear of the subject. Likewise, administration of the vector systems and compositions of the disclosure may be used to treat or ameliorate symptoms of autosomal recessive isolated deafness (DFNB2), hearing loss, and/or vision loss. As an example, administration of the vector systems and compositions of the disclosure may be used to treat or ameliorate hearing loss associated with insufficiency of MYO7A protein expression (which may present in a USH1B patient). In some embodiments, administration of the vector systems and compositions of the disclosure may be used to treat or ameliorate age-related hearing loss presenting in carriers of a recessive defective MYO7A allele (i.e., USH1B carriers) or age-related hearing loss as the consequence of non-genetic deficiency or insufficiency in MYO7A expression.

As another example, administration of the vector systems and compositions of the disclosure may provide a restoration of melanosome migration in retinal pigment epithelium (RPE) cells.

In some embodiments, the disclosure provides rAAV nucleic acid vectors that include at least a first nucleic acid segment that encodes one or more diagnostic or therapeutic agents that alter, inhibit, reduce, prevent, eliminate, or impair the activity of one or more endogenous biological processes in a mammalian cell suitably transformed with the vector of interest. In certain embodiments, such diagnostic or therapeutic agents may include a molecule that selectively inhibits or reduces the effects of one or more metabolic processes, dysfunctions, disorders, or diseases. In certain embodiments, the defect may be caused by injury or trauma to the mammal for which treatment is desired. In other embodiments, the defect may be caused the over-expression of an endogenous biological compound, while in other embodiments still; the defect may be caused by the under-expression or even lack of one or more endogenous biological compounds.

Regulatory Elements of rAAV Vectors

Any of the vector systems of the disclosure may include regulatory elements that are functional in the intended host cell in which the vector is to be expressed. A person of ordinary skill in the art can select regulatory elements for use in appropriate host cells, for example, mammalian or human host cells. Regulatory elements include, for example, promoters, transcription termination sequences, translation termination sequences, enhancers, and polyadenylation elements.

Any of the vector systems of the disclosure may include a promoter sequence operably linked to a nucleotide sequence encoding a desired polypeptide. Promoters contemplated for use in the disclosure include, but are not limited to, cytomegalovirus (CMV) promoter, SV40 promoter, human myosin 7a gene-derived promoter, Rous sarcoma virus (RSV) promoter, chimeric CMV/chicken β-actin promoter (CBA) and the truncated form of CBA (smCBA) (see, e.g., Haire et al. 2006 and U.S. Pat. No. 8,298,818, each of which is incorporated herein by reference). Additional photoreceptor-specific, human rhodopsin kinase (hGRK1) promoter, a synapsin promoter, a glial fibrillary acidic protein (GFAP) promoter, rod specific IRBP promoter, VMD2 (vitelliform macular dystrophy/Best disease) promoter, a RPE-specific vitelliform macular dystrophy-2 [VMD2] promoter, and EF1-alpha promoter sequences are also contemplated to be useful in the practice of various aspects of the disclosure. Exemplary photoreceptor-cell-specific promoters include, but are not limited to, hGRK1, IRBP, rod opsin, NRL, GNAT2e-IRBP, L/M opsin, and cone arrestin promoters.

In particular embodiments, the promoter is a chimeric CMV-β-actin promoter. In particular embodiments, the promoter is a tissue-specific promoter that shows selective activity in one or a group of tissues but is less active or not active in other tissue. In particular embodiments, the promoter is a photoreceptor-specific promoter. In a further embodiment, the promoter is preferably a cone cell-specific promoter or a rod cell-specific promoter, or any combination thereof. In particular embodiments, the promoter is the promoter for human MYO7A gene. In a further embodiment, the promoter comprises a cone transducin a (TαC) gene-derived promoter. In particular embodiments, the promoter is a human GNAT2-derived promoter. Other promoters contemplated within the scope of the disclosure include, without limitation, a rhodopsin promoter (human or mouse), a cGMP-phosphodiesterase β-subunit promoter, a retinitis pigmentosa-specific promoter, an RPE cell-specific promoter [such as a vitelliform macular dystrophy-2 (VMD2) promoter (Best1) (Esumi et al., 2004)], or any combination thereof.

Promoters can be incorporated into a vector using standard techniques known to those of ordinary skill in the molecular biology and/or virology arts. Multiple copies of promoters, and/or multiple distinct promoters can be used in the vectors of the disclosure. In one such embodiment, a promoter may be positioned about the same distance from the transcription start site as it is from the transcription start site in its natural genetic environment, although some variation in this distance is permitted, of course, without a substantial decrease in promoter activity. In the practice of the disclosure, one or more transcription start site(s) are typically included within the disclosed vectors.

The vectors of the disclosure may further include one or more transcription termination sequences, one or more translation termination sequences, one or more signal peptide sequences, one or more internal ribosome entry sites (IRES), and/or one or more enhancer elements, or any combination thereof. Transcription termination regions can typically be obtained from the 3'-untranslated region of a eukaryotic or viral gene sequence. Transcription termination sequences can be positioned downstream of a coding sequence to provide for efficient termination.

Any of the disclosed polynucleotide vectors may also further include one or more post-transcriptional regulatory sequences or one or more polyadenylation signals, including, for example, but not limited to, a woodchuck hepatitis virus post-transcription regulatory element (WRPE), a polyadenylation signal sequence, or an intron/exon junctions/splicing signals, or any combination thereof.

Signal peptide sequences are amino-terminal peptidic sequences that encode information responsible for the location of an operably-linked polypeptide to one or more post-translational cellular destinations, including, for example, specific organelle compartments, or to the sites of protein synthesis and/or activity, and even to the extracellular environment.

Enhancers—cis-acting regulatory elements that increase gene transcription—may also be included in one of the disclosed AAV-based vector systems. A variety of enhancer elements are known to those of ordinary skill in the relevant arts, and include, without limitation, a CaMV 35S enhancer element, a cytomegalovirus (CMV) early promoter enhancer element, an SV40 enhancer element, as well as combinations and/or derivatives thereof. One or more nucleic acid sequences that direct or regulate polyadenylation of the mRNA encoded by a structural gene of interest, may also be optionally included in one or more of the vectors of the disclosure.

Host Cells and Methods for Transducing Cells

The disclosure provides host cells comprising vectors of the disclosed polynucleotide vector systems. In some embodiments, an isolated host cell comprising an overlap polynucleotide vector system is provided. In some embodiments, an isolated host cell comprising a hybrid polynucleotide vector system is provided. In particular embodiments, isolated host cells comprising second generation hybrid and isolated host cells comprising second generation overlap vectors are provided.

Examples of suitable host cells that comprise any of the disclosed dual vector systems include, but are not limited to, photoreceptor cells, cone cells, rod cells, retinal cells (e.g., ganglion cells, retinal pigment epithelium cells), or any combination thereof. Examples of retinal cells include retinal ganglion cells (RGCs), Muller cells, astrocytes, and bipolar cells.

Additional examples of suitable host cells are vestibular hair cells, inner ear hair cells, outer ear hair cells, or any combination thereof.

The disclosure also provides methods for expressing or transducing a selected polypeptide in a cell. In particular embodiments, the method comprises incorporating in the cell an AAV-based, dual vector system as disclosed herein, wherein the vector system includes a polynucleotide sequence that encodes a selected polypeptide and of interest, and expressing the polynucleotide sequences in the cell.

In certain embodiments, the selected polypeptide may be a polypeptide that is heterologous to the cell. In particular embodiments, the cell is a mammalian cell, and preferably, a human cell. In particular embodiments, the cell is a human photoreceptor cell, and preferably a human photoreceptor cone cell or a photoreceptor rod cell. In particular embodiments, the cell expresses a wild type, functional, and/or biologically-active hMYO7A polypeptide that is encoded by a nucleic acid segment present in a vector system as disclosed herein. In particular embodiments, the hMYO7A polypeptide is encoded by the nucleotide sequence shown in SEQ ID NO: 5 or SEQ ID NO: 7.

In particular embodiments, the cell is a photoreceptor cell. In particular embodiments, the cell is a cone cell; preferably, it is a human cone cell or a human rod cell. Such cells may express one or more nucleotide sequences provided in at least a first AAV-based, dual vector system of the disclosure. In particular embodiments, the cell expresses a wild-type, functional, and/or biologically active hMYO7A polypeptide that is encoded by a nucleic acid segment comprised within one or more of the AAV-based vector systems as disclosed herein. In particular embodiments, the hMYO7A polypeptide is encoded by the nucleotide sequence of SEQ ID NO: 5 or SEQ ID NO: 7.

Accordingly, in certain embodiments, the disclosure provides for methods for transducing or expressing a polynucleotide vector system in one or more photoreceptor cells or one or more RPE cells of a mammal (e.g., a human). In an overall and general sense, such a method includes administering (for example, directly administering subretinally) to one or both eyes of the mammal one or more of the rAAV particles disclosed herein, wherein the polynucleotide further comprises at least a first polynucleotide that comprises a PR- or an RPE-cell-specific promoter operably linked to at least a first heterologous nucleic acid segment that encodes a therapeutic agent (full-length polypeptide), for a time effective to produce the therapeutic agent in the one or more PR cells or RPE cells of the mammal. In certain embodiments, the therapeutic polypeptide is stably expressed in a photoreceptor cell, retinal pigment epithelium cell, retinal ganglion cell, bipolar cell, Müller glial cell or astrocyte cell, or combinations thereof. In certain embodiments, the therapeutic polypeptide is stably expressed in a vestibular hair cell, inner ear hair cell, or outer ear hair cell.

Methods of Treatment and Transduction

In some aspects, the disclosure provides methods for treating or ameliorating a disease or condition, such as an eye disease, in a human or animal using gene therapy and an AAV-based dual vector system of the disclosure. In particular embodiments, a method of the disclosure comprises administering a vector system of the disclosure that encodes a polypeptide that provides for treatment or amelioration of the disease or condition. In particular embodiments, the vectors of the disclosure are provided in an AAV virus or virion. The vector system can be administered in vivo or ex vivo.

In particular embodiments, a vector system of the disclosure is administered in a recombinant AAV particle by parenteral administration, such as intravitreal, subretinal, intravenous, intramuscular, intraocular, utricle, or intranasal injection. In some embodiments, vector systems are administered to, e.g., hair cells of the ear, by injection into the utricle, which is one of two sac-like otolith organs sensitive to gravity, as described in Lee et al., Hearing Research Vol. 394 (2020) 107882, incorporated by reference herein. Administration to, e.g., hair cells of the ear may be by a round window injection, or during cochlear implant surgery. In particular embodiments, a vector system of the disclosure is administered to the human or animal by intraocular, intravitreal or subretinal injection.

In some embodiments, the recombinant AAV particle of the disclosure is administered via subretinal injection in a titer of about $1\times10^8$ vg/ml, $5\times10^8$ vg/ml, $8\times10^8$ vg/ml, $1\times10^9$ vg/ml, $5\times10^9$ vg/ml, $1\times10^{10}$ vg/ml, $5\times10^{10}$ vg/ml, $1\times10^{11}$ vg/ml, $5\times10^{11}$ vg/ml, $1\times10^{12}$ vg/ml, $2\times10^{12}$ vg/ml, $3\times10^{12}$ vg/ml, $4\times10^{12}$ vg/ml, about $5\times10^{12}$ vg/ml, about $1\times10^{13}$ vg/ml, or about $5\times10^{13}$ vg/ml. In particular embodiments, the rAAV particle is administered in a titer of $5.0\times10^8$ vg or $8.0\times10^8$ vg.

In some embodiments, the subretinal injection is provided in a volume of about 200 µL, about 175 µL, about 160 µL, about 145 µL, about 130 µL, about 115 µL, about 100 µL, about 90 µL, about 80 µL, about 70 µL, about 60 µL, about 55 µL, about 50 µL, about 45 µL, about 35 µL, about 20 µL, about 10 µL, or about 5 µL. In particular embodiments, the injection is provided in a volume of about 50 µL. Dosage regimes and effective amounts to be administered can be determined by ordinarily skilled clinicians. Administration may be in the form of a single dose or multiple doses. General methods for performing gene therapy using polynucleotides, expression constructs, and vectors are known in the art (see, e.g., Gene Therapy: Principles and Applications (1999); and U.S. Pat. Nos. 6,461,606; 6,204,251 and 6,106,826, each of which is specifically incorporated herein in its entirety by express reference thereto).

In particular embodiments, the disease, disorder or condition to be treated is Usher Syndrome. In some embodiments, the disease or disorder to be treated is autosomal recessive isolated deafness (DFNB2). In other embodiments, the disease, disorder or condition such as age-related macular degeneration (AMD), wet AMD, dry AMD, or geographic atrophy. In certain embodiments, the disease or disorder is retinitis pigmentosa or glaucoma.

The disclosed dual vector systems may be introduced into one or more selected mammalian cells using any one or more of the methods that are known to those of ordinary skill in the gene therapy and/or viral arts. Such methods include, without limitation, transfection, microinjection, electroporation, lipofection, cell fusion, and calcium phosphate precipitation, as well as biolistic methods. In particular embodiments, the vectors of the disclosure may be introduced in vivo, including, for example, by lipofection (for example, DNA transfection via liposomes prepared from one or more cationic lipids) (see, e.g., Felgner et al., 1987). Synthetic cationic lipids (LIPOFECTIN®, Invitrogen Corp., La Jolla, CA, USA) may be used to prepare liposomes that will encapsulate the vectors to facilitate their introduction into one or more selected cells. A vector system of the disclosure can also be introduced in vivo as "naked" DNA using methods known to those of ordinary skill in the art.

In an overall and general sense, the disclosed methods include at least the step of administering to one or both eyes of the mammal in need thereof, one or more of the disclosed rAAV particles herein, in an amount and for a time sufficient to treat or ameliorate the one or more symptoms of the disease, the disorder, the dysfunction, the injury, the abnormal condition, or the trauma in the mammal. In some embodiments, the mammal is a human. In some embodiments, the human is a neonate, a newborn, an infant, or a juvenile. In the practice of the present disclosure, it is contemplated that suitable patients will include, for example, humans that have, are suspected of having, are at risk for developing, or have been diagnosed with one or more retinal disorders, diseases, or dystrophies, including, without limitation, retinal disorders, diseases, and dystrophies that are genetically linked, or inheritable.

In some aspects, the present disclosure provides methods of use of the particles, vectors, virions, expression systems, compositions, and host cells described herein in a method for treating or ameliorating the symptoms, or in the preparation of medicaments for, treating or ameliorating the symptoms of various deficiencies in an eye of a mammal, and in particular one or more deficiencies in human photoreceptors or RPE cells. Exemplary diseases and disorders of the eye (e.g., caused by one or more genetic deficiencies in a PR or RPE cell) for treatment or amelioration of symptoms include Retinitis pigmentosa, Leber Congenital Amaurosis (e.g., LCA10), Age Related Macular Degeneration (AMD), wet AMD, dry AMD, uveitis, Best disease, Stargardt disease, Usher Syndrome, Geographic Atrophy, Diabetic Retinopathy, Retinoschisis, Achromatopsia, Choroideremia, Bardet Biedl Syndrome, and glycogen storage diseases (ocular manifestation).

In some embodiments, administration of any of the disclosed vectors, virions, or compositions to a subject in need thereof provides a partial or complete restoration of melanosome migration in retinal pigment epithelium (RPE) cells. In exemplary embodiments, administration of any of the polynucleotide vector systems, virions, or compositions provides a partial or complete restoration of vision loss.

In some aspects, the present disclosure provides methods of use of the particles, vectors, virions, expression systems, compositions, and host cells described herein in a method for treating or ameliorating the symptoms, or in the preparation of medicaments for, treating or ameliorating the symptoms of various deficiencies in an ear of a mammal, and in particular one or more deficiencies in hair cells of the auditory and hair cells of the vestibular systems. In exemplary embodiments, the subject in need thereof suffers from a disease or disorder selected from Usher syndrome or autosomal recessive isolated deafness (DFNB2). In some embodiments, the subject suffers from Usher Syndrome type 1B, 1D, 1F, or 2A.

In some embodiments, the subject suffers from a disease or condition of the eye, and/or a disease or disorder of the ear, selected from Stargardt Disease; LCA10; Retinitis Pigmentosa, Alstrom syndrome; Usher Syndrome type 1B, 1D, 1F, or 2A; Duchenne muscular dystrophy; Cystic fibrosis; Glycogen storage disease III; non-syndromic deafness; Hemophilia A, or a dysferlinopathy.

Such methods may involve intravitreal or subretinal administration to one or both eyes of a subject in need thereof, one or more of the disclosed particles vectors, virions, host cells, or compositions, in an amount and for a time sufficient to treat or ameliorate the symptoms of such a deficiency in the affected mammal. The methods may also encompass prophylactic treatment of animals suspected of having such conditions, or administration of such compositions to those animals at risk for developing such conditions either following diagnosis, or prior to the onset of symptoms.

Pharmaceutical Compositions and Kits

Pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (e.g., glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, e.g., parabens, chlorobutanol, phenol, sorbic acid, thimerosal, and the like. In many cases, it will be preferable to include isotonic agents, e.g., sugars, buffers or sodium chloride. Prolonged absorption of the injectable compositions can be brought about by the inclusion of agents that delay absorption, e.g., aluminum monostearate and gelatin.

The disclosure also provides pharmaceutical compositions comprising a vector system of the disclosure in combination with a pharmaceutically acceptable carrier. Pharmaceutical compositions adapted for topical or parenteral administration, comprising an amount of a compound constitute a preferred embodiment of the disclosure. The dose administered to a patient, particularly a human, in the context of the disclosure should be sufficient to achieve a therapeutic response in the patient over a reasonable timeframe, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

The disclosure also provides kits comprising a vector system of the disclosure in one or more containers. Kits of the disclosure can optionally include pharmaceutically acceptable carriers and/or diluents. In particular embodiments, a kit of the disclosure includes one or more other components, adjuncts, or adjuvants as described herein. In particular embodiments, a kit of the disclosure includes instructions or packaging materials that describe how to administer a vector system contained within the kit to a selected mammalian recipient.

Containers of the disclosed kits may be of any suitable material, e.g., glass, plastic, metal, etc., and of any suitable size, shape, or configuration. In particular embodiments, a vector system of the disclosure is provided in the kit as a solid. In another embodiment, a vector system of the disclosure is provided in the kit as a liquid or solution. In certain embodiments, the kits may include one or more ampoules or syringes that contain a vector system of the disclosure in a suitable liquid or solution form.

Further contemplated herein are kits containing a pre-mixture of any of the disclosed dual vectors (front half vector and back half vector). These pre-mixtures may be in a single container and/or a single drug product in a suitable liquid or solution form.

The disclosure also provides for the use of the buffers and compositions disclosed herein in the manufacture of a medicament for treating, preventing or ameliorating the symptoms of a disease, disorder, dysfunction, injury or trauma, including, but not limited to, the treatment, prevention, and/or prophylaxis of a disease, disorder or dysfunction, and/or the amelioration of one or more symptoms of such a disease, disorder or dysfunction.

The amount of AAV compositions and time of administration of such compositions will be within the purview of the skilled artisan having benefit of the present teachings. The administration of therapeutically-effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the AAV vector compositions, either over a relatively short, or over a relatively prolonged period, as may be determined by the medical practitioner overseeing the administration of such compositions.

For example, the number of infectious particles administered to a mammal may be approximately $10^7$, $10^8$, $10^9$, $10^{10}$, $10^{11}$, $10^{12}$, $10^{13}$, or even higher, infectious particles/mL, given either as a single dose (or divided into two or more administrations, etc.) as may be required to achieve therapy of the particular disease or disorder being treated. In fact, in certain embodiments, it may be desirable to administer two or more different rAAV particle- or vector-based compositions, either alone, or in combination with one or more other diagnostic agents, drugs, bioactives, or such like, to achieve the desired effects of a particular regimen or therapy. In most rAAV-vectored, gene therapy-based regimens, the inventors contemplate that lower titers of infectious particles will be required when practicing the disclosed methods of pre-treating and co-administering AAV capsids with HA.

To express a therapeutic agent in accordance with the present disclosure one may prepare a rAAV particle that comprises a therapeutic agent-encoding nucleic acid segment under the control of one or more promoters. To bring a sequence "under the control of" a promoter, one positions the 5' end of the transcription initiation site of the transcriptional reading frame generally between about 1 and about 50 nucleotides "downstream" of (for example, 3' of) the chosen promoter. The "upstream" promoter stimulates transcription of the DNA and promotes expression of the encoded polypeptide. This is the meaning of "recombinant expression" in this context. In some embodiments, recombinant vector constructs are those that include a capsid-protein modified rAAV vector that contains an RPE cell- or a photoreceptor cell-specific promoter, operably linked to at least one nucleic acid segment encoding one or more diagnostic, and/or therapeutic agents.

When the use of such vectors is contemplated for introduction of one or more exogenous proteins, polypeptides, peptides, ribozymes, and/or antisense oligonucleotides, to a particular cell transfected with the vector, one may employ the rAAV particles disclosed herein to deliver one or more exogenous polynucleotides to a selected host cell, e.g., to one or more selected cells within the mammalian eye.

In some embodiments, the number of viral particles administered to a subject may be on the order ranging from $10^6$ to $10^{14}$ particles/ml or $10^3$ to $10^{15}$ particles/ml, or any values therebetween for either range, such as for example, about $10^6$, $10^7$, $10^8$, $10^9$, $10^{10}$, $10^{11}$, $10^{12}$, $10^{13}$, or $10^{14}$ particles/ml. In one embodiment, viral particles of higher than $10^{13}$ particles/ml may be administered. In some embodiments, the number of viral particles administered to a subject may be on the order ranging from $10^6$ to $10^{14}$ vector genomes (vgs)/ml or $10^3$ to $10^{15}$ vgs/ml, or any values therebetween for either range, such as for example, about $10^6$, $10^7$, $10^8$, $10^9$, $10^{10}$, $10^{11}$, $10^{12}$, $10^{13}$, or $10^{14}$ vgs/ml. In one embodiment, viral particles of higher than $10^{13}$ vgs/ml are administered. The viral particles can be administered as a single dose, or divided into two or more administrations as may be required to achieve therapy of the particular disease or disorder being treated. In some embodiments, doses of 0.0001 ml to 10 ml, e.g., 0.001 ml, 0.01 ml, 0.1 ml, 1 ml, 2 ml, 5 ml or 10 ml, are delivered to a subject.

In some embodiments, the disclosure provides formulations of one or more viral-based compositions disclosed herein in pharmaceutically acceptable solutions for administration to a cell or an animal, either alone or in combination with one or more other modalities of therapy, and in particular, for therapy of human cells, tissues, and diseases affecting man.

If desired, rAAV particles described herein may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles may thus be delivered along with various other agents as required in the particular instance. Such compositions may be purified from host cells or other biological sources, or alternatively may be chemically synthesized as described herein.

Formulation of pharmaceutically-acceptable buffer, excipients and carrier solutions is well known to those of skill in the art, as is the development of suitable dosing and treatment regimens for using the particular compositions described herein in a variety of treatment regimens, including e.g., oral, parenteral, intraocular (e.g., subretinal or intravitreal), intravenous, intranasal, intra-articular, intra-utricle, intracochlear and intramuscular administration and formulation.

Typically, these formulations may contain at least about 0.1% of the therapeutic agent (e.g., rAAV particle) or more, although the percentage of the active ingredient(s) may, of course, be varied and may conveniently be between about 1 or 2% and about 70% or 80% or more of the weight or volume of the total formulation. Naturally, the amount of therapeutic agent(s) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The term "excipient" refers to a diluent, adjuvant, carrier, or vehicle with which the rAAV particle is administered. Such pharmaceutical excipients can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers. Exemplary excipients and vehicles include, but are not limited to, HA, BSS, artificial CSF, PBS, Ringer's lactate solution, TMN200 solution, polysorbate 20, and poloxamer 100.

The amount of rAAV particle compositions and time of administration of such compositions will be within the purview of the skilled artisan having benefit of the present teachings. It is likely, however, that the administration of therapeutically-effective amounts of the disclosed compositions may be achieved by a single administration, such as for example, a single injection of sufficient numbers of viral particles to provide therapeutic benefit to the patient undergoing such treatment. Alternatively, in some circumstances, it may be desirable to provide multiple, or successive administrations of the compositions, either over a relatively short, or a relatively prolonged period of time, as may be determined by the medical practitioner overseeing the administration of such compositions.

Exemplary compositions may include rAAV particles or nucleic acid vectors either alone, or in combination with one or more additional active ingredients, which may be obtained from natural or recombinant sources or chemically synthesized.

Methods of Manufacturing rAAV Particles

Recombinant adeno-associated virus (rAAV) vectors have been used successfully for in vivo gene transfer in numerous pre-clinical animal models of human disease, and have been used successfully for long-term expression of a wide variety of therapeutic genes (Daya and Berns, 2008; Niemeyer et al., 2009; Owen et al., 2002; Keen-Rhinehart et al., 2005; Scallan et al., 2003; Song et al., 2004). AAV vectors have also generated long-term clinical benefit in humans when targeted to immune-privileged sites, for example, ocular delivery for Leber congenital amaurosis (Bainbridge et al., 2008; Maguire et al., 2008; Cideciyan et al., 2008). A major advantage of this vector is its comparatively low immune profile, eliciting only limited inflammatory responses and, in some cases, even directing immune tolerance to transgene products (LoDuca et al., 2009). Nonetheless, the therapeutic efficiency, when targeted to non-immune privileged organs, has been limited in humans due to antibody and CD8$^+$ T cell responses against the viral capsid, while in animal models, adaptive responses to the transgene product have also been reported (Manno et al., 2006; Mingozzi et al., 2007; Muruve et al., 2008; Vandenberghe and Wilson, 2007; Mingozzi and High, 2007). These results suggested that immune responses remain a concern for AAV vector-mediated gene transfer.

Adeno-associated virus (AAV) is considered the optimal vector for ocular gene therapy due to its efficiency, persistence and low immunogenicity (Daya and Berns, 2008). Identifying vectors capable of transducing PRs via the vitreous has historically relied on identifying which serotypes have native tropism for this cell type following local delivery. Several serotypes have been used to successfully target transgene to PRs following subretinal injection (including, e.g., AAV2, AAV5 and AAV8) with all three demonstrating efficacy in experiments performed across multiple mammalian species (e.g., mouse, rat, dog, pig and non-human primate) (Ali et al., 1996; Auricchio et al., 2001; Weber et al., 2003; Yang et al., 2002; Acland et al., 2001; Vandenberghe et al., 2011; Bennett et al., 1999; Allocca et al., 2007; Petersen-Jones et al., 2009; Lotery et al., 2003; Boye et al., 2012; Stieger et al., 2008; Mussolino et al., 2011; Vandenberghe et al., 2011).

Studies comparing their relative efficiency following subretinal delivery in the rodent show that both AAV5 and AAV8 transduce PRs more efficiently than AAV2, with AAV8 being the most efficient (Yang et al., 2002; Allocca et al., 2007; Rabinowitz et al., 2002; Boye et al., 2011; Pang et al., 2011). It was previously shown that AAV2 and AAV8 vectors containing point mutations of surface-exposed tyrosine residues (tyrosine to phenylalanine, Y-F) display increased transgene expression in a variety of retinal cell types relative to unmodified vectors following both subretinal and intravitreal injection (Petrs-Silva et al., 2009; Petrs-Silva et al., 2011). Of the vectors initially tested by those authors, an AAV2 triple mutant (designated "triple Y-F") exhibited the highest transduction efficiency following intravitreal injection, whereas an AAV2 quadruple mutant ("quad Y-F") exhibited the novel property of enhanced transduction of outer retina (Petrs-Silva et al., 2011).

Further improvements in transduction efficiency have been achieved via directed mutagenesis of surface-exposed threonine (T) or serine (S) residues to non-native amino acids at one of more of those amino acids. Both Y-F and T-V/T-A mutations have been shown to increase efficiency by decreasing phosphorylation of capsid and subsequent ubiquitination as part of the proteosomal degradation pathway (Zhong et al., 2008; Aslanidi et al., In Press; Gabriel et al., 2013). It has been found that the transduction profile of intravitreally-delivered AAV is heavily dependent upon the injection procedure itself. Due to the small size of the mouse eye, it is not uncommon for trans-scleral, intravitreal injections to result in damage to the retina that might allow delivery of some vector directly to the subretinal space.

Exemplary rAAV nucleic acid vectors useful according to the disclosure include single-stranded (ss) or self-complementary (sc) AAV nucleic acid vectors, such as single-stranded or self-complementary recombinant viral genomes.

Methods of producing rAAV particles and nucleic acid vectors are also known in the art and commercially available (see, e.g., Zolotukhin et al., Production and purification of serotype 1, 2, and 5 recombinant adeno-associated viral vectors, *Methods* 28 (2002) 158-167; and U.S. Patent Publication Nos. US 2007/0015238 and US 2012/0322861, which are incorporated herein by reference; and plasmids and kits available from ATCC and Cell Biolabs, Inc.). For example, a plasmid containing the nucleic acid vector sequence may be combined with one or more helper plasmids, e.g., that contain a rep gene (e.g., encoding Rep78, Rep68, Rep52 and Rep40) and a cap gene (encoding VP1, VP2, and VP3, including a modified VP3 region as described herein), and transfected into a producer cell line such that the rAAV particle can be packaged and subsequently purified.

In some embodiments, the one or more helper plasmids includes a first helper plasmid comprising a rep gene and a cap gene and a second helper plasmid comprising a Ela gene, a E1b gene, a E4 gene, a E2a gene, and a VA gene. In some embodiments, the rep gene is a rep gene derived from AAV2 and the cap gene is derived from AAV2 and includes modifications to the gene in order to produce a modified capsid protein described herein. Helper plasmids, and methods of making such plasmids, are known in the art and commercially available (see, e.g., pDM, pDG, pDPlrs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, CA; and Addgene, Cambridge, MA; pxx6; Grimm et al. (1998), Novel Tools for Production and Purification of Recombinant Adenoassociated Virus Vectors, *Human Gene Therapy*, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188).

An exemplary, non-limiting, rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. The cap ORF may also comprise one or more modifications to produce a modified capsid protein as described herein. HEK293 cells (available from ATCC®) are transfected via CaPO4-mediated transfection, lipids or polymeric molecules such as Polyethylenimine (PEI) with the helper plasmid(s) and a plasmid containing a nucleic acid vector described herein. The HEK293 cells are then incubated for at least 60 hours to allow for rAAV particle production. Alternatively, in another example Sf9-based producer stable cell lines are infected with a single recombinant baculovirus containing the nucleic acid vector. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known the art or described herein, e.g., by iodixanol step gradient, CsCl gradient, chromatography, or polyethylene glycol (PEG) precipitation.

Exemplary Definitions

In accordance with the disclosure, polynucleotides, nucleic acid segments, nucleic acid sequences, and the like, include, but are not limited to, DNAs (including, but not limited to, genomic and/or extragenomic DNAs), genes, peptide nucleic acids (PNAs) RNAs (including, but not limited to, rRNAs, mRNAs, and/or tRNAs), nucleosides, as well as one or more nucleic acid segments obtained from natural sources, chemically synthesized, genetically modified, or otherwise prepared or synthesized in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the disclosure, the preferred methods and compositions are described herein. For purposes of the disclosure, the following terms are defined below:

As used herein, the terms "nucleic acid" and "polynucleotide sequence" refer to a deoxyribonucleotide or ribonucleotide polymer in either single- or double-stranded form, and unless otherwise limited, encompass known analogs of natural nucleotides that can function in a similar manner as naturally occurring nucleotides. The polynucleotide sequences include both full-length sequences, as well as shorter sequences derived from the full-length sequences. It is understood that a particular polynucleotide sequence includes the degenerate codons of the native sequence or sequences that may be introduced to provide codon preference in a specific host cell. The polynucleotide sequences falling within the scope of the disclosure further include sequences that specifically hybridize with the sequences coding for a peptide of the disclosure. The polynucleotide includes both the sense and antisense strands, either as individual strands or in the duplex.

Fragments and variants of a polynucleotide of the disclosure can be generated as described herein and tested for the presence of function using standard techniques known in the art. Thus, an ordinarily skilled artisan can readily prepare and test fragments and variants of a polynucleotide or polypeptide of the disclosure and determine whether the fragment or variant retains functional activity that is the same or similar to a full-length or a non-variant polynucleotide or polypeptide, such as a myosin VIIa polynucleotide or polypeptide.

Also within the scope of the disclosure are polynucleotides that have the same, or substantially the same, nucleotide sequence of a polynucleotide exemplary herein, except for the presence of one or more nucleotide substitutions, additions, or deletions within the sequence of the polynucleotide, so long as these variant polynucleotides retain substantially the same relevant functional activity as the polynucleotides exemplary herein (for example, they encode a protein having the same amino acid sequence or the same functional activity as one of the polynucleotides specifically exemplary herein). Thus, the polynucleotides disclosed herein should also be understood to include variants and fragments thereof.

As one of ordinary skill in the molecular biological arts can readily appreciate, there can be a number of variant sequences of a gene or polynucleotide found in nature, in addition to those variants that may be artificially prepared or synthesized by an ordinary-skilled artisan in a laboratory environment. The polynucleotides of the disclosure encompasses those specifically exemplary herein, as well as any natural variants thereof, as well as any variants which can be created artificially, so long as those variants retain the desired biological activity.

Also within the scope of the disclosure are polynucleotides which have the same nucleotide sequences of a polynucleotide exemplary herein except for nucleotide substitutions, additions, or deletions within the sequence of the polynucleotide, as long as these variant polynucleotides retain substantially the same relevant biological activity as the polynucleotides specifically exemplary herein. Thus, the polynucleotides disclosed herein should be understood to include variants and fragments, as discussed above, of the specifically exemplary sequences.

Polynucleotides described herein can also be defined in terms of more particular identity and/or similarity ranges with those exemplary herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or greater as compared to a sequence exemplary herein.

Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described (Altschul et al., 1997). When utilizing BLAST and Gapped BLAST programs, the default parameters of the respective programs (NBLAST and XBLAST) can be used in accordance with published methods.

The disclosure also contemplates those polynucleotide molecules having sequences that are sufficiently homologous with the polynucleotide sequences of the disclosure to permit hybridization with that sequence under standard stringent conditions and standard methods (Maniatis et al., 1982). As used herein, "stringent" conditions for hybridization refers to conditions wherein hybridization is typically carried out overnight at 20-25 degrees Celsius below the melting temperature (Tm) of the DNA hybrid in 6×SSPE, 5×Denhardt's solution, and 0.1% SDS, containing 0.1 mg/mL of a suitable non-specific denatured DNA.

The term "effective amount," as used herein, refers to an amount that is capable of treating or ameliorating a disease or condition or otherwise capable of producing an intended therapeutic effect.

The term "operably linked," as used herein, refers to that the nucleic acid sequences being linked are typically contiguous, or substantially contiguous, and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

The term "promoter," as used herein, refers to a region or regions of a nucleic acid sequence that regulates transcription. Exemplary promoters provided herein include, but are not limited to, a CMV promoter, an EF-1 alpha promoter, a cone arrestin promoter, a chimeric CMV β actin promoter (CBA), a truncated chimeric CMV β actin (smCBA) promoter, a human myosin 7a gene-derived promoter, a TαC gene-derived promoter, a rhodopsin promoter, a cGMP-phosphodiesterase β-subunit promoter, human or mouse rhodopsin promoter, a hGRK1 promoter, a synapsin promoter, a glial fibrillary acidic protein (GFAP) promoter, a rod specific IRBP promoter, a VMD2 promoter.

The term "regulatory element," as used herein, refers to a region or regions of a nucleic acid sequence that regulates transcription. Exemplary regulatory elements include, but are not limited to, enhancers, post-transcriptional elements, transcriptional control sequences, and such like.

The term "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences will be at least about 80%, preferably at least about 85%, and more preferably about 90% or 95% or higher, as readily determined by one or more of the sequence comparison algorithms well-known to those of ordinary skill in the art, such as e.g., the FASTA program analysis described by Pearson and Lipman (1988).

The term "subject," as used herein, describes an organism, including mammals such as primates, to which treatment with the compositions according to the disclosure can be provided. Mammalian species that can benefit from the disclosed methods of treatment include, but are not limited to, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like.

The term "treatment" or any grammatical variation thereof (e.g., treat, treating, and treatment, etc.), as used herein, includes but is not limited to, alleviating a symptom of a disease or condition; and/or reducing, suppressing, inhibiting, lessening, ameliorating or affecting the progression, severity, and/or scope of a disease or condition.

The term "vector," as used herein, refers to a nucleic acid molecule (typically one containing DNA) that is capable of replication in a suitable host cell, or one to which another nucleic acid segment can be operatively linked so as to facilitate replication of the operably-linked nucleic acid segment. Exemplary vectors include, without limitation, plasmids, cosmids, viruses and the like.

As used herein, the term "variant" refers to a molecule (e.g., a polynucleotide) having characteristics that deviate from what occurs in nature, e.g., a "variant" is at least about 80% identical, at least about 90% identical, at least about 95% identical, at least about 96% identical, at least about 97% identical, at least about 98% identical, at least about 99% identical, at least about 99.5% identical, or at least about 99.9% identical to the wild type polynucleotide. Variants of a protein molecule, e.g. a capsid, may contain modifications to the amino acid sequence (e.g., having 1, 2, 3, 4, 5, 6, 7, 8, 9, 10, 10-15, or 15-20 amino acid substitutions) relative to the wild type protein sequence, which arise from point mutations installed into the nucleic acid sequence encoding the capsid protein. These modifications include chemical modifications as well as truncations.

Variants of a nucleic acid molecule, e.g. a polynucleotide vector system, may contain modifications to the sequence (e.g., having 1, 2, 3, 4, 5, 6, 7, 8, 9, 10, 10-15, or 15-20 nucleotide substitutions) relative to the wild type nucleic acid sequence. These modifications may comprise truncations at a 5' terminus or a 3' terminus.

Examples

The following examples are included to demonstrate preferred embodiments of the disclosure. It should be appreciated by those of skill in the art that the techniques disclosed in the examples that follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

EXAMPLE 1 shows an exemplary Overlap Dual Vector System, which has a hMYO7A coding overlap. In an exemplary overlap system (FIG. 2), the overlapping DNA sequence shared by both vector A and vector B consists of a 1350-bp coding region for the human MYO7A gene. This is the simplest system of the disclosure, and appears to be highly efficient in terms of full-length gene reconstitution, and MYO7A expression. Advantageously, each vector is of standard AAV packaging size, and as such, each packages DNA with a high degree of efficiency, and is readily adaptable to conventional GMP standards. Such vectors are also readily characterized to permit requisite regulatory approval prior to use in humans.

Figure 3:
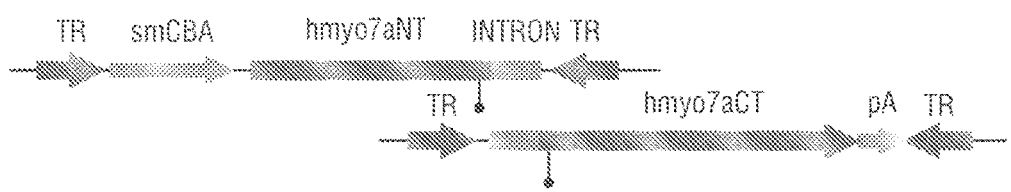
FIG. 3 shows a schematic of the two vector components that make up an exemplary Hybrid Dual Vector System containing a native intron. Native hMYO7A intron 23 in shown in light shading; splice donor and splice acceptor sequences are shown in darker shading and indicated with a (•).
Figure 4:
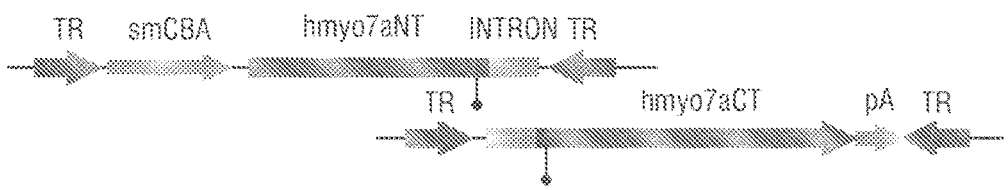
FIG. 4 shows the schematic of the two vector components that make up an exemplary Hybrid Dual Vector System containing a synthetic intron. This is an exemplary standard trans splicing dual vector system, with the "intron" referring to the synthetic alkaline phosphatase splice donor and acceptor sites. Synthetic alkaline phosphatase (AP) intron is shown in light shading; AP splice donor and splice acceptor sequences are shown in darker shading and indicated with a (•).

EXAMPLE 2 shows an exemplary hybrid dual-AAV vector system, which utilizes hMYO7A intron 23 splicing. In an exemplary system (FIG. 3) the overlapping DNA sequence is composed of the native intron 23 of human MYO7A. Vector A contains the coding sequence corresponding to the amino-terminal portion of the hMYO7A cDNA relative to intron 23 (hMYO7ANT) and the native splice-donor site, followed by a 250 bp fragment of intron 23 of hMYO7A (minus the native acceptor site). Vector B contains the carboxyl-terminal portion of the hMYO7A cDNA relative to intron 23 (hMYO7ACT), and a 250 bp fragment of intron 23 of MYO7A (minus the native splice-donor site), followed by the native splice-acceptor site. Upon co-delivery to suitable mammalian host cells, the DNA of vectors A and B recombine to form a reconstituted full-length gene cassette. The resulting RNA transcript will then 'splice out' the native intron. Alternatively, recombination and formation of the gene cassette can occur via the AAV TRs. In this case, the RNA transcript will 'splice out' the native intron23-TR-intron23 motif. In both cases, however, the resulting mRNA is that of the reconstituted full-length hMYO7A gene sequence.

Figure 6A:
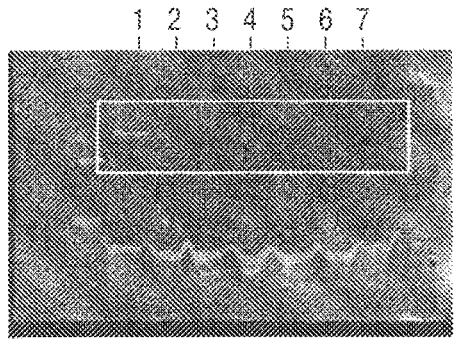
FIG. 6A and FIG. 6B show immunoblot to detect the presence of MYO7A in HEK293 cells infected with an exemplary Overlap Dual Vector System. Results are presented as a time course from 3-7 days post infection (lanes 3-7) and are compared to cells transfected with MYO7A plasmid (lane 1) and uninfected control (lane 2). An area of interest in FIG. 6A is magnified and presented at higher contrast in FIG. 6B. Starting at 3 days post-infection, full-length human MYO7A protein was visible, with peak expression occurring around day 5.
Figure 6B:
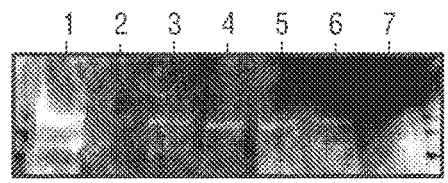

EXAMPLE 3 shows in vitro performance of an exemplary overlap vector system, which contains the hMYO7A coding overlap. HEK293 cells were infected simultaneously with vector A and vector B of an overlap dual vector system (FIG. 2) at a ratio of 10000:1 vg/cell for each vector. The AAV vectors were packaged in AAV2 virions that contain three Y-F mutations in the capsid protein (see, e.g., Zhong et al., 2008). As a positive control, cells were transfected with plasmid containing full-length hMYO7A under the control of smCBA. Protein was recovered from cells at 3-, 4-, 5-, 6- and 7-days post-infection, and an antibody directed against MYO7A was used to assay for its presence in the infected cells via immunoblotting. The results are shown in FIG. 6A and FIG. 6B. An area of interest from inside FIG. 6A is magnified, and presented at higher contrast in FIG. 6B. Starting at 3-days post-infection, the full-length human MYO7A protein was visible; peak expression of the protein occurred around Day 5.

Figure 7A:
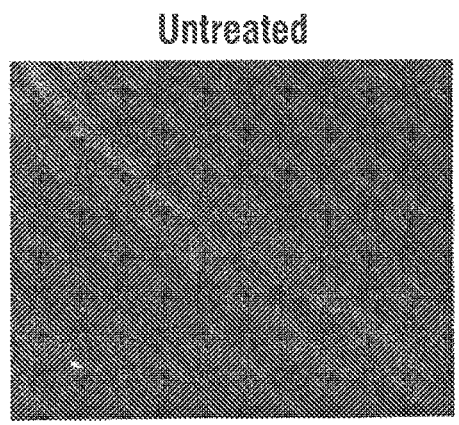
FIG. 7A and FIG. 7B show retinas from untreated mice and mice treated subretinally with an exemplary Overlap Dual Vector System. Immunohistochemistry (IHC) was performed using an antibody directed against MYO7A. MYO7A stains and nuclear (DAPI) stains are indicated.
Figure 7B:
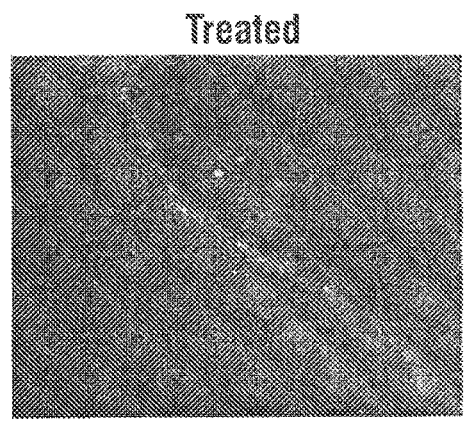

EXAMPLE 4 shows in vivo performance of an exemplary overlap vector system, which contains the hMYO7A coding overlap. Six week old shaker-1 (MYO7A null) mice were sub-retinally co-injected with 1 μL of the same preparations of vector A and vector B used in the above in vitro study. Both vectors were delivered at ~1×10$^{12}$ vg/mL. Four weeks post-injection, retinas from treated and untreated eyes were collected and immunohistochemistry (IHC) was performed using an antibody directed against MYO7A (see FIG. 7A and FIG. 7B). Brighter areas indicated MYO7A-specific staining, while the darker areas correspond to the nuclear-specific, DAPI stain. In the treated eye, MYO7A expression was clearly visible, and it appeared to be restricted to photoreceptors—more precisely to the juncture of the photoreceptor inner and outer segments.

EXAMPLE 5 shows that AAV dual vectors efficiently deliver oversized genes.
Methods and Materials Animals. Shaker-1 mice carrying the 4626SB allele, an effective null mutation (Liu et al., 1999; Hasson et al., 1997), were used on the C57BL6 genetic background, and maintained and genotyped as described (Liu et al., 1999; Gibbs et al., 2003a). They were maintained on a 12-hr light/12-hr dark cycle, with exposure to 10-50 lux of fluorescent lighting during the light phase, and were treated according to federal and institutional animal care guidelines. Homozygous mutants were distinguished from the heterozygous controls by their hyperactivity, head-tossing and circling behavior (Gibson et al., 1995), and/or by a PCR/restriction digest assay.

Construction of AAV Vectors. Single-vector platform: AAV vector plasmid, containing the truncated chimeric CMV/chicken β-actin promoter (smCBA) (Haire et al., 2006) and MYO7A cDNA was constructed by removing the full MYO7A cDNA from pEGFP-C2 by EagI and SalI digest, and then ligating into pTR-smCBA-GFP that had been digested with NotI and SalI to remove GFP. The MYO7A cDNA (~6.7 kb) corresponded to isoform 2 of human MYO7A, and was the same as that described previously by Hashimoto et al. (2007), which was based on the sequence published by Chen et al. (1996) (see SEQ ID NO: 8). MYO7A isoform 2 is 114-kb shorter than isoform 1 (Chen et al., 1996; Weil et al., 1996). Both the MYO7A cDNA, and the resulting junctions were fully sequenced prior to packaging. All vectors intended for in vitro analyses were separately packaged in wild type AAV2, or alternatively in the AAV2 (tripleY-F) capsid mutant vector (Petrs-Silva et al., 2011).

As noted above, AAV2-based vectors were chosen for the in vitro experiments due to their increased transduction efficiency relative to other serotypes (Ryals et al., 2011). All vectors were packaged, purified, and titered using standard methods as previously described (Zolotukhin et al., 2002; Jacobson et al., 2006). Human embryonic kidney (HEK293) cells were transfected by the calcium phosphate method with vector plasmid carrying the full-length MYO7A coding sequence of variant 2 (the plasmid used to package fragmented AAV). These transfected cells were then used as a positive control throughout immunoblot analyses to indicate the appropriate size of full-length MYO7A protein. Vector infections were carried out in HEK293 cells with titer-matched AAV vectors. In brief, cells were grown to 60-70% confluency. All vectors were diluted in a balanced salt solution to achieve the desired multiplicity of infection (MOI). If not specifically mentioned, cells were infected at 10,000 genome-containing particles/cell of each vector, resulting in an MOI of 20,000 total for each vector pair. Cells were incubated in medium containing 10% serum for 3 days post-infection at 37 degrees C. under 7% $CO_2$, and then analyzed via immunoblot. Titers of $10^{12}$ to $10^{13}$ particles/mL were obtained for different lots of AAV2-MYO7A and AAV5-MYO7A.

Oligonucleotide Sequences. For in vivo studies, a human influenza hemagglutinin (HA) tag was added to the 3' termini of the full-length, simple overlap, trans-splicing, and hybrid 3' vectors by utilizing a unique BamHI site (P19), and replacing the non-tagged 3'-end with an HA-tagged (P20) version. All constructs were sequence verified by Sanger sequencing.

AAV Vector Plasmid Design and Cloning. The full-length coding sequence of MYO7A (human isoform 2; GenBank Accession No. NM_001127180) was cloned into a vector plasmid containing the strong, ubiquitous CMV/chicken β-actin (smCBA) promoter (Haire et al., 2006), a polyadenylation signal, and the AAV2 ITRs.

Figure 22A:
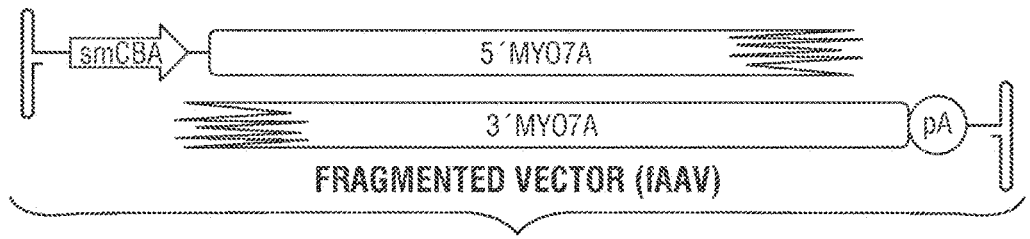
FIGS. 22A-22E show a schematic representation of the dual-AAV-vector pairs created for this study.

Packaging of this plasmid generated the fAAV vector (FIG. 22A). In all systems, the 5' vectors shared the smCBA promoter and a 5' portion of MYO7A, whereas the 3' vectors contained a 3'-portion of MYO7A, and a bovine growth hormone (bGH) polyadenylation signal. Oligonucleotides used for vector construction are listed in Table 1. The simple overlap contained nucleotides 1 through 3644 of MYO7A cDNA from the ATG in the 5' vector, and nucleotides 2279 through 6534 in the 3' vector. The fragments were amplified with oligonucleotides P1 and P3 by polymerase chain reaction (PCR) and cloned into the 5' vector via NotI and NheI, and the 3' vector with P3 (AflII) and P4 (KpnI), respectively.

Figure 22B:
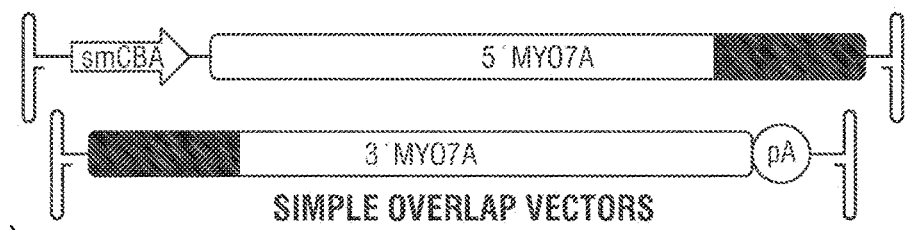

The resulting two vector plasmids share 1365 bp of overlapping MYO7A sequence (FIG. 22B). The trans-splicing and hybrid vectors utilize splice junctions composed of either ideal splice donor and acceptor sites derived from AP coding sequence or native MYO7A splice junctions from exons 23 and 24 (Yan et al., 2002). To create the 5' trans-splicing vector, the splice-acceptor site was amplified using oligonucleotides P5 and P6 (NheI), and the amplicon was then used in a second reaction with oligonucleotide P7 (NsiI) to add a part of the MYO7A coding sequence for cloning.

Figure 22C:
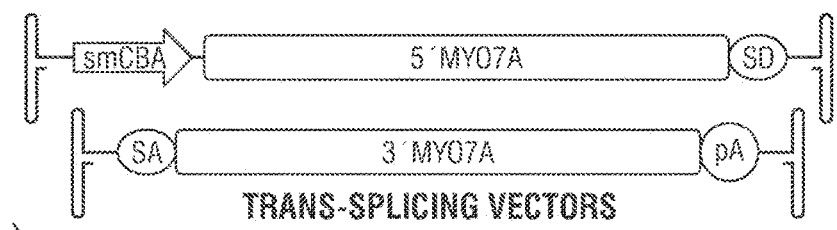
Figure 22D:
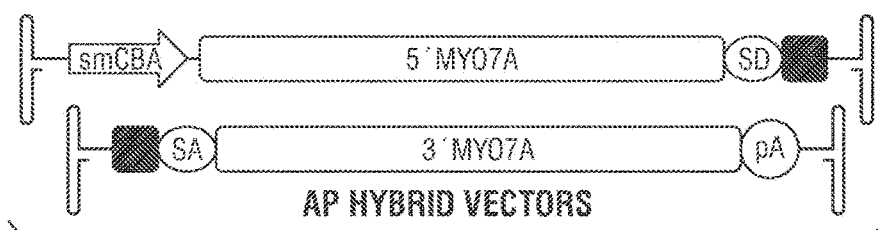

The corresponding 3' vector was similarly created by amplifying the splice-acceptor site with oligonucleotides P8 (AflII) and P9 in a first PCR, and adding part of the 3' MYO7A coding sequence with oligonucleotide P10 (AgeI) in a second PCR (see FIG. 22C). The AP hybrid vectors were created by adding 270 bp of AP overlap sequence to the respective trans-splicing vectors (Ghosh et al., 2011). The sequence was amplified by PCR and, in so doing, appropriate restriction endonuclease sites were added. For the 5' vector oligonucleotides P11 (NheI) and P12 (SalI) were used, while oligonucleotides P13 (NotI) and P14 (AflII) were used for the 3' vector (FIG. 22D).

Figure 22E:

A fourth vector pair, "native intron hybrid" vector, was also created to exploit the natural sequence in and around intron 23 of MYO7A as a recombination locus, and subsequent splicing signal. The 5'-portion was created by amplifying intron 23 with oligonucleotides P15 and P16 (NheI) first, and then using the resulting amplicon in a second reaction with oligonucleotide P7 (NsiI) to facilitate cloning. The corresponding 3'-vector was constructed by amplifying the intron 23 with oligonucleotides P17 and P18 (AflII), and the resulting amplicon, with oligonucleotide P10 (AgeI) in a second reaction (see FIG. 22E).

TABLE 1

Oligonucleotides used in this study

| OliGo | 5'-3' sequence (restriction sites underlined) | Restriction site | (SEQ ID NO:) |
|---|---|---|---|
| P1 | GCGGCGGCCGCCACCATGGTGATTCTTCAGCAGGGGAC | NotI | SEQ ID NO: 9 |
| P2 | GCGGCTAGCGAAGTTCCGCAGGTACTTGAC | NheI | SEQ ID NO: 10 |
| P3 | GCGCTTAAGCAGGTCTAACTTTCTGAAGCTG | AflII | SEQ ID NO: 11 |
| P4 | GCGGGTACCTCACTTGCCGCTCCTGGAGCC | KpnI | SEQ ID NO: 12 |
| P5 | GGCACCTAGTGGCTTTGAGGTAAGTATCAAGGTTACAAGAC | | SEQ ID NO: 13 |
| P6 | GCGGCTAGCTCAGAAACGCAAGAGTCTTC | NheI | SEQ ID NO: 14 |
| P7 | CTTCTTTGTGCGATGCATCAAG | NsiI | SEQ ID NO: 15 |
| P8 | GCGCTTAAGCGACGCATGCTCGCGATAG | AflII | SEQ ID NO: 16 |
| P9 | CGCCCTCGCTCCAGGTCCTGTGGAGAGAAAGGCAAAG | | SEQ ID NO: 17 |
| P10 | GAACCCGAACCGGTCCTTG | AgeI | SEQ ID NO: 18 |
| P11 | GCGGCTAGCCCCCGGGTGCGCGGC | NheI | SEQ ID NO: 19 |
| P12 | GCGGTCGACGAAACGGTCCAGGCTATGTG | SalI | SEQ ID NO: 20 |
| P13 | GCGGCGGCCGCCCCCGGGTGCGCGGCG | NotI | SEQ ID NO: 21 |
| P14 | GCGCTTAAGGAAACGGTCCAGGCTATGTG | AflII | SEQ ID NO: 22 |
| P15 | CAGGCACCTAGTGGCTTTGAGGTACCAGGCTAGGGACAGG | | SEQ ID NO: 23 |
| P16 | GCGGCTAGCCGCCTGAGCCCAGAAGTTC | NheI | SEQ ID NO: 24 |
| P17 | CGCCCTCGCTCCAGGTCCTGAAGGAGACAAGAGGTATG | | SEQ ID NO: 25 |
| P18 | GCGCTTAAGCACCGCTTGTGTTGATCCTC | AflII | SEQ ID NO: 26 |
| P19 | GCCAGGGAAGGATCCCATG | BamHI | SEQ ID NO: 27 |
| P20 | GCGGGTACCTCATGCGTAATCCGGTACATCGTAAGGGTACTTGCCGCACCAGGAGCC | KpnI | SEQ ID NO: 28 |
| P21 | AGCTTCGTAGAGTTTGTGGAGCGG | | SEQ ID NO: 29 |
| P22 | GAGGGGCAAACAACAGATG | | SEQ ID NO: 30 |

Oligonucleotides were used to make 5' and 3' vectors of the dual vector platforms (P1-P20). Oligonucleotides were used to characterize the fidelity of the overlap in simple overlap, trans-splicing and AP hybrid vector platforms (P21-P22). Restriction sites used for cloning are underlined and the introduced hemagglutinin (HA) tag is noted in italics (P19).

Dual Vector Platform. Two separate vector plasmids were constructed: Vector A contains the strong, ubiquitous "smCBA" promoter and MYO7A cDNA encoding the N-terminal portion. Vector B contains MYO7A cDNA encoding the C-terminal portion and a poly-A signal sequence. Each vector plasmid contained both inverted terminal repeats (ITRs). Using PCR with full-length MYO7A cDNA as a template, the MYO7A cDNA was divided roughly in half with amplicons encompassing nucleotide positions 1 through 3644 (Vector A) and 2279 through 6647 (Vector B) relative to ATG start position 1. The resulting two-vector plasmids shared 1365 bp of overlapping MYO7A sequence, and were 5.0- and 4.9-Kb in length, respectively. This was well within the size limitation of standard AAV vectors. Both vector plasmids were sequence verified and separately packaged by standard AAV production methods (Zolotukhin et al., 2002; Jacobson et al., 2006). The titer of the first lot contained $2.5 \times 10^{12}$ particles/mL of each vector, and the second lot contained $4 \times 10^{12}$ particles/mL of each vector.

Reverse Transcription and Characterization of Overlap Region. HEK293 cells were infected with dual vectors, and total RNA was extracted with the RNeasy® kit (Qiagen, Hilden, Germany) according to the manufacturer's recommended protocol. Two micrograms of RNA were then subjected to DNaseI (NEB) digestion for 30 min at 37 degrees Celsius, followed by heat inactivation at 75 degrees Celsius for 10 min. Reverse transcription to cDNA was achieved with the SuperscriptIII® kit (Life Technologies, Grand Island, NY, USA) according to the standard protocol utilizing the oligo dT primer. Two microliters of cDNA was used as template in a PCR (95 degrees Celsius for 3 min. initial denature, 35 cycles of 95 degrees Celsius for 45 sec., 55 degrees Celsius for 45 sec., 72 degrees Celsius for 12 min., and a final 72 degrees Celsius for 15 min.) using oligonucleotide primers P21 and P22 (see Table 1). Annealing sites for these primers are located 5' and 3', respectively, of the area of cDNA overlap (in other words, outside the region of overlap) in the simple overlap and hybrid vector pairs. The 3'-primer annealed to sequence that was complimentary to the bGH polyA. Resulting products were digested with either PpuMI or BglII, separated on a 1.5% agarose gel, and subsequently analyzed on a UV screen. Separately, products were digested with KpnI and AgeI, and subsequently cloned into a pUC vector for sequencing of the entire overlap region. M13~forward and reverse primers that were specific for the vector were used to obtain sense and antisense reads resulting in an 140 bp overlap of the sense and antisense reads. To demonstrate that these methods were capable of detecting aberrant sequence (for example, for quality control), a MYO7A sequence was generated using either an artificial insertion (HindIII fill-in at position 2635) or a point mutation (T→C) at position 2381, and the analyses were repeated.

Viral Delivery in Vitro. HEK293A cells (Invitrogen), grown in DMEM with 10% FBS and 1×NEAA and Pen/Strep (Invitrogen) were plated in 6 well-plates. The next day cells were incubated, at 37 degrees Celsius and 5% $CO_2$, with AAV2- and AAV5-MYO7A at an MOI of 10,000 viral particles/cell in 500 µL of complete medium, containing also 40 µM of calpain inhibitor (Roche, Pleasanton, CA, USA). Two hours later complete medium was added. The next day, the medium was changed and cells were incubated for an additional 48 hrs. Alternatively, some cells were transfected with 1 µg of vector pTR-smCBA-MYO7A, complexed with Lipofectamine 2000 (ratio 1:3), according to the manufacturer's instructions (Invitrogen).

Primary mouse RPE cells were derived from P14-P16 MYO7A-null animals and cultured in 24-well dishes, as described (Gibbs et al., 2003a; Gibbs and Williams, 2003b). After 48 hrs. in culture, cells were transduced with viruses. Cells were incubated in 100 µL of complete medium containing 40 µM of calpain inhibitor, and 10,000 viral particles/cell from full-strength AAV stocks. After 2 hrs, 400 µL of complete medium was added to each well, and incubated overnight. The medium was changed the following day, and cells were incubated for an additional 48 hrs.

ARPE19 cells (American Type Culture Collection, Manassas, VA, USA) were cultivated in DMEM/F-12 with 10% FBS and split into 24-well plates with glass coverslips. Cells were grown to confluency and then transduced in the same manner, as were the primary RPE cells.

MYO7A expression analysis by Western blot and Immunofluorescence. HEK293A and primary mouse RPE cells that were transduced with AAV-MYO7A were collected 3 days post-transduction. For western blot analyses, cells were collected and lysed in 20 mM TRIS, pH 7.4, 5 mM $MgCl_2$, 10 mM NaCl, 1 mM DTT and 1× protease inhibitor cocktail (Sigma-Aldrich Chemical Co., St. Louis, MO, USA). Equivalent amounts of total protein were separated on a 7.5% SDS-PAGE gel. After transfer, blots were blocked with 5% non-fat milk, and probed with mouse anti-MYO7A antibody, generated against residues 927-1203 of human MYO7A (Developmental Studies Hybridoma Bank, Iowa City, Iowa USA) (Soni et al., 2005), and mouse anti-actin antibody (Sigma-Aldrich) as a loading control.

Immunofluorescence was performed with ARPE19 and mouse RPE primary cells, 3 days after infection. Cells were fixed in 4% formaldehyde, blocked with blocking solution (0.5% BSA/0.05% saponin in PBS), incubated with the mouse anti-MYO7A followed by goat anti-mouse Alexa-568 (Molecular Probes, Carlsbad, CA, USA). Coverslips were mounted with mounting medium containing DAPI (Fluorogel II, Electron Microscopy Sciences, Hatfield, PA, USA) and visualized on a Leica confocal system.

Protein extraction and immunoblotting. Transfected and infected HEK293 cells were harvested and washed twice in PBS and processed as previously reported with minor modifications (Boye et al., 2012). The cells were lysed by 3×30 second pulses of sonication in 200 µL of sucrose buffer (0.23 M sucrose, 2 mM EDTA, 5 mM Tris-HCl, pH 7.5) containing protease inhibitors (Roche, Mannheim, Germany). Unlysed cells and cell debris were removed by centrifugation at 14,000 rpm for 10 min. The protein concentration of the supernatant was measured with BCA (Thermo Fisher Scientific, Rockland, IL, USA). Equal amounts of protein were then loaded on 7.5% sodium dodecyl sulfate polyacrylamide gel electrophoresis gels (BioRad, Hercules, CA, USA) and transferred in CAPS buffer (pH 11) onto PVDF membranes (Millipore, Billerica, MA). Blots were then labeled with antibodies against MYO7A (monoclonal antibody raised against amino acids 11-70 of human MYO7A; Santa Cruz, Dallas, TX, USA; 1:1000) or HA (MMS-101P; Covance, Gaithersburg, MD, USA; 1:500) and β-actin (ab 34731; Abcam, Cambridge, MA, USA; 1:5000). For visualization with the Odyssey system (Li-Cor, Lincoln, NE, USA), an anti-mouse and an anti-rabbit secondary antibody conjugated with CW800 and IR680 dyes (Li-Cor), respectively, were used. Semi-quantitative densitometric measurements were performed with Odyssey acquisition and analysis software (Li-Cor). The dual-color images were separated in their respective channels and converted to gray scale for presentation purposes. Size markers present in one channel of each blot were added to both channels for visualization of protein sizes.

Viral Delivery in vivo. Mice were anesthetized with 2.0-3.0% isoflurane inhalation. The pupils of the animals were dilated with 1% (wt./vol.) atropine sulfate and 2.5% phenylephrine. A local anesthetic (0.5% proparacaine hydrochloride) was also administered. A sclerotomy in the temporal limbus was performed with a 27-Ga needle. A 32-Ga blunt needle, attached to a microsyringe pump (WPI, Sarasota, FL, USA) was inserted and 1 µL of viral solution was injected into the ventral subretinal space of P14-P16 animals. Retinal detachment was visualized under a dissecting microscope, and registered as indication of a positive subretinal injection. One microliter of the following AAV8 (Y733F)-based vectors was injected subretinally in one eye of C57BL/6 mice: single fAAV ($1 \times 10^{13}$ vg/mL), front and back half "hybrid" vectors combined equally (each vector=$1 \times 10^{13}$ vg/mL), or front and back half "simple overlap" vectors combined equally (each vector=$1 \times 10^{13}$ vg/mL). Subretinal injections were performed as previously described (Timmers et al., 2001). Further analysis was carried out only on animals that received comparable, successful injections (>60% retinal detachment with minimal surgical complications).

Light Microscopy and Immunoelectron Microscopy of Retinas. Eyecups were processed for embedment in either LR White or Epon, and semithin and ultrathin sections were prepared. Semithin sections were stained with toluidine blue and visualized on a Leica confocal system. Ultrathin sections were labeled with purified MYO7A pAb 2.2 (Liu et al., 1997) and monoclonal anti-opsin (1D4, R. Molday), followed by gold-conjugated secondary antibodies (Electron Microscopy Sciences), as described previously (Lopes et al., 2011). Negative control sections processed at the same time included those from MYO7A-null retinas, and, as positive control, WT animals were used.

MYO7A immunogold density was determined on sections of age-matched WT, MYO7A-null retinas and retinas of MYO7A-null animals that had been injected with AAV-MYO7A at P14-16 and dissected three weeks later. For quantification of the immunolabel, all of the gold particles in a complete section of each RPE cell were counted. The area of each cell's profile was determined using ImageJ software. For background labeling, the concentration of label in sections of untreated MYO7A-null animals was measured. Data were expressed with this background labeling subtracted.

The concentration of MYO7A and opsin immunogold labeling in the connecting cilia of photoreceptor cells was determined by counting gold particles along longitudinal profiles of connecting cilia and measuring the length of each profile. Analysis and quantifications were performed in a minimum of three different retinas, from three different animals. Statistical analysis was performed using one-tail Student's t-test.

Six weeks post-injection, C57BL/6 mice were enucleated and their eyes processed and immunostained as previously described (Boye et al., 2011) with minor modifications. Retinas were immunostained with an antibody specific for hemagglutinin (HA) (monoclonal Ab clone 12CA5; Roche), counterstained with DAPI, and imaged with a spinning disk confocal microscope (Nikon Eclipse TE2000 microscope equipped with Perkin Elmer Ultraview Modular Laser System and Hamamatsu O-RCA-R2 camera). Images were obtained sequentially using a 20× (air) objective lens. All settings (exposure, gain, laser power) were identical across images. All image analysis was performed using Volocity 5.5 software (Perkin Elmer, Waltham, MA, USA).

Results

Figure 10A:
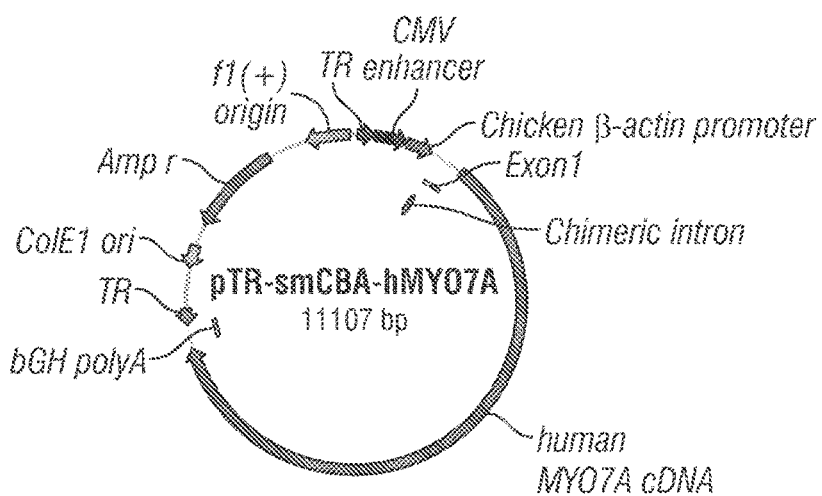
FIGS. 10A-10F illustrate the expression of MYO7A from single AAV2 and AAV5 vectors in cultured cells.

AAV-MYO7A single vector preparations. AAV vector plasmid was engineered to contain a truncated chimeric CMV/chicken β-actin promoter, smCBA (Haire et al., 2006) and the 6.7-kb cDNA encoding the full-length isoform 2 of human MYO7A (NCBI #NM_001127180) (FIG. 10A). The smCBA promoter exhibits the same tropism and activity in mouse retinas as that of the full-length CBA promoter (Haire et al., 2006; Pang et al., 2008). Titers of $10^{12}$ to $10^{13}$ particles/mL were obtained for different lots of AAV2-MYO7A and AAV5-MYO7A. A concentration of $10^{12}$ particles/mL was regarded as the standard concentration (1x), from which dilutions were made. The experiments were performed with virus obtained from three separate preparations. No differences in expression or phenotype correction, as described below, were observed among the different lots for AAV2-MYO7A or AAV5-MYO7A at a given concentration.

Figure 10B:
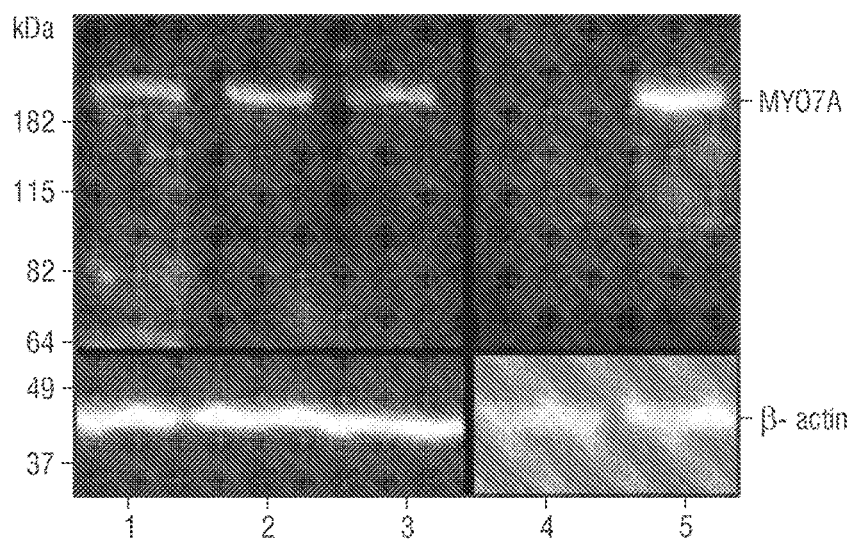
Figure 10C:
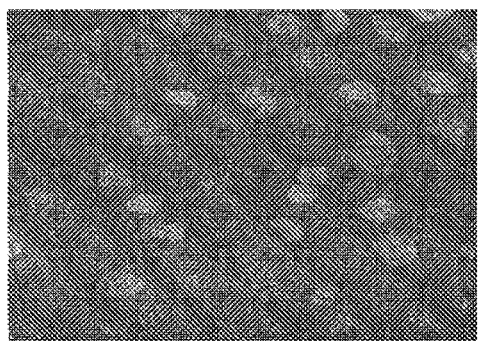
Figure 10D:
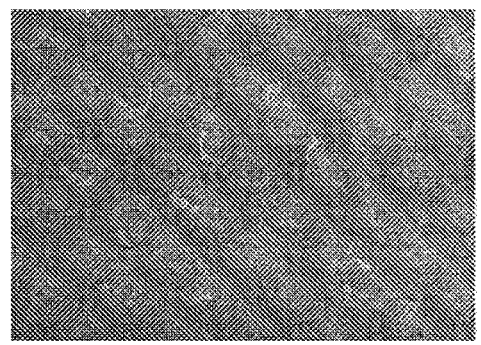
Figure 10E:
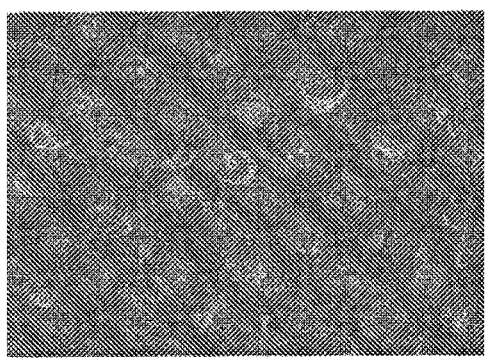
Figure 10F:
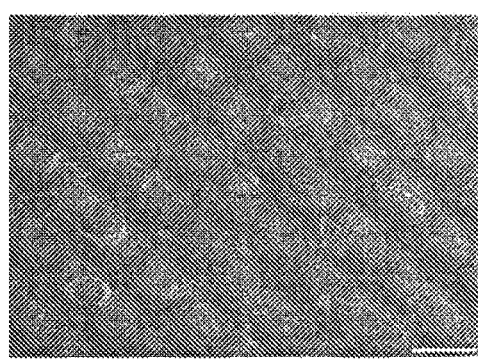

MYO7A Expression in Cell Culture. Transduction of primary cultures of MYO7A-null RPE cells with 1× single AAV2-MYO7A or AAV5-MYO7A resulted in the expression of a polypeptide that, by western blot analysis, had an apparent mass that was comparable to that of WT MYO7A protein, and was present at similar levels to that found in primary cultures of MYO7A$^{+/-}$ RPE cells (FIG. 10B). Likewise, a single band of appropriate size was detected on western blots of HEK293A cells. Immunofluorescence of the primary RPE cells showed that the MYO7A protein, resulting from 1× single AAV-MYO7A treatment of MYO7A-null cells, had a subcellular localization pattern that was comparable to that of endogenous MYO7A in control cells, indicating the generation of appropriately targeted protein (FIGS. 10C-10F). ARPE19 cells were also infected with 1× or diluted (1:100) AAV2-MYO7A or AAV5-MYO7A, and compared with non-treated cells. An increase in MYO7A immunofluorescence was detected in the treated cells, and the intracellular localization of the label was comparable to that in untreated cells (FIGS. 17A-17F).

Localization of MYO7A in Vivo. Most retinal MYO7A is found in the RPE (Hasson et al., 1995), however, the protein is also present in the connecting cilium and pericilium of the photoreceptor cells (Liu et al., 1997; Williams, 2008). A diagram illustrating this distribution and the retinal functions of MYO7A has been published in a recent review (Williams and Lopes, 2011).

Three weeks following injection of 1×AAV2-MYO7A or AAV5-MYO7A into the subretinal space of MYO7A-null mice, retinal tissue was examined by immunoelectron microscopy to test for MYO7A expression. Immunogold label was evident in the photoreceptor cells, where it was localized in the connecting cilium and pericilium, comparable to that in WT retinas (FIGS. 11A-E). Label was also present throughout the RPE cells, particularly in the apical cell body region (FIG. 11F, FIG. 11F-1, FIG. 11G, and FIG. 11G-1; see FIGS. 18A-18D for controls), as found in WT retinas (Gibbs et al., 2004; Liu et al., 1997).

Figure 11A:
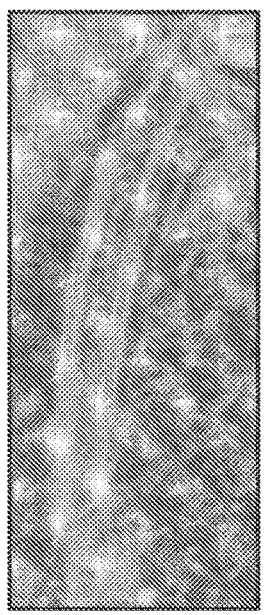
FIGS. 11A-11M show the expression of MYO7A from AAV2 and AAV5 dual vectors in vivo.
Figure 11B:
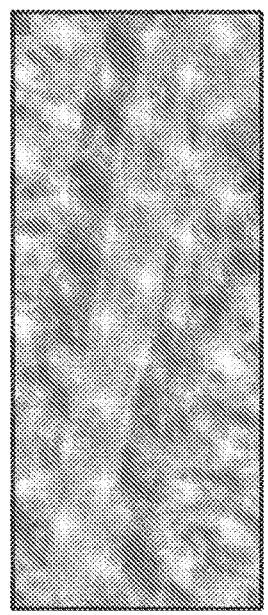
Figure 11C:
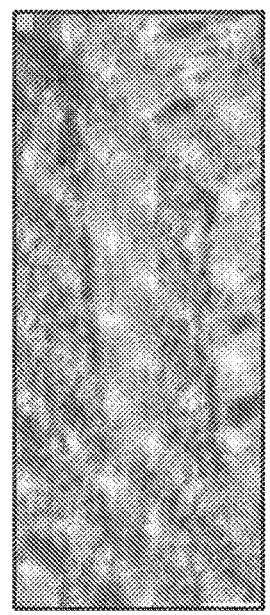
Figure 11D:
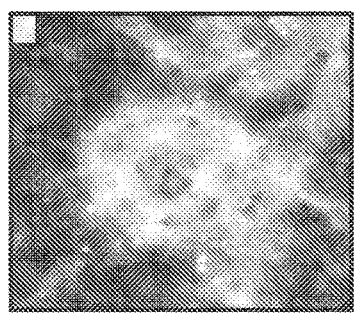
Figure 11E:
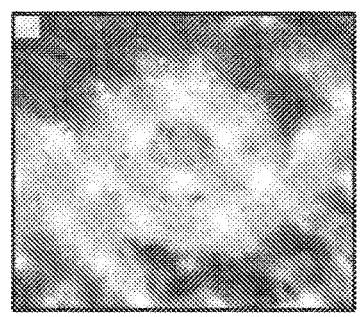
Figure 11I:
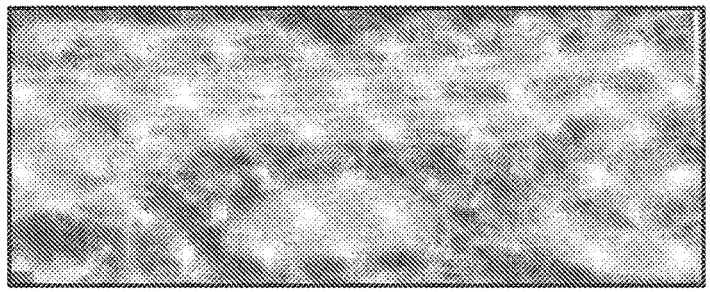
Figure 11H:
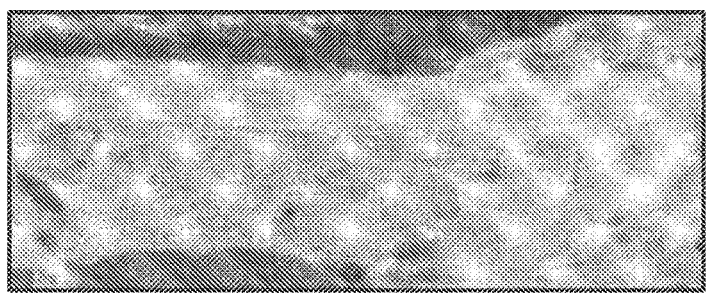
Figure 11G:
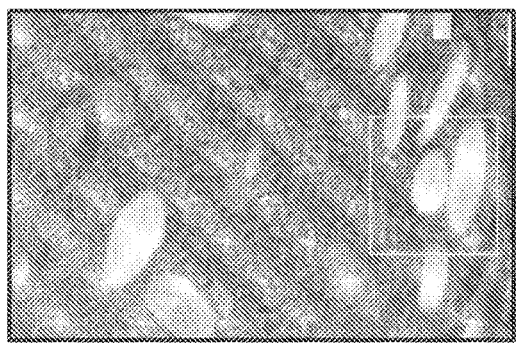
Figures 1, 11G:
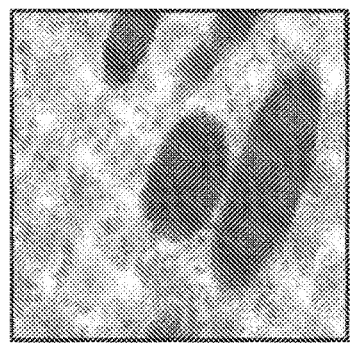
Figure 11F:
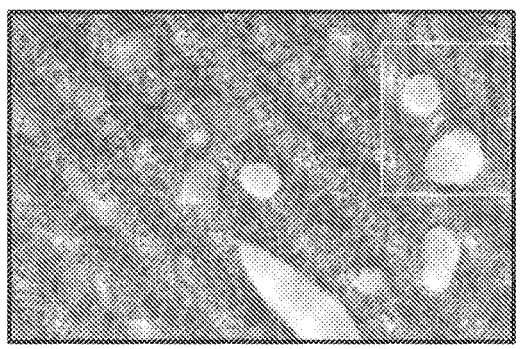
Figures 1, 11F:
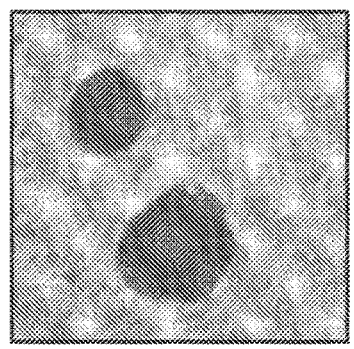

MYO7A has a similar distribution in both rod and cone photoreceptor cells (Liu et al., 1999). To test whether treatment with AAV-MYO7A also affected cone photoreceptor cells, it was determined whether MYO7A was also present in the ciliary region of cone photoreceptors. Double immunoEM of treated retinas was performed, using a MYO7A antibody together with an antibody specific for rod opsin. Although there are only a small number of cones with aligned connecting cilia found in each ultrathin section, MYO7A immunogold label was evident in the connecting cilium and periciliary region of these cones, which were identified by lack of rod opsin labeling in their outer segments (in contrast to the surrounding rod outer segments) (FIG. 11H and FIG. 11I). Hence, AAV2-MYO7A and AAV5-MYO7A can transduce cone as well as rod photoreceptor cells.

Dose-dependent MYO7A expression in photoreceptor and RPE cells. To determine the levels of MYO7A expression following treatment with different concentrations of AAV2-MYO7A and AAV5-MYO7A (lx, 1:10 or 1:100 dilutions), MYO7A immunogold labeling was quantified in EM images, taken within 1.4 mm of the injection site. Reliable detection of MYO7A in the photoreceptor cells, where its distribution is limited to the connecting cilium and pericilium, requires the higher resolution provided by electron microscopy (Liu et al., 1997). Immunogold particle density was measured in images of the photoreceptor connecting cilium and pericilium, shown in complete longitudinal section (from the basal bodies to the base of the outer segment), and in images showing the RPE cells in apical to basal section. Particle density was expressed as particles per length of cilium for the photoreceptor cells (each connecting cilium is ~1.2 m long), and as particles per area for the RPE cells (the entire area between the apical and basal surfaces was included). Particle density is dependent on exposure of epitopes on the surface of the section, and, as such, provides a relative linear measure of antigen density under the conditions used here (for example, grids were etched and labeled in an identical manner, and the labeling was not so dense as to be affected by steric hindrance).

Figure 11J:
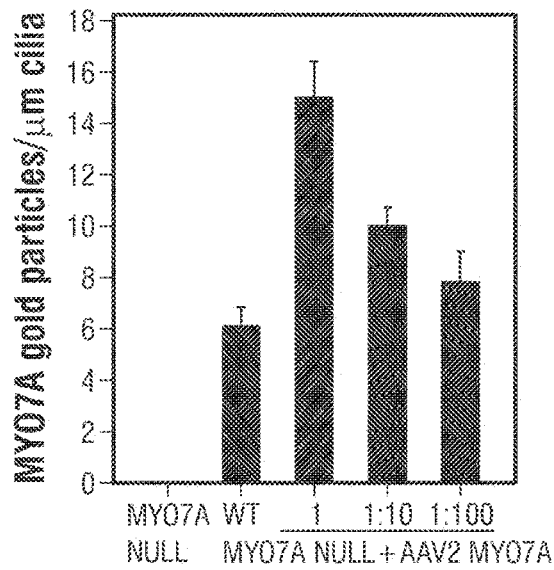
Figure 11K:
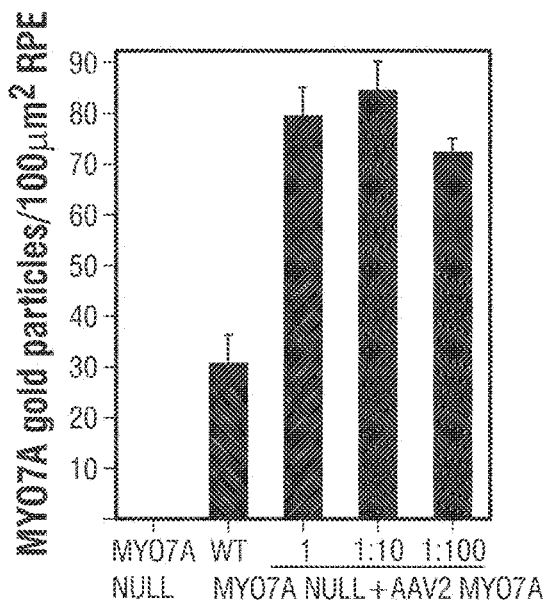
Figure 11L:
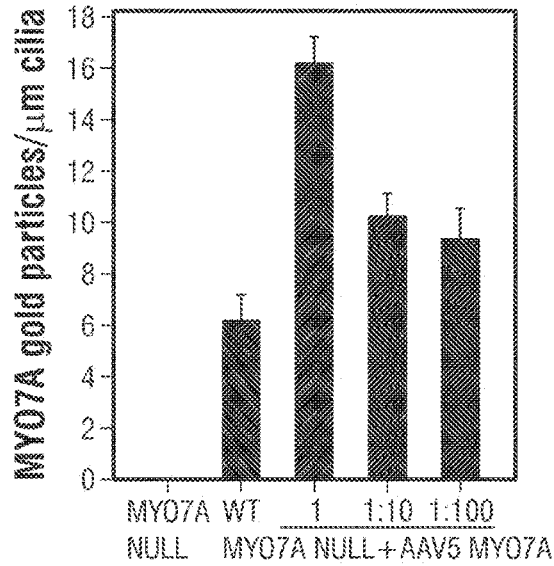
Figure 11M:
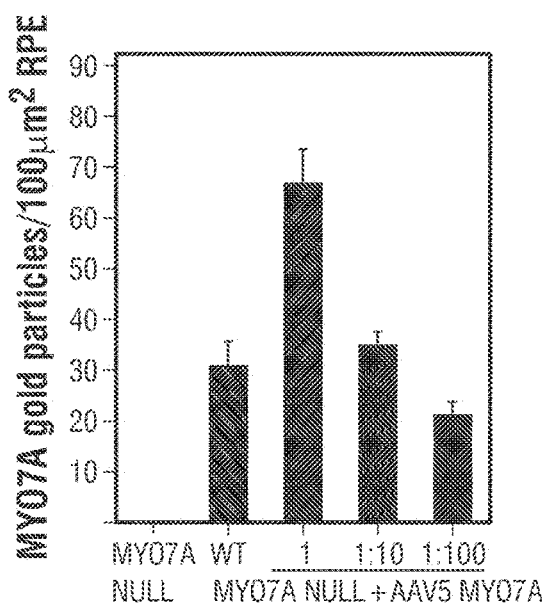

Treatment with 1×AAV2-MYO7A or AAV5-MYO7A resulted in 2.5-2.7 times the density of immunolabel in the photoreceptor cilium, compared with that found in WT retinas, while the 1:10 and 1:100 dilutions resulted in a density of immunolabel that was more comparable to WT levels (FIG. 11J, FIG. 11L, and FIG. 19). Quantification of immunogold label in the RPE showed that injection of AAV2-MYO7A resulted in 2.7 times more label than in WT, with the 1:10 and 1:100 dilutions showing no significant difference (FIG. 11K). In contrast, the level of MYO7A immunolabel in the RPE of retinas injected with AAV5-MYO7A varied in relation to virus titer, with the full dose virus effecting 2.2-fold more MYO7A than that found in WT RPE, the 1:10 dilution effecting WT levels, and the 1:100 dilution resulting, on average, ~60% of WT levels (FIG. 11M).

These counts of labeling density indicate that 1×AAV-MYO7A resulted in more than double the normal level of MYO7A expression in both the photoreceptor and RPE cells. The distribution of MYO7A was not affected by this overexpression in the photoreceptor cells. In the RPE cells, the overall distribution of MYO7A was comparable to WT, with a higher concentration in the apical cell body region. However, with 1×AAV2-MYO7A or 1×AAV5-MYO7A, the proportion of MYO7A that was associated with melanosomes was only 55% of that in WT RPE. This difference is possibly because the proteins that link MYO7A to the melanosomes, MYRIP and RAB27A (Klomp et al., 2007; Lopes et al., 2007), may have remained near WT levels, and thus limited the absolute amount of MYO7A that could associate with the melanosomes.

Despite the overexpression of MYO7A, no pathology was evident in retinas, up to 3 months after injection of 1× (or 1:10) AAV2-MYO7A. However, two out of six retinas injected with $10^{13}$ particles/mL of AAV5-MYO7A (for example, 10×) showed evidence of photoreceptor cell loss across the retina after 3 weeks (AAV2-MYO7A was not tested at this titer) (FIG. 19).

Figure 12A:
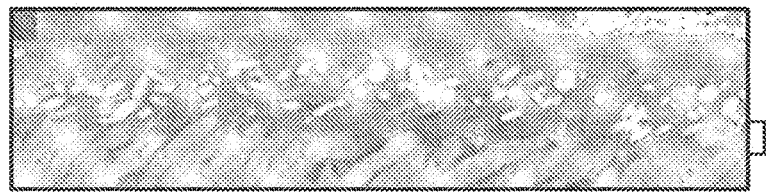
FIGS. 12A-12F show correction of melanosome localization, following subretinal injections with AAV2-MYO7A or AAV5-MYO7A. Light micrographs showing the presence of melanosomes in the apical processes of the RPE in a WT retina (FIG. 12A) and retinas injected with AAV2-MYO7A (FIG. 12B) or AAV5-MYO7A (FIG. 12C). Further away from the injection site (FIG. 12D), melanosomes are present in the apical processes of some RPE cells, but not in others (arrows indicate apical melanosomes; white lines indicate regions where melanosomes are absent from the apical processes).
Figure 12B:
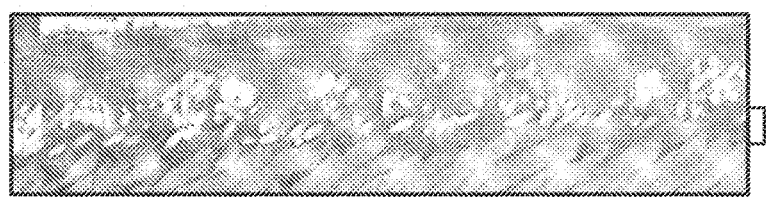
Figure 12C:
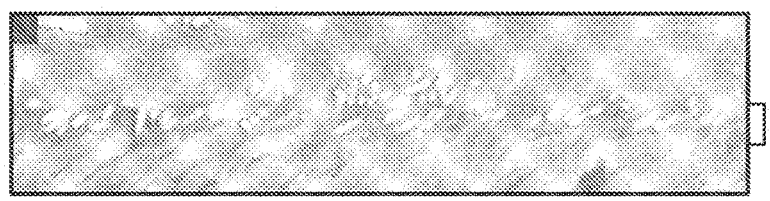
Figure 12D:
Figure 12E:
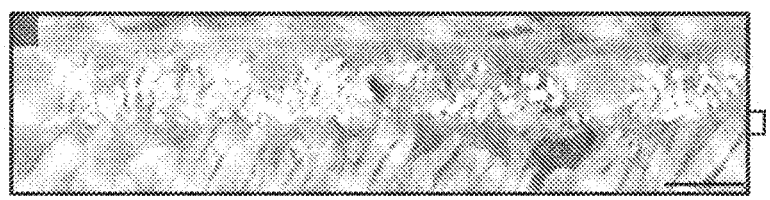
Figure 12F:
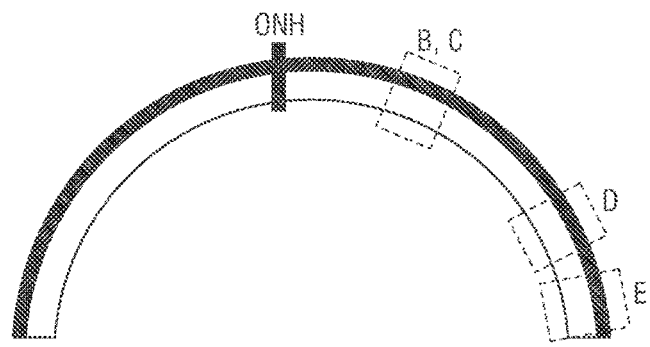
Figure 13:
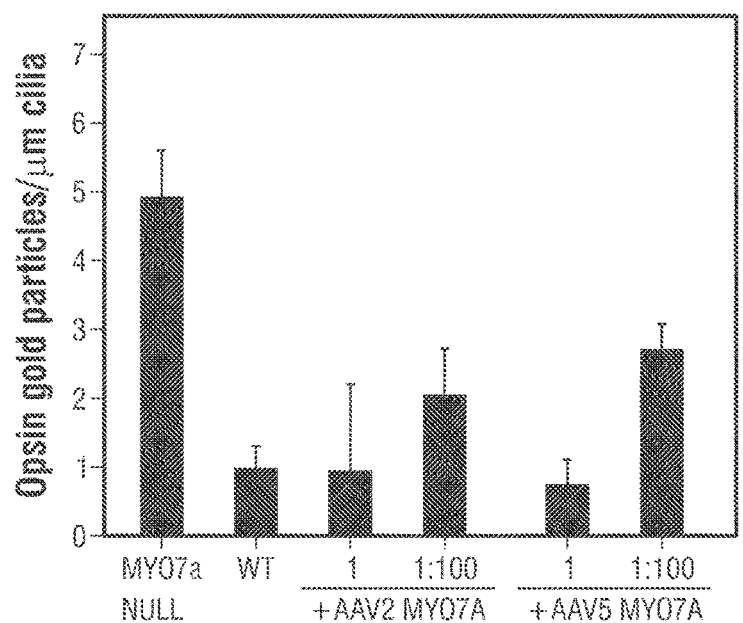
FIG. 13 shows the correction of abnormal levels of opsin in the connecting cilium and pericilium of rod photoreceptors, following subretinal injections with AAV2-MYO7A or AAV5-MYO7A. The bar graph shows opsin immunogold gold particle density along the length of the connecting cilium. Ultrathin sections of retinas from MYO7A-null and WT mice were stained with rod opsin antibody. The MYO7A-null retinas had been untreated, or treated with either 1× or 1:100 AAV2-MYO7A or AAV5-MYO7A. n=3 animals per condition. Bars indicate SEM.

Correction of melanosome localization in the RPE. In MYO7A-mutant mice, melanosomes are absent from the apical processes of the RPE cells (Liu et al., 1998). This mutant phenotype is evident at all neonatal ages, and is due to loss of actin-based transport of the melanosomes by the myosin 7a motor (Gibbs et al., 2004). Three weeks following injection of 1×AAV2-MYO7A or AAV5-MYO7A into the subretinal space of MYO7A-null mice, melanosomes were observed to have a normal distribution in all RPE cells near the site of injection (within 1.4 mm) (n=10 each for AAV2-MYO7A and AAV5-MYO7A) (FIGS. 12A-12C). Well away from the injection site, a mixture of corrected and uncorrected RPE cells was evident, while, at the periphery of the retina, the cells all exhibited the MYO7A-mutant phenotype, indicating lack of correction in this region (FIGS. 12D-12F). The correction of melanosomes was still evident in retinas that were fixed 3 months after injection (FIG. 20). Correction was also observed in all eyes injected with 1:10 dilution AAV2-MYO7A (n=6) or AAV5-MYO7A (n=6), as well as in all eyes injected with 1:100 dilution AAV2-MYO7A (n=6) or AAV5-MYO7A (n=6), although with the 1:100 dilution some of the RPE cells near the site of injection were not corrected.

Correction of opsin distribution. MYO7A-mutant mice have an abnormal accumulation of opsin in the connecting cilia of the photoreceptor cells, a phenotype that is evident by immunoEM with opsin antibodies (Liu et al., 1999). This mutant phenotype suggested that myosin 7a functions in the vectorial delivery of opsin to the outer segment (Liu et al., 1999). Quantification of immunogold opsin labeling in the connecting cilia, demonstrated that this phenotype was corrected with 1×AAV2-MYO7A or AAV5-MYO7A (FIG. 13 and FIGS. 21A-21D). This analysis also showed phenotype correction with 1:100 dilutions, although the data indicated that a full WT phenotype was not achieved (FIG. 13), despite WT levels of MYO7A (FIG. 11J and FIG. 11L), suggesting that some of the MYO7A may not be fully functional.

Figures 1, 14A:
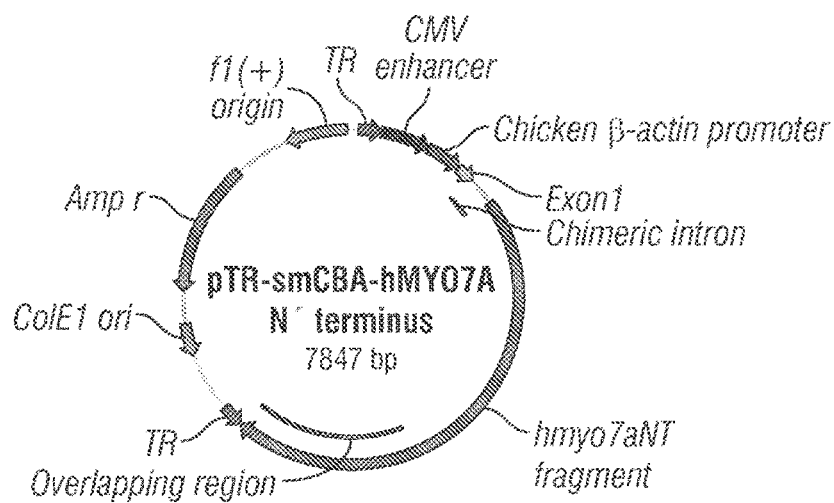
FIGS. 14A-14G show the expression of MYO7A from the overlapping AAV2-MYO7A dual vectors.
Figures 2, 14A:
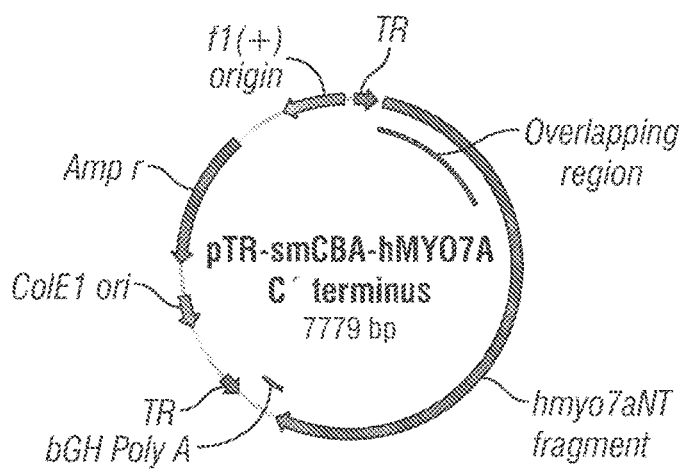

AAV2-MYO7A dual vector preparations. The preceding results demonstrate that a single AAV vector is capable of delivering functional MYO7A to the RPE and photoreceptor cells in vivo. Because the size of smCBA-MYO7A is ~2 kb larger than the nominal carrying capacity of an AAV (Grieger and Samulski, 2005), this transduction may involve undefined fragmentation of the smCBA-MYO7A cDNA followed by reassembly of plus and minus cDNA strands after delivery to the cell as shown for other large genes (Dong et al., 2010; Lai et al., 2010; Wu et al., 2010). To evaluate whether two AAV vectors containing defined, overlapping fragments of MYO7A cDNA (1365 bases) were also capable of mediating full-length MYO7A expression, an AAV2-based dual vector system (FIG. 14A-1 and FIG. 14A-2) was developed. Two separate lots of the AAV2-MYO7A (dual vector) were prepared, each containing equal concentrations of AAV2-smCBA-MYO7A(5'-half) and AAV2-MYO7A(3'-half). The titer of the first lot contained $2.5 \times 10^{12}$ particles/mL of each vector, and the second lot contained $4 \times 10^{12}$ particles/mL.

Figure 14B:
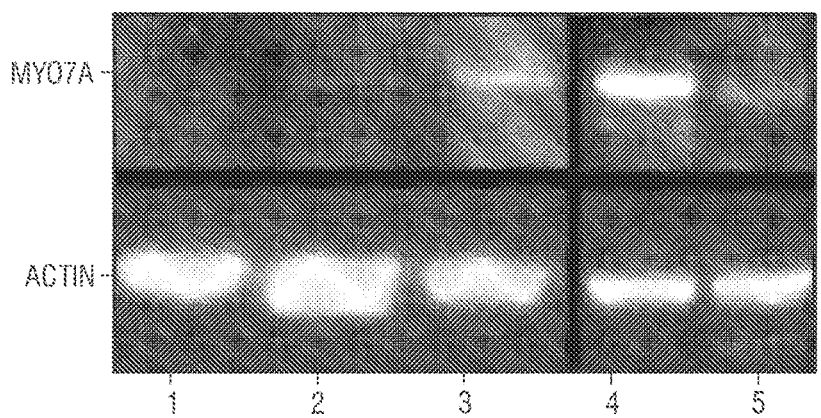

MYO7A expression with AAV2 dual vectors. Western blot analysis of primary cultures of MYO7A-null RPE cells, infected with AAV2-MYO7A (dual vector) of either lot, showed that the cells expressed a MYO7A-immunolabeled polypeptide of comparable mass to that of WT MYO7A (FIG. 14B). However, the expression level of MYO7A in the MYO7A-null RPE cells was significantly less than that found in primary cultures of MYO7A$^{+/-}$ RPE cells (cf. lanes 2 and 3 in FIG. 14B), unlike that found for the single AAV2 or AAV5 vectors (FIG. 10B). Quantitative analysis of western blots showed that MYO7A-null RPE cells, transduced with the single vectors (lx), AAV2-MYO7A or AAV5-MYO7A, or with AAV2-MYO7A (dual vector), expressed MYO7A at levels that were 82%, 111%, and 10%, respectively, of the level of MYO7A in MYO7A$^{+/-}$ RPE cells.

Figure 16:
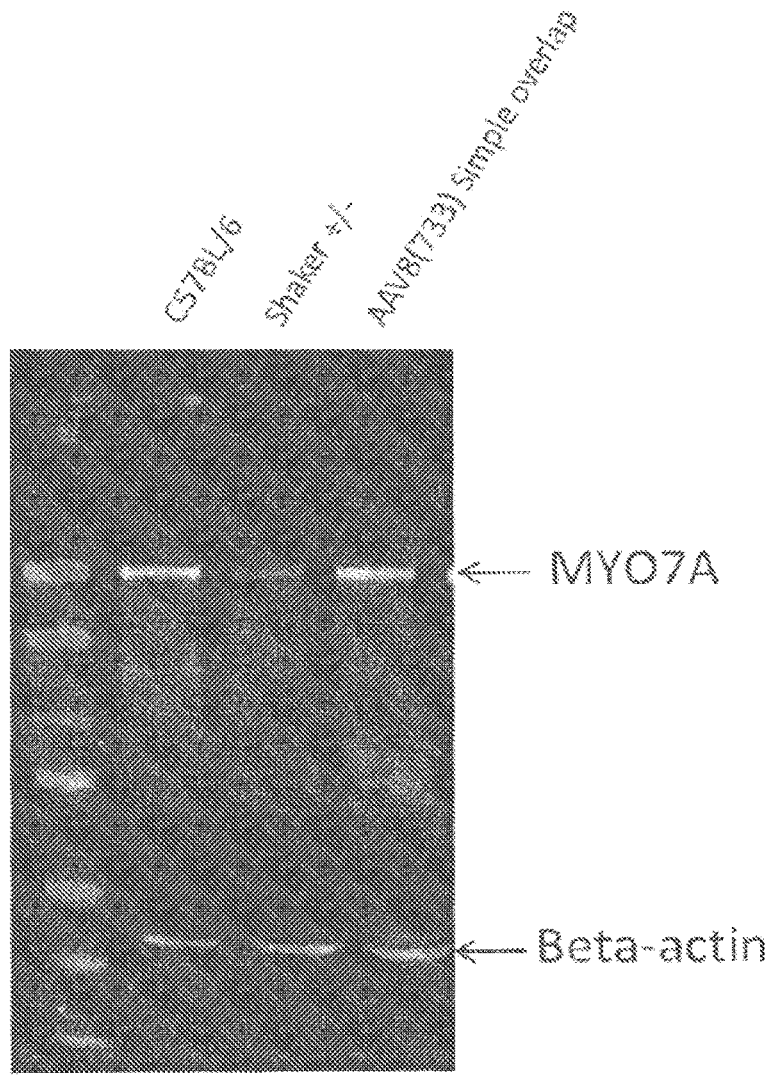
FIG. 16 shows the validation of dual AAV vectors for delivery of full-length MYO7A in vivo. Immunoblot showing expression of MYO7A in retinas of wild type (C57BL/6) mice (lane 1), heterozygous shaker-1$^{+/-}$ mice (lane 2) and shaker-1$^{-/-}$ mice injected with 'simple overlap' MYO7A vectors packaged in AAV8(733) vectors. Both N-terminal and C-terminal vectors of the 'simple overlap' system were injected at a concentration of $3\times10^{10}$ vector genomes/μL. Dual AAV vectors mediated expression of a MYO7A that was identical in size to that found in WT and shaker-1$^{+/-}$ mice. β-actin (visualized here in red) was used as a loading control to validate that equal amounts of protein were loaded in each well.

FIG. 16 is a Western blot using the same dual vector system as above except in an AAV8 serotype. FIG. 16 shows expression level of MYO7A using the dual vector system that was nearly equivalent to the wild type MYO7A expression level. While the reasons for the discrepancy are unclear, much better results were obtained by the inventors using the dual vector systems than were obtained by several outside collaborators. Wild-type-like levels of MYO7A expression were observed in shaker-1 retinas following injection with dual-AAV8(Y733F) vectors. Thus, very good expression of MYO7A with the dual AAV platform has been achieved.

Figure 14C:
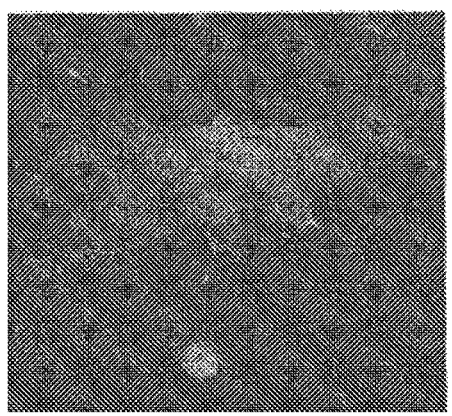
Figure 14D:
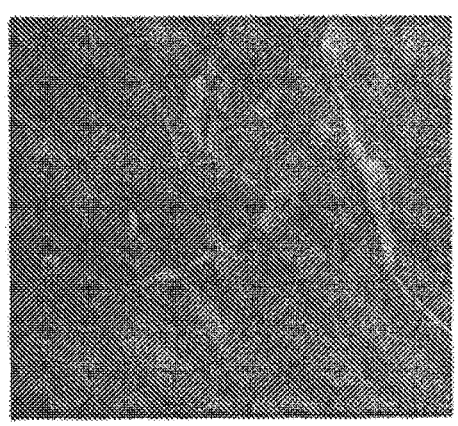
Figure 14E:
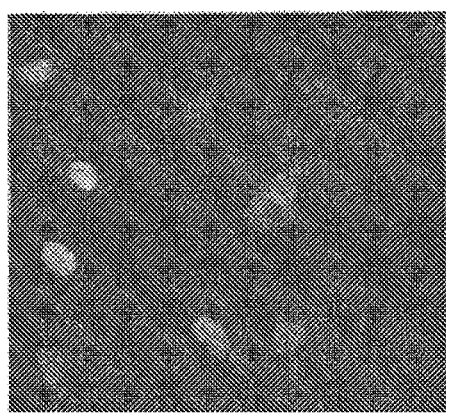
Figure 14F:
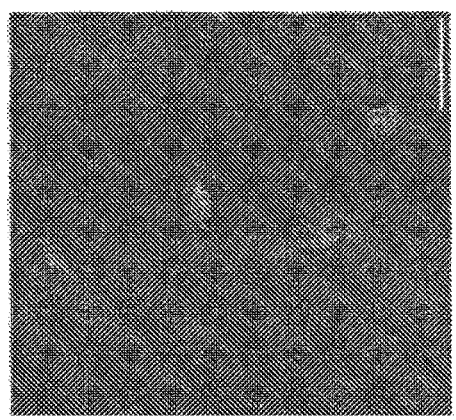
Figure 17A:
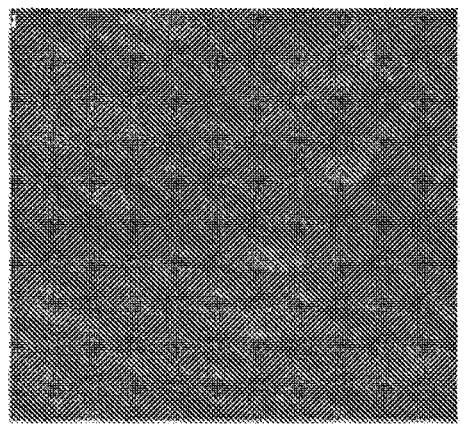
FIGS. 17A-17F show AAV-mediated MYO7A expression in ARPE-19 with fragmented vectors and the simple overlap dual-vector system. Cells were transduced with fragmented vectors: 1×AAV2-MYO7A (FIG. 17A), AAV5-MYO7A (FIG. 17B), 1/100 dilutions thereof (FIG. 17C and FIG. 17D), and the simple overlap dual-vector system: AAV2-MYO7A (dual) (FIG. 17F). Non-transduced cells were used as a control (FIG. 17E); lighter color, MYO7A; darker color, DAPI. Scale=10 μm.
Figure 17B:
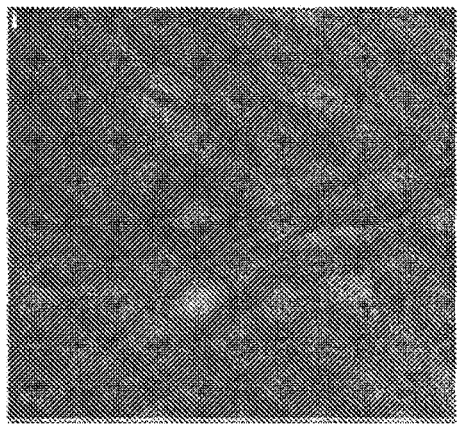
Figure 17C:
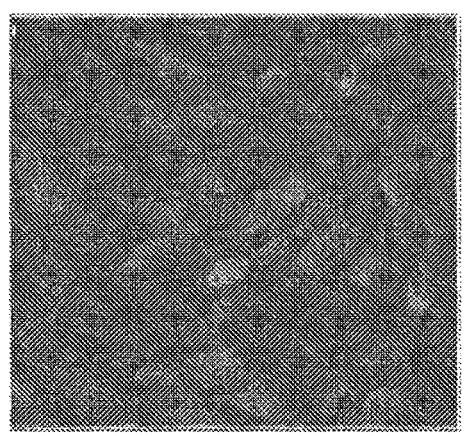
Figure 17D:
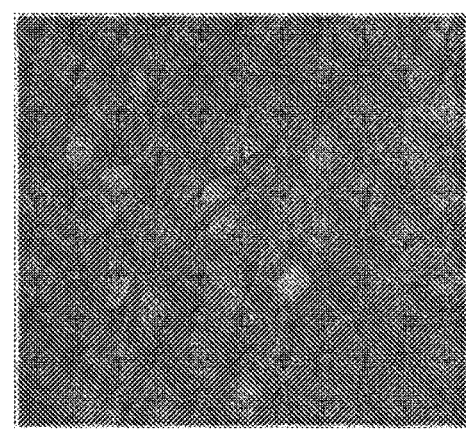
Figure 17E:
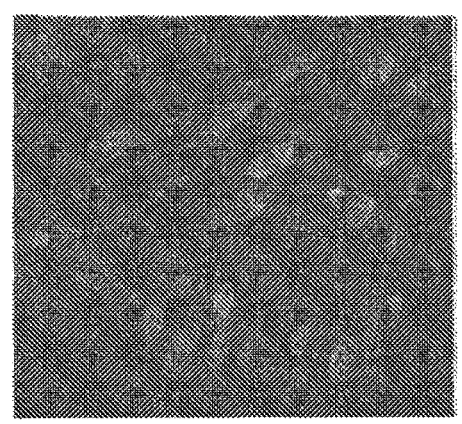
Figure 17F:
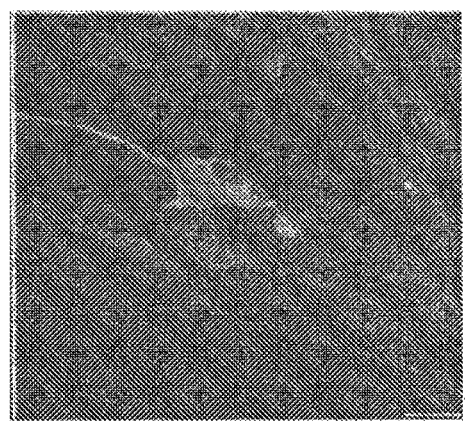

Immunofluorescence of primary MYO7A-null RPE cells, infected with AAV2-MYO7A (dual vector), showed that a few cells scattered throughout the culture exhibited very high levels of MYO7A, but all other cells contained insignificant levels (FIGS. 14C-14E). The cells overexpressing MYO7A typically had altered morphology, suggesting that the high levels of MYO7A may be toxic. Similarly, immunofluorescence of ARPE19 cells, infected with AAV2-MYO7A (dual vector), resulted in a minority of cells that were labeled intensely with MYO7A antibody, with most of the cells appearing to express only endogenous levels of MYO7A (FIG. 14F and FIG. 17F).

Figure 14G:
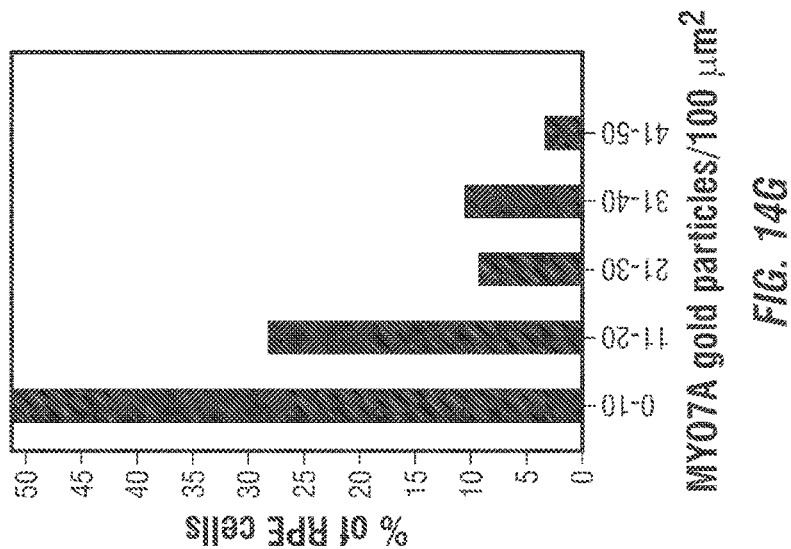

Immunolabeling of retinas, prepared 3 weeks after subretinal injection with AAV2-MYO7A (dual vector) of either lot, also showed only a few RPE cells and photoreceptor cells with clear MYO7A expression, although significant overexpression was not evident in this in vivo experiment. Immunogold particle counts from images of ultrathin sections were used to quantify the level of MYO7A expression in MYO7A-null retinas that were treated with the second lot of AAV2-MYO7A (dual vector). Within 1.4 mm of the injection site, MYO7A immunolabeling of the connecting cilium and pericilium of the photoreceptor cells was a mean of 48% of that in WT retinas: 2.8 particles/µm (n=3 retinas) compared with 6.5 particles/µm for WT (n=3 retinas). The mean label density in apical-basal sections of the RPE was 35% of that in WT retinas: 11 particles/100 µm$^2$ compared with 31 particles/100 µm$^2$ for WT. However, it was clear that these lower means were achieved by some cells expressing near normal amounts of MYO7A and the majority expressing very little; over half the cells had fewer than 10 particles/100 µm$^2$ (FIG. 14G).

Figure 15A:
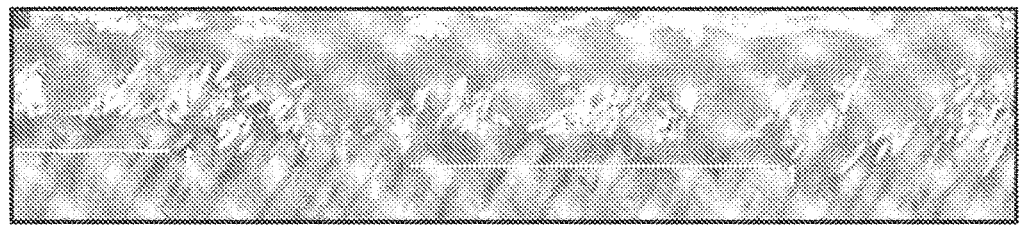
FIGS. 15A-15G illustrate correction of mutant phenotypes, following subretinal injections with AAV2-MYO7A (overlap dual).
Figure 15B:
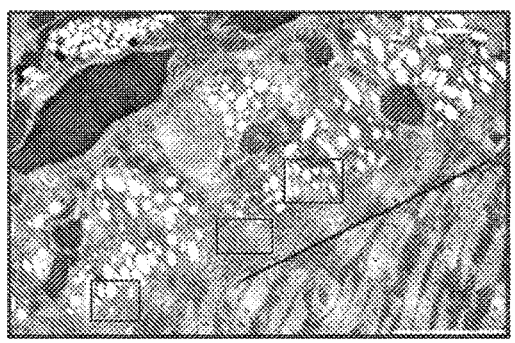
Figure 15C:
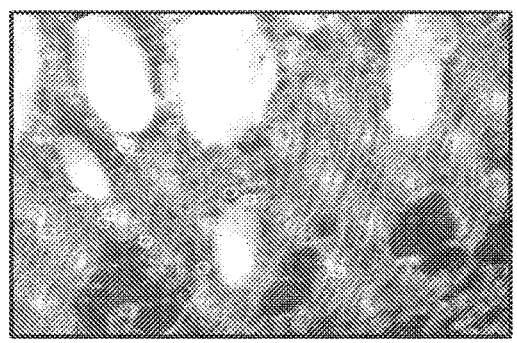
Figure 15D:
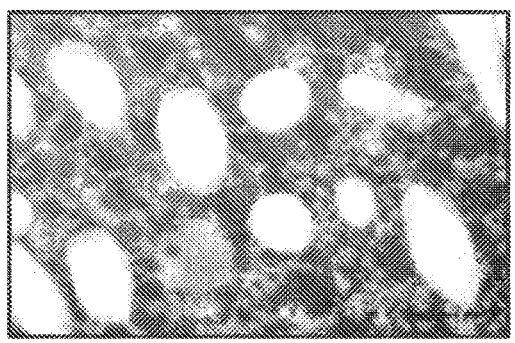
Figure 15E:
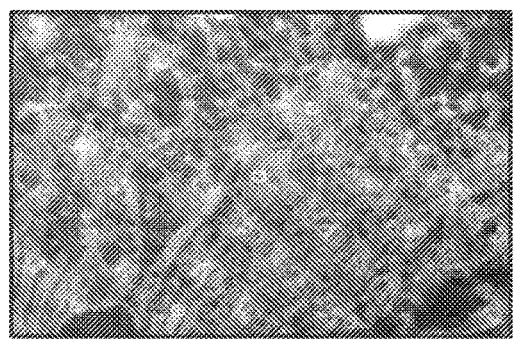

Correction of MYO7A-mutant phenotypes with AAV2 dual vectors. Eyes were analyzed for correction of melanosome localization and ciliary opsin distribution within 1.4 mm of the injection site. With either lot of AAV2-MYO7A (dual vector), some RPE cells (29% for lot 1 treatment [n=6 retinas], 35% for lot 2 treatment [n=9 retinas]) were observed to have a normal apical melanosome distribution, but most of the cells in this region retained the MYO7A-mutant phenotype, resulting in a mosaic effect (FIG. 15A) that contained a much lower proportion of corrected cells than that observed with a 1:100 dilution of either of the single vectors. The only correction observed in 3 eyes injected with a 1:10 dilution of AAV2-MYO7A (dual vector) (first lot), was in 18% of the RPE cells in one of the retinas. With full-strength of AAV2-MYO7A (dual vector) (second lot), opsin immunogold density averaged 3.2±0.4 particles/µm of cilium length, which was reduced from untreated retinas (4.2±0.8 particles/µm; p=0.003), but still greater than WT levels (1.1±0.2 particles/µm), suggesting that most cells were not corrected.

Figure 15F:
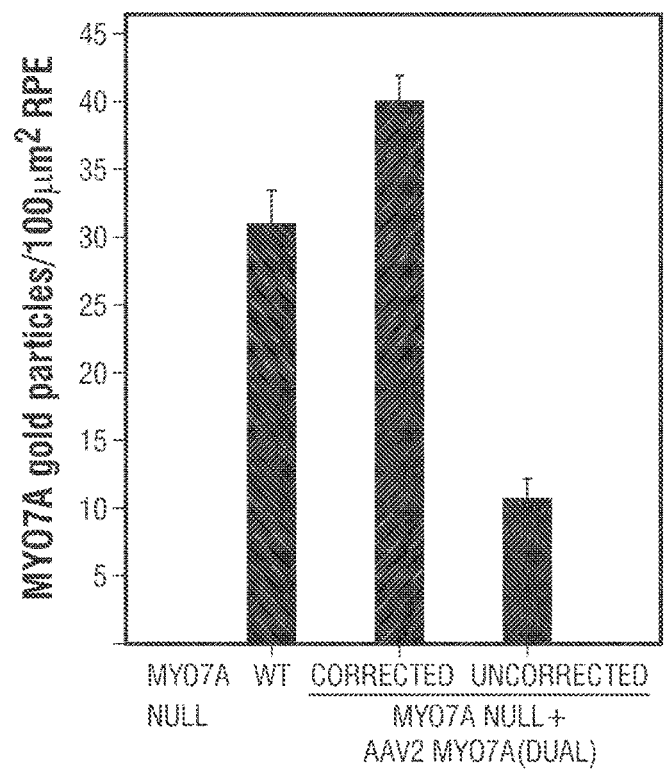
Figure 15G:
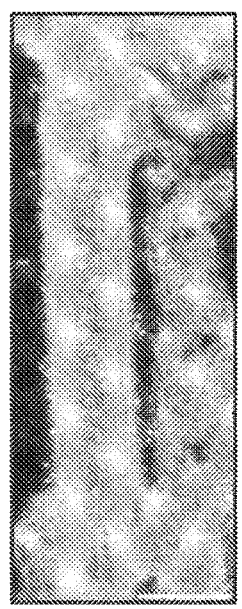

Using immunoelectron microscopy, a correlation between phenotype correction and the expression level of MYO7A was identified (determined by the mean concentration of immunogold particles in an apical-basal section of each RPE cell) (FIGS. 15B-15E). From the eyes injected with AAV2-MYO7A (dual vector) (second lot), it was shown that the corrected RPE cells contained a mean of 108% of the WT level of MYO7A (the minimum level was 82%). RPE cells that were not corrected contained a mean of 26% of the WT level of MYO7A (the maximum level was 92%). While these data showed that higher expression of MYO7A is correlated with phenotype correction (FIG. 15F), it also indicated that some of the labeled MYO7A protein was not functional, given that melanosomes are localized normally in mice that are heterozygous for the MYO7A-null allele and have only ~50% of the WT level of MYO7A.

Figure 23A:
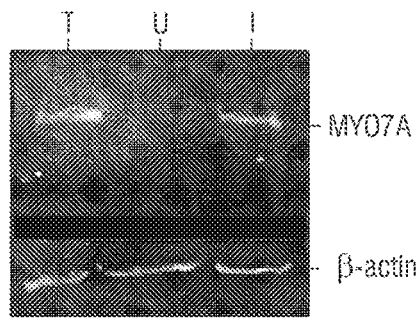
FIGS. 23A-23C show cells expressing human MYO7A after infection with the simple overlap vectors of the present disclosure.
Figure 23B:
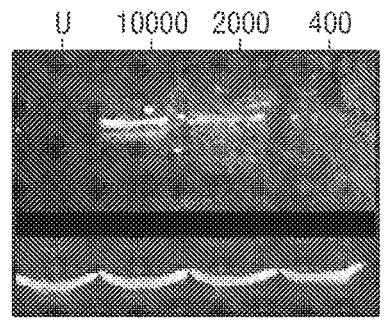
Figure 23C:
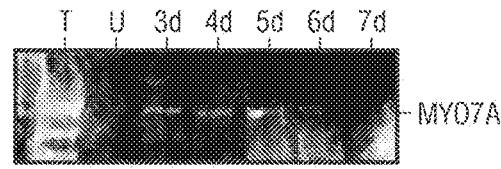

Expression of MYO7A with simple overlap vectors. AAV2-based simple overlap vectors were evaluated in vitro at a variety of MOIs to evaluate how the concentration of vector pairs related to MYO7A expression. How levels of MYO7A changed over time was also evaluated in infected cells. HEK293 cells were infected with simple overlap vector pairs packaged in AAV2(tripleY-F) vector (FIG. 23A). A preliminary co-infection with AAV2(tripleY-F) simple overlap vectors (MOI of 10,000 for each vector) indicated that MYO7A is expressed, and that migration of the protein on gel is identical to a full-length transfection control (FIG. 23A). Coinfection at MOIs of 400, 2000, and 10,000 of each vector shows that the efficiency of the simple overlap system is proportional to the amount of 5' and 3' vectors used (FIG. 23B). MYO7A expression increased as a function of incubation time up to 5 days post-injection in HEK293 cells (FIG. 23C). The visible expression decline was because of a reduction of viable cells in the culture vessel at the later times.

Figure 24:
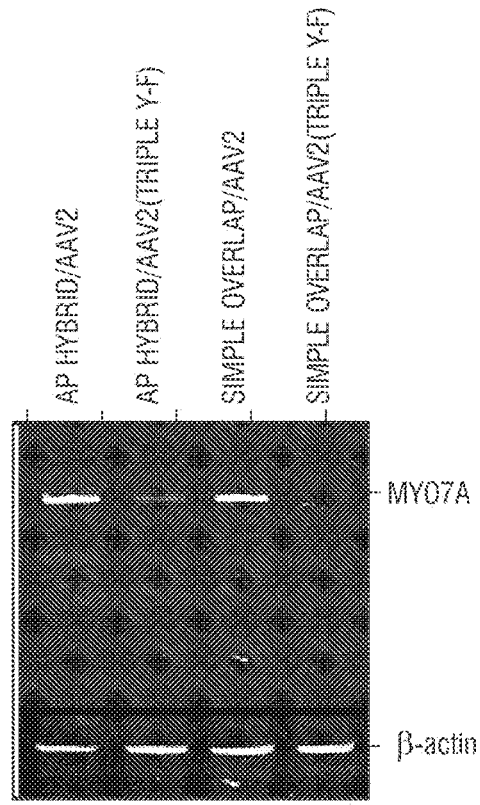
FIG. 24 shows the comparison of AAV2 and AAV2 (tripleY-F mutant capsid)-based vectors in HEK293 cells. Cells were infected with AP hybrid and simple overlap MYO7A dual vector platforms packaged in AAV2 or AAV2 (tripleY-F) at an MOI of 10,000 for each vector.

Comparison of fAAV-MYO7A to dual-AAV-MYO7A expression and evaluation of AA V serotype efficiency. Previously, it was shown that fragmented AAV encoding MYO7A was able to ameliorate the retinal phenotype of the shaker1 mouse (Colella et al., 2013; Lopes et al., 2013; Trapani et al., 2013). To provide a basis for comparison dual-AAV-vector expression was evaluated relative to fAAV in vitro. After infection in HEK293 cells, all dual vector systems expressed MYO7A more efficiently than fAAV (FIG. 24). The AP hybrid platform showed the strongest expression, followed by the simple overlap system.

Other studies have shown, in the context of a conventionally sized DNA payload, that the transduction efficiency and kinetics of AAV2(tripleY-F) vectors are increased relative to standard AAV2 both in vitro and in vivo (Li et al., 2010; Markusic et al., 2010; Ryals et al., 2011). The efficiency of AAV2 versus AAV2(tripleY-F) dual vectors was directly compared in HEK293 cells. Surprisingly, standard AAV2-mediated MYO7A expression was higher than that seen with titer-matched AAV2(tripleY-F) (FIG. 24). Identical results were obtained when comparing different AAV2 and AAV2(tripleY-F) dual vector preparation packaged with identical vector plasmid.

Figure 25A:
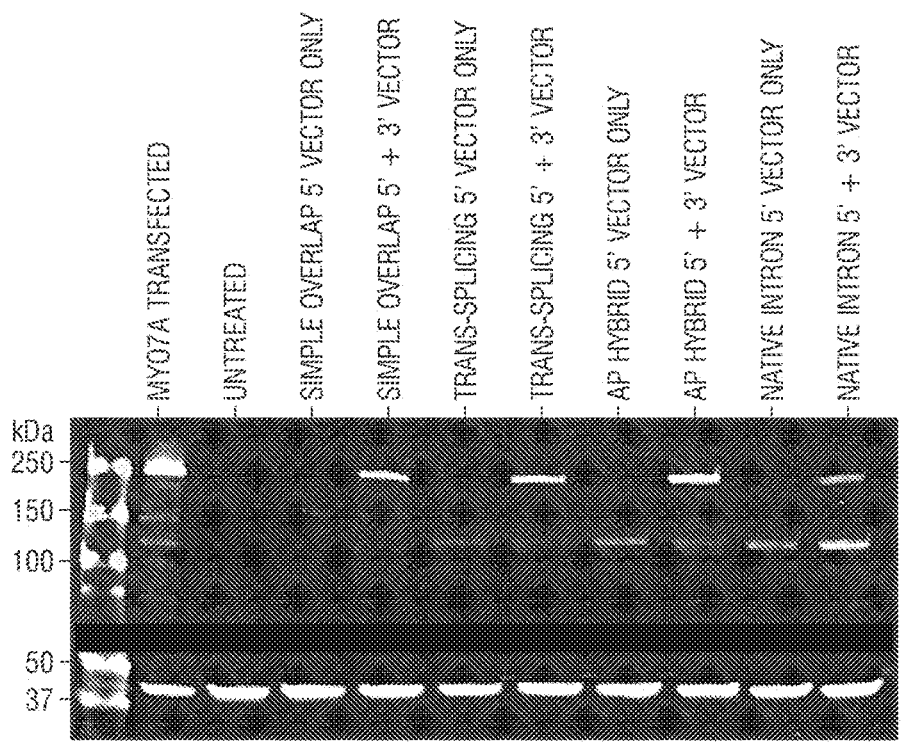
FIGS. 25A-25C show human MYO7A expressed in HEK293 cells. Cells were infected with AAV2-based vector platforms. For each of the dual vector systems, the corresponding 5' and 3' vectors (or the 5' vector alone) were used for infection. HEK293 cells transfected with MYO7A plasmid were used as a positive control. Cells were infected with the MYO7A dual vector pairs at an MOI of 10,000 for each vector. Protein samples were analyzed on Western blot with an antibody against MYO7A (FIG. 25A). Each dual vector platform's relative ability to promote reconstitution was compared by quantifying the amount of 5' vector-mediated truncated protein product in the presence or absence of the respective 3' vector (FIG. 25B). Full-length MYO7A expression mediated by dual vectors was quantified relative to transfection control (FIG. 25C).
Figure 25B:
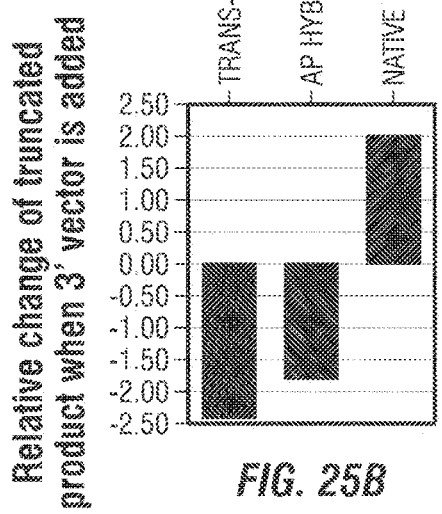
Figure 25C:
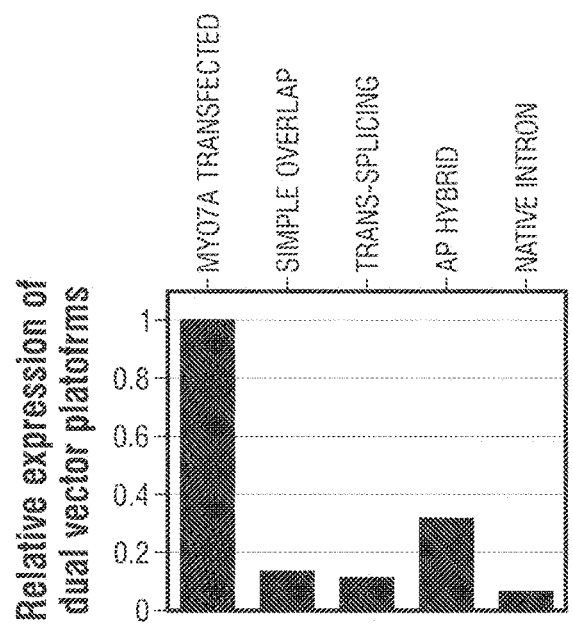

Comparison of relative efficiencies and specificity of full-length MYO7A expression. To quantitatively evaluate the relative expression efficiencies of the dual vector platforms and to assess specificity of full-length protein, HEK293 cells were infected with either the 5' and 3' AAV2-based vector pairs combined or the corresponding 5' vector alone. An additional hybrid vector pair was included that incorporated native MYO7A intronic sequence (intron 23) that served as overlapping sequence and provided appropriate splicing signals. All 5' vectors produced low amounts of a defined, less than full-length peptide detectable on Western blot with the exception of the simple overlap vector (FIG. 25A). However, the trans-splicing and the AP hybrid platforms revealed a distinct decrease of this undesired product when the 3' vector was added to the sample (FIG. 25A). The native intron hybrid platform also showed this secondary band on Western blots, again suggestive of a truncated protein originating from the 5' vector alone. In contrast to all other platforms tested, this band intensity increased with the addition of the 3' vector. Each platform's relative ability to promote reconstitution was compared by quantifying the amount of 5' vector-mediated truncated protein product in the presence or absence of the respective 3' vector (FIG. 25B). Full-length MYO7A expression on Western blot was then quantified relative to transfection control (FIG. 25C). AP hybrid-mediated MYO7A was the strongest followed by simple overlap, trans-splicing, and native intron hybrid (FIG. 25C).

Figure 26A:
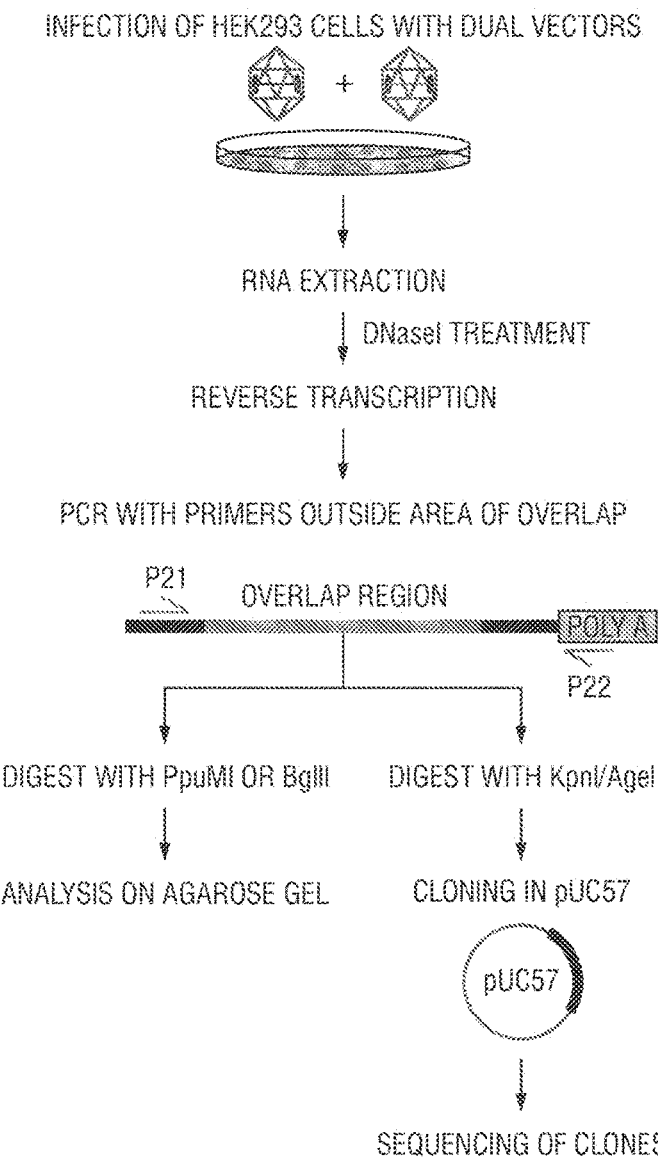
FIGS. 26A-26C show the ability of MYO7A dual vectors to recombine and properly restore coding sequence. The experimental plan is shown in FIG. 26A. HEK293 cells were infected with AAV2-based dual vector platforms, RNA was extracted, and gene-specific primers amplified the sequences using PCR. Control digests with BglII (B) and PpuMI (P) revealed the predicted banding pattern shown in FIGS. 26B-26C. Undigested (U) PCR product is shown as control and a DNA size marker for reference (M). Separately, products were digested with KpnI and AgeI, and then cloned into pUC57 for sequencing of the entire overlap region. Ten clones per vector platform were analyzed. M13 forward- and reverse-primers specific for the subclone vector were used to obtain sense and antisense reads (each 1,000 bp) resulting in 140 bp for which the sense and antisense reads overlapped (FIG. 26C; Table). PCR=polymerase chain reaction.
Figure 26B:
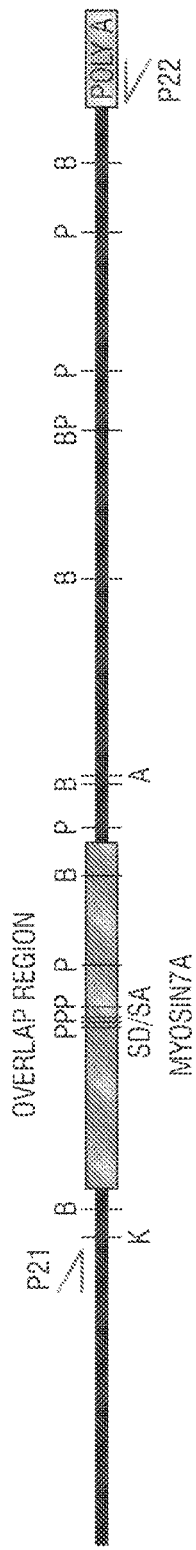
Figure 26C:
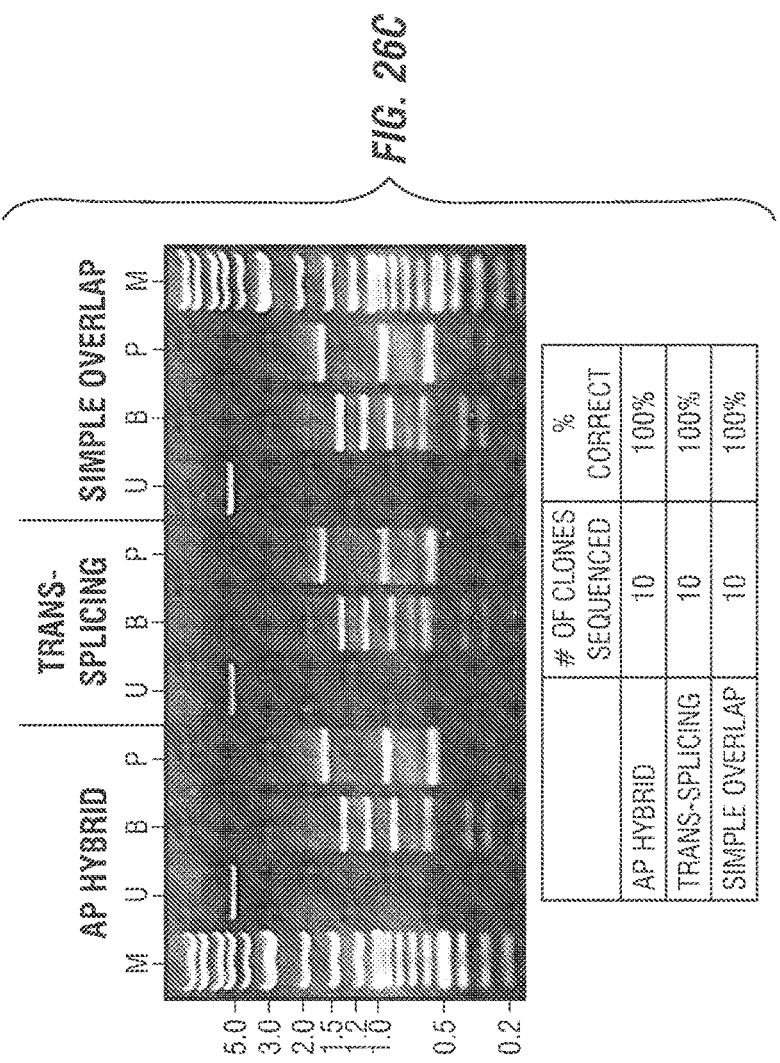
Figure 27A:
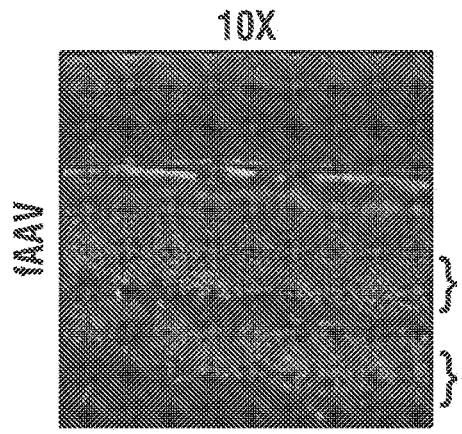
FIGS. 27A-27H show the dual vector-mediated MYO7A expression in vivo. C57BL/6J mice were injected subretinally with AAV2-based dual vectors containing a C-terminal hemagglutinin (HA) tag. Retinal protein expression was analyzed four weeks post-injection by immunohistochemistry and western blot. Ten-micron frozen retinal cross sections were stained with an antibody for HA and imaged at 10× (FIG. 27A, FIG. 27C, and FIG. 27E) and 60× (FIG. 27B, FIG. 27D, and FIG. 27F). An untreated C57BL/6J retina was also stained with an antibody against HA (FIG. 27G). Equal amounts of protein were separated on a 4-15% polyacrylamide gel and stained with an HA antibody (FIG. 27H). For comparison, endogenous MYO7A from C57BL/6J retina was probed with an antibody against MYO7A to confirm that HA-tagged MYO7A migrated at the appropriate size. RPE—retinal pigment epithelium, IS—inner segments, OS—outer segments, ONL—outer nuclear layer, INL—inner nuclear layer, GCL—ganglion cell layer, PR—photoreceptors. Nuclear (DAPI) stains are indicated with brackets ({}).
Figure 27B:
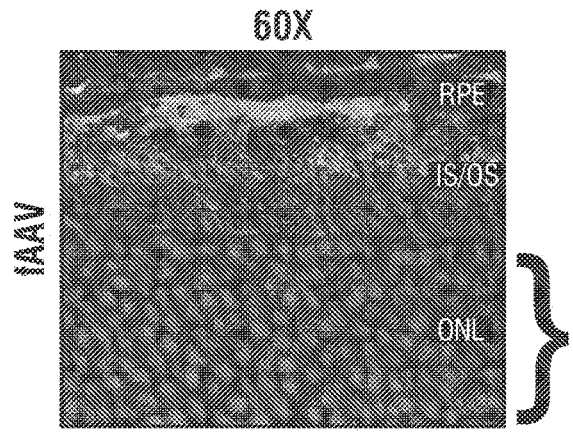
Figure 27C:
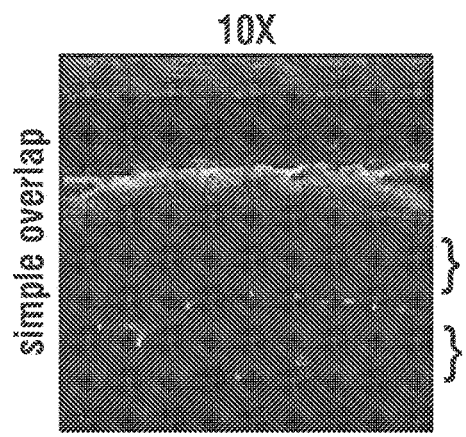
Figure 27D:
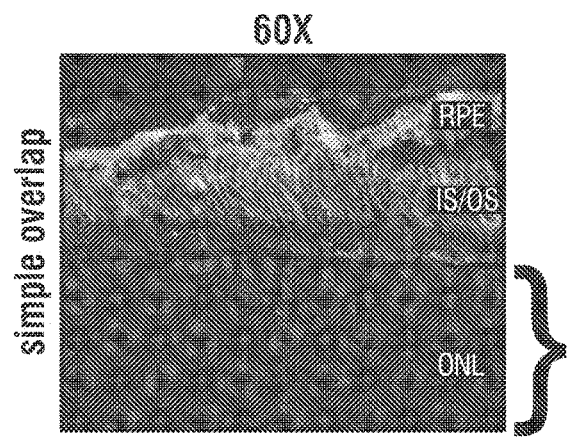
Figure 27E:
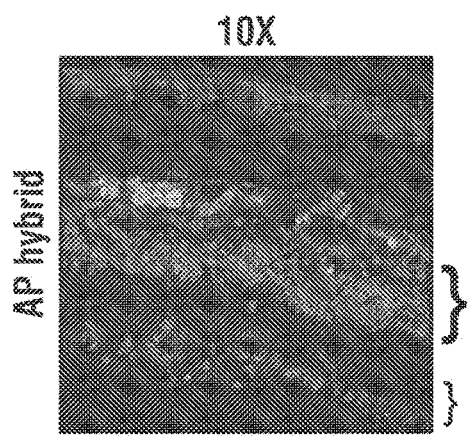
Figure 27F:
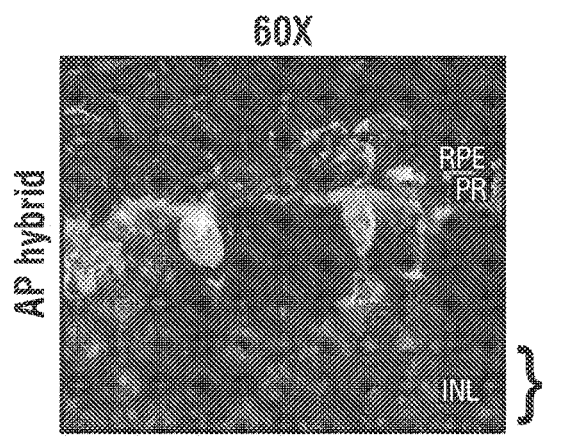
Figure 27G:
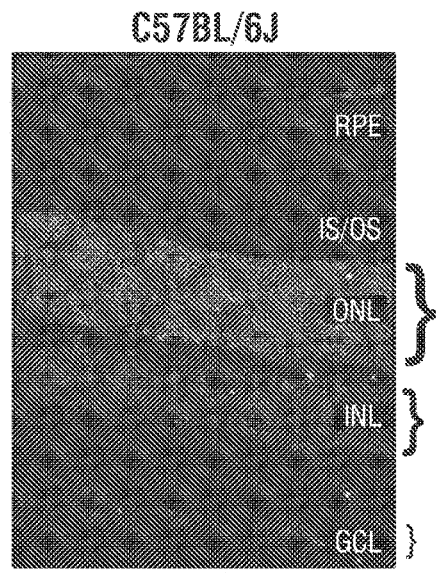
Figure 27H:
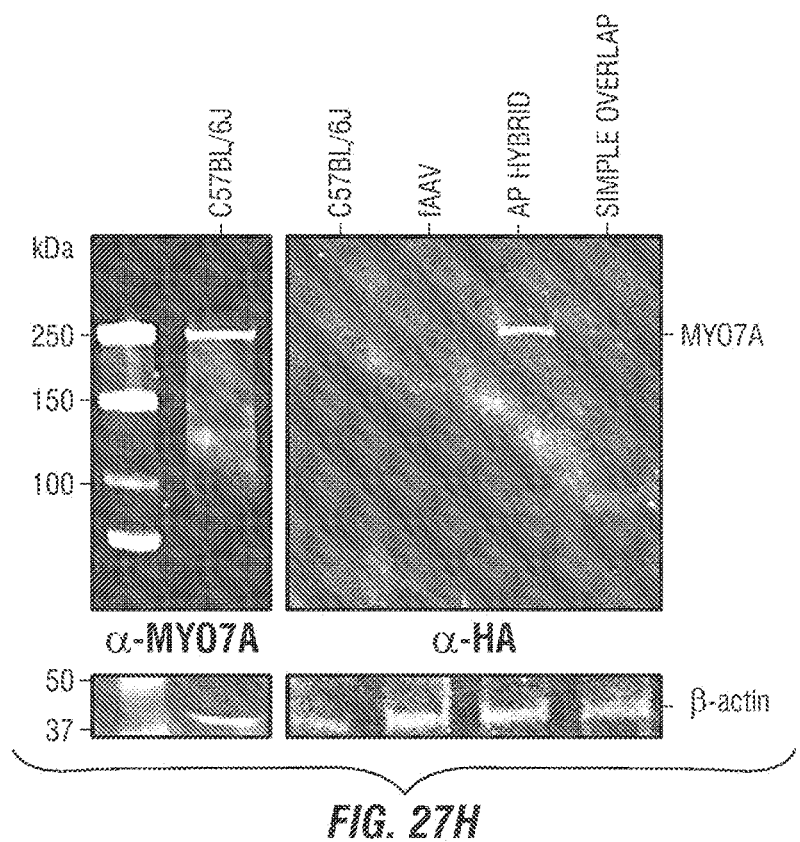

Characterization of the overlap/splice region of the expressed MYO7A. To characterize the fidelity of the mRNA arising from dual vectors, HEK293 cells were infected with dual vectors and RNA extracted, reverse transcribed, and subjected to PCR utilizing primers binding upstream of the overlap region and in the bGH polyA signal region producing a 4.5 kb PCR fragment (FIG. 26A). An identically treated sample not containing reverse transcriptase was used as control for chromosomal DNA contamination. Plasmid containing the full-length MYO7A coding sequence was used as positive control for PCR. A preliminary screen of AAV-mediated MYO7A mRNA was performed by analyzing the pattern of fragment migration on agarose gel following restriction endonuclease digests with PpuMI and BglII (FIG. 26A). Identical banding patterns, consistent with the predicted pattern (PpuMI: 1591, 876, 556, 548, 541, 238, 168, 42, and 36 bp; BglII: 1335, 1074, 827, 583, 360, 272, and 146 bp), were observed following digests of amplicons from each dual vector platform tested, indicating that no gross alterations (deletions/insertions) occurred as a consequence of either homologous recombination of vector pairs and/or RNA splicing (FIG. 26B). To further characterize the fidelity of the overlap region, a fragment containing the complete overlap area (1829 bp) was restricted and cloned into pUC57 (FIG. 26A). Sequencing results of 10 clones picked at random per vector platform revealed that the overlap region was 100% identical to the consensus/predicted MYO7A sequence (FIG. 26C). This indicated that, in the context of the simple overlap platform, homologous recombination was accurate. Additionally, in the context of trans-splicing vectors, accurate splicing occurred. Finally, for the AP hybrid vectors, a combination of accurate homologous recombination and/or splicing took place. To determine whether this protocol was capable of detecting aberrant sequence in reconstituted MYO7A, a sequence that contained either an insertion of a HindIII recognition site (TAGC) at position 2635 or a point mutation (T-C) at position 2381 was also generated.

MYO7A expression mediated by dual vectors in mouse retina. To investigate the expression of MYO7A from the two best performing dual vector platforms in vivo, C57BL/6J mice were subretinally injected with $1 \times 10^{10}$ vector genomes per eye of simple overlap and AP hybrid systems packaged in AAV8(733) and analyzed 4 weeks later by Western blot and immunohistochemistry. AAV8(733)-fAAV-MYO7A vector was also injected to provide a basis for comparison. To distinguish between endogenous MYO7A and exogenous expression mediated by vectors, sequence coding for an HA tag was added to the C prime terminus of the MYO7A cDNA in all constructs. Resulting retinas were immunostained for HA to reveal that fAAV vector along with both dual vector platforms mediated expression of MYO7A in photoreceptors and RPE. A recent report concluded that simple overlap vectors were more efficient for gene transfer to the RPE than photoreceptors (Trapani et al., 2013). Simple overlap-mediated MYO7A expression was observed in both RPE and photoreceptors. In contrast to previous results showing "spotty" MYO7A expression mediated by AAV2-based simple overlap vectors (Lopes et al., 2013), it was found, when packaged in AAV8(733), that simple overlap vectors mediated MYO7A expression in the majority of RPE and photoreceptor cells. Photoreceptor degeneration/outer nuclear layer thinning was apparent in eyes injected with the AP hybrid vector system. Despite the observed degeneration, AP hybrid-mediated MYO7A was clearly detected in residual PR cell bodies and RPE and was sufficient to be detected by immunoblot. By Western blot analysis using HA antibody, simple overlap-mediated MYO7A was present in just detectable amounts. In contrast, fAAV-mediated protein levels were insufficient to be detected in this assay. Using an antibody against MYO7A, immunoblot of WT mouse retina revealed that both endogenous MYO7A and dual vector-mediated, HA-tagged MYO7A migrated similarly.

Discussion

In this example, it was shown that dual AAV vectors with defined genetic payloads can be used to deliver a large transgene in vitro and in vivo. The initial experiments using the simplest of all dual vector platforms revealed that efficiency of AAV2-based simple overlap vectors is proportional to the amount of 5' and 3' vectors used and that MYO7A expression mediated by this system increased as a function of incubation time in HEK293 cells. Next, three distinct dual vector platforms were evaluated and compared to single, fragmented fAAV vector in vitro. All dual vectors analyzed drove higher levels of MYO7A expression than fAAV. Of all platforms tested, a hybrid vector system containing overlapping, recombinogenic sequence and splice donor/acceptor sites from the AP gene (AP hybrid) was the most efficient.

Regarding the specificity with which the dual vector platforms express the correct-sized gene product, it was noted in vitro that trans-splicing and hybrid dual vector platforms generated an additional band of lower molecular weight as detected by immunoblot (monoclonal antibody used was raised against the amino terminus MYO7A). The expression of this truncated protein product was much more pronounced for infections with 5' vectors alone.

After entry into the host cell, the virus capsid is removed and the single-stranded DNA payload is released. The ITRs carried by the single strand serve as primer for DNA polymerases to produce a double strand. The resulting circular intermediates consist mainly of monomers that, over time, convert into multimeric concatemers through intermolecular recombination (Duan et al., 1998; Yang et al., 1999). The dual vector systems of this disclosure utilize this strategy to achieve full-length protein expression. A limiting factor lies in the fact that the highly recombinogenic ITRs flanking the expression cassettes are identical in nature leading to a random recombination and consequently a random orientation of the vector parts relative to each other. This random recombination inevitably results in reduced efficiency because only concatemers that have the two vector parts in 5' to 3' orientation are able to express the full-length protein. This concatemerization over time is consistent with the observation that the amount of single-vector product is reduced in favor of the full-length protein when both 5' and 3' vectors are combined. Interestingly, the simple overlap system does not generate truncated product, even when only the 5' vector is used for infections. In contrast to the trans-splicing and hybrid vectors, there is virtually no intervening sequence between the end of the MYO7A coding sequence and the right-hand ITR.

Notably, in this disclosure, it was found that the sequence in the overlap region of all dual vectors tested in vitro was 100% identical to the consensus/predicted MYO7A sequence. This indicates that homologous recombination and/or splicing was accurate in each dual vector platform.

Similar to the in vitro results, the highest levels of MYO7A expression was found in retinas of mice subretinally injected with AAV8-based AP hybrid vectors (as assessed by probing for HA on Western blot). Notably, no truncated proteins were evident in retinas expressing either simple overlap or AP-hybrid mediated MYO7A. The reason for this observed difference remains to be elucidated but may involve differences in the DNA repair machinery that mediate recombination in actively dividing cells versus post-mitotic photoreceptors/RPE (Hirsch et al., 2013). Dual vector-mediated MYO7A-HA expression was observed in the photoreceptors and RPE of WT mice, locations where MYO7A is thought to have a functional role (Williams and Lopes, 2011). In eyes injected with AP hybrid vectors, marked thinning of the outer nuclear layer was observed. It has previously been shown that vector-mediated overexpression of MYO7A leads to retinal toxicity (Hashimoto et al. 2007). Taken together with the high efficiency of transduction observed in vitro for the AP hybrid platform, the most likely explanation for the observed pathology is excessive production of MYO7A. Despite the marked degeneration, significant amounts of AP hybrid-mediated, full-length MYO7A-HA were detected on Western blot. As high concentrations of vectors were used in these experiments, a simple solution to circumvent cytotoxicity could be to reduce vector genomes injected or replace the strong, ubiquitous smCBA promoter with an endogenous or homologous promoter, and/or a promoter with attenuated strength; or reduce expression of undesired products, like the observed protein expressed from the 5' vectors alone in vitro. However, it was noted that only full-size MYO7A-HA was apparent on Western blot of the AP hybrid-treated retina.

With the goal of developing an AAV-based treatment for USH1B, animal models of this disease have provided an abundance of useful information. Similar to previous observations that fAAV-MYO7A and simple-overlap, dual vectors were capable of restoring melanosome migration and opsin localization in the shaker1 mouse (Lopes et al., 2013), a recent study by an independent lab confirmed the usefulness of the vectors disclosed herein, when it was reported that they were capable of restoring the ultrastructural retinal phenotypes in the animal model. Notably, shaker1 mice lack retinal degeneration, and the severe functional abnormalities seen in USH1B patients (Liu et al., 1997). This fact renders in vivo analysis of therapeutic outcomes in the shaker retina problematic. Alternative animal models for evaluating a treatment for this devastating disease may be useful in adaptation of the present methods to human clinical use.

The results presented here also demonstrated that MYO7A can be efficiently expressed using dual-AAV-vector systems. The platforms containing overlapping elements, namely, the simple overlap system, and the AP hybrid system were both highly efficient. AP hybrid vectors showed the strongest expression of all systems tested, with little observable truncated protein in vitro and none observed in vivo. Simple overlap vectors showed good expression and were the most specific (no truncated protein products were observed) even when the 5'-only vector was used to infect cells. AAV has emerged as the preferred clinical vector and it efficiently transduces both photoreceptors and RPE. Because it has now been demonstrated that MYO7A sequence fidelity is preserved following recombination and/or splicing of dual-AAV-vector platforms and because only full-length MYO7A was detectable in mouse retinas injected with dual vectors, the dual-AAV-vector strategy presented herein represents a valid option for the treatment of retinal disorders associated with mutations in large genes such as USH1B.

Nucleotide Sequences of the Vectors Used in Examples 1-5

```
SEQ ID NO: 1 is the nucleotide sequence of the first generation front-half vector of the
overlap system (i.e., AAV-smCBA-hMYO7A-NTlong; "hMyo7a coding overlap vector A");
CTCCCTCTCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCC

ATCACTAGGGGTTCTCAGATCTGGCGCGCCCAATTCGGTACCCTAGTTATTAATAGTAATCA

ATTACGGGGTCATTAGTTCATAGCCCATATATGGAGTTCCGCGTTACATAACTTACGGTAAA

TGGCCCGCCTGGCTGACCGCCCAACGACCCCCGCCCATTGACGTCAATAATGACGTATGTTC

CCATAGTAACGCCAATAGGGACTTTCCATTGACGTCAATGGGTGGACTATTTACGGTAAAC

TGCCCACTTGGCAGTACATCAAGTGTATCATATGCCAAGTACGCCCCCTATTGACGTCAATG

ACGGTAAATGGCCCGCCTGGCATTATGCCCAGTACATGACCTTATGGGACTTTCCTACTTGG

CAGTACATCTACGTATTAGTCATCGCTATTACCATGGTCGAGGTGAGCCCACGTTCTGCTT

CACTCTCCCCATCTCCCCCCCCTCCCCACCCCCAATTTTGTATTTATTTATTTTTTAATTATTT

TGTGCAGCGATGGGGGCGGGGGGGGGGGGGGGCGCGCGCCAGGCGGGGCGGGGCGGGG

CGAGGGGCGGGGCGGGGCGAGGCGGAGAGGTGCGGCGGCAGCCAATCAGAGCGGCGCGC

TCCGAAAGTTTCCTTTTATGGCGAGGCGGCGGCGGCGGCGGCCCTATAAAAAGCGAAGCGC

GCGGCGGGCGGGAGTCGCTGCGCGCTGCCTTCGCCCCGTGCCCCGCTCCGCCGCCGCCTCG
```

-continued

```
CGCCGCCCGCCCCGGCTCTGACTGACCGCGTTACTCCCACAGGTGAGCGGGCGGGACGGCC
CTTCTCCTCCGGGCTGTAATTAGCGCTTGGTTTAATGACGGCTTGTTTCTTTTCTGTGGCTGC
GTGAAAGCCTTGAGGGGCTCCGGGAGCTAGAGCCTCTGCTAACCATGTTCATGCCTTCTTCT
TTTTCCTACAGCTCCTGGGCAACGTGCTGGTTATTGTGCTGTCTCATCATTTTGGCAAAGAA
TTCTAGCGGCCGCCACCATGGTGATTCTTCAGCAGGGGACCATGTGTGGATGGACCTGAG
ATTGGGGCAGGAGTTCGACGTGCCCATCGGGGCGGTGGTGAAGCTCTGCGACTCTGGGCAG
GTCCAGGTGGTGGATGATGAAGACAATGAACACTGGATCTCTCCGCAGAACGCAACGCACA
TCAAGCCTATGCACCCCACGTCGGTCCACGGCGTGGAGGACATGATCCGCCTGGGGGACCT
CAACGAGGCGGGCATCTTGCGCAACCTGCTTATCCGCTACCGGGACCACCTCATCTACACG
TATACGGGCTCCATCCTGGTGGCTGTGAACCCCTACCAGCTGCTCTCCATCTACTCGCCAGA
GCACATCCGCCAGTATACCAACAAGAAGATTGGGGAGATGCCCCCCCACATCTTTGCCATT
GCTGACAACTGCTACTTCAACATGAAACGCAACAGCCGAGACCAGTGCTGCATCATCAGTG
GGGAATCTGGGGCCGGGAAGACGGAGAGCACAAAGCTGATCCTGCAGTTCCTGGCAGCCA
TCAGTGGGCAGCACTCGTGGATTGAGCAGCAGGTCTTGGAGGCCACCCCCATTCTGGAAGC
ATTTGGGAATGCCAAGACCATCCGCAATGACAACTCAAGCCGTTTCGGAAAGTACATCGAC
ATCCACTTCAACAAGCGGGGCGCCATCGAGGGCGCGAAGATTGAGCAGTACCTGCTGGAA
AAGTCACGTGTCTGTCGCCAGGCCCTGGATGAAAGGAACTACCACGTGTTCTACTGCATGC
TGGAGGGTATGAGTGAGGATCAGAAGAAGAAGCTGGGCTTGGGCCAGGCCTCTGACTACA
ACTACTTGGCCATGGGTAACTGCATAACCTGTGAGGGCCGGGTGGACAGCCAGGAGTACGC
CAACATCCGCTCCGCCATGAAGGTGCTCATGTTCACTGACACCGAGAACTGGGAGATCTCG
AAGCTCCTGGCTGCCATCCTGCACCTGGGCAACCTGCAGTATGAGGCACGCACATTTGAAA
ACCTGGATGCCTGTGAGGTTCTCTTCTCCCCATCGCTGGCCACAGCTGCATCCCTGCTTGAG
GTGAACCCCCCAGACCTGATGAGCTGCCTGACTAGCCGCACCCTCATCACCCGCGGGGAGA
CGGTGTCCACCCCACTGAGCAGGGAACAGGCACTGGACGTGCGCGACGCCTTCGTAAAGGG
GATCTACGGGCGGCTGTTCGTGTGGATTGTGGACAAGATCAACGCAGCAATTTACAAGCCT
CCCTCCCAGGATGTGAAGAACTCTCGCAGGTCCATCGGCCTCCTGGACATCTTTGGGTTTGA
GAACTTTGCTGTGAACAGCTTTGAGCAGCTCTGCATCAACTTCGCCAATGAGCACCTGCAGC
AGTTCTTTGTGCGGCACGTGTTCAAGCTGGAGCAGGAGGAATATGACCTGGAGAGCATTGA
CTGGCTGCACATCGAGTTCACTGACAACCAGGATGCCCTGGACATGATTGCCAACAAGCCC
ATGAACATCATCTCCCTCATCGATGAGGAGAGCAAGTTCCCCAAGGGCACAGACACCACCA
TGTTACACAAGCTGAACTCCCAGCACAAGCTCAACGCCAACTACATCCCCCCCAAGAACAA
CCATGAGACCCAGTTTGGCATCAACCATTTTGCAGGCATCGTCTACTATGAGACCCAAGGCT
TCCTGGAGAAGAACCGAGACACCCTGCATGGGGACATTATCCAGCTGGTCCACTCCTCCAG
GAACAAGTTCATCAAGCAGATCTTCCAGGCCGATGTCGCCATGGGCGCCGAGACCAGGAAG
CGCTCGCCCACACTTAGCAGCCAGTTCAAGCGGTCACTGGAGCTGCTGATGCGCACGCTGG
GTGCCTGCCAGCCCTTCTTTGTGCGATGCATCAAGCCCAATGAGTTCAAGAAGCCCATGCTG
TTCGACCGGCACCTGTGCGTGCGCCAGCTGCGGTACTCAGGAATGATGGAGACCATCCGAA
TCCGCCGAGCTGGCTACCCCATCCGCTACAGCTTCGTAGAGTTTGTGGAGCGGTACCGTGTG
CTGCTGCCAGGTGTGAAGCCGGCCTACAAGCAGGGCGACCTCCGCGGGACTTGCCAGCGCA
TGGCTGAGGCTGTGCTGGGCACCCACGATGACTGGCAGATAGGCAAAACCAAGATCTTTCT
GAAGGACCACCATGACATGCTGCTGGAAGTGGAGCGGGACAAAGCCATCACCGACAGAGT
```

```
CATCCTCCTTCAGAAAGTCATCCGGGGATTCAAAGACAGGTCTAACTTTCTGAAGCTGAAG

AACGCTGCCACACTGATCCAGAGGCACTGGCGGGGTCACAACTGTAGGAAGAACTACGGG

CTGATGCGTCTGGGCTTCCTGCGGCTGCAGGCCCTGCACCGCTCCCGGAAGCTGCACCAGC

AGTACCGCCTGGCCCGCCAGCGCATCATCCAGTTCCAGGCCCGCTGCCGCGCCTATCTGGTG

CGCAAGGCCTTCCGCCACCGCCTCTGGGCTGTGCTCACCGTGCAGGCCTATGCCCGGGGCA

TGATCGCCCGCAGGCTGCACCAACGCCTCAGGGCTGAGTATCTGTGGCGCCTCGAGGCTGA

GAAAATGCGGCTGGCGGAGGAAGAGAAGCTTCGGAAGGAGATGAGCGCCAAGAAGGCCA

AGGAGGAGGCCGAGCGCAAGCATCAGGAGCGCCTGGCCCAGCTGGCTCGTGAGGACGCTG

AGCGGGAGCTGAAGGAGAAGGAGGCCGCTCGGCGGAAGAAGGAGCTCCTGGAGCAGATG

GAAAGGGCCCGCCATGAGCCTGTCAATCACTCAGACATGGTGGACAAGATGTTTGGCTTCC

TGGGGACTTCAGGTGGCCTGCCAGGCCAGGAGGGCCAGGCACCTAGTGGCTTTGAGGACCT

GGAGCGAGGGCGGAGGGAGATGGTGGAGGAGGACCTGGATGCAGCCCTGCCCCTGCCTGA

CGAGGATGAGGAGGACCTCTCTGAGTATAAATTTGCCAAGTTCGCGGCCACCTACTTCCAG

GGGACAACCACGCACTCCTACACCCGGCGGCCACTCAAACAGCCACTGCTCTACCATGACG

ACGAGGGTGACCAGCTGGCAGCCCTGGCGGTCTGGATCACCATCCTCCGCTTCATGGGGGA

CCTCCCTGAGCCCAAGTACCACACAGCCATGAGTGATGGCAGTGAGAAGATCCCTGTGATG

ACCAAGATTTATGAGACCCTGGGCAAGAAGACGTACAAGAGGGAGCTGCAGGCCCTGCAG

GGCGAGGGCGAGGCCCAGCTCCCCGAGGGCCAGAAGAAGAGCAGTGTGAGGCACAAGCTG

GTGCATTTGACTCTGAAAAAGAAGTCCAAGCTCACAGAGGAGGTGACCAAGAGGCTGCAT

GACGGGGAGTCCACAGTGCAGGGCAACAGCATGCTGGAGGACCGGCCCACCTCCAACCTG

GAGAAGCTGCACTTCATCATCGGCAATGGCATCCTGCGGCCAGCACTCCGGGACGAGATCT

ACTGCCAGATCAGCAAGCAGCTGACCCACAACCCCTCCAAGAGCAGCTATGCCCGGGGCTG

GATTCTCGTGTCTCTCTGCGTGGGCTGTTTCGCCCCCTCCGAGAAGTTTGTCAAGTACCTGC

GGAACTTCGCTAGCGGGCACTAGTCCGTCGACTGTTAATTAAGCATGCTGGGGAGAGATCT

AGGAAACCCCTAGTGATGGAGTTGGCCACTCCCTCTCTGCGCGCTCGCTCGCTCACTGAGGC

CGGGCGACCAAAGGTCGCCCGACGCCCGGGCTTTGCCCGGGCGGCCTCAGTGAGCGAGCG

AGCGCGCAGAGAGGGAG
```

SEQ ID NO: 2 is the nucleotide sequence of the first generation back-half vector of the overlap system (i.e., AAV-hMYO7A-CTlong.HA; "hMyo7a coding overlap vector B");

```
CTCCCTCTCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCC

ATCACTAGGGGTTCAGATCTGGCGCGCCCAATTGGCTTCGAATTCTAGCGGCCGCTGCTTAA

GCAGGTCTAACTTTCTGAAGCTGAAGAACGCTGCCACACTGATCCAGAGGCACTGGCGGGG

TCACAACTGTAGGAAGAACTACGGGCTGATGCGTCTGGGCTTCCTGCGGCTGCAGGCCCTG

CACCGCTCCCGGAAGCTGCACCAGCAGTACCGCCTGGCCCGCCAGCGCATCATCCAGTTCC

AGGCCCGCTGCCGCGCCTATCTGGTGCGCAAGGCCTTCCGCCACCGCCTCTGGGCTGTGCTC

ACCGTGCAGGCCTATGCCCGGGGCATGATCGCCCGCAGGCTGCACCAACGCCTCAGGGCTG

AGTATCTGTGGCGCCTCGAGGCTGAGAAAATGCGGCTGGCGGAGGAAGAGAAGCTTCGGA

AGGAGATGAGCGCCAAGAAGGCCAAGGAGGAGGCCGAGCGCAAGCATCAGGAGCGCCTG

GCCCAGCTGGCTCGTGAGGACGCTGAGCGGGAGCTGAAGGAGAAGGAGGCCGCTCGGCGG

AAGAAGGAGCTCCTGGAGCAGATGGAAAGGGCCCGCCATGAGCCTGTCAATCACTCAGAC
```

-continued

```
ATGGTGGACAAGATGTTTGGCTTCCTGGGGACTTCAGGTGGCCTGCCAGGCCAGGAGGGCC

AGGCACCTAGTGGCTTTGAGGACCTGGAGCGAGGGCGGAGGGAGATGGTGGAGGAGGACC

TGGATGCAGCCCTGCCCCTGCCTGACGAGGATGAGGAGGACCTCTCTGAGTATAAATTTGC

CAAGTTCGCGGCCACCTACTTCCAGGGGACAACCACGCACTCCTACACCCGGCGGCCACTC

AAACAGCCACTGCTCTACCATGACGACGAGGGTGACCAGCTGGCAGCCCTGGCGGTCTGGA

TCACCATCCTCCGCTTCATGGGGGACCTCCCTGAGCCCAAGTACCACACAGCCATGAGTGA

TGGCAGTGAGAAGATCCCTGTGATGACCAAGATTTATGAGACCCTGGGCAAGAAGACGTAC

AAGAGGGAGCTGCAGGCCCTGCAGGGCGAGGGCGAGGCCCAGCTCCCCGAGGGCCAGAAG

AAGAGCAGTGTGAGGCACAAGCTGGTGCATTTGACTCTGAAAAAGAAGTCCAAGCTCACA

GAGGAGGTGACCAAGAGGCTGCATGACGGGGAGTCCACAGTGCAGGGCAACAGCATGCTG

GAGGACCGGCCCACCTCCAACCTGGAGAAGCTGCACTTCATCATCGGCAATGGCATCCTGC

GGCCAGCACTCCGGGACGAGATCTACTGCCAGATCAGCAAGCAGCTGACCCACAACCCCTC

CAAGAGCAGCTATGCCCGGGGCTGGATTCTCGTGTCTCTCTGCGTGGGCTGTTTCGCCCCCT

CCGAGAAGTTTGTCAAGTACCTGCGGAACTTCATCCACGGGGGCCCGCCCGGCTACGCCCC

GTACTGTGAGGAGCGCCTGAGAAGGACCTTTGTCAATGGGACACGGACACAGCCGCCCAGC

TGGCTGGAGCTGCAGGCCACCAAGTCCAAGAAGCCAATCATGTTGCCCGTGACATTCATGG

ATGGGACCACCAAGACCCTGCTGACGGACTCGGCAACCACGGCCAAGGAGCTCTGCAACG

CGCTGGCCGACAAGATCTCTCTCAAGGACCGGTTCGGGTTCTCCCTCTACATTGCCCTGTTT

GACAAGGTGTCCTCCCTGGGCAGCGGCAGTGACCACGTCATGGACGCCATCTCCCAGTGCG

AGCAGTACGCCAAGGAGCAGGGCGCCCAGGAGCGCAACGCCCCCTGGAGGCTCTTCTTCCG

CAAAGAGGTCTTCACGCCCTGGCACAGCCCCTCCGAGGACAACGTGGCCACCAACCTCATC

TACCAGCAGGTGGTGCGAGGAGTCAAGTTTGGGGAGTACAGGTGTGAGAAGGAGGACGAC

CTGGCTGAGCTGGCCTCCCAGCAGTACTTTGTAGACTATGGCTCTGAGATGATCCTGGAGCG

CCTCCTGAACCTCGTGCCCACCTACATCCCCGACCGCGAGATCACGCCCCTGAAGACGCTG

GAGAAGTGGGCCCAGCTGGCCATCGCCGCCCACAAGAAGGGGATTTATGCCCAGAGGAGA

ACTGATGCCCAGAAGGTCAAAGAGGATGTGGTCAGTTATGCCCGCTTCAAGTGGCCCTTGC

TCTTCTCCAGGTTTTATGAAGCCTACAAATTCTCAGGCCCCAGTCTCCCCAAGAACGACGTC

ATCGTGGCCGTCAACTGGACGGGTGTGTACTTTGTGGATGAGCAGGAGCAGGTACTTCTGG

AGCTGTCCTTCCCAGAGATCATGGCCGTGTCCAGCAGCAGGGGAGCGAAAACGACGGCCCC

CAGCTTCACGCTGGCCACCATCAAGGGGGACGAATACACCTTCACCTCCAGCAATGCTGAG

GACATTCGTGACCTGGTGGTCACCTTCCTAGAGGGGCTCCGGAAGAGATCTAAGTATGTTG

TGGCCCTGCAGGATAACCCCAACCCCGCAGGCGAGGAGTCAGGCTTCCTCAGCTTTGCCAA

GGGAGACCTCATCATCCTGGACCATGACACGGGCGAGCAGGTCATGAACTCGGGCTGGGCC

AACGGCATCAATGAGAGGACCAAGCAGCGTGGGGACTTCCCCACCGACAGTGTGTACGTCA

TGCCCACTGTCACCATGCCACCGCGGGAGATTGTGGCCCTGGTCACCATGACTCCCGATCA

GAGGCAGGACGTTGTCCGGCTCTTGCAGCTGCGAACGGCGGAGCCCGAGGTGCGTGCCAAG

CCCTACACGCTGGAGGAGTTTTCCTATGACTACTTCAGGCCCCCCACCCAAGCACACGCTGA

GCCGTGTCATGGTGTCCAAGGCCCGAGGCAAGGACCGGCTGTGGAGCCACACGCGGGAAC

CGCTCAAGCAGGCGCTGCTCAAGAAGCTCCTGGGCAGTGAGGAGCTCTCGCAGGAGGCCTG

CCTGGCCTTCATTGCTGTGCTCAAGTACATGGGCGACTACCCGTCCAAGAGGACACGCTCC

GTCAACGAGCTCACCGACCAGATCTTTGAGGGTCCCCTGAAAGCCGAGCCCCTGAAGGACG
```

```
AGGCATATGTGCAGATCCTGAAGCAGCTGACCGACAACCACATCAGGTACAGCGAGGAGC

GGGGTTGGGAGCTGCTCTGGCTGTGCACGGGCCTTTTCCCACCCAGCAACATCCTCCTGCCC

CACGTGCAGCGCTTCCTGCAGTCCCGAAAGCACTGCCCACTCGCCATCGACTGCCTGCAAC

GGCTCCAGAAAGCCCTGAGAAACGGGTCCCGGAAGTACCCTCCGCACCTGGTGGAGGTGG

AGGCCATCCAGCACAAGACCACCCAGATTTTCCACAAAGTCTACTTCCCTGATGACACTGA

CGAGGCCTTCGAAGTGGAGTCCAGCACCAAGGCCAAGGACTTCTGCCAGAACATCGCCACC

AGGCTGCTCCTCAAGTCCTCAGAGGGATTCAGCCTCTTTGTCAAAATTGCAGACAAGGTCAT

CAGCGTTCCTGAGAATGACTTCTTCTTTGACTTTGTTCGACACTTGACAGACTGGATAAAGA

AAGCTCGGCCCATCAAGGACGGAATTGTGCCCTCACTCACCTACCAGGTGTTCTTCATGAA

GAAGCTGTGGACCACCACGGTGCCAGGGAAGGATCCCATGGCCGATTCCATCTTCCACTAT

TACCAGGAGTTGCCCAAGTATCTCCGAGGCTACCACAAGTGCACGCGGGAGGAGGTGCTGC

AGCTGGGGCGCTGATCTACAGGGTCAAGTTCGAGGAGGACAAGTCCTACTTCCCCAGCAT

CCCCAAGCTGCTGCGGGAGCTGGTGCCCCAGGACCTTATCCGGCAGGTCTCACCTGATGAC

TGGAAGCGGTCCATCGTCGCCTACTTCAACAAGCACGCAGGGAAGTCCAAGGAGGAGGCC

AAGCTGGCCTTCCTGAAGCTCATCTTCAAGTGGCCCACCTTTGGCTCAGCCTTCTTCGAGGT

GAAGCAAACTACGGAGCCAAACTTCCCTGAGATCCTCCTAATTGCCATCAACAAGTATGGG

GTCAGCCTCATCGATCCCAAAACGAAGGATATCCTCACCACTCATCCCTTCACCAAGATCTC

CAACTGGAGCAGCGGCAACACCTACTTCCACATCACCATTGGGAACTTGGTGCGCGGGAGC

AAACTGCTCTGCGAGACGTCACTGGGCTACAAGATGGATGACCTCCTGACTTCCTACATTA

GCCAGATGCTCACAGCCATGAGCAAACAGCGGGGCTCCAGGAGCGGCAAGTACCCTTACG

ATGTACCGGATTACGCATGAGGTACCAAGGGCGAATTCTGCAGTCGACTAGAGCTCGCTGA

TCAGCCTCGACTGTGCCTTCTAGTTGCCAGCCATCTGTTGTTTGCCCCTCCCCCGTGCCTTCC

TTGACCCTGGAAGGTGCCACTCCCACTGTCCTTTCCTAATAAAATGAGGAAATTGCATCGCA

TTGTCTGAGTAGGTGTCATTCTATTCTGGGGGGTGGGGTGGGGCAGGACAGCAAGGGGGAG

GATTGGGAAGACAATAGCAGGCATGCTGGGGAGAGATCTGAGGACTAGTCCGTCGACTGTT

AATTAAGCATGCTGGGGAGAGATCTAACCCCTAGTGATGGAGTTGGCCACTCCCTCTCTGC

GCGCTCGCTCGCTCACTGAGGCCGGGCGACCAAAGGTCGCCCGACGCCCGGGCTTTGCCCG

GGCGGCCTCAGTGAGCGAGCGAGCGCGCAGAGAGGGAG

SEQ ID NO: 3 is the nucleotide sequence of the front-half vector of the exon 23/24 hybrid
vector system (i.e., AAV-smCBA-hMYO7ANT-APSD-ApHead);
CTCCCTCTCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCC

ATCACTAGGGGTTCTCAGATCTGGCGCGCCCAATTCGGTACCCTAGTTATTAATAGTAATCA

ATTACGGGGTCATTAGTTCATAGCCCATATATGGAGTTCCGCGTTACATAACTTACGGTAAA

TGGCCCGCCTGGCTGACCGCCCAACGACCCCCGCCCATTGACGTCAATAATGACGTATGTTC

CCATAGTAACGCCAATAGGGACTTTCCATTGACGTCAATGGGTGGACTATTTACGGTAAAC

TGCCCACTTGGCAGTACATCAAGTGTATCATATGCCAAGTACGCCCCCTATTGACGTCAATG

ACGGTAAATGGCCCGCCTGGCATTATGCCCAGTACATGACCTTATGGGACTTTCCTACTTGG

CAGTACATCTACGTATTAGTCATCGCTATTACCATGGTCGAGGTGAGCCCCACGTTCTGCTT

CACTCTCCCCATCTCCCCCCCCTCCCCACCCCCAATTTTGTATTTATTTATTTTTTAATTATTT

TGTGCAGCGATGGGGGCGGGGGGGGGGGGGGGCGCGCGCCAGGCGGGGCGGGGCGGGG
```

-continued

```
CGAGGGGCGGGGCGGGGCGAGGCGGAGAGGTGCGGCGGCAGCCAATCAGAGCGGCGCGC

TCCGAAAGTTTCCTTTTATGGCGAGGCGGCGGCGGCGGCCCTATAAAAAGCGAAGCGC

GCGGCGGGCGGGAGTCGCTGCGCGCTGCCTTCGCCCCGTGCCCCGCTCCGCCGCCGCCTCG

CGCCGCCCGCCCCGGCTCTGACTGACCGCGTTACTCCCACAGGTGAGCGGGCGGGACGGCC

CTTCTCCTCCGGGCTGTAATTAGCGCTTGGTTTAATGACGGCTTGTTTCTTTTCTGTGGCTGC

GTGAAAGCCTTGAGGGGCTCCGGGAGCTAGAGCCTCTGCTAACCATGTTCATGCCTTCTTCT

TTTTCCTACAGCTCCTGGGCAACGTGCTGGTTATTGTGCTGTCTCATCATTTTGGCAAAGAA

TTCTAGCGGCCGCCACCATGGTGATTCTTCAGCAGGGGGACCATGTGTGGATGGACCTGAG

ATTGGGGCAGGAGTTCGACGTGCCCATCGGGGCGGTGGTGAAGCTCTGCGACTCTGGGCAG

GTCCAGGTGGTGGATGATGAAGACAATGAACACTGGATCTCTCCGCAGAACGCAACGCACA

TCAAGCCTATGCACCCCACGTCGGTCCACGGCGTGGAGGACATGATCCGCCTGGGGGACCT

CAACGAGGCGGGCATCTTGCGCAACCTGCTTATCCGCTACCGGGACCACCTCATCTACACG

TATACGGGCTCCATCCTGGTGGCTGTGAACCCCTACCAGCTGCTCTCCATCTACTCGCCAGA

GCACATCCGCCAGTATACCAACAAGAAGATTGGGGAGATGCCCCCCCACATCTTTGCCATT

GCTGACAACTGCTACTTCAACATGAAACGCAACAGCCGAGACCAGTGCTGCATCATCAGTG

GGGAATCTGGGCCGGGAAGACGGAGAGCACAAAGCTGATCCTGCAGTTCCTGGCAGCCA

TCAGTGGGCAGCACTCGTGGATTGAGCAGCAGGTCTTGGAGGCCACCCCCATTCTGGAAGC

ATTTGGGAATGCCAAGACCATCCGCAATGACAACTCAAGCCGTTTCGGAAAGTACATCGAC

ATCCACTTCAACAAGCGGGGCGCCATCGAGGGCGCGAAGATTGAGCAGTACCTGCTGGAA

AAGTCACGTGTCTGTCGCCAGGCCCTGGATGAAAGGAACTACCACGTGTTCTACTGCATGC

TGGAGGGTATGAGTGAGGATCAGAAGAAGAAGCTGGGCTTGGGCCAGGCCTCTGACTACA

ACTACTTGGCCATGGGTAACTGCATAACCTGTGAGGGCCGGGTGGACAGCCAGGAGTACGC

CAACATCCGCTCCGCCATGAAGGTGCTCATGTTCACTGACACCGAGAACTGGGAGATCTCG

AAGCTCCTGGCTGCCATCCTGCACCTGGGCAACCTGCAGTATGAGGCACGCACATTTGAAA

ACCTGGATGCCTGTGAGGTTCTCTTCTCCCCATCGCTGGCCACAGCTGCATCCCTGCTTGAG

GTGAACCCCCCAGACCTGATGAGCTGCCTGACTAGCCGCACCCTCATCACCCGCGGGGAGA

CGGTGTCCACCCCACTGAGCAGGGAACAGGCACTGGACGTGCGCGACGCCTTCGTAAAGGG

GATCTACGGGCGGCTGTTCGTGTGGATTGTGGACAAGATCAACGCAGCAATTTACAAGCCT

CCCTCCCAGGATGTGAAGAACTCTCGCAGGTCCATCGGCCTCCTGGACATCTTTGGGTTTGA

GAACTTTGCTGTGAACAGCTTTGAGCAGCTCTGCATCAACTTCGCCAATGAGCACCTGCAGC

AGTTCTTTGTGCGGCACGTGTTCAAGCTGGAGCAGGAGGAATATGACCTGGAGAGCATTGA

CTGGCTGCACATCGAGTTCACTGACAACCAGGATGCCCTGGACATGATTGCCAACAAGCCC

ATGAACATCATCTCCCTCATCGATGAGGAGAGCAAGTTCCCCAAGGGCACAGACACCACCA

TGTTACACAAGCTGAACTCCCAGCACAAGCTCAACGCCAACTACATCCCCCCCAAGAACAA

CCATGAGACCCAGTTTGGCATCAACCATTTTGCAGGCATCGTCTACTATGAGACCCAAGGCT

TCCTGGAGAAGAACCGAGACACCCTGCATGGGACATTATCCAGCTGGTCCACTCCTCCAG

GAACAAGTTCATCAAGCAGATCTTCCAGGCCGATGTCGCCATGGGCGCCGAGACCAGGAAG

CGCTCGCCCACACTTAGCAGCCAGTTCAAGCGGTCACTGGAGCTGCTGATGCGCACGCTGG

GTGCCTGCCAGCCCTTCTTTGTGCGATGCATCAAGCCCAATGAGTTCAAGAAGCCCATGCTG

TTCGACCGGCACCTGTGCGTGCGCCAGCTGCGGTACTCAGGAATGATGGAGACCATCCGAA

TCCGCCGAGCTGGCTACCCCATCCGCTACAGCTTCGTAGAGTTTGTGGAGCGGTACCGTGTG
```

```
CTGCTGCCAGGTGTGAAGCCGGCCTACAAGCAGGGCGACCTCCGCGGGACTTGCCAGCGCA

TGGCTGAGGCTGTGCTGGGCACCCACGATGACTGGCAGATAGGCAAAACCAAGATCTTTCT

GAAGGACCACCATGACATGCTGCTGGAAGTGGAGCGGGACAAAGCCATCACCGACAGAGT

CATCCTCCTTCAGAAAGTCATCCGGGGATTCAAAGACAGGTCTAACTTTCTGAAGCTGAAG

AACGCTGCCACACTGATCCAGAGGCACTGGCGGGTCACAACTGTAGGAAGAACTACGGG

CTGATGCGTCTGGGCTTCCTGCGGCTGCAGGCCCTGCACCGCTCCCGGAAGCTGCACCAGC

AGTACCGCCTGGCCCGCCAGCGCATCATCCAGTTCCAGGCCCGCTGCCGCGCCTATCTGGTG

CGCAAGGCCTTCCGCCACCGCCTCTGGGCTGTGCTCACCGTGCAGGCCTATGCCCGGGGCA

TGATCGCCCGCAGGCTGCACCAACGCCTCAGGGCTGAGTATCTGTGGCGCCTCGAGGCTGA

GAAAATGCGGCTGGCGGAGGAAGAGAAGCTTCGGAAGGAGATGAGCGCCAAGAAGGCCA

AGGAGGAGGCCGAGCGCAAGCATCAGGAGCGCCTGGCCCAGCTGGCTCGTGAGGACGCTG

AGCGGGAGCTGAAGGAGAAGGAGGCCGCTCGGCGGAAGAAGGAGCTCCTGGAGCAGATG

GAAAGGGCCCGCCATGAGCCTGTCAATCACTCAGACATGGTGGACAAGATGTTTGGCTTCC

TGGGGACTTCAGGTGGCCTGCCAGGCCAGGAGGGCCAGGCACCTAGTGGCTTTGAGGTAAG

TATCAAGGTTACAAGACAGGTTTAAGGAGACCAATAGAAACTGGGCTTGTCGAGACAGAG

AAGACTCTTGCGTTTCTGAGCTAGCCCCCGGGTGCGCGGCGTCGGTGGTGCCGGCGGGGGG

CGCCAGGTCGCAGGCGGTGTAGGGCTCCAGGCAGGCGGCGAAGGCCATGACGTGCGCTAT

GAAGGTCTGCTCCTGCACGCCGTGAACCAGGTGCGCCTGCGGGCCGCGCGCGAACACCGCC

ACGTCCTCGCCTGCGTGGGTCTCTTCGTCCAGGGGCACTGCTGACTGCTGCCGATACTCGGG

GCTCCCGCTCTCGCTCTCGGTAACATCCGGCCGGGCGCCGTCCTTGAGCACATAGCCTGGAC

CGTTTCGTCGACTGTTAATTAAGCATGCTGGGGAGAGATCTAGGAACCCCTAGTGATGGAG

TTGGCCACTCCCTCTCTGCGCGCTCGCTCGCTCACTGAGGCCGGGCGACCAAAGGTCGCCCG

ACGCCCGGGCTTTGCCCGGGCGGCCTCAGTGAGCGAGCGAGCGCGCAGAGAGGGAG
```

SEQ ID NO: 67 (only the N-myosin7A portion of SEQ ID NO: 3 (AAV-smCBA-hMYO7ANT-APSD-ApHead))

```
ATGGTGATTCTTCAGCAGGGGGACCATGTGTGGATGGACCTGAGATTGGGGCAGGAGTTCG

ACGTGCCCATCGGGGCGGTGGTGAAGCTCTGCGACTCTGGGCAGGTCCAGGTGGTGGATGA

TGAAGACAATGAACACTGGATCTCTCCGCAGAACGCAACGCACATCAAGCCTATGCACCCC

ACGTCGGTCCACGGCGTGGAGGACATGATCCGCCTGGGGGACCTCAACGAGGCGGGCATCT

TGCGCAACCTGCTTATCCGCTACCGGGACCACCTCATCTACACGTATACGGGCTCCATCCTG

GTGGCTGTGAACCCCTACCAGCTGCTCTCCATCTACTCGCCAGAGCACATCCGCCAGTATAC

CAACAAGAAGATTGGGGAGATGCCCCCCCACATCTTTGCCATTGCTGACAACTGCTACTTC

AACATGAAACGCAACAGCCGAGACCAGTGCTGCATCATCAGTGGGGAATCTGGGGCCGGG

AAGACGGAGAGCACAAAGCTGATCCTGCAGTTCCTGGCAGCCATCAGTGGGCAGCACTCGT

GGATTGAGCAGCAGGTCTTGGAGGCCACCCCCATTCTGGAAGCATTTGGGAATGCCAAGAC

CATCCGCAATGACAACTCAAGCCGTTTCGGAAAGTACATCGACATCCACTTCAACAAGCGG

GGCGCCATCGAGGGCGCGAAGATTGAGCAGTACCTGCTGGAAAAGTCACGTGTCTGTCGCC

AGGCCCTGGATGAAAGGAACTACCACGTGTTCTACTGCATGCTGGAGGGTATGAGTGAGGA

TCAGAAGAAGAAGCTGGGCTTGGGCCAGGCCTCTGACTACAACTACTTGGCCATGGGTAAC

TGCATAACCTGTGAGGGCCGGGTGGACAGCCAGGAGTACGCCAACATCCGCTCCGCCATGA

AGGTGCTCATGTTCACTGACACCGAGAACTGGGAGATCTCGAAGCTCCTGGCTGCCATCCT
```

-continued

```
GCACCTGGGCAACCTGCAGTATGAGGCACGCACATTTGAAAACCTGGATGCCTGTGAGGTT

CTCTTCTCCCCATCGCTGGCCACAGCTGCATCCCTGCTTGAGGTGAACCCCCCAGACCTGAT

GAGCTGCCTGACTAGCCGCACCCTCATCACCCGCGGGGAGACGGTGTCCACCCCACTGAGC

AGGGAACAGGCACTGGACGTGCGCGACGCCTTCGTAAAGGGGATCTACGGGCGGCTGTTCG

TGTGGATTGTGGACAAGATCAACGCAGCAATTTACAAGCCTCCCTCCCAGGATGTGAAGAA

CTCTCGCAGGTCCATCGGCCTCCTGGACATCTTTGGGTTTGAGAACTTTGCTGTGAACAGCT

TTGAGCAGCTCTGCATCAACTTCGCCAATGAGCACCTGCAGCAGTTCTTTGTGCGGCACGTG

TTCAAGCTGGAGCAGGAGGAATATGACCTGGAGAGCATTGACTGGCTGCACATCGAGTTCA

CTGACAACCAGGATGCCCTGGACATGATTGCCAACAAGCCCATGAACATCATCTCCCTCAT

CGATGAGGAGAGCAAGTTCCCCAAGGGCACAGACACCACCATGTTACACAAGCTGAACTCC

CAGCACAAGCTCAACGCCAACTACATCCCCCCCAAGAACAACCATGAGACCCAGTTTGGCA

TCAACCATTTTGCAGGCATCGTCTACTATGAGACCCAAGGCTTCCTGGAGAAGAACCGAGA

CACCCTGCATGGGACATTATCCAGCTGGTCCACTCCTCCAGGAACAAGTTCATCAAGCAG

ATCTTCCAGGCCGATGTCGCCATGGGCGCCGAGACCAGGAAGCGCTCGCCCACACTTAGCA

GCCAGTTCAAGCGGTCACTGGAGCTGCTGATGCGCACGCTGGGTGCCTGCCAGCCCTTCTTT

GTGCGATGCATCAAGCCCAATGAGTTCAAGAAGCCCATGCTGTTCGACCGGCACCTGTGCG

TGCGCCAGCTGCGGTACTCAGGAATGATGGAGACCATCCGAATCCGCCGAGCTGGCTACCC

CATCCGCTACAGCTTCGTAGAGTTTGTGGAGCGGTACCGTGTGCTGCTGCCAGGTGTGAAG

CCCGGCCTACAAGCAGGGCGACCTCCGCGGGACTTGCCAGCGCATGGCTGAGGCTGTGCTGG

GCACCCACGATGACTGGCAGATAGGCAAAACCAAGATCTTTCTGAAGGACCACCATGACAT

GCTGCTGGAAGTGGAGCGGGACAAAGCCATCACCGACAGAGTCATCCTCCTTCAGAAAGTC

ATCCGGGGATTCAAAGACAGGTCTAACTTTCTGAAGCTGAAGAACGCTGCCACACTGATCC

AGAGGCACTGGCGGGGTCACAACTGTAGGAAGAACTACGGGCTGATGCGTCTGGGCTTCCT

GCGGCTGCAGGCCCTGCACCGCTCCCGGAAGCTGCACCAGCAGTACCGCCTGGCCCGCCAG

CGCATCATCCAGTTCCAGGCCCGCTGCCGCGCCTATCTGGTGCGCAAGGCCTTCCGCCACCG

CCTCTGGGCTGTGCTCACCGTGCAGGCCTATGCCCGGGGCATGATCGCCCGCAGGCTGCAC

CAACGCCTCAGGGCTGAGTATCTGTGGCGCCTCGAGGCTGAGAAAATGCGGCTGGCGGAGG

AAGAGAAGCTTCGGAAGGAGATGAGCGCCAAGAAGGCCAAGGAGGAGGCCGAGCGCAAG

CATCAGGAGCGCCTGGCCCAGCTGGCTCGTGAGGACGCTGAGCGGGAGCTGAAGGAGAAG

GAGGCCGCTCGGCGGAAGAAGGAGCTCCTGGAGCAGATGGAAAGGGCCCGCCATGAGCCT

GTCAATCACTCAGACATGGTGGACAAGATGTTTGGCTTCCTGGGGACTTCAGGTGGCCTGC

CAGGCCAGGAGGGCCAGGCACCTAGTGGCTTTGAG
```

SEQ ID NO: 68 (only the N-myosin7A portion encoded by SEQ ID NO: 3 (AAV-smCBA-hMYO7ANT-APSD-APhead))

```
MVILQQGDHVWMDLRLGQEFDVPIGAVVKLCDSGQVQVVDDEDNEHWISPQNATHIKPMHPT

SVHGVEDMIRLGDLNEAGILRNLLIRYRDHLIYTYTGSILVAVNPYQLLSIYSPEHIRQYTNKKIG

EMPPHIFAIADNCYFNMKRNSRDQCCIISGESGAGKTESTKLILQFLAAISGQHSWIEQQVLEATP

ILEAFGNAKTIRNDNSSRFGKYIDIHFNKRGAIEGAKIEQYLLEKSRVCRQALDERNYHVFYCML

EGMSEDQKKKLGLGQASDYNYLAMGNCITCEGRVDSQEYANIRSAMKVLMFTDTENWEISKL

LAAILHLGNLQYEARTFENLDACEVLFSPSLATAASLLEVNPPDLMSCLTSRTLITRGETVSTPLS

REQALDVRDAFVKGIYGRLFVWIVDKINAAIYKPPSQDVKNSRRSIGLLDIFGFENFAVNSFEQL

CINFANEHLQQFFVRHVFKLEQEEYDLESIDWLHIEFTDNQDALDMIANKPMNIISLIDEESKFPK
```

GTDTTMLHKLNSQHKLNANYIPPKNNHETQFGINHFAGIVYYETQGFLEKNRDTLHGDIIQLVH

SSRNKFIKQIFQADVAMGAETRKRSPTLSSQFKRSLELLMRTLGACQPFFVRCIKPNEFKKPMLF

DRHLCVRQLRYSGMMETIRIRRAGYPIRYSFVEFVERYRVLLPGVKPAYKQGDLRGTCQRMAE

AVLGTHDDWQIGKTKIFLKDHHDMLLEVERDKAITDRVILLQKVIRGFKDRSNFLKLKNAATLI

QRHWRGHNCRKNYGLMRLGFLRLQALHRSRKLHQQYRLARQRIIQFQARCRAYLVRKAFRHR

LWAVLTVQAYARGMIARRLHQRLRAEYLWRLEAEKMRLAEEEKLRKEMSAKKAKEEAERKH

QERLAQLAREDAERELKEKEAARRKKELLEQMERARHEPVNHSDMVDKMFGFLGTSGGLPGQ

EGQAPSGFE

SEQ ID NO: 69 (Alkaline phosphatase head sequence (APhead)(e.g., AAV-
smCBA-hMYO7A-NT-APSD-APhead, AAV-smCBA-hMYO7A-NT-Ex21-APSD-APhead,
AAV-smCBA-hMYO7A-NT-Ex21-APSD-APhead CMv1, AAV-APhead-APSA-
hMYO7ACTex22.HA-MIN, AAV-APhead-APSA-hMYO7ACTex22-MIN))
CCCCGGGTGCGCGGCGTCGGTGGTGCCGGCGGGGGGCGCCAGGTCGCAGGCGGTGTAGGG

CTCCAGGCAGGCGGCGAAGGCCATGACGTGCGCTATGAAGGTCTGCTCCTGCACGCCGTGA

ACCAGGTGCGCCTGCGGGCCGCGCGCGAACACCGCCACGTCCTCGCCTGCGTGGGTCTCTT

CGTCCAGGGGCACTGCTGACTGCTGCCGATACTCGGGGCTCCCGCTCTCGCTCTCGGTAACA

TCCGGCCGGGCGCCGTCCTTGAGCACATAGCCTGGACCGTTTC

SEQ ID NO: 70 Alkaline phosphatase head sequence (APhead)(e.g., AAV-
smCBA-hMYO7A-NT-ex21-APSD-APhead-CMv2, AAV-smCBA-hMYO7A-NT-ex21-APSD-
APhead-CMv3, AAV-APhead-APSA-hMYO7ACT-ex22-APSD-CMv2.HA, AAV-APhead-
APSA-hMYO7ACT-ex22-APSD-CMv2.HA-MIN, AAV-APhead-APSA-hMYO7ACT-ex22-
APSD-CMv2-MIN)
CCCCGGGTGCGCGGCGTCGGTGGTGCCGGCGGGGGGCGCCAGGTCGCAGGCGGTGTAGGG

CTCCAGGCAGGCGGCGAAGGCCATGACGTGCGCTATGAAGGTCTGCTCCTGCACGCCGTGA

ACCAGGTGCGCCTGCGGGCCGCGCGCGAACACCGCCACGTCCTCGCCTGCGTGGGTCTCTT

CGTCCAGGGGCACTGCGCACTGCTGCCGATACTCGGGGCTCCCGCTCTCGCTCTCGGTAACA

TCCGGCCGGGCGCCGTCCTTGAGCACATAGCCTGGACCGTTTC

SEQ ID NO: 4 is the nucleotide sequence of the back-half vector of the exon 23/24 hybrid
vector system (i.e., AAV-APhead-APSA-hMYO7ACT.HA);
CTCCCTCTCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCC

ATCACTAGGGGTTCTCAGATCTGGCGCGCCCAATTGGCTTCGAATTCTAGCGGCCGCCCCCG

GGTGCGCGGCGTCGGTGGTGCCGGCGGGGGGCGCCAGGTCGCAGGCGGTGTAGGGCTCCA

GGCAGGCGGCGAAGGCCATGACGTGCGCTATGAAGGTCTGCTCCTGCACGCCGTGAACCAG

GTGCGCCTGCGGGCCGCGCGCGAACACCGCCACGTCCTCGCCTGCGTGGGTCTCTTCGTCCA

GGGGCACTGCTGACTGCTGCCGATACTCGGGGCTCCCGCTCTCGCTCTCGGTAACATCCGGC

CGGGCGCCGTCCTTGAGCACATAGCCTGGACCGTTTCCTTAAGCGACGCATGCTCGCGATA

GGCACCTATTGGTCTTACTGACATCCACTTTGCCTTTCTCTCCACAGGACCTGGAGCGAGGG

CGGAGGGAGATGGTGGAGGAGGACCTGGATGCAGCCCTGCCCCTGCCTGACGAGGATGAG

GAGGACCTCTCTGAGTATAAATTTGCCAAGTTCGCGGCCACCTACTTCCAGGGGACAACCA

CGCACTCCTACACCCGGCGGCCACTCAAACAGCCACTGCTCTACCATGACGACGAGGGTGA

CCAGCTGGCAGCCCTGGCGGTCTGGATCACCATCCTCCGCTTCATGGGGGACCTCCCTGAGC

CCAAGTACCACACAGCCATGAGTGATGGCAGTGAGAAGATCCCTGTGATGACCAAGATTTA

TGAGACCCTGGGCAAGAAGACGTACAAGAGGGAGCTGCAGGCCCTGCAGGGCGAGGGCGA

GGCCCAGCTCCCCGAGGGCCAGAAGAAGAGCAGTGTGAGGCACAAGCTGGTGCATTTGAC

TCTGAAAAAGAAGTCCAAGCTCACAGAGGAGGTGACCAAGAGGCTGCATGACGGGGAGTC

```
CACAGTGCAGGGCAACAGCATGCTGGAGGACCGGCCCACCTCCAACCTGGAGAAGCTGCA

CTTCATCATCGGCAATGGCATCCTGCGGCCAGCACTCCGGGACGAGATCTACTGCCAGATC

AGCAAGCAGCTGACCCACAACCCCTCCAAGAGCAGCTATGCCCGGGGCTGGATTCTCGTGT

CTCTCTGCGTGGGCTGTTTCGCCCCCTCCGAGAAGTTTGTCAAGTACCTGCGGAACTTCATC

CACGGGGGCCCGCCCGGCTACGCCCCGTACTGTGAGGAGCGCCTGAGAAGGACCTTTGTCA

ATGGGACACGGACACAGCCGCCCAGCTGGCTGGAGCTGCAGGCCACCAAGTCCAAGAAGC

CAATCATGTTGCCCGTGACATTCATGGATGGGACCACCAAGACCCTGCTGACGGACTCGGC

AACCACGGCCAAGGAGCTCTGCAACGCGCTGGCCGACAAGATCTCTCTCAAGGACCGGTTC

GGGTTCTCCCTCTACATTGCCCTGTTTGACAAGGTGTCCTCCCTGGGCAGCGGCAGTGACCA

CGTCATGGACGCCATCTCCCAGTGCGAGCAGTACGCCAAGGAGCAGGGCGCCCAGGAGCG

CAACGCCCCTGGAGGCTCTTCTTCCGCAAAGAGGTCTTCACGCCCTGGCACAGCCCCTCCG

AGGACAACGTGGCCACCAACCTCATCTACCAGCAGGTGGTGCGAGGAGTCAAGTTTGGGGA

GTACAGGTGTGAGAAGGAGGACGACCTGGCTGAGCTGGCCTCCCAGCAGTACTTTGTAGAC

TATGGCTCTGAGATGATCCTGGAGCGCCTCCTGAACCTCGTGCCCACCTACATCCCCGACCG

CGAGATCACGCCCCTGAAGACGCTGGAGAAGTGGGCCCAGCTGGCCATCGCCGCCCACAA

GAAGGGGATTTATGCCCAGAGGAGAACTGATGCCCAGAAGGTCAAAGAGGATGTGGTCAG

TTATGCCCGCTTCAAGTGGCCCTTGCTCTTCTCCAGGTTTTATGAAGCCTACAAATTCTCAG

GCCCCAGTCTCCCCAAGAACGACGTCATCGTGGCCGTCAACTGGACGGGTGTGTACTTTGT

GGATGAGCAGGAGCAGGTACTTCTGGAGCTGTCCTTCCCAGAGATCATGGCCGTGTCCAGC

AGCAGGGGAGCGAAAACGACGGCCCCCAGCTTCACGCTGGCCACCATCAAGGGGGACGAA

TACACCTTCACCTCCAGCAATGCTGAGGACATTCGTGACCTGGTGGTCACCTTCCTAGAGGG

GCTCCGGAAGAGATCTAAGTATGTTGTGGCCCTGCAGGATAACCCCAACCCCGCAGGCGAG

GAGTCAGGCTTCCTCAGCTTTGCCAAGGGAGACCTCATCATCCTGGACCATGACACGGGCG

AGCAGGTCATGAACTCGGGCTGGGCCAACGGCATCAATGAGAGGACCAAGCAGCGTGGGG

ACTTCCCCACCGACAGTGTGTACGTCATGCCCACTGTCACCATGCCACCGCGGGAGATTGTG

GCCCTGGTCACCATGACTCCCGATCAGAGGCAGGACGTTGTCCGGCTCTTGCAGCTGCGAA

CGGCGGAGCCCGAGGTGCGTGCCAAGCCCTACACGCTGGAGGAGTTTTCCTATGACTACTT

CAGGCCCCCACCCAAGCACACGCTGAGCCGTGTCATGGTGTCCAAGGCCCGAGGCAAGGAC

CGGCTGTGGAGCCACACGCGGGAACCGCTCAAGCAGGCGCTGCTCAAGAAGCTCCTGGGC

AGTGAGGAGCTCTCGCAGGAGGCCTGCCTGGCCTTCATTGCTGTGCTCAAGTACATGGGCG

ACTACCCGTCCAAGAGGACACGCTCCGTCAACGAGCTCACCGACCAGATCTTTGAGGGTCC

CCTGAAAGCCGAGCCCCTGAAGGACGAGGCATATGTGCAGATCCTGAAGCAGCTGACCGA

CAACCACATCAGGTACAGCGAGGAGCGGGGTTGGGAGCTGCTCTGGCTGTGCACGGGCCTT

TTCCCACCCAGCAACATCCTCCTGCCCCACGTGCAGCGCTTCCTGCAGTCCCGAAAGCACTG

CCCACTCGCCATCGACTGCCTGCAACGGCTCCAGAAAGCCCTGAGAAACGGGTCCCGGAAG

TACCCTCCGCACCTGGTGGAGGTGGAGGCCATCCAGCACAAGACCACCCAGATTTTCCACA

AAGTCTACTTCCCTGATGACACTGACGAGGCCTTCGAAGTGGAGTCCAGCACCAAGGCCAA

GGACTTCTGCCAGAACATCGCCACCAGGCTGCTCCTCAAGTCCTCAGAGGGATTCAGCCTCT

TTGTCAAAATTGCAGACAAGGTCATCAGCGTTCCTGAGAATGACTTCTTCTTTGACTTTGTT

CGACACTTGACAGACTGGATAAAGAAAGCTCGGCCCATCAAGGACGGAATTGTGCCCTCAC
```

-continued

TCACCTACCAGGTGTTCTTCATGAAGAAGCTGTGGACCACCACGGTGCCAGGGAAGGATCC

CATGGCCGATTCCATCTTCCACTATTACCAGGAGTTGCCCAAGTATCTCCGAGGCTACCACA

AGTGCACGCGGGAGGAGGTGCTGCAGCTGGGGGCGCTGATCTACAGGGTCAAGTTCGAGG

AGGACAAGTCCTACTTCCCCAGCATCCCCAAGCTGCTGCGGGAGCTGGTGCCCCAGGACCT

TATCCGGCAGGTCTCACCTGATGACTGGAAGCGGTCCATCGTCGCCTACTTCAACAAGCAC

GCAGGGAAGTCCAAGGAGGAGGCCAAGCTGGCCTTCCTGAAGCTCATCTTCAAGTGGCCCA

CCTTTGGCTCAGCCTTCTTCGAGGTGAAGCAAACTACGGAGCCAAACTTCCCTGAGATCCTC

CTAATTGCCATCAACAAGTATGGGGTCAGCCTCATCGATCCCAAAACGAAGGATATCCTCA

CCACTCATCCCTTCACCAAGATCTCCAACTGGAGCAGCGGCAACACCTACTTCCACATCACC

ATTGGGAACTTGGTGCGCGGGAGCAAACTGCTCTGCGAGACGTCACTGGGCTACAAGATGG

ATGACCTCCTGACTTCCTACATTAGCCAGATGCTCACAGCCATGAGCAAACAGCGGGGCTC

CAGGAGCGGCAAGTACCCTTACGATGTACCGGATTACGCATGAGGTACCAAGGGCGAATTC

TGCAGTCGACTAGAGCTCGCTGATCAGCCTCGACTGTGCCTTCTAGTTGCCAGCCATCTGTT

GTTTGCCCCTCCCCCGTGCCTTCCTTGACCCTGGAAGGTGCCACTCCCACTGTCCTTTCCTAA

TAAAATGAGGAAATTGCATCGCATTGTCTGAGTAGGTGTCATTCTATTCTGGGGGGTGGGG

TGGGGCAGGACAGCAAGGGGGAGGATTGGGAAGACAATAGCAGGCATGCTGGGGAGAGA

TCTGAGGACTAGTCCGTCGACTGTTAATTAAGCATGCTGGGGAGAGATCTAGGAAACCCCT

AGTGATGGAGTTGGCCACTCCCTCTCTGCGCGCTCGCTCGCTCACTGAGGCCGGGCGACCA

AAGGTCGCCCGACGCCCGGGCTTTGCCCGGGCGGCCTCAGTGAGCGAGCGAGCGCGCAGA

GAGGGAG

SEQ ID NO: 71 myosin7A (e.g., AAV-APhead-APSA-hMYO7ACT.HA)
GACCTGGAGCGAGGGCGGAGGGAGATGGTGGAGGAGGACCTGGATGCAGCCCTGCCCCTG

CCTGACGAGGATGAGGAGGACCTCTCTGAGTATAAATTTGCCAAGTTCGCGGCCACCTACT

TCCAGGGGACAACCACGCACTCCTACACCCGGCGGCCACTCAAACAGCCACTGCTCTACCA

TGACGACGAGGGTGACCAGCTGGCAGCCCTGGCGGTCTGGATCACCATCCTCCGCTTCATG

GGGGACCTCCCTGAGCCCAAGTACCACACAGCCATGAGTGATGGCAGTGAGAAGATCCCTG

TGATGACCAAGATTTATGAGACCCTGGGCAAGAAGACGTACAAGAGGGAGCTGCAGGCCC

TGCAGGGCGAGGGCGAGGCCCAGCTCCCCGAGGGCCAGAAGAAGAGCAGTGTGAGGCACA

AGCTGGTGCATTTGACTCTGAAAAAGAAGTCCAAGCTCACAGAGGAGGTGACCAAGAGGC

TGCATGACGGGGAGTCCACAGTGCAGGGCAACAGCATGCTGGAGGACCGGCCCACCTCCA

ACCTGGAGAAGCTGCACTTCATCATCGGCAATGGCATCCTGCGGCCAGCACTCCGGGACGA

GATCTACTGCCAGATCAGCAAGCAGCTGACCCACAACCCCTCCAAGAGCAGCTATGCCCGG

GGCTGGATTCTCGTGTCTCTCTGCGTGGGCTGTTTCGCCCCCTCCGAGAAGTTTGTCAAGTA

CCTGCGGAACTTCATCCACGGGGCCCGCCCGGCTACGCCCCGTACTGTGAGGAGCGCCTG

AGAAGGACCTTTGTCAATGGGACACGGACACAGCCGCCCAGCTGGCTGGAGCTGCAGGCC

ACCAAGTCCAAGAAGCCAATCATGTTGCCCGTGACATTCATGGATGGGACCACCAAGACCC

TGCTGACGGACTCGGCAACCACGGCCAAGGAGCTCTGCAACGCGCTGGCCGACAAGATCTC

TCTCAAGGACCGGTTCGGGTTCTCCCTCTACATTGCCCTGTTTGACAAGGTGTCCTCCCTGG

GCAGCGGCAGTGACCACGTCATGGACGCCATCTCCCAGTGCGAGCAGTACGCCAAGGAGC

AGGGCGCCCAGGAGCGCAACGCCCCCTGGAGGCTCTTCTTCCGCAAAGAGGTCTTCACGCC

CTGGCACAGCCCCTCCGAGGACAACGTGGCCACCAACCTCATCTACCAGCAGGTGGTGCGA

-continued

```
GGAGTCAAGTTTGGGGAGTACAGGTGTGAGAAGGAGGACGACCTGGCTGAGCTGGCCTCC

CAGCAGTACTTTGTAGACTATGGCTCTGAGATGATCCTGGAGCGCCTCCTGAACCTCGTGCC

CACCTACATCCCCGACCGCGAGATCACGCCCCTGAAGACGCTGGAGAAGTGGGCCCAGCTG

GCCATCGCCGCCCACAAGAAGGGGATTTATGCCCAGAGGAGAACTGATGCCCAGAAGGTC

AAAGAGGATGTGGTCAGTTATGCCCGCTTCAAGTGGCCCTTGCTCTTCTCCAGGTTTTATGA

AGCCTACAAATTCTCAGGCCCCAGTCTCCCCAAGAACGACGTCATCGTGGCCGTCAACTGG

ACGGGTGTGTACTTTGTGGATGAGCAGGAGCAGGTACTTCTGGAGCTGTCCTTCCCAGAGA

TCATGGCCGTGTCCAGCAGCAGGGGAGCGAAAACGACGGCCCCAGCTTCACGCTGGCCAC

CATCAAGGGGACGAATACACCTTCACCTCCAGCAATGCTGAGGACATTCGTGACCTGGTG

GTCACCTTCCTAGAGGGGCTCCGGAAGAGATCTAAGTATGTTGTGGCCCTGCAGGATAACC

CCAACCCCGCAGGCGAGGAGTCAGGCTTCCTCAGCTTTGCCAAGGGAGACCTCATCATCCT

GGACCATGACACGGGCGAGCAGGTCATGAACTCGGGCTGGGCCAACGGCATCAATGAGAG

GACCAAGCAGCGTGGGGACTTCCCCACCGACAGTGTGTACGTCATGCCCACTGTCACCATG

CCACCGCGGGAGATTGTGGCCCTGGTCACCATGACTCCCGATCAGAGGCAGGACGTTGTCC

GGCTCTTGCAGCTGCGAACGGCGGAGCCCGAGGTGCGTGCCAAGCCCTACACGCTGGAGGA

GTTTTCCTATGACTACTTCAGGCCCCCACCCAAGCACACGCTGAGCCGTGTCATGGTGTCCA

AGGCCCGAGGCAAGGACCGGCTGTGGAGCCACACGCGGGAACCGCTCAAGCAGGCGCTGC

TCAAGAAGCTCCTGGGCAGTGAGGAGCTCTCGCAGGAGGCCTGCCTGGCCTTCATTGCTGT

GCTCAAGTACATGGGCGACTACCCGTCCAAGAGGACACGCTCCGTCAACGAGCTCACCGAC

CAGATCTTTGAGGGTCCCCTGAAAGCCGAGCCCCTGAAGGACGAGGCATATGTGCAGATCC

TGAAGCAGCTGACCGACAACCACATCAGGTACAGCGAGGAGCGGGGTTGGGAGCTGCTCT

GGCTGTGCACGGGCCTTTTCCCACCCAGCAACATCCTCCTGCCCCACGTGCAGCGCTTCCTG

CAGTCCCGAAAGCACTGCCCACTCGCCATCGACTGCCTGCAACGGCTCCAGAAAGCCCTGA

GAAACGGGTCCCGGAAGTACCCTCCGCACCTGGTGGAGGTGGAGGCCATCCAGCACAAGA

CCACCCAGATTTTCCACAAAGTCTACTTCCCTGATGACACTGACGAGGCCTTCGAAGTGGA

GTCCAGCACCAAGGCCAAGGACTTCTGCCAGAACATCGCCACCAGGCTGCTCCTCAAGTCC

TCAGAGGGATTCAGCCTCTTTGTCAAAATTGCAGACAAGGTCATCAGCGTTCCTGAGAATG

ACTTCTTCTTTGACTTTGTTCGACACTTGACAGACTGGATAAAGAAAGCTCGGCCCATCAAG

GACGGAATTGTGCCCTCACTCACCTACCAGGTGTTCTTCATGAAGAAGCTGTGGACCACCA

CGGTGCCAGGGAAGGATCCCATGGCCGATTCCATCTTCCACTATTACCAGGAGTTGCCCAA

GTATCTCCGAGGCTACCACAAGTGCACGCGGGAGGAGGTGCTGCAGCTGGGGGCGCTGATC

TACAGGGTCAAGTTCGAGGAGGACAAGTCCTACTTCCCCAGCATCCCCAAGCTGCTGCGGG

AGCTGGTGCCCCAGGACCTTATCCGGCAGGTCTCACCTGATGACTGGAAGCGGTCCATCGT

CGCCTACTTCAACAAGCACGCAGGGAAGTCCAAGGAGGAGGCCAAGCTGGCCTTCCTGAA

GCTCATCTTCAAGTGGCCCACCTTTGGCTCAGCCTTCTTCGAGGTGAAGCAAACTACGGAGC

CAAACTTCCCTGAGATCCTCCTAATTGCCATCAACAAGTATGGGGTCAGCCTCATCGATCCC

AAAACGAAGGATATCCTCACCACTCATCCCTTCACCAAGATCTCCAACTGGAGCAGCGGCA
```

-continued
```
ACACCTACTTCCACATCACCATTGGGAACTTGGTGCGCGGGAGCAAACTGCTCTGCGAGAC

GTCACTGGGCTACAAGATGGATGACCTCCTGACTTCCTACATTAGCCAGATGCTCACAGCC

ATGAGCAAACAGCGGGCTCCAGGAGCGGCAAG
```

SEQ ID NO: 72 (hemagglutinin (HA) tag (AAV-APhead-APSA-hMYO7ACT.HA, AAV-hMYO7A-CTlong.HA)
```
TACCCTTACGATGTACCGGATTACGCATGA
```

EXAMPLE 6 shows second generation hybrid vectors that minimize expression of truncated MYO7A protein.

Figure 28:
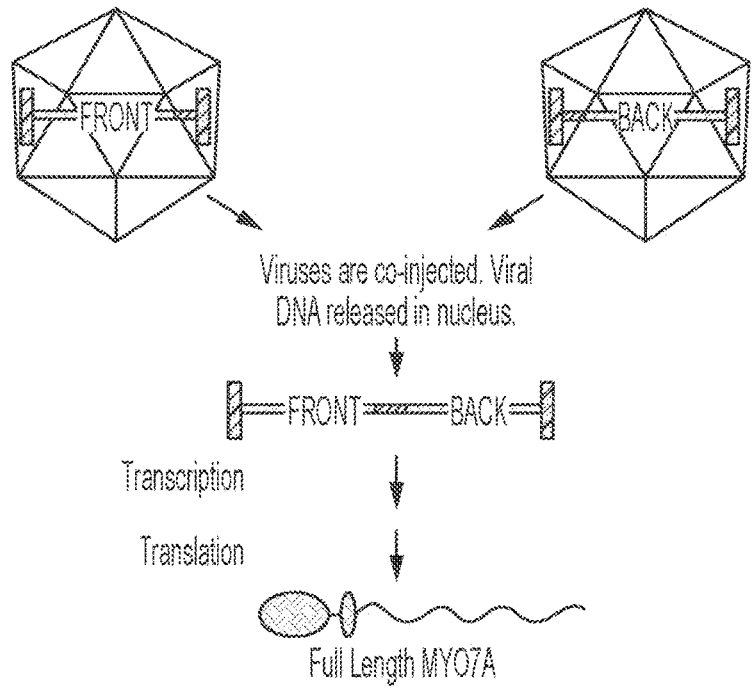
FIG. 28 is a representative schematic of how the dual vector systems deliver, recombine, and produce full-length transgene. MYO7A cDNA is split into two parts, or "halves," and each half is delivered via a separate AAV vector. Following co-infection, gene halves recombine via their shared/overlapping sequence to form full-length MYO7A. The recombined transgene can then be transcribed and translated into the desired protein product.
Figure 29A:
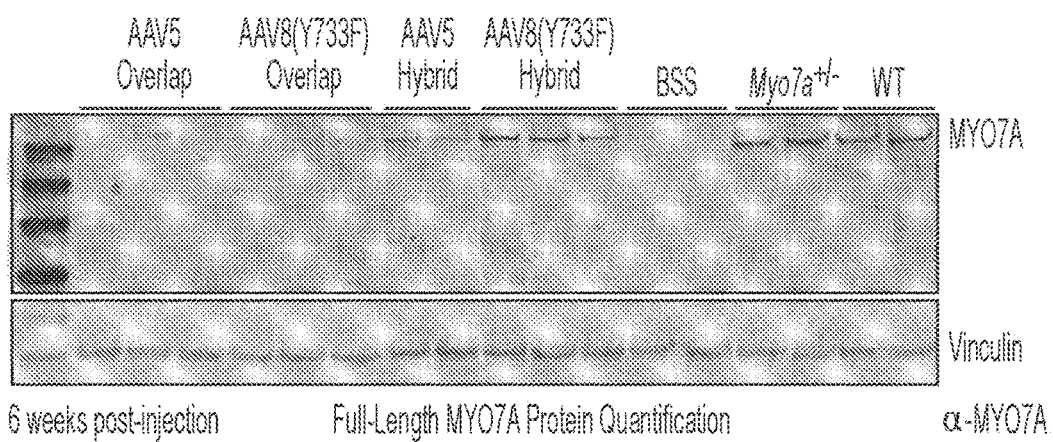
FIGS. 29A-29B show the dual vector-mediated MYO7A expression Myo7a$^{-/-}$ mice.
Figure 29B:
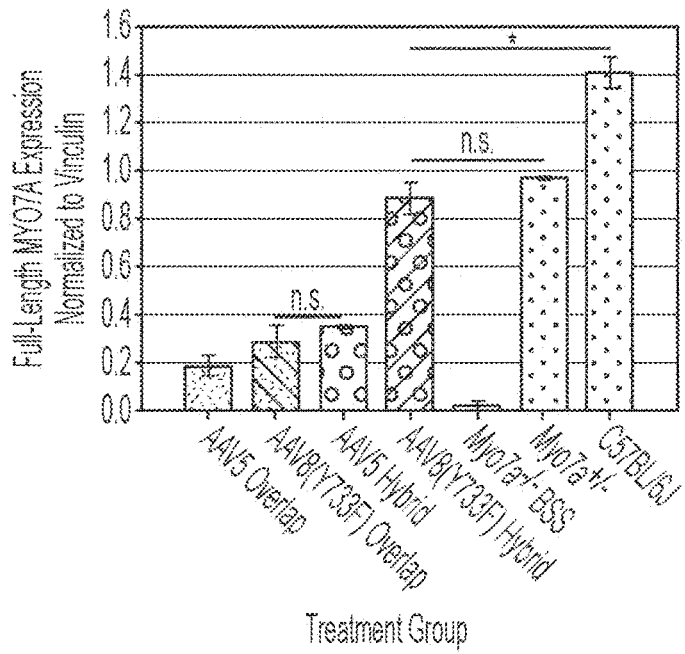
Figure 30:
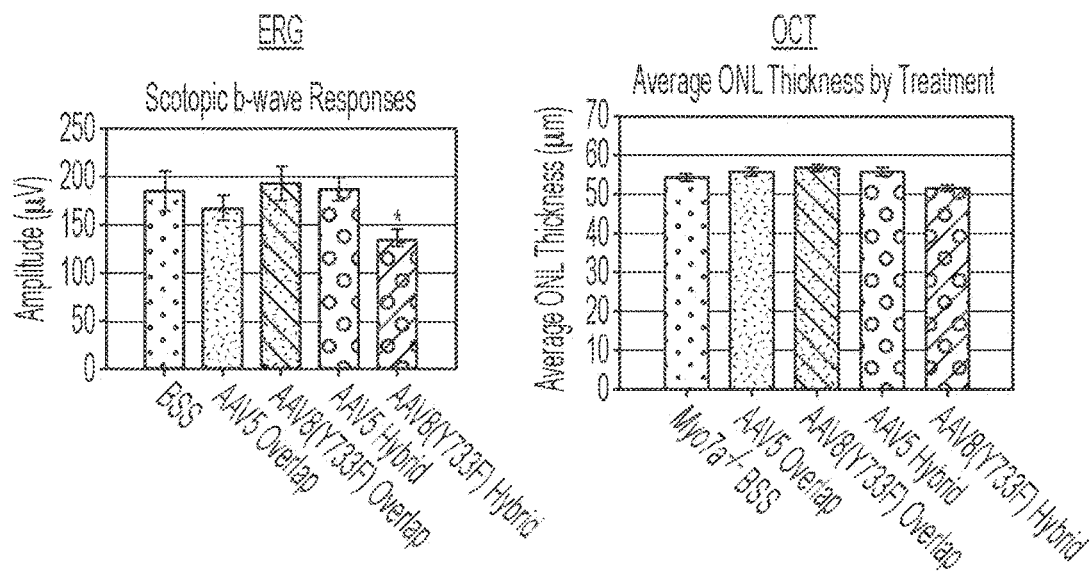
FIG. 30 shows two bar graphs illustrating the scotopic b-wave responses and average ONL thickness by treatment at 6 weeks post-injection, in order to evaluate the safety of dual AAV-MYO7A vectors. All treatments were delivered at 5.0×10$^8$ vg total (2.5×10$^8$ vg each).
Figure 31A:
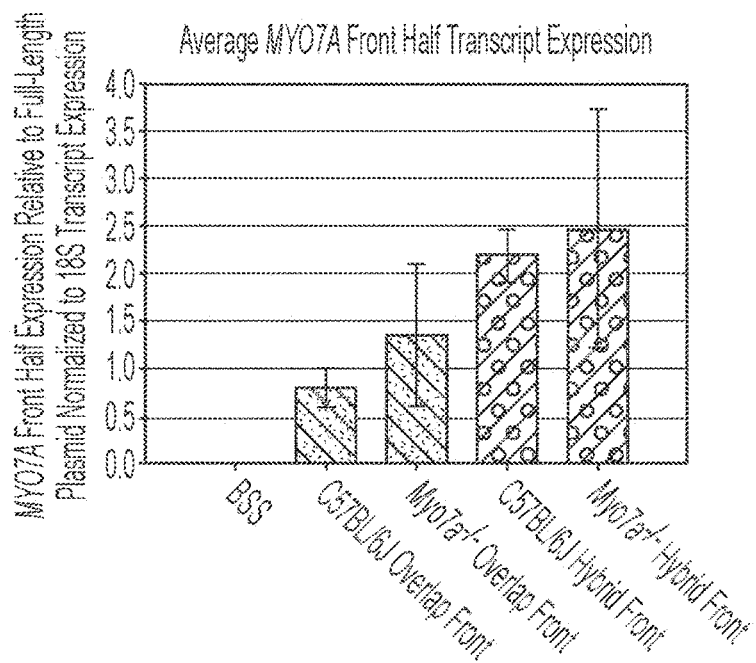
FIGS. 31A-31B show that only the front half hybrid vectors produced truncated protein.
Figure 31B:
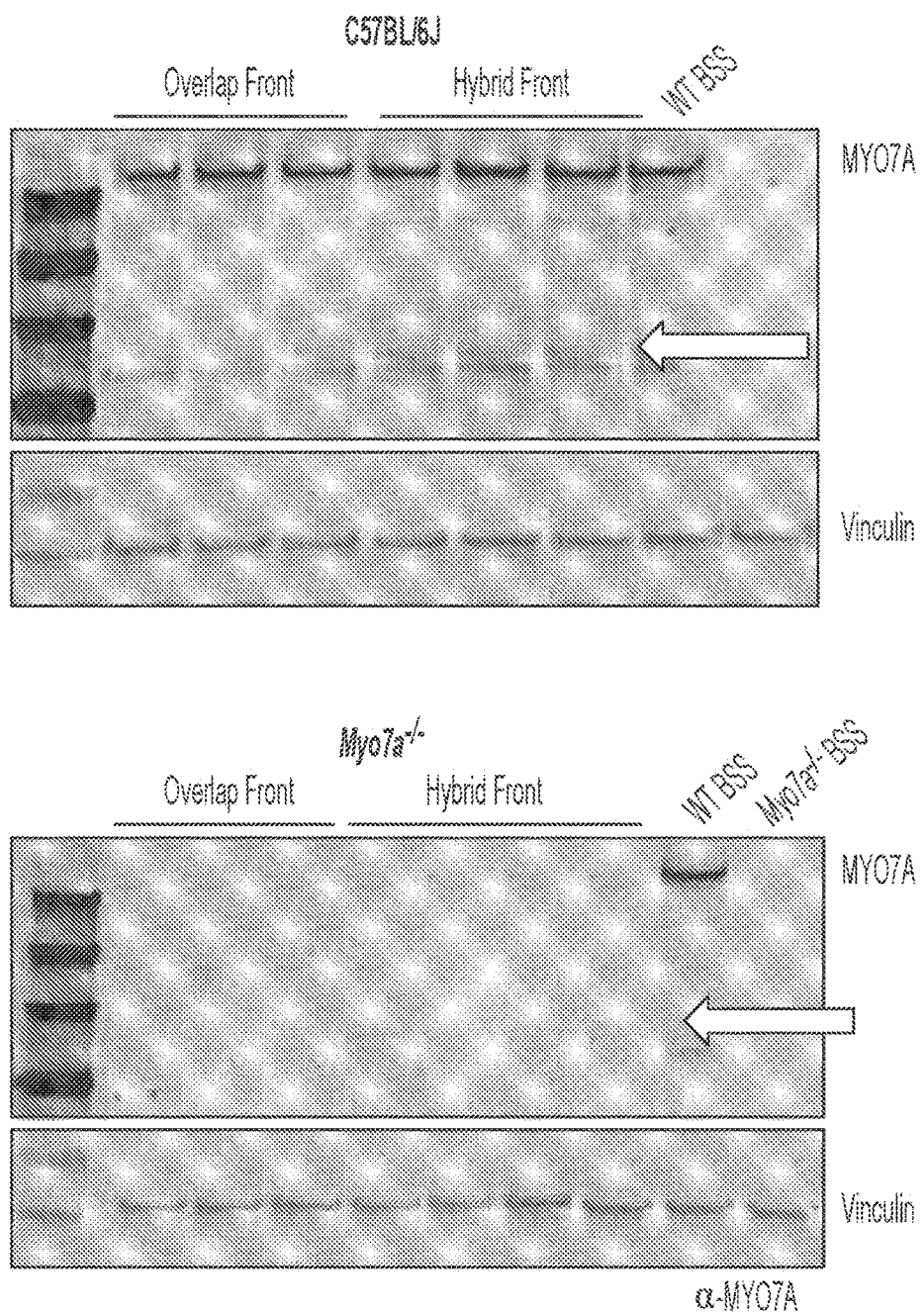
Figure 32:
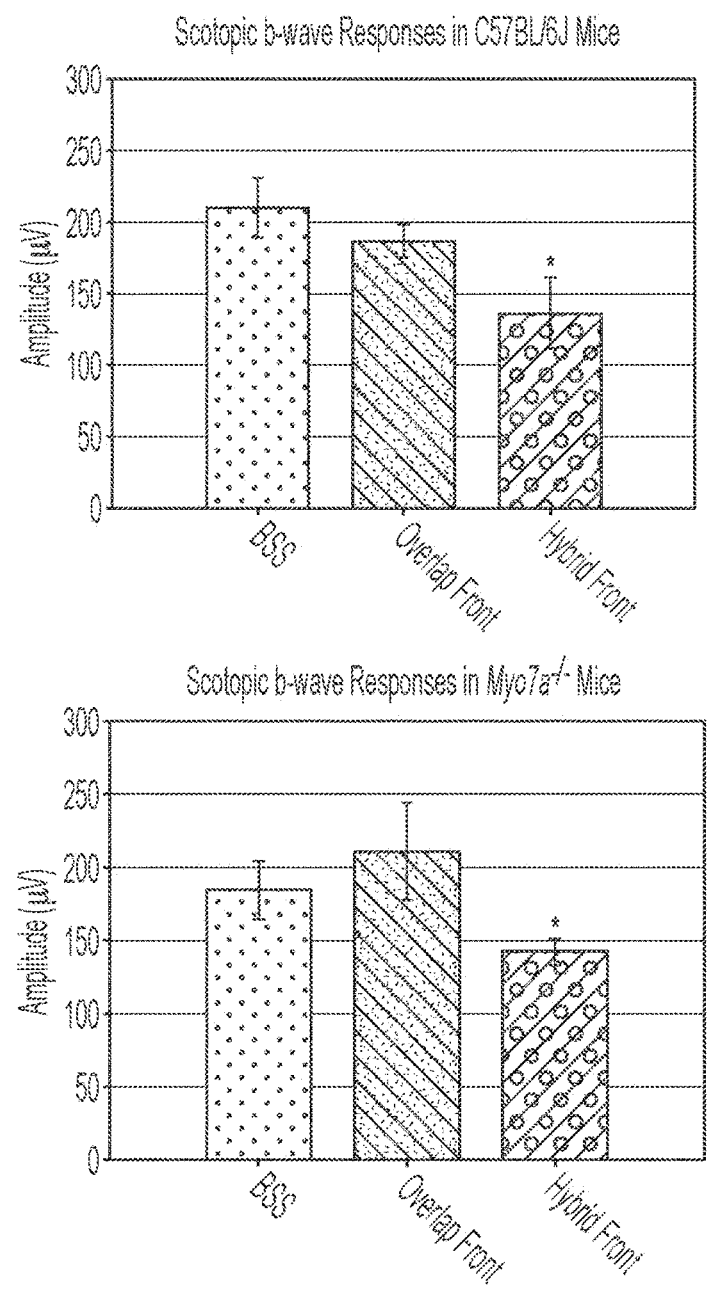
FIG. 32 shows two bar graphs illustrating the scotopic b-wave responses in C57BL/6J and Myo7a$^{-/-}$ mice at 6 weeks post-injection. These results show that only the front half hybrid vectors led to a loss of retinal function. All vectors were delivered at 5.0×10$^8$ vg.
Figure 33:
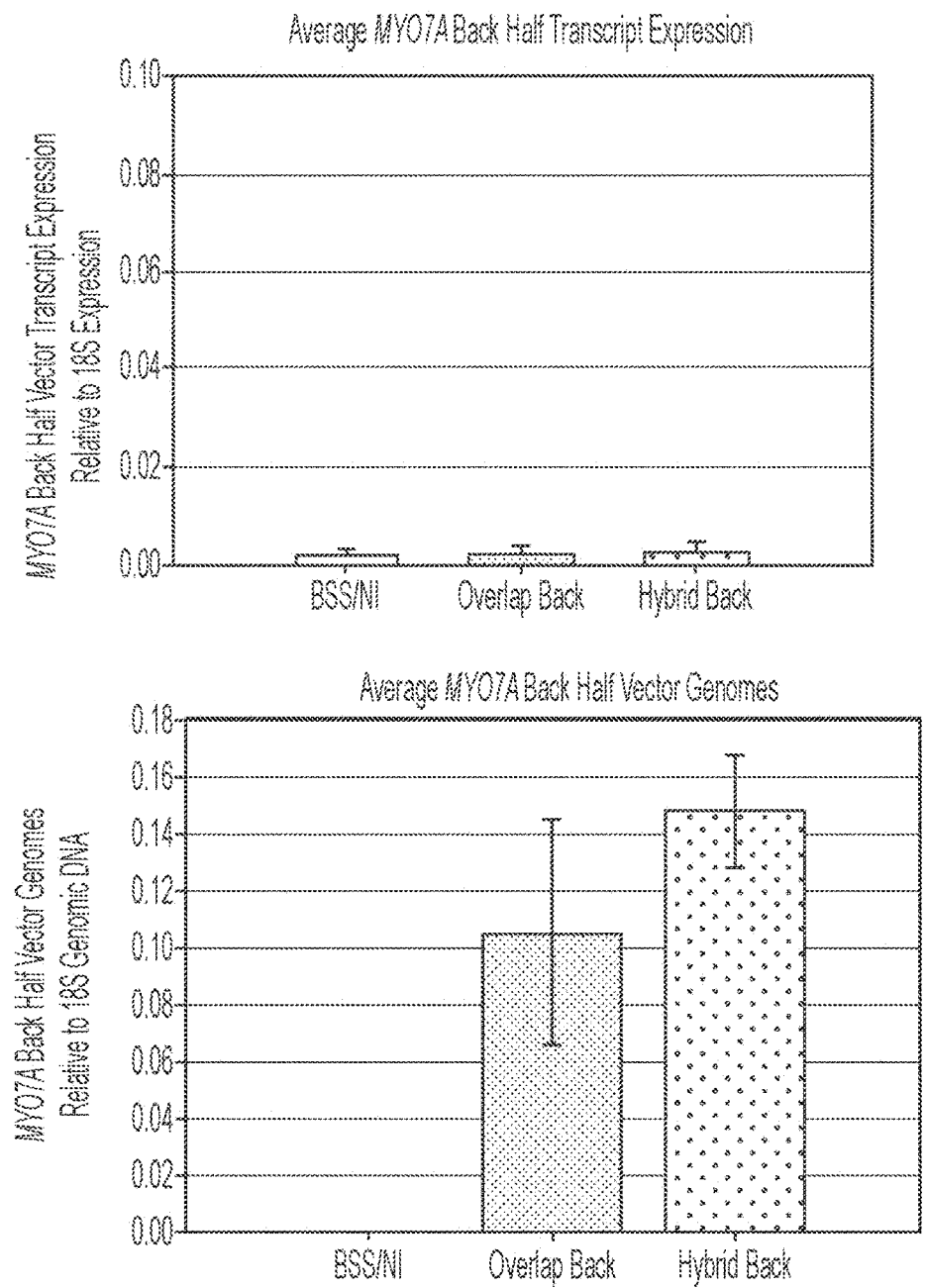
FIG. 33 shows two bar graphs illustrating the average MYO7A back half transcript expression and vector genomes at 6 weeks post-injection. These results show that the back half vectors do not produce transcript or truncated protein. All vectors were delivered at 8.0×10$^8$ vg.

The hybrid and simple overlap front half vectors as described in Examples 1-5 contained a MYO7A cDNA sequence that encoded a portion of the MYO7A protein tail domain. The tail domain of MYO7A is known for its ability to bind other cellular proteins. In Examples 1-5 of the present application, it is shown that the original hybrid front half vector was capable of encoding a MYO7A protein (FIGS. 28-30) (Dyka, et al. 2014). However, some loss of retinal structure/function was observed following injection of original hybrid front half vectors into mouse retina. This loss of retinal structure/function was hypothesized to be a result of the gain of function, which is exerted by the truncated MYO7A protein containing a partial tail domain. The truncated MYO7A protein was shown to be produced from only the front-half vectors (FIGS. 31-32). As a control, the expression levels of any truncated protein encoded by the back-half vectors was also measured. These results demonstrate that back-half vectors do not produce a truncated product and do not lead to a loss of retinal structure/function (FIG. 33).

To eliminate this gain of function toxicity associated with the truncated MYO7A protein fragment, improved, second generation hybrid and simple overlap vectors were developed with the goal of eliminating the formation of the truncated protein from the front-half vectors. Though the previously developed simple overlap vector did not produce observable quantities of truncated MYO7A protein, and did not exhibit observable loss of structure/function following its injection in mice, a second generation simple overlap vector was nevertheless developed in conjunction with the second generation hybrid vector. This was done as a precaution to hedge against the possibility that the original simple overlap front-half vector may express truncated MYO7A at levels unable to be detected via immunoblot and tolerability studies in mouse.

Figure 34:
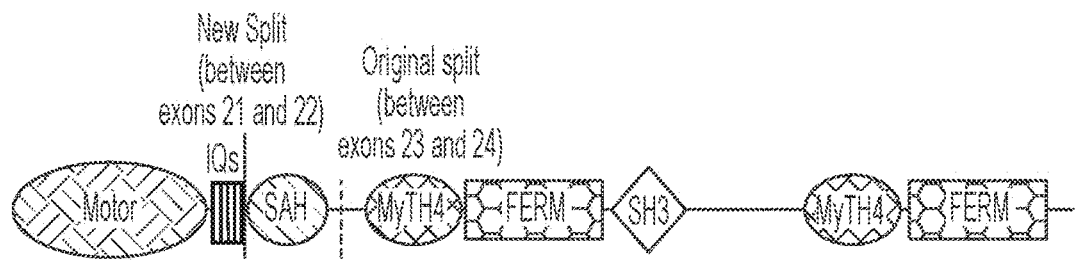
FIG. 34 is a diagram showing the split site relocation from the original site, between exons 23 and 24, to a new split site, between exons 21 and 22, in order to prevent a loss of function observed following injection with front half hybrid vectors. The hybrid vector system with the new split site between exons 21 and 22 will be hereinafter referred to as the "second generation" hybrid.

In both the hybrid and simple overlap platforms, sequence corresponding to the tail domain from the front-half vectors was moved to the back-half vectors. The MYO7A protein is an actin-based molecular motor, wherein the N-terminal (head) contains an actin-binding site and an ATP-binding site. The 5IQ (neck) is stabilized by calmodulin, and there is a single a-helix (SAH) that acts as a lever. The C-terminal (tail) domain of the MYO7A protein determines the functional specificity. Notably, in the hybrid vector, the 'split point' was moved from exon 23/24 in the original to exon 21/22 in the second generation (FIGS. 34 and 50A), such that the second generation vector systems have the split point moved from one side of the single alpha-helix (SAH) to the other. This new split between exons 21 and 22 is positioned between the 5IQ (neck) and SAH.

In the simple overlap vector, the amount of overlap sequence was reduced such that no sequence corresponding to the tail domain remained in the front vector (this new vector construct will be hereinafter referred to as the "second generation overlap"). Thus, the second generation overlap vector would contain a shorter segment of overlapping sequence such that the overlap ended at the split point between exons 21 and 22. The second generation hybrid and second generation overlap vectors described herein ensure that no portion of tail domain is encoded by either the hybrid front-, or simple overlap front-half vector. The vector systems were altered in this way to reduce production of truncated MYO7A protein.

Figure 35A:
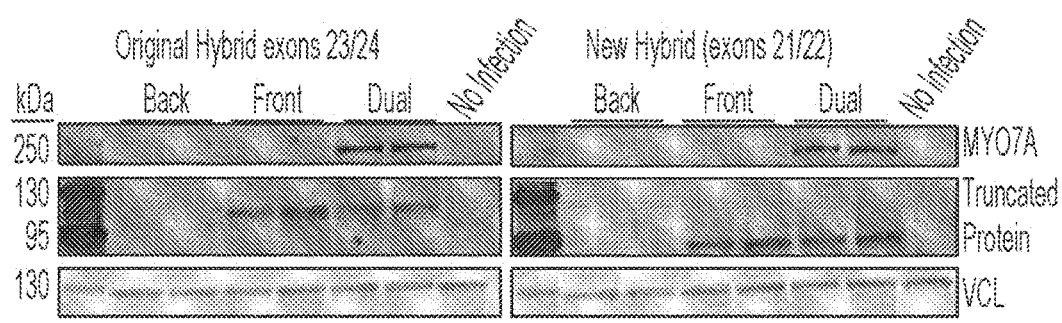
FIGS. 35A-35B show in vitro results after administration of first and second generation hybrid vectors in HEK293 cells.
Figure 35B:
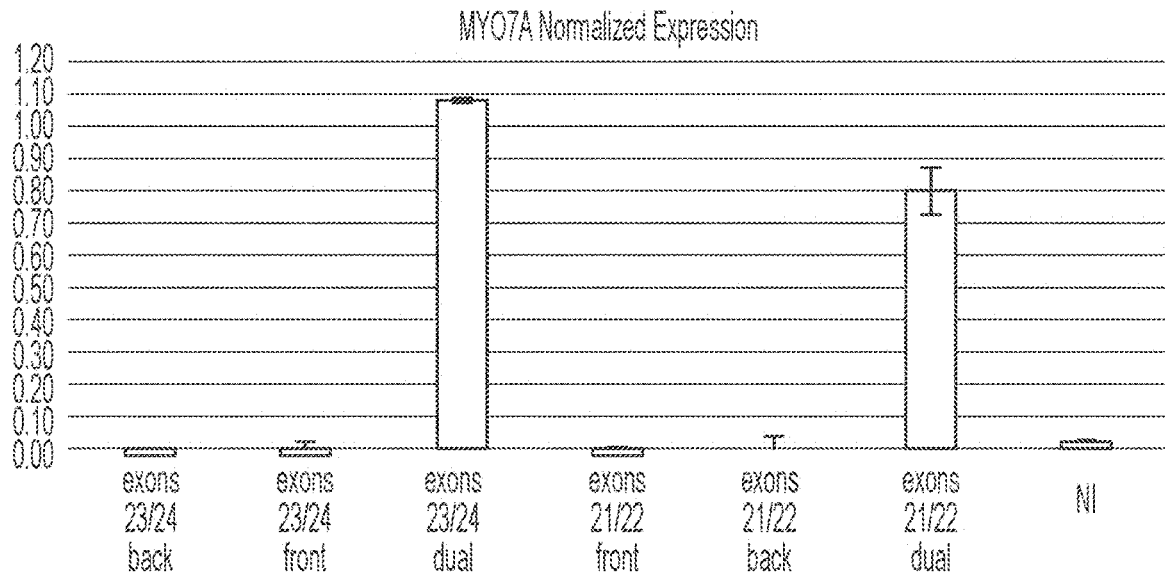
Figures 36A, 36B:
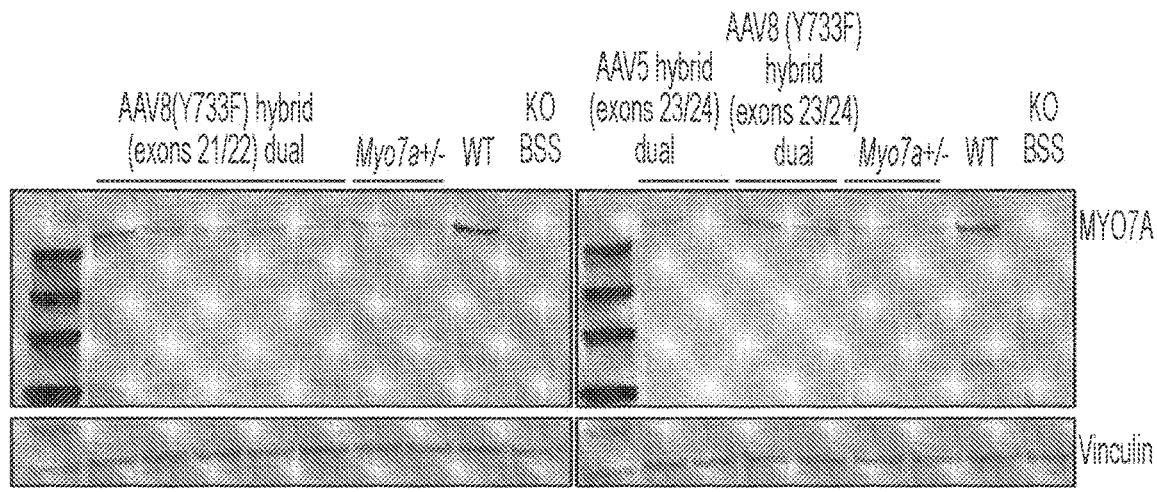
FIGS. 36A-36C show in vivo results from the subretinal injection of second generation dual hybrid vectors in Myo7a$^{-/-}$ mice. The injection dose was 5×10$^8$ vg total.
Figure 36C:
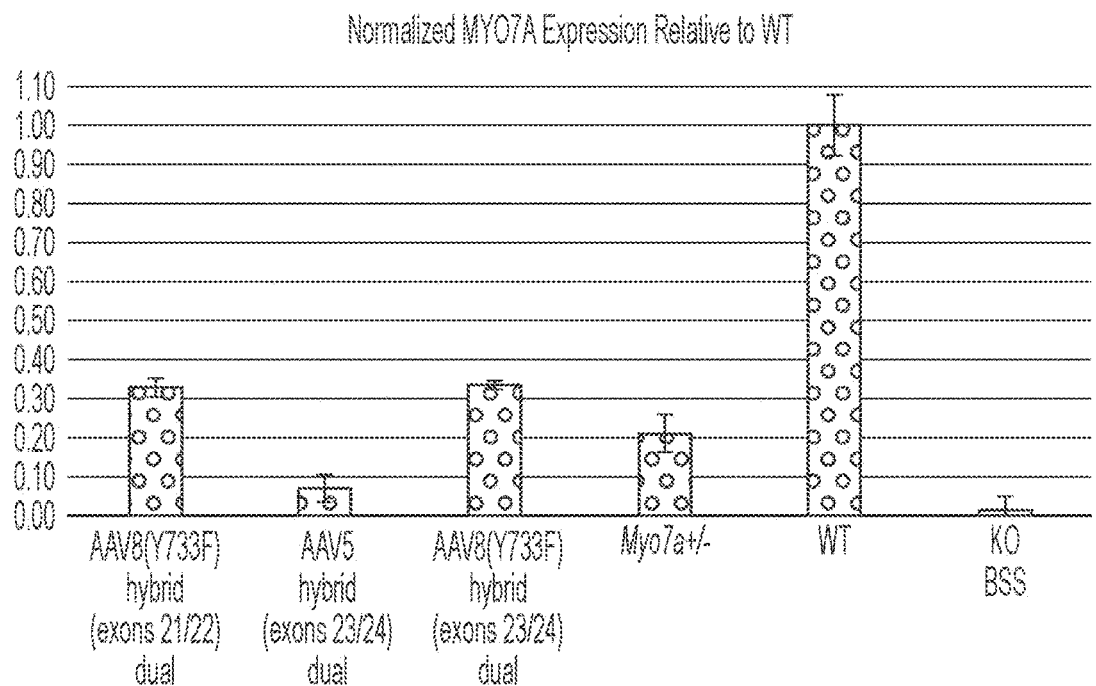
Figure 38:
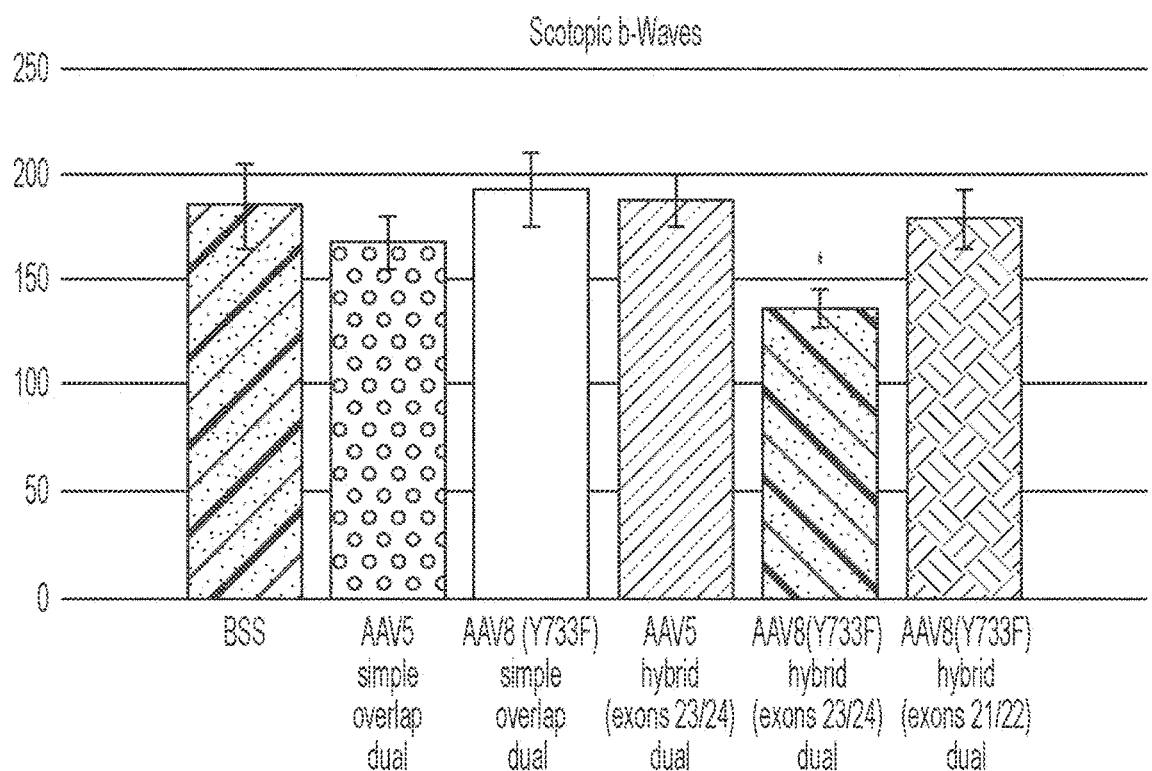
FIG. 38 is a bar graph showing the results from in vivo hybrid AAV-MYO7A injections. The second generation Ex21/22 hybrid vectors express equivalent amounts of full-length MYO7A compared to the first generation Ex23/24 hybrid vectors, but do not cause the production of a truncated protein fragment observed in the first generation Ex23/24 hybrid vectors.
Figure 39A:
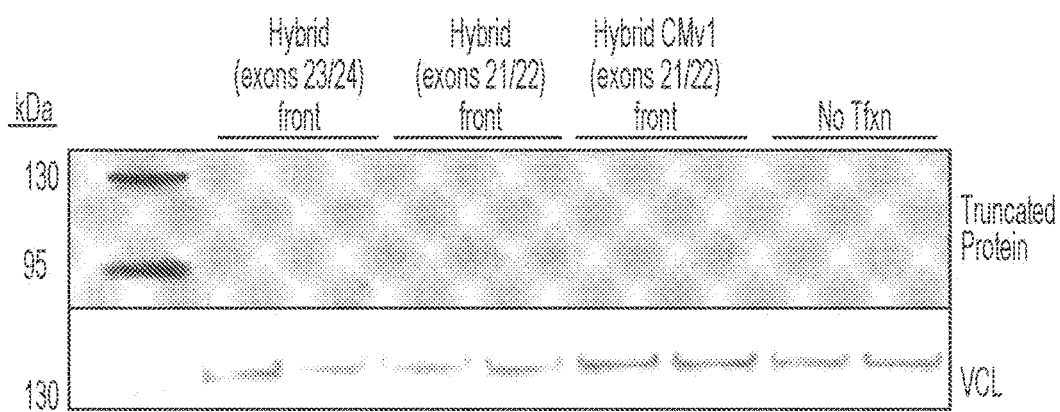
FIGS. 39A-39B show in vitro results of expression of a truncated MYO7A protein in HEK293 cells.
Figure 39B:
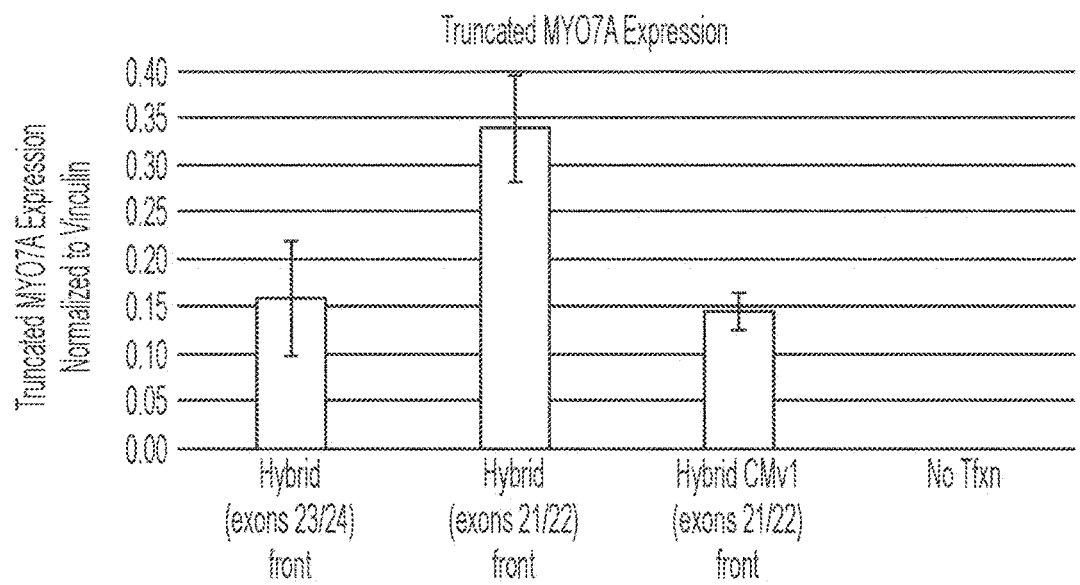

When the second generation hybrid vectors containing the exon 21/22 split point were administered in vitro to HEK293 cells, a truncated MYO7A protein of smaller size, corresponding to the change in vector sequence was observed (FIGS. 35 and 39). When the second generation hybrid vectors containing the exon 21/22 split point were administered in vivo via subretinal injection in Myo7a$^{-/-}$ mice, the smaller sized MYO7A protein was also observed (FIGS. 36 and 38). The second generation hybrid vectors containing the exon 21/22 split point express equivalent amounts of full-length MYO7A compared to original hybrid vectors containing the exon 23/24 split point (see, e.g., FIGS. 35 and 36), but do not produce the MYO7A tail protein fragment observed in original hybrid vectors (FIG. 38). In sum, it is demonstrated herein that the second generation hybrid and simple overlap vectors that do not express a tail domain sequence in the front half vectors result in a MYO7A protein product that is better tolerated in retina.

The front half AAV-MYO7A vectors (both hybrid and simple overlap) contain promoters and inverted terminal repeats (ITRs). It is possible that the ITRs provide a polyadenylation signal that, together with the promoter, leads to the production and maturation of messenger RNA for translation. In the context of the hybrid vectors, it is also possible that the alkaline phosphatase (AP) splice donor and APhead 'intron' sequence are also facilitating maturation of the mRNA by providing a splicing signal. While the exact mechanism promoting mRNA maturation is unclear, it is observable that hybrid front half vectors do produce truncated protein (FIGS. 31-33).

Figure 42:
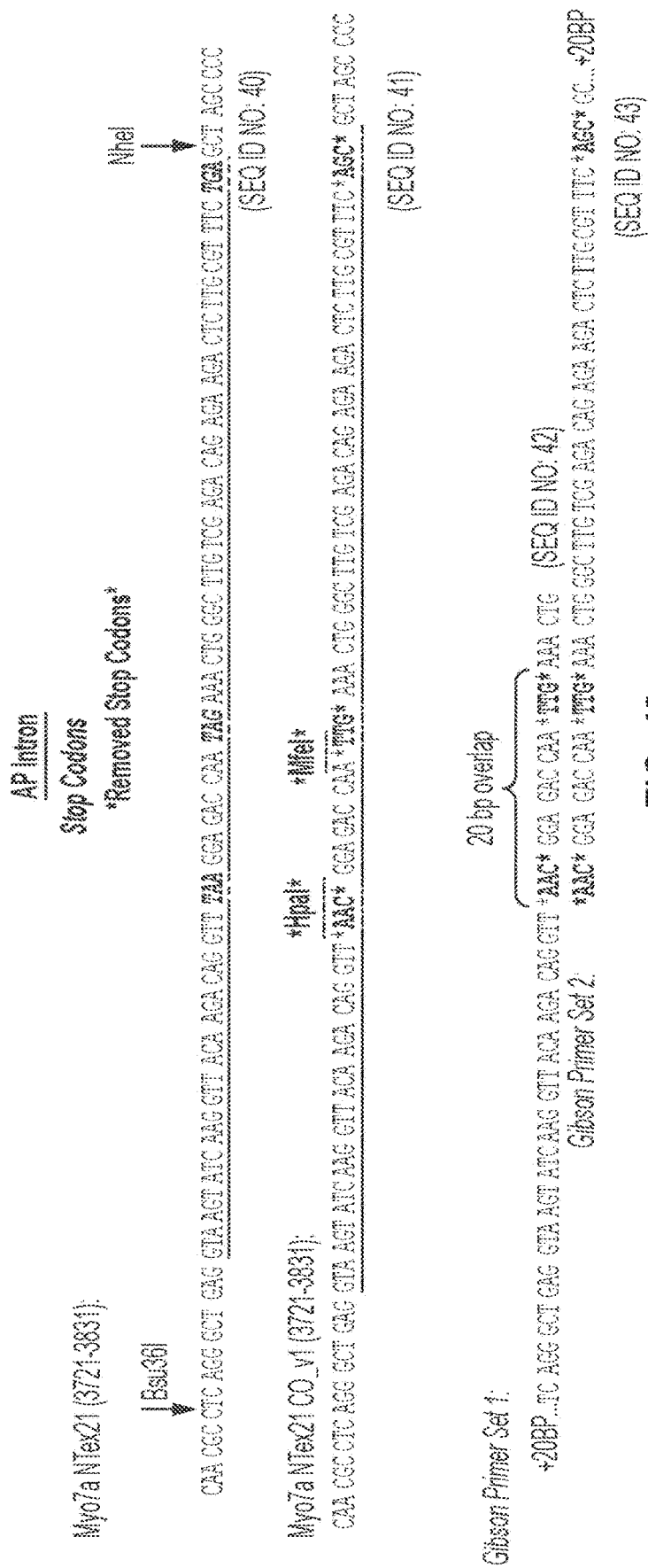
FIG. 42 shows the procedure for removal of the stop codons from the second generation hybrid front-half vector ("Myo7a NT-Ex21") to create the CMv1 hybrid front-half vector. The second generation hybrid front-half vector (relevant fragment of SEQ ID NO: 31 shown as SEQ ID NO: 40) contained three stop codons within the AP intron (potential stop codons shown in red). The restriction enzymes Bsu36I and NheI were used to excise the region containing the stop codons. Gibson primer sets (SEQ ID NO: 42, SEQ ID NO: 43) were then used to replace the excised sequence. The new sequence had all three of the potential in-frame stop codons removed (are indicated with asterisks (*)) (relevant fragment of SEQ ID NO: 33 shown as SEQ ID NO: 41). In addition to modifying the potential stop codons, two restriction sites, HpaI and MfeI, were added to the new sequence to simplify the screening of the resultant clones.

Though it is demonstrated herein that the second generation hybrid vectors result in diminished production of undesired products, additional improvements were made to the vectors to reduce the production of truncated MYO7A, thereby further increasing safety and efficiency. In the hybrid vectors, which contain the second generation exon 21/22 split point as described above, potential in-frame stop codons located downstream of the MYO7A sequence were removed from the front hybrid vector plasmids (FIG. 42). The single nucleotide substitutions removing these potential stop codons are designed to take advantage of the 'non-stop' decay mechanism of the cell, thereby eliminating the spurious RNA before it can be translated. In-frame stop codons were removed in two stages. First, three potential stop codons within the AP splice donor sequence were removed from the second generation hybrid vector to create a further improved vector still containing the exon 21/22 split point ("CMv1 hybrid"; SEQ ID NOs: 33 and 32; FIG. 42).

An additional potential in-frame stop codon was located within the shared recombinogenic AP region. Thus, a separate, further improved vector was generated wherein there were functional improvements made in both the front-half and back-half second generation hybrid vectors containing the exon 21/22 split point ("CMv2 hybrid"; SEQ ID NOs: 34 and 35). The CMv2 hybrid front half vector has the three potential stop codons located in the AP splice donor sequence, as well as the one potential stop codon located in the APhead recombinogenic sequence, removed. The CMv2 hybrid back half vector has an identical change made in the APhead recombinogenic sequence so as to match the front half vector.

Upon making the modifications that result in the CMv2 hybrid back-half vector as described herein, the CMv2 hybrid back-half vector becomes close to exceeding, but does not actually exceed, the packaging limit of an AAV vector construct. To mitigate the possibility that the back-half vector is too large, a construct was designed that modifies the CMv2 hybrid back-half vector to remove any extraneous sequence existing between elements in the construct, as well as the HA sequence. Once modified, the resulting back-half vector is designated as the CMv2.1 hybrid back-half vector (SEQ ID NO: 44).

Figure 40:
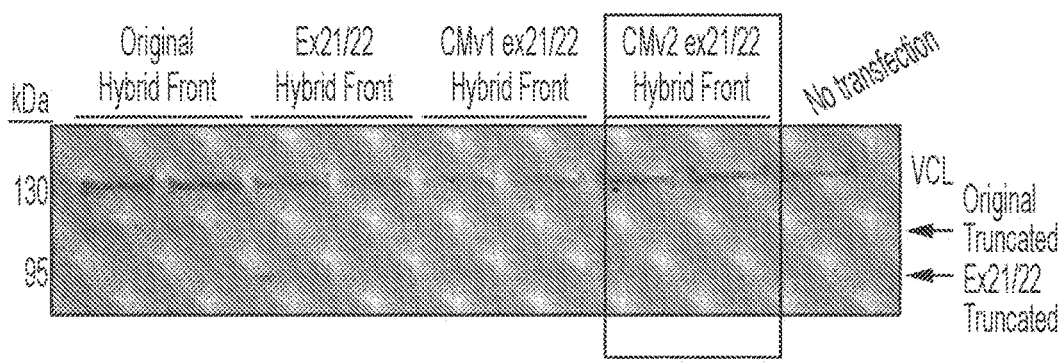
FIG. 40 shows the western blot results for the original hybrid front vector, second generation ex21/22 hybrid front vector, CMv1 ex21/22 hybrid front vector, and the CMv2 ex21/22 hybrid front vector. As used herein, "CMv2" (may be referred to herein as "COv2") refers to the human codon-modified version 2 hybrid vector.

The CMv1 and CMv2 hybrid vectors were tested in vitro, by transfecting these plasmids into HEK293 cells. The first generation hybrid front half vector ("original") and the second generation hybrid front half vector ("ex21/22") were also used for comparison (FIG. 40). It was found that the CMv1 hybrid front half vector still produced truncated MYO7A. However, the CMv2 hybrid front half vector did not produce any truncated protein. Vinculin (VCL) was used as a loading control in all samples.

Figure 43:
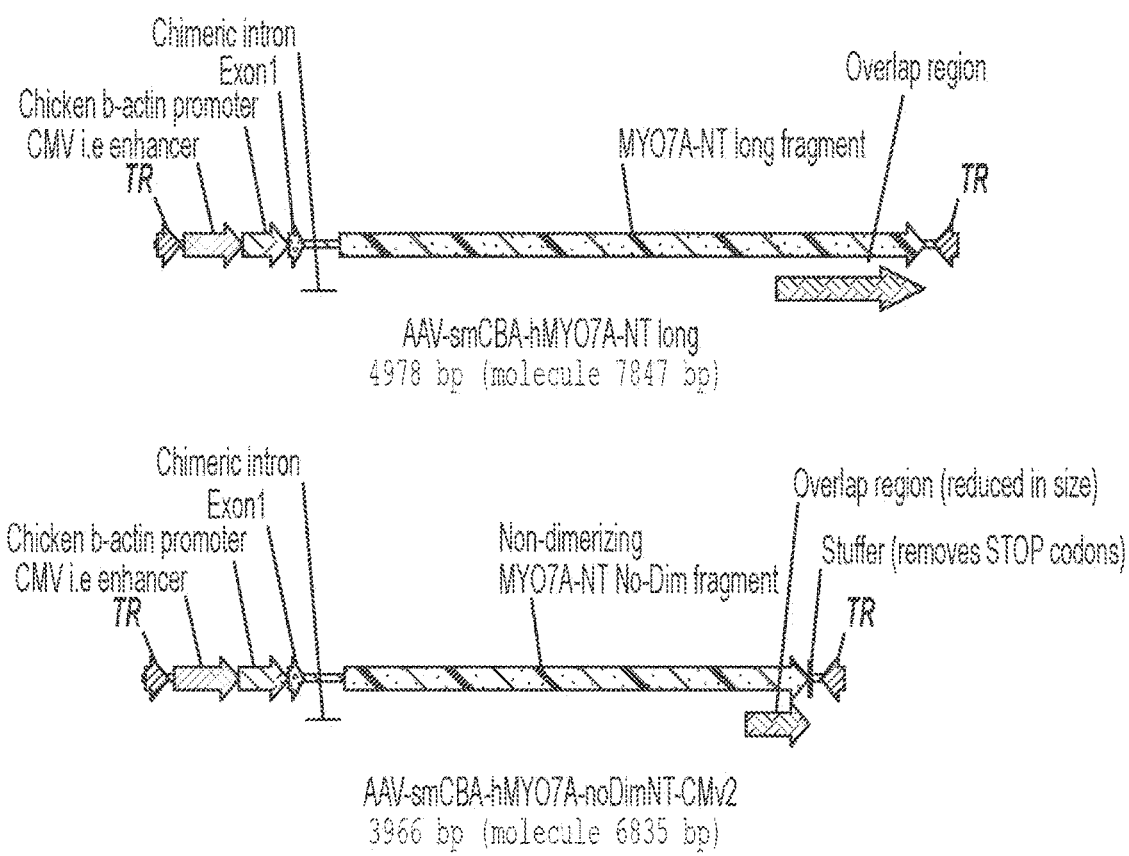
FIG. 43 shows the changes made in the second generation overlap front-half vector to create the CMv1 overlap front-half vector.

Corresponding changes were made in the simple overlap vector, despite the absence of truncated protein encoded by this vector (FIG. 43). Because the putative stop codons that were removed in the CMv1 and CMv2 hybrid vectors do not exist in the front-half of the simple overlap vectors, slightly different modifications were made to the simple overlap vectors. In the CMv1 overlap vector, the simple overlap vector has been modified in the 3' untranslated region, between the MYO7A partial coding sequence and the 3' AAV ITR, to remove potential in-frame stop codons ("CMv1 overlap"; SEQ ID NOs: 36 and 38; FIG. 43).

As shown in FIG. 41, AAV-mediated MYO7A transcript is expressed in macaque retina, and tolerability of dual AAV5-MYO7A vectors in subretinally injected macaque retinas is shown. Macaque retinas were evaluated 2 months after injection.

These data show great promise for application of the technology to human patients.

Figure 47:
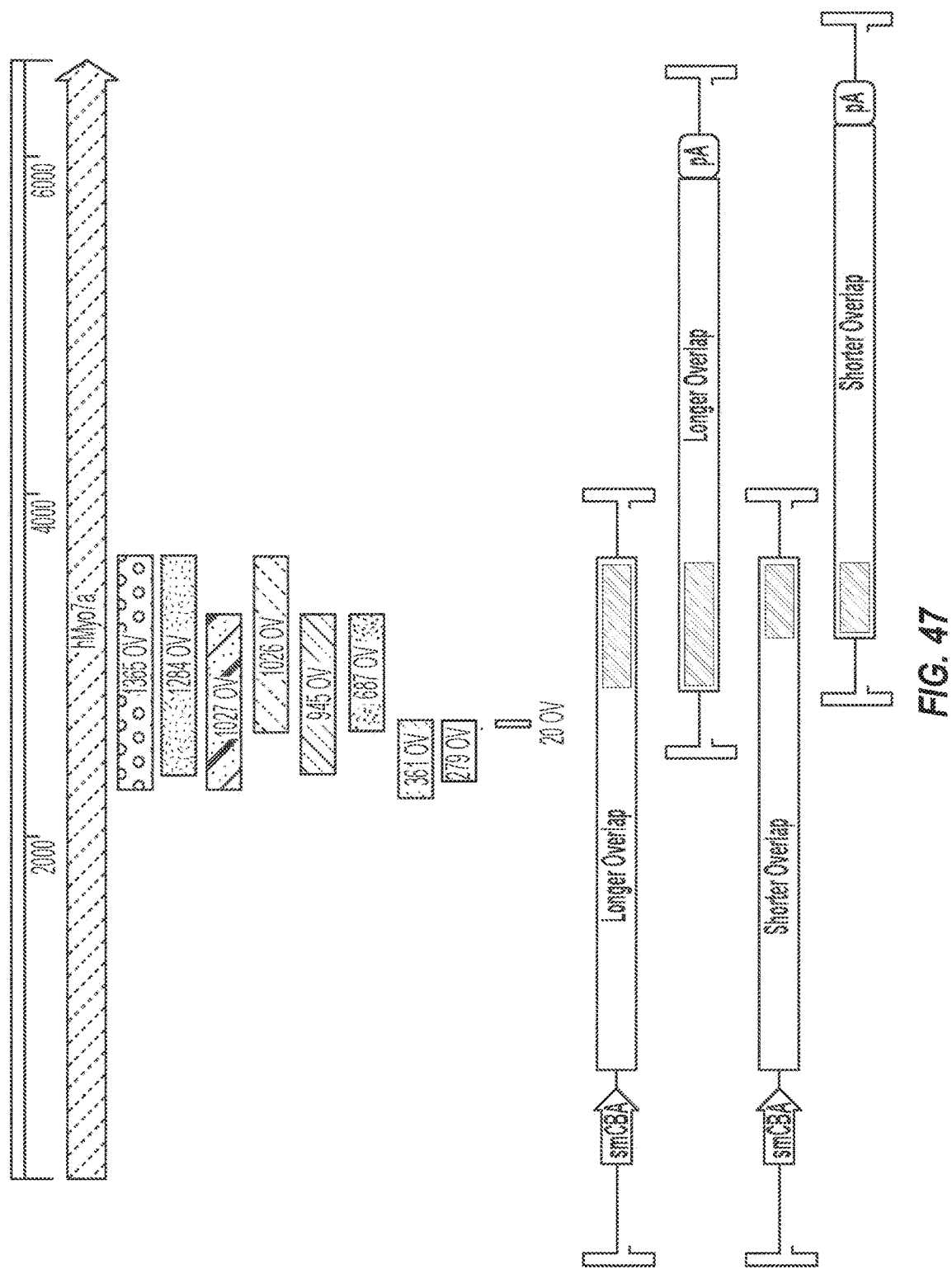
FIG. 47 shows length and location of overlap. Shorter overlap lengths result in less shared sequence between front and back half vectors.

EXAMPLE 7 provides third generation hybrid vectors.
Third Generation Overlap Vectors An improved third generation (V3) overlap vector pair was generated by altering the overlapping regions of the MYO7A coding sequence. This V3 overlap pair consists of a front half vector ("AAV-smCBA-hMYO7A-NTlong-v3") comprising the nucleotide sequence of SEQ ID NO: 50, and a back half vector ("AAV-smCBA-hMYO7A-CTlong-v3.HA") comprising the nucleotide sequence of SEQ ID NO: 51. This V3 overlap pair contains an N-terminal myosin 7A coding sequence comprising SEQ ID NO: 66 and a C-terminal myosin 7A coding sequence comprising SEQ ID NO: 80. These vectors contain shortened overlapping region length (see FIGS. 46 and 47), such as overlapping region lengths of 945 bp and 687 bp. Reduction of the length of the overlapping region has the effect of reducing the size of the vector genome overall.

Figure 49A:
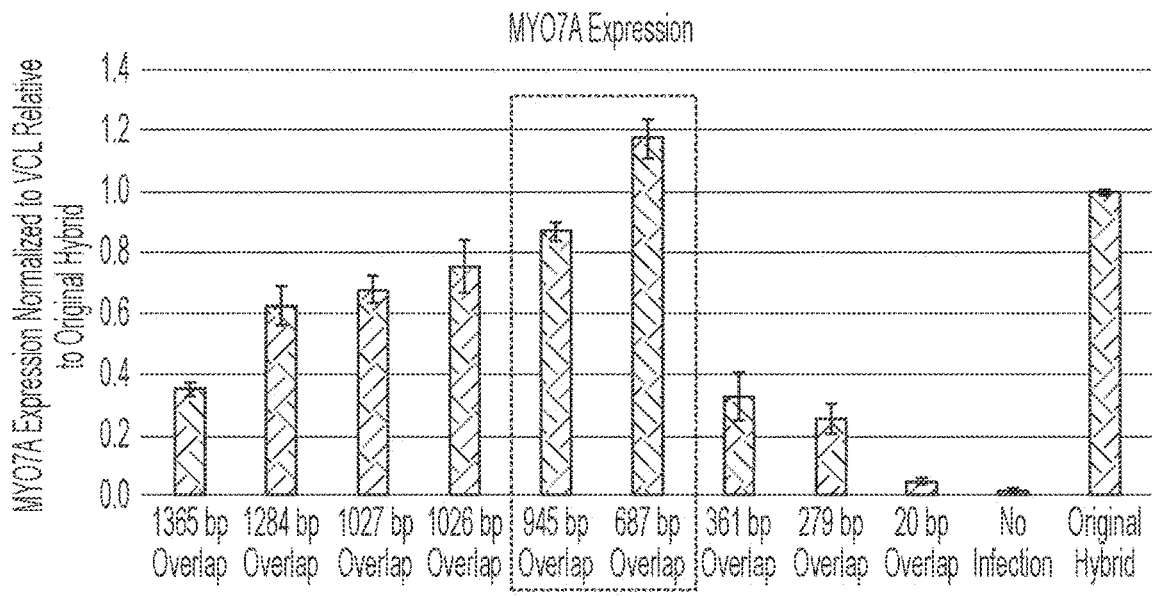
FIGS. 49A-49B show overlap panel quantification. Overlap vectors containing 687 or 945 bp of overlapping MYO7A sequence produce as much or more full length MYO7A as original hybrid vectors.

The V3 Overlap dual vector system was shown to produce increased levels of full-length MYO7A protein as compared to the original vectors, as quantified by the Protein Simple Jess system, as shown in FIGS. 48A and 49A. Overlap vectors containing 687 bp and 945 bp of overlapping MYO7A sequence provided optimal expression levels.

Figure 49B:
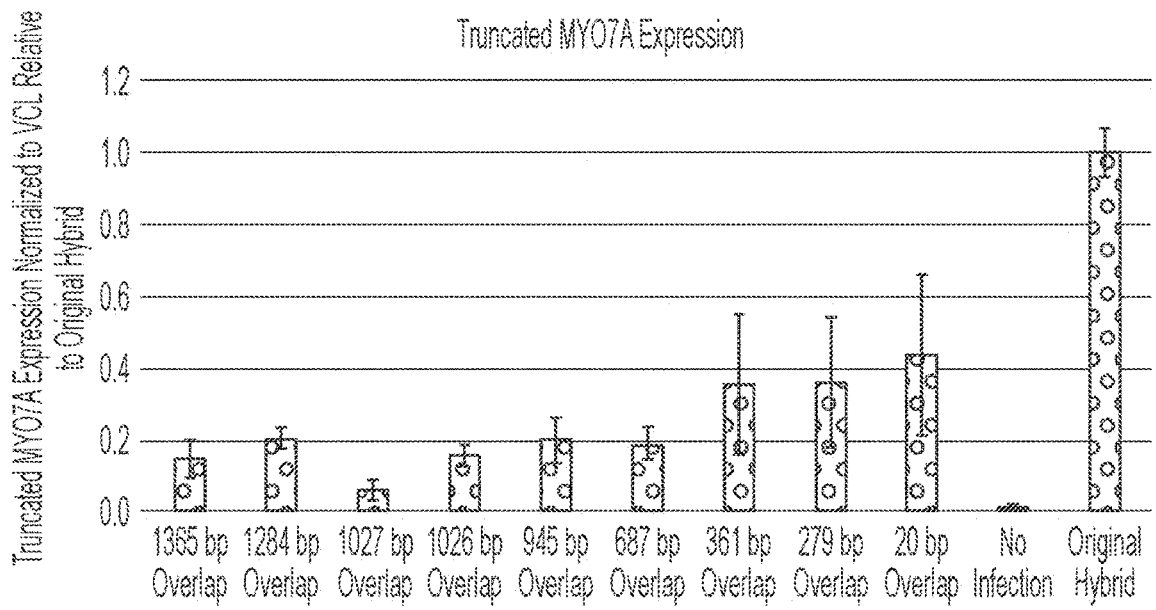

As shown in FIG. 49B, the V3 overlap vectors do not produce an appreciable amount of undesired truncated MYO7A fragment when their overlapping region length remains above 361 bp. Thus, reducing overlap length to a certain point, and therefore ensuring neither vector genome is pushing the packaging capacity of AAV capsid (4.7 to 4.9 kb), leads to increased expression of full length MYO7A. If overlap length is too small (<361 bp), full length MYO7A expression is reduced, and truncated protein may appear.

By virtue of the shorter length of their overlapping regions, these improved, third generation overlap vectors contain shorter ITR to ITR (ITR-ITR) lengths (see FIG. 48B). In particular embodiments, the length between the inverted terminal repeats at each end of the first AAV vector polynucleotide is about 4615 nucleotides (nt) or fewer. The ITR-ITR length in the improved first vector polynucleotide is 4615 nt. In particular embodiments, the length between the inverted terminal repeats at each end of the second AAV vector polynucleotide is about 4800 nt or fewer. The ITR-ITR length in the improved second vector polynucleotide is about 4560 nt.

hMYO7A overlapping regions, e.g., SEQ ID NOs: 39 and 53-59, may be used as the polynucleotide sequence that overlaps in additional overlap dual vectors expressing large genes (other than MYO7A). In particular, disclosed herein are overlap dual vectors that express a large gene other than MYO7A and that comprises a nucleotide sequence having at least 80%, 85%, 90%, 95%, 98%, or 99% identity to any one of SEQ ID NOs: 39 and 52-59. In particular embodiments, these overlap dual vectors comprises the nucleotide sequence of any one of SEQ ID NOs: 39 and 53-59, e.g., SEQ ID NO: 56 or 57, and express a large gene selected from ABCA4, CEP290, EYS, RP1, ALMS1, CDH23, PCDH15, USH1C, USH1G, USH2A, DNFB31, DMD, CFTR, GDE, DYSF, F8, and DFNB2. In some embodiments, these overlap vectors contain two overlapping sequences disclosed herein, e.g., the mutually exclusive sequences SEQ ID NOs: 39 and 56, or the mutually exclusive sequences SEQ ID NOs: 39 and 57. rAAV virions containing V3 overlap vector pairs containing 687 bp and 945 bp of overlapping region length are packaged and administered to retinal cells. rAAV virions containing V3 overlap vector pairs containing 687 bp and 945 bp of overlapping region length are packaged and administered to auditory hair cells.

Overlap vectors containing the following pairs of myosin7A-encoding nucleotide sequences are evaluated in their abilities to produce full-length MYO7A polypeptide, in vitro or in vivo. In vitro evaluation may be performed using Protein Simple Jess Western blotting.

the first AAV vector polynucleotide comprises the nucleotide sequence of SEQ ID NO: 63, and the second AAV vector polynucleotide comprises the nucleotide sequence of SEQ ID NO: 83;

the first AAV vector polynucleotide comprises the nucleotide sequence of SEQ ID NO: 63, and the second AAV vector polynucleotide comprises the nucleotide sequence of SEQ ID NO: 90;

the first AAV vector polynucleotide comprises the nucleotide sequence of SEQ ID NO: 101, and the second AAV vector polynucleotide comprises the nucleotide sequence of SEQ ID NO: 83;

the first AAV vector polynucleotide comprises the nucleotide sequence of SEQ ID NO: 101, and the second AAV vector polynucleotide comprises the nucleotide sequence of SEQ ID NO: 90;

the first AAV vector polynucleotide comprises the nucleotide sequence of SEQ ID NO: 66, and the second AAV vector polynucleotide comprises the nucleotide sequence of SEQ ID NO: 83; and the first AAV vector polynucleotide comprises the nucleotide sequence of SEQ ID NO: 66, and the second AAV vector polynucleotide comprises the nucleotide sequence of SEQ ID NO: 90.

Accordingly, in some embodiments, provided herein are polynucleotide vector systems in which the first AAV vector polynucleotide comprises a nucleotide sequence that is at least about 80%, at least 85%, at least 90%, at least 95%, at least 98%, or at least 99% identical to the SEQ ID NO: 63, and the second AAV vector polynucleotide comprises a nucleotide sequence that is at least about 80%, at least 85%, at least 90%, at least 95%, at least 98%, or at least 99% identical to nucleotide sequence of SEQ ID NO: 83. In some embodiments, the second AAV vector polynucleotide comprises a nucleotide sequence that is at least about 80%, at least 85%, at least 90%, at least 95%, at least 98%, or at least 99% identical to SEQ ID NO: 90.

In some embodiments, the first AAV vector polynucleotide comprises a nucleotide sequence that is at least about 80%, at least 85%, at least 90%, at least 95%, at least 98%, or at least 99% identical to SEQ ID NO: 101. In some embodiments, the first AAV vector polynucleotide comprises a nucleotide sequence that is at least about 80%, at least 85%, at least 90%, at least 95%, at least 98%, or at least 99% identical to SEQ ID NO: 66. In some embodiments, provided herein are polynucleotide vector systems in which the first AAV vector polynucleotide comprises a nucleotide sequence that is at least about 80%, at least 85%, at least 90%, at least 95%, at least 98%, or at least 99% identical to the SEQ ID NO: 66, and the second AAV vector polynucleotide comprises a nucleotide sequence that is at least about 80%, at least 85%, at least 90%, at least 95%, at least 98%, or at least 99% identical to nucleotide sequence of SEQ ID NO: 90.

The following overlap vectors are evaluated in their abilities to produce full-length MYO7A polypeptide, in vitro or in vivo. In vitro evaluation may be performed using Protein Simple Jess Western blotting.

the first AAV vector comprises the nucleotide sequence of SEQ ID NO: 50, and the second AAV vector comprises the nucleotide sequence of SEQ ID NO: 51;

the first AAV vector comprises the nucleotide sequence of SEQ ID NO: 50, and the second AAV vector comprises the nucleotide sequence of SEQ ID NO: 38;

the first AAV vector comprises the nucleotide sequence of SEQ ID NO: 1, and the second AAV vector comprises the nucleotide sequence of SEQ ID NO: 38;

the first AAV vector comprises the nucleotide sequence of SEQ ID NO: 50, and the second AAV vector comprises the nucleotide sequence of SEQ ID NO: 2;

the first AAV vector comprises the nucleotide sequence of SEQ ID NO: 1, and the second AAV vector comprises the nucleotide sequence of SEQ ID NO: 51;

the first AAV vector comprises the nucleotide sequence of SEQ ID NO: 36, and the second AAV vector comprises the nucleotide sequence of SEQ ID NO: 2;

the first AAV vector comprises the nucleotide sequence of SEQ ID NO: 36, and the second AAV vector comprises the nucleotide sequence of SEQ ID NO: 38;

the first AAV vector comprises the nucleotide sequence of SEQ ID NO: 36, and the second AAV vector comprises the nucleotide sequence of SEQ ID NO: 51;

the first AAV vector comprises the nucleotide sequence of SEQ ID NO: 37, and the second AAV vector comprises the nucleotide sequence of SEQ ID NO: 38; and the first AAV vector comprises the nucleotide sequence of SEQ ID NO: 37, and the second AAV vector comprises the nucleotide sequence of SEQ ID NO: 51.

Accordingly, in some embodiments, provided herein are polynucleotide vector systems in which the first AAV vector polynucleotide comprises a nucleotide sequence that is at least about 80%, at least 85%, at least 90%, at least 95%, at least 98%, or at least 99% identical to the SEQ ID NO: 50, and the second AAV vector polynucleotide comprises a nucleotide sequence that is at least about 80%, at least 85%, at least 90%, at least 95%, at least 98%, or at least 99% identical to nucleotide sequence of SEQ ID NO: 51. In some embodiments, the second AAV vector polynucleotide comprises a nucleotide sequence that is at least about 80%, at least 85%, at least 90%, at least 95%, at least 98%, or at least 99% identical to SEQ ID NO: 38. In some embodiments, the second AAV vector polynucleotide comprises a nucleotide sequence that is at least about 80%, at least 85%, at least 90%, at least 95%, at least 98%, or at least 99% identical to SEQ ID NO: 2.

In some embodiments, the first AAV vector polynucleotide comprises a nucleotide sequence that is at least about 80%, at least 85%, at least 90%, at least 95%, at least 98%, or at least 99% identical to SEQ ID NO: 1. In some embodiments, the first AAV vector polynucleotide comprises a nucleotide sequence that is at least about 80%, at least 85%, at least 90%, at least 95%, at least 98%, or at least 99% identical to SEQ ID NO: 36. In some embodiments, the first AAV vector polynucleotide comprises a nucleotide sequence that is at least about 80%, at least 85%, at least 90%, at least 95%, at least 98%, or at least 99% identical to SEQ ID NO: 37. In some embodiments, provided herein are polynucleotide vector systems in which the first AAV vector polynucleotide comprises a nucleotide sequence that is at least about 80%, at least 85%, at least 90%, at least 95%, at least 98%, or at least 99% identical to the SEQ ID NO: 37, and the second AAV vector polynucleotide comprises a nucleotide sequence that is at least about 80%, at least 85%, at least 90%, at least 95%, at least 98%, or at least 99% identical to nucleotide sequence of SEQ ID NO: 38 or SEQ ID NO: 51.

Third Generation Hybrid Vectors

An improved third generation (CMv3) hybrid system, or vector pair, was generated by making substitutions into three putative stop codons in the 3' untranslated region (UTR) of the front-half vector of the CMv2 hybrid system. As such, the CMv3 Hybrid Front Half vector contains substitutions in (i.e., removal of) one in-frame stop codon in the APhead sequence, three in-frame stop codons in the AP intron sequence, and three in-frame stop codons in the 3' UTR sequence. In exemplary embodiments, the CMv3 hybrid system is a CMv3 MIN system as residual, unseeded legacy sequences (such as restriction enzyme sites) have been removed.

Exemplary CMv3 hybrid systems consist of i) the front half vector ("AAV-smCBA-hMYO7A-NT-Ex21-APSD-APhead-CMv3") comprising the nucleotide sequence of SEQ ID NO: 46, and ii) a CMv2 back half vector ("AAV-APhead-APSA-ex22hMYO7A-CT.HA-CMv2)") comprising the nucleotide sequence of SEQ ID NO: 35, a CMv2.1 back half vector ("AAV-APhead-APSA-hMYO7ACTex22-CMv2.1") comprising the nucleotide sequence of SEQ ID NO: 44, or a minimized version of either vector, e.g. a CMv2 (or V2-)Back MIN comprising the nucleotide sequence of SEQ ID NO: 49.

To generate the Hybrid-CMv3 back MIN and Hybrid-CMv2 back MIN vectors, an 'unneeded legacy' sequence was removed from the back half vector to ensure the vector size did not exceed the packaging capacity of an AAV capsid. By virtue of the removal of unseeded legacy sequences from the back, these improved, third generation hybrid vectors contain shorter ITR to ITR (ITR-ITR) lengths (see FIGS. 50C and 51B). In particular embodiments, the length between the inverted terminal repeats at each end of a first AAV vector polynucleotide of the hybrid vectors is about 4279 nucleotides (nt) or fewer. This has the effect of minimizing the length of the back half vector, which improved packaging efficiency. The Hybrid-V2 back MIN is 122 bp smaller (4981 vs. 4859 bp) than the associated original vector, and the Hybrid_CMv2 back MIN is 121 bp smaller (4982 vs. 4861 bp) than the associated original vector. For the Hybrid-V2 back MIN HA and Hybrid-CMV2 back MIN HA vectors, a hemagglutinin (HA) tag was added to the minimized back half vectors (Hybrid-V2 back MIN and Hybrid-CMV2 back MIN) to allow for detection in normal monkeys.

Figure 50D:
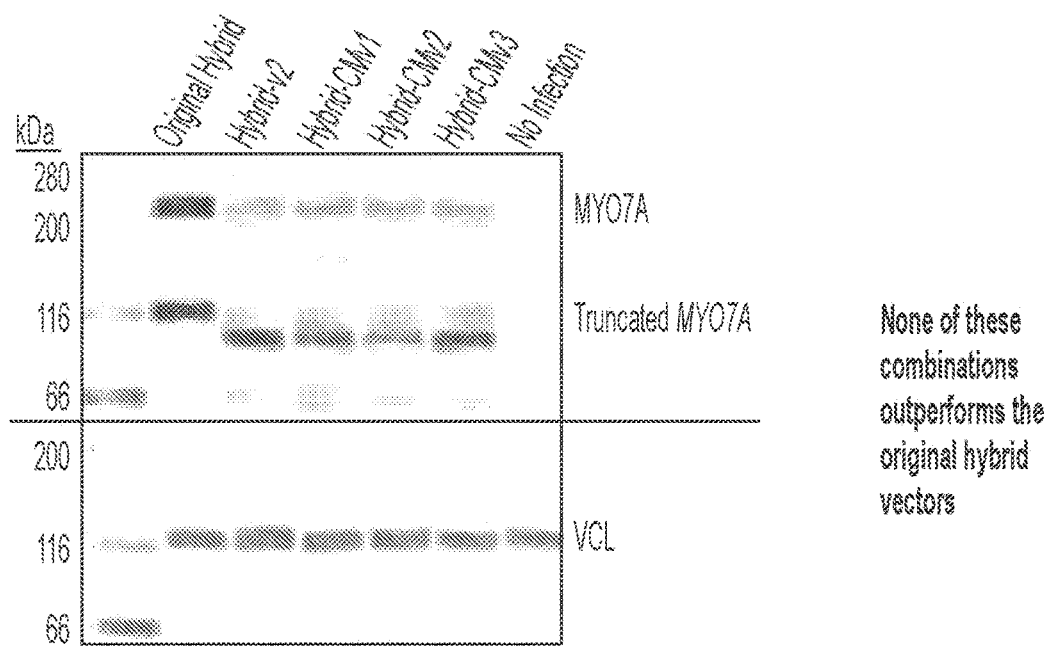
Figure 51A:
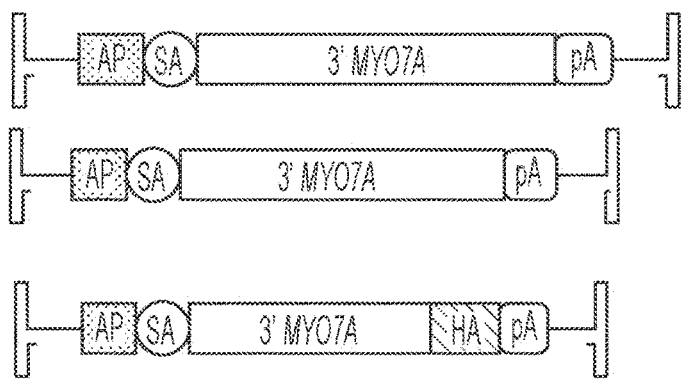
Figure 51D:
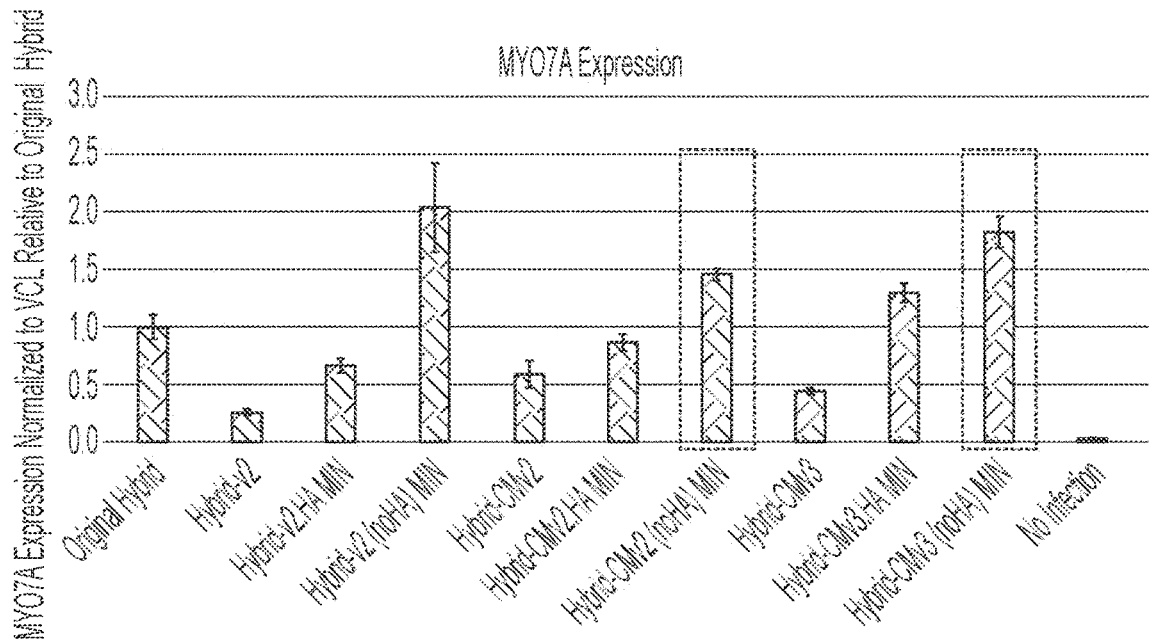
Figure 51E:
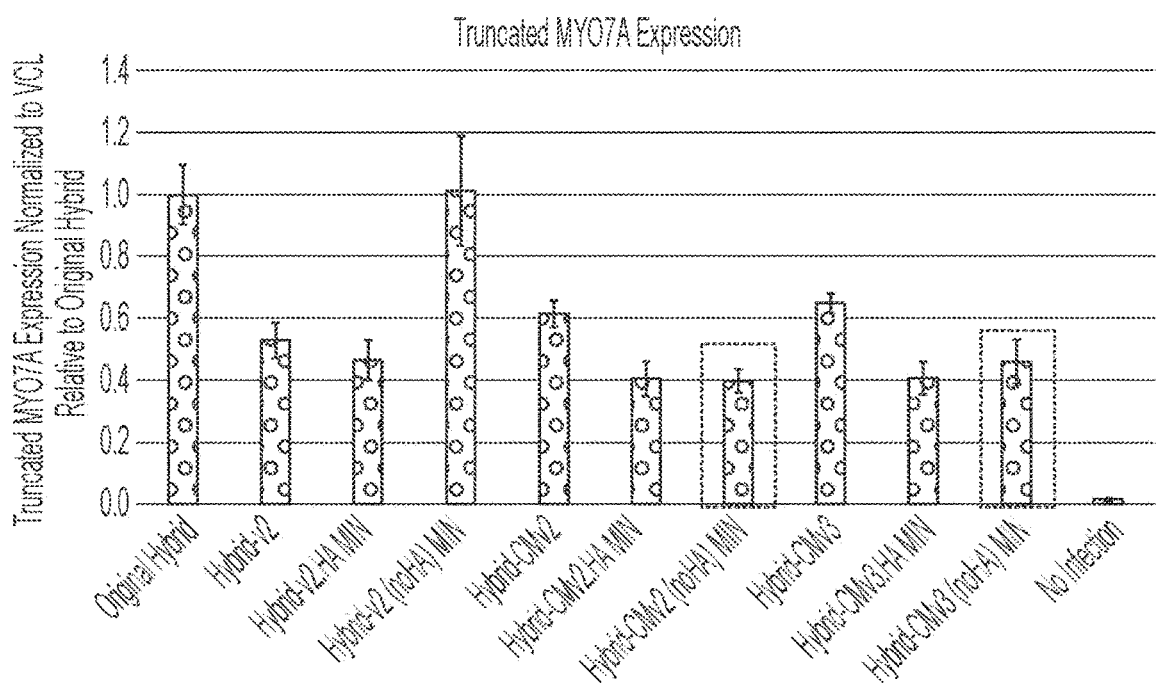

The CMv3 Hybrid vector system was shown to produce comparably low levels of the truncated MYO7A fragment as compared to Hybrid CMv1 and Hybrid CMv2 vectors, as shown in FIG. 50D. Further, as shown in FIGS. 51C and 51D, the pairing the hybrid CMv3 front half vector with a CMv3 MIN back half vector produced full-length MYO7A at levels equal to or above that seen with the original ($1^{st}$ generation) hybrid vectors. This pair of vectors produced comparably low levels of truncated fragment, as shown in FIG. 51E.

The inventors have also discovered that wherein a hMYO7A sequence may be used as the intronic sequence mediating recombination in the cell following administration in hybrid dual vectors expressing large genes (other than MYO7A). Such hybrid vectors are generated to contain one or more overlapping regions identified through improvement of the MYO7A overlap vectors provided herein. (Such vectors may or do not contain an APhead sequence and/or an AP intronic sequence, to allow for the insertion of one of these overlapping regions.) In particular, disclosed herein are hybrid dual vectors that contain a sequence between the first intron and second intron of the first and second AAV vector polynucleotides, respectively, that comprises a nucleotide sequence having at least 80%, 85%, 90%, 95%, 98%, or 99% identity to any one of SEQ ID NOs: 39 and 52-59. In particular embodiments, hybrid dual vectors contain a sequence between the first intron and second intron of the first and second AAV vector polynucleotides, respectively, that comprises the nucleotide sequence of any one of SEQ ID NOs: 39 and 53-59, e.g., SEQ ID NO: 56 or 57. Additional large genes that may be delivered with these hybrid vectors include ABCA4, CEP290, EYS, RP1, ALMS1, CDH23, PCDH15, USH1C, USH1G, USH2A, DNFB31, DMD, CFTR, GDE, DYSF, F8, and DFNB2. In some embodiments, these hybrid dual vectors contain an intron sequence containing two overlapping sequences disclosed herein, e.g., the mutually exclusive sequences SEQ ID NOs: 39 and 56, or the mutually exclusive sequences SEQ ID NOs: 39 and 57.

rAAV virions containing CMv3 hybrid vector pairs comprising the SEQ ID NO: 46 front-half vector and SEQ ID NO: 35 back-half vector are packaged and administered to retinal cells. rAAV virions containing CMv3 hybrid vector pairs comprising the SEQ ID NO: 46 front-half vector and SEQ ID NO: 35 back-half vector are packaged and administered to auditory hair cells.

Hybrid vectors containing the following pair of myosin7A-encoding nucleotide sequences are evaluated in their abilities to produce full-length MYO7A polypeptide, in vitro or in vivo:
the first AAV vector polynucleotide comprises the nucleotide sequence of SEQ ID NO: 73, and the second AAV vector polynucleotide comprises the nucleotide sequence of SEQ ID NO: 75.

Accordingly, in some embodiments, provided herein are polynucleotide vector systems in which the first AAV vector polynucleotide comprises a nucleotide sequence that is at least about 80%, at least 85%, at least 90%, at least 95%, at least 98%, or at least 99% identical to the SEQ ID NO: 73, and the second AAV vector polynucleotide comprises a nucleotide sequence that is at least about 80%, at least 85%, at least 90%, at least 95%, at least 98%, or at least 99% identical to nucleotide sequence of SEQ ID NO: 75.

Hybrid vector systems comprising the following pairs of vector sequences are evaluated in their abilities to produce full-length MYO7A polypeptide, in vitro or in vivo.
the first AAV vector comprises the nucleotide sequence of SEQ ID NO: 31, and the second AAV vector comprises the nucleotide sequence of SEQ ID NO: 32;
the first AAV vector comprises the nucleotide sequence of SEQ ID NO: 46, and the second AAV vector comprises the nucleotide sequence of SEQ ID NO: 35;
the first AAV vector comprises the nucleotide sequence of SEQ ID NO: 46, and the second AAV vector comprises the nucleotide sequence of SEQ ID NO: 49;
the first AAV vector comprises the nucleotide sequence of SEQ ID NO: 34, and the second AAV vector comprises the nucleotide sequence of SEQ ID NO: 47;
the first AAV vector comprises the nucleotide sequence of SEQ ID NO: 31, and the second AAV vector comprises the nucleotide sequence of SEQ ID NO: 48;
the first AAV vector comprises the nucleotide sequence of SEQ ID NO: 31, and the second AAV vector comprises the nucleotide sequence of SEQ ID NO: 49;
the first AAV vector comprises the nucleotide sequence of SEQ ID NO: 33, and the second AAV vector comprises the nucleotide sequence of SEQ ID NO: 32;
the first AAV vector comprises the nucleotide sequence of SEQ ID NO: 34, and the second AAV vector comprises the nucleotide sequence of SEQ ID NO: 35; and
the first AAV vector comprises the nucleotide sequence of SEQ ID NO: 34, and the second AAV vector comprises the nucleotide sequence of SEQ ID NO: 44.

Accordingly, in some embodiments, provided herein are polynucleotide vector systems in which the first AAV vector polynucleotide comprises a nucleotide sequence that is at least about 80%, at least 85%, at least 90%, at least 95%, at least 98%, or at least 99% identical to the SEQ ID NO: 31, and the second AAV vector polynucleotide comprises a nucleotide sequence that is at least about 80%, at least 85%, at least 90%, at least 95%, at least 98%, or at least 99% identical to nucleotide sequence of SEQ ID NO: 32. In some embodiments, the second AAV vector polynucleotide comprises a nucleotide sequence that is at least about 80%, at least 85%, at least 90%, at least 95%, at least 98%, or at least 99% identical to SEQ ID NO: 48 or SEQ ID NO: 49. In some embodiments, the first AAV vector polynucleotide comprises a nucleotide sequence that is at least about 80%, at least 85%, at least 90%, at least 95%, at least 98%, or at least 99% identical to SEQ ID NO: 33.

In some embodiments, provided herein are polynucleotide vector systems in which the first AAV vector polynucleotide comprises a nucleotide sequence that is at least about 80%, at least 85%, at least 90%, at least 95%, at least 98%, or at least 99% identical to the SEQ ID NO: 46, and the second AAV vector polynucleotide comprises a nucleotide sequence that is at least about 80%, at least 85%, at least 90%, at least 95%, at least 98%, or at least 99% identical to nucleotide sequence of SEQ ID NO: 35. In some embodiments, the second AAV vector polynucleotide comprises a nucleotide sequence that is at least about 80%, at least 85%, at least 90%, at least 95%, at least 98%, or at least 99% identical to SEQ ID NO: 49. In some embodiments, the first AAV vector polynucleotide comprises a nucleotide sequence that is at least about 80%, at least 85%, at least 90%, at least 95%, at least 98%, or at least 99% identical to SEQ ID NO: 34.

In some embodiments, provided herein are polynucleotide vector systems in which the first AAV vector polynucleotide comprises a nucleotide sequence that is at least about 80%, at least 85%, at least 90%, at least 95%, at least 98%, or at least 99% identical to the SEQ ID NO: 34, and the second AAV vector polynucleotide comprises a nucleotide sequence that is at least about 80%, at least 85%, at least 90%, at least 95%, at least 98%, or at least 99% identical to nucleotide sequence of SEQ ID NO: 47. In some embodiments, the second AAV vector polynucleotide comprises a nucleotide sequence that is at least about 80%, at least 85%, at least 90%, at least 95%, at least 98%, or at least 99% identical to SEQ ID NO: 35 or 44.

The polynucleotide vector systems of the disclosure may comprise a nucleotide sequence that is at least 80%, 85%, 90%, 92.5%, 95%, 96%, 97%, 98%, 99%, or 99.5% identical to any of the following sequences (e.g., any of SEQ ID NOs: 31-38, 44, and 46-51). In some embodiments, the vectors comprise a sequence comprising any one of SEQ ID NOs: 31-38, 44, and 46-51. In some embodiments, the vector systems of the disclosure comprise a nucleotide sequence that contains that differs from any of the sequences of SEQ ID NOs: 31-38, 44, and 46-51 by 1, 2, 3, 4, 5, 5-10, 10-15, 15-20, 20-25, 25-30, 30-35, 35-40, 40-45, 45-50, or more than 50 nucleotides. The disclosed vectors may differ in any of the following vector sequences in the presence, or absence, of a tag such as an HA tag. The disclosed vectors may contain stretches of 5-10, 10-15, 15-20, 20-25, 25-35, 35-45, 45-60, 60-75 or more than 75 consecutive nucleotides in common with any of SEQ ID NOs: 31-38, 44, and 46-51.

The myosin7a-encoding sequences of any of the polynucleotide vectors provided herein may comprise a nucleotide sequence that is at least 80%, 85%, 90%, 92.5%, 95%, 96%, 97%, 98%, 99%, or 99.5% identical to any of the hMyosin7a-encoding sequences in the N-terminal (front half, "—NT") or C-terminal (back half, "—CT") vectors that follow, e.g., SEQ ID NOs: 63, 66, 73, 75, 77, 80, and 90. The disclosed N-terminal and C-terminal myosin7a-encoding sequences may contain stretches of 5-10, 10-15, 15-20, 20-25, 25-35, 35-45, 45-60, 60-75 or more than 75 consecutive nucleotides in common with any of SEQ ID NOs: 63, 66, 73, 75, 77, 80, and 90.

The polynucleotide vectors and myosin7a-encoding sequences provided herein may comprise a nucleotide sequence that differs from any of the following sequences (e.g., any of the vectors of SEQ ID NOs: 31-38, 44, and 46-51; or any of the hMyosin7a-encoding sequences in the N-terminal (front half, "—NT") or C-terminal (back half, "—CT") vectors set forth as SEQ ID NOs: 63, 66, 73, 75, 77, 80, and 90) by 1, 2, 3, 4, 5, 6, 7, 8, 9, 10, 10-15, 15-20, 20-25, or more than 25 nucleotides. The polynucleotide vectors provided herein may comprise a nucleotide sequence that differs from any of the following sequences by 1, 2, 3, 4, 5, 6, 7, 8, 9, 10, or more than 10 nucleotides at or near the 5' terminus of the vector; and may differ from any of these sequences by 1, 2, 3, 4, 5, 6, 7, 8, 9, 10, or more than 10 nucleotides at or near the 3' terminus. The vectors provided herein may comprise truncations by 1, 2, 3, 4, 5, 6, 7, 8, 9, or 10 nucleotides at the 5' or 3' terminus.

Nucleotide Sequences of the Vectors Provided in Examples 6 and 7

```
SEQ ID NO: 31 is the nucleotide sequence of the second generation hybrid front-half
vector (i.e., AAV-smCBA-hMYO7A-NT-Ex21-APSD-APhead):
CTCCCTCTCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCC

ATCACTAGGGGTTCTCAGATCTGGCGCGCCCAATTCGGTACCCTAGTTATTAATAGTAATCA

ATTACGGGGTCATTAGTTCATAGCCCATATATGGAGTTCCGCGTTACATAACTTACGGTAAA

TGGCCCGCCTGGCTGACCGCCCAACGACCCCCGCCCATTGACGTCAATAATGACGTATGTTC

CCATAGTAACGCCAATAGGGACTTTCCATTGACGTCAATGGGTGGACTATTTACGGTAAAC

TGCCCACTTGGCAGTACATCAAGTGTATCATATGCCAAGTACGCCCCCTATTGACGTCAATG

ACGGTAAATGGCCCGCCTGGCATTATGCCCAGTACATGACCTTATGGGACTTTCCTACTTGG

CAGTACATCTACGTATTAGTCATCGCTATTACCATGGTCGAGGTGAGCCCCACGTTCTGCTT

CACTCTCCCCATCTCCCCCCCCTCCCCACCCCCAATTTTGTATTTATTTATTTTTTAATTATTT

TGTGCAGCGATGGGGGCGGGGGGGGGGGGGGGCGCGCGCCAGGCGGGGCGGGGCGGGG

CGAGGGGCGGGGCGGGGCGAGGCGGAGAGGTGCGGCGGCAGCCAATCAGAGCGGCGCGC

TCCGAAAGTTTCCTTTTATGGCGAGGCGGCGGCGGCGGCGGCCCTATAAAAAGCGAAGCGC
```

-continued

```
GCGGCGGGCGGGAGTCGCTGCGCGCTGCCTTCGCCCCGTGCCCCGCTCCGCCGCCGCCTCG

CGCCGCCCGCCCCGGCTCTGACTGACCGCGTTACTCCCACAGGTGAGCGGGCGGGACGGCC

CTTCTCCTCCGGGCTGTAATTAGCGCTTGGTTTAATGACGGCTTGTTTCTTTTCTGTGGCTGC

GTGAAAGCCTTGAGGGGCTCCGGGAGCTAGAGCCTCTGCTAACCATGTTCATGCCTTCTTCT

TTTTCCTACAGCTCCTGGGCAACGTGCTGGTTATTGTGCTGTCTCATCATTTTGGCAAAGAA

TTCTAGCGGCCGCCACCATGGTGATTCTTCAGCAGGGGACCATGTGTGGATGGACCTGAG

ATTGGGGCAGGAGTTCGACGTGCCCATCGGGGCGGTGGTGAAGCTCTGCGACTCTGGGCAG

GTCCAGGTGGTGGATGATGAAGACAATGAACACTGGATCTCTCCGCAGAACGCAACGCACA

TCAAGCCTATGCACCCCACGTCGGTCCACGGCGTGGAGGACATGATCCGCCTGGGGGACCT

CAACGAGGCGGGCATCTTGCGCAACCTGCTTATCCGCTACCGGGACCACCTCATCTACACG

TATACGGGCTCCATCCTGGTGGCTGTGAACCCCTACCAGCTGCTCTCCATCTACTCGCCAGA

GCACATCCGCCAGTATACCAACAAGAAGATTGGGGAGATGCCCCCCCACATCTTTGCCATT

GCTGACAACTGCTACTTCAACATGAAACGCAACAGCCGAGACCAGTGCTGCATCATCAGTG

GGGAATCTGGGCCGGGAAGACGGAGAGCACAAAGCTGATCCTGCAGTTCCTGGCAGCCA

TCAGTGGGCAGCACTCGTGGATTGAGCAGCAGGTCTTGGAGGCCACCCCCATTCTGGAAGC

ATTTGGGAATGCCAAGACCATCCGCAATGACAACTCAAGCCGTTTCGGAAAGTACATCGAC

ATCCACTTCAACAAGCGGGCGCCATCGAGGGCGCGAAGATTGAGCAGTACCTGCTGGAA

AAGTCACGTGTCTGTCGCCAGGCCCTGGATGAAAGGAACTACCACGTGTTCTACTGCATGC

TGGAGGGTATGAGTGAGGATCAGAAGAAGAAGCTGGGCTTGGGCCAGGCCTCTGACTACA

ACTACTTGGCCATGGGTAACTGCATAACCTGTGAGGGCCGGGTGGACAGCCAGGAGTACGC

CAACATCCGCTCCGCCATGAAGGTGCTCATGTTCACTGACACCGAGAACTGGGAGATCTCG

AAGCTCCTGGCTGCCATCCTGCACCTGGGCAACCTGCAGTATGAGGCACGCACATTTGAAA

ACCTGGATGCCTGTGAGGTTCTCTTCTCCCCATCGCTGGCCACAGCTGCATCCCTGCTTGAG

GTGAACCCCCCAGACCTGATGAGCTGCCTGACTAGCCGCACCCTCATCACCCGCGGGGAGA

CGGTGTCCACCCCACTGAGCAGGGAACAGGCACTGGACGTGCGCGACGCCTTCGTAAAGGG

GATCTACGGGCGGCTGTTCGTGTGGATTGTGGACAAGATCAACGCAGCAATTTACAAGCCT

CCCTCCCAGGATGTGAAGAACTCTCGCAGGTCCATCGGCCTCCTGGACATCTTTGGGTTTGA

GAACTTTGCTGTGAACAGCTTTGAGCAGCTCTGCATCAACTTCGCCAATGAGCACCTGCAGC

AGTTCTTTGTGCGGCACGTGTTCAAGCTGGAGCAGGAGGAATATGACCTGGAGAGCATTGA

CTGGCTGCACATCGAGTTCACTGACAACCAGGATGCCCTGGACATGATTGCCAACAAGCCC

ATGAACATCATCTCCCTCATCGATGAGGAGAGCAAGTTCCCCAAGGGCACAGACACCACCA

TGTTACACAAGCTGAACTCCCAGCACAAGCTCAACGCCAACTACATCCCCCCCAAGAACAA

CCATGAGACCCAGTTTGGCATCAACCATTTTGCAGGCATCGTCTACTATGAGACCCAAGGCT

TCCTGGAGAAGAACCGAGACACCCTGCATGGGACATTATCCAGCTGGTCCACTCCTCCAG

GAACAAGTTCATCAAGCAGATCTTCCAGGCCGATGTCGCCATGGGCGCCGAGACCAGGAAG

CGCTCGCCCACACTTAGCAGCCAGTTCAAGCGGTCACTGGAGCTGCTGATGCGCACGCTGG

GTGCCTGCCAGCCCTTCTTTGTGCGATGCATCAAGCCCAATGAGTTCAAGAAGCCCATGCTG

TTCGACCGGCACCTGTGCGTGCGCCAGCTGCGGTACTCAGGAATGATGGAGACCATCCGAA

TCCGCCGAGCTGGCTACCCCATCCGCTACAGCTTCGTAGAGTTTGTGGAGCGGTACCGTGTG

CTGCTGCCAGGTGTGAAGCCGGCCTACAAGCAGGGCGACCTCCGCGGGACTTGCCAGCGCA
```

TGGCTGAGGCTGTGCTGGGCACCCACGATGACTGGCAGATAGGCAAAACCAAGATCTTTCT

GAAGGACCACCATGACATGCTGCTGGAAGTGGAGCGGGACAAAGCCATCACCGACAGAGT

CATCCTCCTTCAGAAAGTCATCCGGGGATTCAAAGACAGGTCTAACTTTCTGAAGCTGAAG

AACGCTGCCACACTGATCCAGAGGCACTGGCGGGGTCACAACTGTAGGAAGAACTACGGG

CTGATGCGTCTGGGCTTCCTGCGGCTGCAGGCCCTGCACCGCTCCCGGAAGCTGCACCAGC

AGTACCGCCTGGCCCGCCAGCGCATCATCCAGTTCCAGGCCCGCTGCCGCGCCTATCTGGTG

CGCAAGGCCTTCCGCCACCGCCTCTGGGCTGTGCTCACCGTGCAGGCCTATGCCCGGGGCA

TGATCGCCCGCAGGCTGCACCAACGCCTCAGGGCTGAGGTAAGTATCAAGGTTACAAGACA

GGTTTAAGGAGACCAATAGAAACTGGGCTTGTCGAGACAGAGAAGACTCTTGCGTTTCTGA

GCTAGCCCCGGGTGCGCGGCGTCGGTGGTGCCGGCGGGGGGCGCCAGGTCGCAGGCGGT

GTAGGGCTCCAGGCAGGCGGCGAAGGCCATGACGTGCGCTATGAAGGTCTGCTCCTGCACG

CCGTGAACCAGGTGCGCCTGCGGGCCGCGCGCGAACACCGCCACGTCCTCGCCTGCGTGGG

TCTCTTCGTCCAGGGGCACTGCTGACTGCTGCCGATACTCGGGGCTCCCGCTCTCGCTCTCG

GTAACATCCGGCCGGGCGCCGTCCTTGAGCACATAGCCTGGACCGTTTCGTCGACTGTTAAT

TAAGCATGCTGGGGAGAGATCTAGGAAACCCCTAGTGATGGAGTTGGCCACTCCCTCTCTG

CGCGCTCGCTCGCTCACTGAGGCCGGGCGACCAAAGGTCGCCCGACGCCCGGGCTTTGCCC

GGGCGGCCTCAGTGAGCGAGCGAGCGCGCAGAGAGGGAG

SEQ ID NO: 73 (hMYO7A-NT (AAV-smCBA-hMYO7A-NT-Ex21-APSD-APhead),
(AAV-smCBA-hMYO7A-NT-Ex21-APSD-APhead CMv1), (AAV-smCBA-hMYO7A-NT-
Ex21-APSD-APhead CMv2), and (AAV-smCBA-hMY07A- NT-Ex21-APSD-APhead-CMv3))
ATGGTGATTCTTCAGCAGGGGGACCATGTGTGGATGGACCTGAGATTGGGGCAGGAGTTCG

ACGTGCCCATCGGGGCGGTGGTGAAGCTCTGCGACTCTGGGCAGGTCCAGGTGGTGGATGA

TGAAGACAATGAACACTGGATCTCTCCGCAGAACGCAACGCACATCAAGCCTATGCACCCC

ACGTCGGTCCACGCGTGGAGGACATGATCCGCCTGGGGGACCTCAACGAGGCGGGCATCT

TGCGCAACCTGCTTATCCGCTACCGGGACCACCTCATCTACACGTATACGGGCTCCATCCTG

GTGGCTGTGAACCCCTACCAGCTGCTCTCCATCTACTCGCCAGAGCACATCCGCCAGTATAC

CAACAAGAAGATTGGGGAGATGCCCCCCCACATCTTTGCCATTGCTGACAACTGCTACTTC

AACATGAAACGCAACAGCCGAGACCAGTGCTGCATCATCAGTGGGGAATCTGGGGCCGGG

AAGACGGAGAGCACAAAGCTGATCCTGCAGTTCCTGGCAGCCATCAGTGGGCAGCACTCGT

GGATTGAGCAGCAGGTCTTGGAGGCCACCCCCATTCTGGAAGCATTTGGGAATGCCAAGAC

CATCCGCAATGACAACTCAAGCCGTTTCGGAAAGTACATCGACATCCACTTCAACAAGCGG

GGCGCCATCGAGGGCGCGAAGATTGAGCAGTACCTGCTGGAAAAGTCACGTGTCTGTCGCC

AGGCCCTGGATGAAAGGAACTACCACGTGTTCTACTGCATGCTGGAGGGTATGAGTGAGGA

TCAGAAGAAGAAGCTGGGCTTGGGCCAGGCCTCTGACTACAACTACTTGGCCATGGGTAAC

TGCATAACCTGTGAGGGCCGGGTGGACAGCCAGGAGTACGCCAACATCCGCTCCGCCATGA

AGGTGCTCATGTTCACTGACACCGAGAACTGGGAGATCTCGAAGCTCCTGGCTGCCATCCT

GCACCTGGGCAACCTGCAGTATGAGGCACGCACATTTGAAAACCTGGATGCCTGTGAGGTT

CTCTTCTCCCCATCGCTGCCACAGCTGCATCCCTGCTTGAGGTGAACCCCCCAGACCTGAT

GAGCTGCCTGACTAGCCGCACCCTCATCACCCGCGGGGAGACGGTGTCCACCCCACTGAGC

AGGGAACAGGCACTGGACGTGCGCGACGCCTTCGTAAAGGGGATCTACGGGCGGCTGTTCG

TGTGGATTGTGGACAAGATCAACGCAGCAATTTACAAGCCTCCCTCCCAGGATGTGAAGAA

CTCTCGCAGGTCCATCGGCCTCCTGGACATCTTTGGGTTTGAGAACTTTGCTGTGAACAGCT

-continued

```
TTGAGCAGCTCTGCATCAACTTCGCCAATGAGCACCTGCAGCAGTTCTTTGTGCGGCACGTG

TTCAAGCTGGAGCAGGAGGAATATGACCTGGAGAGCATTGACTGGCTGCACATCGAGTTCA

CTGACAACCAGGATGCCCTGGACATGATTGCCAACAAGCCCATGAACATCATCTCCCTCAT

CGATGAGGAGAGCAAGTTCCCCAAGGGCACAGACACCACCATGTTACACAAGCTGAACTCC

CAGCACAAGCTCAACGCCAACTACATCCCCCCCAAGAACAACCATGAGACCCAGTTTGGCA

TCAACCATTTTGCAGGCATCGTCTACTATGAGACCCAAGGCTTCCTGGAGAAGAACCGAGA

CACCCTGCATGGGACATTATCCAGCTGGTCCACTCCTCCAGGAACAAGTTCATCAAGCAG

ATCTTCCAGGCCGATGTCGCCATGGGCGCCGAGACCAGGAAGCGCTCGCCCACACTTAGCA

GCCAGTTCAAGCGGTCACTGGAGCTGCTGATGCGCACGCTGGGTGCCTGCCAGCCCTTCTTT

GTGCGATGCATCAAGCCCAATGAGTTCAAGAAGCCCATGCTGTTCGACCGGCACCTGTGCG

TGCGCCAGCTGCGGTACTCAGGAATGATGGAGACCATCCGAATCCGCCGAGCTGGCTACCC

CATCCGCTACAGCTTCGTAGAGTTTGTGGAGCGGTACCGTGTGCTGCTGCCAGGTGTGAAG

CCGGCCTACAAGCAGGGCGACCTCCGCGGGACTTGCCAGCGCATGGCTGAGGCTGTGCTGG

GCACCCACGATGACTGGCAGATAGGCAAAACCAAGATCTTTCTGAAGGACCACCATGACAT

GCTGCTGGAAGTGGAGCGGGACAAAGCCATCACCGACAGAGTCATCCTCCTTCAGAAAGTC

ATCCGGGGATTCAAAGACAGGTCTAACTTTCTGAAGCTGAAGAACGCTGCCACACTGATCC

AGAGGCACTGGCGGGGTCACAACTGTAGGAAGAACTACGGGCTGATGCGTCTGGGCTTCCT

GCGGCTGCAGGCCCTGCACCGCTCCCGGAAGCTGCACCAGCAGTACCGCCTGGCCCGCCAG

CGCATCATCCAGTTCCAGGCCCGCTGCCGCGCCTATCTGGTGCGCAAGGCCTTCCGCCACCG

CCTCTGGGCTGTGCTCACCGTGCAGGCCTATGCCCGGGGCATGATCGCCCGCAGGCTGCAC

CAACGCCTCAGGGCTGAG
```

SEQ ID NO: 74 (hMYO7A-NT (AAV-smCBA-hMYO7A-NT-Ex21-APSD-APhead), (AAV-smCBA-hMYO7A-NT-Ex21-APSD-APhead CMv1), (AAV-smCBA-hMYO7A-NT-Ex21-APSD-APhead-CMv3))

```
MVILQQGDHVWMDLRLGQEFDVPIGAVVKLCDSGQVQVVDDEDNEHWISPQNATHIKPMHPT

SVHGVEDMIRLGDLNEAGILRNLLIRYRDHLIYTYTGSILVAVNPYQLLSIYSPEHIRQYTNKKIG

EMPPHIFAIADNCYFNMKRNSRDQCCIISGESGAGKTESTKLILQFLAAISGQHSWIEQQVLEATP

ILEAFGNAKTIRNDNSSRFGKYIDIHFNKRGAIEGAKIEQYLLEKSRVCRQALDERNYHVFYCML

EGMSEDQKKKLGLGQASDYNYLAMGNCITCEGRVDSQEYANIRSAMKVLMFTDTENWEISKL

LAAILHLGNLQYEARTFENLDACEVLFSPSLATAASLLEVNPPDLMSCLTSRTLITRGETVSTPLS

REQALDVRDAFVKGIYGRLFVWIVDKINAAIYKPPSQDVKNSRRSIGLLDIFGFENFAVNSFEQL

CINFANEHLQQFFVRHVFKLEQEEYDLESIDWLHIEFTDNQDALDMIANKPMNIISLIDEESKFPK

GTDTTMLHKLNSQHKLNANYIPPKNNHETQFGINHFAGIVYYETQGFLEKNRDTLHGDIIQLVH

SSRNKFIKQIFQADVAMGAETRKRSPTLSSQFKRSLELLMRTLGACQPFFVRCIKPNEFKKPMLF

DRHLCVRQLRYSGMMETIRIRRAGYPIRYSFVEFVERYRVLLPGVKPAYKQGDLRGTCQRMAE

AVLGTHDDWQIGKTKIFLKDHHDMLLEVERDKAITDRVILLQKVIRGFKDRSNFLKLKNAATLI

QRHWRGHNCRKNYGLMRLGFLRLQALHRSRKLHQQYRLARQRIIQFQARCRAYLVRKAFRHR

LWAVLTVQAYARGMIARRLHQRLRAE
```

SEQ ID NO: 32 is the nucleotide sequence of the second generation hybrid back-half vector (i.e., AAV-APhead-APSA-ex22hMYO7A-CT.HA (with hemagglutinin (HA) tag)):

```
CTCCCTCTCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCC

ATCACTAGGGGTTCTCAGATCTGGCGCGCCCAATTGGCTTCGAATTCTAGCGGCCGCCCCCG
```

-continued

```
GGTGCGCGGCGTCGGTGGTGCCGGCGGGGGCGCCAGGTCGCAGGCGGTGTAGGGCTCCA

GGCAGGCGGCGAAGGCCATGACGTGCGCTATGAAGGTCTGCTCCTGCACGCCGTGAACCAG

GTGCGCCTGCGGGCCGCGCGCGAACACCGCCACGTCCTCGCCTGCGTGGGTCTCTTCGTCCA

GGGGCACTGCTGACTGCTGCCGATACTCGGGGCTCCCGCTCTCGCTCTCGGTAACATCCGGC

CGGGCGCCGTCCTTGAGCACATAGCCTGGACCGTTTCCTTAAGCGACGCATGCTCGCGATA

GGCACCTATTGGTCTTACTGACATCCACTTTGCCTTTCTCTCCACAGTATCTGTGGCGCCTCG

AGGCTGAGAAAATGCGGCTGGCGGAGGAAGAGAAGCTTCGGAAGGAGATGAGCGCCAAG

AAGGCCAAGGAGGAGGCCGAGCGCAAGCATCAGGAGCGCCTGGCCCAGCTGGCTCGTGAG

GACGCTGAGCGGGAGCTGAAGGAGAAGGAGGCCGCTCGGCGGAAGAAGGAGCTCCTGGAG

CAGATGGAAAGGGCCCGCCATGAGCCTGTCAATCACTCAGACATGGTGGACAAGATGTTTG

GCTTCCTGGGGACTTCAGGTGGCCTGCCAGGCCAGGAGGGCCAGGCACCTAGTGGCTTTGA

GGACCTGGAGCGAGGGCGGAGGGAGATGGTGGAGGAGGACCTGGATGCAGCCCTGCCCCT

GCCTGACGAGGATGAGGAGGACCTCTCTGAGTATAAATTTGCCAAGTTCGCGGCCACCTAC

TTCCAGGGGACAACCACGCACTCCTACACCCGGCGGCCACTCAAACAGCCACTGCTCTACC

ATGACGACGAGGGTGACCAGCTGGCAGCCCTGGCGGTCTGGATCACCATCCTCCGCTTCAT

GGGGGACCTCCCTGAGCCCAAGTACCACACAGCCATGAGTGATGGCAGTGAGAAGATCCCT

GTGATGACCAAGATTTATGAGACCCTGGGCAAGAAGACGTACAAGAGGGAGCTGCAGGCC

CTGCAGGGCGAGGGCGAGGCCCAGCTCCCCGAGGGCCAGAAGAAGAGCAGTGTGAGGCAC

AAGCTGGTGCATTTGACTCTGAAAAAGAAGTCCAAGCTCACAGAGGAGGTGACCAAGAGG

CTGCATGACGGGGAGTCCACAGTGCAGGGCAACAGCATGCTGGAGGACCGGCCCACCTCC

AACCTGGAGAAGCTGCACTTCATCATCGGCAATGGCATCCTGCGGCCAGCACTCCGGGACG

AGATCTACTGCCAGATCAGCAAGCAGCTGACCCACAACCCCTCCAAGAGCAGCTATGCCCG

GGGCTGGATTCTCGTGTCTCTCTGCGTGGGCTGTTTCGCCCCCTCCGAGAAGTTTGTCAAGT

ACCTGCGGAACTTCATCCACGGGGGCCCGCCCGGCTACGCCCCGTACTGTGAGGAGCGCCT

GAGAAGGACCTTTGTCAATGGGACACGGACACAGCCGCCCAGCTGGCTGGAGCTGCAGGC

CACCAAGTCCAAGAAGCCAATCATGTTGCCCGTGACATTCATGGATGGGACCACCAAGACC

CTGCTGACGGACTCGGCAACCACGGCCAAGGAGCTCTGCAACGCGCTGGCCGACAAGATCT

CTCTCAAGGACCGGTTCGGGTTCTCCCTCTACATTGCCCTGTTTGACAAGGTGTCCTCCCTG

GGCAGCGGCAGTGACCACGTCATGGACGCCATCTCCCAGTGCGAGCAGTACGCCAAGGAG

CAGGGCGCCCAGGAGCGCAACGCCCCTGGAGGCTCTTCTTCCGCAAAGAGGTCTTCACGC

CCTGGCACAGCCCCTCCGAGGACAACGTGGCCACCAACCTCATCTACCAGCAGGTGGTGCG

AGGAGTCAAGTTTGGGGAGTACAGGTGTGAGAAGGAGGACGACCTGGCTGAGCTGGCCTC

CCAGCAGTACTTTGTAGACTATGGCTCTGAGATGATCCTGGAGCGCCTCCTGAACCTCGTGC

CCACCTACATCCCCGACCGCGAGATCACGCCCCTGAAGACGCTGGAGAAGTGGGCCCAGCT

GGCCATCGCCGCCCACAAGAAGGGGATTTATGCCCAGAGGAGAACTGATGCCCAGAAGGT

CAAAGAGGATGTGGTCAGTTATGCCCGCTTCAAGTGGCCCTTGCTCTTCTCCAGGTTTTATG

AAGCCTACAAATTCTCAGGCCCCAGTCTCCCCAAGAACGACGTCATCGTGGCCGTCAACTG

GACGGGTGTGTACTTTGTGGATGAGCAGGAGCAGGTACTTCTGGAGCTGTCCTTCCCAGAG

ATCATGGCCGTGTCCAGCAGCAGGGGAGCGAAAACGACGGCCCCAGCTTCACGCTGGCCA

CCATCAAGGGGGACGAATACACCTTCACCTCCAGCAATGCTGAGGACATTCGTGACCTGGT

GGTCACCTTCCTAGAGGGGCTCCGGAAGAGATCTAAGTATGTTGTGGCCCTGCAGGATAAC
```

-continued

```
CCCAACCCCGCAGGCGAGGAGTCAGGCTTCCTCAGCTTTGCCAAGGGAGACCTCATCATCC
TGGACCATGACACGGGCGAGCAGGTCATGAACTCGGGCTGGGCCAACGGCATCAATGAGA
GGACCAAGCAGCGTGGGGACTTCCCCACCGACAGTGTGTACGTCATGCCCACTGTCACCAT
GCCACCGCGGGAGATTGTGGCCCTGGTCACCATGACTCCCGATCAGAGGCAGGACGTTGTC
CGGCTCTTGCAGCTGCGAACGGCGGAGCCCGAGGTGCGTGCCAAGCCCTACACGCTGGAGG
AGTTTTCCTATGACTACTTCAGGCCCCCACCCAAGCACACGCTGAGCCGTGTCATGGTGTCC
AAGGCCCGAGGCAAGGACCGGCTGTGGAGCCACACGCGGGAACCGCTCAAGCAGGCGCTG
CTCAAGAAGCTCCTGGGCAGTGAGGAGCTCTCGCAGGAGGCCTGCCTGGCCTTCATTGCTG
TGCTCAAGTACATGGGCGACTACCCGTCCAAGAGGACACGCTCCGTCAACGAGCTCACCGA
CCAGATCTTTGAGGGTCCCCTGAAAGCCGAGCCCCTGAAGGACGAGGCATATGTGCAGATC
CTGAAGCAGCTGACCGACAACCACATCAGGTACAGCGAGGAGCGGGGTTGGGAGCTGCTC
TGGCTGTGCACGGGCCTTTTCCCACCCAGCAACATCCTCCTGCCCCACGTGCAGCGCTTCCT
GCAGTCCCGAAAGCACTGCCCACTCGCCATCGACTGCCTGCAACGGCTCCAGAAAGCCCTG
AGAAACGGGTCCCGGAAGTACCCTCCGCACCTGGTGGAGGTGGAGGCCATCCAGCACAAG
ACCACCCAGATTTTCCACAAAGTCTACTTCCCTGATGACACTGACGAGGCCTTCGAAGTGG
AGTCCAGCACCAAGGCCAAGGACTTCTGCCAGAACATCGCCACCAGGCTGCTCCTCAAGTC
CTCAGAGGGATTCAGCCTCTTTGTCAAAATTGCAGACAAGGTCATCAGCGTTCCTGAGAAT
GACTTCTTCTTTGACTTTGTTCGACACTTGACAGACTGGATAAAGAAAGCTCGGCCCATCAA
GGACGGAATTGTGCCCTCACTCACCTACCAGGTGTTCTTCATGAAGAAGCTGTGGACCACC
ACGGTGCCAGGGAAGGATCCCATGGCCGATTCCATCTTCCACTATTACCAGGAGTTGCCCA
AGTATCTCCGAGGCTACCACAAGTGCACGCGGGAGGAGGTGCTGCAGCTGGGGCGCTGAT
CTACAGGGTCAAGTTCGAGGAGGACAAGTCCTACTTCCCCAGCATCCCCAAGCTGCTGCGG
GAGCTGGTGCCCCAGGACCTTATCCGGCAGGTCTCACCTGATGACTGGAAGCGGTCCATCG
TCGCCTACTTCAACAAGCACGCAGGGAAGTCCAAGGAGGAGGCCAAGCTGGCCTTCCTGAA
GCTCATCTTCAAGTGGCCCACCTTTGGCTCAGCCTTCTTCGAGGTGAAGCAAACTACGGAGC
CAAACTTCCCTGAGATCCTCCTAATTGCCATCAACAAGTATGGGGTCAGCCTCATCGATCCC
AAAACGAAGGATATCCTCACCACTCATCCCTTCACCAAGATCTCCAACTGGAGCAGCGGCA
ACACCTACTTCCACATCACCATTGGGAACTTGGTGCGCGGGAGCAAACTGCTCTGCGAGAC
GTCACTGGGCTACAAGATGGATGACCTCCTGACTTCCTACATTAGCCAGATGCTCACAGCC
ATGAGCAAACAGCGGGGCTCCAGGAGCGGCAAGTACCCTTACGATGTACCGGATTACGCAT
GAGGTACCAAGGGCGAATTCTGCAGTCGACTAGAGCTCGCTGATCAGCCTCGACTGTGCCT
TCTAGTTGCCAGCCATCTGTTGTTTGCCCCTCCCCCGTGCCTTCCTTGACCCTGGAAGGTGCC
ACTCCCACTGTCCTTTCCTAATAAAATGAGGAAATTGCATCGCATTGTCTGAGTAGGTGTCA
TTCTATTCTGGGGGGTGGGGTGGGGCAGGACAGCAAGGGGGAGGATTGGGAAGACAATAG
CAGGCATGCTGGGGAGAGATCTGGAGGACTAGTCCGTCGACTGTTAATTAAGCATGCTGGG
GAGAGATCTAGGAAACCCCTAGTGATGGAGTTGGCCACTCCCTCTCTGCGCGCTCGCTCGCT
CACTGAGGCCGGGCGACCAAAGGTCGCCCGACGCCCGGGCTTTGCCCGGGCGGCCTCAGTG
AGCGAGCGAGCGCGCAGAGAGGGAG
```

-continued

SEQ ID NO: 75, ex22hMYO7A (e.g., AAV-APhead-APSA-ex22hMYO7A-CT.HA,
AAV-APhead-APSA-ex22hMYO7A -CT.HA-CMv2, AAV-APhead-APSA-hMYO7ACTex22-
CMv2.1.HA, AAV-APhead-APSA-hMYO7ACTex22-CMv2, AAV-APhead-APSA-
hMYO7ACTex 22.HA-MIN, and AAV-APhead-APSA-hMYO7ACTex 22-MIN))
TATCTGTGGCGCCTCGAGGCTGAGAAAATGCGGCTGGCGGAGGAAGAGAAGCTTCGGAAG

GAGATGAGCGCCAAGAAGGCCAAGGAGGAGGCCGAGCGCAAGCATCAGGAGCGCCTGGCC

CAGCTGGCTCGTGAGGACGCTGAGCGGGAGCTGAAGGAGAAGGAGGCCGCTCGGCGGAAG

AAGGAGCTCCTGGAGCAGATGGAAAGGGCCCGCCATGAGCCTGTCAATCACTCAGACATGG

TGGACAAGATGTTTGGCTTCCTGGGGACTTCAGGTGGCCTGCCAGGCCAGGAGGGCCAGGC

ACCTAGTGGCTTTGAGGACCTGGAGCGAGGGCGGAGGGAGATGGTGGAGGAGGACCTGGA

TGCAGCCCTGCCCCTGCCTGACGAGGATGAGGAGGACCTCTCTGAGTATAAATTTGCCAAGT

TCGCGGCCACCTACTTCCAGGGGACAACCACGCACTCCTACACCCGGCGGCCACTCAAACA

GCCACTGCTCTACCATGACGACGAGGGTGACCAGCTGGCAGCCCTGGCGGTCTGGATCACC

ATCCTCCGCTTCATGGGGGACCTCCCTGAGCCCAAGTACCACACAGCCATGAGTGATGGCA

GTGAGAAGATCCCTGTGATGACCAAGATTTATGAGACCCTGGGCAAGAAGACGTACAAGAG

GGAGCTGCAGGCCCTGCAGGGCGAGGGCGAGGCCCAGCTCCCCGAGGGCCAGAAGAAGAG

CAGTGTGAGGCACAAGCTGGTGCATTTGACTCTGAAAAAGAAGTCCAAGCTCACAGAGGAG

GTGACCAAGAGGCTGCATGACGGGGAGTCCACAGTGCAGGGCAACAGCATGCTGGAGGAC

CGGCCCACCTCCAACCTGGAGAAGCTGCACTTCATCATCGGCAATGGCATCCTGCGCCAG

CACTCCGGGACGAGATCTACTGCCAGATCAGCAAGCAGCTGACCCACAACCCCTCCAAGAG

CAGCTATGCCCGGGGCTGGATTCTCGTGTCTCTCTGCGTGGGCTGTTTCGCCCCCTCCGAGA

AGTTTGTCAAGTACCTGCGGAACTTCATCCACGGGGCCCGCCCGGCTACGCCCCGTACTGT

GAGGAGCGCCTGAGAAGGACCTTTGTCAATGGGACACGGACACAGCCGCCCAGCTGGCTGG

AGCTGCAGGCCACCAAGTCCAAGAAGCCAATCATGTTGCCCGTGACATTCATGGATGGGAC

CACCAAGACCCTGCTGACGGACTCGGCAACCACGGCCAAGGAGCTCTGCAACGCGCTGGCC

GACAAGATCTCTCTCAAGGACCGGTTCGGGTTCTCCCTCTACATTGCCCTGTTTGACAAGGT

GTCCTCCCTGGGCAGCGGCAGTGACCACGTCATGGACGCCATCTCCCAGTGCGAGCAGTAC

GCCAAGGAGCAGGGCGCCCAGGAGCGCAACGCCCCCTGGAGGCTCTTCTTCCGCAAAGAGG

TCTTCACGCCCTGGCACAGCCCCTCCGAGGACAACGTGGCCACCAACCTCATCTACCAGCAG

GTGGTGCGAGGAGTCAAGTTTGGGGAGTACAGGTGTGAGAAGGAGGACGACCTGGCTGAG

CTGGCCTCCCAGCAGTACTTTGTAGACTATGGCTCTGAGATGATCCTGGAGCGCCTCCTGAA

CCTCGTGCCCACCTACATCCCCGACCGCGAGATCACGCCCCTGAAGACGCTGGAGAAGTGG

GCCCAGCTGGCCATCGCCGCCCACAAGAAGGGGATTTATGCCCAGAGGAGAACTGATGCCC

AGAAGGTCAAAGAGGATGTGGTCAGTTATGCCCGCTTCAAGTGGCCCTTGCTCTTCTCCAGG

TTTTATGAAGCCTACAAATTCTCAGGCCCCAGTCTCCCCAAGAACGACGTCATCGTGGCCGT

CAACTGGACGGGTGTGTACTTTGTGGATGAGCAGGAGCAGGTACTTCTGGAGCTGTCCTTCC

CAGAGATCATGGCCGTGTCCAGCAGCAGGGGAGCGAAAACGACGGCCCCCAGCTTCACGCT

GGCCACCATCAAGGGGGACGAATACACCTTCACCTCCAGCAATGCTGAGGACATTCGTGAC

CTGGTGGTCACCTTCCTAGAGGGGCTCCGGAAGAGATCTAAGTATGTTGTGGCCCTGCAGG

ATAACCCCAACCCCGCAGGCGAGGAGTCAGGCTTCCTCAGCTTTGCCAAGGGAGACCTCAT

CATCCTGGACCATGACACGGGCGAGCAGGTCATGAACTCGGGCTGGGCCAACGGCATCAAT

GAGAGGACCAAGCAGCGTGGGGACTTCCCCACCGACAGTGTGTACGTCATGCCCACTGTCA

CCATGCCACCGCGGGAGATTGTGGCCCTGGTCACCATGACTCCCGATCAGAGGCAGGACGT

```
TGTCCGGCTCTTGCAGCTGCGAACGGCGGAGCCCGAGGTGCGTGCCAAGCCCTACACGCTG

GAGGAGTTTTCCTATGACTACTTCAGGCCCCCACCCAAGCACACGCTGAGCCGTGTCATGGT

GTCCAAGGCCCGAGGCAAGGACCGGCTGTGGAGCCACACGCGGGAACCGCTCAAGCAGGC

GCTGCTCAAGAAGCTCCTGGGCAGTGAGGAGCTCTCGCAGGAGGCCTGCCTGGCCTTCATT

GCTGTGCTCAAGTACATGGGCGACTACCCGTCCAAGAGGACACGCTCCGTCAACGAGCTCA

CCGACCAGATCTTTGAGGGTCCCCTGAAAGCCGAGCCCCTGAAGGACGAGGCATATGTGCA

GATCCTGAAGCAGCTGACCGACAACCACATCAGGTACAGCGAGGAGCGGGGTTGGGAGCT

GCTCTGGCTGTGCACGGGCCTTTTCCCACCCAGCAACATCCTCCTGCCCCACGTGCAGCGCT

TCCTGCAGTCCCGAAAGCACTGCCCACTCGCCATCGACTGCCTGCAACGGCTCCAGAAAGC

CCTGAGAAACGGGTCCCGGAAGTACCCTCCGCACCTGGTGGAGGTGGAGGCCATCCAGCAC

AAGACCACCCAGATTTTCCACAAAGTCTACTTCCCTGATGACACTGACGAGGCCTTCGAAGT

GGAGTCCAGCACCAAGGCCAAGGACTTCTGCCAGAACATCGCCACCAGGCTGCTCCTCAAG

TCCTCAGAGGGATTCAGCCTCTTTGTCAAAATTGCAGACAAGGTCATCAGCGTTCCTGAGAA

TGACTTCTTCTTTGACTTTGTTCGACACTTGACAGACTGGATAAAGAAAGCTCGGCCCATCA

AGGACGGAATTGTGCCCTCACTCACCTACCAGGTGTTCTTCATGAAGAAGCTGTGGACCACC

ACGGTGCCAGGGAAGGATCCCATGGCCGATTCCATCTTCCACTATTACCAGGAGTTGCCCAA

GTATCTCCGAGGCTACCACAAGTGCACGCGGGAGGAGGTGCTGCAGCTGGGGGCGCTGATC

TACAGGGTCAAGTTCGAGGAGGACAAGTCCTACTTCCCCAGCATCCCCAAGCTGCTGCGGG

AGCTGGTGCCCCAGGACCTTATCCGGCAGGTCTCACCTGATGACTGGAAGCGGTCCATCGTC

GCCTACTTCAACAAGCACGCAGGGAAGTCCAAGGAGGAGGCCAAGCTGGCCTTCCTGAAGC

TCATCTTCAAGTGGCCCACCTTTGGCTCAGCCTTCTTCGAGGTGAAGCAAACTACGGAGCCA

AACTTCCCTGAGATCCTCCTAATTGCCATCAACAAGTATGGGGTCAGCCTCATCGATCCCAA

AACGAAGGATATCCTCACCACTCATCCCTTCACCAAGATCTCCAACTGGAGCAGCGGCAAC

ACCTACTTCCACATCACCATTGGGAACTTGGTGCGCGGGAGCAAACTGCTCTGCGAGACGTC

ACTGGGCTACAAGATGGATGACCTCCTGACTTCCTACATTAGCCAGATGCTCACAGCCATGA

GCAAACAGCGGGGCTCCAGGAGCGGCAAG

SEQ ID NO: 76, ex22hMYO7A (e.g., AAV-APhead-APSA-ex22hMYO7A-CT.HA,
AAV-APhead-APSA-ex22hMYO7A -CT.HA-CMv2, and AAV-APhead-APSA-
hMYO7ACTex22-CMv2.1 .HA))
YLWRLEAEKMRLAEEEKLRKEMSAKKAKEEAERKHQERLAQLAREDAERELKEKEAARRKKE

LLEQMERARHEPVNHSDMVDKMFGFLGTSGGLPGQEGQAPSGFEDLERGRREMVEEDLDAAL

PLPDEDEEDLSEYKFAKFAATYFQGTTTHSYTRRPLKQPLLYHDDEGDQLAALAVWITILRFMG

DLPEPKYHTAMSDGSEKIPVMTKIYETLGKKTYKRELQALQGEGEAQLPEGQKKSSVRHKLVH

LTLKKKSKLTEEVTKRLHDGESTVQGNSMLEDRPTSNLEKLHFIIGNGILRPALRDEIYCQISKQL

THNPSKSSYARGWILVSLCVGCFAPSEKFVKYLRNFIHGGPPGYAPYCEERLRRTFVNGTRTQPP

SWLELQATKSKKPIMLPVTFMDGTTKTLLTDSATTAKELCNALADKISLKDRFGFSLYIALFDK

VSSLGSGSDHVMDAISQCEQYAKEQGAQERNAPWRLFFRKEVFTPWHSPSEDNVATNLIYQQV

VRGVKFGEYRCEKEDDLAELASQQYFVDYGSEMILERLLNLVPTYIPDREITPLKTLEKWAQLAI

AAHKKGIYAQRRTDAQKVKEDVVSYARFKWPLLFSRFYEAYKFSGPSLPKNDVIVAVNWTGV

YFVDEQEQVLLELSFPEIMAVSSSRGAKTTAPSFTLATIKGDEYTFTSSNAEDIRDLVVTFLEGLR

KRSKYVVALQDNPNPAGEESGFLSFAKGDLIILDHDTGEQVMNSGWANGINERTKQRGDFPTD

SVYVMPTVTMPPREIVALVTMTPDQRQDVVRLLQLRTAEPEVRAKPYTLEEFSYDYFRPPPKHT
```

-continued

LSRVMVSKARGKDRLWSHTREPLKQALLKKLLGSEELSQEACLAFIAVLKYMGDYPSKRTRSV

NELTDQIFEGPLKAEPLKDEAYVQILKQLTDNHIRYSEERGWELLWLCTGLFPPSNILLPHVQRF

LQSRKHCPLAIDCLQRLQKALRNGSRKYPPHLVEVEAIQHKTTQIFHKVYFPDDTDEAFEVESST

KAKDFCQNIATRLLLKSSEGFSLFVKIADKVISVPENDFFFDFVRHLTDWIKKARPIKDGIVPSLT

YQVFFMKKLWTTTVPGKDPMADSIFHYYQELPKYLRGYHKCTREEVLQLGALIYRVKFEEDKS

YFPSIPKLLRELVPQDLIRQVSPDDWKRSIVAYFNKHAGKSKEEAKLAFLKLIFKWPTFGSAFFE

VKQTTEPNFPEILLIAINKYGVSLIDPKTKDILTTHPFTKISNWSSGNTYFHITIGNLVRGSKLLCET

SLGYKMDDLLTSYISQMLTAMSKQRGSRSGK

SEQ ID NO: 33 is the nucleotide sequence of the CMv1 hybrid front-half vector (i.e.,
AAV-smCBA-hMYO7A-NT-Ex21-APSD-APhead CMv1):
CTCCCTCTCTGCGCGCTCGCTCGCTCACTGAGGCCGCCCGGGCAAAGCCCGGGCGTCGGGCG

ACCTTTGGTCGCCCGGCCTCAGTGAGCGAGCGAGCGCGCAGAGAGGGAGTGGCCAACTCCA

TCACTAGGGGTTCTCAGATCTGGCGCGCCCAATTCGGTACCCTAGTTATTAATAGTAATCAA

TTACGGGGTCATTAGTTCATAGCCCATATATGGAGTTCCGCGTTACATAACTTACGGTAAAT

GGCCCGCCTGGCTGACCGCCCAACGACCCCCGCCCATTGACGTCAATAATGACGTATGTTCC

CATAGTAACGCCAATAGGGACTTTCCATTGACGTCAATGGGTGGACTATTTACGGTAAACTG

CCCACTTGGCAGTACATCAAGTGTATCATATGCCAAGTACGCCCCCTATTGACGTCAATGAC

GGTAAATGGCCCGCCTGGCATTATGCCCAGTACATGACCTTATGGGACTTTCCTACTTGGCA

GTACATCTACGTATTAGTCATCGCTATTACCATGGTCGAGGTGAGCCCCACGTTCTGCTTCA

CTCTCCCCATCTCCCCCCCCTCCCCACCCCCAATTTTGTATTTATTTATTTTTTAATTATTTTG

TGCAGCGATGGGGGCGGGGGGGGGGGGGGGCGCGCGCCAGGCGGGGCGGGGCGGGGCG

AGGGGCGGGGCGGGGCGAGGCGGAGAGGTGCGGCGGCAGCCAATCAGAGCGGCGCGCTCC

GAAAGTTTCCTTTTATGGCGAGGCGGCGGCGGCGGCCCTATAAAAAGCGAAGCGCGCG

GCGGGCGGGAGTCGCTGCGCGCTGCCTTCGCCCCGTGCCCCGCTCCGCCGCCGCCTCGCGCC

GCCCGCCCCGGCTCTGACTGACCGCGTTACTCCCACAGGTGAGCGGGCGGGACGGCCCTTCT

CCTCCGGGCTGTAATTAGCGCTTGGTTTAATGACGGCTTGTTTCTTTTCTGTGGCTGCGTGAA

AGCCTTGAGGGGCTCCGGGAGCTAGAGCCTCTGCTAACCATGTTCATGCCTTCTTCTTTTTCC

TACAGCTCCTGGGCAACGTGCTGGTTATTGTGCTGTCTCATCATTTTGGCAAAGAATTCTAG

CGGCCGCCACCATGGTGATTCTTCAGCAGGGGACCATGTGTGGATGGACCTGAGATTGGG

GCAGGAGTTCGACGTGCCCATCGGGCGGTGGTGAAGCTCTGCGACTCTGGGCAGGTCCAG

GTGGTGGATGATGAAGACAATGAACACTGGATCTCTCCGCAGAACGCAACGCACATCAAGC

CTATGCACCCCACGTCGGTCCACGGCGTGGAGGACATGATCCGCCTGGGGGACCTCAACGA

GGCGGGCATCTTGCGCAACCTGCTTATCCGCTACCGGGACCACCTCATCTACACGTATACGG

GCTCCATCCTGGTGGCTGTGAACCCCTACCAGCTGCTCTCCATCTACTCGCCAGAGCACATC

CGCCAGTATACCAACAAGAAGATTGGGGAGATGCCCCCCCACATCTTTGCCATTGCTGACA

ACTGCTACTTCAACATGAAACGCAACAGCCGAGACCAGTGCTGCATCATCAGTGGGGAATC

TGGGGCCGGGAAGACGGAGAGCACAAAGCTGATCCTGCAGTTCCTGGCAGCCATCAGTGGG

CAGCACTCGTGGATTGAGCAGCAGGTCTTGGAGGCCACCCCCATTCTGGAAGCATTTGGA

ATGCCAAGACCATCCGCAATGACAACTCAAGCCGTTTCGGAAAGTACATCGACATCCACTT

CAACAAGCGGGGCGCCATCGAGGGCGCGAAGATTGAGCAGTACCTGCTGGAAAAGTCACG

TGTCTGTCGCCAGGCCCTGGATGAAAGGAACTACCACGTGTTCTACTGCATGCTGGAGGGTA

-continued

```
TGAGTGAGGATCAGAAGAAGAAGCTGGGCTTGGGCCAGGCCTCTGACTACAACTACTTGGC
CATGGGTAACTGCATAACCTGTGAGGGCCGGGTGGACAGCCAGGAGTACGCCAACATCCGC
TCCGCCATGAAGGTGCTCATGTTCACTGACACCGAGAACTGGGAGATCTCGAAGCTCCTGG
CTGCCATCCTGCACCTGGGCAACCTGCAGTATGAGGCACGCACATTTGAAAACCTGGATGC
CTGTGAGGTTCTCTTCTCCCCATCGCTGGCCACAGCTGCATCCCTGCTTGAGGTGAACCCCC
CAGACCTGATGAGCTGCCTGACTAGCCGCACCCTCATCACCCGCGGGGAGACGGTGTCCAC
CCCACTGAGCAGGGAACAGGCACTGGACGTGCGCGACGCCTTCGTAAAGGGGATCTACGGG
CGGCTGTTCGTGTGGATTGTGGACAAGATCAACGCAGCAATTTACAAGCCTCCCTCCCAGGA
TGTGAAGAACTCTCGCAGGTCCATCGGCCTCCTGGACATCTTTGGGTTTGAGAACTTTGCTG
TGAACAGCTTTGAGCAGCTCTGCATCAACTTCGCCAATGAGCACCTGCAGCAGTTCTTTGTG
CGGCACGTGTTCAAGCTGGAGCAGGAGGAATATGACCTGGAGAGCATTGACTGGCTGCACA
TCGAGTTCACTGACAACCAGGATGCCCTGGACATGATTGCCAACAAGCCCATGAACATCAT
CTCCCTCATCGATGAGGAGAGCAAGTTCCCCAAGGGCACAGACACCACCATGTTACACAAG
CTGAACTCCCAGCACAAGCTCAACGCCAACTACATCCCCCCCAAGAACAACCATGAGACCC
AGTTTGGCATCAACCATTTTGCAGGCATCGTCTACTATGAGACCCAAGGCTTCCTGGAGAAG
AACCGAGACACCCTGCATGGGACATTATCCAGCTGGTCCACTCCTCCAGGAACAAGTTCA
TCAAGCAGATCTTCCAGGCCGATGTCGCCATGGGCGCCGAGACCAGGAAGCGCTCGCCCAC
ACTTAGCAGCCAGTTCAAGCGGTCACTGGAGCTGCTGATGCGCACGCTGGGTGCCTGCCAG
CCCTTCTTTGTGCGATGCATCAAGCCCAATGAGTTCAAGAAGCCCATGCTGTTCGACCGGCA
CCTGTGCGTGCGCCAGCTGCGGTACTCAGGAATGATGGAGACCATCCGAATCCGCCGAGCT
GGCTACCCCATCCGCTACAGCTTCGTAGAGTTTGTGGAGCGGTACCGTGTGCTGCTGCCAGG
TGTGAAGCCGGCCTACAAGCAGGGCGACCTCCGCGGGACTTGCCAGCGCATGGCTGAGGCT
GTGCTGGGCACCCACGATGACTGGCAGATAGGCAAAACCAAGATCTTTCTGAAGGACCACC
ATGACATGCTGCTGGAAGTGGAGCGGGACAAAGCCATCACCGACAGAGTCATCCTCCTTCA
GAAAGTCATCCGGGGATTCAAAGACAGGTCTAACTTTCTGAAGCTGAAGAACGCTGCCACA
CTGATCCAGAGGCACTGGCGGGGTCACAACTGTAGGAAGAACTACGGGCTGATGCGTCTGG
GCTTCCTGCGGCTGCAGGCCCTGCACCGCTCCCGGAAGCTGCACCAGCAGTACCGCCTGGCC
CGCCAGCGCATCATCCAGTTCCAGGCCCGCTGCCGCGCCTATCTGGTGCGCAAGGCCTTCCG
CCACCGCCTCTGGGCTGTGCTCACCGTGCAGGCCTATGCCCGGGGCATGATCGCCCGCAGGC
TGCACCAACGCCTCAGGGCTGAGGTAAGTATCAAGGTTACAAGACAGGTTAACGGAGACCA
ATTGAAACTGGGCTTGTCGAGACAGAGAAGACTCTTGCGTTTCAGCGCTAGCCCCCGGGTG
CGCGGCGTCGGTGGTGCCGGCGGGGGGCGCCAGGTCGCAGGCGGTGTAGGGCTCCAGGCA
GGCGGCGAAGGCCATGACGTGCGCTATGAAGGTCTGCTCCTGCACGCCGTGAACCAGGTGC
GCCTGCGGGCCGCGCGCGAACACCGCCACGTCCTCGCCTGCGTGGGTCTCTTCGTCCAGGGG
CACTGCTGACTGCTGCCGATACTCGGGGCTCCCGCTCTCGCTCTCGGTAACATCCGGCCGGG
CGCCGTCCTTGAGCACATAGCCTGGACCGTTTCGTCGACTGTTAATTAAGCATGCTGGGGAG
AGATCTGAGGAAACCCCTAGTGATGGAGTTGGCCACTCCCTCTCTGCGCGCTCGCTCGCTCA
CTGAGGCCGGGCGACCAAAGGTCGCCCGACGCCCGGGCTTTGCCCGGGCGGCCTCAGTGAG
CGAGCGAGCGCGCAGAGAGGGAG
```

SEQ ID NO: 34 is the nucleotide sequence of the CMv2 hybrid front-half vector (i.e.,
AAV-smCBA-hMYO7A-NT-Ex21-APSD-APhead CMv2):
CTCCCTCTCTGCGCGCTCGCTCGCTCACTGAGGCCGCCCGGGCAAAGCCCGGGCGTCGGCG

ACCTTTGGTCGCCCGGCCTCAGTGAGCGAGCGAGCGCGCAGAGAGGGAGTGGCCAACTCCA

TCACTAGGGGTTCTCAGATCTGGCGCGCCCAATTCGGTACCCTAGTTATTAATAGTAATCAA

TTACGGGGTCATTAGTTCATAGCCCATATATGGAGTTCCGCGTTACATAACTTACGGTAAAT

GGCCCGCCTGGCTGACCGCCCAACGACCCCCGCCCATTGACGTCAATAATGACGTATGTTCC

CATAGTAACGCCAATAGGGACTTTCCATTGACGTCAATGGGTGGACTATTTACGGTAAACTG

CCCACTTGGCAGTACATCAAGTGTATCATATGCCAAGTACGCCCCCTATTGACGTCAATGAC

GGTAAATGGCCCGCCTGGCATTATGCCCAGTACATGACCTTATGGGACTTTCCTACTTGGCA

GTACATCTACGTATTAGTCATCGCTATTACCATGGTCGAGGTGAGCCCCACGTTCTGCTTCA

CTCTCCCCATCTCCCCCCCCTCCCCACCCCCAATTTTGTATTTATTTATTTTTTAATTATTTTG

TGCAGCGATGGGGCGGGGGGGGGGGGGGGGCGCGCGCCAGGCGGGGCGGGGCGGGGCG

AGGGGCGGGGCGGGGCGAGGCGGAGAGGTGCGGCGGCAGCCAATCAGAGCGGCGCGCTCC

GAAAGTTTCCTTTTATGGCGAGGCGGCGGCGGCGGCGGCCCTATAAAAAGCGAAGCGCGCG

GCGGGCGGGAGTCGCTGCGCGCTGCCTTCGCCCCGTGCCCCGCTCCGCCGCCGCCTCGCGCC

GCCCGCCCCGGCTCTGACTGACCGCGTTACTCCCACAGGTGAGCGGGCGGGACGGCCCTTCT

CCTCCGGGCTGTAATTAGCGCTTGGTTTAATGACGGCTTGTTTCTTTTCTGTGGCTGCGTGAA

AGCCTTGAGGGGCTCCGGGAGCTAGAGCCTCTGCTAACCATGTTCATGCCTTCTTCTTTTTCC

TACAGCTCCTGGGCAACGTGCTGGTTATTGTGCTGTCTCATCATTTTGGCAAAGAATTCTAG

CGGCCGCCACCATGGTGATTCTTCAGCAGGGGACCATGTGTGGATGGACCTGAGATTGGG

GCAGGAGTTCGACGTGCCCATCGGGGCGGTGGTGAAGCTCTGCGACTCTGGGCAGGTCCAG

GTGGTGGATGATGAAGACAATGAACACTGGATCTCTCCGCAGAACGCAACGCACATCAAGC

CTATGCACCCCACGTCGGTCCACGGCGTGGAGGACATGATCCGCCTGGGGGACCTCAACGA

GGCGGGCATCTTGCGCAACCTGCTTATCCGCTACCGGGACCACCTCATCTACACGTATACGG

GCTCCATCCTGGTGGCTGTGAACCCCTACCAGCTGCTCTCCATCTACTCGCCAGAGCACATC

CGCCAGTATACCAACAAGAAGATTGGGGAGATGCCCCCCCACATCTTTGCCATTGCTGACA

ACTGCTACTTCAACATGAAACGCAACAGCCGAGACCAGTGCTGCATCATCAGTGGGGAATC

TGGGGCCGGGAAGACGGAGAGCACAAAGCTGATCCTGCAGTTCCTGGCAGCCATCAGTGGG

CAGCACTCGTGGATTGAGCAGCAGGTCTTGGAGGCCACCCCCATTCTGGAAGCATTTGGGA

ATGCCAAGACCATCCGCAATGACAACTCAAGCCGTTTCGGAAAGTACATCGACATCCACTT

CAACAAGCGGGGCGCCATCGAGGGCGCGAAGATTGAGCAGTACCTGCTGGAAAAGTCACG

TGTCTGTCGCCAGGCCCTGGATGAAAGGAACTACCACGTGTTCTACTGCATGCTGGAGGGTA

TGAGTGAGGATCAGAAGAAGAAGCTGGGCTTGGGCCAGGCCTCTGACTACAACTACTTGGC

CATGGGTAACTGCATAACCTGTGAGGGCCGGGTGGACAGCCAGGAGTACGCCAACATCCGC

TCCGCCATGAAGGTGCTCATGTTCACTGACACCGAGAACTGGGAGATCTCGAAGCTCCTGG

CTGCCATCCTGCACCTGGGCAACCTGCAGTATGAGGCACGCACATTTGAAAACCTGGATGC

CTGTGAGGTTCTCTTCTCCCCATCGCTGGCCACAGCTGCATCCCTGCTTGAGGTGAACCCCC

CAGACCTGATGAGCTGCCTGACTAGCCGCACCCTCATCACCCGCGGGGAGACGGTGTCCAC

CCCACTGAGCAGGGAACAGGCACTGGACGTGCGCGACGCCTTCGTAAAGGGGATCTACGGG

CGGCTGTTCGTGTGGATTGTGGACAAGATCAACGCAGCAATTTACAAGCCTCCCTCCCAGGA

TGTGAAGAACTCTCGCAGGTCCATCGGCCTCCTGGACATCTTTGGGTTTGAGAACTTTGCTG

TGAACAGCTTTGAGCAGCTCTGCATCAACTTCGCCAATGAGCACCTGCAGCAGTTCTTTGTG

CGGCACGTGTTCAAGCTGGAGCAGGAGGAATATGACCTGGAGAGCATTGACTGGCTGCACA

TCGAGTTCACTGACAACCAGGATGCCCTGGACATGATTGCCAACAAGCCCATGAACATCAT

CTCCCTCATCGATGAGGAGAGCAAGTTCCCCAAGGGCACAGACACCACCATGTTACACAAG

CTGAACTCCCAGCACAAGCTCAACGCCAACTACATCCCCCCCAAGAACAACCATGAGACCC

AGTTTGGCATCAACCATTTTGCAGGCATCGTCTACTATGAGACCCAAGGCTTCCTGGAGAAG

AACCGAGACACCCTGCATGGGACATTATCCAGCTGGTCCACTCCTCCAGGAACAAGTTCA

TCAAGCAGATCTTCCAGGCCGATGTCGCCATGGGCGCCGAGACCAGGAAGCGCTCGCCCAC

ACTTAGCAGCCAGTTCAAGCGGTCACTGGAGCTGCTGATGCGCACGCTGGGTGCCTGCCAG

CCCTTCTTTGTGCGATGCATCAAGCCCAATGAGTTCAAGAAGCCCATGCTGTTCGACCGGCA

CCTGTGCGTGCGCCAGCTGCGGTACTCAGGAATGATGGAGACCATCCGAATCCGCCGAGCT

GGCTACCCCATCCGCTACAGCTTCGTAGAGTTTGTGGAGCGGTACCGTGTGCTGCTGCCAGG

TGTGAAGCCGGCCTACAAGCAGGGCGACCTCCGCGGGACTTGCCAGCGCATGGCTGAGGCT

GTGCTGGGCACCCACGATGACTGGCAGATAGGCAAAACCAAGATCTTTCTGAAGGACCACC

ATGACATGCTGCTGGAAGTGGAGCGGGACAAAGCCATCACCGACAGAGTCATCCTCCTTCA

GAAAGTCATCCGGGGATTCAAAGACAGGTCTAACTTTCTGAAGCTGAAGAACGCTGCCACA

CTGATCCAGAGGCACTGGCGGGGTCACAACTGTAGGAAGAACTACGGGCTGATGCGTCTGG

GCTTCCTGCGGCTGCAGGCCCTGCACCGCTCCCGGAAGCTGCACCAGCAGTACCGCCTGGCC

CGCCAGCGCATCATCCAGTTCCAGGCCCGCTGCCGCGCCTATCTGGTGCGCAAGGCCTTCCG

CCACCGCCTCTGGGCTGTGCTCACCGTGCAGGCCTATGCCCGGGGCATGATCGCCCGCAGGC

TGCACCAACGCCTCAGGGCTGAGGTAAGTATCAAGGTTACAAGACAGGTTAACGGAGACCA

ATTGAAACTGGCTTGTCGAGACAGAGAAGACTCTTGCGTTTCAGCGCTAGCCCCCGGGTG

CGCGGCGTCGGTGGTGCCGGCGGGGGCGCCAGGTCGCAGGCGGTGTAGGGCTCCAGGCA

GGCGGCGAAGGCCATGACGTGCGCTATGAAGGTCTGCTCCTGCACGCCGTGAACCAGGTGC

GCCTGCGGGCCGCGCGCGAACACCGCCACGTCCTCGCCTGCGTGGGTCTCTTCGTCCAGGGG

CACTGCGCACTGCTGCCGATACTCGGGGCTCCCGCTCTCGCTCTCGGTAACATCCGGCCGGG

CGCCGTCCTTGAGCACATAGCCTGGACCGTTTCGTCGACTGTTAATTAAGCATGCTGGGGAG

AGATCTGTAACCCCTAGTGATGGAGTTGGCCACTCCCTCTCTGCGCGCTCGCTCGCTCACTG

AGGCCGGGCGACCAAAGGTCGCCCGACGCCCGGGCTTTGCCCGGGCGGCCTCAGTGAGCGA

GCGAGCGCGCAGAGAGGGAG

SEQ ID NO: 35 is the nucleotide sequence of the CMv2 hybrid back-half vector (i.e., AAV-APhead-APSA-ex22hMYO7A-CT.HA-CMv2):
CTCCCTCTCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCC

ATCACTAGGGGTTCAGATCTGGCGCGCCCAATTGGCTTCGAATTCTAGCGGCCGCCCCCGG

GTGCGCGGCGTCGGTGGTGCCGGCGGGGGCGCCAGGTCGCAGGCGGTGTAGGGCTCCAG

GCAGGCGGCGAAGGCCATGACGTGCGCTATGAAGGTCTGCTCCTGCACGCCGTGAACCAGG

TGCGCCTGCGGGCCGCGCGCGAACACCGCCACGTCCTCGCCTGCGTGGGTCTCTTCGTCCAG

GGGCACTGCGCACTGCTGCCGATACTCGGGGCTCCCGCTCTCGCTCTCGGTAACATCCGGCC

GGGCGCCGTCCTTGAGCACATAGCCTGGACCGTTTCTCTTAAGCGACGCATGCTCGCGATA

GGCACCTATTGGTCTTACTGACATCCACTTTGCCTTTCTCTCCACAGTATCTGTGGCGCCTCG

-continued

```
AGGCTGAGAAAATGCGGCTGGCGGAGGAAGAGAAGCTTCGGAAGGAGATGAGCGCCAAG

AAGGCCAAGGAGGAGGCCGAGCGCAAGCATCAGGAGCGCCTGGCCCAGCTGGCTCGTGAG

GACGCTGAGCGGGAGCTGAAGGAGAAGGAGGCCGCTCGGCGGAAGAAGGAGCTCCTGGAG

CAGATGGAAAGGGCCCGCCATGAGCCTGTCAATCACTCAGACATGGTGGACAAGATGTTTG

GCTTCCTGGGGACTTCAGGTGGCCTGCCAGGCCAGGAGGGCCAGGCACCTAGTGGCTTTGA

GGACCTGGAGCGAGGGCGGAGGGAGATGGTGGAGGAGGACCTGGATGCAGCCCTGCCCCT

GCCTGACGAGGATGAGGAGGACCTCTCTGAGTATAAATTTGCCAAGTTCGCGGCCACCTAC

TTCCAGGGGACAACCACGCACTCCTACACCCGGCGGCCACTCAAACAGCCACTGCTCTACC

ATGACGACGAGGGTGACCAGCTGGCAGCCCTGGCGGTCTGGATCACCATCCTCCGCTTCAT

GGGGGACCTCCCTGAGCCCAAGTACCACACAGCCATGAGTGATGGCAGTGAGAAGATCCCT

GTGATGACCAAGATTTATGAGACCCTGGGCAAGAAGACGTACAAGAGGGAGCTGCAGGCC

CTGCAGGGCGAGGGCGAGGCCCAGCTCCCCGAGGGCCAGAAGAAGAGCAGTGTGAGGCAC

AAGCTGGTGCATTTGACTCTGAAAAAGAAGTCCAAGCTCACAGAGGAGGTGACCAAGAGG

CTGCATGACGGGGAGTCCACAGTGCAGGGCAACAGCATGCTGGAGGACCGGCCCACCTCC

AACCTGGAGAAGCTGCACTTCATCATCGGCAATGGCATCCTGCGGCCAGCACTCCGGGACG

AGATCTACTGCCAGATCAGCAAGCAGCTGACCCACAACCCCTCCAAGAGCAGCTATGCCCG

GGGCTGGATTCTCGTGTCTCTGCGTGGGCTGTTTCGCCCCCTCCGAGAAGTTTGTCAAGT

ACCTGCGGAACTTCATCCACGGGGCCCGCCCGGCTACGCCCCGTACTGTGAGGAGCGCCT

GAGAAGGACCTTTGTCAATGGGACACGGACACAGCCGCCCAGCTGGCTGGAGCTGCAGGC

CACCAAGTCCAAGAAGCCAATCATGTTGCCCGTGACATTCATGGATGGGACCACCAAGACC

CTGCTGACGGACTCGGCAACCACGGCCAAGGAGCTCTGCAACGCGCTGGCCGACAAGATCT

CTCTCAAGGACCGGTTCGGGTTCTCCCTCTACATTGCCCTGTTTGACAAGGTGTCCTCCCTG

GGCAGCGGCAGTGACCACGTCATGGACGCCATCTCCCAGTGCGAGCAGTACGCCAAGGAG

CAGGGCGCCCAGGAGCGCAACGCCCCCTGGAGGCTCTTCTTCCGCAAAGAGGTCTTCACGC

CCTGGCACAGCCCCTCCGAGGACAACGTGGCCACCAACCTCATCTACCAGCAGGTGGTGCG

AGGAGTCAAGTTTGGGGAGTACAGGTGTGAGAAGGAGGACGACCTGGCTGAGCTGGCCTC

CCAGCAGTACTTTGTAGACTATGGCTCTGAGATGATCCTGGAGCGCCTCCTGAACCTCGTGC

CCACCTACATCCCCGACCGCGAGATCACGCCCCTGAAGACGCTGGAGAAGTGGGCCCAGCT

GGCCATCGCCGCCCACAAGAAGGGGATTTATGCCCAGAGGAGAACTGATGCCCAGAAGGT

CAAAGAGGATGTGGTCAGTTATGCCCGCTTCAAGTGGCCCTTGCTCTTCTCCAGGTTTTATG

AAGCCTACAAATTCTCAGGCCCCAGTCTCCCCAAGAACGACGTCATCGTGGCCGTCAACTG

GACGGGTGTGTACTTTGTGGATGAGCAGGAGCAGGTACTTCTGGAGCTGTCCTTCCCAGAG

ATCATGGCCGTGTCCAGCAGCAGGGGAGCGAAAACGACGGCCCCAGCTTCACGCTGGCCA

CCATCAAGGGGACGAATACACCTTCACCTCCAGCAATGCTGAGGACATTCGTGACCTGGT

GGTCACCTTCCTAGAGGGGCTCCGGAAGAGATCTAAGTATGTTGTGGCCCTGCAGGATAAC

CCCAACCCCGCAGGCGAGGAGTCAGGCTTCCTCAGCTTTGCCAAGGGAGACCTCATCATCC

TGGACCATGACACGGGCGAGCAGGTCATGAACTCGGGCTGGGCCAACGGCATCAATGAGA

GGACCAAGCAGCGTGGGGACTTCCCCACCGACAGTGTGTACGTCATGCCCACTGTCACCAT

GCCACCGCGGGAGATTGTGGCCCTGGTCACCATGACTCCCGATCAGAGGCAGGACGTTGTC

CGGCTCTTGCAGCTGCGAACGGCGGAGCCCGAGGTGCGTGCCAAGCCCTACACGCTGGAGG

AGTTTTCCTATGACTACTTCAGGCCCCCACCCAAGCACACGCTGAGCCGTGTCATGGTGTCC
```

-continued

AAGGCCCGAGGCAAGGACCGGCTGTGGAGCCACACGCGGGAACCGCTCAAGCAGGCGCTG

CTCAAGAAGCTCCTGGGCAGTGAGGAGCTCTCGCAGGAGGCCTGCCTGGCCTTCATTGCTG

TGCTCAAGTACATGGGCGACTACCCGTCCAAGAGGACACGCTCCGTCAACGAGCTCACCGA

CCAGATCTTTGAGGGTCCCCTGAAAGCCGAGCCCTGAAGGACGAGGCATATGTGCAGATC

CTGAAGCAGCTGACCGACAACCACATCAGGTACAGCGAGGAGCGGGGTTGGGAGCTGCTC

TGGCTGTGCACGGGCCTTTTCCCACCCAGCAACATCCTCCTGCCCCACGTGCAGCGCTTCCT

GCAGTCCCGAAAGCACTGCCCACTCGCCATCGACTGCCTGCAACGGCTCCAGAAAGCCCTG

AGAAACGGGTCCCGGAAGTACCCTCCGCACCTGGTGGAGGTGGAGGCCATCCAGCACAAG

ACCACCCAGATTTTCCACAAAGTCTACTTCCCTGATGACACTGACGAGGCCTTCGAAGTGG

AGTCCAGCACCAAGGCCAAGGACTTCTGCCAGAACATCGCCACCAGGCTGCTCCTCAAGTC

CTCAGAGGGATTCAGCCTCTTTGTCAAAATTGCAGACAAGGTCATCAGCGTTCCTGAGAAT

GACTTCTTCTTTGACTTTGTTCGACACTTGACAGACTGGATAAAGAAAGCTCGGCCCATCAA

GGACGGAATTGTGCCCTCACTCACCTACCAGGTGTTCTTCATGAAGAAGCTGTGGACCACC

ACGGTGCCAGGGAAGGATCCCATGGCCGATTCCATCTTCCACTATTACCAGGAGTTGCCCA

AGTATCTCCGAGGCTACCACAAGTGCACGCGGGAGGAGGTGCTGCAGCTGGGGCGCTGAT

CTACAGGGTCAAGTTCGAGGAGGACAAGTCCTACTTCCCCAGCATCCCCAAGCTGCTGCGG

GAGCTGGTGCCCCAGGACCTTATCCGGCAGGTCTCACCTGATGACTGGAAGCGGTCCATCG

TCGCCTACTTCAACAAGCACGCAGGGAAGTCCAAGGAGGAGGCCAAGCTGGCCTTCCTGAA

GCTCATCTTCAAGTGGCCCACCTTTGGCTCAGCCTTCTTCGAGGTGAAGCAAACTACGGAGC

CAAACTTCCCTGAGATCCTCCTAATTGCCATCAACAAGTATGGGGTCAGCCTCATCGATCCC

AAAACGAAGGATATCCTCACCACTCATCCCTTCACCAAGATCTCCAACTGGAGCAGCGGCA

ACACCTACTTCCACATCACCATTGGGAACTTGGTGCGCGGGAGCAAACTGCTCTGCGAGAC

GTCACTGGGCTACAAGATGGATGACCTCCTGACTTCCTACATTAGCCAGATGCTCACAGCC

ATGAGCAAACAGCGGGGCTCCAGGAGCGGCAAGTACCCTTACGATGTACCGGATTACGCAT

GAGGTACCAAGGGCGAATTCTGCAGTCGACTAGAGCTCGCTGATCAGCCTCGACTGTGCCT

TCTAGTTGCCAGCCATCTGTTGTTTGCCCCTCCCCCGTGCCTTCCTTGACCCTGGAAGGTGCC

ACTCCCACTGTCCTTTCCTAATAAAATGAGGAAATTGCATCGCATTGTCTGAGTAGGTGTCA

TTCTATTCTGGGGGGTGGGGTGGGGCAGGACAGCAAGGGGGAGGATTGGGAAGACAATAG

CAGGCATGCTGGGGAGAGATCTGGAGGACTAGTCCGTCGACTGTTAATTAAGCATGCTGGG

GAGAGATCTAGGAAACCCCTAGTGATGGAGTTGGCCACTCCCTCTCTGCGCGCTCGCTCGCT

CACTGAGGCCGGGCGACCAAAGGTCGCCCGACGCCCGGGCTTTGCCCGGGCGGCCTCAGTG

AGCGAGCGAGCGCGCAGAGAGGGAG

SEQ ID NO: 36 is the nucleotide sequence of the CMv1 overlap front-half vector (i.e., AAV-smCBA-hMYO7A-noDimNT-CMv1):
CTCCCTCTCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCC

ATCACTAGGGGTTCTCAGATCTGGCGCGCCCAATTCGGTACCCTAGTTATTAATAGTAATCA

ATTACGGGGTCATTAGTTCATAGCCCATATATGGAGTTCCGCGTTACATAACTTACGGTAAA

TGGCCCGCCTGGCTGACCGCCCAACGACCCCCGCCCATTGACGTCAATAATGACGTATGTTC

CCATAGTAACGCCAATAGGGACTTTCCATTGACGTCAATGGGTGGACTATTTACGGTAAAC

TGCCCACTTGGCAGTACATCAAGTGTATCATATGCCAAGTACGCCCCCTATTGACGTCAATG

-continued

```
ACGGTAAATGGCCCGCCTGGCATTATGCCCAGTACATGACCTTATGGGACTTTCCTACTTGG
CAGTACATCTACGTATTAGTCATCGCTATTACCATGGTCGAGGTGAGCCCCACGTTCTGCTT
CACTCTCCCCATCTCCCCCCCCTCCCCACCCCCAATTTTGTATTTATTTATTTTTTAATTATTT
TGTGCAGCGATGGGGGCGGGGGGGGGGGGGGCGCGCGCCAGGCGGGGCGGGGCGGGG
CGAGGGGCGGGGCGGGGCGAGGCGGAGAGGTGCGGCGGCAGCCAATCAGAGCGGCGCGC
TCCGAAAGTTTCCTTTTATGGCGAGGCGGCGGCGGCGGCCCTATAAAAAGCGAAGCGC
GCGGCGGGCGGGAGTCGCTGCGCGCTGCCTTCGCCCCGTGCCCCGCTCCGCCGCCGCCTCG
CGCCGCCCGCCCCGGCTCTGACTGACCGCGTTACTCCCACAGGTGAGCGGGCGGGACGGCC
CTTCTCCTCCGGGCTGTAATTAGCGCTTGGTTTAATGACGGCTTGTTTCTTTTCTGTGGCTGC
GTGAAAGCCTTGAGGGGCTCCGGGAGCTAGAGCCTCTGCTAACCATGTTCATGCCTTCTTCT
TTTTCCTACAGCTCCTGGGCAACGTGCTGGTTATTGTGCTGTCTCATCATTTTGGCAAAGAA
TTCTAGCGGCCGCCACCATGGTGATTCTTCAGCAGGGGGACCATGTGTGGATGGACCTGAG
ATTGGGGCAGGAGTTCGACGTGCCCATCGGGCGGTGGTGAAGCTCTGCGACTCTGGGCAG
GTCCAGGTGGTGGATGATGAAGACAATGAACACTGGATCTCTCCGCAGAACGCAACGCACA
TCAAGCCTATGCACCCCACGTCGGTCCACGGCGTGGAGGACATGATCCGCCTGGGGGACCT
CAACGAGGCGGGCATCTTGCGCAACCTGCTTATCCGCTACCGGGACCACCTCATCTACACG
TATACGGGCTCCATCCTGGTGGCTGTGAACCCCTACCAGCTGCTCTCCATCTACTCGCCAGA
GCACATCCGCCAGTATACCAACAAGAAGATTGGGGAGATGCCCCCCCACATCTTTGCCATT
GCTGACAACTGCTACTTCAACATGAAACGCAACAGCCGAGACCAGTGCTGCATCATCAGTG
GGGAATCTGGGCCGGGAAGACGGAGAGCACAAAGCTGATCCTGCAGTTCCTGGCAGCCA
TCAGTGGGCAGCACTCGTGGATTGAGCAGCAGGTCTTGGAGGCCACCCCCATTCTGGAAGC
ATTTGGGAATGCCAAGACCATCCGCAATGACAACTCAAGCCGTTTCGGAAAGTACATCGAC
ATCCACTTCAACAAGCGGGGCGCCATCGAGGGCGCGAAGATTGAGCAGTACCTGCTGGAA
AAGTCACGTGTCTGTCGCCAGGCCCTGGATGAAAGGAACTACCACGTGTTCTACTGCATGC
TGGAGGGTATGAGTGAGGATCAGAAGAAGAAGCTGGGCTTGGGCCAGGCCTCTGACTACA
ACTACTTGGCCATGGGTAACTGCATAACCTGTGAGGGCCGGGTGGACAGCCAGGAGTACGC
CAACATCCGCTCCGCCATGAAGGTGCTCATGTTCACTGACACCGAGAACTGGGAGATCTCG
AAGCTCCTGGCTGCCATCCTGCACCTGGGCAACCTGCAGTATGAGGCACGCACATTTGAAA
ACCTGGATGCCTGTGAGGTTCTCTTCTCCCCATCGCTGGCCACAGCTGCATCCCTGCTTGAG
GTGAACCCCCAGACCTGATGAGCTGCCTGACTAGCCGCACCCTCATCACCCGCGGGGAGA
CGGTGTCCACCCCACTGAGCAGGGAACAGGCACTGGACGTGCGCGACGCCTTCGTAAAGGG
GATCTACGGGCGGCTGTTCGTGTGGATTGTGGACAAGATCAACGCAGCAATTTACAAGCCT
CCCTCCCAGGATGTGAAGAACTCTCGCAGGTCCATCGGCCTCCTGGACATCTTTGGGTTTGA
GAACTTTGCTGTGAACAGCTTTGAGCAGCTCTGCATCAACTTCGCCAATGAGCACCTGCAGC
AGTTCTTTGTGCGGCACGTGTTCAAGCTGGAGCAGGAGGAATATGACCTGGAGAGCATTGA
CTGGCTGCACATCGAGTTCACTGACAACCAGGATGCCCTGGACATGATTGCCAACAAGCCC
ATGAACATCATCTCCCTCATCGATGAGGAGAGCAAGTTCCCCAAGGGCACAGACACCACCA
TGTTACACAAGCTGAACTCCCAGCACAAGCTCAACGCCAACTACATCCCCCCAAGAACAA
CCATGAGACCCAGTTTGGCATCAACCATTTTGCAGGCATCGTCTACTATGAGACCCAAGGCT
TCCTGGAGAAGAACCGAGACACCCTGCATGGGGACATTATCCAGCTGGTCCACTCCTCCAG
GAACAAGTTCATCAAGCAGATCTTCCAGGCCGATGTCGCCATGGGCGCCGAGACCAGGAAG
```

CGCTCGCCCACACTTAGCAGCCAGTTCAAGCGGTCACTGGAGCTGCTGATGCGCACGCTGG

GTGCCTGCCAGCCCTTCTTTGTGCGATGCATCAAGCCCAATGAGTTCAAGAAGCCCATGCTG

TTCGACCGGCACCTGTGCGTGCGCCAGCTGCGGTACTCAGGAATGATGGAGACCATCCGAA

TCCGCCGAGCTGGCTACCCCATCCGCTACAGCTTCGTAGAGTTTGTGGAGCGGTACCGTGTG

CTGCTGCCAGGTGTGAAGCCGGCCTACAAGCAGGGCGACCTCCGCGGGACTTGCCAGCGCA

TGGCTGAGGCTGTGCTGGGCACCCACGATGACTGGCAGATAGGCAAAACCAAGATCTTTCT

GAAGGACCACCATGACATGCTGCTGGAAGTGGAGCGGGACAAAGCCATCACCGACAGAGT

CATCCTCCTTCAGAAAGTCATCCGGGGATTCAAAGACAGGTCTAACTTTCTGAAGCTGAAG

AACGCTGCCACACTGATCCAGAGGCACTGGCGGGGTCACAACTGTAGGAAGAACTACGGG

CTGATGCGTCTGGGCTTCCTGCGGCTGCAGGCCCTGCACCGCTCCCGGAAGCTGCACCAGC

AGTACCGCCTGGCCCGCCAGCGCATCATCCAGTTCCAGGCCCGCTGCCGCGCCTATCTGGTG

CGCAAGGCCTTCCGCCACCGCCTCTGGGCTGTGCTCACCGTGCAGGCCTATGCCCGGGGCA

TGATCGCCCGCAGGCTGCACCAACGCCTCAGGGCTGAGTATCTGTGGCGCCTCGAGGCTGA

GAAAATGCGGCTGGCGGAGGAAGAGAAGCTTAGAGGATCCTCCCGTCGACTGTTTAAGCAT

GCTGGGGAGAGATCTGAGGAAACCCCTAGTGATGGAGTTGGCCACTCCCTCTCTGCGCGCT

CGCTCGCTCACTGAGGCCGGGCGACCAAAGGTCGCCCGACGCCCGGGCTTTGCCCGGGCGG

CCTCAGTGAGCGAGCGAGCGCGCAGAGAGGGAG

SEQ ID NO: 62 (peptide encoded by the N-myosin7A portion of SEQ ID NO: 36
(AAV-smCBA-hMYO7A-noDimNT-CMv1))
MVILQQGDHVWMDLRLGQEFDVPIGAVVKLCDSGQVQVVDDEDNEHWISPQNATHIKPMHPT

SVHGVEDMIRLGDLNEAGILRNLLIRYRDHLIYTYTGSILVAVNPYQLLSIYSPEHIRQYTNKKIG

EMPPHIFAIADNCYFNMKRNSRDQCCIISGESGAGKTESTKLILQFLAAISGQHSWIEQQVLEATP

ILEAFGNAKTIRNDNSSRFGKYIDIHFNKRGAIEGAKIEQYLLEKSRVCRQALDERNYHVFYCML

EGMSEDQKKKLGLGQASDYNYLAMGNCITCEGRVDSQEYANIRSAMKVLMFTDTENWEISKL

LAAILHLGNLQYEARTFENLDACEVLFSPSLATAASLLEVNPPDLMSCLTSRTLITRGETVSTPLS

REQALDVRDAFVKGIYGRLFVWIVDKINAAIYKPPSQDVKNSRRSIGLLDIFGFENFAVNSFEQL

CINFANEHLQQFFVRHVFKLEQEEYDLESIDWLHIEFTDNQDALDMIANKPMNIISLIDEESKFPK

GTDTTMLHKLNSQHKLNANYIPPKNNHETQFGINHFAGIVYYETQGFLEKNRDTLHGDIIQLVH

SSRNKFIKQIFQADVAMGAETRKRSPTLSSQFKRSLELLMRTLGACQPFFVRCIKPNEFKKPMLF

DRHLCVRQLRYSGMMETIRIRRAGYPIRYSFVEFVERYRVLLPGVKPAYKQGDLRGTCQRMAE

AVLGTHDDWQIGKTKIFLKDHHDMLLEVERDKAITDRVILLQKVIRGFKDRSNFLKLKNAATLI

QRHWRGHNCRKNYGLMRLGFLRLQALHRSRKLHQQYRLARQRIIQFQARCRAYLVRKAFRHR

LWAVLTVQAYARGMIARRLHQRLRAEYLWRLEAEKMRLAEEEKL

SEQ ID NO: 63 (only the N-myosin7A portion of SEQ ID NO: 36 (AAV-smCBA-
hMYO7A-noDimNT-CMv1))
ATGGTGATTCTTCAGCAGGGGACCATGTGTGGATGGACCTGAGATTGGGGCAGGAGTTCG

ACGTGCCCATCGGGCGGTGGTGAAGCTCTGCGACTCTGGGCAGGTCCAGGTGGTGGATGA

TGAAGACAATGAACACTGGATCTCTCCGCAGAACGCAACGCACATCAAGCCTATGCACCCC

ACGTCGGTCCACGGCGTGGAGGACATGATCCGCCTGGGGGACCTCAACGAGGCGGGCATCT

TGCGCAACCTGCTTATCCGCTACCGGGACCACCTCATCTACACGTATACGGGCTCCATCCTG

GTGGCTGTGAACCCCTACCAGCTGCTCTCCATCTACTCGCCAGAGCACATCCGCCAGTATAC

CAACAAGAAGATTGGGGAGATGCCCCCCCACATCTTTGCCATTGCTGACAACTGCTACTTC

-continued

```
AACATGAAACGCAACAGCCGAGACCAGTGCTGCATCATCAGTGGGGAATCTGGGGCCGGG

AAGACGGAGAGCACAAAGCTGATCCTGCAGTTCCTGGCAGCCATCAGTGGGCAGCACTCGT

GGATTGAGCAGCAGGTCTTGGAGGCCACCCCCATTCTGGAAGCATTTGGGAATGCCAAGAC

CATCCGCAATGACAACTCAAGCCGTTTCGGAAAGTACATCGACATCCACTTCAACAAGCGG

GGCGCCATCGAGGGCGCGAAGATTGAGCAGTACCTGCTGGAAAAGTCACGTGTCTGTCGCC

AGGCCCTGGATGAAAGGAACTACCACGTGTTCTACTGCATGCTGGAGGGTATGAGTGAGGA

TCAGAAGAAGAAGCTGGGCTTGGGCCAGGCCTCTGACTACAACTACTTGGCCATGGGTAAC

TGCATAACCTGTGAGGGCCGGGTGGACAGCCAGGAGTACGCCAACATCCGCTCCGCCATGA

AGGTGCTCATGTTCACTGACACCGAGAACTGGGAGATCTCGAAGCTCCTGGCTGCCATCCT

GCACCTGGGCAACCTGCAGTATGAGGCACGCACATTTGAAAACCTGGATGCCTGTGAGGTT

CTCTTCTCCCCATCGCTGGCCACAGCTGCATCCCTGCTTGAGGTGAACCCCCCAGACCTGAT

GAGCTGCCTGACTAGCCGCACCCTCATCACCCGCGGGGAGACGGTGTCCACCCCACTGAGC

AGGGAACAGGCACTGGACGTGCGCGACGCCTTCGTAAAGGGGATCTACGGGCGGCTGTTCG

TGTGGATTGTGGACAAGATCAACGCAGCAATTTACAAGCCTCCCTCCCAGGATGTGAAGAA

CTCTCGCAGGTCCATCGGCCTCCTGGACATCTTTGGGTTTGAGAACTTTGCTGTGAACAGCT

TTGAGCAGCTCTGCATCAACTTCGCCAATGAGCACCTGCAGCAGTTCTTTGTGCGGCACGTG

TTCAAGCTGGAGCAGGAGGAATATGACCTGGAGAGCATTGACTGGCTGCACATCGAGTTCA

CTGACAACCAGGATGCCCTGGACATGATTGCCAACAAGCCCATGAACATCATCTCCCTCAT

CGATGAGGAGAGCAAGTTCCCCAAGGGCACAGACACCACCATGTTACACAAGCTGAACTCC

CAGCACAAGCTCAACGCCAACTACATCCCCCCCAAGAACAACCATGAGACCCAGTTTGGCA

TCAACCATTTTGCAGGCATCGTCTACTATGAGACCCAAGGCTTCCTGGAGAAGAACCGAGA

CACCCTGCATGGGACATTATCCAGCTGGTCCACTCCTCCAGGAACAAGTTCATCAAGCAG

ATCTTCCAGGCCGATGTCGCCATGGGCGCCGAGACCAGGAAGCGCTCGCCCACACTTAGCA

GCCAGTTCAAGCGGTCACTGGAGCTGCTGATGCGCACGCTGGGTGCCTGCCAGCCCTTCTTT

GTGCGATGCATCAAGCCCAATGAGTTCAAGAAGCCCATGCTGTTCGACCGGCACCTGTGCG

TGCGCCAGCTGCGGTACTCAGGAATGATGGAGACCATCCGAATCCGCCGAGCTGGCTACCC

CATCCGCTACAGCTTCGTAGAGTTTGTGGAGCGGTACCGTGTGCTGCTGCCAGGTGTGAAG

CCGGCCTACAAGCAGGGCGACCTCCGCGGGACTTGCCAGCGCATGGCTGAGGCTGTGCTGG

GCACCCACGATGACTGGCAGATAGGCAAAACCAAGATCTTTCTGAAGGACCACCATGACAT

GCTGCTGGAAGTGGAGCGGGACAAAGCCATCACCGACAGAGTCATCCTCCTTCAGAAAGTC

ATCCGGGGATTCAAAGACAGGTCTAACTTTCTGAAGCTGAAGAACGCTGCCACACTGATCC

AGAGGCACTGGCGGGGTCACAACTGTAGGAAGAACTACGGGCTGATGCGTCTGGGCTTCCT

GCGGCTGCAGGCCCTGCACCGCTCCCGGAAGCTGCACCAGCAGTACCGCCTGGCCCGCCAG

CGCATCATCCAGTTCCAGGCCCGCTGCCGCGCCTATCTGGTGCGCAAGGCCTTCCGCCACCG

CCTCTGGGCTGTGCTCACCGTGCAGGCCTATGCCCGGGGCATGATCGCCCGCAGGCTGCAC

CAACGCCTCAGGGCTGAGTATCTGTGGCGCCTCGAGGCTGAGAAAATGCGGCTGGCGGAGG

AAGAGAAGCTT

SEQ ID NO: 37 is the nucleotide sequence of the second generation overlap front-half
vector (i.e., AAV-smCBA-hMYO7A-noDIM-NTlong):
CTCCCTCTCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCC

ATCACTAGGGGTTCTCAGATCTGGCGCGCCCAATTCGGTACCCTAGTTATTAATAGTAATCA
```

-continued

```
ATTACGGGGTCATTAGTTCATAGCCCATATATGGAGTTCCGCGTTACATAACTTACGGTAAA

TGGCCCGCCTGGCTGACCGCCCAACGACCCCCGCCCATTGACGTCAATAATGACGTATGTTC

CCATAGTAACGCCAATAGGGACTTTCCATTGACGTCAATGGGTGGACTATTTACGGTAAAC

TGCCCACTTGGCAGTACATCAAGTGTATCATATGCCAAGTACGCCCCCTATTGACGTCAATG

ACGGTAAATGGCCCGCCTGGCATTATGCCCAGTACATGACCTTATGGGACTTTCCTACTTGG

CAGTACATCTACGTATTAGTCATCGCTATTACCATGGTCGAGGTGAGCCCCACGTTCTGCTT

CACTCTCCCCATCTCCCCCCCCTCCCCACCCCCAATTTTGTATTTATTTATTTTTTAATTATTT

TGTGCAGCGATGGGGGCGGGGGGGGGGGGGGGCGCGCGCCAGGCGGGGCGGGGCGGGG

CGAGGGGCGGGGCGGGGCGAGGCGGAGAGGTGCGGCGGCAGCCAATCAGAGCGGCGCGC

TCCGAAAGTTTCCTTTTATGGCGAGGCGGCGGCGGCGGCCCTATAAAAAGCGAAGCGC

GCGGCGGGCGGGAGTCGCTGCGCGCTGCCTTCGCCCCGTGCCCCGCTCCGCCGCCGCCTCG

CGCCGCCCGCCCCGGCTCTGACTGACCGCGTTACTCCCACAGGTGAGCGGGCGGGACGGCC

CTTCTCCTCCGGGCTGTAATTAGCGCTTGGTTTAATGACGGCTTGTTTCTTTTCTGTGGCTGC

GTGAAAGCCTTGAGGGGCTCCGGGAGCTAGAGCCTCTGCTAACCATGTTCATGCCTTCTTCT

TTTTCCTACAGCTCCTGGGCAACGTGCTGGTTATTGTGCTGTCTCATCATTTTGGCAAAGAA

TTCTAGCGGCCGCCACCATGGTGATTCTTCAGCAGGGGGACCATGTGTGGATGGACCTGAG

ATTGGGGCAGGAGTTCGACGTGCCCATCGGGGCGGTGGTGAAGCTCTGCGACTCTGGGCAG

GTCCAGGTGGTGGATGATGAAGACAATGAACACTGGATCTCTCCGCAGAACGCAACGCACA

TCAAGCCTATGCACCCCACGTCGGTCCACGGCGTGGAGGACATGATCCGCCTGGGGGACCT

CAACGAGGCGGGCATCTTGCGCAACCTGCTTATCCGCTACCGGGACCACCTCATCTACACG

TATACGGGCTCCATCCTGGTGGCTGTGAACCCCTACCAGCTGCTCTCCATCTACTCGCCAGA

GCACATCCGCCAGTATACCAACAAGAAGATTGGGGAGATGCCCCCCCACATCTTTGCCATT

GCTGACAACTGCTACTTCAACATGAAACGCAACAGCCGAGACCAGTGCTGCATCATCAGTG

GGGAATCTGGGGCCGGGAAGACGGAGAGCACAAAGCTGATCCTGCAGTTCCTGGCAGCCA

TCAGTGGGCAGCACTCGTGGATTGAGCAGCAGGTCTTGGAGGCCACCCCCATTCTGGAAGC

ATTTGGGAATGCCAAGACCATCCGCAATGACAACTCAAGCCGTTTCGGAAAGTACATCGAC

ATCCACTTCAACAAGCGGGGCGCCATCGAGGGCGCGAAGATTGAGCAGTACCTGCTGGAA

AAGTCACGTGTCTGTCGCCAGGCCCTGGATGAAAGGAACTACCACGTGTTCTACTGCATGC

TGGAGGGTATGAGTGAGGATCAGAAGAAGAAGCTGGGCTTGGGCCAGGCCTCTGACTACA

ACTACTTGGCCATGGGTAACTGCATAACCTGTGAGGGCCGGGTGGACAGCCAGGAGTACGC

CAACATCCGCTCCGCCATGAAGGTGCTCATGTTCACTGACACCGAGAACTGGGAGATCTCG

AAGCTCCTGGCTGCCATCCTGCACCTGGGCAACCTGCAGTATGAGGCACGCACATTTGAAA

ACCTGGATGCCTGTGAGGTTCTCTTCTCCCCATCGCTGGCCACAGCTGCATCCCTGCTTGAG

GTGAACCCCCAGACCTGATGAGCTGCCTGACTAGCCGCACCCTCATCACCCGCGGGGAGA

CGGTGTCCACCCCACTGAGCAGGGAACAGGCACTGGACGTGCGCGACGCCTTCGTAAAGGG

GATCTACGGGCGGCTGTTCGTGTGGATTGTGGACAAGATCAACGCAGCAATTTACAAGCCT

CCCTCCCAGGATGTGAAGAACTCTCGCAGGTCCATCGGCCTCCTGGACATCTTTGGGTTTGA

GAACTTTGCTGTGAACAGCTTTGAGCAGCTCTGCATCAACTTCGCCAATGAGCACCTGCAGC

AGTTCTTTGTGCGGCACGTGTTCAAGCTGGAGCAGGAGGAATATGACCTGGAGAGCATTGA

CTGGCTGCACATCGAGTTCACTGACAACCAGGATGCCCTGGACATGATTGCCAACAAGCCC
```

-continued

ATGAACATCATCTCCCTCATCGATGAGGAGAGCAAGTTCCCCAAGGGCACAGACACCACCA

TGTTACACAAGCTGAACTCCCAGCACAAGCTCAACGCCAACTACATCCCCCCCAAGAACAA

CCATGAGACCCAGTTTGGCATCAACCATTTTGCAGGCATCGTCTACTATGAGACCCAAGGCT

TCCTGGAGAAGAACCGAGACACCCTGCATGGGACATTATCCAGCTGGTCCACTCCTCCAG

GAACAAGTTCATCAAGCAGATCTTCCAGGCCGATGTCGCCATGGGCGCCGAGACCAGGAAG

CGCTCGCCCACACTTAGCAGCCAGTTCAAGCGGTCACTGGAGCTGCTGATGCGCACGCTGG

GTGCCTGCCAGCCCTTCTTTGTGCGATGCATCAAGCCCAATGAGTTCAAGAAGCCCATGCTG

TTCGACCGGCACCTGTGCGTGCGCCAGCTGCGGTACTCAGGAATGATGGAGACCATCCGAA

TCCGCCGAGCTGGCTACCCCATCCGCTACAGCTTCGTAGAGTTTGTGGAGCGGTACCGTGTG

CTGCTGCCAGGTGTGAAGCCGGCCTACAAGCAGGGCGACCTCCGCGGGACTTGCCAGCGCA

TGGCTGAGGCTGTGCTGGGCACCCACGATGACTGGCAGATAGGCAAAACCAAGATCTTTCT

GAAGGACCACCATGACATGCTGCTGGAAGTGGAGCGGGACAAAGCCATCACCGACAGAGT

CATCCTCCTTCAGAAAGTCATCCGGGGATTCAAAGACAGGTCTAACTTTCTGAAGCTGAAG

AACGCTGCCACACTGATCCAGAGGCACTGGCGGGTCACAACTGTAGGAAGAACTACGGG

CTGATGCGTCTGGGCTTCCTGCGGCTGCAGGCCCTGCACCGCTCCCGGAAGCTGCACCAGC

AGTACCGCCTGGCCCGCCAGCGCATCATCCAGTTCCAGGCCCGCTGCCGCGCCTATCTGGTG

CGCAAGGCCTTCCGCCACCGCCTCTGGGCTGTGCTCACCGTGCAGGCCTATGCCCGGGGCA

TGATCGCCCGCAGGCTGCACCAACGCCTCAGGGCTGAGTATCTGTGGCGCCTCGAGGCTGA

GAAAATGCGGCTGGCGGAGGAAGAGAAGCTTTGAAAGTGACATTAGGCTCCCGTCGACTGT

TAATTAAGCATGCTGGGGAGAGATCTGAGGAAACCCCTAGTGATGGAGTTGGCCACTCCCT

CTCTGCGCGCTCGCTCGCTCACTGAGGCCGGGCGACCAAAGGTCGCCCGACGCCCGGGCTT

TGCCCGGGCGGCCTCAGTGAGCGAGCGAGCGCGCAGAGAGGGAG

SEQ ID NO: 90 (only the N-myosin7A portion of SEQ ID NO: 37 (AAV-smCBA-hMYO7A-
noDIM-NTlong))
ATGGTGATTCTTCAGCAGGGGGACCATGTGTGGATGGACCTGAGATTGGGGCAGGAGTTCG

ACGTGCCCATCGGGGCGGTGGTGAAGCTCTGCGACTCTGGGCAGGTCCAGGTGGTGGATGA

TGAAGACAATGAACACTGGATCTCTCCGCAGAACGCAACGCACATCAAGCCTATGCACCCC

ACGTCGGTCCACGGCGTGGAGGACATGATCCGCCTGGGGGACCTCAACGAGGCGGGCATCT

TGCGCAACCTGCTTATCCGCTACCGGGACCACCTCATCTACACGTATACGGGCTCCATCCTG

GTGGCTGTGAACCCCTACCAGCTGCTCTCCATCTACTCGCCAGAGCACATCCGCCAGTATAC

CAACAAGAAGATTGGGGAGATGCCCCCCCACATCTTTGCCATTGCTGACAACTGCTACTTC

AACATGAAACGCAACAGCCGAGACCAGTGCTGCATCATCAGTGGGGAATCTGGGGCCGGG

AAGACGGAGAGCACAAAGCTGATCCTGCAGTTCCTGGCAGCCATCAGTGGGCAGCACTCGT

GGATTGAGCAGCAGGTCTTGGAGGCCACCCCCATTCTGGAAGCATTTGGGAATGCCAAGAC

CATCCGCAATGACAACTCAAGCCGTTTCGGAAAGTACATCGACATCCACTTCAACAAGCGG

GGCGCCATCGAGGGCGCGAAGATTGAGCAGTACCTGCTGGAAAAGTCACGTGTCTGTCGCC

AGGCCCTGGATGAAAGGAACTACCACGTGTTCTACTGCATGCTGGAGGGTATGAGTGAGGA

TCAGAAGAAGAAGCTGGGCTTGGGCCAGGCCTCTGACTACAACTACTTGGCCATGGGTAAC

TGCATAACCTGTGAGGGCCGGGTGGACAGCCAGGAGTACGCCAACATCCGCTCCGCCATGA

AGGTGCTCATGTTCACTGACACCGAGAACTGGGAGATCTCGAAGCTCCTGGCTGCCATCCT

GCACCTGGGCAACCTGCAGTATGAGGCACGCACATTTGAAAACCTGGATGCCTGTGAGGTT

CTCTTCTCCCCATCGCTGGCCACAGCTGCATCCCTGCTTGAGGTGAACCCCCCAGACCTGAT

```
GAGCTGCCTGACTAGCCGCACCCTCATCACCCGCGGGGAGACGGTGTCCACCCCACTGAGC

AGGGAACAGGCACTGGACGTGCGCGACGCCTTCGTAAAGGGGATCTACGGGCGGCTGTTCG

TGTGGATTGTGGACAAGATCAACGCAGCAATTTACAAGCCTCCCTCCCAGGATGTGAAGAA

CTCTCGCAGGTCCATCGGCCTCCTGGACATCTTTGGGTTTGAGAACTTTGCTGTGAACAGCT

TTGAGCAGCTCTGCATCAACTTCGCCAATGAGCACCTGCAGCAGTTCTTTGTGCGGCACGTG

TTCAAGCTGGAGCAGGAGGAATATGACCTGGAGAGCATTGACTGGCTGCACATCGAGTTCA

CTGACAACCAGGATGCCCTGGACATGATTGCCAACAAGCCCATGAACATCATCTCCCTCAT

CGATGAGGAGAGCAAGTTCCCCAAGGGCACAGACACCACCATGTTACACAAGCTGAACTCC

CAGCACAAGCTCAACGCCAACTACATCCCCCCCAAGAACAACCATGAGACCCAGTTTGGCA

TCAACCATTTTGCAGGCATCGTCTACTATGAGACCCAAGGCTTCCTGGAGAAGAACCGAGA

CACCCTGCATGGGGACATTATCCAGCTGGTCCACTCCTCCAGGAACAAGTTCATCAAGCAG

ATCTTCCAGGCCGATGTCGCCATGGGCGCCGAGACCAGGAAGCGCTCGCCCACACTTAGCA

GCCAGTTCAAGCGGTCACTGGAGCTGCTGATGCGCACGCTGGGTGCCTGCCAGCCCTTCTTT

GTGCGATGCATCAAGCCCAATGAGTTCAAGAAGCCCATGCTGTTCGACCGGCACCTGTGCG

TGCGCCAGCTGCGGTACTCAGGAATGATGGAGACCATCCGAATCCGCCGAGCTGGCTACCC

CATCCGCTACAGCTTCGTAGAGTTTGTGGAGCGGTACCGTGTGCTGCTGCCAGGTGTGAAG

CCGGCCTACAAGCAGGGCGACCTCCGCGGGACTTGCCAGCGCATGGCTGAGGCTGTGCTGG

GCACCCACGATGACTGGCAGATAGGCAAAACCAAGATCTTTCTGAAGGACCACCATGACAT

GCTGCTGGAAGTGGAGCGGGACAAAGCCATCACCGACAGAGTCATCCTCCTTCAGAAAGTC

ATCCGGGGATTCAAAGACAGGTCTAACTTTCTGAAGCTGAAGAACGCTGCCACACTGATCC

AGAGGCACTGGCGGGGTCACAACTGTAGGAAGAACTACGGGCTGATGCGTCTGGGCTTCCT

GCGGCTGCAGGCCCTGCACCGCTCCCGGAAGCTGCACCAGCAGTACCGCCTGGCCCGCCAG

CGCATCATCCAGTTCCAGGCCCGCTGCCGCGCCTATCTGGTGCGCAAGGCCTTCCGCCACCG

CCTCTGGGCTGTGCTCACCGTGCAGGCCTATGCCCGGGGCATGATCGCCCGCAGGCTGCAC

CAACGCCTCAGGGCTGAGTATCTGTGGCGCCTCGAGGCTGAGAAAATGCGGCTGGCGGAGG

AAGAGAAGCTT
```

SEQ ID NO: 91 (only the N-myosin7A portion of SEQ ID NO: 37 (AAV-smCBA-hMYO7A-noDIM-NTlong))

MVILQQGDHVWMDLRLGQEFDVPIGAVVKLCDSGQVQVVDDEDNEHWISPQNATHIKPMHPT

SVHGVEDMIRLGDLNEAGILRNLLIRYRDHLIYTYTGSILVAVNPYQLLSIYSPEHIRQYTNKKIG

EMPPHIFAIADNCYFNMKRNSRDQCCIISGESGAGKTESTKLILQFLAAISGQHSWIEQQVLEATP

ILEAFGNAKTIRNDNSSRFGKYIDIHFNKRGAIEGAKIEQYLLEKSRVCRQALDERNYHVFYCML

EGMSEDQKKKLGLGQASDYNYLAMGNCITCEGRVDSQEYANIRSAMKVLMFTDTENWEISKL

LAAILHLGNLQYEARTFENLDACEVLFSPSLATAASLLEVNPPDLMSCLTSRTLITRGETVSTPLS

REQALDVRDAFVKGIYGRLFVWIVDKINAAIYKPPSQDVKNSRRSIGLLDIFGFENFAVNSFEQL

CINFANEHLQQFFVRHVFKLEQEEYDLESIDWLHIEFTDNQDALDMIANKPMNIISLIDEESKFPK

GTDTTMLHKLNSQHKLNANYIPPKNNHETQFGINHFAGIVYYETQGFLEKNRDTLHGDIIQLVH

SSRNKFIKQIFQADVAMGAETRKRSPTLSSQFKRSLELLMRTLGACQPFFVRCIKPNEFKKPMLF

DRHLCVRQLRYSGMMETIRIRRAGYPIRYSFVEFVERYRVLLPGVKPAYKQGDLRGTCQRMAE

AVLGTHDDWQIGKTKIFLKDHHDMLLEVERDKAITDRVILLQKVIRGFKDRSNFLKLKNAATLI

-continued

QRHWRGHNCRKNYGLMRLGFLRLQALHRSRKLHQQYRLARQRIIQFQARCRAYLVRKAFRHR

LWAVLTVQAYARGMIARRLHQRLRAEYLWRLEAEKMRLAEEEKL

SEQ ID NO: 38 is the nucleotide sequence of the second generation overlap back-half vector (i.e., AAV-hMYO7A-CTlong-v2.HA).

CTCCCTCTCTGCGCGCTCGCTCGCTCACTGAGGCCGCCCGGGCAAAGCCCGGGCGTCGGGC

GACCTTTGGTCGCCCGGCCTCAGTGAGCGAGCGAGCGCGCAGAGAGGGAGTGGCCAACTCC

ATCACTAGGGGTTCAGATCTGGCGCGCCGGATCCGGGCTGATGCGTCTGGGCTTCCTGCGG

CTGCAGGCCCTGCACCGCTCCCGGAAGCTGCACCAGCAGTACCGCCTGGCCCGCCAGCGCA

TCATCCAGTTCCAGGCCCGCTGCCGCGCCTATCTGGTGCGCAAGGCCTTCCGCCACCGCCTC

TGGGCTGTGCTCACCGTGCAGGCCTATGCCCGGGGCATGATCGCCCGCAGGCTGCACCAAC

GCCTCAGGGCTGAGTATCTGTGGCGCCTCGAGGCTGAGAAAATGCGGCTGGCGGAGGAAG

AGAAGCTTCGGAAGGAGATGAGCGCCAAGAAGGCCAAGGAGGAGGCCGAGCGCAAGCAT

CAGGAGCGCCTGGCCCAGCTGGCTCGTGAGGACGCTGAGCGGGAGCTGAAGGAGAAGGAG

GCCGCTCGGCGGAAGAAGGAGCTCCTGGAGCAGATGGAAAGGGCCCGCCATGAGCCTGTC

AATCACTCAGACATGGTGGACAAGATGTTTGGCTTCCTGGGGACTTCAGGTGGCCTGCCAG

GCCAGGAGGGCCAGGCACCTAGTGGCTTTGAGGACCTGGAGCGAGGGCGGAGGGAGATGG

TGGAGGAGGACCTGGATGCAGCCCTGCCCCTGCCTGACGAGGATGAGGAGGACCTCTCTGA

GTATAAATTTGCCAAGTTCGCGGCCACCTACTTCCAGGGGACAACCACGCACTCCTACACC

CGGCGGCCACTCAAACAGCCACTGCTCTACCATGACGACGAGGGTGACCAGCTGGCAGCCC

TGGCGGTCTGGATCACCATCCTCCGCTTCATGGGGGACCTCCCTGAGCCCAAGTACCACAC

AGCCATGAGTGATGGCAGTGAGAAGATCCCTGTGATGACCAAGATTTATGAGACCCTGGGC

AAGAAGACGTACAAGAGGGAGCTGCAGGCCCTGCAGGGCGAGGGCGAGGCCCAGCTCCCC

GAGGGCCAGAAGAAGAGCAGTGTGAGGCACAAGCTGGTGCATTTGACTCTGAAAAAGAAG

TCCAAGCTCACAGAGGAGGTGACCAAGAGGCTGCATGACGGGGAGTCCACAGTGCAGGGC

AACAGCATGCTGGAGGACCGGCCCACCTCCAACCTGGAGAAGCTGCACTTCATCATCGGCA

ATGGCATCCTGCGGCCAGCACTCCGGGACGAGATCTACTGCCAGATCAGCAAGCAGCTGAC

CCACAACCCCTCCAAGAGCAGCTATGCCCGGGGCTGGATTCTCGTGTCTCTCTGCGTGGGCT

GTTTCGCCCCCTCCGAGAAGTTTGTCAAGTACCTGCGGAACTTCATCCACGGGGCCCGCCC

GGCTACGCCCCGTACTGTGAGGAGCGCCTGAGAAGGACCTTTGTCAATGGGACACGGACAC

AGCCGCCCAGCTGGCTGGAGCTGCAGGCCACCAAGTCCAAGAAGCCAATCATGTTGCCCGT

GACATTCATGGATGGGACCACCAAGACCCTGCTGACGGACTCGGCAACCACGGCCAAGGA

GCTCTGCAACGCGCTGGCCGACAAGATCTCTCTCAAGGACCGGTTCGGGTTCTCCCTCTACA

TTGCCCTGTTTGACAAGGTGTCCTCCCTGGGCAGCGGCAGTGACCACGTCATGGACGCCATC

TCCCAGTGCGAGCAGTACGCCAAGGAGCAGGGCGCCCAGGAGCGCAACGCCCCCTGGAGG

CTCTTCTTCCGCAAAGAGGTCTTCACGCCCTGGCACAGCCCCTCCGAGGACAACGTGGCCA

CCAACCTCATCTACCAGCAGGTGGTGCGAGGAGTCAAGTTTGGGGAGTACAGGTGTGAGAA

GGAGGACGACCTGGCTGAGCTGGCCTCCCAGCAGTACTTTGTAGACTATGGCTCTGAGATG

ATCCTGGAGCGCCTCCTGAACCTCGTGCCCACCTACATCCCCGACCGCGAGATCACGCCCCT

GAAGACGCTGGAGAAGTGGGCCCAGCTGGCCATCGCCGCCCACAAGAAGGGGATTTATGC

CCAGAGGAGAACTGATGCCCAGAAGGTCAAAGAGGATGTGGTCAGTTATGCCCGCTTCAAG

TGGCCCTTGCTCTTCTCCAGGTTTTATGAAGCCTACAAATTCTCAGGCCCCAGTCTCCCCAA

GAACGACGTCATCGTGGCCGTCAACTGGACGGGTGTGTACTTTGTGGATGAGCAGGAGCAG

-continued

```
GTACTTCTGGAGCTGTCCTTCCCAGAGATCATGGCCGTGTCCAGCAGCAGGGGAGCGAAAA

CGACGGCCCCCAGCTTCACGCTGGCCACCATCAAGGGGGACGAATACACCTTCACCTCCAG

CAATGCTGAGGACATTCGTGACCTGGTGGTCACCTTCCTAGAGGGGCTCCGGAAGAGATCT

AAGTATGTTGTGGCCCTGCAGGATAACCCCAACCCCGCAGGCGAGGAGTCAGGCTTCCTCA

GCTTTGCCAAGGGAGACCTCATCATCCTGGACCATGACACGGGCGAGCAGGTCATGAACTC

GGGCTGGGCCAACGGCATCAATGAGAGGACCAAGCAGCGTGGGGACTTCCCCACCGACAG

TGTGTACGTCATGCCCACTGTCACCATGCCACCGCGGGAGATTGTGGCCCTGGTCACCATGA

CTCCCGATCAGAGGCAGGACGTTGTCCGGCTCTTGCAGCTGCGAACGGCGGAGCCCGAGGT

GCGTGCCAAGCCCTACACGCTGGAGGAGTTTTCCTATGACTACTTCAGGCCCCCACCCAAG

CACACGCTGAGCCGTGTCATGGTGTCCAAGGCCCGAGGCAAGGACCGGCTGTGGAGCCACA

CGCGGGAACCGCTCAAGCAGGCGCTGCTCAAGAAGCTCCTGGGCAGTGAGGAGCTCTCGCA

GGAGGCCTGCCTGGCCTTCATTGCTGTGCTCAAGTACATGGGCGACTACCCGTCCAAGAGG

ACACGCTCCGTCAACGAGCTCACCGACCAGATCTTTGAGGGTCCCCTGAAAGCCGAGCCCC

TGAAGGACGAGGCATATGTGCAGATCCTGAAGCAGCTGACCGACAACCACATCAGGTACA

GCGAGGAGCGGGGTTGGGAGCTGCTCTGGCTGTGCACGGGCCTTTTCCCACCCAGCAACAT

CCTCCTGCCCCACGTGCAGCGCTTCCTGCAGTCCCGAAAGCACTGCCCACTCGCCATCGACT

GCCTGCAACGGCTCCAGAAAGCCCTGAGAAACGGGTCCCGGAAGTACCCTCCGCACCTGGT

GGAGGTGGAGGCCATCCAGCACAAGACCACCCAGATTTTCCACAAAGTCTACTTCCCTGAT

GACACTGACGAGGCCTTCGAAGTGGAGTCCAGCACCAAGGCCAAGGACTTCTGCCAGAAC

ATCGCCACCAGGCTGCTCCTCAAGTCCTCAGAGGGATTCAGCCTCTTTGTCAAAATTGCAGA

CAAGGTCATCAGCGTTCCTGAGAATGACTTCTTCTTTGACTTTGTTCGACACTTGACAGACT

GGATAAAGAAAGCTCGGCCCATCAAGGACGGAATTGTGCCCTCACTCACCTACCAGGTGTT

CTTCATGAAGAAGCTGTGGACCACCACGGTGCCAGGGAAGGATCCCATGGCCGATTCCATC

TTCCACTATTACCAGGAGTTGCCCAAGTATCTCCGAGGCTACCACAAGTGCACGCGGGAGG

AGGTGCTGCAGCTGGGGGCGCTGATCTACAGGGTCAAGTTCGAGGAGGACAAGTCCTACTT

CCCCAGCATCCCCAAGCTGCTGCGGGAGCTGGTGCCCCAGGACCTTATCCGGCAGGTCTCA

CCTGATGACTGGAAGCGGTCCATCGTCGCCTACTTCAACAAGCACGCAGGGAAGTCCAAGG

AGGAGGCCAAGCTGGCCTTCCTGAAGCTCATCTTCAAGTGGCCCACCTTTGGCTCAGCCTTC

TTCGAGGTGAAGCAAACTACGGAGCCAAACTTCCCTGAGATCCTCCTAATTGCCATCAACA

AGTATGGGGTCAGCCTCATCGATCCCAAAACGAAGGATATCCTCACCACTCATCCCTTCACC

AAGATCTCCAACTGGAGCAGCGGCAACACCTACTTCCACATCACCATTGGGAACTTGGTGC

GCGGGAGCAAACTGCTCTGCGAGACGTCACTGGGCTACAAGATGGATGACCTCCTGACTTC

CTACATTAGCCAGATGCTCACAGCCATGAGCAAACAGCGGGGCTCCAGGAGCGGCAAGTA

CCCTTACGATGTACCGGATTACGCATGAGGTACCAAGGGCGAATTCTGCAGTCGACTAGAG

CTCGCTGATCAGCCTCGACTGTGCCTTCTAGTTGCCAGCCATCTGTTGTTTGCCCCTCCCCG

TGCCTTCCTTGACCCTGGAAGGTGCCACTCCCACTGTCCTTTCCTAATAAAATGAGGAAATT

GCATCGCATTGTCTGAGTAGGTGTCATTCTATTCTGGGGGGTGGGTGGGCAGGACAGCA

AGGGGGAGGATTGGGAAGACAATAGCAGGCATGCTGGGGAGAGATCTGAGGATCCTTAAT

TAAGCATGCTGGGGAGAGATCTGAACCCCTAGTGATGGAGTTGGCCACTCCCTCTCTGCGC
```

-continued

GCTCGCTCGCTCACTGAGGCCGGGCGACCAAAGGTCGCCCGACGCCCGGGCTTTGCCCGGG

CGGCCTCAGTGAGCGAGCGAGCGCGCAGAGAGGGAG

SEQ ID NO: 77 (C-term myosin7A (e.g., AAV-hMYO7A-CTlong-v2.HA))
GGGCTGATGCGTCTGGGCTTCCTGCGGCTGCAGGCCCTGCACCGCTCCCGGAAGCTGCACC

AGCAGTACCGCCTGGCCCGCCAGCGCATCATCCAGTTCCAGGCCCGCTGCCGCGCCTATCT

GGTGCGCAAGGCCTTCCGCCACCGCCTCTGGGCTGTGCTCACCGTGCAGGCCTATGCCCGG

GGCATGATCGCCCGCAGGCTGCACCAACGCCTCAGGGCTGAGTATCTGTGGCGCCTCGAGG

CTGAGAAAATGCGGCTGGCGGAGGAAGAGAAGCTTCGGAAGGAGATGAGCGCCAAGAAG

GCCAAGGAGGAGGCCGAGCGCAAGCATCAGGAGCGCCTGGCCCAGCTGGCTCGTGAGGAC

GCTGAGCGGGAGCTGAAGGAGAAGGAGGCCGCTCGGCGGAAGAAGGAGCTCCTGGAGCAG

ATGGAAAGGGCCCGCCATGAGCCTGTCAATCACTCAGACATGGTGGACAAGATGTTTGGCT

TCCTGGGGACTTCAGGTGGCCTGCCAGGCCAGGAGGGCCAGGCACCTAGTGGCTTTGAGGA

CCTGGAGCGAGGGCGGAGGGAGATGGTGGAGGAGGACCTGGATGCAGCCCTGCCCCTGCC

TGACGAGGATGAGGAGGACCTCTCTGAGTATAAATTTGCCAAGTTCGCGGCCACCTACTTC

CAGGGGACAACCACGCACTCCTACACCCGGCGGCCACTCAAACAGCCACTGCTCTACCATG

ACGACGAGGGTGACCAGCTGGCAGCCCTGGCGGTCTGGATCACCATCCTCCGCTTCATGGG

GGACCTCCCTGAGCCCAAGTACCACACAGCCATGAGTGATGGCAGTGAGAAGATCCCTGTG

ATGACCAAGATTTATGAGACCCTGGGCAAGAAGACGTACAAGAGGGAGCTGCAGGCCCTG

CAGGGCGAGGGCGAGGCCCAGCTCCCCGAGGGCCAGAAGAAGAGCAGTGTGAGGCACAAG

CTGGTGCATTTGACTCTGAAAAAGAAGTCCAAGCTCACAGAGGAGGTGACCAAGAGGCTGC

ATGACGGGGAGTCCACAGTGCAGGGCAACAGCATGCTGGAGGACCGGCCCACCTCCAACC

TGGAGAAGCTGCACTTCATCATCGGCAATGGCATCCTGCGGCCAGCACTCCGGGACGAGAT

CTACTGCCAGATCAGCAAGCAGCTGACCCACAACCCCTCCAAGAGCAGCTATGCCCGGGGC

TGGATTCTCGTGTCTCTCTGCGTGGGCTGTTTCGCCCCCTCCGAGAAGTTTGTCAAGTACCT

GCGGAACTTCATCCACGGGGCCCGCCCGGCTACGCCCCGTACTGTGAGGAGCGCCTGAGA

AGGACCTTTGTCAATGGGACACGGACACAGCCGCCCAGCTGGCTGGAGCTGCAGGCCACCA

AGTCCAAGAAGCCAATCATGTTGCCCGTGACATTCATGGATGGGACCACCAAGACCCTGCT

GACGGACTCGGCAACCACGGCCAAGGAGCTCTGCAACGCGCTGGCCGACAAGATCTCTCTC

AAGGACCGGTTCGGGTTCTCCCTCTACATTGCCCTGTTTGACAAGGTGTCCTCCCTGGGCAG

CGGCAGTGACCACGTCATGGACGCCATCTCCCAGTGCGAGCAGTACGCCAAGGAGCAGGG

CGCCCAGGAGCGCAACGCCCCTGGAGGCTCTTCTTCCGCAAAGAGGTCTTCACGCCCTGG

CACAGCCCCTCCGAGGACAACGTGGCCACCAACCTCATCTACCAGCAGGTGGTGCGAGGAG

TCAAGTTTGGGGAGTACAGGTGTGAGAAGGAGGACGACCTGGCTGAGCTGGCCTCCCAGCA

GTACTTTGTAGACTATGGCTCTGAGATGATCCTGGAGCGCCTCCTGAACCTCGTGCCCACCT

ACATCCCCGACCGCGAGATCACGCCCCTGAAGACGCTGGAGAAGTGGGCCCAGCTGGCCAT

CGCCGCCCACAAGAAGGGGATTTATGCCCAGAGGAGAACTGATGCCCAGAAGGTCAAAGA

GGATGTGGTCAGTTATGCCCGCTTCAAGTGGCCCTTGCTCTTCTCCAGGTTTTATGAAGCCT

ACAAATTCTCAGGCCCCAGTCTCCCCAAGAACGACGTCATCGTGGCCGTCAACTGGACGGG

TGTGTACTTTGTGGATGAGCAGGAGCAGGTACTTCTGGAGCTGTCCTTCCCAGAGATCATGG

CCGTGTCCAGCAGCAGGGGAGCGAAAACGACGGCCCCCAGCTTCACGCTGGCCACCATCAA

GGGGGACGAATACACCTTCACCTCCAGCAATGCTGAGGACATTCGTGACCTGGTGGTCACC

TTCCTAGAGGGGCTCCGGAAGAGATCTAAGTATGTTGTGGCCCTGCAGGATAACCCCAACC

-continued

CCGCAGGCGAGGAGTCAGGCTTCCTCAGCTTTGCCAAGGGAGACCTCATCATCCTGGACCA

TGACACGGGCGAGCAGGTCATGAACTCGGGCTGGGCCAACGGCATCAATGAGAGGACCAA

GCAGCGTGGGGACTTCCCCACCGACAGTGTGTACGTCATGCCCACTGTCACCATGCCACCG

CGGGAGATTGTGGCCCTGGTCACCATGACTCCCGATCAGAGGCAGGACGTTGTCCGGCTCT

TGCAGCTGCGAACGGCGGAGCCCGAGGTGCGTGCCAAGCCCTACACGCTGGAGGAGTTTTC

CTATGACTACTTCAGGCCCCCACCCAAGCACACGCTGAGCCGTGTCATGGTGTCCAAGGCC

CGAGGCAAGGACCGGCTGTGGAGCCACACGCGGGAACCGCTCAAGCAGGCGCTGCTCAAG

AAGCTCCTGGGCAGTGAGGAGCTCTCGCAGGAGGCCTGCCTGGCCTTCATTGCTGTGCTCA

AGTACATGGGCGACTACCCGTCCAAGAGGACACGCTCCGTCAACGAGCTCACCGACCAGAT

CTTTGAGGGTCCCCTGAAAGCCGAGCCCCTGAAGGACGAGGCATATGTGCAGATCCTGAAG

CAGCTGACCGACAACCACATCAGGTACAGCGAGGAGCGGGGTTGGGAGCTGCTCTGGCTGT

GCACGGGCCTTTTCCCACCCAGCAACATCCTCCTGCCCCACGTGCAGCGCTTCCTGCAGTCC

CGAAAGCACTGCCCACTCGCCATCGACTGCCTGCAACGGCTCCAGAAAGCCCTGAGAAACG

GGTCCCGGAAGTACCCTCCGCACCTGGTGGAGGTGGAGGCCATCCAGCACAAGACCACCCA

GATTTTCCACAAAGTCTACTTCCCTGATGACACTGACGAGGCCTTCGAAGTGGAGTCCAGC

ACCAAGGCCAAGGACTTCTGCCAGAACATCGCCACCAGGCTGCTCCTCAAGTCCTCAGAGG

GATTCAGCCTCTTTGTCAAAATTGCAGACAAGGTCATCAGCGTTCCTGAGAATGACTTCTTC

TTTGACTTTGTTCGACACTTGACAGACTGGATAAAGAAAGCTCGGCCCATCAAGGACGGAA

TTGTGCCCTCACTCACCTACCAGGTGTTCTTCATGAAGAAGCTGTGGACCACCACGGTGCCA

GGGAAGGATCCCATGGCCGATTCCATCTTCCACTATTACCAGGAGTTGCCCAAGTATCTCCG

AGGCTACCACAAGTGCACGCGGGAGGAGGTGCTGCAGCTGGGGGCGCTGATCTACAGGGT

CAAGTTCGAGGAGGACAAGTCCTACTTCCCCAGCATCCCCAAGCTGCTGCGGGAGCTGGTG

CCCCAGGACCTTATCCGGCAGGTCTCACCTGATGACTGGAAGCGGTCCATCGTCGCCTACTT

CAACAAGCACGCAGGGAAGTCCAAGGAGGAGGCCAAGCTGGCCTTCCTGAAGCTCATCTTC

AAGTGGCCCACCTTTGGCTCAGCCTTCTTCGAGGTGAAGCAAACTACGGAGCCAAACTTCC

CTGAGATCCTCCTAATTGCCATCAACAAGTATGGGGTCAGCCTCATCGATCCCAAAACGAA

GGATATCCTCACCACTCATCCCTTCACCAAGATCTCCAACTGGAGCAGCGGCAACACCTACT

TCCACATCACCATTGGGAACTTGGTGCGCGGGAGCAAACTGCTCTGCGAGACGTCACTGGG

CTACAAGATGGATGACCTCCTGACTTCCTACATTAGCCAGATGCTCACAGCCATGAGCAAA

CAGCGGGGCTCCAGGAGCGGCAAG

SEQ ID NO: 78 (N-term myosin7A (e.g., AAV-hMYO7A-CTlong.HA)
GLMRLGFLRLQALHRSRKLHQQYRLARQRIIQFQARCRAYLVRKAFRHRLWAVLTVQAYARG

MIARRLHQRLRAEYLWRLEAEKMRLAEEEKLRKEMSAKKAKEEAERKHQERLAQLAREDAER

ELKEKEAARRKKELLEQMERARHEPVNHSDMVDKMFGFLGTSGGLPGQEGQAPSGFEDLERG

RREMVEEDLDAALPLPDEDEEDLSEYKFAKFAATYFQGTTTHSYTRRPLKQPLLYHDDEGDQL

AALAVWITILRFMGDLPEPKYHTAMSDGSEKIPVMTKIYETLGKKTYKRELQALQGEGEAQLPE

GQKKSSVRHKLVHLTLKKKSKLTEEVTKRLHDGESTVQGNSMLEDRPTSNLEKLHFIIGNGILRP

ALRDEIYCQISKQLTHNPSKSSYARGWILVSLCVGCFAPSEKFVKYLRNFIHGGPPGYAPYCEER

LRRTFVNGTRTQPPSWLELQATKSKKPIMLPVTFMDGTTKTLLTDSATTAKELCNALADKISLK

DRFGFSLYIALFDKVSSLGSGSDHVMDAISQCEQYAKEQGAQERNAPWRLFFRKEVFTPWHSPS

EDNVATNLIYQQVVRGVKFGEYRCEKEDDLAELASQQYFVDYGSEMILERLLNLVPTYIPDREI

-continued

```
TPLKTLEKWAQLAIAAHKKGIYAQRRTDAQKVKEDVVSYARFKWPLLFSRFYEAYKFSGPSLP

KNDVIVAVNWTGVYFVDEQEQVLLELSFPEIMAVSSSRGAKTTAPSFTLATIKGDEYTFTSSNAE

DIRDLVVTFLEGLRKRSKYVVALQDNPNPAGEESGFLSFAKGDLIILDHDTGEQVMNSGWANGI

NERTKQRGDFPTDSVYVMPTVTMPPREIVALVTMTPDQRQDVVRLLQLRTAEPEVRAKPYTLE

EFSYDYFRPPPKHTLSRVMVSKARGKDRLWSHTREPLKQALLKKLLGSEELSQEACLAFIAVLK

YMGDYPSKRTRSVNELTDQIFEGPLKAEPLKDEAYVQILKQLTDNHIRYSEERGWELLWLCTGL

FPPSNILLPHVQRFLQSRKHCPLAIDCLQRLQKALRNGSRKYPPHLVEVEAIQHKTTQIFHKVYFP

DDTDEAFEVESSTKAKDFCQNIATRLLLKSSEGFSLFVKIADKVISVPENDFFFDFVRHLTDWIKK

ARPIKDGIVPSLTYQVFFMKKLWTTTVPGKDPMADSIFHYYQELPKYLRGYHKCTREEVLQLG

ALIYRVKFEEDKSYFPSIPKLLRELVPQDLIRQVSPDDWKRSIVAYFNKHAGKSKEEAKLAFLKLI

FKWPTFGSAFFEVKQTTEPNFPEILLIAINKYGVSLIDPKTKDILTTHPFTKISNWSSGNTYFHITIG

NLVRGSKLLCETSLGYKMDDLLTSYISQMLTAMSKQRGSRSGK
```

In some embodiments, the vectors provided herein comprise a truncated chimeric CBA promoter. The vectors provided herein may comprise a promoter having a nucleotide sequence that differs from the smCBA promoter set forth as SEQ ID NO: 64 by 1, 2, or 3 nucleotides. In some embodiments, the vectors provided herein comprise a promoter that is not an smCBA promoter. In some embodiments, the vectors provided herein comprise a promoter selected from selected from the group consisting of a CMV promoter, an EF-1 alpha promoter, a cone arrestin promoter, a human myosin 7a gene-derived promoter, a TαC gene-derived promoter, a rhodopsin promoter, a cGMP-phosphodiesterase β-subunit promoter, human or mouse rhodopsin promoter, a hGRK1 promoter, a synapsin promoter, a glial fibrillary acidic protein (GFAP) promoter, a rod specific IRBP promoter, a VMD2 promoter, and combinations thereof. In some embodiments, the promoter is a rhodopsin promoter. In some embodiments, the promoter is a CMV promoter. In some embodiments, the promoter is not a CMV promoter.

In some embodiments, the promoter is a tissue-specific promoter. In some embodiments, the promoter mediates expression in ocular tissue. In some embodiments, the promoter does not mediate expression in ocular tissue. In some embodiments, the promoter mediates expression in hair cells of the auditory system and/or the vestibular system.

```
SEQ ID NO: 64 smCBA promoter
AATTCGGTACCCTAGTTATTAATAGTAATCAATTACGGGGTCATTAGTTCATAGCCCATATA
TGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATT
GACGTCAATGGGTGGACTATTTACGGTAAACTGCCCACTTGGCAGTACATCAAGTGTATCA
TATGCCAAGTACGCCCCCTATTGACGTCAATGACGGTAAATGGCCCGCCTGGCATTATGCCC
AGTACATGACCTTATGGGACTTTCCTACTTGGCAGTACATCTACGTATTAGTCATCGCTATT
ACCATGGTCGAGGTGAGCCCCACGTTCTGCTTCACTCTCCCCATCTCCCCCCCCTCCCCACC
CCCAATTTTGTATTTATTTATTTTTTAATTATTTTGTGCAGCGATGGGGCGGGGGGGGGG
GGGGGCGCGCGCCAGGCGGGGCGGGGCGGGGCGAGGGGCGGGGCGGGGCGAGGCGGAGA
GGTGCGGCGGCAGCCAATCAGAGCGGCGCGCTCCGAAAGTTTCCTTTTATGGCGAGGCGGC
GGCGGCGGCGGCCCTATAAAAAGCGAAGCGCGCGGCGGGCGGGAGTCGCTGCGCGCTGCC
TTCGCCCCGTGCCCCGCTCCGCCGCCGCCTCGCGCCGCCCGCCCCGGCTCTGACTGACCGCG
TTACTCCCACAGGTGAGCGGGCGGGACGGCCCTTCTCCTCCGGGCTGTAATTAGCGCTTGGT
TTAATGACGGCTTGTTTCTTTTCTGTGGCTGCGTGAAAGCCTTGAGGGGCTCCGGGAGCTAG
AGCCTCTGCTAACCATGTTCATGCCTTCTTCTTTTTCCTACAGCTCCTGGGCAACGTGCTGGT
TATTGTGCTGTCTCATCATTTTGGCAAAG SEQ ID NO: 39 is the nucleotide sequence of second generation overlapping portion of the
overlap vector system:
CAGGTCTAACTTTCTGAAGCTGAAGAACGCTGCCACACTGATCCAGAGGCACTGGC
GGGGTCACAACTGTAGGAAGAACTACGGGCTGATGCGTCTGGGCTTCCTGCGGCTG
CAGGCCCTGCACCGCTCCCGGAAGCTGCACCAGCAGTACCGCCTGGCCCGCCAGCG
CATCATCCAGTTCCAGGCCCGCTGCCGCGCCTATCTGGTGCGCAAGGCCTTCCGCCA
CCGCCTCTGGGCTGTGCTCACCGTGCAGGCCTATGCCCGGGGCATGATCGCCCGCA
GGCTGCACCAACGCCTCAGGGCTGAGTATCTGTGGCGCCTCGAGGCTGAGAAAATG
CGGCTGGCGGAGGAAGAGAAGCTT SEQ ID NO: 79 (associated protein sequence from SEQ ID NO: 39)
RSNFLKLKNAATLIQRHWRGHNCRKNYGLMRLGFLRLQALHRSRKLHQQYRLARQRII
QFQARCRAYLVRKAFRHRLWAVLTVQAYARGMIARRLHQRLRAEYLWRLEAEKMRL
AEEEKL
```

SEQ ID NO: 40 is the relevant fragment of SEQ ID NO: 31 where potential in-frame stop codons are located in the second generation hybrid front half AP splice donor region (see, e.g. FIG. 42).
CAACGCCTCAGGGCTGAGGTAAGTATCAAGGTTACAAGACAGGTTTAAGGAGACCA
ATAGAAACTGGGCTTGTCGAGACAGAGAAGACTCTTGCGTTTCTGAGCTAGCCCC SEQ ID NO: 41 is the relevant fragment of SEQ ID NO: 33 where potential in-frame stop codons are removed in the CMv1 hybrid front half AP splice donor region (see, e.g., FIG. 42).
CAACGCCTCAGGGCTGAGGTAAGTATCAAGGTTACAAGACAGGTTAACGGAGACCA
ATTGAAACTGGGCTTGTCGAGACAGAGAAGACTCTTGCGTTTCAGCGCTAGCCCC SEQ ID NO: 42 is the forward primer sequence of Gibson Primer Set 1 (reverse primer sequence is the reverse compliment of the forward primer (not shown))(see, e.g., FIG. 42).
CCGCAGGCTGCACCAACGCCTCAGGGCTGAGGTAAGTATCAAGGTTACAAGACAG
GTTAACGGAGACCAATTGAAACT SEQ ID NO: 43 is the forward primer sequence of Gibson Primer Set 2 (reverse primer sequence is the reverse compliment of the forward primer (not shown))(see, e.g., FIG. 42).
AACGGAGACCAATTGAAACTGGGCTTGTCGAGACAGAGAAGACTCTTGCGTTTCAG
CGCTAGCCCCCGGGTGCGCGGCG SEQ ID NO: 44 is the polynucleotide sequence of the CMv2.1 hybrid back half vector (i.e., AAV-APhead-APSA-hMYO7ACTex22-CMv2.1).
CTCCCTCTCTGCGCGCTCGCTCGCTCACTGAGGCCGCCCGGGCAAAGCCCGGGCGTCGGGC
GACCTTTGGTCGCCCGGCCTCAGTGAGCGAGCGAGCGCGCAGAGAGGGAGTGGCCAACTCC
ATCACTAGGGGTTCTCAGATCTGGCGCGCCCCCCGGGTGCGCGGCGTCGGTGGTGCCGGCG
GGGGGCGCCAGGTCGCAGGCGGTGTAGGGCTCCAGGCAGGCGGCGAAGGCCATGACGTGC
GCTATGAAGGTCTGCTCCTGCACGCCGTGAACCAGGTGCGCCTGCGGGCCGCGCGCGAACA
CCGCCACGTCCTCGCCTGCGTGGGTCTCTTCGTCCAGGGGCACTGCGCACTGCTGCCGATAC
TCGGGGCTCCCGCTCTCGCTCTCGGTAACATCCGGCCGGGCGCCGTCCTTGAGCACATAGCC
TGGACCGTTTCTCTTAAGCGACGCATGCTCGCGATAGGCACCTATTGGTCTTACTGACATCC
ACTTTGCCTTTCTCTCCACAGTATCTGTGGCGCCTCGAGGCTGAGAAAATGCGGCTGGCGGA
GGAAGAGAAGCTTCGGAAGGAGATGAGCGCCAAGAAGGCCAAGGAGGAGGCCGAGCGCA
AGCATCAGGAGCGCCTGGCCCAGCTGGCTCGTGAGGACGCTGAGCGGGAGCTGAAGGAGA
AGGAGGCCGCTCGGCGGAAGAAGGAGCTCCTGGAGCAGATGGAAAGGGCCCGCCATGAGC
CTGTCAATCACTCAGACATGGTGGACAAGATGTTTGGCTTCCTGGGGACTTCAGGTGGCCTG
CCAGGCCAGGAGGGCCAGGCACCTAGTGGCTTTGAGGACCTGGAGCGAGGGCGGAGGGAG
ATGGTGGAGGAGGACCTGGATGCAGCCCTGCCCCTGCCTGACGAGGATGAGGAGGACCTCT
CTGAGTATAAATTTGCCAAGTTCGCGGCCACCTACTTCCAGGGGACAACCACGCACTCCTA
CACCCGGCGGCCACTCAAACAGCCACTGCTCTACCATGACGACGAGGGTGACCAGCTGGCA
GCCCTGGCGGTCTGGATCACCATCCTCCGCTTCATGGGGGACCTCCCTGAGCCCAAGTACCA
CACAGCCATGAGTGATGGCAGTGAGAAGATCCCTGTGATGACCAAGATTTATGAGACCCTG
GGCAAGAAGACGTACAAGAGGGAGCTGCAGGCCCTGCAGGGCGAGGGCGAGGCCCAGCTC
CCCGAGGGCCAGAAGAAGAGCAGTGTGAGGCACAAGCTGGTGCATTTGACTCTGAAAAAG
AAGTCCAAGCTCACAGAGGAGGTGACCAAGAGGCTGCATGACGGGGAGTCCACAGTGCAG
GGCAACAGCATGCTGGAGGACCGGCCCACCTCCAACCTGGAGAAGCTGCACTTCATCATCG
GCAATGGCATCCTGCGGCCAGCACTCCGGGACGAGATCTACTGCCAGATCAGCAAGCAGCT
GACCCACAACCCCTCCAAGAGCAGCTATGCCCGGGGCTGGATTCTCGTGTCTCTGCGTGG
GCTGTTTCGCCCCCTCCGAGAAGTTTGTCAAGTACCTGCGGAACTTCATCCACGGGGGCCCG
CCCGGCTACGCCCCGTACTGTGAGGAGCGCCTGAGAAGGACCTTTGTCAATGGGACAGGA
CACAGCCGCCCAGCTGGCTGGAGCTGCAGGCCACCAAGTCCAAGAAGCCAATCATGTTGCC
CGTGACATTCATGGATGGGACCACCAAGACCCTGCTGACGGACTCGGCAACCACGGCCAAG
GAGCTCTGCAACGCGCTGGCCGACAAGATCTCTCTCAAGGACCGGTTCGGGTTCTCCCTCTA
CATTGCCCTGTTTGACAAGGTGTCCTCCTGGGCAGCGGCAGTGACCACGTCATGAGCGCC
ATCTCCCAGTGCGAGCAGTACGCCAAGGAGCAGGGCGCCCAGGAGCGCAACGCCCCTGG
AGGCTCTTCTTCCGCAAAGAGGTCTTCACGCCCTGGCACAGCCCTCCGAGGACAACGTGG
CCACCAACCTCATCTACCAGCAGGTGGTGCGAGGAGTCAAGTTTGGGGAGTACAGGTGTGA
GAAGGAGGACGACCTGGCTGAGCTGGCCTCCCAGCAGTACTTTGTAGACTATGGCTCTGAG
ATGATCCTGGAGCGCCTCCTGAACCTCGTGCCCACCTACATCCCGACCGCGAGATCACGC
CCCTGAAGACGCTGGAGAAGTGGGCCCAGCTGGCCATCGCCGCCCACAAGAAGGGGATTT
ATGCCCAGAGGAGAACTGATGCCCAGAAGGTCAAAGAGGATGTGGTCAGTTATGCCCGCTT
CAAGTGGCCCTTGCTCTTCTCCAGGTTTTATGAAGCCTACAAATTCTCAGGCCCCAGTCTCC
CCAAGAACGACGTCATCGTGGCCGTCAACTGGACGGGTGTGTACTTTGTGGATGAGCAGGA
GCAGGTACTTCTGGAGCTGTCCTTCCCAGAGATCATGGCCGTGTCCAGCAGCAGGGGAGCG
AAAACGACGGCCCCAGCTTCACGCTGGCCACCATCAAGGGGACGAATACACCTTCACCT
CCAGCAATGCTGAGGACATTCGTGACCTGGTGGTCACCTTCCTAGAGGGGCTCCGGAAGAG
ATCTAAGTATGTTGTGGCCCTGCAGGATAACCCCAACCCCGCAGGCGAGGAGTCAGGCTTC
CTCAGCTTTGCCAAGGGAGACCTCATCATCCTGGACCATGACACGGGCGAGCAGGTCATGA
ACTCGGGCTGGGCCAACGGCATCAATGAGAGGACCAAGCAGCGTGGGGACTTCCCCACCG
ACAGTGTGTACGTCATGCCCACTGTCACCATGCCACCGCGGGAGATTGTGGCCCTGGTCAC
CATGACTCCCGATCAGAGGCAGGACGTTGTCCGGCTCTTGCAGCTGCGAACGGCGGAGCCC
GAGGTGCGTGCCAAGCCCTACACGCTGGAGGAGTTTTCCTATGACTACTTCAGGCCCCCAC
CCAAGCACACGCTGAGCCGTGTCATGGTGTCCAAGGCCCGAGGCAAGGACCGGCTGTGGA
GCCACACGCGGGAACCGCTCAAGCAGGCGCTGCTCAAGAAGCTCCTGGGCAGTGAGGAGC
TCTCGCAGGAGGCCTGCCTGGCCTTCATTGCTGTGCTTCAGTACATGGGCGACTACCCGTCC
AAGAGGACACGCTCCGTCAACGAGCTCACCGACCAGATCTTTGAGGGTCCCCCTGAAAGCCG
AGCCCCTGAAGGACGAGGCATATGTGCAGATCCTGAAGCAGCTGACCGACAACCACATCA
GGTACAGCGAGGAGCGGGGTTGGGAGCTGCTCTGGCTGTGCACGGGCCTTTTCCCACCCAG
CAACATCCTCCTGCCCCACGTGCAGCGCTTCCTGCAGTCCCGAAAGCACTGCCCACTCGCCA
TCGACTGCCTGCAACGGCTCCAGAAAGCCCTGAGAAACGGGTCCCGGAAGTACCCTCCGCA -continued
CCTGGTGGAGGTGGAGGCCATCCAGCACAAGACCACCCAGATTTTCCACAAAGTCTACTTC
CCTGATGACACTGACGAGGCCTTCGAAGTGGAGTCCAGCACCAAGGCCAAGGACTTCTGCC
AGAACATCGCCACCAGGCTGCTCCTCAAGTCCTCAGAGGGATTCAGCCTCTTTGTCAAAATT
GCAGACAAGGTCATCAGCGTTCCTGAGAATGACTTCTTCTTTGACTTTGTTCGACACTTGAC
AGACTGGATAAAGAAAGCTCGGCCCATCAAGGACGGAATTGTGCCCTCACTCACCTACCAG
GTGTTCTTCATGAAGAAGCTGTGGACCACCACGGTGCCAGGGAAGGATCCCATGGCCGATT
CCATCTTCCACTATTACCAGGAGTTGCCCAAGTATCTCCGAGGCTACCACAAGTGCACGCG
GGAGGAGGTGCTGCAGCTGGGGGCGCTGATCTACAGGGTCAAGTTCGAGGAGGACAAGTC
CTACTTCCCCAGCATCCCCAAGCTGCTGCGGGAGCTGGTGCCCCAGGACCTTATCCGGCAG
GTCTCACCTGATGACTGGAAGCGGTCCATCGTCGCCTACTTCAACAAGCACGCAGGGAAGT
CCAAGGAGGAGGCCAAGCTGGCCTTCCTGAAGCTCATCTTCAAGTGGCCCACCTTTGGCTC
AGCCTTCTTCGAGGTGAAGCAAACTACGGAGCCAAACTTCCCTGAGATCCTCCTAATTGCC
ATCAACAAGTATGGGGTCAGCCTCATCGATCCCAAAACGAAGGATATCCTCACCACTCATC
CCTTCACCAAGATCTCCAACTGGAGCAGCGGCAACACCTACTTCCACATCACCATTGGGAA
CTTGGTGCGCGGGAGCAAACTGCTCTGCGAGACGTCACTGGGCTACAAGATGGATGACCTC
CTGACTTCCTACATTAGCCAGATGCTCACAGCCATGAGCAAACAGCGGGGCTCCAGGAGCG
GCAAGAGAGCTCGCTGATCAGCCTCGACTGTGCCTTCTAGTTGCCAGCCATCTGTTGTTTGC
CCCTCCCCCGTGCCTTCCTTGACCCTGGAAGGTGCCACTCCCACTGTCCTTTCCTAATAAAA
TGAGGAAATTGCATCGCATTGTCTGAGTAGGTGTCATTCTATTCTGGGGGGTGGGGTGGGG
CAGGACAGCAAGGGGGAGGATTGGGAAGACAATAGCAGGCATTTAATTAAGCATGCTGGG
GAGAGATCTGAGGAAACCCCTAGTGATGGAGTTGGCCACTCCCTCTCTGCGCGCTCGCTCG
CTCACTGAGGCCGGGCGACCAAAGGTCGCCCGACGCCCGGGCTTTGCCCGGGCGGCCTCAG
TGAGCGAGCGAGCGCGCAGAGAGGGAG SEQ ID NO: 45 is the portion of overlapping sequence from the original overlap vectors.
CAGGTCTAACTTTCTGAAGCTGAAGAACGCTGCCACACTGATCTCAGAGGCACTGGCGGGT
CACAACTGTAGGAAGAACTACGGGCTGATGCGTCTGGGCTTCCTGCGGCTGCAGGCCCTGC
ACCGCTCCCGGAAGCTGCACCAGCAGTACCGCCTGGCCCGCCAGCGCATCATCCAGTTCCA
GGCCCGCTGCCGCGCCTATCTGGTGCGCAAGGCCTTCCGCCACCGCCTCTGGGCTGTGCTCA
CCGTGCAGGCCTATGCCCGGGGCATGATCGCCCGCAGGCTGCACCAACGCCTCAGGGCTGA
GTATCTGTGGCGCCTCGAGGCTGAGAAAATGCGGCTGGCGGAGGAAGAGAAGCTTCGGAA
GGAGATGAGCGCCAAGAAGGCCAAGGAGGAGGCCGAGCGCAAGCATCAGGAGCGCCTGG
CCCAGCTGGCTCGTGAGGACGCTGAGCGGGAGCTGAAGGAGAAGGAGGCCGCTCGGCGGA
AGAAGGAGCTCCTGGAGCAGATGGAAAAGGGCCCGCCATGAGCCTGTCAATCACTCAGACA
TGGTGGACAAGATGTTTGGCTTCCTGGGGACTTCAGGTGGCCTGCCAGGCCAGGAGGGCCA
GGCACCTAGTGGCTTTGAGGACCTGGAGCGAGGGCGGAGGGAGATGGTGGAGGAGGACCT
GGATGCAGCCCTGCCCCTGCCTGACGAGGATGAGGAGGACCTCTCTGAGTATAAATTTGCC
AAGTTCGCGGCCACCTACTTCCAGGGGACAACCACGCACTCCTACACCCGGCGGCCACTCA
AACAGCCACTGCTCTACCATGACGACGAGGGTGACCAGCTGGCAGCCCTGGCGGTCTGGAT
CACCATCCTCCGCTTCATGGGGGACCTCCCTGAGCCCAAGTACCACACAGCCATGAGTGAT
GGCAGTGAGAAGATCCCTGTGATGACCAAGATTTATGAGACCCTGGGCAAGAAGACGTAC
AAGAGGGAGCTGCAGGCCCTGCAGGGCGAGGGCGAGGCCCAGCTCCCGAGGGCCAGAAG
AAGAGCAGTGTGAGGCACAAGCTGGTGCATTTGACTCTGAAAAAGAAGTCCAAGCTCACA
GAGGAGGTGACCAAGAGGCTGCATGACGGGGAGTCCACAGTGCAGGGCAACAGCATGCTG
GAGGACCGGCCCACCTCCAACCTGGAGAAGCTGCACTTCATCATCGGCAATGGCATCCTGC
GGCCAGCACTCCGGGACGAGATCTACTGCCAGATCAGCAAGCAGCTGACCCACAACCCCTC
CAAGAGCAGCTATGCCCGGGGCTGGATTCTCGTGTCTCTCTGCGTGGGCTGTTTCGCCCCCT
CCGAGAAGTTTGTCAAGTACCTGCGGAACTTC SEQ ID NO: 46 is the polynucleotide sequence of the CMv3 hybrid front half vector (i.e.,
AAV-smCBA-hMYO7A-NT-Ex21-APSD-APhead-CMv3)(pairs with CMv2 back half
vector).
CTCCCTCTCTGCGCGCTCGCTCGCTCACTGAGGCCGCCCGGGCAAAGCCCGGGCGTCGGGC
GACCTTTGGTCGCCCGGCCTCAGTGAGCGAGCGAGCGCGCAGAGAGGGAGTGGCCAACTCC
ATCACTAGGGGTTCTCAGATCTGGCGCGCCCAATTCGGTACCCTAGTTATTAATAGTAATCA
ATTACGGGGTCATTAGTTCATAGCCCATATATGGAGTTCCGCGTTACATAACTTACGGTAAA
TGGCCCGCCTGGCTGACCGCCCAACGACCCCCGCCCATTGACGTCAATAATGACGTATGTTC
CCATAGTAACGCCAATAGGGACTTTCCATTGACGTCAATGGGTGGACTATTTACGGTAAAC
TGCCCACTTGGCAGTACATCAAGTGTATCATATGCCAAGTACGCCCCCTATTGACGTCAATG
ACGGTAAATGGCCCGCCTGGCATTATGCCCAGTACATGACCTTATGGGACTTTCCTACTTGG
CAGTACATCTACGTATTAGTCATCGCTATTACCATGGTCGAGGTGAGCCCCACGTTCTGCTT
CACTCTCCCCATCTCCCCCCCCTCCCCACCCCCAATTTTGTATTTATTTATTTTTTAATTATTT
TGTGCAGCGATGGGGGCGGGGGGGGGGGGGGGCGCGCGCCAGGCGGGGCGGGCGGGG
CGAGGGGCGGGCGGGGCGAGGCGGAGAGGTGCGGCGGCAGCCAATCAGAGCGGCGCGC
TCCGAAAGTTTCCTTTTATGGCGAGGCGGCGGCGGCGGCGGCCCTATAAAAAGCGAAGCGC
GCGGCGGGCGGGAGTCGCTGCGCGCTGCCTTCGCCCCGTGCCCCGCTCCGCCGCCGCCTCG
CGCCGCCCGCCCCGGCTCTGACTGACCGCGTTACTCCCACAGGTGAGCGGGCGGGACGGCC
CTTCTCCTCCGGGCTGTAATTAGCGCTTGGTTTAATGACGGCTTGTTTCTTTTCTGTGGCTGC
GTGAAAGCCTTGAGGGGCTCCGGGAGCTAGAGCCTCTGCTAACCATGTTCATGCCTTCTTCT
TTTTCCTACAGCTCCTGGGCAACGTGCTGGTTATTGTGCTGTCTCATCATTTTGGCAAAGAA
TTCTAGCGGCCGCCACCATGGTGATTCTTCAGCAGGGGACCATGTGTGGATGGACCTGAG
ATTGGGGCAGGAGTTCGACGTGCCCATCGGGGCGGTGGTGAAGCTCTGCGACTCTGGGCAG
GTCCAGGTGGTGGATGATGAAGACAATGAACACTGGATCTCTCCGCAGAACGCAACGCACA
TCAAGCCTATGCACCCCACGTCGGTCCACGGCGTGGAGGACATGATCCGCCTGGGGGACCT
CAACGAGGCGGGCATCTTGCGCAACCTGCTTATCCGCTACCGGGACCACCTCATCTACACG
TATACGGGCTCCATCCTGGTGGCTGTGAACCCCTACCAGCTGCTCTCCATCTACTCGCCAGA
GCACATCCGCCAGTATACCAACAAGAAGATTGGGGAGATGCCCCCCCACATCTTTGCCATT
GCTGACAACTGCTACTTCAACATGAAACGCAACAGCCGAGACCAGTGCTGCATCATCAGTG
GGGAATCTGGGGCCGGGAAGACGGAGAGCACAAAGCTGATCCTGCAGTTCCTGGCAGCCA
TCAGTGGGCAGCACTCGTGGATTGAGCAGCAGGTCTTGGAGGCCACCCCCATTCTGGAAGC
ATTTGGGAATGCCAAGACCATCCGCAATGACAACTCAAGCCGTTTCGGAAAGTACATCGAC -continued

```
ATCCACTTCAACAAGCGGGGCGCCATCGAGGGCGCGAAGATTGAGCAGTACCTGCTGGAA
AAGTCACGTGTCTGTCGCCAGGCCCTGGATGAAAGGAACTACCACGTGTTCTACTGCATGC
TGGAGGGTATGAGTGAGGATCAGAAGAAGAAGCTGGGCTTGGGCCAGGCCTCTGACTACA
ACTACTTGGCCATGGGTAACTGCATAACCTGTGAGGGCCGGGTGGACAGCCAGGAGTACGC
CAACATCCGCTCCGCCATGAAGGTGCTCATGTTCACTGACACCGAGAACTGGGAGATCTCG
AAGCTCCTGGCTGCCATCCTGCGCACCTGGGCAACCTGCAGTATGAGGCACGCACATTTGAAA
ACCTGGATGCCTGTGAGGTTCTCTTCTCCCCATCGCTGGCCACAGCTGCATCCCTGCTTGAG
GTGAACCCCCCAGACCTGATGAGCTGCCTGACTAGCCGCACCCTCATCACCCGCGGGGAGA
CGGTGTCCACCCCACTGAGCAGGGAACAGGCACTGGACGTGCGCGACGCCTTCGTAAAGGG
GATCTACGGGCGGCTGTTCGTGTGGATTGTGGACAAGATCAACGCAGCAATTTACAAGCCT
CCCTCCCAGGATGTGAAGAACTCTCGCAGGTCCATCGGCCTCCTGGACATCTTTGGGTTTGA
GAACTTTGCTGTGAACAGCTTTGAGCAGCTCTGCATCAACTTCGCCAATGAGCACCTGCAGC
AGTTCTTTGTGCGGCACGTGTTCAAGCTGGAGCAGGAGGAATATGACCTGGAGAGCATTGA
CTGGCTGCACATCGAGTTCACTGACAACCAGGATGCCCTGGACATGATTGCCAACAAGCCC
ATGAACATCATCTCCCTCATCGATGAGGAGAGCAAGTTCCCCAAGGGCACAGACACCACCA
TGTTACACAAGCTGAACTCCCAGCACAAGCTCAACGCCAACTACATCCCCCCCAAGAACAA
CCATGAGACCCAGTTTGGCATCAACCATTTTGCAGGCATCGTCTACTATGAGACCCAAGGCT
TCCTGGAGAAGAACCGAGACACCCTGCATGGGACATTATCCGACTGGTTGGTTCCACTCCTCCAG
GAACAAGTTCATCAAGCAGATCTTCCAGGCCGATGTCGCCATGGGCGCCGAGACCAGGAAG
CGCTCGCCCACACTTAGCAGCCAGTTCAAGCGGTCACTGGAGCTGCTGATGCGCACGCTGG
GTGCCTGCCAGCCCTTCTTTGTGCGATGCATCAAGCCCAATGAGTTCAAGAAGCCCATGCTG
TTCGACCGGCACCTGTGCGTGCGCCAGCTGCGGTACTCAGGAATGATGGAGACCATCCGAA
TCCGCCGAGCTGGCTACCCCATCCGCTACAGCTTCGTAGAGTTTGTGGAGCGGTACCGTGTG
CTGCTGCCAGGTGTGAAGCCGGCCTACAAGCAGGGCGACCTCCGCGGGACTTGCCAGCGCA
TGGCTGAGGCTGTGCTGGGCACCCACGATGACTGGCAGATAGGCAAAACCAAGATCTTTCT
GAAGGACCACCATGACATGCTGCTGGAAGTGGAGCGGGACAAAGCCATCACCGACAGAGT
CATCCTCCTTCAGAAAGTCATCCGGGGATTCAAAGACAGGTCTAACTTTCTGAAGCTGAAG
AACGCTGCCACACTGATCCAGAGGCACTGGCGGGGTCACAACTGTAGGAAGAACTACGGG
CTGATGCGTCTGGGCTTCCTGCGGCTGCAGGCCCTGCACCGCTCCCGGAAGCTGCACCAGC
AGTACCGCCTGGCCCGCCAGCGCATCATCCAGTTCCAGGCCCGCTGCCGCGCCTATCTGGTG
CGCAAGGCCTTCCGCCACCGCCTCTGGGCTGTGCTCACCGTGCAGGCCTATGCCCGGGGCA
TGATCGCCCGCAGGCTGCACCAACGCCTCAGGGCTGAGGTAAGTATCAAGGTTACAAGACA
GGTTAACGGAGACCAATTGAAACTGGGCTTGTCGAGACAGAGAAGACTCTTGCGTTTCAGC
GCTAGCCCCCGGGTGCGGGCGTCGGTGGTGCCGGCGGGGGGCGCCCAGGTCGCAGGCGT
GTAGGGCTCCAGGCAGGCGGCGAAGGCCATGACGTGCGCTATGAAGGTCTGCTCCTGCACG
CCGTGAACCAGGTGCGCCTGCGGGCCGCGCGCGAACACCGCCACGTCCTCGCCTGCGTGGG
TCTCTTCGTCCAGGGGCACTGCGCACTGCTGCCGATACTCGGGGCTCCCGCTCTCGCTCTCG
GTAACATCCGGCCGGGCGCCGTCCTTGAGCACATAGCCTGGACCGTTTCGTCGACGGATCC
GCATGCTGGGGAGAGATCTGAGGAAACCCCTAGTGATGGAGTTGGCCACTCCCTCTCTGCG
CGCTCGCTCGCTCACTGAGGCCGGGCGACCAAAGGTCGCCCGACGCCCGGGCTTTGCCCGG
GCGGCCTCAGTGAGCGAGCGAGCGCGCAGAGAGGGAG
```

SEQ ID NO: 47 is the polynucleotide sequence of the CMv2.1 hybrid back half vector, containing the HA tag (i.e., AAV-APhead-APSA-hMYO7ACTex22-CMv2.1.HA) (pairs with CMv2 front half vector).

```
CTCCCTCTCTGCGCGCTCGCTCGCTCACTGAGGCCGCCCGGGCAAAGCCCGGGCGTCGGGC
GACCTTTGGTCGCCCGGCCTCAGTGAGCGAGCGAGCGCGCAGAGAGGGAGTGGCCAACTCC
ATCACTAGGGGTTCTCAGATCTGGCGCGCCCCCGGGTGCGCGGCGTCGGTGGTGCCGGCG
GGGGGCGCCAGGTCGCAGGCGGTGTAGGGCTCCAGGCAGGCGGCGAAGGCCATGACGTGC
GCTATGAAGGTCTGCTCCTGCACGCCGTGAACCAGGTGCGCCTGCGGGCCGCGCGCGAACA
CCGCCACGTCCTCGCCTGCGTGGGTCTCTTCGTCCAGGGGCACTGCGCACTGCTGCCGATAC
TCGGGGCTCCCGCTCTCGCTCTCGGTAACATCCGGCCGGGCGCCGTCCTTGAGCACATAGCC
TGGACCGTTTCTCTTAAGCGACGCATGCTCGCGATAGGCACCTATTGGTCTTACTGACATCC
ACTTTGCCTTTCTCTCCACAGTATCTGTGGCGCCTCGAGGCTGAGAAAATGCGGCTGGCGGA
GGAAGAGAAGCTTCGGAAGGAGATGAGCGCCAAGAAGGCCAAGGAGGAGGCCGAGCGCA
AGCATCAGGAGCGCCTGGCCCAGCTGGCTCGTGAGGACGCTGAGCGGGAGCTGAAGGAGA
AGGAGGCCGCTCGGCGGAAGAAGGAGCTCCTGGAGCAGATGGAAAGGGCCCGCCATGAGC
CTGTCAATCACTCAGACATGGTGGACAAGATGTTTGGCTTCCTGGGGACTTCAGGTGGCCTG
CCAGGCCAGGAGGGCCAGGCACCTAGTGGCTTTGAGGACCTGGAGCGAGGGCGGAGGGAG
ATGGTGGAGGAGGACCTGGATGCAGCCCTGCCCCTGCCTGACGAGGATGAGGAGGACCTCT
CTGAGTATAAATTTGCCAAGTTCGCGGCCACCTACTTCCAGGGGACAACCACGCACTCCTA
CACCCGGCGGCCACTCAAACAGCCACTGCTCTACCATGACGACGAGGGTGACCAGCTGGCA
GCCCTGGCGGTCTGGATCACCATCCTCCGCTTCATGGGGGACCTCCCTGAGCCCAAGTACCA
CACAGCCATGAGTGATGGCAGTGAGAAGATCCCTGTGATGACCAAGATTTATGAGACCCTG
GGCAAGAAGACGTACAAGAGGGAGCTGCAGGCCCTGCAGGGCGAGGGCGAGGCCCAGCTC
CCCGAGGGCCAGAAGAAGAGCAGTGTGAGGCACAAGCTGGTGCATTTGACTCTGAAAAAG
AAGTCCAAGCTCACAGAGGAGGTGACCAAGAGGCTGCATGACGGGGAGTCCACAGTGCAG
GGCAACAGCATGCTGGAGGACCGGCCCACCTCCAACCTGGAGAAGCTGCACTTCATCATCG
GCAATGGCATCCTGCGGCCAGCACTCCGGGACGAGATCTACTGCCAGATCAGCAAGCAGCT
GACCCACAACCCCTCCAAGAGCAGCTATGCCCGGGGCTGGATTCTCGTGTCTCTGCGTGG
GCTGTTTCGCCCCCTCCGAGAAGTTTGTCAAGTACCTGCGGAACTTCATCCACGGGGCCCG
CCCGGCTACGCCCCGTACTGTGAGGAGCGCCTGAGAAGGACCCTTTGTCAATGGGACACGGA
CACAGCCGCCCAGCTGGCTGGAGCTGCAGGCCACCAAGTCCAAGAAGCCAATCATGTTGCC
CGTGACATTCATGGATGGGACCACCAAGACCCTGCTGACGGACTCGGCAACCACGGCCAAG
GAGTCTGCAACGCGCTGGCCGACAAGATCTCTCAAGGACCGGTTCGGGTTCTCCCTCTA
CATTGCCCTGTTTGACAAGGTGTCCTCCCTGGGCAGCGGCAGTGACCACGTCATGGACGCC
ATCTCCCAGTGCGAGCAGTACGCCAAGGAGCAGGGCGCCCAGGAGCGCAACGCCCCTGG
AGGCTCTTCTTCCGCAAAGAGGTCTTCACGCCCTGGCACAGCCCTCCGAGGACAACGTGG
CCACCAACCTCATCTACCAGCAGGTGGTGCGAGGAGTCAAGTTTGGGGAGTACAGGTGTGA
GAAGGAGGACGACCTGGCTGAGCTGGCCTCCCAGCAGTACTTTGTAGACTATGGCTCTGAG
ATGATCCTGGAGCGCCTCCTGAACCTCGTGCCCACCTACATCCCCGACCGCGAGATCACGC
```

-continued

```
CCCTGAAGACGCTGGAGAAGTGGGCCCAGCTGGCCATCGCCGCCCACAAGAAGGGGATTT
ATGCCCAGAGGAGAACTGATGCCCAGAAGGTCAAAGAGGATGTGGTCAGTTATGCCCGCTT
CAAGTGGCCCTTGCTCTTCTCCAGGTTTTATGAAGCCTACAAATTCTCAGGCCCCAGTCTCC
CCAAGAACGACGTCATCGTGGCCGTCAACTGGACGGGTGTGTACTTTGTGGATGAGCAGGA
GCAGGTACTTCTGGAGCTGTCCTTCCCAGAGATCATGGCCGGTGTCCAGCAGCAGGGGAGCG
AAAACGACGGCCCCCAGCTTCACGCTGGCCACCATCAAGGGGGACGAATACACCTTCACCT
CCAGCAATGCTGAGGACATTCGTGACCTGGTGGTCACCTTCCTAGAGGGGCTCCGGAAGAG
ATCTAAGTATGTTGTGGCCCTGCAGGATAACCCCAACCCCGCAGGCGAGGAGTCAGGCTTC
CTCAGCTTTGCCAAGGGAGACCTCATCATCCTGGACCATGACACGGGCGAGCAGGTCATGA
ACTCGGGCTGGGCCAACGGCATCAATGAGAGGACCAAGCAGCGTGGGGACTTCCCCACCG
ACAGTGTGTACGTCATGCCCACTGTCACCATGCCACCGCGGGAGATTGTGGCCCTGGTCAC
CATGACTCCCGATCAGAGGCAGGACGTTGTCCGGCTCTTGCAGCTGCAACGGCGGAGCCC
GAGGTGCGTGCCAAGCCCTACACGCTGGAGGAGTTTTCCTATGACTACTTCAGGCCCCCAC
CCAAGCACACGCTGAGCCGTGTCATGGTGTCCAAGGCCCGAGGCAAGGACCGGCTGTGGA
GCCACACGCGGGAACCGCTCAAGCAGGCGCTGCTCAAGAAGCTCCTGGGCAGTGAGGAGC
TCTCGCAGGAGGCCTGCCTGGCCTTCATTGCTGTGCTCAAGTACATGGGCGACTACCCGTCC
AAGAGGACACGCTCCGTCAACGAGCTCACCGACCAGATCTTTGAGGGTCCCCTGAAAGCCG
AGCCCCTGAAGGACGAGGCATATGTGCAGATCCTGAAGCAGCGTGACCGACAACCACATCA
GGTACAGCGAGGAGCGGGGTTGGGAGCTGCTCTGGCTGTGCACGGGCCTTTTCCCACCCAG
CAACATCCTCCTGCCCCACGTGCAGCGCTTCCTGCAGTCCCGAAAGCACTGCCCACTCGCCA
TCGACTGCCTGCAACGGCTCCAGAAAGCCCTGAGAAACGGGTCCCGGAAGTACCCTCCGCA
CCTGGTGGAGGTGGAGGCCATCCAGCACAAGACCACCCAGATTTTCACAAAGTCTACTTC
CCTGATGACACTGACGAGGCCTTCGAAGTGGAGTCCAGCACCAAGGCCAAGGACTTCTGCC
AGAACATCGCCACCAGGCTGCTCCTCAAGTCCTCAGAGGGATTCAGCCTCTTTGTCAAAATT
GCAGACAAGGTCATCAGCGTTCCTGAGAATGACTTCTTCTTTGACTTTGTTCGACACTTGAC
AGACTGGATAAAGAAAGCTCGGCCCATCAAGGACGGAATTGTGCCTCACTCACCTACCAG
GTGTTCTTCATGAAGAAGCTGTGGACCACCACGGTGCCAGGGAAGGATCCCATGGCCGATT
CCATCTTCCACTATTACCAGGAGTTGCCCAAGTATCTCCGAGGCTACCACAAGTGCACGCG
GGAGGAGGTGCTGCAGCTGGGGGCGCTGATCTACAGGGTCAAGTTCGAGGAGGACAAGTC
CTACTTCCCCAGCATCCCCAAGCTGCTGCGGGAGCTGGTGCCCCAGGACCTTATCCGGCAG
GTCTCACCTGATGACTGGAAGCGGTCCATCGTCGCCTACTTCAACAAGCACGCAGGGAAGT
CCAAGGAGGAGGCCAAGCTGGCCTTCCTGAAGCTCATCTTCAAGTGGCCCACCTTTGGCTC
AGCCTTCTTCGAGGTGAAGCAAACTACGGAGCCAAACTTCCTGAGATCCTCCTAATTGCC
ATCAACAAGTATGGGGTCAGCCTCATCGATCCCAAAACGAAGGATATCCTCACCACTCATC
CCTTCACCAAGATCTCCAACTGGAGCAGCGGCAACACCTACTTCCACATCACCATTGGGAA
CTTGGTGCGCGGGAGCAAACTGCTCTGCGAGACGTCACTGGGCTACAAGATGGATGACCTC
CTGACTTCCTACATTAGCCAGATGCTCACAGCCATGAGCAAACAGCGGGGCTCCAGGAGCG
GCAAGTACCCTTACGATGTACCGGATTACGCATGAAGAGCTCGCTGATCAGCCTCGACTGT
GCCTTCTAGTTGCCAGCCATCTGTTGTTTGCCCCTCCCCCGTGCCTTCCTTGACCCTGGAAGG
TGCCACTCCCACTGTCCTTTCCTAATAAAATGAGGAAATTGCATCGCATTGTCTGAGTAGGT
GTCATTCTATTCTGGGGGGTGGGGTGGGCAGGACAGCAAGGGGGAGGATTGGGAAGACA
ATAGCAGGCATTTAATTAAGCATGCTGGGGAGAGATCTGAGGAAACCCCTAGTGATGGAGT
TGGCCACTCCCTCTCTGCGCGCTCGCTCGCTCACTGAGGCCGGGCGACCAAAGGTCGCCCG
ACGCCCGGGCTTTGCCCGGGCGGCCTCAGTGAGCGAGCGAGCGCGCAGAGAGGGAG
```

SEQ ID NO: 48 is the polynucleotide sequence of the minimized second-generation hybrid back half vector, containing the HA tag (i.e., AAV-APhead-APSA-hMYO7ACTex22.HA-MIN) (pairs with second generation front half hybrid vector).

```
CTCCCTCTCTGCGCGCTCGCTCGCTCACTGAGGCCGCCCGGGCAAAGCCCGGGCGTCGGGC
GACCTTTGGTCGCCCGGCCTCAGTGAGCGAGCGAGCGCGCAGAGAGGGAGTGGCCAACTCC
ATCACTAGGGGTTCTCAGATCTGGCGCGCCCCCCGGGTGCGCGGCGTCGGTGGTGCCGGCG
GGGGCGCCAGGTCGCAGGCGGTGTAGGGCTCCAGGCAGGCGGCGAAGGCCATGACGTGC
GCTATGAAGGTCTGCTCCTGCACGCCGTGAACCAGGTGCGCCTGCGGGCCGCGCGCGAACA
CCGCCACGTCCTCGCCTGCGTGGGTCTCTTCGTCCAGGGGCACTGCTGACTGCTGCCGATAC
TCGGGGCTCCCGCTCTCGCTCTCGGTAACATCCGGCCGGCGCCGTCCTTGAGCACATAGCC
TGGACCGTTTCCTTAAGCGACGCATGCTCGCGATAGGCACCTATTGGTCTTACTGACATCCA
CTTTGCCTTTCTCTCCACAGTATCTGTGGCGCCTCGAGGCTGAGAAAATGCGGCTGGCGGAG
GAAGAGAAGCTTCGGAAGGAGATGAGCGCCAAGAAGGCCAAGGAGGAGGCCGAGCGCAA
GCATCAGGAGCGCCTGGCCCAGCTGGCTCGTGAGGACGCTGAGCGGGAGCTGAAGGAGAA
GGAGGCCGCTCGGCGGAAGAAGGAGCTCCTGGAGCAGATGGAAAGGGCCCGCCATGAGCC
TGTCAATCACTCAGACATGGTGGACAAGATGTTTGGCTTCCTGGGGACTTCAGGTGGCCTGC
CAGGCCAGGAGGGCCAGGCACCTAGTGGCTTTGAGGACCTGGAGCGAGGGCGGAGGGAGA
TGGTGGAGGAGGACCTGGATGCAGCCCTGCCCCTGCCTGACGAGGATGAGGAGGACCTCTC
TGAGTATAAATTTGCCAAGTTCGCGGCCACCTACTTCCAGGGGACAACCACGCACTCCTAC
ACCCGGCGGCCACTCAAACAGCCACTGCTCTACCATGACGACGAGGGTGACCAGCTGGCAG
CCCTGGCGGTCTGGATCACCATCCTCCGCTTCATGGGGGACCTCCCTGAGCCCAAGTACCAC
ACAGCCATGAGTGATGGCAGTGAGAAGATCCCTGTGATGACCAAGATTTATGAGACCCTGG
GCAAGAAGACGTACAAGAGGGAGCTGCAGGCCCTGCAGGGCGAGGGCGAGGCCCAGCTCC
CCGAGGGCCAGAAGAAGAGCAGTGTGAGGCACAAGCTGGTGCATTTGACTCTGAAAAAGA
AGTCCAAGCTCACAGAGGAGGTGACCAAGAGGCTGCATGACGGGGAGTCCACAGTGCAGG
GCAACAGCATGCTGGAGGACCGGCCCACCTCCAACCTGGAGAAGCTGCACTTCATCATCGG
CAATGGCATCCTGCGGCCAGCACTCCGGGACGAGATCTACTGCCAGATCAGCAAGCAGCTG
ACCCACAACCCCTCCAAGAGCAGCTATGCCCGGGGCTGGATTCTCGTGTCTCTCTGCGTGGG
CTGTTTCGCCCCCTCCGAGAAGTTTGTCAAGTACCTGCGCGAACTTCATCACGGGGGCCCGC
CCGGCTACGCCCCGTACTGTGAGGAGCGCCTGAGAAGGACCTTTGTCAATGGACACGGAC
ACAGCCGCCAGCTGGCTGGAGCTGCAGGCCACCAAGTCCAAGAAGCCAATCATGTTGCCC
GTGACATTCATGGATGGGACCACCAAGACCCTGCTGACGGACTCGGCAACCACGGCCAAGG
AGCTCTGCAACGCGCTGGCCGACAAGATCTCTCTCAAGGACCGGTTCGGGTTCTCCCTCTAC
ATTGCCCTGTTTGACAAGGTGTCCTCCCTGGGCAGCGGCAGTGACCACGTCATGGACGCCA
TCTCCCAGTGCGAGCAGTACGCCAAGGAGCAGGGCGCCCAGGAGCGCAACGCCCCTGGA
GGCTCTTCTTCCGCAAAGAGGTCTTCACGCCCTGGCACAGCCCCTCCGAGGACAACGTGGC
```

-continued

```
CACCAACCTCATCTACCAGCAGGTGGTGCGAGGAGTCAAGTTTGGGGAGTACAGGTGTGAG
AAGGAGGACGACCTGGCTGAGCTGGCCTCCCAGCAGTACTTTGTAGACTATGGCTCTGAGA
TGATCCTGGAGCGCCTCCTGAACCTCGTGCCCACCTACATCCCCGACCGCGAGATCACGCCC
CTGAAGACGCTGGAGAAGTGGGCCCAGCTGGCCATCGCCGCCCACAAGAAGGGGATTTAT
GCCCAGAGGAGAACTGATGCCCAGAAGGTCAAAGAGGATGTGGTCAGTTATGCCCGCTTCA
AGTGGCCCTTGCTCTTCTCCAGGTTTTATGAAGCCTACAAATTCTCAGGCCCCAGTCTCCCC
AAGAACGACGTCATCGTGGCCGTCAACTGGACGGGTGTGTACTTTGTGGATGAGCAGGAGC
AGGTACTTCTGGAGCTGTCCTTCCCAGAGATCATGGCCGTGTCCAGCAGCAGGGGAGCGAA
AACGACGGCCCCCAGCTTCACGCTGGCCACCATCAAGGGGGACGAATACACCTTCACCTCC
AGCAATGCTGAGGACATTCGTGACCTGGTGGTCACCTTCCTAGAGGGGCTCCGGAAGAGAT
CTAAGTATGTTGTGGCCCTGCAGGATAACCCCAACCCCGCAGGCGAGGAGTCAGGCTTCCT
CAGCTTTGCCAAGGGAGACCTCATCATCCTGGACCATGACACGGGCGAGCAGGTCATGAAC
TCGGGCTGGGCCAACGGCATCAATGAGAGGACCAAGCAGCGTGGGGACTTCCCCACCGAC
AGTGTGTACGTCATGCCCACTGTCACCATGCCACCGCGGGAGATTGTGGCCCTGGTCACCAT
GACTCCCGATCAGAGGCAGGACGTTGTCCGGCTCTTGCAGCTGCGAACGGCGGAGCCCGAG
GTGCGTGCCAAGCCCTACACGCTGGAGGAGTTTTCCTATGACTACTTCAGGCCCCCACCCAA
GCACACGCTGAGCCGTGTCATGGTGTCCAAGGCCCGAGGCAAGGACCGGCTGTGGAGCCAC
ACGCGGGAACGCTCAAGCAGGCGCTGCTCAAGAAGCTCCTGGGCAGTGAGGAGCTCTCGC
AGGAGGCCTGCCTGGCCTTCATTGCTGTGCTCAAGTACATGGGCGACTACCCGTCCAAGAG
GACACGCTCCGTCAACGAGCTCACCGACCAGATCTTTGAGGGTCCCCTGAAAGCCGAGCCC
CTGAAGGACGAGGCATATGTGCAGATCCTGAAGCAGCTGACCGACAACCACATCAGGTAC
AGCGAGGAGCGGGGTTGGGAGCTGCTCTGGCTGTGCACGGGCCTTTTCCCACCCAGCAACA
TCCTCCTGCCCCACGTGCAGCGCTTCCTGCAGTCCCGAAAGCACTGCCCACTCGCCATCGAC
TGCCTGCAACGGCTCCAGAAAGCCCTGAGAAACGGGTCCCGGAAGTACCCTCCGCACCTGG
TGGAGGTGGAGGCCATCCAGCACAAGACCACCCAGATTTTCCACAAAGTCTACTTCCCTGA
TGACACTGACGAGGCCTTCGAAGTGGAGTCCAGCACCAAGGCCAAGGACTTCTGCCAGAAC
ATCGCCACCAGGCTGCTCCTCAAGTCCTCAGAGGGATTCAGCCTCTTTGTCAAAATTGCAGA
CAAGGTCATCAGCGTTCCTGAGAATGACTTCTTCTTTGACTTTGTTCGACACTTGACAGACT
GGATAAAGAAAGCTCGGCCCATCAAGGACGGAATTGTGCCCTCACTCACCTACCAGGTGTT
CTTCATGAAGAAGCTGTGGACCACCACGGTGCCAGGGAAGGATCCCATGGCCGATTCCATC
TTCCACTATTACCAGGAGTTGCCCAAGTATCTCCGAGGCTACCACAAGTGCACGCGGGAGG
AGGTGCTGCAGCTGGGGGCGCTGATCTACAGGGTCAAGTTCGAGGAGGACAAGTCCTACTT
CCCCAGCATCCCCAAGCTGCTGCGGGAGCTGGTGCCCCAGGACCTTATCGGCAGGTCTCA
CCTGATGACTGGAAGCGGTCCATCGTCGCCTACTTCAACAAGCACGCAGGGAAGTCCAAGG
AGGAGGCCAAGCTGGCCTTCCTGAAGCTCATCTTCAAGTGGCCCACCTTTGGCTCAGCCTTC
TTCGAGGTGAAGCAAACTACGGAGCCAAACTTCCCTGAGATCCTCCTAATTGCCATCAACA
AGTATGGGGTCAGCCTCATCGATCCCAAAACGAAGGATATCCTCACCACTCATCCCTTCACC
AAGATCTCCAACTGGAGCAGCGGCAACACCTACTTCCACATCACCATTGGGAACTTGGTGC
GCGGGAGCAAACTGCTCTGCGAGACGTCACTGGGCTACAAGATGGATGACCTCCTGACTTC
CTACATTAGCCAGATGCTCACAGCCATGAGCAAACAGCGGGGCTCCAGGAGCGGCAAGTA
CCCTTACGATGTACCGGATTACGCATGAAGAGCTCGCTGATCAGCCTCGACTGTGCCTTCTA
GTTGCCAGCCATCTGTTGTTTGCCCCTCCCCCGTGCCTTCCTTGACCCTGGAAGGTGCCACTC
CCACTGTCCTTTCCTAATAAAATGAGGAAATTGCATCGCATTGTCTGAGTAGGTGTCATTCT
ATTCTGGGGGGTGGGGTGGGCAGGACAGCAAGGGGGAGGATTGGGAAGACAATAGCAGG
CATTTAATTAAGCATGCTGGGGAGAGATCTGAGGAAACCCCTAGTGATGGAGTTGGCCACT
CCCTCTCTGCGCGCTCGCTCGCTCACTGAGGCCGGGCGACCAAAGGTCGCCCGACGCCCGG
GCTTTGCCCGGGCGGCCTCAGTGAGCGAGCGAGCGCGCAGAGAGGGAG
```

SEQ ID NO: 49 is the polynucleotide sequence of the minimized second-generation hybrid back half vector, not containing the HA tag (i.e., AAV-APhead-APSA-hMYO7ACTex22-MIN)(pairs with second generation front half hybrid vector).

```
CTCCCTCTCTGCGCGCTCGCTCGCTCACTGAGGCCGCCCGGGCAAAGCCCGGGCGTCGGGC
GACCTTTGGTCGCCCGGCCTCAGTGAGCGAGCGAGCGCGCAGAGAGGGAGTGGCCAACTCC
ATCACTAGGGGTTCTCAGATCTGGCGCGCCCCCGGGTGCGCGGCGTCGGTGGTGCCGGCG
GGGGGCGCCAGGTCGCAGGCGGTGTAGGGCTCCAGGCAGGCGGCGAAGGCCATGACGTGC
GCTATGAAGGTCTGCTCCTGCACGCCGTGAACCAGGTGCGCCTGCGGGCCGCGCGCGAACA
CCGCCACGTCCTCGCCTGCGTGGGTCTCTTCGTCCAGGGGCACTGCTGACTGCTGCCGATAC
TCGGGGCTCCCGCTCTCGCTCTCGGTAACATCCGGCCGGGCGCCGTCCTTGAGCACATAGCC
TGGACCGTTTCCTTAAGCGACGCATGCTCGCGATAGGCACCTATTGTCTTACTGACATCCA
CTTTGCCTTTCTCTCCACAGTATCTGTGGCGCCTCGAGGCTGAGAAAATGCGGCTGGCGGAG
GAAGAGAAGCTTCGGAAGGAGATGAGCGCCAAGAAGGCCAAGGAGGAGGCCGAGCGCAA
GCATCAGGAGCGCCTGGCCCAGCTGGCTCGTGAGGACGCTGAGCGGGAGCTGAAGGAGAA
GGAGGCCGCTCGGCGGAAGAAGGAGCTCCTGGAGCAGATGGAAAGGGCCCGCCATGAGCC
TGTCAATCACTCAGACATGGTGGACAAGATGTTTGGCTTCCTGGGGACTTCAGGTGGCCTGC
CAGGCCAGGAGGGCCAGGCACCTAGTGGCTTTGAGGACCTGGAGCGAGGGCGGAGGGAGA
TGGTGGAGGAGGACCTGGATGCAGCCCTGCCCCTGCCTGACGAGGATGAGGAGGACCTCTC
TGAGTATAAATTTGCCAAGTTCGCGGCCACCTACTTCCAGGGACAACCACGCACTTCCTAC
ACCCGGCGGCCACTCAAACAGCCACTGCTCTACCATGACGACGAGGGTGACCAGCTGGCAG
CCCTGGCCGGTCTGGATCACCATCCTCCGCTTCATGGGGGACCTCCCTGAGCCCAAGTACCAC
ACAGCCATGAGTGATGGCAGTGAGAAGATCCCTGTGATGACCAAGATTTATGAGACCCTGG
GCAAGAAGACGTACAAGAGGGAGCTGCAGGCCCTGCAGGGCGAGGGCGAGGCCCAGCTCC
CCGAGGGCCAGAAGAAGAGCAGTGTGAGGCACAAGCTGGTGCATTTGACTCTGAAAAAGA
AGTCCAAGCTCACAGAGGAGGTGACCAAGAGGCTGCATGACGGGGAGTCCACAGTGCAGG
GCAACAGCATGCTGGAGGACCGGCCCACCTCCAACCTGGAGAAGCTGCACTTCATCATCGG
CAATGGCATCCTGCGGCCAGCACTCCGGGACGAGATCTACTGCCAGATCAGCAAGCAGCTG
ACCCACAACCCCTCCAAGAGCAGCTATGCCCGGGGCTGGATTCTCGTGTCTCTCTGCGTGGG
CTGTTTCGCCCCCTCCGAGAAGTTTGTCAAGTACCTGCGCGAACTTCATCCACGGGGCCCGC
CCGGCTACGCCCCGTACTGTGAGGAGCGCTGAGAAGGACCTTTGTCAATGGGACACGGAC
ACAGCCGCCCAGCTGGCTGGAGCTGCAGGCCACCAAGTCCAAGAAGCCAATCATGTTGCCC
GTGCACTTCATGGATGGGACCACCAAGACCCTGCTGACGGACTCGGCAACCACGGCCAAGG
AGCTCTGCAACGCGCTGGCCGACAAGATCTCTCTCAAGGACCGGTTCGGGTTCTCCCTCTAC
```

-continued

```
ATTGCCCTGTTTGACAAGGTGTCCTCCCTGGGCAGCGGCAGGTGACCACGTCATGGACGCCA
TCTCCCAGTGCGAGCAGTACGCCAAGGAGCAGGGCGCCCAGGAGCGCAACGCCCCCTGGA
GGCTCTTCTTCCGCAAAGAGGTCTTCACGCCCTGGCACAGCCCCTCCGAGGACAACGTGGC
CACCAACCTCATCTACCAGCAGGTGGTGCGAGGAGTCAAGTTTGGGGAGTACAGGTGTGAG
AAGGAGGACGACCTGGCTGAGCTGGCCTCCCAGCAGTACTTTGTAGACTATGGCTCTGAGA
TGATCCTGGAGCGCCTCCTGAACCTCGTGCCCACCTACATCCCCGACCGCGAGATCACGCCC
CTGAAGACGCTGGAGAAGTGGGCCCAGCTGGCCATCGCCGCCCACAAGAAGGGGATTTAT
GCCCAGAGGAGAACTGATGCCCAGAAGGTCAAAGAGGATGTGGTCAGTTATGCCCGCTTCA
AGTGGCCCTTGCTCTTCTCCAGGTTTTATGAAGCCTACAAATTCTCAGGCCCCAGTCTCCCC
AAGAACGACGTCATCGTGGCCGTCAACTGGACGGGTGTGTACTTTGTGGATGAGCAGGAGC
AGGTACTTCTGGAGCTGTCCTTCCCAGAGATCATGGCCGTGTCCAGCAGCAGGGGAGCGAA
AACGACGGCCCCAGCTTCACGCTGGCCACCATCAAGGGGGACGAATACACCTTCACCTCC
AGCAATGCTGAGGACATTCGTGACCTGGTGGTCACCTTCCTAGAGGGGCTCCGGAAGAGAT
CTAAGTATGTTGTGGCCCTGCAGGATAACCCCAACCCCGCAGGCGAGGAGTCAGGCTTCCT
CAGCTTTGCCAAGGGAGACCTCATCATCCTGGACCATGACACGGGCGAGCAGGTCATGAAC
TCGGGCTGGGCCAACGGCATCAATGAGAGGACCAAGCAGCGTGGGGACTTCCCCACCGAC
AGTGTGTACGTCATGCCCACTGTCACCATGCCACCGCGGGAGATTGTGGCCCTGGTCACCAT
GACTCCCGATCAGAGGCAGGACGTTGTCCGGCTCTTGCAGCTGCGAACGGCGGAGCCCGAG
GTGCGTGCCAAGCCCTACACGCTGGAGGAGTTTTCCTATGACTACTTCAGGCCCCCACCCAA
GCACACGCTGAGCCGTGTCATGGTGTCCAAGGCCCGAGGCAAGGACCGGCTGTGGACCAC
ACGCGGGAACCGCTCAAGCAGGCGCTGCTCAAGAAGCTCCTGGGCAGTGAGGAGCTCTCGC
AGGAGGCCTGCCTGGCCTTCATTGCTGTGCTCAAGTACATGGGCGACTACCCGTCCAAGAG
GACACGCTCCGTCAACGAGCTCACCGACCAGATCTTTGAGGGTCCCCTGAAAGCCGAGCCC
CTGAAGGACGAGGCATATGTGCAGATCCTGAAGCAGCTGACCGACAACCACATCAGGTAC
AGCGAGGAGCGGGGTTGGGAGCTGCTCTGGCTGTGCACGGGCCTTTTCCCACCCAGCAACA
TCCTCCTGCCCCACGTGCAGCGCTTCCTGCAGTCCCGAAAGCACTGCCCACTCGCCATCGAC
TGCCTGCAACGGCTCCAGAAAGCCCTGAGAAACGGGTCCCGGAAGTACCCTCCGCACCTGG
TGGAGGTGGAGGCCATCCAGCACAAGACCACCCAGATTTTCCACAAAGTCTACTTCCCTGA
TGACACTGACGAGGCCTTCGAAGTGGAGTCCAGCACCAAGGCCAAGGACTTCTGCCAGAAC
ATCGCCACCAGGCTGCTCCTCAAGTCCTCAGAGGGATTCAGCCTCTTTGTCAAAATTGCAGA
CAAGGTCATCAGCGTTCCTGAGAATGACTTCTTCTTTGACTTTGTTCGACACTTGACAGACT
GGATAAAGAAAGCTCGGCCCATCAAGGACGGAATTGTGCCCTCACTCACCTACCAGGTGTT
CTTCATGAAGAAGCTGTGGACCACCACGGTGCCAGGGAAGGATCCCATGGCCGATTCCATC
TTCCACTATTACCAGGAGTTGCCCAAGTATCTCCGAGGCTACCACAAGTGCACGCGGGAGG
AGGTGCTGCAGCTGGGGCGCTGATCTACAGGGTCAAGTTCGAGGAGGACAAGTCCTACTT
CCCCAGCATCCCCAAGCTGCTGCGGGAGCTGGTGCCCCAGGACCTTATCCGGCAGGTCTCA
CCTGATGACTGGAAGCGGTCCATCGTCGCCTACTTCAACAAGCACGCAGGGAAGTCCAAGG
AGGAGGCCAAGCTGGCCCTTCCTGAAGCTCATCTTCAAGTGGCCCACCTTTGGCTCAGCCTTC
TTCGAGGTGAAGCAAACTACGGAGCCAAACTTCCCTGAGATCCTCCTAATTGCCATCAACA
AGTATGGGGTCAGCCTCATCGATCCCAAAACGAAGGATATCCTCACCCACTCATCCCTTCACC
AAGATCTCCAACTGGAGCAGCGGCAACACCCTACTTCCACATCACCATTGGGAACTTGGTGC
GCGGGAGCAAACTGCTCTGCGAGACGTCACTGGGCTACAAGATGGATGACCTCCTGACTTC
CTACATTAGCCAGATGCTCACAGCCATGAGCAAACAGCGGGCTCCAGGAGCGGCAAGAG
AGCTCGCTGATCAGCCTCGACTGTGCCTTCTAGTTGCCAGCCATCTGTTGTTTGCCCCTCCCC
CGTGCCTTCCTTGACCCTGGAAGGTGCCACTCCCACTGTCCTTTCCTAATAAAATGAGGAAA
TTGCATCGCATTGTCTGAGTAGGTGTCATTCTATTCTGGGGGTGGGGTGGGCAGGACAG
CAAGGGGGAGGATTGGGAAGACAATAGCAGGCATTTAATTAAGCATGCTGGGGAGAGATC
TAGGAAACCCCTAGTGATGGAGTTGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGAGCG
AGCGCGCAGAGAGGGAG
```

SEQ ID NO: 50 is the polynucleotide sequence of the third generation overlap front half vector (i.e., AAV-smCBA-hMYO7A-NTlong-v3).

```
CTCCCTCTCTGCGCGCTCGCTCGCTCACTGAGGCCGCCCGGGCAAAGCCCGGGCGTCGGGC
GACCTTTGGTCGCCCGGCCTCAGTGAGCGAGCGAGCGCGCAGAGAGGGAGTGGCCAACTCC
ATCACTAGGGGTTCAGATCTGGCGCGCCCAATTCGGTACCCTAGTTATTAATAGTAATCAAT
TACGGGGTCATTAGTTCATAGCCCATATATGGAGTTCCGCGTTACATAACTTACGGTAAATG
GCCCGCCTGGCTGACCGCCCAACGACCCCCGCCCATTGACGTCAATAATGACGTATGTTCCC
ATAGTAACGCCAATAGGGACTTTCCATTGACGTCAATGGGTGGACTATTTACGGTAAACTG
CCCACTTGGCAGTACATCAAGTGTATCATATGCCAAGTACGCCCCCTATTGACGTCAATGAC
GGTAAATGGCCCGCCTGGCATTATGCCCAGTACATGACCTTATGGGACTTTCCTACTTGGCA
GTACATCTACGTATTAGTCATCGCTATTACCATGGTCGAGGTGAGCCCCACGTTCTGCTTCA
CTCTCCCCATCTCCCCCCCCCTCCCCACCCCCAATTTTGTATTTATTTATTTTTTAATTATTTTG
TGCAGCGATGGGGGCGGGGGGGGGGGGGGCGCGCGCCAGGCGGGCGGGGCGGGGCG
AGGGGCGGGGCGGGGCGAGGCGGAGAGGTGCGGCGGCAGCCAATCAGAGCGGCGCGCTCC
GAAAGTTTCCTTTTATGGCGAGGCGGCGGCGGCGGCGGCCCTATAAAAAGCGAAGCGCGCG
GCGGGCGGGAGTCGCTGCGCGCTGCCTTCGCCCCGTGCCCCGCTCCGCCGCCGCCTCGCGC
CGCCCGCCCCGGCTCTGACTGACCGCGTTACTCCCACAGGTGAGCGGGCGGGACGGCCCTT
CTCCTCCGGGCTGTAATTAGCGCTTGGTTTAATGACGGCTTGTTTCTTTTCTGTGGCTGCGTG
AAAGCCTTGAGGGGCTCCGGGAGCTAGAGCCTCTGCTAACCATGTTCATGCCTTCTTCTTTTT
TCCTACAGCTCCTGGGCAACGTGCTGGTTATTGTGCTGTCTCATCATTTTGGCAAAGAATTC
TAGCGGCCGCCACCATGGTGATTCTTCAGCAGGGGACCATGTGTGATGGACCTGAGATT
GGGGCAGGAGTTCGACGTGCCCATCGGGGCGGTGGTGAAGCTCTGCGACTCTGGGCAGGTC
CAGGTGGTGGATGATGAAGACAATGAACACTGGATCTCTCCGCAGAACGCAACGCACATCA
AGCCTATGCACCCCACGTCGGTCCACGGCGTGGAGGACATGATCCGCCTGGGGGACCTCAA
CGAGGCGGCATCTTTGCGCAACCTGCTTATCCGCTACCGGGACCACCTCATCTACACGTATA
CGGGGCTCCATCCTGGTGGCTGTGAACCCCTACCAGCTGCTCTCCATCTACTCGCCAGAGCAC
ATCCGCCAGTATACCAACAAGAAGATTGGGGAGATGCCCCCCACATCTTTGCCATTGCTG
ACAACTGCTACTTCAACATGAAACGCAACAGCCGAGACCAGTGCTGCATCATCAGTGGGA
ATCTGGGCCGGAAGACGGAGAGCACAAAGCTGATCCTGCAGTTCCTGGCAGCCATCAGT
GGGCAGCACTCGTGGATTGAGCAGCAGGTCTTGGAGGCCACCCCCATTCTGGAAGCATTTG
```

-continued

GGAATGCCAAGACCATCCGCAATGACAACTCAAGCCGTTTCGGAAAGTACATCGACATCCA
CTTCAACAAGCGGGGCGCCATCGAGGGCGCGAAGATTGAGCAGTACCTGCTGGAAAAGTC
ACGTGTCTGTCGCCAGGCCCTGGATGAAAGGAACTACCACGTGTTCTACTGCATGCTGGAG
GGTATGAGTGAGGATCAGAAGAAGAAGCTGGGCTTGGGCCAGGCCTCTGACTACAACTACT
TGGCCATGGGTAACTGCATAACCTGTGAGGGCCGGGTGGACAGCCAGGAGTACGCCAACAT
CCGCTCCGCCATGAAGGTGCTCATGTTCACTGACACCGAGAACTGGGAGATCTCGAAGCTC
CTGGCTGCCATCCTGCACCTGGGCAACCTGCAGTATGAGGCACGCACATTTGAAAACCTGG
ATGCCTGTGAGGTTCTCTTCTCCCCATCGCTGGCCACAGCTGCATCCCTGCTTGAGGTGAAC
CCCCCAGACCTGATGAGCTGCCTGACTAGCCGCACCCTCATCACCCGCGGGGAGACGGTGT
CCACCCCACTGAGCAGGGAACAGGCACTGGACGTGCGCGACGCCTTCGTAAAGGGGATCTA
CGGGCGGCTGTTCGTGTGGATTGTGGACAAGATCAACGCAGCAATTTACAAGCCTCCCTCC
CAGGATGTGAAGAACTCTCGCAGGTCCATCGGCCTCCTGGACATCTTTGGGTTTGAGAACTT
TGCTGTGAACAGCTTTGAGCAGCTCTGCATCAACTTCGCCAATGAGCACCTGCAGCAGTTCT
TTGTGCGGCACGTGTTCAAGCTGGAGCAGGAGGAATATGACCTGGAGAGCATTGACTGGCT
GCACATCGAGTTCACTGACAACCAGGATGCCCTGGACATGATTGCCAACAAGCCCATGAAC
ATCATCTCCCTCATCGATGAGGAGAGCAAGTTCCCCAAGGGCACAGACACCACCATGTTAC
ACAAGCTGAACTCCCAGCACAAGCTCAACGCCAACTACATCCCCCCCAAGAACAACCATGA
GACCCAGTTTGGCATCAACCATTTTGCAGGCATCGTCTACTATGAGACCCAAGGCTTCCTGG
AGAAGAACCGAGACACCCTGCATGGGGACATTATCCAGCTGGTCCACTCCTCCAGGAACAA
GTTCATCAAGCAGATCTTCCAGGCCGATGTCGCCATGGGCGCCGAGACCAGGAAGCGCTCG
CCCACACTTAGCAGCCAGTTCAAGCGGTCACTGGAGCTGCTGATGCGCACGCTGGGTGCCT
GCCAGCCCTTCTTTGTGCGATGCATCAAGCCCAATGAGTTCAAGAAGCCCATGCTGTTCGAC
CGGCACCTGTGCGTGCGCCAGCTGCGGTACTCAGGAATGATGGAGACCATCCGAATCCGCC
GAGCTGGCTACCCCATCCGCTACAGCTTCGTAGAGTTTGTGGAGCGGTACCGTGTGCTGCTG
CCAGGTGTGAAGCCGGCCTACAAGCAGGGCGACCTCCGCGGGACTTGCCAGCGCATGGCTG
AGGCTGTGCTGGGCACCCACGATGACTGGCAGATAGGCAAAACCAAGATCTTTCTGAAGGA
CCACCATGACATGCTGCTGGAAGTGGAGCGGGACAAAGCCATCACCGACAGAGTCATCCTC
CTTCAGAAAGTCATCCGGGGATTCAAAGACAGGTCTAACTTTCTGAAGCTGAAGAACGCTG
CCACACTGATCCAGAGGCACTGGCGGGGTCACAACTGTAGGAAGAACTACGGGCTGATGC
GTCTGGGCTTCCTGCGGCTGCAGGCCCTGCACCGCTCCCGGAAGCTGCACCAGCAGTACCG
CCTGGCCCGCCAGCGCATCATCCAGTTCCAGGCCCGCTGCCGCGCCTATCTGGTGCGCAAG
GCCTTCCGCCACCGCCTCTGGGCTGTGCTCACCGTGCAGGCCTATGCCCGGGGCATGATCGC
CCGCAGGCTGCACCAACGCCTCAGGGCTGAGTATCTGTGGCGCCTCGAGGCTGAGAAAATG
CGGCTGGCGGAGGAAGAGAAGCTTCGGAAGGAGATGAGCGCCAAGAAGGCCAAGGAGGA
GGCCGAGCGCAAGCATCAGGAGCGCCTGGCCCAGCTGGCTCGTGAGGACGCTGAGCGGGA
GCTGAAGGAGAAGGAGGCCGCTCGGCGGAAGAAGGAGCTCCTGGAGCAGATGGAAAGGG
CCCGCCATGAGCCTGTCAATCACTCAGACATGGTGGACAAGATGTTTGGCTTCCTGGGGAC
TTCAGGTGGCCTGCCAGGCCAGGAGGGCCAGGCACCTAGTGGCTTTGAGGACCTGGAGCGA
GGGCGGAGGGAGATGGTGGAGGAGGACCTGGATGCAGCCCTGCCCCTGCCTGACGAGGAT
GAGGAGGACCTCTCTGAGTATAAATTTGCCAAGTTCGCGGCCACCTACTTCCAGGGGACAA
CCACGCACTCCTACACCCGGCGGCCACTCAAACAGCCACTGCTCTACCATGACGACGAGGG
TGACCAGCTGGCAGCCCTGGCGGTCTGGATCACCATCCTCCGCTTCATGGGGGACCTCCCTG
AGCCCAAGTACCACACAGCCATGAGTGATGGCAGTGAGAAGATCCCTGTGATGACCAAGAT
TTATGAGACCCTGGGCAAGAAGACGTACAAGAGGGAGCTGCAGGCCCTGCAGGGCGAGGG
CGAGGCCCAGCTCCCCGAGGGCCAGTTAATTAAGCATGCTGGGGAGAGATCTGAACCCCTA
GTGATGGAGTTGGCCACTCCCTCTCTGCGCGCTCGCTCGCTCACTGAGGCCGGGCGACCAA
AGGTCGCCCGACGCCCGGGCTTTGCCCGGGCGGCCTCAGTGAGCGAGCGAGCGCGCAGAG
AGGGAG

SEQ ID NO: 66 (only the N-myosin7A portion of SEQ ID NO: 50)
ATGGTGATTCTTCAGCAGGGGGACCATGTGTGGATGGACCTGAGATTGGGGCAGGAGTTCG
ACGTGCCCATCGGGGCGGTGGTGAAGCTCTGCGACTCTGGGCAGGTCCAGGTGGTGGATGA
TGAAGACAATGAACACTGGATCTCTCCGCAGAACGCAACGCACATCAAGCCTATGCACCCC
ACGTCGGTCCACGGCGTGGAGGACATGATCCGCCTGGGGGACCTCAACGAGGCGGGCATCT
TGCGCAACCTGCTTATCCGCTACCGGGACCACCTCATCTACACGTATACGGGCTCCATCCTG
GTGGCTGTGAACCCCTACCAGCTGCTCTCCATCTACTCGCCAGAGCACATCCGCCAGTATAC
CAACAAGAAGATTGGGGAGATGCCCCCCCACATCTTTGCCATTGCTGACAACTGCTACTTC
AACATGAAACGCAACAGCCGAGACCAGTGCTGCATCATCAGTGGGGAATCTGGGGCCGGG
AAGACGGAGAGCACAAAGCTGATCCTGCAGTTCCTGGCAGCCATCAGTGGGCAGCACTCGT
GGATTGAGCAGCAGGTCTTGGAGGCCACCCCCATTCTGGAAGCATTTGGGAATGCCAAGAC
CATCCGCAATGACAACTCAAGCCGTTTCGGAAAGTACATCGACATCCACTTCAACAAGCGG
GGCGCCATCGAGGGCGCGAAGATTGAGCAGTACCTGCTGGAAAAGTCACGTGTCTGTCGCC
AGGCCCTGGATGAAAGGAACTACCACGTGTTCTACTGCATGCTGGAGGGTATGAGTGAGGA
TCAGAAGAAGAAGCTGGGCTTGGGCCAGGCCTCTGACTACAACTACTTGGCCATGGGTAAC
TGCATAACCTGTGAGGGCCGGGTGGACAGCCAGGAGTACGCCAACATCCGCTCCGCCATGA
AGGTGCTCATGTTCACTGACACCGAGAACTGGGAGATCTCGAAGCTCCTGGCTGCCATCCT
GCACCTGGGCAACCTGCAGTATGAGGCACGCACATTTGAAAACCTGGATGCCTGTGAGGTT
CTCTTCTCCCCATCGCTGGCCACAGCTGCATCCCTGCTTGAGGTGAACCCCCCAGACCTGAT
GAGCTGCCTGACTAGCCGCACCCTCATCACCCGCGGGGAGACGGTGTCCACCCCACTGAGC
AGGGAACAGGCACTGGACGTGCGCGACGCCTTCGTAAAGGGGATCTACGGGCGGCTGTTCG
TGTGGATTGTGGACAAGATCAACGCAGCAATTTACAAGCCTCCCTCCCAGGATGTGAAGAA
CTCTCGCAGGTCCATCGGCCTCCTGGACATCTTTGGGTTTGAGAACTTTGCTGTGAACAGCT
TTGAGCAGCTCTGCATCAACTTCGCCAATGAGCACCTGCAGCAGTTCTTTGTGCGGCACGTG
TTCAAGCTGGAGCAGGAGGAATATGACCTGGAGAGCATTGACTGGCTGCACATCGAGTTCA
CTGACAACCAGGATGCCCTGGACATGATTGCCAACAAGCCCATGAACATCATCTCCCTCAT
CGATGAGGAGAGCAAGTTCCCCAAGGGCACAGACACCACCATGTTACACAAGCTGAACTCC
CAGCACAAGCTCAACGCCAACTACATCCCCCCCAAGAACAACCATGAGACCCAGTTTGGCA
TCAACCATTTTGCAGGCATCGTCTACTATGAGACCCAAGGCTTCCTGGAGAAGAACCGAGA
CACCCTGCATGGGGACATTATCCAGCTGGTCCACTCCTCCAGGAACAAGTTCATCAAGCAG
ATCTTCCAGGCCGATGTCGCCATGGGCGCCGAGACCAGGAAGCGCTCGCCCACACTTAGCA
GCCAGTTCAAGCGGTCACTGGAGCTGCTGATGCGCACGCTGGGTGCCTGCCAGCCCTTCTTT -continued
```
GTGCGATGCATCAAGCCCAATGAGTTCAAGAAGCCCATGCTGTTCGACCGGCACCTGTGCG
TGCGCCAGCTGCGGTACTCAGGAATGATGGAGACCATCCGAATCCGCCGAGCTGGCTACCC
CATCCGCTACAGCTTCGTAGAGTTTGTGGAGCGGTACCGTGTGCTGCTGCCAGGTGTGAAG
CCCGGCCTACAAGCAGGGCGACCTCCGCGGGACTTGCCAGCGCATGGCTGAGGCTGTGCTG
GCACCCACGATGACTGGCAGATAGGCAAAACCAAGATCTTTCTGAAGGACCACCATGACAT
GCTGCTGGAAGTGGAGCGGGACAAAGCCATCACCGACAGAGTCATCCTCCTTCAGAAAGTC
ATCCGGGGATTCAAAGACAGGTCTAACTTTCTGAAGCTGAAGAACGCTGCCACACTGATCC
AGAGGCACTGGCGGGGTCACAACTGTAGGAAGAACTACGGGCTGATGCGTCTGGGCTTCCT
GCGGCTGCAGGCCCTGCACCGCTCCCGGAAGCTGCACCAGCAGTACCGCCTGGCCCGCCAG
CGCATCATCCAGTTCCAGGCCCGCTGCCGCGCCTATCTGGTGCGCAAGGCCTTCCGCCACCG
CCTCTGGGCTGTGCTCACCGTGCAGGCCTATGCCCGGGGCATGATCGCCCGCAGGCTGCAC
CAACGCCTCAGGGCTGAGTATCTGTGGCGCCTCGAGGCTGAGAAAATGCGGCTGGCGGAGG
AAGAGAAGCTTCGGAAGGAGATGAGCGCCAAGAAGGCCAAGGAGGAGGCCGAGCGCAAG
CATCAGGAGCGCCTGGCCCAGCTGGCTCGTGAGGACGCTGAGCGGGAGCTGAAGGAGAAG
GAGGCCGCTCGGCGGAAGAAGGAGCTCCTGGAGCAGATGGAAAGGGCCCGCCATGAGCCT
GTCAATCACTCAGACATGGTGGACAAGATGTTTGGCTTCCTGGGGACTTCAGGTGGCCTGC
CAGGCCAGGAGGGCCAGGCACCTAGTGGCTTTGAGGACCTGGAGCGAGGGCGGAGGGAGA
TGGTGGAGGAGGACCTGGATGCAGCCCTGCCCCTGCCTGACGAGGATGAGGAGGACCTCTC
TGAGTATAAATTTGCCAAGTTCGCGGCCACCTACTTCCAGGGGACAACCACGCACTCCTAC
ACCCGGCGGCCACTCAAACAGCCACTGCTCTACCATGACGACGAGGGTGACCAGCTGGCAG
CCCTGGCGGTCTGGATCACCATCCTCCGCTTCATGGGGGACCTCCCTGAGCCCAAGTACCAC
ACAGCCATGAGTGATGGCAGTGAGAAGATCCCTGTGATGACCAAGATTTATGAGACCCTGG
GCAAGAAGACGTACAAGAGGGAGCTGCAGGCCCTGCAGGGCGAGGGCGAGGCCCAGCTCC
CCGAGGGCCAG
```

SEQ ID NO: 65 (peptide encoded by the N-myosin7A portion of SEQ ID NO: 50)
```
MVILQQGDHVWMDLRLGQEFDVPIGAVVKLCDSGQVQVVDDEDNEHWISPQNATHIKPMHPT
SVHGVEDMIRLGDLNEAGILRNLLIRYRDHLIYTYTGSILVAVNPYQLLSIYSPEHIRQYTNKKIG
EMPPHIFAIADNCYFNMKRNSRDQCCIISGESGAGKTESTKLILQFLAAISGQHSWIEQQVLEATP
ILEAFGNAKTIRNDNSSRFGKYIDIHFNKRGAIEGAKIEQYLLEKSRVCRQALDERNYHVFYCML
EGMSEDQKKKLGLGQASDYNYLAMGNCITCEGRVDSQEYANIRSAMKVLMFTDTENWEISKL
LAAILHLGNLQYEARTFENLDACEVLFSPSLATAASLLEVNPPDLMSCLTSRTLITRGETVSTPLS
REQALDVRDAFVKGIYGRLFVWIVDKINAAIYKPPSQDVKNSRRSIGLLDIFGFENFAVNSFEQL
CINFANEHLQQFFVRHVFKLEQEEYDLESIDWLHIEFTDNQDALDMIANKPMNIISLIDEESKFPK
GTDTTMLHKLNSQHKLNANYIPPKNNHETQFGINHFAGIVYYETQGFLEKNRDTLHGDIIQLVH
SSRNKFIKQIFQADVAMGAETRKRSPTLSSQFKRSLELLMRTLGACQPFFVRCIKPNEFKKPMLF
DRHLCVRQLRYSGMMETIRIRRAGYPIRYSFVEFVERYRVLLPGVKPAYKQGDLRGTCQRMAE
AVLGTHDDWQIGKTKIFLKDHHDMLLEVERDKAITDRVILLQKVIRGFKDRSNFLKLKNAATLI
QRHWRGHNCRKNYGLMRLGFLRLQALHRSRKLHQQYRLARQRIIQFQARCRAYLVRKAFRHR
LWAVLTVQAYARGMIARRLHQRLRAEYLWRLEAEKMRLAEEEKLRKEMSAKKAKEEAERKH
QERLAQLAREDAERELKEKEAARRKKELLEQMERARHEPVNHSDMVDKMFGFLGTSGGLPGQ
EGQAPSGFEDLERGRREMVEEDLDAALPLPDEDEEDLSEYKFAKFAATYFQGTTTHSYTRRPLK
QPLLYHDDEGDQLAALAVWITILRFMGDLPEPKYHTAMSDGSEKIPVMTKIYETLGKKTYKREL
QALQGEGEAQLPEGQ
```

SEQ ID NO: 51 is the polynucleotide sequence of the third generation overlap back half vector (i.e., AAV-hMYO7A-CTlong-v3.HA).
```
CTCCCTCTCTGCGCGCTCGCTCGCTCACTGAGGCCGCCCGGGCAAAGCCCGGGCGTCGGGC
GACCTTTGGTCGCCCGGCCTCAGTGAGCGAGCGAGCGCGCAGAGAGGGAGTGGCCAACTCC
ATCACTAGGGGTTCAGATCTGGCGCGCCCTGGCGGAGGAAGAGAAGCTTCGGAAGGAGAT
GAGCGCCAAGAAGGCCAAGGAGGAGGCCGAGCGCAAGCATCAGGAGCGCCTGGCCCAGCT
GGCTCGTGAGGACGCTGAGCGGGAGCTGAAGGAGAAGGAGGCCGCTCGGCGGAAGAAGG
AGCTCCTGGAGCAGATGGAAAGGGCCCGCCATGAGCCTGTCAATCACTCAGACATGGTGGA
CAAGATGTTTGGCTTCCTGGGGACTTCAGGTGGCCTGCCAGGCCAGGAGGGCCAGGCACCT
AGTGGCTTTGAGGACCTGGAGCGAGGGCGGAGGGAGATGGTGGAGGAGGACCTGGATGCA
GCCCTGCCCCTGCCTGACGAGGATGAGGAGGACCTCTCTGAGTATAAATTTGCCAAGTTCG
CGGCCACCTACTTCCAGGGGACAACCACGCACTCCTACACCCGGCGGCCACTCAAACAGCC
ACTGCTCTACCATGACGACGAGGGTGACCAGCTGGCAGCCCTGGCGGTCTGGATCACCATC
CTCCGCTTCATGGGGGACCTCCCTGAGCCCAAGTACCACACAGCCATGAGTGATGGCAGTG
AGAAGATCCCTGTGATGACCAAGATTTATGAGACCCTGGGCAAGAAGACGTACAAGAGGG
AGCTGCAGGCCCTGCAGGGCGAGGGCGAGGCCCAGCTCCCCGAGGGCCAGAAGAAGAGCA
GTGTGAGGCACAAGCTGGTGCATTTGACTCTGAAAAAGAAGTCCAAGCTCACAGAGGAGGT
GACCAAGAGGCTGCATGACGGGGAGTCCACAGTGCAGGGCAACAGCATGCTGGAGGACCG
GCCCACCTCCAACCTGGAGAAGCTGCACTTCATCATCGGCAATGGCATCCTGCGGCCAGCA
CTCCGGGACGAGATCTACTGCCAGATCAGCAAGCAGCTGACCCACAACCCCTCCAAGAGCA
GCTATGCCCGGGGCTGGATTCTCGTGTCTCTGCGTGGGCTGTTTCGCCCCTCCGAGAAG
TTTGTCAAGTACCTGCGGAACTTCATCCACGGGGCCCGCCCGGCTACGCCCCGTACTGTGA
GGAGCGCCTGAGAAGGACCTTTGTCAATGGGACACGGACACGCCGCCCAGCTGGCTGGA
GCTGCAGGCCACCAAGTCCAAGAAGCCAATCATGTTGCCCGTGACATTCATGGATGGGACC
ACCAAGACCCTGCTGACGGACTCGGCAACCACGGCCAAGGAGTCTGCAACGCGCTGGCCG
ACAAGATCTCTCAAGGACCGGTTCGGGTTCTCCCTCTACATTGCCCTGTTTGACAAGGTG
TCCTCCCTGGGCAGCGGCAGTGACCACGTCATGAGCGCCATCTCCCAGTGCGAGCAGTACG
CCAAGGAGCAGGGCGCCCAGGAGCGCAACGCCCCTGGAGGCTCTTCTTCCGCAAAGAGGT
CTTCACGCCCTGGCACAGCCCCTCCGAGGACAACGTGGCCACCAACCTCATCTACCAGCAG
GTGGTGCGAGGAGTCAAGTTTGGGGAGTACAGGTGTGAGAAGGAGGACGACCTGGCTGAG
CTGGCCTCCCAGCAGTACTTTGTAGACATGGCTCTGAGATGATCCTGGAGCGCCTTCGAA
CCTCGTGCCCACCTACATCCCCGACCGCGAGATCACGCCCCTGAAGACGCTGGAGAAGTGG
GCCCAGCTGGCCATCGCCGCCCACAAGAAGGGGATTTATGCCCAGAGGAGAACTGATGCCC
AGAAGGTCAAAGAGGATGTGGTCAGTTATGCCCGCTTCAAGTGGCCCTTGCTCTTCTCCAG
GTTTTATGAAGCCTACAAATTCTCAGGCCCCAGTCTCCCCAAGAACGACGTCATCGTGGCC
TCAACTGGACGGGTGTGTACTTTGTGGATGAGCAGGAGCAGGTACTTCTGGAGCTGTCCTTC
```

-continued

```
CCAGAGATCATGGCCGTGTCCAGCAGCAGGGGGAGCGAAAACGACGGCCCCCAGCTTCACG
CTGGCCACCATCAAGGGGGACGAATACACCTTCACCTCCAGCAATGCTGAGGACATTCGTG
ACCTGGTGGTCACCTTCCTAGAGGGGCTCCGGAAGAGATCTAAGTATGTTGTGGCCCTGCA
GGATAACCCCAACCCCGCAGGCGAGGAGTCAGGCTTCCTCAGCTTTGCCAAGGGAGACCTC
ATCATCCTGGACCATGACACGGGCGAGCAGGTCATGAACTCGGGCTGGGCCAACGGCATCA
ATGAGAGGACCAAGCAGCGTGGGGACTTCCCCACCGACAGTGTGTACGTCATGCCCACTGT
CACCATGCCACCGCGGGAGATTGTGGCCCTGGTCACCATGACTCCCGATCAGAGGCAGGAC
GTTGTCCGGCTCTTGCAGCTGCGAACGGCGGAGCCCGAGGTGCGTGCCAAGCCCTACACGC
TGGAGGAGTTTTCCTATGACTACTTCAGGCCCCCACCCAAGCACACGCTGAGCCGTGTCATG
GTGTCCAAGGCCCGAGGCAAGGACCGGCTGTGGAGCCACACGCGGGAACCGCTCAAGCAG
GCGCTGCTCAAGAAGCTCCTGGGCAGTGAGGAGCTCTCGCAGGAGGCCTGCCTGGCCTTCA
TTGCTGTGCTCAAGTACATGGGCGACTACCCGTCCAAGAGGACACGCTCCGTCAACGAGCT
CACCGACCAGATCTTTGAGGGTCCCCTGAAAGCCGAGCCCCTGAAGGACGAGGCATATGTG
CAGATCCTGAAGCAGCTGACCGACAACCACATCAGGTACAGCGAGGAGCAGGAGCGGGGTTGGGAG
CTGCTCTGGCTGTGCACGGGCCTTTTCCCACCCAGCAACATCCTCCTGCCCCACGTGCAGCG
CTTCCTGCAGTCCCGAAAGCACTGCCCACTCGCCATCGACTGCCTGCAACGGCTCCAGAAA
GCCCTGAGAAACGGGTCCCGGAAGTACCCTCCGCACCTGGTGGAGGTGGAGGCCATCCAGC
ACAAGACCACCCAGATTTTCCACAAAGTCTACTTCCCTGATGACACTGACGAGGCCTTCGA
AGTGGAGTCCAGCACCAAGGCCAAGGACTTCGCCAGAACATCGCCACCAGGCTGCTCCTC
AAGTCCTCAGAGGGATTCAGCCTCTTTGTCAAAATTGCAGACAAGGTCATCAGCGTTCCTG
AGAATGACTTCTTCTTTGACTTTGTTCGACACTTGACAGACTGGATAAAGAAAGCTCGGCCC
ATCAAGGACGGAATTGTGCCCTCACTCACCTACCAGGTGTTCTTCATGAAGAAGCTGTGGA
CCACCACGGTGCCAGGGAAGGATCCCATGGCCGATTCCATCTTCCACTATTACCAGGAGTT
GCCCAAGTATCTCCGAGGCTACCACAAGTGCACGCGGGAGGAGGTGCTGCAGCTGGGGGC
GCTGATCTACAGGGTCAAGTTCGAGGAGGACAAGTCCTACTTCCCCAGCATCCCCAAGCTG
CTGCGGGAGCTGGTGCCCCAGGACCTTATCCGGCAGGTCTCACCTGATGACTGGAAGCGGT
CCATCGTCGCCTACTTCAACAAGCACGCAGGGAAGTCCAAGGAGGAGGCCAAGCTGGCCTTT
CCTGAAGCTCATCTTCAAGTGGCCCACCTTTGGCTCAGCCTTCTTCGAGGTGAAGCAAACTA
CGGAGCCAAACTTCCCTGAGATCCTCCTAATTGCCATCAACAAGTATGGGGTCAGCCTCATC
GATCCCAAAACGAAGGATATCCTCACCACTCATCCCTTCACCAAGATCTCCAACTGGAGCA
GCGGCAACACCTACTTCCACATCACCATTGGGAACTTGGTGCGCGGGAGCAAACTGCTCTG
CGAGACGTCACTGGGCTACAAGATGGATGACCTCCTGACTTCCTACATTAGCCAGATGCTC
ACAGCCATGAGCAAACAGCGGGGCTCCAGGAGCGGCAAGTACCCTTACGATGTACCGGATT
ACGCATGAGGTACCAAGGGCGAATTCTGCAGTCGACTAGAGCTCGCTGATCAGCCTCGACT
GTGCCTTCTAGTTGCCAGCCATCTGTTGTTTGCCCCTCCCCGTGCCTTCCTTGACCCTGGAA
GGTGCCACTCCCACTGTCCTTTCCTAATAAAATGAGGAAATTGCATCGCATTGTCTGAGTAG
GTGTCATTCTATTCTGGGGGGTGGGTGGGGCAGGACAGCAAGGGGGAGGATTGGGAAGA
CAATAGCAGGCATGCTGGGGAGAGATCTGAGGACTAGTCCGTCGACTGTTAATTAAGCATG
CTGGGGAGAGATCTGAACCCCTAGTGATGGAGTTGGCCACTCCCTCTCTGCGCGCTCGCTCG
CTCACTGAGGCCGGGCGACCAAAGGTCGCCCGACGCCCGGGCTTTGCCCGGGCGGCCTCAG
TGAGCGAGCGAGCGCGCAGAGAGGGAG

SEQ ID NO: 80 (hMYO7A c-term (e.g., AAV-hMYO7A-CTlong-v3.HA)
CTGGCGGAGGAAGAGAAGCTTCGGAAGGAGATGAGCGCCAAGAAGGCCAAGGAGGAGGC
CGAGCGCAAGCATCAGGAGCGCCTGGCCCAGCTGGCTCGTGAGGACGCTGAGCGGGAGCT
GAAGGAGAAGGAGGCCGCTCGGCGGAAGAAGGAGCTCCTGGAGCAGATGGAAAGGGCCC
GCCATGAGCCTGTCAATCACTCAGACATGGTGGACAAGATGTTTGGCTTCCTGGGGACTTC
AGGTGGCCTGCCAGGCCAGGAGGGCCAGGCACCTAGTGGCTTTGAGGACCTGGAGCGAGG
GCGGAGGGAGATGGTGGAGGAGGACCTGGATGCAGCCCTGCCCCTGCCTGACGAGGATGA
GGAGGACCTCTCTGAGTATAAATTTGCCAAGTTCGCGGCCACCTACTTCCAGGGGACAACC
ACGCACTCCTACACCCGGCGGCCACTCAAACAGCCACTGCTCTACCATGACGACGAGGGTG
ACCAGCTGGCAGCCCTGGCGGTCTGGATCACCATCCTCCGCTTCATGGGGGACCTCCCTGA
GCCCAAGTACCACACAGCCATGAGTGATGGCAGTGAGAAGATCCCTGTGATGACCAAGATT
TATGAGACCCTGGGCAAGAAGACGTACAAGAGGGAGCTGCAGGCCCTGCAGGGCGAGGGC
GAGGCCCAGCTCCCCGAGGGCCAGAAGAAGAGCAGTGTGAGGCACAAGCTGGTGCATTTG
ACTCTGAAAAAGAAGTCCAAGCTCACAGAGGAGGTGACCAAGAGGCTGCATGACGGGGAG
TCCACAGTGCAGGGCAACAGCATGCTGGAGGACCGGCCCACCTCCAACCTGGAGAAGCTGC
ACTTCATCATCGGCAATGGCATCCTGCGGCCAGCACTCCGGGACGAGATCTACTGCCAGAT
CAGCAAGCAGCTGACCCACAACCCCTCCAAGAGCAGCTATGCCCGGGGCTGGATTCTCGTG
TCTCTCTGCGTGGGCTGTTTCGCCCCCTCCGAGAAGTTTGTCAAGTACCTGCGGAACTTCAT
CCACGGGGGCCCGCCCGGCTACGCCCCGTACTGTGAGGAGCGCCTGAGAAGGACCTTTGTC
AATGGGACACGGACACAGCCGCCAGCTGGCTGGAGCTGCAGGCCACCAAGTCCAAGAAG
CCAATCATGTTGCCCGTGACATTCATGGATGGGACCACCAAGACCCTGCTGACGGACTCGG
CAACCACGGCCAAGGAGCTCTGCAACGCGCTGGCCGACAAGATCTCTCTCAAGGACCGGTT
CGGGTTCTCCCTCTACATTGCCCTGTTTGACAAGGTGTCCTCCTGGGCAGCGGCAGTGACC
ACGTCATGGACGCCATCTCCCAGTGCGAGCAGTACGCCAAGGAGCAGGGCGCCCAGGAGC
GCAACGCCCCTGGAGGCTCTTCTTCCGCAAAGAGGTCTTCACGCCCTGGCACAGCCCTCC
GAGGACAACGTGGCCACCAACCTCATCTACCAGCAGGTGGTGCGAGGAGTCAAGTTTGGGG
AGTACAGGCTGTGAAGGAGGACGACCTGGCTGAGCTGGCCTCCCAGCAGTACTTTGTAGA
CTATGGCTCTGAGATGATCCTGGAGCGCCTCCTGAACCTCGTGCCCACCTACATCCCCGACC
GCGAGATCACGCCCCTGAAGACGCTGGAGAAGTGGGCCCAGCTGGCCATCGCCGCCCACA
AGAAGGGGATTTATGCCCAGAGGAGAACTGATGCCCAGAAGGTCAAGAGGATGTGGTCA
GTTATGCCCGCTTCAAGTGGCCCTTGCTCTTCTCCAGGTTTTATGAAGCCTACAAATTCTCA
GGCCCCAGTCTCCCCAAGAACGACGTCATCGTGGCCGTCAACTGACGGGTGTGTACTTTG
TGGATGAGCAGGAGCAGGTACTTCTGGAGCTGTCCTTCCCAGAGATCATGGCCGTGTCCAG
CAGCAGGGGAGCGAAAACGACGGCCCCCAGCTTCACGCTGGCCACCATCAAGGGGGACGA
ATACACCTTCACCTCCAGCAATGCTGAGGACATTCGTGACCTGGTGGTCACCTTCCTAGAGG
GGCTCCGGAAGAGATCTAAGTATGTTGTGGCCCTGCAGGATAACCCCAACCCCGCAGGCGA
GGAGTCAGGCTTCCTCAGCTTTGCCAAGGGAGACCTCATCATCCTGGACCATGACACGGGC
GAGCAGGTCATGAACTCGGGCTGGGCCAACGGCATCAATGAGAGGACCAAGCAGCGTGGG
GACTTCCCCACCGACAGTGTGTACGTCATGCCCACTGTCACCATGCCACCGCGGGAGATTGT
```

-continued
```
GGCCCTGGTCACCATGACTCCCGATCAGAGGCAGGACGTTGTCCGGCTCTTGCAGCTGCGA
ACGGCGGAGCCCGAGGTGCGTGCCAAGCCCTACACGCTGGAGGAGTTTTCCTATGACTACT
TCAGGCCCCCACCCAAGCACACGCTGAGCCGTGTCATGGTGTCCAAGGCCCGAGGCAAGGA
CCGGCTGTGGAGCCACACGCGGGAACCGCTCAAGCAGGCGCTGCTCAAGAAGCTCCTGGGC
AGTGAGGAGCTCTCGCAGGAGGCCTGCCTGGCCTTCATTGCTGTGCTCAAGTACATGGGCG
ACTACCCGTCCAAGAGGACACGCTCCGTCAACGAGCTCACCGACCAGATCTTTGAGGGTCC
CCTGAAAGCCGAGCCCCTGAAGGACGAGGCATATGTGCAGATCCTGAAGCAGCTGACCGA
CAACCACATCAGGTACAGCGAGGAGCGGGGTTGGGAGCTGCTCTGGCTGTGCACGGGCCTT
TTCCCACCCAGCAACATCCTCCTGCCCCACGTGCAGCGCTTCCTGCAGTCCCGAAAGCACTG
CCCACTCGCCATCGACTGCCTGCAACGGCTCCAGAAAGCCCTGAGAAACGGGTCCCGGAAG
TACCCTCCGCACCTGGTGGAGGTGGAGGCCATCCAGCACAAGACCACCCAGATTTTCCACA
AAGTCTACTTCCCTGATGACACTGACGAGGCCTTCGAAGTGGAGTCCAGCACCAAGGCCAA
GGACTTCTGCCAGAACATCGCCACCAGGCTGCTCCTCAAGTCCTCAGAGGGATTCAGCCTCT
TTGTCAAAATTGCAGACAAGGTCATCAGCGTTCCTGAGAATGACTTCTTCTTTGACTTTGTT
CGACACTTGACAGACTGGATAAAGAAAGCTCGGCCCATCAAGGACGGAATTGTGCCCTCAC
TCACCTACCAGGTGTTCTTCATGAAGAAGCTGTGGACCACCACGGTGCCAGGGAAGGATCC
CATGGCCGATTCCATCTTCCACTATTACCAGGAGTTGCCCAAGTATCTCCGAGGCTACCACA
AGTGCACGCGGGAGGAGGTGCTGCAGCTGGGGGCGCTGATCTACAGGGTCAAGTTCGAGG
AGGACAAGTCCTACTTCCCCAGCATCCCCAAGCTGCTGCGGGAGCTGGTGCCCCAGGACCT
TATCCGGCAGGTCTCACCTGATGACTGGAAGCGGTCCATCGTCGCCTACTTCAACAAGCAC
GCAGGGAAGTCCAAGGAGGAGGCCAAGCTGGCCTTCCTGAAGCTCATCTTCAAGTGGCCCA
CCTTTGGCTCAGCCTTCTTCGAGGTGAAGCAAACTACGGAGCCAAACTTCCCTGAGATCCTC
CTAATTGCCATCAACAAGTATGGGGTCAGCCTCATCGATCCCAAAACGAAGGATATCCTCA
CCACTCATCCCTTCACCAAGATCTCCAACTGGAGCAGCGGCAACACCTACTTCCACATCACC
ATTGGGAACTTGGTGCGCGGGAGCAAACTGCTCTGCGAGACGTCACTGGGCTACAAGATGG
ATGACCTCCTGACTTCCTACATTAGCCAGATGCTCACAGCCATGAGCAAACAGCGGGGCTC
CAGGAGCGGCAAG SEQ ID NO: 81 (hMYO7A c-term (e.g., AAV-hMYO7A-CTlong-v3.HA)
LAEEEKLRKEMSAKKAKEEAERKHQERLAQLAREDAERELKEKEAARRKKELLEQMERARHE
PVNHSDMVDKMFGFLGTSGGLPGQEGQAPSGFEDLERGRREMVEEDLDAALPLPDEDEEDLSE
YKFAKFAATYFQGTTTHSYTRRPLKQPLLYHDDEGDQLAALAVWITILRFMGDLPEPKYHTAM
SDGSEKIPVMTKIYETLGKKTYKRELQALQGEGEAQLPEGQKKSSVRHKLVHLTLKKKSKLTEE
VTKRLHDGESTVQGNSMLEDRPTSNLEKLHFIIGNGILRPALRDEIYCQISKQLTHNPSKSSYARG
WILVSLCVGCFAPSEKFVKYLRNFIHGGPPGYAPYCEERLRRTFVNGTRTQPPSWLELQATKSK
KPIMLPVTFMDGTTKTLLTDSATTAKELCNALADKISLKDRFGFSLYIALFDKVSSLGSGSDHVM
DAISQCEQYAKEQGAQERNAPWRLFFRKEVFTPWHSPSEDNVATNLIYQQVVRGVKFGEYRCE
KEDDLAELASQQYFVDYGSEMILERLLNLVPTYIPDREITPLKTLEKWAQLAIAAHKKGIYAQR
RTDAQKVKEDVVSYARFKWPLLFSRFYEAYKFSGPSLPKNDVIVAVNWTGVYFVDEQEQVLLE
LSFPEIMAVSSSRGAKTTAPSFTLATIKGDEYTFTSSNAEDIRDLVVTFLEGLRKRSKYVVALQD
NPNPAGEESGFLSFAKGDLIILDHDTGEQVMNSGWANGINERTKQRGDFPTDSVYVMPTVTMP
PREIVALVTMTPDQRQDVVRLLQLRTAEPEVRAKPYTLEEFSYDYFRPPPKHTLSRVMVSKARG
KDRLWSHTREPLKQALLKLLGSEELSQEACLAFIAVLKYMGDYPSKRTRSVNELTDQIFEGPL
KAEPLKDEAYVQILKQLTDNHIRYSEERGWELLWLCTGLFPPSNILLPHVQRFLQSRKHCPLAID
CLQRLQKALRNGSRKYPPHLVEVEAIQHKTTQIFHKVYFPDDTDEAFEVESSTKAKDFCQNIAT
RLLLKSSEGFSLFVKIADKVISVPENDFFFDFVRHLTDWIKKARPIKDGIVPSLTYQVFFMKKLW
TTTVPGKDPMADSIFHYYQELPKYLRGYHKCTREEVLQLGALIYRVKFEEDKSYFPSIPKLLREL
VPQDLIRQVSPDDWKRSIVAYFNKHAGKSKEEAKLAFLKLIFKWPTFGSAFFEVKQTTEPNFPEI
LLIAINKYGVSLIDPKTKDILTTHPFTKISNWSSGNTYFHITIGNLVRGSKLLCETSLGYKMDDLL
TSYISQMLTAMSKQRGSRSGK
```

In some embodiments, the overlap polynucleotide vectors provided herein comprise a region of overlap that comprises a nucleotide sequence having 80%, 85%, 90%, 92.5%, 95%, 98%, or 99% sequence identity to any of the overlap sequences provided herein. In some embodiments, the overlapping regions comprises a nucleotide sequence having 80%, 85%, 90%, 92.5%, 95%, 98%, or 99% sequence identity to any one of SEQ ID NOs: 39 and 52-59. In some embodiments, the overlapping regions comprises a nucleotide sequence having 80%, 85%, 90%, 92.5%, 95%, 98%, or 99% sequence identity to any one of SEQ ID NOs: 39 and 53-59. In some embodiments, the overlapping regions (or polynucleotide sequence that overlaps) comprises a nucleotide sequence having 80%, 85%, 90%, 92.5%, 95%, 98%, or 99% sequence identity to SEQ ID NO: 39, 56 or 57. In some embodiments, the polynucleotide sequence that overlaps comprises a nucleotide sequence selected from any of SEQ ID NOs: 39 and 52-59. The overlap vectors provided herein may comprise a polynucleotide sequence that overlaps that differs from any of SEQ ID NOs: 39 and 52-59 by 1, 2, 3, 4, 5, 6, 7, 8, 9, 10, 10-15, 15-20, 20-25, or more than 25 nucleotides. In some embodiments, these overlap vectors contain two overlapping sequences disclosed herein, e.g., the mutually exclusive sequences SEQ ID NOs: 39 and 56, or the mutually exclusive sequences SEQ ID NOs: 39 and 57.

In exemplary embodiments, the polynucleotide sequence that overlaps comprises SEQ ID NO: 56. In some embodiments, the polynucleotide sequence that overlaps comprises SEQ ID NO: 57. In some embodiments, the polynucleotide sequence that overlaps comprises SEQ ID NO: 39. In some embodiments, the polynucleotide sequence that overlaps does not comprise SEQ ID NO: 52.

In some embodiments, the overlap polynucleotide vectors provided herein comprise a region of overlap (polynucleotide sequence that overlaps) that encodes a protein having an amino acid sequence comprising 95%, 98%, or 99% or greater sequence identity to any of SEQ ID NOs: 79 and 82-89. In exemplary embodiments, these vectors comprise a region of overlap (polynucleotide sequence that overlaps) that encodes a protein having the amino acid sequence of any one of SEQ ID NOs: 79 and 82-89. In exemplary embodiments, these vectors comprise a region of overlap (polynucleotide sequence that overlaps) that encodes a protein having the amino acid sequence of any one of SEQ ID NOs: 79 and 83-89. In some embodiments, the polynucleotide sequence that overlaps does not encode the amino acid sequence of SEQ ID NO: 82.

In various embodiments, the overlap polynucleotide vectors provided herein contain a region of overlap in the polypeptide coding sequence having a length of about 1365 bp, 1284 bp, 1027 bp, 1026 bp, 945 bp, 687 bp, 361 bp, 279 bp, or 20 bp. In some embodiments, overlap vectors contain a region of overlap of less than 1000 bp in length. In some embodiments, overlap vectors contain a region of overlap of less than 1365 bp. In some embodiments, overlap vectors contain a region of overlap of less than 700 bp. In some embodiments, the region of overlap has a length of between about 20 to 100 nucleotides, about 100 to 500 nucleotides, about 100 to 200 nucleotides, about 200 to 300 nucleotides, or about 300 to 400 nucleotides.

In various embodiments, the overlap polynucleotide vectors provided herein contain a region of overlap having a length of exactly 1365 bp, 1284 bp, 1027 bp, 1026 bp, 945 bp, 687 bp, 361 bp, 279 bp, or 20 bp. It will be understood that these regions of overlap may be mutually exclusive of one another in the coding sequence. In some embodiments, the overlap polynucleotide vectors contain one or more regions of overlap, e.g., contain two regions of overlap. In some embodiments, the overlap vectors contain two regions of overlap having lengths of 361 bp and 687 bp.

In exemplary embodiments, the overlap polynucleotide vectors provided herein contain a region of overlap having a length of 687 or 945 bp. In some embodiments, these vectors contain a region of overlapping MYO7A sequence having a length of 687 or 945 bp. In some embodiments, overlap vectors contain a region of overlap having a length of 361 bp.

```
1365 bp Overlap. (SEQ ID NO: 52)
CAGGTCTAACTTTCTGAAGCTGAAGAACGCTGCCACACTGATCCAGAGGCACTGGC

GGGGTCACAACTGTAGGAAGAACTACGGGCTGATGCGTCTGGGCTTCCTGCGGCTG

CAGGCCCTGCACCGCTCCCGGAAGCTGCACCAGCAGTACCGCCTGGCCCGCCAGCG

CATCATCCAGTTCCAGGCCCGCTGCCGCGCCTATCTGGTGCGCAAGGCCTTCCGCCA

CCGCCTCTGGGCTGTGCTCACCGTGCAGGCCTATGCCCGGGGCATGATCGCCCGCA

GGCTGCACCAACGCCTCAGGGCTGAGTATCTGTGGCGCCTCGAGGCTGAGAAAATG

CGGCTGGCGGAGGAAGAGAAGCTTCGGAAGGAGATGAGCGCCAAGAAGGCCAAG

GAGGAGGCCGAGCGCAAGCATCAGGAGCGCCTGGCCCAGCTGGCTCGTGAGGACG

CTGAGCGGGAGCTGAAGGAGAAGGAGGCCGCTCGGCGGAAGAAGGAGCTCCTGGA

GCAGATGGAAAGGGCCCGCCATGAGCCTGTCAATCACTCAGACATGGTGGACAAG

ATGTTTGGCTTCCTGGGGACTTCAGGTGGCCTGCCAGGCCAGGAGGGCCAGGCACC

TAGTGGCTTTGAGGACCTGGAGCGAGGGCGGAGGGAGATGGTGGAGGAGGACCTG

GATGCAGCCCTGCCCCTGCCTGACGAGGATGAGGAGGACCTCTCTGAGTATAAATT

TGCCAAGTTCGCGGCCACCTACTTCCAGGGGACAACCACGCACTCCTACACCCGGC

GGCCACTCAAACAGCCACTGCTCTACCATGACGACGAGGGTGACCAGCTGGCAGCC

CTGGCGGTCTGGATCACCATCCTCCGCTTCATGGGGGACCTCCCTGAGCCCAAGTA

CCACACAGCCATGAGTGATGGCAGTGAGAAGATCCCTGTGATGACCAAGATTTATG

AGACCCTGGGCAAGAAGACGTACAAGAGGGAGCTGCAGGCCCTGCAGGGCGAGGG

CGAGGCCCAGCTCCCCGAGGGCCAGAAGAAGAGCAGTGTGAGGCACAAGCTGGTG

CATTTGACTCTGAAAAAGAAGTCCAAGCTCACAGAGGAGGTGACCAAGAGGCTGC

ATGACGGGGAGTCCACAGTGCAGGGCAACAGCATGCTGGAGGACCGGCCCACCTC

CAACCTGGAGAAGCTGCACTTCATCATCGGCAATGGCATCCTGCGGCCAGCACTCC

GGGACGAGATCTACTGCCAGATCAGCAAGCAGCTGACCCACAACCCCTCCAAGAG

CAGCTATGCCCGGGGCTGGATTCTCGTGTCTCTCTGCGTGGGCTGTTTCGCCCCCTC

CGAGAAGTTTGTCAAGTACCTGCGGAACTTC

SEQ ID NO: 82
(protein sequence that corresponds to SEQ ID NO: 52)
RSNFLKLKNAATLIQRHWRGHNCRKNYGLMRLGFLRLQALHRSRKLHQQYRLARQRII

QFQARCRAYLVRKAFRHRLWAVLTVQAYARGMIARRLHQRLRAEYLWRLEAEKMRL

AEEEKLRKEMSAKKAKEEAERKHQERLAQLAREDAERELKEKEAARRKKELLEQMER

ARHEPVNHSDMVDKMFGFLGTSGGLPGQEGQAPSGFEDLERGRREMVEEDLDAALPL
```

-continued

PDEDEEDLSEYKFAKFAATYFQGTTTHSYTRRPLKQPLLYHDDEGDQLAALAVWITILR

FMGDLPEPKYHTAMSDGSEKIPVMTKIYETLGKKTYKRELQALQGEGEAQLPEGQKKS

SVRHKLVHLTLKKKSKLTEEVTKRLHDGESTVQGNSMLEDRPTSNLEKLHFIIGNGILR

PALRDEIYCQISKQLTHNPSKSSYARGWILVSLCVGCFAPSEKFVKYLRNF 1284 bp Overlap. (SEQ ID NO: 53)
GGGCTGATGCGTCTGGGCTTCCTGCGGCTGCAGGCCCTGCACCGCTCCCGGAAGCT

GCACCAGCAGTACCGCCTGGCCCGCCAGCGCATCATCCAGTTCCAGGCCCGCTGCC

GCGCCTATCTGGTGCGCAAGGCCTTCCGCCACCGCCTCTGGGCTGTGCTCACCGTGC

AGGCCTATGCCCGGGGCATGATCGCCCGCAGGCTGCACCAACGCCTCAGGGCTGAG

TATCTGTGGCGCCTCGAGGCTGAGAAAATGCGGCTGGCGGAGGAAGAGAAGCTTC

GGAAGGAGATGAGCGCCAAGAAGGCCAAGGAGGAGGCCGAGCGCAAGCATCAGG

AGCGCCTGGCCCAGCTGGCTCGTGAGGACGCTGAGCGGGAGCTGAAGGAGAAGGA

GGCCGCTCGGCGGAAGAAGGAGCTCCTGGAGCAGATGGAAAGGGCCCGCCATGAG

CCTGTCAATCACTCAGACATGGTGGACAAGATGTTTGGCTTCCTGGGGACTTCAGG

TGGCCTGCCAGGCCAGGAGGGCCAGGCACCTAGTGGCTTTGAGGACCTGGAGCGA

GGGCGGAGGGAGATGGTGGAGGAGGACCTGGATGCAGCCCTGCCCCTGCCTGACG

AGGATGAGGAGGACCTCTCTGAGTATAAATTTGCCAAGTTCGCGGCCACCTACTTC

CAGGGGACAACCACGCACTCCTACACCCGGCGGCCACTCAAACAGCCACTGCTCTA

CCATGACGACGAGGGTGACCAGCTGGCAGCCCTGGCGGTCTGGATCACCATCCTCC

GCTTCATGGGGGACCTCCCTGAGCCCAAGTACCACACAGCCATGAGTGATGGCAGT

GAGAAGATCCCTGTGATGACCAAGATTTATGAGACCCTGGGCAAGAAGACGTACA

AGAGGGAGCTGCAGGCCCTGCAGGGCGAGGGCGAGGCCCAGCTCCCCGAGGGCCA

GAAGAAGAGCAGTGTGAGGCACAAGCTGGTGCATTTGACTCTGAAAAAGAAGTCC

AAGCTCACAGAGGAGGTGACCAAGAGGCTGCATGACGGGGAGTCCACAGTGCAGG

GCAACAGCATGCTGGAGGACCGGCCCACCTCCAACCTGGAGAAGCTGCACTTCATC

ATCGGCAATGGCATCCTGCGGCCAGCACTCCGGGACGAGATCTACTGCCAGATCAG

CAAGCAGCTGACCCACAACCCCTCCAAGAGCAGCTATGCCCGGGGCTGGATTCTCG

TGTCTCTCTGCGTGGGCTGTTTCGCCCCCTCCGAGAAGTTTGTCAAGTACCTGCGGA

ACTTC

SEQ ID NO: 83
(protein sequence that corresponds to SEQ ID NO: 53)
GLMRLGFLRLQALHRSRKLHQQYRLARQRIIQFQARCRAYLVRKAFRHRLWAVLTVQ

AYARGMIARRLHQRLRAEYLWRLEAEKMRLAEEEKLRKEMSAKKAKEEAERKHQER

LAQLAREDAERELKEKEAARRKKELLEQMERARHEPVNHSDMVDKMFGFLGTSGGLP

GQEGQAPSGFEDLERGRREMVEEDLDAALPLPDEDEEDLSEYKFAKFAATYFQGTTTH

SYTRRPLKQPLLYHDDEGDQLAALAVWITILRFMGDLPEPKYHTAMSDGSEKIPVMTKI

YETLGKKTYKRELQALQGEGEAQLPEGQKKSSVRHKLVHLTLKKKSKLTEEVTKRLH

DGESTVQGNSMLEDRPTSNLEKLHFIIGNGILRPALRDEIYCQISKQLTHNPSKSSYARG

WILVSLCVGCFAPSEKFVKYLRNF 1027 bp Overlap. (SEQ ID NO: 54)
CAGGTCTAACTTTCTGAAGCTGAAGAACGCTGCCACACTGATCCAGAGGCACTGGC

GGGGTCACAACTGTAGGAAGAACTACGGGCTGATGCGTCTGGGCTTCCTGCGGCTG

CAGGCCCTGCACCGCTCCCGGAAGCTGCACCAGCAGTACCGCCTGGCCCGCCAGCG

```
CATCATCCAGTTCCAGGCCCGCTGCCGCGCCTATCTGGTGCGCAAGGCCTTCCGCCA

CCGCCTCTGGGCTGTGCTCACCGTGCAGGCCTATGCCCGGGGCATGATCGCCCGCA

GGCTGCACCAACGCCTCAGGGCTGAGTATCTGTGGCGCCTCGAGGCTGAGAAAATG

CGGCTGGCGGAGGAAGAGAAGCTTCGGAAGGAGATGAGCGCCAAGAAGGCCAAG

GAGGAGGCCGAGCGCAAGCATCAGGAGCGCCTGGCCCAGCTGGCTCGTGAGGACG

CTGAGCGGGAGCTGAAGGAGAAGGAGGCCGCTCGGCGGAAGAAGGAGCTCCTGGA

GCAGATGGAAAGGGCCCGCCATGAGCCTGTCAATCACTCAGACATGGTGGACAAG

ATGTTTGGCTTCCTGGGGACTTCAGGTGGCCTGCCAGGCCAGGAGGGCCAGGCACC

TAGTGGCTTTGAGGACCTGGAGCGAGGGCGGAGGGAGATGGTGGAGGAGGACCTG

GATGCAGCCCTGCCCCTGCCTGACGAGGATGAGGAGGACCTCTCTGAGTATAAATT

TGCCAAGTTCGCGGCCACCTACTTCCAGGGGACAACCACGCACTCCTACACCCGGC

GGCCACTCAAACAGCCACTGCTCTACCATGACGACGAGGGTGACCAGCTGGCAGCC

CTGGCGGTCTGGATCACCATCCTCCGCTTCATGGGGGACCTCCCTGAGCCCAAGTA

CCACACAGCCATGAGTGATGGCAGTGAGAAGATCCCTGTGATGACCAAGATTTATG

AGACCCTGGGCAAGAAGACGTACAAGAGGGAGCTGCAGGCCCTGCAGGGCGAGGG

CGAGGCCCAGCTCCCCGAGGGCCAG

SEQ ID NO: 84
(protein sequence that corresponds to SEQ ID NO: 54)
RSNFLKLKNAATLIQRHWRGHNCRKNYGLMRLGFLRLQALHRSRKLHQQYRLARQRII

QFQARCRAYLVRKAFRHRLWAVLTVQAYARGMIARRLHQRLRAEYLWRLEAEKMRL

AEEEKLRKEMSAKKAKEEAERKHQERLAQLAREDAERELKEKEAARRKKELLEQMER

ARHEPVNHSDMVDKMFGFLGTSGGLPGQEGQAPSGFEDLERGRREMVEEDLDAALPL

PDEDEEDLSEYKFAKFAATYFQGTTTHSYTRRPLKQPLLYHDDEGDQLAALAVWITILR

FMGDLPEPKYHTAMSDGSEKIPVMTKIYETLGKKTYKRELQALQGEGEAQLPEGQ 1026 bp Overlap. (SEQ ID NO: 55)
CTGGCGGAGGAAGAGAAGCTTCGGAAGGAGATGAGCGCCAAGAAGGCCAAGGAG

GAGGCCGAGCGCAAGCATCAGGAGCGCCTGGCCCAGCTGGCTCGTGAGGACGCTG

AGCGGGAGCTGAAGGAGAAGGAGGCCGCTCGGCGGAAGAAGGAGCTCCTGGAGC

AGATGGAAAGGGCCCGCCATGAGCCTGTCAATCACTCAGACATGGTGGACAAGAT

GTTTGGCTTCCTGGGGACTTCAGGTGGCCTGCCAGGCCAGGAGGGCCAGGCACCTA

GTGGCTTTGAGGACCTGGAGCGAGGGCGGAGGGAGATGGTGGAGGAGGACCTGGA

TGCAGCCCTGCCCCTGCCTGACGAGGATGAGGAGGACCTCTCTGAGTATAAATTTG

CCAAGTTCGCGGCCACCTACTTCCAGGGGACAACCACGCACTCCTACACCCGGCGG

CCACTCAAACAGCCACTGCTCTACCATGACGACGAGGGTGACCAGCTGGCAGCCCT

GGCGGTCTGGATCACCATCCTCCGCTTCATGGGGGACCTCCCTGAGCCCAAGTACC

ACACAGCCATGAGTGATGGCAGTGAGAAGATCCCTGTGATGACCAAGATTTATGAG

ACCCTGGGCAAGAAGACGTACAAGAGGGAGCTGCAGGCCCTGCAGGGCGAGGGCG

AGGCCCAGCTCCCCGAGGGCCAGAAGAAGAGCAGTGTGAGGCACAAGCTGGTGCA

TTTGACTCTGAAAAAGAAGTCCAAGCTCACAGAGGAGGTGACCAAGAGGCTGCAT

GACGGGAGTCCACAGTGCAGGGCAACAGCATGCTGGAGGACCGGCCCACCTCCA

ACCTGGAGAAGCTGCACTTCATCATCGGCAATGGCATCCTGCGGCCAGCACTCCGG

GACGAGATCTACTGCCAGATCAGCAAGCAGCTGACCCACAACCCCTCCAAGAGCA
```

```
GCTATGCCCGGGGCTGGATTCTCGTGTCTCTCTGCGTGGGCTGTTTCGCCCCCTCCG

AGAAGTTTGTCAAGTACCTGCGGAACTTC

SEQ ID NO: 85
(protein sequence that corresponds to SEQ ID NO: 55)
LAEEEKLRKEMSAKKAKEEAERKHQERLAQLAREDAERELKEKEAARRKKELLEQME

RARHEPVNHSDMVDKMFGFLGTSGGLPGQEGQAPSGFEDLERGRREMVEEDLDAALP

LPDEDEEDLSEYKFAKFAATYFQGTTTHSYTRRPLKQPLLYHDDEGDQLAALAVWITIL

RFMGDLPEPKYHTAMSDGSEKIPVMTKIYETLGKKTYKRELQALQGEGEAQLPEGQKK

SSVRHKLVHLTLKKKSKLTEEVTKRLHDGESTVQGNSMLEDRPTSNLEKLHFIIGNGIL

RPALRDEIYCQISKQLTHNPSKSSYARGWILVSLCVGCFAPSEKFVKYLRNF 945 bp Overlap. (SEQ ID NO: 56)
GGGCTGATGCGTCTGGGCTTCCTGCGGCTGCAGGCCCTGCACCGCTCCCGGAAGCT

GCACCAGCAGTACCGCCTGGCCCGCCAGCGCATCATCCAGTTCCAGGCCCGCTGCC

GCGCCTATCTGGTGCGCAAGGCCTTCCGCCACCGCCTCTGGGCTGTGCTCACCGTGC

AGGCCTATGCCCGGGGCATGATCGCCCGCAGGCTGCACCAACGCCTCAGGGCTGAG

TATCTGTGGCGCCTCGAGGCTGAGAAAATGCGGCTGGCGGAGGAAGAGAAGCTTC

GGAAGGAGATGAGCGCCAAGAAGGCCAAGGAGGAGGCCGAGCGCAAGCATCAGG

AGCGCCTGGCCCAGCTGGCTCGTGAGGACGCTGAGCGGGAGCTGAAGGAGAAGGA

GGCCGCTCGGCGGAAGAAGGAGCTCCTGGAGCAGATGGAAAGGGCCCGCCATGAG

CCTGTCAATCACTCAGACATGGTGGACAAGATGTTTGGCTTCCTGGGGACTTCAGG

TGGCCTGCCAGGCCAGGAGGGCCAGGCACCTAGTGGCTTTGAGGACCTGGAGCGA

GGGCGGAGGGAGATGGTGGAGGAGGACCTGGATGCAGCCCTGCCCCTGCCTGACG

AGGATGAGGAGGACCTCTCTGAGTATAAATTTGCCAAGTTCGCGGCCACCTACTTC

CAGGGGACAACCACGCACTCCTACACCCGGCGGCCACTCAAACAGCCACTGCTCTA

CCATGACGACGAGGGTGACCAGCTGGCAGCCCTGGCGGTCTGGATCACCATCCTCC

GCTTCATGGGGGACCTCCCTGAGCCCAAGTACCACACAGCCATGAGTGATGGCAGT

GAGAAGATCCCTGTGATGACCAAGATTTATGAGACCCTGGGCAAGAAGACGTACA

AGAGGGAGCTGCAGGCCCTGCAGGGCGAGGGCGAGGCCCAGCTCCCCGAGGGCCA

G

SEQ ID NO: 86
(protein sequence that corresponds to SEQ ID NO: 56)
GLMRLGFLRLQALHRSRKLHQQYRLARQRIIQFQARCRAYLVRKAFRHRLWAVLTVQ

AYARGMIARRLHQRLRAEYLWRLEAEKMRLAEEEKLRKEMSAKKAKEEAERKHQER

LAQLAREDAERELKEKEAARRKKELLEQMERARHEPVNHSDMVDKMFGFLGTSGGLP

GQEGQAPSGFEDLERGRREMVEEDLDAALPLPDEDEEDLSEYKFAKFAATYFQGTTTH

SYTRRPLKQPLLYHDDEGDQLAALAVWITILRFMGDLPEPKYHTAMSDGSEKIPVMTKI

YETLGKKTYKRELQALQGEGEAQLPEGQ 687 bp Overlap. (SEQ ID NO: 57)
CTGGCGGAGGAAGAGAAGCTTCGGAAGGAGATGAGCGCCAAGAAGGCCAAGGAG

GAGGCCGAGCGCAAGCATCAGGAGCGCCTGGCCCAGCTGGCTCGTGAGGACGCTG

AGCGGGAGCTGAAGGAGAAGGAGGCCGCTCGGCGGAAGAAGGAGCTCCTGGAGC

AGATGGAAAGGGCCCGCCATGAGCCTGTCAATCACTCAGACATGGTGGACAAGAT

GTTTGGCTTCCTGGGGACTTCAGGTGGCCTGCCAGGCCAGGAGGGCCAGGCACCTA
```

-continued
GTGGCTTTGAGGACCTGGAGCGAGGGCGGAGGGAGATGGTGGAGGAGGACCTGGA

TGCAGCCCTGCCCCTGCCTGACGAGGATGAGGAGGACCTCTCTGAGTATAAATTTG

CCAAGTTCGCGGCCACCTACTTCCAGGGGACAACCACGCACTCCTACACCCGGCGG

CCACTCAAACAGCCACTGCTCTACCATGACGACGAGGGTGACCAGCTGGCAGCCCT

GGCGGTCTGGATCACCATCCTCCGCTTCATGGGGGACCTCCCTGAGCCCAAGTACC

ACACAGCCATGAGTGATGGCAGTGAGAAGATCCCTGTGATGACCAAGATTTATGAG

ACCCTGGGCAAGAAGACGTACAAGAGGGAGCTGCAGGCCCTGCAGGGCGAGGGCG

AGGCCCAGCTCCCCGAGGGCCAG

SEQ ID NO: 87
(protein sequence that corresponds to SEQ ID NO: 57)
LAEEEKLRKEMSAKKAKEEAERKHQERLAQLAREDAERELKEKEAARRKKELLEQME

RARHEPVNHSDMVDKMFGFLGTSGGLPGQEGQAPSGFEDLERGRREMVEEDLDAALP

LPDEDEEDLSEYKFAKFAATYFQGTTTHSYTRRPLKQPLLYHDDEGDQLAALAVWITIL

RFMGDLPEPKYHTAMSDGSEKIPVMTKIYETLGKKTYKRELQALQGEGEAQLPEGQ 361 bp Overlap (same as SEQ ID NO: 39)
CAGGTCTAACTTTCTGAAGCTGAAGAACGCTGCCACACTGATCCAGAGGCACTGGC

GGGGTCACAACTGTAGGAAGAACTACGGGCTGATGCGTCTGGGCTTCCTGCGGCTG

CAGGCCCTGCACCGCTCCCGGAAGCTGCACCAGCAGTACCGCCTGGCCCGCCAGCG

CATCATCCAGTTCCAGGCCCGCTGCCGCGCCTATCTGGTGCGCAAGGCCTTCCGCCA

CCGCCTCTGGGCTGTGCTCACCGTGCAGGCCTATGCCCGGGGCATGATCGCCCGCA

GGCTGCACCAACGCCTCAGGGCTGAGTATCTGTGGCGCCTCGAGGCTGAGAAAATG

CGGCTGGCGGAGGAAGAGAAGCTT 279 bp Overlap (SEQ ID NO: 58)
GGGCTGATGCGTCTGGGCTTCCTGCGGCTGCAGGCCCTGCACCGCTCCCGGAAGCT

GCACCAGCAGTACCGCCTGGCCCGCCAGCGCATCATCCAGTTCCAGGCCCGCTGCC

GCGCCTATCTGGTGCGCAAGGCCTTCCGCCACCGCCTCTGGGCTGTGCTCACCGTGC

AGGCCTATGCCCGGGGCATGATCGCCCGCAGGCTGCACCAACGCCTCAGGGCTGAG

TATCTGTGGCGCCTCGAGGCTGAGAAAATGCGGCTGGCGGAGGAAGAGAAGCTT

SEQ ID NO: 88
(protein sequence that corresponds to SEQ ID NO: 58)
GLMRLGFLRLQALHRSRKLHQQYRLARQRIIQFQARCRAYLVRKAFRHRLWAVLTVQ

AYARGMIARRLHQRLRAEYLWRLEAEKMRLAEEEKL 20 bp Overlap (SEQ ID NO: 59):
TGGCGGAGGAAGAGAAGCTT SEQ ID NO: 89 (protein sequence that corresponds to SEQ ID NO: 59):
AEEEKL In some embodiments of the disclosed hybrid and overlap vectors, any of the disclosed front half vectors (5' AAV) comprise a left inverted terminal repeat sequence that comprises a nucleotide sequence having at least 95% or 98% identity to SEQ ID NO: 60. In some embodiments of the disclosed hybrid and overlap vectors, any of the disclosed front half vectors comprise a left inverted terminal repeat sequence that comprises SEQ ID NO: 60. In some embodiments of the disclosed hybrid and overlap vectors, any of the disclosed back half vectors (3' AAV) comprise a right inverted terminal repeat sequence that comprises SEQ ID NO: 61. In some embodiments of the disclosed hybrid and overlap vectors, any of the disclosed back half vectors comprise a right inverted terminal repeat sequence that comprises a nucleotide sequence having at least 95% or 98% identity to SEQ ID NO: 61. In various embodiments, any of the disclosed dual hybrid and overlap vector pairs comprise a left ITR sequence comprising SEQ ID NO: 60 and a right ITR sequence comprising SEQ ID NO: 61.

Left ITR Sequence(SEQ ID NO: 60).
CTCCCTCTCTGCGCGCTCGCTCGCTCACTGAGGCCGCCCGGGCAAAGCCC

GGGCGTCGGGCGACCTTTGGTCGCCCGGCCTCAGTGAGCGAGCGAGCGCG

CAGAGAGGGAGTGGCCAACTCCATCACTAGGGGTT

-continued

Right ITR Sequence(SEQ ID NO: 61).
AACCCCTAGTGATGGAGTTGGCCACTCCCTCTCTGCGCGCTCGCTCGCTC

ACTGAGGCCGGGCGACCAAAGGTCGCCCGACGCCCGGGCTTTGCCCGGGC

GGCCTCAGTGAGCGAGCGAGCGCGCAGAGAGGGAG

TABLE 2

Overlap Region Information & Sequences

| Overlap Fragment Name/Length: | Position in hMYO7A cDNA Start: | End: |
|---|---|---|
| 1365 | 2281 | 3645 |
| 1284 | 2362 | 3645 |
| 1027 | 2281 | 3306 |
| 1026 | 2620 | 3645 |
| 945 | 2362 | 3306 |
| 687 | 2620 | 3306 |
| 361 | 2280 | 2640 |
| 279 | 2362 | 2640 |
| 20 | 2621 | 2640 |

TABLE 3

Select Examples 6 and 7 AAV Sequences and Components (amino acid (aa), nucleic acid (nt))

| SEQUENCE | FULL-LENGTH AAV SEQUENCE |
|---|---|
| \multicolumn{2}{c}{Myosin7A N-terminus} |
| SEQ ID NO: 62 (aa) SEQ ID NO: 63 (nt) | AAV-smCBA-hMYO7A-noDimNT-CMv1 (SEQ ID NO: 36) |
| SEQ ID NO: 91 (aa) SEQ ID NO: 90 (nt) | AAV-smCBA-hMYO7A-noDIM-NTlong (SEQ ID NO: 37) |
| SEQ ID NO: 65 (aa) SEQ ID NO: 66 (nt) | AAV-smCBA-hMYO7A-NTlong-v3 (SEQ ID NO: 50) |
| SEQ ID NO: 74 (aa) SEQ ID NO: 73 (nt) | AAV-smCBA-hMYO7A-NT-Ex21-APSD-APhead (SEQ ID NO: 31) AAV-smCBA-hMYO7A-NT-Ex21-APSD-APhead CMv1 (SEQ ID NO: 33) AAV-smCBA-hMYO7A-NT-Ex21-APSD-APhead CMv2 (SEQ ID NO: 34) AAV-smCBA-hMYO7A- NT-Ex21-APSD-APhead-CMv3 (SEQ ID NO: 46) |
| \multicolumn{2}{c}{Myosin7A C-terminus} |
| SEQ ID NO: 78 (aa) SEQ ID NO: 77 (nt) SEQ ID NO: 81 (aa) SEQ ID NO: 80 (nt) | AAV-hMYO7A-CTlong-v2.HA (SEQ ID NO: 38) AAV-hMYO7A-CTlong-v3.HA (SEQ ID NO: 51) |
| SEQ ID NO: 76 (aa) SEQ ID NO: 75 (nt) | AAV-APhead-APSA-ex22hMYO7A-CT.HA (SEQ ID NO: 32) AAV-APhead-APSA-ex22hMYO7A-CT.HA-CMv2 (SEQ ID NO: 35) AAV-APhead-APSA-hMYO7ACTex22-CMv2.1 (SEQ ID NO: 44) AAV-APhead-APSA-hMYO7ACTex22-CMv2.1.HA (SEQ ID NO: 47) AAV-APhead-APSA-hMYO7ACTex22.HA-MIN (SEQ ID NO: 48) AAV-APhead-APSA-hMYO7ACTex22-MIN (SEQ ID NO: 49) |
| \multicolumn{2}{c}{Myosin7A overlap} |
| SEQ ID NO: 79 (aa) SEQ ID NO: 39 (nt) | AAV-smCBA-hMYO7A-noDIM-NTlong (SEQ ID NO: 37) + AAV-hMYO7A-CTlong.HA (SEQ ID NO: 2) AAV-smCBA-hMYO7A-noDIM-NTlong-CMv1 (SEQ ID NO: 36) + AAV-hMYO7A-CTlong.HA (SEQ ID NO: 2) |
| SEQ ID NO: 82 (aa) SEQ ID NO: 52 (nt) | AAV-smCBA-hMYO7A-NTlong (SEQ ID NO: 1) + AAV-hMYO7A-CTlong.HA (SEQ ID NO: 2) |
| SEQ ID NO: 83 (aa) SEQ ID NO: 53 (nt) | AAV-smCBA-hMYO7A-NTlong (SEQ ID NO: 1) + AAV-hMYO7A-CTlong-v2.HA (SEQ ID NO: 38) |
| SEQ ID NO: 84 (aa) SEQ ID NO: 54 (nt) | AAV-smCBA-hMYO7A-NTlong-v3 (SEQ ID NO: 50) + AAV-hMYO7A-CTlong.HA (SEQ ID NO: 2) |
| SEQ ID NO: 85 (aa) SEQ ID NO: 55 (nt) | AAV-smCBA-hMYO7A-NTlong (SEQ ID NO: 1) + AAV-hMYO7A-CTlong-v3.HA (SEQ ID NO: 51) |
| SEQ ID NO: 86 (aa) SEQ ID NO: 56 (nt) | AAV-smCBA-hMYO7A-NTlong-v3 (SEQ ID NO: 50) + AAV-hMYO7A-CTlong-v2.HA (SEQ ID NO: 38) |
| SEQ ID NO: 87 (aa) SEQ ID NO: 57 (nt) | AAV-smCBA-hMYO7A-NTlong-v3 (SEQ ID NO: 50) + AAV-hMYO7A-CTlong-v3.HA (SEQ ID NO: 51) |
| SEQ ID NO: 88 (aa) SEQ ID NO: 58 (nt) | AAV-smCBA-hMYO7A-noDIM-NTlong (SEQ ID NO: 37) + AAV-hMYO7A-CTlong-v2.HA (SEQ ID NO: 38) AAV-smCBA-hMYO7A-noDimNT-CMv1 (SEQ ID NO: 36) + AAV-hMYO7A-CTlong-v2.HA (SEQ ID NO: 38) |
| SEQ ID NO: 89 (aa) SEQ ID NO: 59 (nt) | AAV-smCBA-hMYO7A-noDIMNTlong (SEQ ID NO: 37) + (AAV-hMYO7A-CTlong-v3.HA (SEQ ID NO: 51) AAV-smCBA-hMYO7A-noDIMNTlong-CMv1 (SEQ ID NO: 36) + (AAV-hMYO7A-CTlong-v3.HA (SEQ ID NO: 51) |
| \multicolumn{2}{c}{smCBA Promoter} |
| SEQ ID NO: 64 (nt) | (SEQ ID NO: 1) AAV-smCBA-hMYO7A-NT-Ex21-APSD-APhead (SEQ ID NO: 31) (SEQ ID NO: 34) (SEQ ID NO: 3) (SEQ ID NO: 33) (SEQ ID NO: 37) |

TABLE 3-continued

Select Examples 6 and 7 AAV Sequences and Components (amino acid (aa), nucleic acid (nt)

| SEQUENCE | FULL-LENGTH AAV SEQUENCE |
|---|---|
| | (SEQ ID NO: 36)<br>(SEQ ID NO: 50) |
| | HA tag |
| SEQ ID<br>NO: 72 (nt) | AAV-APhead-APSA-ex22hMYO7A-CT.HA<br>(SEQ ID NO: 32)<br>AAV-APhead-APSA-ex22hMYO7A-CT.HA-<br>CMv2 (SEQ ID NO: 35)<br>AAV-hMYO7A-CTlong-v2.HA<br>(SEQ ID NO: 38)<br>AAV-APhead-APSA-hMYO7ACTex22-<br>CMv2.1 (SEQ ID NO: 44)<br>AAV-APhead-APSA-hMYO7ACT<br>ex22-CMv2.1.HA (SEQ ID NO: 47)<br>AAV-APhead-APSA-hMYO7ACTex<br>22.HA-MIN (SEQ ID NO: 48) |

REFERENCES

The following references, to the extent that they provide exemplary procedural or other details supplementary to those set forth herein, are specifically incorporated herein by reference:

Allocca, M et al., "Novel adeno-associated virus serotypes efficiently transduce murine photoreceptors," *J. Virol.*, 81(20):11372-80 (2007).

Allocca, M et al., "Serotype-dependent packaging of large genes in adeno-associated viral vectors results in effective gene delivery in mice," *J. Clin. Invest.*, 118(5): 1955-1964 (2008).

Altschul, S F et al., "Basic local alignment search tool," *J. Mol. Biol.*, 215:403-410 (1990).

Altschul, S F et al., "Gapped BLAST and PSI-BLAST: A new generation of protein database search programs," *Nucl. Acids Res.*, 25:3389-3402 (1997).

Astuto, L M et al., "Genetic heterogeneity of Usher syndrome: analysis of 151 families with Usher type I," *Am. J. Hum. Genet.*, 67:1569-1574 (2000).

Bainbridge, J W et al., "Effect of gene therapy on visual function in Leber's congenital amaurosis," *N. Engl. J. Med.*, 358:2231-2239 (2008).

Beltz, G A et al., "Isolation of multigene families and determination of homologies by filter hybridization methods," *Meth. Enzymol.*, 100:266-285 (1983).

Bharadwaj, A K et al., "Evaluation of the myosin VIIA gene and visual function in patients with Usher syndrome type I," *Exp. Eye Res.*, 71:173-181 (2000).

Bowles, D E et al., "Phase I gene therapy for Duchenne muscular dystrophy using a translational optimized AAV vector," *Mol. Ther.*, 20:443-455 (2012).

Boye, S E et al., "A comprehensive review of retinal gene therapy," *Mol. Ther.*, 21:509-519 (2013).

Boye, S L et al., "AAV-mediated gene therapy in the guanylate cyclase (RetGC1/RetGC2) double knockout mouse model of Leber congenital amaurosis," *Hum. Gene Ther.*, 24:189-202 (2012).

Boye, S L et al., "Long-term preservation of cone photoreceptors and restoration of cone function by gene therapy in the guanylate cyclase-1 knockout (GC1KO) mouse," *Invest. Ophthalmol. Vis. Sci.*, 52:7098-7108 (2011).

Chen, Z Y et al., "Molecular cloning and domain structure of human myosin-VIIa, the gene product defective in Usher syndrome 1B," *Genomics*, 36:440-448 (1996).

Cideciyan, A V et al., "Human RPE65 gene therapy for Leber congenital amaurosis: persistence of early visual improvements and safety at 1 year," *Hum. Gene Ther.*, 20:999-1004 (2009).

Dong, B et al., "Characterization of genome integrity for oversized recombinant AAV vector," *Mol. Ther.*, 18(1): 87-92 (2010).

Duan, D et al., "Circular intermediates of recombinant adeno-associated virus have defined structural characteristics responsible for long-term episomal persistence in muscle tissue," *J. Virol.*, 72:8568-8577 (1998).

Duan, D et al., "Expanding AAV packaging capacity with trans-splicing or overlapping vectors: a quantitative comparison," *Mol. Ther.*, 4:383-391 (2001).

Duan, D et al., "Trans-splicing vectors expand the packaging limits of adeno-associated virus for gene therapy applications," *Methods Mol. Med.*, 76:287-307 (2003).

Dyka, F M et al., "Dual adeno-associated virus vectors result in efficient in vitro and in vivo expression of an oversized gene, MYO7A," *Hum. Gene Ther. Methods*, 25(2):166-177 (2014).

Esumi, N et al., "Analysis of the VMD2 promoter and implication of E-box binding factors in its regulation," *J. Biol. Chem.*, 279:19064-19073 (2004).

Felgner, P L et al., "Lipofection: a highly efficient, lipid-mediated DNA-transfection procedure," *Proc. Nat'l. Acad. Sci. USA*, 84(21):7413-7417 (1987).

Flotte, T R et al., "Phase 2 clinical trial of a recombinant adeno-associated viral vector expressing alpha1-antitrypsin: interim results," *Hum. Gene Ther.*, 22:1239-1247 (2011).

*Gene Therapy: Principles and Applications*, Blankenstein, T. (Ed.), Birkhauser-Verlag, Basel, Switzerland (1999).

Ghosh, A et al., "A hybrid vector system expands adeno-associated viral vector packaging capacity in a trans-gene-independent manner," *Mol. Ther.*, 16:124-130 (2008).

Ghosh, A et al., "Efficient transgene reconstitution with hybrid dual AAV vectors carrying the minimized bridging sequences," *Hum. Gene Ther.*, 22:77-83 (2011).

Gibbs, D and Williams, D S, "Isolation and culture of primary mouse retinal pigmented epithelial cells," *Adv. Exp. Med. Biol.*, 533:347-352 (2003b).

Gibbs, D et al., "Abnormal phagocytosis by retinal pigmented epithelium that lacks myosin VIIa, the Usher syndrome 1B protein," *Proc. Nat'l. Acad. Sci. USA*, 100:6481-6486 (2003a).

Gibbs, D et al., "Role of myosin VIIa and Rab27a in the motility and localization of RPE melanosomes," *J. Cell Sci.*, 117:6473-6483 (2004).

Gibson, F et al., "A type VII myosin encoded by mouse deafness gene shaker-1," *Nature*, 374:62-64 (1995).

Grieger, J C and Samulski, R J, "Packaging capacity of adeno-associated virus serotypes: impact of larger genomes on infectivity and postentry steps," *J. Virol.*, 79:9933-9944 (2005).

Haire, S E et al., "Light-driven cone arrestin translocation in cones of postnatal guanylate cyclase-1 knockout mouse retina treated with AAV-GC1," *Invest. Ophthalmol. Vis. Sci.*, 47:3745-3753 (2006).

Halbert, C L et al., "Efficient mouse airway transduction following recombination between AAV vectors carrying parts of a larger gene," *Nat. Biotechnol.*, 20:697-701 (2002).

Hashimoto, T et al., "Lentiviral gene replacement therapy of retinas in a mouse model for Usher syndrome type 1B," *Gene Ther.*, 14(7):584-594 (2007).

Hasson, T et al., "Effects of shaker-1 mutations on myosin-VIIa protein and mRNA expression," *Cell Motil. Cytoskeleton*, 37:127-138 (1997).

Hasson, T et al., "Expression in cochlea and retina of myosin VIIa, the gene product defective in Usher syndrome type 1B," *Proc. Nat'l. Acad. Sci. USA*, 92:9815-9819 (1995).

Hauswirth, W W et al., "Treatment of leber congenital amaurosis due to RPE65 mutations by ocular subretinal injection of adeno-associated virus gene vector: short-term results of a phase I trial," *Hum. Gene Ther.*, 19:979-990 (2008).

Hirsch, M L et al., "AAV recombineering with single strand oligonucleotides," *PLoS One* 4:e7705 (2009).

Hirsch, M L et al., "Little vector, big gene transduction: fragmented genome reassembly of adeno-associated virus," *Mol. Ther.*, 18(1):6-8 (2010).

Hirsch, M L et al., "Oversized AAV transduction is mediated via a DNA-PKcs-independent, Rad51C-dependent repair pathway," *Mol. Ther.*, 21:2205-2216 (2013).

Jacobson, S G et al., "Retinal disease course in Usher syndrome 1B due to MYO7A mutations," *Invest. Ophthalmol. Vis. Sci.*, 52:7924-7936 (2011).

Jacobson, S G et al., "Safety of recombinant adeno-associated virus type 2-RPE65 vector delivered by ocular subretinal injection," *Molec. Ther.*, 13:1074-1084 (2006).

Jacobson, S G et al., "Usher syndromes due to MYO7A, PCDH15, USH2A or GPR98 mutations share retinal disease mechanism," *Hum. Mol. Genet.*, 17:2405-2415 (2008).

Kapranov, P et al., "Native molecular state of adeno-associated viral vectors revealed by single-molecule sequencing," *Hum. Gene Ther.*, 23:46-55 (2012).

Karlin, S and Altschul, S F "Applications and statistics for multiple high-scoring segments in molecular sequences," *Proc. Nat'l. Acad. Sci. USA*, 90:5873-5877 (1993).

Karlin, S and Altschul, S F, "Methods for assessing the statistical significance of molecular sequence features by using general scoring schemes," *Proc. Nat'l. Acad. Sci. USA*, 87:2264-2268 (1990).

Keats, B J and Corey, D P "The usher syndromes," *Am. J. Med. Genet.*, 89:158-166 (1999). Klomp, A E et al., "Analysis of the linkage of MYRIP and MYO7A to melanosomes by RAB27A in retinal pigment epithelial cells," *Cell Motil. Cytoskeleton*, 64:474-487 (2007).

Lai, Y et al., "Design of trans-splicing adeno-associated viral vectors for Duchenne muscular dystrophy gene therapy," *Methods Mol. Biol.*, 433:259-275 (2008).

Lai, Y et al., "Efficient in vivo gene expression by trans-splicing adeno-associated viral vectors," *Nat. Biotechnol.*, 23:1435-1439 (2005).

Lai, Y et al., "Evidence for the failure of adeno-associated virus serotype 5 to package a viral genome ≥8.2 kb," *Mol. Ther.*, 18(1):75-79 (2010).

Lai, Y et al., "Synthetic intron improves transduction efficiency of trans-splicing adeno-associated viral vectors," *Hum. Gene Ther.*, 17:1036-1042 (2006).

Li, M et al., "High-efficiency transduction of fibroblasts and mesenchymal stem cells by tyrosine-mutant AAV2 vectors for their potential use in cellular therapy," *Hum. Gene Ther.*, 21:1527-1543 (2010).

Liu, X et al., "Mutant myosin VIIa causes defective melanosome distribution in the RPE of shaker-1 mice," *Nat. Genet.*, 19:117-118 (1998).

Liu, X et al., "Myosin VIIa participates in opsin transport through the photoreceptor cilium," *J. Neurosci.*, 19:6267-6274 (1999).

Liu, X et al., "Myosin VIIa, the product of the Usher 1B syndrome gene, is concentrated in the connecting cilia of photoreceptor cells," *Cell Motil. Cytoskel.*, 37:240-252 (1997).

Liu, X Z et al., "Mutations in the myosin VIIA gene cause non-syndromic recessive deafness," *Nat. Genet.*, 16:188-190 (1997).

Lopes, V S et al., "Retinal gene therapy with a large MYO7A cDNA using adeno-associated virus," *Gene Ther.*, 20:824-833 (2013).

Lopes, V S et al., "The ternary Rab27a-Myrip-Myosin VIIa complex regulates melanosome motility in the retinal pigment epithelium," *Traffic*, 8:486-499 (2007).

Lopes, V S et al., "The Usher 1B protein, MYO7A, is required for normal localization and function of the visual retinoid cycle enzyme, RPE65," *Hum. Mol. Genet.*, 20(13):2560-2570 (2011).

Lostal, W et al., "Efficient recovery of dysferlin deficiency by dual adeno-associated vector-mediated gene transfer," *Hum. Mol. Genet.*, 19:1897-1907 (2010).

Maguire, A M et al., "Age-dependent effects of RPE65 gene therapy for Leber's congenital amaurosis: a phase 1 dose-escalation trial," *Lancet*, 374:1597-1605 (2009).

Markusic, D M et al., "High-efficiency transduction and correction of murine hemophilia B using AAV2 vectors devoid of multiple surface-exposed tyrosines," *Mol. Ther.*, 18:2048-2056 (2010).

*Molecular Cloning: A Laboratory Manual*, (Maniatis, T, Fritsch, E F, and Sambrook, J), Cold Spring Harbor Laboratory, Cold Spring Harbor, NY (1982).

Nathwani, A C et al., "Adenovirus-associated virus vector-mediated gene transfer in hemophilia B," *N. Engl. J. Med.*, 365:2357-2365 (2011).

Ouyang, X M et al., "Characterization of Usher syndrome type I gene mutations in an Usher syndrome patient population," *Hum. Genet.*, 116:292-299 (2005).

Pang, J J et al., "Comparative analysis of in vivo and in vitro AAV vector transduction in the neonatal mouse retina: effects of serotype and site of administration," *Vision Res.*, 48:377-385 (2008).

Petrs-Silva, H et al., "High-efficiency transduction of the mouse retina by tyrosine-mutant AAV serotype vectors." *Mol. Ther.* 17:463-471 (2009).

Petrs-Silva, H et al., "Novel properties of tyrosine-mutant AAV2 vectors in the mouse retina," *Mol. Ther.*, 19:293-301 (2011).

Ryals, R C et al., "Quantifying transduction efficiencies of unmodified and tyrosine capsid mutant AAV vectors in vitro using two ocular cell lines," *Mol. Vis.*, 17:1090-1102 (2011).

Sahly, I et al., "Localization of Usher 1 proteins to the photoreceptor calyceal processes, which are absent from mice," *J. Cell Biol.*, 199:381-399 (2012).

Saihan, Z et al., "Update on Usher syndrome," *Curr. Opin. Neurol.*, 22:19-27 (2009).

Simonelli, F et al., "Gene therapy for Leber's congenital amaurosis is safe and effective through 1.5 years after vector administration," *Mol. Ther.*, 18:643-650 (2010).

Smith, R J et al., "Clinical diagnosis of the Usher syndromes," *Usher Syndrome Consortium. Am. J. Med. Genet.*, 50:32-38 (1994).

Soni, L E et al., "The unconventional myosin-VIIa associates with lysosomes," *Cell Motil. Cytoskeleton*, 62:13-26 (2005).

Timmers, A M et al., "Subretinal injections in rodent eyes: effects on electrophysiology and histology of rat retina," *Mol. Vis.*, 7:131-137 (2001).

Trapani, I et al., "Effective delivery of large genes to the retina by dual AAV vectors," *EMBO Mol. Med.*, 6:194-211 (2014).

Trapani, I, et al., "Improved dual AAV vectors with reduced expression of truncated proteins are safe and effective in the retina of a mouse model of Stargardt disease," *Hum. Mol. Gen.*, 24(23): 8811-6825 (2015).

Weil, D et al., "Defective myosin VIIA gene responsible for Usher syndrome type 1B," *Nature*, 374:60-61 (1995).

Weil, D et al., "Human myosin VIIA responsible for the Usher 1B syndrome: a predicted membrane-associated motor protein expressed in developing sensory epithelia," *Proc. Nat'l. Acad. Sci. USA*, 93:3232-3237 (1996).

Williams, D S and Lopes, V S "The many different cellular functions of MYO7A in the retina," *Biochem. Soc. Trans.*, 39:1207-1210 (2011).

Williams, D S, "Usher syndrome: Animal models, retinal function of Usher proteins, and prospects for gene therapy," *Vision Res.*, 48:433-441 (2008).

Wolfrum, U et al., "Myosin VIIa as a common component of cilia and microvilli," *Cell Motil. Cytoskeleton*, 40:261-271 (1998).

Wu, Z et al., "Effect of genome size on AAV vector packaging," *Mol. Ther.*, 18(1):80-86 (2010).

Yan, Z et al., "Inverted terminal repeat sequences are important for intermolecular recombination and circularization of adeno-associated virus genomes," *J. Virol.*, 79:364-379 (2005).

Yan, Z et al., "Recombinant AAV-mediated gene delivery using dual vector heterodimerization," *Methods Enzymol.*, 346:334-357 (2002).

Yan, Z et al., "Trans-splicing vectors expand the utility of adeno-associated virus for gene therapy," *Proc. Nat'l. Acad. Sci. USA*, 97:6716-6721 (2000).

Yang, J et al., "Concatemerization of adeno-associated virus circular genomes occurs through intermolecular recombination," *J. Virol.*, 73:9468-9477 (1999).

Zhang, Y and Duan, D "Novel mini-dystrophin gene dual adeno-associated virus vectors restore neuronal nitric oxide synthase expression at the sarcolemma," *Hum. Gene Ther.*, 23:98-103 (2012).

Zhong, L et al., "Next generation of adeno-associated virus 2 vectors: point mutations in tyrosines lead to high-efficiency transduction at lower doses," *Proc. Nat'l. Acad. Sci. USA*, 105(22):7827-7832 (2008).

Zolotukhin, S et al., "Production and purification of serotype 1, 2, and 5 recombinant adeno-associated viral vectors," *Methods*, 28:158-167 (2002).

EQUIVALENTS

It should be understood that the examples and embodiments described herein are for illustrative purposes only and that various modifications or changes in light thereof will be suggested to persons skilled in the art and are to be included within the spirit and purview of this application and the scope of the appended claims.

All references cited herein (including publications, patent applications and patents) are incorporated by reference to the same extent as if each reference was individually and specifically incorporated by reference, and was set forth in its entirety herein.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order, unless otherwise indicated herein, or unless otherwise clearly contradicted by context.

The use of any examples, or exemplary language (e.g., "such as") provided herein, is intended merely to better illustrate the disclosure and does not pose a limitation on the scope of the disclosure unless otherwise indicated. No language in the specification should be construed as indicating any element is essential to the practice of the disclosure unless as much is explicitly stated.

The description herein of any aspect or embodiment of the disclosure using terms such as "comprising", "having", "including" or "containing" with reference to an element or elements is intended to provide support for a similar aspect or embodiment of the disclosure that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context). For example, a nucleotide sequence described herein as comprising a particular element should be understood as also describing a nucleotide sequence consisting of that element, unless otherwise stated or clearly contradicted by context.

All of the compositions and methods disclosed and claimed herein can be made and executed without undue experimentation in light of the present disclosure. While the compositions and methods of this invention have been described in terms of preferred embodiments, it will be apparent to those of ordinary skill in the art that variations may be applied to the compositions and/or methods disclosed herein, and/or to the steps or the sequence of steps of the methods described herein without departing from the concept, spirit and/or scope of the disclosure. More specifically, it will be apparent that certain agents that are chemically- and/or physiologically-related may be substituted for the agents described herein while the same or similar results would be achieved. All such similar substitutes and modifications apparent to those skilled in the art are deemed to be within the spirit, scope and concept of the disclosure as defined by the appended claims.

What is claimed is:

1. A polynucleotide vector system comprising:
   i) a first AAV vector polynucleotide comprising an inverted terminal repeat at each end of a polynucleotide comprising a promoter followed by a first partial coding sequence that encodes an N-terminal part of a full-length myosin polypeptide, and
   ii) a second AAV vector polynucleotide comprising an inverted terminal repeat at each end of a polynucleotide comprising a second partial coding sequence that encodes a C-terminal part of the full-length myosin polypeptide, and wherein the N-terminal part of the full-length myosin polypeptide comprises an amino acid sequence having at least 90% identity to the amino acid sequence of SEQ ID NO: 62; and
   the C-terminal part of the full-length myosin polypeptide comprises an amino acid sequence having at least 90% identity to the amino acid sequence of SEQ ID NO: 81,
   wherein the first partial coding sequence does not encode the single-alpha helix (SAH) domain of the full-length myosin polypeptide, and the first partial coding sequence and the second partial coding sequence encode the full-length myosin polypeptide.

2. The polynucleotide vector system of claim 1, wherein the promoter is selected from the group consisting of: a CMV promoter, an EF-1 alpha promoter, a cone arrestin promoter, a smCBA promoter, a human myosin 7a gene-derived promoter, a TαC gene-derived promoter, a rhodopsin promoter, a cGMP-phosphodiesterase β-subunit promoter, human or mouse rhodopsin promoter, a hGRK1 promoter, a rod specific IRBP promoter, a VMD2 promoter, a synapsin promoter, a glial fibrillary acidic protein (GFAP) promoter, and combinations thereof.

3. The polynucleotide vector system of claim 1, comprising a 3' untranslated region downstream of the second partial coding sequence.

4. The polynucleotide vector system of claim 3, wherein the 3' untranslated region comprises a substitution as compared to the wild-type myosin 3' untranslated region.

5. The polynucleotide vector system of claim 1, wherein the first AAV vector polynucleotide comprises an overlap sequence and the second AAV vector polynucleotide comprises the overlap sequence, wherein the overlap sequence is an intron of a gene encoding the full-length myosin polypeptide, the AK sequence of the F1 phage, or a synthetic alkaline phosphatase (AP) intron.

6. The polynucleotide vector system of claim 5, wherein the first AAV vector polynucleotide comprises a splice donor site and the second AAV vector polynucleotide comprises a splice acceptor site.

7. A viral particle comprising the polynucleotide vector system of claim 1, wherein the viral particle comprises an AAV2, AAV5, AAV7, AAV8, AAV44.9, AAV44.9 (E531D), AAV9-PHP.B, or AAV44.9 (Y733F) capsid.

8. The polynucleotide vector system of claim 1, wherein the N-terminal part of the full-length myosin polypeptide is at least 95% identical to the amino acid sequence of SEQ ID NO: 62.

9. The polynucleotide vector system of claim 1, wherein the N-terminal part of the full-length myosin polypeptide consists of amino acid residues 1-862 of SEQ ID NO: 62.

10. The polynucleotide vector system of claim 8, wherein the C-terminal part of the full-length myosin polypeptide comprises an amino acid sequence that is at least 95% identical to the amino acid sequence of SEQ ID NO: 81.

11. The polynucleotide vector system of claim 8, wherein the C-terminal part of the full-length myosin polypeptide comprises the amino acid sequence of SEQ ID NO: 81.

12. The polynucleotide vector system of claim 11, wherein the full-length myosin polypeptide is a biologically-active MYO7A polypeptide.

13. The polynucleotide vector system of claim 12, wherein the promoter is a smCBA promoter.

14. A viral particle comprising the polynucleotide vector system of claim 13, wherein the viral particle comprises an AAV44.9 (E531D) capsid.

* * * * *